(12) United States Patent
Patek et al.

(10) Patent No.: US 7,354,933 B2
(45) Date of Patent: Apr. 8, 2008

(54) CYCLIC UREA DERIVATIVES, PREPARATION THEREOF AND PHARMACEUTICAL USE THEREOF AS KINASE INHIBITORS

(75) Inventors: Marcel Patek, Tucson, AZ (US); Anil Nair, Tucson, AZ (US); Augustin Hittinger, Igny (FR); Conception Nemecek, Thiais (FR); Daniel Bond, Tucson, AZ (US); Greg Harlow, Boulder, CO (US); Herve Bouchard, Thiais (FR); Jacques Mauger, Tucson, AZ (US); Jean-Luc Malleron, Marcoussis (FR); Mark Palermo, Rindge, NH (US); Fahad Al-Obeidi, Tucson, AZ (US); Thomas Faitg, Exton, PA (US); Hartmut Strobel, Liederbach (DE); Sven Ruf, Floersheim (DE); Kurt Ritter, Frankfurt Am Main (DE); Youssef El-Ahmad, Creteil (FR); Dominique Lesuisse, Montreuil (FR); Didier Bénard, Attainville (FR)

(73) Assignee: Aventis Pharma SA, Antony (FR)

( * ) Notice: Subject to any disclaimer, the term of this patent is extended or adjusted under 35 U.S.C. 154(b) by 294 days.

(21) Appl. No.: 10/770,382

(22) Filed: Feb. 2, 2004

(65) Prior Publication Data
US 2004/0248884 A1 Dec. 9, 2004

Related U.S. Application Data

(60) Provisional application No. 60/468,685, filed on May 7, 2003.

(30) Foreign Application Priority Data

Jan. 31, 2003 (FR) .................................. 03 01098

(51) Int. Cl.
*C07D 401/06* (2006.01)
*C07D 403/06* (2006.01)
*A61K 31/41* (2006.01)

(52) U.S. Cl. ..................... 514/314; 514/341; 514/389; 514/391; 546/172; 546/274.4; 548/319.1

(58) Field of Classification Search ................ 546/172, 546/274.4; 548/319.1; 514/314, 341, 389, 514/391
See application file for complete search history.

(56) References Cited

U.S. PATENT DOCUMENTS

| 4,097,578 | A | 6/1978 | Perronnet et al. |
| 5,276,049 | A | 1/1994 | Himmelsbach et al. |
| 6,022,875 | A | 2/2000 | Zimmer et al. |
| 6,759,415 | B1 * | 7/2004 | Poitout et al. ............... 514/274 |

FOREIGN PATENT DOCUMENTS

| EP | 0 503 548 A1 | 9/1992 |
| EP | 0584694 | 3/1994 |
| EP | 0770613 | 5/1997 |
| WO | WO 97/38984 | 10/1997 |
| WO | WO 98/39303 | 9/1998 |
| WO | WO 01/09090 | * 2/2001 |
| WO | WO 01/56996 A1 | 8/2001 |
| WO | WO 01/92253 | 12/2001 |

OTHER PUBLICATIONS

Fabbro et al., Protein kinases as targets for anticancer agents: from inhibitors to useful drugs, Pharmacology & Therapeutics, 93, pp. 79-98, 2002.*
Traxler, Protein tyrosine kinase inhibitors in cancer treatment, Exp. Opin. Ther. Patents, 7(6), pp. 571-588, 1997.*
Layzer, Degenerative diseases of the nervous system, Cecil Textbook of Medicine, 20th Edition, vol. 2, pp. 2050-2057, 1996.*
Damasio, Alzheimer's Disease and related dementias, Cecil Textbook of Medicine, 20th Edition, vol. 2, pp. 1992-1996, 1996.*
Simone, Oncology: Introduction, 20th Edition, vol. 1, pp. 1004-1010, 1996.*
Cressey et al., Medline Abstract (BMC Cancer, vol. 5, p. 128) Oct. 2005.*
Yano et al., Medline Abstract (Clinical Cancer Research: An Official Journal of The American Association for Cancer Research, vol. 6, Issue 3, pp. 957-965) Mar. 2000.*

* cited by examiner

*Primary Examiner*—Deepak Rao
(74) *Attorney, Agent, or Firm*—Kelly L. Bender; Paul R. Darkes

(57) ABSTRACT

The present invention relates to a cyclic urea compound of formula I:

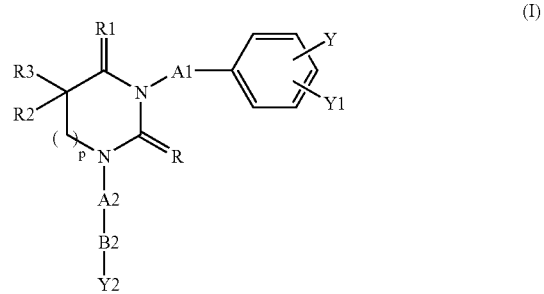

as defined herein. The invention is also directed to the process for its preparation, pharmaceutical composition comprising it and its pharmaceutical use, as an inhibitor on a protein kinase. Thus, it is useful for preventing or treating a physiological disorder capable of being modulated by inhibiting the activity of a protein kinase, such as a solid tumor.

58 Claims, No Drawings

CYCLIC UREA DERIVATIVES, PREPARATION THEREOF AND PHARMACEUTICAL USE THEREOF AS KINASE INHIBITORS

This application claims benefit of Provisional Application No. 60/468,685 filed May 7, 2003.

FIELD OF THE INVENTION

The present invention relates to a cyclic urea compound, process for its preparation, pharmaceutical composition comprising it and its pharmaceutical use, as an inhibitor on a protein kinase. Thus, it is useful for preventing or treating a physiological disorder capable of being modulated by inhibiting the activity of a protein kinase, such as a solid tumor.

BACKGROUND OF THE INVENTION

Protein kinases belong especially to the following group: EGFR, Fak, FLK-1, FGFR1, FGFR2, FGFR3, FGFR4, FGFR5, flt-1, IGF-1R, KDR, PLK, PDGFR, tie2, VEGFR, AKT, and Raf.

Cancer remains a disease for which the existing treatments are clearly insufficient. Certain protein kinases, especially including IGF-1R (Insulin Growth Factor 1 Receptor), play an important role in many cancers. The inhibition of such protein kinases is potentially important in the chemotherapy of cancers, especially for suppressing the growth or survival of tumors.

Protein kinases participate in signaling events that control the activation, growth and differentiation of cells in response either to extracellular mediators or to changes in the environment. In general, these kinases belong to two groups: those that preferentially phosphorylate serine and/or threonine residues and those that preferentially phosphorylate tyrosine residues [S. K. Hanks and T. Hunter, FASEB. J., 1995, 9, pages 576-596]. The serine/threonine kinases are, for example, the isoforms of the protein kinases C [A. C. Newton, J. Biol. Chem., 1995, 270, pages 28495-28498] and a group of cycline-dependent kinases, for instance cdc2 [J. Pines, Trends in Biochemical Sciences, 1995, 18, pages 195-197]. The tyrosine kinases comprise growth factor receptors, for instance the epidermal growth factor (EGF) receptor [S. Iwashita and M. Kobayashi, Cellular Signalling, 1992, 4, pages 123-132], and cytosol kinases, for instance p56tck, p59fYn and ZAP-70 and the kinases csk [C. Chan et. al., Ann. Rev. Immunol., 1994, 12, pages 555-592].

Abnormally high levels of kinase protein activity have been implicated in many diseases, resulting from abnormal cellular functions. This may arise either directly or indirectly from a dysfunction in the mechanisms for controlling the kinase activity, linked, for example, to a mutation, an overexpression or an inappropriate activation of the enzyme, or an over- or underproduction of cytokines or of growth factors, also involved in the transduction of the signals upstream or downstream of the kinases. In all these cases, a selective inhibition of the action of the kinases offers hope of a beneficial effect.

The type 1 receptor for in the insulin-like growth factor (IGF-I-R) is a transmembrane receptor with tyrosine kinase activity which binds firstly to IGFI, but also to IGFII and to insulin with lower affinity. The binding of IGF1 to its receptor results in oligomerization of the receptor, the activation of tyrosine kinase, intermolecular autophosphorylation and the phosphorylation of cell substrates (main substrates: IRS1 and Shc). The receptor activated by its ligand induces mitogenic activity in normal cells. However, IGF-I-R plays an important role in "abnormal" growth.

Several clinical reports underline the important role of the IGF-I route in the development of human cancers.

IGF-I-R is often found overexpressed in many types of tumors (breast, colon, lung, sarcoma, etc.) and its presence is often associated with a more aggressive phenotype.

High concentrations of circulating IGF1 are strongly correlated with a risk of prostate cancer, lung cancer and breast cancer.

Furthermore, it has been widely documented that IGF-I-R is necessary for establishing and maintaining the transformed phenotype in vitro as in vivo [Baserga R, Exp. Cell. Res., 1999, 253, pages 1-6]. The kinase activity of IGF-I-R is essential for the transformation activity of several oncogenes: EGFR, PDGFR, the large T antigen of the SV40 virus, activated Ras, Raf, and v-Src. The expression of IGF-I-R in normal fibroblasts induces a neoplastic phenotype, which may then result in the formation of a tumor in vivo. The expression of IGF-I-R plays an important role in substrate-independent growth. IGF-I-R has also been shown to be a protector in chemotherapy-induced and radiation-induced apoptosis, and cytokine-induced apoptosis. Furthermore, the inhibition of endogenous IGF-I-R with a negative dominant, the formation of a triple helix or the expression of an antisense sequence brings about suppression of the transforming activity in vitro and reduction of tumor growth in animal models.

FAK is a cytoplasmic tyrosine kinase that plays an important role in transducing the signal transmitted by the integrins, a family of heterodimeric receptors of cellular adhesion. FAK and the integrins are colocalized in perimembrane structures known as adhesion plaques. It has been shown in many cell types that the activation of FAK and its phosphorylation on tyrosine residues and in particular its autophosphorylation on tyrosine 397 were dependent on the binding of the integrins to their extracellular ligands and thus induced during cellular adhesion [L. Kornberg, et al. J. Biol. Chem. 267(33): 23439-442 (1992)]. The autophosphorylation on tyrosine 397 of FAK is a binding site for another tyrosine kinase, Src, via its SH2 domain [Schaller et al. Mol. Cell. Biol. 14: 1680-1688 1994; Xing et al. Mol. Cell. Biol. 5: 413-421 1994]. Src can then phosphorylate FAK on tyrosine 925, thus recruiting the adapter protein Grb2 and inducing in certain cells activation of the ras and MAP kinase pathway involved in controlling cellular proliferation [Schlaepfer et al. Nature; 372: 786-791 1994; Schlaepfer et al. Prog. Biophy. Mol. Biol. 71: 435-478 1999; Schlaepfer and Hunter, J. Biol. Chem. 272: 13189-13195 1997].

The activation of FAK can thus induce the jun $NH_2$-terminal kinase (JNK) signaling pathway and result in the progression of the cells to the G1 phase of the cellular cycle [Oktay et al., J. Cell. Biol. 145: 1461-1469 1999]. Phosphatidylinositol-3-OH kinase (PI3-kinase) also binds to FAK on tyrosine 397 and this interaction might be necessary for the activation of P13-kinase [Chen and Guan, Proc. Nat. Acad. Sci. USA. 91: 10148-10152 1994; Ling et al. J. Cell. Biochem. 73: 533-544 1999]. The FAK/Src complex phosphorylates various substrates, for instance paxillin and p130CAS in fibroblasts [Vuori et al. Mol. Cell. Biol. 16: 2606-2613 1996].

The results of numerous studies support the hypothesis that FAK inhibitors might be useful in treating cancer. Studies have suggested that FAK might play an important role in in vitro cell proliferation and/or survival. For example, in CHO cells, certain authors have demonstrated that the overexpression of p125FAK induces an acceleration of the G1 to S transition, suggesting that p125FAK promotes cellular proliferation [J.-H. Zhao et al. J. Cell Biol. 143: 1997-2008 1998]. Other authors have shown that tumor cells treated with FAK antisense oligonucleotides lose their adhesion and go into apoptosis (Xu et al, Cell Growth Differ. 4: 413-418 1996). It has also been demonstrated that FAK promotes the migration of cells in vitro. Thus, fibroblasts that are deficient for the expression of FAK ("knockout" mice for FAK) show a rounded morphology and deficiencies in cell migration in response to chemotactic signals, and these defects are suppressed by reexpression of FAK [D J. Sieg et al., J. Cell Science. 112: 2677-91 1999]. The overexpression of the C-terminal domain of FAK (FRNK) blocks the stretching of adherent cells and reduces cellular migration in vitro [A. Richardson and J. T. Parsons Nature. 380: 538-540 1996]. The overexpression of FAK in CHO or COS cells or in human astrocytoma cells promotes migration of the cells. The involvement of FAK in promoting the proliferation and migration of cells in numerous cell types in vitro suggests the potential role of FAK in neoplastic processes. A recent study has effectively demonstrated the increase in the proliferation of tumor cells in vivo after induction of the expression of FAK in human astrocytoma cells [L. A. Cary et al. J. Cell Sci. 109: 1787-94 1996; D. Wang et al. J. Cell Sci. 113: 4221-4230 2000]. Furthermore, immunohistochemical studies on human biopsies have demonstrated that FAK is overexpressed in prostate cancer, breast cancer, thyroid cancer, cancer of the colon, melanoma, brain cancer and lung cancer, the level of expression of FAK being directly correlated to the tumors having the most aggressive phenotype [T M Weiner et al. Lancet. 342 (8878): 1024-1025 1993; Owens et al. Cancer Research. 55: 2752-2755 1995; K. Maung et al. Oncogene 18: 6824-6828 1999; D. Wang et al. J. Cell Sci. 113: 4221-4230 2000]. Protein kinase AKT (also known as PKB) and phosphoinositide 3-kinase (PI3K) are involved in a cell signaling pathway that transmits signals from growth factors activating membrane receptors.

This transduction pathway is involved in numerous cellular functions: regulation of apoptosis, control of transcription and translation, glucose metabolism, angiogenesis and mitochondrial integrity. First identified as an important component of insulin-dependent signaling pathways regulating metabolic responses, serine/threonine kinase AKT was then identified as a mediator playing a key role in survival induced with growth factors. It has been shown that AKT can inhibit death by apoptosis induced by various stimuli, in a certain number of cell types and tumor cells. In accordance with these findings, it has been shown that AKT can, by phosphorylation of given serine residues, inactivate BAD, GSK3β, caspase-9, and Forkhead transcription factor, and can activate IKKalpha and e-NOS. It is interesting to note that the protein BAD is found hyper-phosphorylated in 11 human tumor cell lines out of 41 studied. Furthermore, it has been shown that hypoxia modulates the induction of VEGF in cells transformed with Ha-ras by activating the PI3K/AKT pathway and by involving the binding sequence of the HIF-1 (hypoxia inducible factor-1) transcription factor known as HRE for "hypoxy-responsive element".

AKT plays a very important role in cancer pathologies. The amplification and/or overexpression of AKT has been reported in many human tumors, for instance gastric carcinoma (amplification of AKT1), ovary carcinoma, breast carcinoma or pancreatic carcinoma (amplification and overexpression of AKT2) and breast carcinomas deficient in estrogen receptors, and also androgen-independent prostate carcinomas (overexpression of AKT3). Furthermore, AKT is constitutively activated in all the PTEN (−/−) tumors, the PTEN phosphatase being deleted or inactivated by mutations in many types of tumors, for instance carcinomas of the ovary, of the prostate, of the endometrium, glioblastomas and melanomas. AKT is also involved in the oncogenic activation of bcr-abl (references: A. Khawaja, Nature 1999, 401, 33-34; Cardone et al. Nature 1998, 282, 1318-1321; S. Kitada et al., Am. J. Pathol. 1998 January; 152(1): 51-61; N M Mazure et al. Blood 1997, 90, 3322-3331; H. Zhong et al. Cancer Res. 2000, 60, 1541-1545).

SUMMARY OF THE INVENTION

The present invention relates to a cyclic urea compound of formula I:

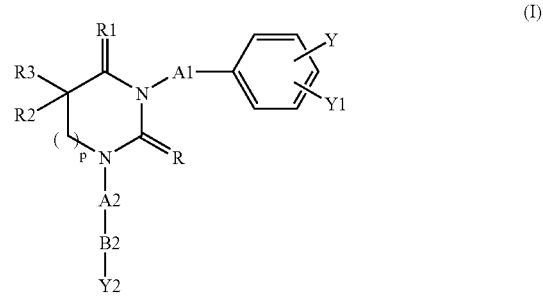

wherein p is 0, 1 or 2,

R and R1, which may be identical or different, are O or NH,

R2 and R3, which may be identical or different, are hydrogen, alkyl, alkenyl, alkynyl, cycloalkyl, aryl and heteroaryl that are optionally substituted, or R2 and R3 taken together with the carbon atom to which they are attached form 3- to 10-membered carbocyclyl that is optionally being substituted or 3- to 10-membered heterocyclyl containing one or more hetero atoms chosen from O, S, N and NR7 that is optionally being substituted, A1 is single bond, alkyl, alkenyl or alkynyl, Y and Y1, which may be identical or different, are such that one of Y and Y1 is —OCF$_3$, —O—F$_2$—CHF$_2$, —O—CHF$_2$, —O—CH$_2$—CF$_3$, —SO$_2$NR5R6, —SF$_5$ and —S(O)$_n$-alkyl and the other of Y and Y1 is —OCF$_3$, —O—F$_2$—CHF$_2$, —O—CHF$_2$, —O—CH$_2$—CF$_3$, SO$_2$NR5R6, —SF$_5$, —S(O)$_n$-alkyl, hydrogen, halogen, hydroxyl, alkoxy, nitro, —CN, —NR5R6, optionally substituted alkyl, optionally substituted aryl, optionally substituted heteroaryl, —CF$_3$, —O-alkenyl, —O-alkynyl, —O-cycloalkyl, —S(O)$_n$-alkenyl, —S(O)$_n$-alkynyl, —S(O)$_n$-cycloalkyl, —CONR5R6, or free, salified or esterified carboxyl, or the

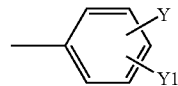

is

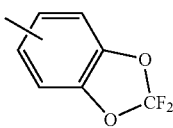 or 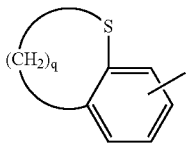

that is optionally substituted with one or more alkyl that are optionally substituted, q is 2, 3 or 4, R5 and R6, which may be identical or different, are hydrogen, alkyl, alkenyl, alkynyl, cycloalkyl, cycloalkenyl, heterocyclyl, optionally substituted aryl or optionally substituted heteroaryl, or R5 and R6 taken together with the nitrogen atom to which they are attached form 3- to 10-membered heterocyclyl containing one or more hetero atoms chosen from O, S, N and NR7 that is optionally being substituted, A2, which may be identical to or different from A1, is defined as A1 or is CO or $SO_2$, B2 is saturated or unsaturated, 3- to 10-membered monocyclic or bicyclic heterocyclyl containing one or more hetero atoms chosen from O, S, N and NR7 that is optionally substituted with one or more identical or different substituents defined as Y2, R7 is hydrogen, alkyl, cycloalkyl, phenyl, acyl, —$S(O)_2$Alk, —$S(O)_2$Aryl, —$S(O)_2$heteroaryl or —$S(O)_2$NR5R6, Y2 is hydrogen, halogen, hydroxyl, cyano, alkyl, alkoxy, cycloalkyl, heterocyclyl, aryl, heteroaryl, —O-alkenyl, —O-alkynyl, —O-cycloalkyl, —$S(O)_n$-alkyl, —$S(O)_n$-alkenyl, —$S(O)_n$-alkynyl, —$S(O)_n$-cycloalkyl, —COOR13, —OCOR13, NR5R6, CONR5R6, —$S(O)_n$—NR5R6, —NR10-CO—R13, —NR10-$SO_2$—R13, NH—$SO_2$—NR5R6, —NR10-CO—NR5R6, —NR10-CS—NR5R6 or —NR10-COOR13, all of which are optionally substituted, all the alkyl, alkenyl, alkynyl and alkoxy above are linear or branched and contain not more than 6 carbon atoms, all the cycloalkyl and heterocyclyl above contain not more than 7 carbon atoms, all the aryl and heteroaryl above contain not more than 10 carbon atoms, all the carbocyclyl, heterocyclyl, alkyl, alkenyl, alkynyl, alkoxy, cycloalkyl, heterocyclyl, aryl and heteroaryl above, and also the ring formed by R5 and R6 with the nitrogen atom to which they are attached, are optionally substituted with one or more substituents, which may be identical or different, selected from the group consisting of halogen, cyano, hydroxyl, alkoxy, —$CF_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-$S(O)_n$—R8, —$S(O)_n$—R8, —N(R10)-$S(O)_n$—NR11R12 and —$S(O)_n$—NR11R12, all the aryl and heteroaryl above are optionally substituted with one or more substituents selected from the group consisting of alkyl, alkoxy and alkylenedioxy, all the cyclic radicals above, and also the ring formed by R5 and R6 with the nitrogen atom to which they are attached, are optionally substituted with one or more substituents selected from the group consisting of oxo and thioxo, n is 0 to 2, R8 is alkyl, alkenyl, cycloalkyl, cycloalkylalkyl, heterocyclyl, heterocyclylalkyl, aryl, arylalkyl, heteroaryl and heteroarylalkyl, R9 is defined as R8 or is hydrogen, R10 is hydrogen or alkyl, R11 and R12, which may be identical or different, are hydrogen, $C_3$-$C_6$ cycloalkyl, $C_1$-$C_4$ alkyl or phenyl, optionally substituted with one or more substituents, which may be identical or different, selected from the group consisting of halogen, cyano, hydroxyl, alkoxy, —$CF_3$, nitro, phenyl, and free, salified, esterified or amidated carboxyl, or R11 and R12 taken together with the nitrogen atom to which they are attached form 5- to 7-membered cyclic radical containing one or more hetero atoms chosen from O, S, N and NR7, preferably a cyclic amine, and R13, which may be identical to or different to R5 or R6, is defined as R5 or R6, or racemic, enantiomeric or diastereoisomeric isomer form of the compound of formula I, addition salt with mineral or organic acid or with mineral or organic base thereof, with the proviso:

a) when p is 0, R and R1 are oxygen, A1 is single bond or alkyl, Y and Y1, which may be identical or different, are at least one is —$OCF_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is single bond or alkyl, Y and Y1, which may be identical or different, are at least one is —$OCF_3$, —SO-Alk, —$S(O)_2$-alk or —$SO_2NH_2$, A2 is $CH_2$ and B2 is an optionally substituted heterocyclyl, then R2 and R3 are not one hydrogen and the other alkyl optionally interrupted with O, S or N-alk; always substituted with a hydroxamate (—CO—NHOH);

c) when p is 0, R and R1 are oxygen, A1 is a single bond or alkyl, Y and Y1, which may be identical or different, are at least one is —$S(O)_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or d) when p is 0 to 2, R and R1 are oxygen, A1 is single bond, Y and Y1, which may be identical or different, are one is —$SO_2$Alk or $SO_2NH_2$ and the other is NR5R6, A2 is single bond or alkylene and B2 is optionally substituted 5- to 10-membered heterocyclyl, then R2 and R3 are not both hydrogen.

The invention is also directed to a pharmaceutical composition comprising a compound of formula I, method of preparation thereof and method for pharmaceutical use of the compound of formula I in a patient.

DETAILED DESCRIPTION OF THE INVENTION

As used above, and throughout the description of the invention, the following terms, unless otherwise indicated, shall be understood to have the following meanings:—

The term "Hal", "Halo" or halogen denotes fluorine, chlorine, bromine or iodine atoms.

The term "alkyl", "alk", "Alk" or "ALK" denotes a linear or branched radical containing not more than 12 carbon atoms, chosen from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl and dodecyl radicals, and also the linear or branched positional isomers thereof.

Mention is made more particularly of alkyl radical containing not more than 6 carbon atoms, and especially methyl, ethyl, propyl, isopropyl, n-butyl, isobutyl, tert-butyl, linear or branched pentyl and linear or branched hexyl.

The term "alkenyl" denotes a linear or branched radical containing not more than 12 carbon atoms and preferably 4 carbon atoms, chosen, for example, from the following values: ethenyl or vinyl, propenyl or allyl, 1-propenyl, n-butenyl, i-butenyl, 3-methyl-2-butenyl, n-pentenyl, hexenyl, heptenyl, octenyl, cyclohexylbutenyl and decenyl, and also the linear or branched positional isomers thereof; more particularly is allyl or butenyl.

The term "alkynyl" denotes a linear or branched radical containing not more than 12 carbon atoms and preferably 4 carbon atoms, chosen, for example, from the following values: ethynyl, propynyl or propargyl, butynyl, n-butynyl, i-butynyl, 3-methyl-2-butynyl, pentynyl or hexynyl, and also the linear or branched positional isomers thereof; more particularly is propargyl.

The term "alkoxy" denotes a linear or branched radical containing not more than 12 carbon atoms and preferably 6 carbon atoms chosen, for example, from methoxy, ethoxy, propoxy, isopropoxy, linear, secondary or tertiary butoxy, pentoxy, hexoxy and heptoxy radicals, and also the linear or branched positional isomers thereof.

The term "alkoxycarbonyl" or alkyl-O—CO— denotes a linear or branched radical containing not more than 12 carbon atoms, in which the alkyl radical has the meaning given above: examples include methoxycarbonyl and ethoxycarbonyl radicals.

The term "alkylenedioxy" or —O-alkylene-O— denotes a linear or branched radical containing not more than 12 carbon atoms, in which the alkylene radical has the meaning given above: examples include methylenedioxy and ethylenedioxy radicals.

The term "alkylsulfinyl" or alkyl-SO— denotes a linear or branched radical containing not more than 12 carbon atoms, in which the alkyl radical has the meaning given above and preferably contains 4 carbon atoms.

The term "alkylsulfonyl" or alkyl-SO$_2$— denotes a linear or branched radical containing not more than 12 carbon atoms, in which the alkyl radical has the meaning given above and preferably contains 4 carbon atoms.

The term "alkylsulfonylcarbamoyl" or alkyl-SO$_2$—NH—C(=O)— denotes a linear or branched radical containing not more than 12 carbon atoms, in which the alkyl radical has the meaning given above and preferably contains 4 carbon atoms.

The term "alkylthio" or alkyl-S— denotes a linear or branched radical containing not more than 12 carbon atoms and especially is methylthio, ethylthio, isopropylthio and heptylthio radicals.

The term "cycloalkyl" denotes a 3- to 10-membered monocyclic or bicyclic carbocyclic or carbocyclyl radical and especially denotes cyclopropyl, cyclobutyl, cyclopentyl and cyclohexyl radicals.

The term "—O-cycloalkyl" denotes a radical in which the cycloalkyl radical has the meaning given above.

The term "cycloalkenyl" denotes a 3- to 10-membered monocyclic or bicyclic nonaromatic carbocyclic or carbocyclyl radical containing at least one double bond, and especially denotes cyclobutenyl, cyclopentenyl and cyclohexenyl radicals.

The term "cycloalkylalkyl" denotes a radical in which cycloalkyl and alkyl are chosen from the values indicated above: this radical thus denotes, for example, cyclopropylmethyl, cyclopentylmethyl, cyclohexylmethyl and cycloheptylmethyl radicals.

The term "acyl" or rad-CO— denotes a linear or branched radical containing not more than 12 carbon atoms, in which the rad is hydrogen, alkyl, cycloalkyl, cycloalkenyl, cycloalkyl, heterocyclyl or aryl radical, these radicals having the values indicated above and being optionally substituted as indicated: examples include the formyl, acetyl, propionyl, butyryl or benzoyl radicals, valeryl, hexanoyl, acryloyl, crotonoyl or carbamoyl.

The term "acyloxy" means acyl-O— radical in which acyl has the meaning given above: examples include acetoxy or propionyloxy radicals.

The term "acylamino" means acyl-NH— radical in which acyl has the meaning given above.

The term "aryl" denotes unsaturated monocyclic radical or unsaturated radical consisting of fused carbocyclic rings. Examples of such aryl radicals that may be mentioned include phenyl or naphthyl radicals.

Mention is made more particularly of the phenyl radical.

The term "arylalkyl" means radical resulting from the combination of the optionally substituted alkyl radicals mentioned above and the optionally substituted aryl radicals also mentioned above: examples include benzyl, phenylethyl, 2-phenethyl, triphenylmethyl or naphthalenemethyl radicals.

The term "heterocyclic" denotes a saturated carbocyclic radical (heterocyclyl) or unsaturated carbocyclic radical (heteroaryl) which is at least 6-membered, interrupted with one or more hetero atoms, which may be identical or different, chosen from oxygen, nitrogen and sulfur atoms.

Heterocyclyl radical that may especially be mentioned include dioxolane, dioxane, dithiolane, thiooxolane, thiooxane, oxiranyl, oxolanyl, dioxolanyl, piperazinyl, piperidyl, pyrrolidyl, imidazolidinyl, pyrazolidinyl, morpholinyl, or tetrahydrofuryl, tetrahydrothienyl, chromanyl, dihydrobenzofuranyl, indolinyl, piperidyl, perhydropyranyl, pyrindolinyl, tetrahydroquinolyl, tetrahydroisoquinolyl and thioazolidinyl radicals, all these radicals being optionally substituted.

Among the heterocyclyl radical that may especially be mentioned are optionally substituted piperazinyl, optionally substituted piperidyl, optionally substituted pyrrolidinyl, imidazolidinyl, pyrazolidinyl, morpholinyl and thioazolidinyl radicals: mention may also be made more particularly of optionally substituted morpholinyl, pyrrolidyl and piperazinyl radicals.

The term "heterocyclylalkyl" means radical in which the heterocyclyl and alkyl residues have the above meanings.

Among the 5-membered heteroaryl radicals that may be mentioned are furyl radicals such as 2-furyl, thienyl radicals such as 2-thienyl and 3-thienyl, and pyrrolyl, diazolyl, thiazolyl, thiadiazolyl, thiatriazolyl, isothiazolyl, oxazolyl, oxadiazolyl, 3- or 4-isoxazolyl, imidazolyl, pyrazolyl and isoxazolyl radicals.

Among the 6-membered heteroaryl radicals that may especially be mentioned are pyridyl radicals such as 2-pyridyl, 3-pyridyl and 4-pyridyl, and pyrimidyl, pyrimidinyl, pyridazinyl, pyrazinyl and tetrazolyl radicals.

Among the fused heteroaryl radicals containing at least one hetero atom chosen from sulfur, nitrogen and oxygen, examples include benzothienyl such as 3-benzothienyl, benzofuryl, benzofuranyl, benzopyrrolyl, benzimidazolyl, benzoxazolyl, thionaphthyl, indolyl, purinyl, quinolyl, isoquinolyl and naphthyridinyl.

Among the fused heteroaryl radicals that may be mentioned more particularly are benzothienyl, benzofuranyl, indolyl, quinolyl, benzimidazolyl, benzothiazolyl, furyl, imidazolyl, indolizinyl, isoxazolyl, isoquinolyl, isothiazolyl, oxadiazolyl, pyrazinyl, pyridazinyl, pyrazolyl, pyridyl, pyrimidinyl, pyrrolyl, quinazolinyl, 1.3.4-thiadiazolyl, thiazolyl and thienyl radicals and triazolyl groups, these radicals optionally being substituted as indicated for the heteroaryl radicals;

The term "cyclic amine" denotes a 3- to 8-membered cycloalkyl radical in which one carbon atom is replaced with a nitrogen atom, the cycloalkyl radical having the meaning given above and also possibly containing one or more other hetero atoms chosen from O, S, $SO_2$, N and NR7 with R7 as defined above; examples of such cyclic amines that may be mentioned include pyrrolidyl, piperidyl, morpholinyl, piperazinyl, indolinyl, pyrindolinyl and tetrahydroquinolyl radicals.

The term "patient" denotes a human being or other mammal.

The term "prodrug" denotes a compound that may be converted in vivo via metabolic mechanisms (such as hydrolysis) into a product of formula I. For example, an ester of a compound of formula I containing a hydroxyl group may be converted by hydrolysis in vivo into its parent molecule. Alternatively, an ester of a compound of formula I containing a carboxyl group may be converted by in vivo hydrolysis into its parent molecule.

Examples of esters of the compound of formula I containing a hydroxyl group that may be mentioned include the acetates, citrates, lactates, tartrates, malonates, oxalates, salicylates, propionates, succinates, fumarates, maleates, methylenebis-β-hydroxynaphthoates, gentisates, isethionates, di-p-tolyltartrates, methanesulfonates, ethanesulfonates, benzenesulfonates, p-toluenesulfonates, cyclohexylsulfamates and quinates.

Esters of products of formula I that are particularly useful, containing a hydroxyl group, may be prepared from acid residues such as those described by Bundgaard et. al., J. Med. Chem., 1989, 32, page 2503-2507: these esters especially include substituted (aminomethyl)benzoates, dialkylaminomethylbenzoates in which the two alkyl groups may be linked together or may be interrupted with an oxygen atom or with an optionally substituted nitrogen atom, i.e., an alkylated nitrogen atom, or (morpholinomethyl)benzoates, e.g., 3- or 4-(morpholinomethyl)benzoates, and (4-alkylpiperazin-1-yl)benzoates, e.g., 3- or 4-(4-alkylpiperazin-1-yl) benzoates.

The carboxyl radical of the compound of formula I may be salified or esterified with various groups known to those skilled in the art, among which nonlimiting examples include the following compounds:

among the salification compounds, mineral bases such as, for example, one equivalent of sodium, potassium, lithium, calcium, magnesium or ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine;

among the esterification compounds, alkyl radicals to form alkoxycarbonyl groups such as, for example, methoxycarbonyl, ethoxycarbonyl, tert-butoxycarbonyl or benzyloxycarbonyl, these alkyl radicals possibly being substituted with radicals chosen, for example, from halogen atoms and hydroxyl, alkoxy, acyl, acyloxy, alkylthio, amino or aryl radicals, such as, for example, in chloromethyl, hydroxypropyl, methoxymethyl, propionyloxymethyl, methylthiomethyl, dimethylaminoethyl, benzyl or phenethyl groups.

The term "esterified carboxyl" means, for example, radical such as alkyloxycarbonyl radical, for example methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl.

Mention may also be made of radicals formed with readily cleavable ester residues, such as methoxymethyl or ethoxymethyl radicals; acyloxyalkyl radicals such as pivaloyloxymethyl, pivaloyloxyethyl, acetoxymethyl or acetoxyethyl; alkyloxycarbonyloxyalkyl radicals such as methoxycarbonyloxy methyl or ethyl radicals, and isopropyloxycarbonyloxy methyl or ethyl radicals.

A list of such ester radicals may be found, for example, in European patent EP 0 034 536.

The term "amidated carboxyl" means radical of the type —CONR5R6 as defined above: also intended are the radicals NCOR6R7 in which the radicals R6 and R7, which may be identical or different, are a hydrogen atom or an alkyl radical containing from 1 to 4 carbon atoms such as methyl, ethyl, propyl, isopropyl, butyl, isobutyl, sec-butyl or tert-butyl radicals and especially amino, alkylamino and dialkylamino radicals.

The term "alkylamino" means linear or branched methylamino, ethylamino, propylamino or butylamino radical. Alkyl radicals containing not more than 4 carbon atoms are preferred, the alkyl radicals possibly being chosen from the alkyl radicals mentioned above.

The term "dialkylamino" means, for example, dimethylamino, diethylamino and methylethylamino radical. As previously, alkyl radicals containing not more than 4 carbon atoms, chosen from the list indicated above, are preferred.

The radicals NR5R6 or NR6R7 may also form a heterocyclyl which may or may not comprise an additional hetero atom. Mention may be made of pyrrolyl, imidazolyl, indolyl, piperidyl, morpholinyl and piperazinyl radicals. The piperidyl, morpholinyl and piperazinyl radicals are preferred.

The term "salified carboxyl" means the salt formed, for example, with one equivalent of sodium, potassium, lithium, calcium, magnesium or ammonium. Mention may also be made of the salts formed with organic bases such as methylamine, propylamine, trimethylamine, diethylamine and triethylamine. The sodium salt is preferred.

When the compound of formula I comprise an amino radical that may be salified with an acid, it is clearly understood that these acid salts also form part of the invention. Mention may be made of the salts obtained, for example, with hydrochloric acid or methanesulfonic acid.

The addition salts with mineral or organic acids of the compound of formula I may be, for example, the salts formed with hydrochloric acid, hydrobromic acid, hydriodic acid, nitric acid, sulfuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids such as, for example, methanesulfonic acid, ethanesulfonic acid or propanesulfonic acid, alkyldisulfonic acids such as, for example, methanedisulfonic acid or alpha,beta-ethanedisulfonic acid, arylmonosulfonic acids such as benzenesulfonic acid, and aryldisulfonic acids.

It may be recalled that stereoisomerism may be defined in its broad sense as the isomerism of compounds having the same structural formulae but whose various groups are arranged differently in space, especially such as in monosubstituted cyclohexanes whose substituent may be in an axial or equatorial position, and the various possible rotational conformations of ethane derivatives. However, there is another type of stereoisomerism, due to the different spatial arrangements of fixed substituents, either on double bonds or on rings, which is often referred to as geometrical isomerism or cis-trans (E and Z) isomerism. The term "stereoisomer" is used in the present patent application in its broadest sense and thus relates to all the compounds indicated above.

EMBODIMENTS

With reference to inventions described herein, below are particular embodiments related thereto.

A particular embodiment according to the invention is the compound of formula I wherein p is 0 to 2, R and R1, which may be identical or different, are O or NH, R2 and R3, which may be identical or different, are hydrogen, alkyl, alkenyl, alkynyl, cycloalkyl, aryl and heteroaryl which are optionally substituted, or R2 and R3 taken together with the carbon atom to which they are attached form 3- to 10-membered optionally substituted carbocyclyl or 3- to 10-membered optionally substituted heterocyclyl containing one or more hetero atoms chosen from O, S, N and NR7, A1 is single bond, alkyl, allyl or propynyl, Y and Y1, which may be identical or different, are such that one from among Y and Y1 is selected from the group consisting of —OCF$_3$, —S(O)$_n$CF$_3$, —S(O)$_n$-alk, —SO$_2$CHF$_2$, —SO$_2$CF$_2$CF$_3$ and —SO$_2$NR5R6 and the other of Y and Y1 is selected from the group consisting of these same definitions and hydrogen, halogen, hydroxyl, alkoxy, —NR5R6, optionally substituted alkyl, optionally substituted aryl, optionally substituted heteroaryl, —CF$_3$, —O-allyl, —O-propynyl, —O-cycloalkyl, —S(O)$_n$-allyl, —S(O)$_n$-propynyl, —S(O)$_n$-cycloalkyl, —CONR5R6 and free, salified or esterified carboxyl, wherein R5 and R6, which may be identical or different, are selected from the group consisting of hydrogen, alkyl, alkenyl, cycloalkyl, cycloalkenyl, heterocyclyl, aryl and heteroaryl, which are optionally substituted, or R5 and R6 taken together with the nitrogen atom to which they are attached form 3- to 10-membered heterocyclyl containing one or more hetero atoms chosen from O, S, N and NR7, which is optionally substituted, A2, which may be identical to or different from A1, is defined as A1 or CO or SO$_2$, B2 is a saturated or unsaturated heterocyclyl containing 1 or more identical or different hetero atoms chosen from O, S, N and NR7, optionally substituted with one or more identical or different substituents chosen from the definition of Y2, R7 is hydrogen, alkyl, cycloalkyl, phenyl, acyl, —S(O)$_2$Alk, —S(O)$_2$Aryl, S(O)$_2$heteroaryl or —S(O)$_2$NR5R6 radical, Y2 is hydrogen, halogen, hydroxyl, alkyl, alkoxy, cycloalkyl, heterocyclyl, aryl, heteroaryl, —O-allyl, —O-propynyl, —O-cycloalkyl, —S(O)$_n$-alkyl, —S(O)$_n$-allyl, —S(O)$_n$-propynyl, —S(O)$_n$-cycloalkyl, —COOR9, —OCOR8, —NR5R6, —CONR5R6, —S(O)$_n$—R5R6, —NHCOR8, —NH—S(O)$_n$R8, —NH—S(O)$_n$CF$_3$ or —NH—SO$_2$—NR5R6, all these radicals being optionally substituted, all the carbocyclyl, heterocyclyl, alkyl, alkenyl, alkynyl, alkoxy, cycloalkyl, heterocyclyl, aryl and heteroaryl above are optionally substituted with one or more substituents, which may be identical or different, selected from the group consisting of halogen, cyano, hydroxyl, alkoxy, —CF$_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, N(R10)-C(=O)—NR11R12, —N(R10)-S(O)$_n$—R8, —S(O)$_n$—R8, —N(R10)-S(O)$_n$—NR11R12 or —S(O)$_n$—NR11R12, and all the aryl and heteroaryl above are optionally substituted with one or more substituents selected from the group consisting of alkyl and alkylenedioxy radicals, or racemic, enantiomeric or diastereoisomeric isomer form of the compound of formula I, addition salt with mineral or organic acid or with mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —OCF$_3$, —SO-Alk, —S(O)$_2$-alk or —SO$_2$NH$_2$, A2 is CH$_2$ and B2 is an optionally substituted heterocyclyl, then R2 and R3 are not one hydrogen and the other alkyl optionally interrupted with O, S or N-alk; always substituted with a hydroxamate (—CO—NHOH);

c) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or d) when p is 0 to 2, R and R1 are oxygen, A1 is single bond, Y and Y1, which may be identical or different, are one is —SO$_2$Alk or SO$_2$NH$_2$ and the other is NR5R6, A2 is single bond or alkylene and B2 is optionally substituted 5- to 10-membered heterocyclyl, then R2 and R3 are not both hydrogen.

Another particular embodiment according to the invention is where p is 0 to 2,

R and R1, which may be identical or different, are O or NH,

R2 and R3, which may be identical or different, are hydrogen, alkyl, alkenyl, cycloalkyl, phenyl and heteroaryl, which are optionally substituted, or R2 and R3 taken together with the carbon atom to which they are attached form, a carbocyclyl or heterocyclyl, these radicals being 3- to 10-membered and the heterocyclyl contains one or more hetero atoms chosen from O, S, N and NR7, all these radicals being optionally substituted, A1 is single bond, alkyl, allyl or propynyl, Y and Y1, which may be identical or different, are one from among Y and Y1 is selected from the group consisting of —OCF$_3$, —S(O)$_n$CF$_3$, S(O)$_n$-alk, —SO$_2$CHF$_2$, —SO$_2$CF$_2$CF$_3$ and —SO$_2$NR5R6 and the other from Y and Y1 is selected from the group consisting of —OCF$_3$, —S(O)$_n$ CF$_3$, S(O)$_n$-alk, —SO$_2$CHF$_2$, —SO$_2$CF$_2$CF$_3$, —SO$_2$NR5R6, hydrogen, halogen, hydroxyl, alkoxy, NR5R6, optionally substituted alkyl, optionally substituted phenyl, optionally substituted pyrazolyl and optionally substituted pyridyl, R5 and R6, which may be identical or different, are hydrogen, alkyl, alkenyl, cycloalkyl, heterocyclyl, phenyl or heteroaryl, which are optionally substituted, or R5 and R6 taken together with the nitrogen atom to which they are attached form, a 3- to 10-membered heterocyclyl that contains one or more hetero atoms chosen from O, S, N and NR7, which is optionally substituted, A2, which may be identical to or different from A1, is defined as A1 or is CO or SO$_2$, B2 is a saturated or unsaturated 3- to 10-membered heterocyclyl that contains one or more hetero atoms, which may be identical or different, chosen from O, S, N and NR7, optionally substituted with one or more substituents, which may be identical or different substituents defined as Y2, R7 is hydrogen or an alkyl, cycloalkyl or phenyl radical, Y2 is hydrogen, halogen, hydroxyl, alkyl, alkoxy, cycloalkyl, heterocyclyl, phenyl, heteroaryl, —O-cycloalkyl, —S(O)$_n$-alk, —S(O)$_n$-cycloalkyl, —COOR9, —OCOR8, —NR5R6, —CONR5R6, S(O)$_n$—R5R6, —NHCOR8 and —NH—S(O)$_n$R8, all these radicals being optionally substituted, all the alkyl, alkenyl, alkynyl and alkoxy radicals above being linear or branched and contain not more than 6 carbon atoms, all the cycloalkyl and heterocyclyl radicals above containing not more than 7 carbon atoms, all the aryl and heteroaryl radicals above containing not more than 10 carbon atoms, all the carbocyclic and heterocyclic alkyl, alkenyl, alkynyl, alkoxy, cycloalkyl, heterocyclyl, aryl and heteroaryl radicals above being optionally substituted with one or more radicals, which may be identical or different, chosen from halogen atoms and cyano, hydroxyl, alkoxy, —CF$_3$, nitro, phenyl, heteroaryl, —C(=O)—OR9, —C(=O)—R8, —NR11R12, —C(=O)—NR11R12, —N(R10)-C(=O)—R8, —N(R10)-C(=O)—OR9, N(R10)-C(=O)—NR11R12, —N(R10)-S(O)$_n$—R8, —S(O)$_n$—R8, —N(R10)-S(O)$_n$—NR11R12 and —S(O)$_n$—NR11R12, all the aryl and heteroaryl radicals above are optionally substituted with one or more radicals chosen from alkyl and alkylenedioxy, n is 0 to 2, R8 is alkyl, cycloalkyl, cycloalkylalkyl, heterocyclyl, heterocyclylalkyl, phenyl or phenylalkyl, R9 is defined as R8 or is hydrogen, R10 is hydrogen or alkyl, and R11 and R12, which may be identical or different, are hydrogen, C$_1$-C$_4$ alkyl and phenyl, which are optionally substituted with one or more radicals, which may be identical or different, chosen from halogen, hydroxyl, alkoxy, —CF$_3$, nitro, phenyl and free, salified, esterified or amidated carboxyl, or R11 and R12 taken together with the nitrogen atom to which they are attached form 5- to 7-membered cyclic radical containing one or more hetero atoms chosen from O, S, N and NR7, preferably a cyclic amine, or racemic, enantiomeric or diastereoisomeric isomer form of the compound of formula I, addition salt with mineral or organic acid or with mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —OCF$_3$, —SO-Alk, —S(O)$_2$-alk or —SO$_2$NH$_2$, A2 is CH$_2$ and B2 is an optionally substituted heterocyclyl, then R2 and R3 are not one hydrogen and the other alkyl optionally interrupted with O, S or N-alk; always substituted with a hydroxamate (CO—NHOH);

c) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or d) when p is 0 to 2, R and R1 are oxygen, A1 is single bond, Y and Y1, which may be identical or different, are one is —SO$_2$Alk or SO$_2$NH$_2$ and the other is NR5R6, A2 is single bond or alkylene and B2 is optionally substituted 5- to 10-membered heterocyclyl, then R2 and R3 are not both hydrogen.

A further particular embodiment according to the invention is where Y and Y1, which may be identical or different, are such that one from among Y and Y1 is selected from the group consisting of OCF$_3$, —O—CF$_2$—CHF$_2$, —O—CHF$_2$, —O—CH$_2$—CF$_3$, —S(O)$_n$CF$_3$, —S—CF$_2$—CF$_2$—CF$_3$, —S(O)$_n$-alk, —S-Alk-O-Alk, —S-Alk-OH, —S-Alk-CN, —S-Alk-heterocyclyl, —SO$_2$CHF$_2$, —SO$_2$CF$_2$CF$_3$, —SO$_2$NR5R6 and —SF$_5$, in which Alk is alkyl containing from 1 to 4 carbon atoms, and the other from among Y and Y1 is chosen from the following values: hydrogen, halogen, nitro, —NR5R6, free or esterified carboxyl, and —CONR5R6, or the

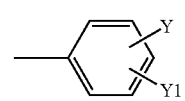

is

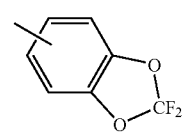 or 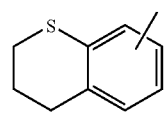

being optionally substituted with one or more alkyl, which are themselves optionally substituted, or racemic, enantiomeric or diastereoisomeric isomer form of the compound of formula I, addition salt with mineral or organic acid or with mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is single bond or alkyl, Y and Y1, which may be identical or different, are at least one is —OCF$_3$, —SO-Alk, —S(O)$_2$-alk or —SO$_2$NH$_2$, A2 is CH$_2$ and B2 is an optionally substituted heterocyclyl, then R2 and R3 are not one hydrogen and the other alkyl optionally interrupted with O, S or N-alk; always substituted with a hydroxamate (—CO—NHOH); or c) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl.

A further particular embodiment according to the invention is where one from among Y and Y1 is hydrogen and the other is chosen from —OCF$_3$, —S(O)$_n$CF$_3$, —S(O)$_n$-alk, —SO$_2$CHF$_2$, —SO$_2$CF$_2$CF$_3$ and —SO$_2$NR5R6, or racemic, enantiomeric or diastereoisomeric isomer form of the compound of formula I, addition salt with mineral or organic acid or with mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is single bond or alkyl, Y and Y1, which may be identical or different, are at least one is —OCF$_3$, —SO-Alk, —S(O)$_2$-alk or —SO$_2$NH$_2$, A2 is CH$_2$ and B2 is an optionally substituted heterocyclyl, then R2 and R3 are not one hydrogen and the other alkyl optionally interrupted with O, S or N-alk; always substituted with a hydroxamate (—CO—NHOH); or c) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl.

A further particular embodiment according to the invention is where one from among Y and Y1 is hydrogen and the other is chosen from —S(O)$_n$CF$_3$, —SO-Alk, —S(O)$_2$Alk, —SO$_2$CHF$_2$, —SO$_2$CF$_2$CF$_3$ and —SO$_2$NR5R6, or racemic, enantiomeric or diastereoisomeric isomer form of the compound of formula I, addition salt with mineral or organic acid or with mineral or organic base thereof, with the proviso:

a) when p is 0, R and R1 are oxygen, A1 is single bond or alkyl, Y and Y1, which may be identical or different, are at least one is —OCF$_3$, —SO-Alk, —S(O)$_2$-alk or —SO$_2$NH$_2$, A2 is CH$_2$ and B2 is an optionally substituted heterocyclyl, then R2 and R3 are not one hydrogen and the other alkyl optionally interrupted with O, S or N-alk; always substituted with a hydroxamate (—CO—NHOH); or b) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl.

A further particular embodiment according to the invention is where one from among Y and Y1 is hydrogen and the other is chosen from —S(O)$_n$CF$_3$, —SO$_2$CHF$_2$, —SO$_2$CF$_2$CF$_3$ and —SO$_2$NR5R6, or racemic, enantiomeric or diastereoisomeric isomer form of the compound of formula I, addition salt with mineral or organic acid or with mineral or organic base thereof, with the proviso:

when p is 0, R and R1 are oxygen, A1 is single bond or alkyl, Y and Y1, which may be identical or different, are such that one is hydrogen and the other is —SO$_2$NR2, A2 is CH$_2$ and B2 is an optionally substituted heterocyclyl, then R2 and R3 are not one hydrogen and the other alkyl optionally interrupted by O, S or N-alk, always substituted with a hydroxamate (—CO—NHOH).

A further particular embodiment according to the invention is where one from among Y and Y1 is hydrogen and the other is chosen from —S(O)$_n$CF$_3$, —SO$_2$CHF$_2$ and —SO$_2$CF$_2$CF$_3$, or racemic, enantiomeric or diastereoisomeric isomer form of the compound of formula I, addition salt with mineral or organic acid or with mineral or organic base thereof.

A further particular embodiment according to the invention is where all the alkyl, alkenyl, alkynyl, cycloalkyl, heterocyclyl, aryl or heteroaryl defined above are optionally substituted with one or more radicals, which may be identical or different, chosen from halogen, cyano, hydroxyl, alkoxy, —CF$_3$, nitro, phenyl, carboxyl which is free, salified, esterified with an alkyl radical or amidated with —NR11aR12a, —C(=O)—R9a, —NR11aR12a, —C(=O)—NR11aR12a, —N(R10a)-C(=O)—R9a, —N(R10a)-C(=O)—OR8a, —N(R10a)-C(=O)—NR11aR12a, —N(R10a)-S(O)$_n$—R9a, —S(O)$_n$—R9a, —N(R10a)—S(O)$_n$—NR11aR12a or —S(O)$_n$—NR11aR12a, all the aryl and heteroaryl above furthermore being optionally substituted with an ethylenedioxy, R8a is hydrogen, alkyl, alkenyl, phenyl, phenylalkyl, heteroaryl or heteroarylalkyl, R9a is alkyl, cycloalkyl, cycloalkylalkyl, heterocyclyl, heterocyclylalkyl, phenyl, phenylalkyl, heteroaryl or heteroarylalkyl, R10a is hydrogen or alkyl, R11a and R12a, which may be identical or different, are hydrogen, alkyl, cycloalkyl, cycloalkylalkyl, phenyl, phenylalkyl, optionally substituted with one or more substituents, which may be identical or different, chosen from halogen, hydroxyl, C$_1$-C$_4$ alkyl and C$_1$-C$_4$ alkoxy, or R11a and R12a taken together with the nitrogen atom to which they are attached form, a cyclic radical chosen from pyrrolidyl, piperidyl, piperazinyl, morpholinyl, indolinyl, pyrindolinyl, tetrahydroquinolyl, thiazolidinyl and naphthyridyl, or racemic, enantiomeric or diastereoisomeric isomer form of the compound of formula I, addition salt with mineral or organic acid or with mineral or organic base thereof.

A further particular embodiment according to the invention is where p is 0.

A further particular embodiment according to the invention is where p is 1.

A further particular embodiment according to the invention is where p is 2.

A further particular embodiment according to the invention is where R1 is 0.

A further particular embodiment according to the invention is where R is 0.

A further particular embodiment according to the invention is where R2 and R3, which may be identical or different, are hydrogen, alkyl, alkenyl, cycloalkyl, cycloalkylalkyl, phenyl, phenylalkyl, heterocyclyl, heterocyclylalkyl, heteroaryl or heteroarylalkyl, which are optionally substituted, or R2 and R3 taken together with the carbon atom to which they are attached form 3- to 10-membered carbocyclyl or heterocyclyl, and the heterocyclyl contains one or more hetero atoms chosen from O, S, N and NR7b, all these radicals being optionally substituted, all the above radicals being optionally substituted with one or more radicals chosen from halogen, cyano, hydroxyl, alkyl and alkoxy containing 1 to 4 carbon atoms, —CF$_3$, nitro, phenyl, carboxyl which is free, salified, esterified with alkyl or amidated with —NR11bR12b, —C(=O)—R9b, —NR11bR12b and —C(=O)—NR11bR12b, R7b is hydrogen, alkyl or phenyl, R9 is hydrogen, alkyl, cycloalkyl, cycloalkylalkyl or phenyl, R11b and R12b, which may be identical or different, are hydrogen, alkyl, cycloalkyl or phenyl, or R11b and R12b taken together with the nitrogen atom to which they are attached form, an optionally substituted piperazinyl.

A further particular embodiment according to the invention is where R2 and R3, which may be identical or different, are chosen from hydrogen, alkyl, phenylalkyl, pyridylalkyl and benzothienylalkyl, which are optionally substituted with one or more radicals chosen from halogen, hydroxyl, alkyl and alkoxy containing from one to 4 carbon atoms, or R2 and R3 taken together with the carbon atom to which they are attached form a 3- to 6-membered cycloalkyl or heterocyclyl containing a nitrogen atom.

A further particular embodiment according to the invention is where R2 and R3, which may be identical or different, are chosen from hydrogen, alkyl, hydroxyalkyl, phenylalkyl, hydroxyphenylalkyl, pyridylalkyl or thienylbenzothienylalkyl, or R2 and R3 taken together with the carbon atom to which they are attached form a cycloalkyl radical containing from 3 to 6 carbon atoms or azetidinyl, pyrrolidyl or piperidyl A further particular embodiment according to the invention is where R2 and R3, which may be identical or different, are chosen from hydrogen, alkyl, hydroxyalkyl, phenylalkyl and hydroxyphenylalkyl, or R2 and R3 taken together with the carbon atom to which they are attached form a cycloalkyl containing from 3 to 6 carbon atoms.

A further particular embodiment according to the invention is where one from among R2 and R3 is chosen from hydrogen and alkyl, and the other from among R2 and R3 is chosen from among the broadest definitions of R2 and R3, or R2 and R3 taken together with the carbon atom to which they are attached form a cycloalkyl containing from 3 to 6 carbon atoms.

A further particular embodiment according to the invention is where R2 and R3, which may be identical or different, are hydrogen and alkyl, or R2 and R3 taken together with the carbon atom to which they are attached form a cycloalkyl containing from 3 to 6 carbon atoms.

A further particular embodiment according to the invention is where R2 and R3, which may be identical or different, are hydrogen and methyl, or R2 and R3 taken together with the carbon atom to which they are attached form cyclopropyl.

A further particular embodiment according to the invention is where A1 is single bond and A2 is chosen from single bond, a linear or branched alkyl containing not more than 6 carbon atoms and allyl, propynyl, C=O and SO$_2$ radicals, the other substituents of said compound of formula I having any one of the values defined above.

A further particular embodiment according to the invention is where A1 is single bond and A2 is chosen from single bond, alkyl, allyl, propynyl, C=O and SO$_2$.

A further particular embodiment according to the invention is where A1 is single bond and A2 is chosen from alkyl, allyl, propynyl, C=O and SO$_2$.

A further particular embodiment according to the invention is where A1 is single bond and A2 is alkyl or C=O.

A further particular embodiment according to the invention is where A1 is single bond and A2 is C=O, ethylene or methylene.

A further particular embodiment according to the invention is where A1 is single bond and A2 is methylene.

A further particular embodiment according to the invention is where Y and Y1 are such that one is hydrogen, halogen or amino and the other is chosen from —OCF$_3$, —O—CF$_2$—CHF$_2$, —O—CHF$_2$, —O—CH$_2$—CF$_3$, —SF$_5$, —S(O)$_n$—CF$_3$, —S(O)$_n$-alk, —SO$_2$CHF$_2$, —SO$_2$CF$_2$CF$_3$, —SO$_2$NH$_2$, —S—CF$_2$—CF$_2$—CF$_3$, —S-Alk-O-Alk, —S-Alk-OH, —S-Alk-CN, —S-Alk-morpholino, —S-Alk-pyrrolidinyl and —S-Alk-piperazinyl, wherein the morpholino, pyrrolidinyl and piperazinyl are optionally substituted with Alk, in which Alk is alkyl containing from 1 to 4 carbon atoms.

A further particular embodiment according to the invention is where Y is hydrogen and Y1 is chosen from —OCF$_3$, S(O)$_n$—CF$_3$, —S(O)$_n$—CH$_3$, —SO$_2$CHF$_2$ and —SO$_2$NH$_2$.

A further particular embodiment according to the invention is where Y is hydrogen and Y1 is chosen from —OCF$_3$, —S(O)$_n$—CF$_3$ and —SO$_2$CHF$_2$.

A further particular embodiment according to the invention is where Y is hydrogen and Y1 is chosen from —OCF$_3$ and S(O)$_n$—CF$_3$.

A further particular embodiment according to the invention is where Y is hydrogen and Y1 is chosen from —OCF$_3$, S—CF$_3$ and S(O)$_2$—CF$_3$.

A further particular embodiment according to the invention is where B2 is monocyclic or bicyclic heteroaryl chosen from pyridyl, pyrimidinyl, quinolyl, azaindolyl, 1H-pyrrolo[2,3-b]pyridinyl, quinazolyl, thiazolyl, imidazolyl, pyrazolyl, furazanyl, isoxazolyl, morpholinyl, pyrrolidinyl, furyl, piperidyl, thienyl, chromenyl, oxochromenyl, indolyl, pyrrolyl, purinyl, benzoxazinyl, benzimidazolyl and benzofuranyl, which are optionally substituted with one or more radicals chosen from the definition of Y2.

A further particular embodiment according to the invention is where B2 is heteroaryl chosen from 3- or 4-pyridyl, 3- or 4-quinolyl, imidazolyl, thiazolyl, indolyl, pyrazolyl, pyrrolyl, pyrimidyl, purinyl, benzoxazinyl, benzimidazolyl and benzofuranyl, which are optionally substituted with one or more radicals chosen from the definition of Y2.

A further particular embodiment according to the invention is where B2 is heteroaryl chosen from 4-pyridyl, 4-quinolyl, imidazolyl, thiazolyl, pyrazolyl, pyrrolyl, pyrimidyl and purinyl radicals, which are optionally substituted with one or more radicals chosen from the definition of Y2.

A further particular embodiment according to the invention is where B2 is heteroaryl chosen from 3- or 4-pyridyl, pyrimidinyl, 3- or 4-quinolyl, azaindolyl, quinazolyl, thiazolyl, imidazolyl, pyrazolyl, furazanyl and isoxazolyl, which are optionally substituted with one or more radicals chosen from the definition of Y2.

A further particular embodiment according to the invention is where B2 is heteroaryl chosen from 3- or 4-pyridyl, pyrimidyl, 3- or 4-quinolyl, azaindolyl and quinazolyl, which are optionally substituted with one or more radicals chosen from the definition of Y2.

A further particular embodiment according to the invention is where B2 is 4-pyridyl, 4-quinolyl or 1H-pyrrolo[2.3-b]pyrid-4-yl, which are optionally substituted with one or more radicals chosen from the definition of Y2.

A further particular embodiment according to the invention is where Y2 is 2-amino-4-pyridyl in which the amino is optionally substituted as indicated for the radical —NR5R6 as defined herein and in the experimental section.

A further particular embodiment according to the invention is where

Y2 is hydrogen, halogen, hydroxyl, cyano, alkyl, alkoxy, phenyl, —COOH, —COOAlk, —CONR5R6, —NR5R6, —NR10-COOR6, —NR10-CO—R6, —NR10-CS—NR5R6, —NR10-CO—NR5R6 or —NR10-SO$_2$—R6, which are all optionally substituted, R5 and R6, which may be identical or different, are chosen from hydrogen, alkyl, cycloalkyl, phenyl and 5- or 6-membered heteroaryl containing 1 to 3 hetero atoms chosen from O, N and S, which are all optionally substituted, or R5 and R6 taken together with the nitrogen atom to which they are attached form an optionally substituted pyrrolidinyl, piperidyl, piperazinyl, morpholinyl or quinazolinyl, R10 is hydrogen or alkyl, all the alkyl, alkoxy, cycloalkyl and phenyl, and also the ring formed by R5 and R6 with the atom to which they are attached, are optionally substituted with one or more radicals, which may be identical or different, chosen from halogen, cyano, hydroxyl, alkyl, alkoxy, OCF$_3$, —CF$_3$, —S(O)$_n$—CF$_3$, nitro, oxo, thioxo, —OCOAlk; and phenyl, which is optionally substituted with one or more radicals chosen from halogen, alkyl, alkoxy; —OCOAlk; —NH$_2$, —NHAlk, —N(Alk)$_2$, —N(alk)(phenylalkyl), —N(Alk)(aminoalkyl), —N(Alk)(alkylaminoalkyl), —N(Alk)(dialkylaminoalkyl), and carboxyl in free form or esterified with an alkyl, all phenyl herein are optionally substituted with alkylenedioxy, all alkyl herein are optionally substituted with one or more saturated or partially unsaturated 4- to 7-membered heterocyclyl containing at least one nitrogen atom N and 0 to 2 other hetero atoms chosen from O, N and S, all the pyrrolidinyl and quinazolinyl herein are optionally substituted with oxo or thioxo, all the alkyl and alkoxy herein being linear or branched and containing not more than 6 carbon atoms, all the cycloalkyl herein containing not more than 7 carbon atoms.

A further particular embodiment according to the invention is where R5 and R6 represent pyridyl, pyrazinyl, pyrimidinyl, thienyl, thiazolyl and oxazolyl, which are all optionally substituted.

A further particular embodiment according to the invention is where the alkyl is optionally substituted with heterocyclyl chosen from thiomorpholin-4-yl, thiazolidin-3-yl, azetidin-1-yl, piperazinyl, imidazolyl, morpholinyl, pyrrolidinyl, piperidyl and azepanyl, all of which are optionally substituted as indicated herein; especially with one or more radicals chosen from alkyl, hydroxyalkyl, oxo, pyridyl and phenyl optionally substituted with one or more radicals chosen from halogen, alkyl, hydroxyl, alkoxy, —CN, carboxyl or amino, which are themselves optionally substituted.

Examples include piperazinyl optionally substituted with Alk, Alk-OH, pyridyl or phenyl, which itself is optionally substituted with one or more radicals chosen from halogen, alkyl, hydroxyl, alkoxy, —CN, carboxyl and amino, which are themselves optionally substituted; piperidyl optionally substituted with one or two Alk; or azepanyl optionally substituted with oxo.

Y2 is hydrogen, halogen, hydroxyl, cyano, alkyl, alkoxy, phenyl, —CONR5R6, —NR5R6, —NR10-COOH, —NR10-COOAlk, —NR10-CO—R6, —NR10-CS—NR5R6, —NR10-CO—NR5R6 or —NR10-SO$_2$—R6, R5 and R6, which may be identical or different, are chosen from hydrogen; alkyl; cycloalkyl; phenyl; pyrimidinyl; thienyl; pyridyl; quinolyl; thiazolyl optionally substituted with one or two halogen; pyran optionally substituted with one or more —OCOAlk; phenyl substituted with one or more radicals chosen from halogen, alkyl, alkoxy, amino, alkylamino, dialkylamino and carboxyl in free form or esterified with an alkyl radical; alkyl substituted with phenyl, which is itself optionally substituted with one or more radicals chosen from halogen, alkyl, alkoxy, amino, alkylamino, dialkylamino, carboxyl in free form or esterified with an alkyl radical; alkyl substituted with piperazinyl, which is itself optionally substituted with one or more radicals chosen from Alk, Alk-OH and pyridyl; alkyl substituted with imidazolyl; alkyl substituted with one or more radicals chosen from —NH$_2$, —NHAlk, —N(Alk)$_2$, —N(alk)(phenylalkyl), —N(Alk)(aminoalkyl), —N(Alk)(alkylaminoalkyl) and —N(Alk)(dialkylaminoalkyl); alkyl substituted with morpholinyl optionally substituted with one or two Alk; alkyl substituted with pyrrolidinyl; alkyl substituted with piperidyl, which is itself optionally substituted with one or two Alk; alkyl substituted with thiomorpholinyl; alkyl substituted with azetidinyl; and alkyl substituted with azepanyl, which is optionally substituted with oxo, or R5 and R6 taken together with the nitrogen atom to which they are attached form pyrrolidinyl; piperidyl; piperazinyl; morpholinyl; or quinazolinyl, all of which are optionally substituted with one or more radicals, which may be identical or different, chosen from halogen, alkyl, hydroxyl and alkoxy, and phenyl which is optionally substituted with one or more radicals chosen from halogen, alkyl and alkoxy, pyrrolidinyl and quinazolinyl are optionally substituted with oxo or thioxo, the piperazinyl itself is optionally substituted with one or more radicals chosen from Alk, Alk-OH and pyridyl, R10 is hydrogen or alkyl, all alkyl, Alk and alkoxy above being linear or branched and containing not more than 6 carbon atoms, all the cycloalkyl herein containing not more than 7 carbon atoms, all the phenyl are optionally substituted with a radical chosen from —$CF_3$, —$OCF_3$, nitro and alkylenedioxy.

Further particular embodiments according to the invention are directed to the three structures below, in which the definition of —NR14R15 is chosen from the definition of

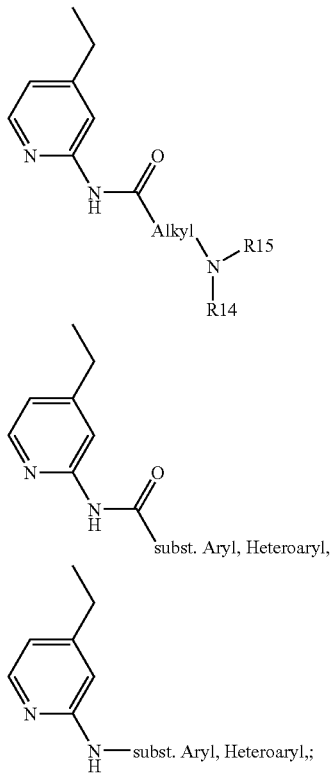

—NR5R6 and the definition for Alkyl, Aryl and Heteroaryl are chosen from the values of the alkyl, aryl and heteroaryl as defined above and optionally substituted as defined herein.

A further particular embodiment according to the invention is where B2 is the 4-pyridyl and 4-quinolyl, which are optionally substituted with one or more radicals chosen from the definition of Y2

A further particular embodiment according to the invention is where Y2 is V1, halogen, hydroxyl, —C(=NH)$NH_2$, OV1, O—CO—V1, COOV1, COV1, CO—NV1V2, —NV1V2, —NH—CO—V1, —NH—COO—V1, —NH—NH—CO—V1, —NV1-CO—NV1V2, —NV1-CO—NHV1, —NH—CO—NHV1, —NH—$SO_2$—NHV1 and —NH—$SO_2$—V1, in which V1 and V2, which may be identical or different, are hydrogen, alkyl, cycloalkyl or phenyl or heterocyclyl such as pyridyl, pyrazolyl, imidazolyl, dihydroimidazolyl, tetrazolyl, morpholinyl, piperazinyl, piperazinylalkyl, alkylpiperazinyl, phenylpiperazinyl, thienyl, furanyl, piperidyl, methylpiperidyl, pyridyl, pyrrolidyl and pyrrolidylalkyl, all the alkyl, phenyl and heterocyclyl being optionally substituted with one or more radicals chosen from halogen, hydroxyl, alkyl, alkoxy, —$CF_3$, —$NH_2$, NH-alk, N$(Alk)_2$ and phenyl, itself optionally substituted with one or more substituents chosen from halogen, hydroxyl and alkoxy radicals, all the phenyl and heterocyclyl herein are optionally substituted with one or more alkyl, the phenyl is optionally substituted with —NR5R6 in which R5 and R6 are as defined herein.

A further particular embodiment according to the invention is where Y2 is hydrogen, halogen, alkyl, cycloalkyl, hydroxyl, alkoxy, carboxyl which is free or esterified with an alkyl or phenyl, —$NH_2$, —NHalk, —N$(Alk)_2$ or phenyl, all the alkyl, alkoxy and phenyl are optionally substituted with one or more radicals chosen from halogen, hydroxyl, $C_1$-$C_4$ alkyl, $C_1$-$C_4$ alkoxy, —$CF_3$, —$NH_2$, —NH-alk, N$(Alk)_2$ and phenyl, which is itself optionally substituted with one or more substituents chosen from halogen, hydroxyl and alkoxy, all the phenyl are optionally substituted with one or more $C_1$-$C_4$ alkyl and optionally substituted with —NR5R6 in which R5 and R6 are as defined herein.

A further particular embodiment according to the invention is where Y2 is hydrogen, F, Cl, —$CH_3$, —$CH_2CH_3$, —OH, —$OCH_3$, —$NH_2$, —NH-Alk and phenyl optionally substituted with —NR5R6 in which R5 and R6 are as defined herein.

A further particular embodiment according to the invention is where B2 is 4-pyridyl and 4-quinolyl substituted with one or two radicals chosen from F, Cl, —OH and —$OCH_3$.

A further particular embodiment according to the invention is where

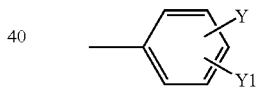

is which is selected from the following

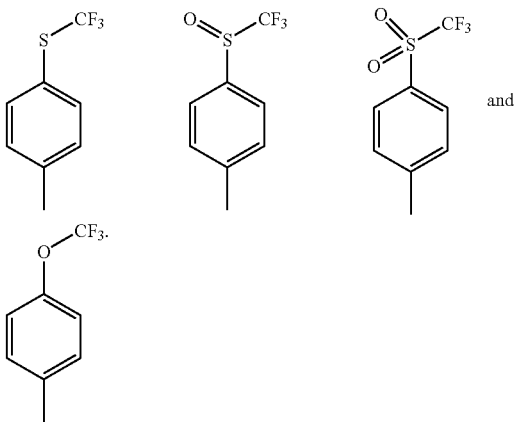

A further particular embodiment according to the invention is where —A2-B2-Y2 are selected from the following radicals:

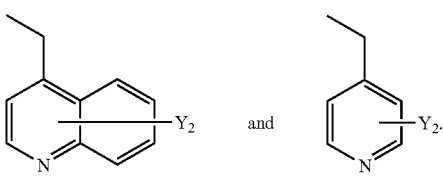

A further particular embodiment according to the invention is where R2 and R3 form together a cycloalkyl or heterocyclyl, or identical or different, are hydrogen or methyl.

A further particular embodiment according to the invention corresponding to formula (IC):

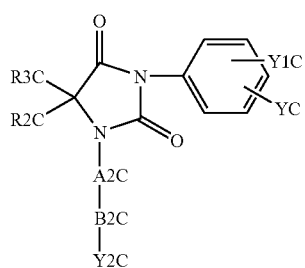

(IC)

in which YC and Y1C are such that one is hydrogen, halogen, or amino and the other is chosen from —OCF$_3$, —O—CF$_2$—CHF$_2$, —O—CHF$_2$, —O—CH$_2$—CF$_3$, —SF$_5$, —S(O)$_n$—CF$_3$, —S(O)$_n$-alk, —SO$_2$CHF$_2$, SO$_2$CF$_2$CF$_3$, —SO$_2$NH$_2$, —S—CF$_2$—CF$_2$—CF$_3$, —S-Alk-O-Alk, —S-Alk-OH, —S-Alk-CN, —S-Alk-morpholino, —S-Alk-pyrrolidyl and —S-Alk-piperazinyl, the morpholino, pyrrolidyl and piperazinyl are optionally substituted with Alk, with Alk being alkyl containing from 1 to 4 carbon atoms, or the phenyl thereof with its substituents YC and Y1C forms one of the two following radicals:

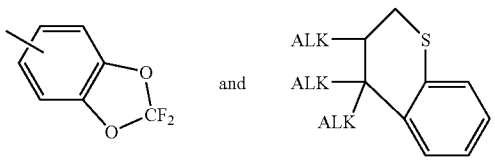

R2C and R3C, which may be identical or different, are hydrogen or optionally substituted alkyl, or R2C and R3C taken together with the carbon atom to which they are attached form, a C$_3$-C$_{10}$ cycloalkyl or heterocyclyl, A2C is single bond or CH$_2$, B2C is pyridyl, pyrimidyl, quinolyl, azaindolyl, quinazolyl, thiazolyl, imidazolyl, pyrazolyl, furazanyl, isoxazolyl, morpholinyl, pyrrolidyl, furyl, piperidyl, chromenyl, oxochromenyl, quinazolyl, thienyl, indolyl, pyrrolyl, purinyl, benzoxazinyl, benzimidazolyl or benzofuryl, that are optionally substituted with one or more radicals chosen from the definition of Y2A, Y2CA is hydrogen, halogen, hydroxyl, cyano, alkyl, alkoxy, phenyl, —COOH, —COOAlk, —CONR5R6, —NR5R6, —NR10-COOH, —NR10-COOAlk, —NR10-CO—R6, —NR10-CS—NR5R6, —NR10-CO—NR5R6 or —NR10-SO$_2$—R6, all these radicals are optionally substituted, R5 and R6, which may be identical or different, are chosen from hydrogen, alkyl, cycloalkyl, phenyl, pyrimidyl, thienyl, pyridyl, quinolyl, thiazolyl and pyran, all these radicals are optionally substituted, or R5 and R6 taken together with the nitrogen atom to which they are attached form optionally substituted pyrrolidyl, piperidyl, piperazinyl, morpholinyl or quinazolinyl, R10 is hydrogen or alkyl, all the alkyl, Alk or ALK, alkoxy, cycloalkyl and phenyl radicals herein, and also the ring formed by R5 and R6 with the atom to which they are attached, are optionally substituted with one or more radicals, which may be identical or different, chosen from halogen, cyano, hydroxyl, alkyl, alkoxy, —OCF$_3$, —CF$_3$, —S(O)$_n$—CF$_3$, nitro, oxo, thioxo, —OCOAlk, and phenyl, itself optionally substituted with one or more radicals chosen from halogen, alkyl, alkoxy; —OCOAlk; —NH$_2$, —NHAlk, —N(Alk)$_2$, —N(alk)(phenylalkyl), —N(Alk)(aminoalkyl) —N(Alk)(alkylaminoalkyl), —N(Alk)(dialkylaminoalkyl); carboxyl in free form or esterified with alkyl, all the phenyl herein are optionally substituted with alkylenedioxy, all the alkyl herein are optionally substituted with one or more radicals chosen from piperazinyl, itself optionally substituted with Alk, Alk-OH and pyridyl; imidazolyl; morpholinyl; pyrrolidyl; piperidyl, itself optionally substituted with one or two alk; azepanyl optionally substituted with oxo, all the pyrrolidyl and quinazolinyl herein are optionally substituted with oxo or thioxo, all the alkyl and alkoxy herein being linear or branched and containing not more than 6 carbon atoms, all the cycloalkyl herein containing not more than 7 carbon atoms, and n is 0 to 2, or racemic, enantiomeric or diastereoisomeric isomer form of the compound of formula I, addition salt with mineral or organic acid or with mineral or organic base thereof.

A further particular embodiment according to the invention is where, the radical below that can be formed by phenyl with its substituents Y and Y1:

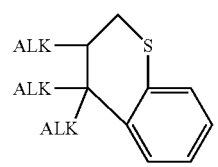

is

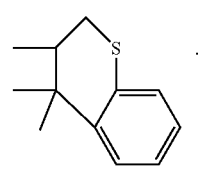

A further particular embodiment according to the invention corresponds to formula (IA):

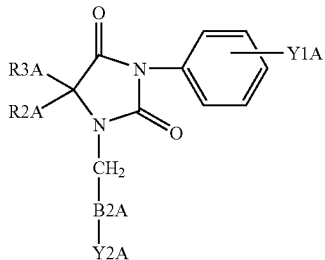

in which:

Y1A is —OCF$_3$, —S(O)$_n$—CF$_3$ and —SO$_2$CHF$_2$,

B2a is 4-quinolyl and 4-pyridyl optionally substituted with one or more radicals chosen from the definition of Y2A, Y2A is defined as Y2, R2A and R3A, which may be identical or different, are hydrogen or optionally substituted alkyl, or R2A and R3A taken together with the carbon atom to which they are attached form a C$_3$-C$_{10}$ cycloalkyl or heterocyclyl, all the alkyl and phenyl are optionally substituted with one or more radicals chosen from halogen, —OH, alk, —O-alk, —OCF$_3$, —S(O)$_n$—CF$_3$, —CF$_3$, —NH$_2$, —NH-Alk and —N(Alk)$_2$, and n is 0 to 2, or racemic, enantiomeric or diastereoisomeric isomer form of the compound of formula I, addition salt with mineral or organic acid or with mineral or organic base thereof.

A further particular embodiment according to the invention is for the compound of formula (IA) as defined above in which Y1A, B2a, R2A and R3A have the meanings given above and Y2A is halogen, —OH, -alk, —Oalk, —Oacyl, —NR5AR6A, —CO2H, —CO2alk, —CO—NR5AR6A, —S(O)$_n$—CF$_3$, —NH—S(O)$_n$—CF$_3$ or phenyl, alk is a linear or branched alkyl radical containing not more than 6 carbon atoms, all the alkyl, alkoxy and phenyl are optionally substituted, R5A and R6A, which may be identical or different, are hydrogen, alkyl, cycloalkyl or phenyl, the alkyl and phenyl are optionally substituted, or R5A and R6A taken together with the nitrogen atom to which they are attached form cyclic radical chosen from pyrrolidyl, piperidyl, piperazinyl, morpholinyl, indolinyl, pyrindolinyl, tetrahydroquinolyl and azetidinyl, all the alkyl, alkoxy and phenyl are optionally substituted with one or more radicals chosen from halogen, —OH, alk, —Oalk, —OCF$_3$, —S(O)$_n$—CF$_3$, —CF$_3$, —NH$_2$, —NH-Alk and —N(Alk)$_2$, and n is 0 to 2, or said products of formula (IA) being in any possible racemic, enantiomeric or diastereoisomeric isomer form, and also the addition salts with mineral and organic acids or with mineral and organic bases of said products of formula (IA).

A subject of the present invention is especially the compound of formula (IA) as defined above in which:

Y1A is —OCF$_3$, SCF$_3$ or S(O)$_2$—CF$_3$,

B2a is a 4-quinolyl or 4-pyridyl radical optionally substituted with one or two radicals chosen from halogen, —OH, alk, —Oalk, —CO2H, —CO2alk, —NR5AR6A, —CF$_3$, —OCF$_3$ and optionally substituted phenyl, R5A and R6A, which may be identical or different, are hydrogen, alkyl, cycloalkyl or phenyl, the alkyl and phenyl radicals being optionally substituted, or R5A and R6A taken together with the nitrogen atom to which they are attached form, a cyclic radical chosen from pyrrolidyl, piperidyl, piperazinyl, morpholinyl, piperazinyl and azetidinyl radicals, R2A and R3A, which may be identical or different, are hydrogen or optionally substituted alkyl, or R2A and R3A taken together with the carbon atom to which they are attached form, a C$_3$-C$_6$ cycloalkyl or heterocyclyl radical, all the alkyl and phenyl radicals being optionally substituted with one or more radicals chosen from halogen, OH, alk, Oalk, OCF$_3$, S(O)$_n$—CF$_3$, —CF$_3$, NH$_2$, NHalk and N(Alk)$_2$, said products of formula (IA) being in any possible racemic, enantiomeric or racemic, enantiomeric or diastereoisomeric isomer form of the compound of formula I, addition salt with mineral or organic acid or with mineral or organic base thereof.

A subject of the present invention is especially the compound of formula (IA) as defined above corresponding to formula (IA) in which:

Y1A is —OCF$_3$, —SCF$_3$ or —S(O)$_2$—CF$_3$,

B2a is 4-quinolyl or 4-pyridyl optionally substituted with one or two radicals chosen from halogen, —OH, alk and —Oalk, and R2A and R3A, which may be identical or different, are hydrogen or linear or branched alkyl containing not more than 4 carbon atoms optionally substituted with hydroxyl, or R2A and R3A taken together with the carbon atom to which they are attached form a C$_3$-C$_6$ cycloalkyl, or said products of formula (IA) being in any possible racemic, enantiomeric or enantiomeric or diastereoisomeric isomer form of the compound of formula I, addition salt with mineral or organic acid or with mineral or organic base thereof.

A subject of the present invention is especially the compound of formula (IA) as defined above corresponding to formula (IA) in which Y1a is —OCF$_3$, —SCF$_3$ or —S(O)$_2$CF$_3$, and R2A and R3A, which may be identical or different, are hydrogen or CH3, or R2A and R3A taken together with the carbon atom to which they are attached form cyclopropyl, or diastereoisomeric isomer form of the compound of formula I, addition salt with mineral or organic acid or with mineral or organic base thereof.

A subject of the present invention is especially the compound of formula (I) as defined above corresponding to formula (IB):

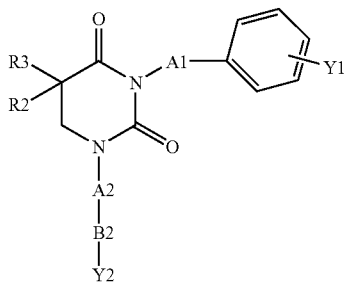

(IB)

in which R2, R3, A1, Y, Y1, A2, B2 and Y2 have the meanings given above or diastereoisomeric isomer form of the compound of formula I, addition salt with mineral or organic acid or with mineral or organic base thereof.

A subject of the present invention is especially the compound of formula (IB) as defined above in which Y1 is —OCF$_3$, —SCF$_3$ or —S(O)$_2$CF$_3$ and R2 and R3, which may be identical or different, are hydrogen or —CH$_3$, or R2 and R3 taken together with the carbon atom to which they are attached form cyclopropyl, or diastereoisomeric isomer form of the compound of formula I, addition salt with mineral or organic acid or with mineral or organic base thereof.

Among the compounds of the invention that are preferred, are given below:
(S)-5-methyl-1-quinol-4-ylmethyl-3-(4-trifluoromethanesulfonylphenyl)imidazolidine-2,4-dione trifluoroacetate;
(S)-5-methyl-1-pyrid-4-ylmethyl-3-(4-trifluoromethanesulfonylphenyl)imidazolidine-2,4-dione trifluoroacetate;
(S)-5-methyl-1-quinol-4-ylmethyl-3-(4-trifluoromethylsulfanylphenyl)imidazolidine-2,4-dione trifluoroacetate;
5,5-dimethyl-1-quinol-4-ylmethyl-3-(4-trifluoromethanesulfonylphenyl)imidazolidine-2,4-dione trifluoroacetate;
(R)-5-methyl-1-quinol-4-ylmethyl-3-(4-trifluoromethanesulfonylphenyl)imidazolidine-2,4-dione trifluoroacetate;
(R)-5-methyl-1-quinol-4-ylmethyl-3-(4-trifluoromethylsulfanylphenyl)imidazolidine-2,4-dione trifluoroacetate;
(R)-5-methyl-1-pyrid-4-ylmethyl-3-(4-trifluoromethanesulfonylphenyl)imidazolidine-2,4-dione trifluoroacetate;
(R)-5-methyl-1-(3-methylpyrid-4-ylmethyl)-3-(4-trifluoromethanesulfonylphenyl)imidazolidine-2,4-dione trifluoroacetate;
(R)-4-methyl-3-quinol-4-ylmethyl-5-thioxo-1-(4-trifluoromethylsulfanylphenyl)imidazolidin-2-one trifluoroacetate;
(R)-5-isopropyl-1-quinol-4-ylmethyl-3-(4-trifluoromethylsulfanylphenyl)imidazolidine-2,4-dione trifluoroacetate;
(R)-5-isopropyl-1-quinol-4-ylmethyl-3-(4-trifluoromethanesulfonylphenyl)imidazolidine-2,4-dione trifluoroacetate;
(R)-5-(4-hydroxybenzyl)-1-quinol-4-ylmethyl-3-(4-trifluoromethanesulfonylphenyl)imidazolidine-2,4-dione trifluoroacetate;
(R)-5-(4-hydroxybenzyl)-1-pyrid-4-ylmethyl-3-(4-trifluoromethanesulfonylphenyl)imidazolidine-2,4-dione trifluoroacetate;
(R)-5-(1-hydroxyethyl)-1-quinol-4-ylmethyl-3-(4-trifluoromethanesulfonylphenyl)imidazolidine-2,4-dione trifluoroacetate;
4-quinol-4-ylmethyl-6-(4-trifluoromethylsulfanylphenyl)-4,6-diazaspiro[2.4]heptane-5,7-dione trifluoroacetate;
4-quinol-4-ylmethyl-6-(4-trifluoromethanesulfonylphenyl)-4,6-diazaspiro[2.4]heptane-5,7-dione trifluoroacetate;
4-pyrid-4-ylmethyl-6-(4-trifluoromethylsulfanylphenyl)-4,6-diazaspiro[2.4]heptane-5,7-dione trifluoroacetate;
4-pyrid-4-ylmethyl-6-(4-trifluoromethanesulfonylphenyl)-4,6-diazaspiro[2.4]heptane-5,7-dione trifluoroacetate;
(R)-1-(3-hydroxypyrid-4-ylmethyl)-5-methyl-3-(4-trifluoromethylsulfanylphenyl)imidazolidine-2,4-dione trifluoroacetate;
5,5-dimethyl-1-quinol-4-ylmethyl-3-(4-trifluoromethoxyphenyl)imidazolidine-2,4-dione trifluoroacetate;
5,5-dimethyl-1-quinol-4-ylmethyl-3-(4-trifluoromethylsulfanylphenyl)imidazolidine-2,4-dione trifluoroacetate;
5,5-dimethyl-1-(3-methylpyrid-4-ylmethyl)-3-(4-trifluoromethoxyphenyl)imidazolidine-2,4-dione trifluoroacetate;
5,5-dimethyl-1-(3-methylpyrid-4-ylmethyl)-3-(4-trifluoromethylsulfanylphenyl)imidazolidine-2,4-dione trifluoroacetate;
5,5-dimethyl-1-(3-methylpyrid-4-ylmethyl)-3-(4-trifluoromethanesulfonylphenyl)imidazolidine-2,4-dione trifluoroacetate;
1-(3-hydroxypyrid-4-ylmethyl)-5,5-dimethyl-3-(4-trifluoromethoxyphenyl)imidazolidine-2,4-dione trifluoroacetate;
1-(3-hydroxypyrid-4-ylmethyl)-5,5-dimethyl-3-(4-trifluoromethylsulfanylphenyl)imidazolidine-2,4-dione trifluoroacetate;
1-(3-hydroxypyrid-4-ylmethyl)-5,5-dimethyl-3-(4-trifluoromethanesulfonylphenyl)imidazolidine-2,4-dione trifluoroacetate;
4-quinol-4-ylmethyl-6-(4-trifluoromethoxyphenyl)-4,6-diazaspiro[2.4]heptane-5,7-dione trifluoroacetate;
4-(3-methylpyrid-4-ylmethyl)-6-(4-trifluoromethylsulfanylphenyl)-4,6-diazaspiro[2.4]heptane-5,7-dione trifluoroacetate;
4-(3-hydroxypyrid-4-ylmethyl)-6-(4-trifluoromethoxyphenyl)-4,6-diazaspiro[2.4]heptane-5,7-dione trifluoroacetate;
4-(3-hydroxypyrid-4-ylmethyl)-6-(4-trifluoromethylsulfanylphenyl)-4,6-diazaspiro[2.4]heptane-5,7-dione trifluoroacetate;
4-(3-hydroxypyrid-4-ylmethyl)-6-(4-trifluoromethanesulfonylphenyl)-4,6-diazaspiro[2.4]heptane-5,7-dione trifluoroacetate, said compound of formula I being in any possible racemic, enantiomeric or diastereoisomeric isomer form, and also the addition salts with mineral and organic acids or with mineral and organic bases of said compound of formula I.

Among the preferred products of the invention, mention may be made more particularly of the compound of formula I as defined above, the names of which are given below:
{4-[5,5-dimethyl-2,4-dioxo-3-(4-trifluoromethylsulfanylphenyl)imidazolidin-1-ylmethyl]pyrid-2-yl}cyclopropanecarboxamide trifluoroacetate;
5,5-dimethyl-1-[2-(pyrid-2-ylamino)pyrid-4-ylmethyl]-3-(4-trifluoromethylsulfanylphenyl)-imidazolidine-2,4-dione; compound with trifluoroacetic acid;
N-{4-[5,5-dimethyl-2,4-dioxo-3-(4-trifluoromethylsulfanylphenyl)imidazolidin-1-ylmethyl]pyrid-2-yl} isobutyramide; compound with trifluoroacetic acid;
N-{4-[5,5-dimethyl-2,4-dioxo-3-(4-trifluoromethylsulfanylphenyl)imidazolidin-1-ylmethyl]pyrid-2-yl}propionamide; compound with trifluoroacetic acid;

1-(2-aminopyrid-4-ylmethyl)-5,5-dimethyl-3-(4-trifluoromethylsulfanylphenyl)imidazolidine-2,4-dione hydrochloride;

{4-[5,5-dimethyl-2,4-dioxo-3-(4-trifluoromethylsulfanylphenyl)imidazolidin-1-ylmethyl]pyrid-2-yl}pyridine-2-carboxamide trifluoroacetate;

N-{4-[5,5-dimethyl-2,4-dioxo-3-(4-trifluoromethylsulfanylphenyl)imidazolidin-1-ylmethyl]pyrid-2-yl}-3-piperid-1-ylpropionamide trifluoroacetate;

N-{4-[5,5-dimethyl-2,4-dioxo-3-(4-trifluoromethylsulfanylphenyl)imidazolidin-1-ylmethyl]pyrid-2-yl}-3-[4-(2-hydroxyethyl)piperazin-1-yl]propionamide trifluoroacetate;

N-{4-[5,5-dimethyl-2,4-dioxo-3-(4-trifluoromethylsulfanylphenyl)imidazolidin-1-ylmethyl]pyrid-2-yl}-3-morpholin-4-ylpropionamide trifluoroacetate;

N-{4-[5,5-dimethyl-2,4-dioxo-3-(4-trifluoromethylsulfanylphenyl)imidazolidin-1-ylmethyl]pyrid-2-yl}-3-pyrrolidin-1-ylpropionamide trifluoroacetate;

N-{4-[5,5-dimethyl-2,4-dioxo-3-(4-trifluoromethylsulfanylphenyl)imidazolidin-1-ylmethyl]pyrid-2-yl}-3-(4-methylpiperazin-1-yl)propionamide trifluoroacetate;

1-{4-[5,5-dimethyl-2,4-dioxo-3-(4-trifluoromethylsulfanylphenyl)imidazolidin-1-ylmethyl]pyrid-2-yl}-3-phenylurea;

1-[2-(6-ethylpyrid-2-ylamino)pyrid-4-ylmethyl]-5,5-dimethyl-3-(4-trifluoromethylsulfanylphenyl)imidazolidine-2,4-dione;

5,5-dimethyl-1-[2-(4-methylpyrid-2-ylamino)pyrid-4-ylmethyl]-3-(4-trifluoromethylsulfanylphenyl)imidazolidine-2,4-dione;

5,5-dimethyl-1-[2-(6-methylpyrid-2-ylamino)pyrid-4-ylmethyl]-3-(4-trifluoromethylsulfanylphenyl)imidazolidine-2,4-dione;

1-[2-(4,6-dimethylpyrid-2-ylamino)pyrid-4-ylmethyl]-5,5-dimethyl-3-(4-trifluoromethylsulfanylphenyl)imidazolidine-2,4-dione;

1-[2-(3,5-dichloropyrid-2-ylamino)pyrid-4-ylmethyl]-5,5-dimethyl-3-(4-trifluoromethylsulfanylphenyl)imidazolidine-2,4-dione;

5,5-dimethyl-1-[2-(pyrid-4-ylamino)pyrid-4-ylmethyl]-3-(4-trifluoromethylsulfanylphenyl)imidazolidine-2,4-dione;

5,5-dimethyl-1-[2-(pyrid-3-ylamino)pyrid-4-ylmethyl]-3-(4-trifluoromethylsulfanylphenyl)imidazolidine-2,4-dione;

N-{4-[5,5-dimethyl-2,4-dioxo-3-(4-trifluoromethylsulfanylphenyl)imidazolidin-1-ylmethyl]pyrid-2-yl}-3-(2-oxoazepan-1-yl)propionamide;

3-(benzylmethylamino)-N-{4-[5,5-dimethyl-2,4-di-oxo-3-(4-trifluoromethylsulfanylphenyl)imidazolidin-1-ylmethyl]pyrid-2-yl}propionamide;

4,5-diacetoxy-6-acetoxymethyl-2-(3-{4-[5,5-dimethyl-2,4-dioxo-3-(4-trifluoromethylsulfanylphenyl)imidazolidin-1-ylmethyl]pyrid-2-yl}thioureidoacetic acid;

5,5-dimethyl-1-[2-(5-methylpyrid-2-ylamino)pyridin-4-ylmethyl]-3-(4-trifluoromethylsulfanylphenyl)imidazolidine-2,4-dione;

N-{4-[5,5-dimethyl-2,4-dioxo-3-(4-trifluoromethylsulfanylphenyl)imidazolidin-1-ylmethyl]pyrid-2-yl}-3,5-dimethoxybenzamide trifluoroacetate;

5,5-dimethyl-1-[2-(pyrazin-2-ylamino)pyrid-4-ylmethyl]-3-(4-trifluoromethylsulfanylphenyl)imidazolidine-2,4-dione trifluoroacetate;

N-{4-[5,5-dimethyl-2,4-dioxo-3-(4-trifluoromethylsulfanylphenyl)imidazolidin-1-ylmethyl]pyrid-2-yl}-3-(3-methylpiperid-1-yl)propionamide trifluoroacetate;

N-{4-[5,5-dimethyl-2,4-dioxo-3-(4-trifluoromethylsulfanylphenyl)imidazolidin-1-ylmethyl]pyrid-2-yl}-3-(3,5-dimethylpiperid-1-yl)propionamide trifluoroacetate;

N-{4-[5,5-dimethyl-2,4-dioxo-3-(4-trifluoromethylsulfanylphenyl)imidazolidin-1-ylmethyl]pyrid-2-yl}-3-methoxybenzamide trifluoroacetate;

{4-[5,5-dimethyl-2,4-dioxo-3-(4-trifluoromethylsulfanylphenyl)imidazolidin-1-ylmethyl]pyrid-2-yl}pyrazine-2-carboxamide trifluoroacetate;

{4-[5,5-dimethyl-2,4-dioxo-3-(4-trifluoromethylsulfanylphenyl)imidazolidin-1-ylmethyl]pyrid-2-yl}thiophene-2-carboxamide trifluoroacetate;

N-{4-[5,5-dimethyl-2,4-dioxo-3-(4-trifluoromethylsulfanylphenyl)imidazolidin-1-ylmethyl]pyrid-2-yl}-4-methylbenzamide; compound with trifluoroacetic acid;

1-isoquinolin-5-yl-5,5-dimethyl-3-(4-trifluoro-methylsulfanylphenyl)imidazolidine-2,4-dione;

3-(4-acetylpiperazin-1-yl)-N-{4-[5,5-dimethyl-2,4-dioxo-3-(4-trifluoromethylsulfanylphenyl)imidazolidin-1-ylmethyl]pyrid-2-yl}propionamide;

3-[4-(2-diethylaminoethyl)piperazin-1-yl]-N-{4-[5,5-dimethyl-2,4-dioxo-3-(4-trifluoromethylsulfanylphenyl)imidazolidin-1-ylmethyl]pyrid-2-yl}propionamide;

N-{4-[5,5-dimethyl-2,4-dioxo-3-(4-trifluoromethylsulfanylphenyl)imidazolidin-1-ylmethyl]pyrid-2-yl}-3-(2,6-dimethylmorpholin-4-yl)propionamide;

N-{4-[5,5-dimethyl-2,4-dioxo-3-(4-trifluoromethylsulfanylphenyl)imidazolidin-1-ylmethyl]pyrid-2-yl}-3-(4-pyrrolidin-1-ylpiperid-1-yl)propionamide;

N-{4-[5,5-dimethyl-2,4-dioxo-3-(4-trifluoromethylsulfanylphenyl)imidazolidin-1-ylmethyl]pyrid-2-yl}-2-(4-pyrrolidin-1-ylpiperid-1-yl)acetamide;

5,5-dimethyl-1-[2-(4-methylpyrid-3-ylamino)pyrid-4-ylmethyl]-3-(4-trifluoromethylsulfanylphenyl)imidazolidine-2,4-dione;

5,5-dimethyl-1-[2-(6-morpholin-4-ylpyrid-3-ylamino)pyrid-4-ylmethyl]-3-(4-trifluoromethylsulfanylphenyl)imidazolidine-2,4-dione;

1-[2-(2,6-dimethylpyrid-3-ylamino)pyrid-4-ylmethyl]-5,5-dimethyl-3-(4-trifluoromethylsulfanylphenyl)imidazolidine-2,4-dione;

methyl 5-{4-[5,5-dimethyl-2,4-dioxo-3-(4-trifluoromethylsulfanylphenyl)imidazolidin-1-ylmethyl]pyrid-2-ylamino}pyridine-2-carboxylate;

1-[2-(2,6-dimethoxypyrid-3-ylamino)pyrid-4-ylmethyl]-5,5-dimethyl-3-(4-trifluoromethylsulfanylphenyl)imidazolidine-2,4-dione;

1-[2-(6-fluoropyrid-3-ylamino)pyrid-4-ylmethyl]-5,5-dimethyl-3-(4-trifluoromethylsulfanylphenyl)imidazolidine-2,4-dione;

1-[2-(6-methoxypyrid-3-ylamino)pyrid-4-ylmethyl]-5,5-dimethyl-3-(4-trifluoromethylsulfanylphenyl)imidazolidine-2,4-dione, said compound of formula I being in any possible racemic, enantiomeric or diastereoisomeric isomer form, and also the addition salts with mineral and organic acids or with mineral and organic bases of said compound of formula I.

A subject of the present invention is also a process for preparing the compound of formula I as defined above, characterized in that:

either a product of formula (II):

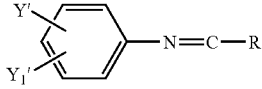

(II)

in which Y' and Y1' have the meanings given above for Y and Y1, respectively, in which the optional reactive functions are optionally protected and R has the meaning given above, is reacted in the presence of a tertiary base with a product of formula (III):

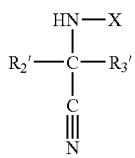

(III)

in which X is —A2'-B2'-Y2' or hydrogen, and A2', B2', Y2', R2' and R3' have the meanings given above, respectively, for A2', B2', Y2', R2' and R3' in which the optional reactive functions are optionally protected above, to obtain a product of formula (IV):

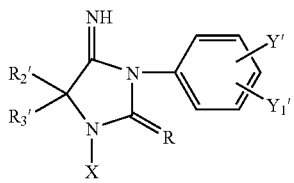

(IV)

in which Y', Y1', X, R, R2' and R3' have the meanings given above, which products of formula (IV) are, if necessary or if desired, subjected to any one or more of the following reactions, in any order:

a) reaction for removal of any protecting groups that may be borne by Y', Y1', R, R2' and R3' and X when X is —A2'-B2'-Y2';

b) reaction for hydrolysis of the >C=NH group to a ketone function c) action on the products of formula (IV) in which X is hydrogen, and after optional hydrolysis of the >C=NH group to a ketone function of a reagent of formula Hal-A2'-B2'-Y2' in which A2', B2' and Y2' have the meanings given above and Hal is a halogen atom, to obtain products of formula (Ii):

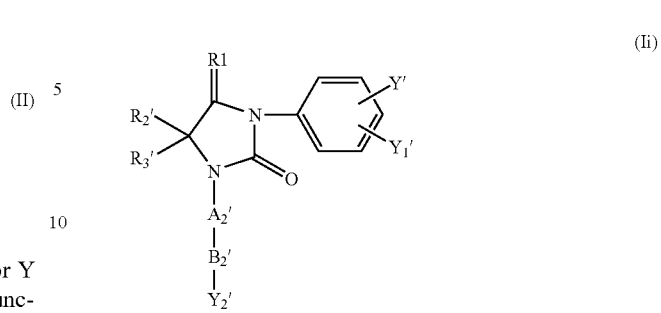

(Ii)

in which Y', Y1', R2', R3', A2', B2' and Y2' have the meanings given above, followed, if desired, by the action on these products of an agent for removing any protecting groups that may be borne by Y', Y1', R2', R3', A2', B2' and Y2' or, where appropriate, the action of an esterification, amidation or salification agent, or the product of formula (II) defined above is reacted in the presence of a tertiary base with a product of formula (III'):

(III')

in which R2' and R3' have the meanings given above and Q is either an alkali metal atom, for example sodium, or an alkyl radical containing from 1 to 6 carbon atoms, to obtain a product of formula (IVa):

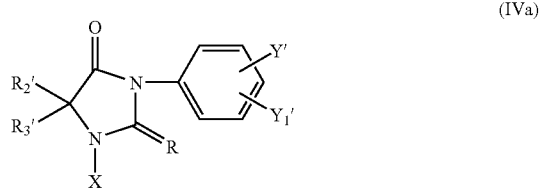

(IVa)

in which Y', Y1', R, R2', R3' and X have the meanings given above, which product, if desired, is subjected to any one or more of the following reactions, in any order:

a) reaction for removal of the possible protecting groups that may be borne by X;

b) action on the products of formula (IVa), in which X is hydrogen, of a reagent of formula Hal-A2'-B2'-Y2' in which A2', B2' and Y2' have the meanings given above and Hal is a halogen atom, to obtain products of formula (Iii):

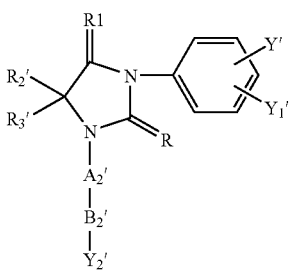

(Iii)

in which Y', Y1', R, R1, R2', R3' and A2', B2' and Y2' have the meanings given above, followed, if desired, by the action on these products of an agent for removing any protecting groups that may be borne by Y', Y1', R2', R3', A2', B2' and Y2' or, where appropriate, the action of an esterification, amidation or salification agent, or a reagent of formula Hal-A2'-B2'-Y2', in which A2', B2', Y2' and Hal have the meanings given above, is reacted with a product of formula (IV'):

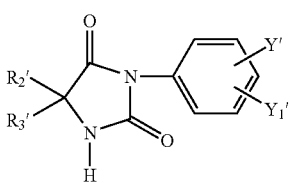

(IV')

in which Y', Y1', R2' and R3' have the meanings given above, to obtain a product of formula (IV"):

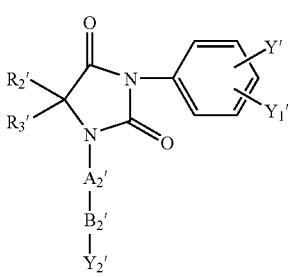

(IV")

in which Y', Y1', R2', R3', A2', B2' and Y2' have the meanings given above, which product of formula (IV") is, if necessary or if desired, subjected to a reaction for removal of any protecting groups that may be borne by —A2'-B2'-Y2', followed, where appropriate, by the action of an esterification, amidation or salification agent.

It may be noted that, depending on the values of Y', Y1', R2', R3', A2', B2' and Y2', the products of formulae (IV), (Ii), (IVa), (Iii) and (IV") may be compound of formula I and that, to obtain products or other compound of formula I, these products may be subjected if desired, and necessary, to one or more of the following conversion reactions, in any order:

a) a reaction for esterification of an acid function, b) a reaction for saponification of an ester function to an acid function, c) a reaction for oxidation of an alkylthio group to the corresponding sulfoxide or sulfone group, d) a reaction for conversion of a ketone function to an oxime function, e) a reaction for reducing a free or esterified carboxyl function to an alcohol function, f) a reaction for conversion of an alkoxy function to a hydroxyl function, or of a hydroxyl function to an alkoxy function, g) a reaction for oxidation of an alcohol function to an aldehyde, acid or ketone function, h) a reaction for conversion of a nitrile radical to a tetrazolyl, i) a reaction for reduction of nitro compounds to amino compounds, j) a reaction for removal of the protecting groups that may be borne by the protected reactive functions, k) a reaction for salification with a mineral or organic acid or with a base to obtain the corresponding salt, l) a reaction for resolution of the racemic forms to resolved products, said compound of formula I thus obtained being in any possible racemic, enantiomeric or diastereoisomeric isomer form.

It may be noted that such reactions for converting substituents into other substituents may also be performed on the starting materials, and also on the intermediates as defined above before continuing the synthesis according to the reactions indicated in the process described above.

The various reactive functions that may be borne by certain compounds of the reactions defined above may, if necessary, be protected: these are, for example, hydroxyl, acyl, free carboxyl or amino and monoalkylamino radicals, which may be protected with the appropriate protecting groups.

The following nonexhaustive list of examples of protection of reactive functions may be mentioned:

The hydroxyl groups may be protected, for example, with alkyl radicals such as tert-butyl, trimethylsilyl, tert-butyldimethylsilyl, methoxymethyl, tetrahydropyranyl, benzyl or acetyl.

The amino groups may be protected, for example, with acetyl, trityl, benzyl, tert-butoxycarbonyl, benzyloxycarbonyl, phthalimido radicals or other radicals known in peptide chemistry.

The acyl groups such as the formyl group may be protected, for example, in the form of cyclic or noncyclic ketals or thioketals such as dimethyl or diethylketal or ethylene dioxyketal, or diethylthioketal or ethylenedithioketal.

The acid functions of the products described above may be, if desired, amidated with a primary or secondary amine, for example in methylene chloride in the presence, for example, of 1-ethyl-3-(dimethylaminopropyl)carbodiimide hydrochloride at room temperature.

The acid functions may be protected, for example, in the form of esters formed with readily cleavable esters such as benzyl esters or tert-butyl esters, or esters known in peptide chemistry.

These reactions a) to k) indicated above may be performed, for example, as indicated below.

a) The products described above may, if desired, undergo, on the possible carboxyl functions, esterification reactions that may be performed according to the usual methods known to those skilled in the art.

b) The possible conversions of ester functions into an acid function of the products described above may be, if desired, performed under the usual conditions known to those skilled in the art, especially by acid or alkaline hydrolysis, for example with sodium hydroxide or potassium hydroxide in alcoholic medium such as, for example, in methanol, or with hydrochloric acid or sulfuric acid.

c) The possible alkylthio groups in the products described above, in which the alkyl radical is optionally substituted with one or more halogen atoms, especially fluorine, may, if desired, be converted into the corresponding sulfoxide or sulfone functions under the usual conditions known to those skilled in the art such as, for example, with peracids such as, for example, peracetic acid or meta-chloroperbenzoic acid, or with ozone, oxone or sodium periodate in a solvent such as, for example, methylene chloride or dioxane at room temperature.

The production of the sulfoxide function may be promoted with an equimolar mixture of the product containing an alkylthio group and the reagent such as, especially, a peracid.

The production of the sulfone function may be promoted with a mixture of the product containing an alkylthio group with an excess of the reagent such as, especially, a peracid.

d) The reaction for conversion of a ketone function into an oxime may be performed under the usual conditions known to those skilled in the art, such as, especially, a reaction in the presence of an optionally O-substituted hydroxylamine in an alcohol such as, for example, ethanol, at room temperature or with heating.

e) The possible free or esterified carboxyl functions of the products described above may be, if desired, reduced to an alcohol function by the methods known to those skilled in the art: the possible esterified carboxyl functions may be, if desired, reduced to an alcohol function by the methods known to those skilled in the art and especially with lithium aluminum hydride in a solvent such as, for example, tetrahydrofuran or dioxane or ethyl ether.

The possible free carboxyl functions of the products described above may be, if desired, reduced to an alcohol function especially with boron hydride.

f) The possible alkoxy functions such as, especially, methoxy, in the products described above, may be, if desired, converted into a hydroxyl function under the usual conditions known to those skilled in the art, for example with boron tribromide in a solvent such as, for example, methylene chloride, with pyridine hydrobromide or hydrochloride or with hydrobromic acid or hydrochloric acid in water or trifluoroacetic acid at reflux.

g) The possible alcohol functions of the products described above may be, if desired, converted into an aldehyde or acid function by oxidation under the usual conditions known to those skilled in the art, such as, for example, by the action of manganese oxide to obtain the aldehydes, or of Jones' reagent to access the acids.

h) The possible nitrile functions of the products described above may be, if desired, converted into tetrazolyl under the usual conditions known to those skilled in the art, such as, for example, by cycloaddition of a metal azide such as, for example, sodium azide or a trialkyltin azide on the nitrile function, as indicated in the method described in the article referenced as follows:

J. Organometallic Chemistry., 33, 337 (1971) KOZIMA S. et al.

It may be noted that the reaction for conversion of a carbamate into urea and especially of a sulfonylcarbamate into sulfonylurea may be performed, for example, at the reflux point of a solvent such as, for example, toluene, in the presence of the appropriate amine.

It is understood that the reactions described above may be performed as indicated or, where appropriate, according to other common methods known to those skilled in the art.

i) The removal of protecting groups such as, for example, those indicated above may be performed under the usual conditions known to those skilled in the art, especially via an acid hydrolysis performed with an acid such as hydrochloric acid, benzenesulfonic acid or paratoluenesulfonic acid, formic acid or trifluoroacetic acid, or via a catalytic hydrogenation. The phthalimido group may be removed with hydrazine.

A list of various protecting groups that may be used will be found, for example, in patent BF 2 499 995.

j) The products described above may, if desired, be subjected to salification reactions, for example with a mineral or organic acid or with a mineral or organic base according to the usual methods known to those skilled in the art.

k) The possible optically active forms of the products described above may be prepared by resolving the racemic mixtures according to the usual methods known to those skilled in the art.

The reaction of the products of formula (II) with the products of formula (III) is preferably performed in an organic solvent such as tetrahydrofuran or dichloroethane, but ethyl ether or isopropyl ether may also be used.

The process is optionally performed in the presence of a tertiary base such as triethylamine or pyridine or methylethylpyridine.

The possible reactive functions that are optionally protected in the product of formula (III), (IVa) or (IV'') are the hydroxyl or amino functions. Usual protecting groups are used to protect these functions. Examples include the following protecting groups for the amino radical: tert-butyl, tert-amyl, trichloroacetyl, chloroacetyl, benzhydryl, trityl, formyl, benzyloxycarbonyl.

Protecting groups for the hydroxyl radical that may be mentioned include radicals such as formyl, chloroacetyl, tetrahydropyranyl, trimethylsilyl and tert-butyldimethylsilyl.

It is clearly understood that the above list is not limiting and that other protecting groups, which are known, for example, in peptide chemistry, may be used. A list of such protecting groups is found, for example, in French patent 2 499 995, the content of which is incorporated herein by reference.

The possible reactions for removal of the protecting groups are performed as indicated in said patent 2 499 995. The preferred method of removal is acid hydrolysis with acids chosen from hydrochloric acid, benzenesulfonic acid or para-toluenesulfonic acid, formic acid or trifluoroacetic acid. Hydrochloric acid is preferred.

The possible reaction for hydrolysis of the >C=NH group to a ketone group is also preferably performed using an acid such as aqueous hydrochloric acid, for example at reflux.

The action on the products of formula (IV), (IVa) or (IV')
of the reagent of formula Hal-A2'-B2'-Y2' is performed in
the presence of a strong base such as sodium hydride or
potassium hydride. The process may be performed by phase-
transfer reaction in the presence of quaternary ammonium
salts such as tert-butylammonium.

An example of removal of the tert-butyldimethylsilyl
group using hydrochloric acid is given below in the
examples.

The possible esterification of a free OH radical is per-
formed under standard conditions. An acid or a functional
derivative, for example an anhydride such as acetic anhy-
dride in the presence of a base such as pyridine, may be used,
for example.

The possible esterification or salification of a COOH
group is performed under the standard conditions known to
those skilled in the art.

The possible amidation of a COOH radical is performed
under standard conditions. A primary or secondary amine
may be used on a functional derivative of the acid, for
example a symmetrical or mixed anhydride.

A subject of the present invention is also a process for
preparing the products of formula (I"):

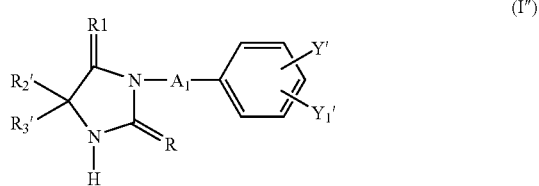

(I")

in which Y', Y1', A1, R, R1, R2' and R3' have the meanings
given above, characterized in that a product of formula (V):

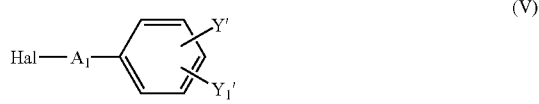

(V)

in which A1, Y1' and Y2' have the above meanings and Hal
is a halogen atom, is reacted with a product of formula (VI):

(VI)

in which R, R1, R2', R3' and X have the above meanings, the
reaction being performed in the presence of a catalyst and
optionally a solvent.

As regards the products of formula (V), the term "Hal"
preferably denotes a chlorine atom, but may also denote a
bromine or iodine atom.

A subject of the invention is, more specifically, a process
as defined above in which the catalyst is a metal in native or
oxidized form or a base.

The catalyst used may be a metal in native form, in metal
oxide form or in the form of metal salts. The catalyst may
also be a base. When the catalyst used is a metal, this metal
may be copper or nickel.

The metal salts may be a chloride or an acetate.

It may be noted that when A1 is single bond, a catalyst
may be used. When A1 is alkyl, it is then an alkylation,
which may be performed especially in the presence of a
reagent such as a base.

When the catalyst is a base, this base may be, for example,
sodium hydroxide or potassium hydroxide and, if desired,
dimethyl sulfoxide may be added to the reaction medium.

A subject of the invention is, more specifically, a process
as defined above in which the catalyst is chosen from
cuprous oxide, cupric oxide, copper in native form and a
base such as sodium hydroxide or potassium hydroxide.

The copper in native form used as catalyst is preferably in
the form of powder.

A subject of the invention is particularly a process as
defined above in which the catalyst is cuprous oxide.

The solvent used is preferably chosen from high-boiling
ethers such as, for example, phenyl oxide, diglyme, triglyme
and dimethyl sulfoxide, but may also be, for example, a
high-boiling oil such as paraffin or liquid petroleum jelly.

It may be noted that, especially when A1 is single bond,
in the reaction of a product of formula (V) with a product of
formula (VI) as defined above, palladium or a salt thereof as
described, for example, in the following articles, or a copper
salt with a ligand, for instance a 1,2-diaminocyclohexane
derivative, may also be used as catalyst: Buchwald S. L., J.
AM. CHEM. SOC., 2002, 6043 and Buchwald S. L., J. AM.
CHEM. SOC., 2001, 7727.

A subject of the invention is, more particularly, a process
as defined above, characterized in that the process is per-
formed in the presence of a solvent of ether type such as
phenyl ether, diglyme, triglyme, dimethyl sulfoxide, toluene
or dioxane.

A subject of the invention is, most particularly, a process
as defined above in which the solvent used is phenyl ether
or triglyme.

The process for preparing the desired product, defined
above, may be performed under pressure or at atmospheric
pressure, preferably at elevated temperature.

A subject of the invention is thus a process as defined
above, characterized in that the reaction is performed at a
temperature above 100° C. and preferably above 150° C.

A subject of the invention is, more specifically, a process
as defined above, characterized in that the reaction is per-
formed for more than 2 hours.

A subject of the invention is, very specifically, a process
as defined above, characterized in that the reaction is per-
formed in the presence of cuprous oxide, in triglyme, at a
temperature of greater than or equal to 200° C. and for more
than 3 hours.

The products that are the subject of the present invention
have advantageous pharmacological properties: it has been
found that they especially have inhibitory properties on
protein kinases.

Among these protein kinases, mention may be made
especially of IGF1R.

FAK may also be mentioned. AKT may also be men-
tioned.

Tests given in the experimental section below illustrate
the inhibitory activity of products of the present invention
with respect to such protein kinases.

These properties thus make the compound of formula I of the present invention usable as medicinal products for treating malignant tumors.

The compound of formula I may also be used in the veterinary field.

A subject of the invention is thus, as medicinal products, pharmaceutically acceptable compound of formula I.

A subject of the invention is, particularly, the use as medicinal products of the products whose names are below:
(S)-5-methyl-1-quinol-4-ylmethyl-3-(4-trifluoromethanesulfonylphenyl)imidazolidine-2,4-dione trifluoroacetate;
(S)-5-methyl-1-pyrid-4-ylmethyl-3-(4-trifluoromethanesulfonylphenyl)imidazolidine-2,4-dione trifluoroacetate;
(S)-5-methyl-1-quinol-4-ylmethyl-3-(4-trifluoromethylsulfanylphenyl)imidazolidine-2,4-dione trifluoroacetate;
5,5-dimethyl-1-quinol-4-ylmethyl-3-(4-trifluoromethanesulfonylphenyl)imidazolidine-2,4-dione trifluoroacetate;
(R)-5-methyl-1-quinol-4-ylmethyl-3-(4-trifluoromethanesulfonylphenyl)imidazolidine-2,4-dione trifluoroacetate;
(R)-5-methyl-1-quinol-4-ylmethyl-3-(4-trifluoromethylsulfanylphenyl)imidazolidine-2,4-dione trifluoroacetate;
(R)-5-methyl-1-pyrid-4-ylmethyl-3-(4-trifluoromethanesulfonylphenyl)imidazolidine-2,4-dione trifluoroacetate;
(R)-5-methyl-1-(3-methylpyrid-4-ylmethyl)-3-(4-trifluoromethanesulfonylphenyl)imidazolidine-2,4-dione trifluoroacetate;
(R)-4-methyl-3-quinol-4-ylmethyl-5-thioxo-1-(4-trifluoromethylsulfanylphenyl)imidazolidin-2-one trifluoroacetate;
(R)-5-isopropyl-1-quinol-4-ylmethyl-3-(4-trifluoromethylsulfanylphenyl)imidazolidine-2,4-dione trifluoroacetate;
(R)-5-isopropyl-1-quinol-4-ylmethyl-3-(4-trifluoromethanesulfonylphenyl)imidazolidine-2,4-dione trifluoroacetate;
(R)-5-(4-hydroxybenzyl)-1-quinol-4-ylmethyl-3-(4-trifluoromethanesulfonylphenyl)imidazolidine-2,4-dione trifluoroacetate;
(R)-5-(4-hydroxybenzyl)-1-pyrid-4-ylmethyl-3-(4-trifluoromethanesulfonylphenyl)imidazolidine-2,4-dione trifluoroacetate;
(R)-5-(1-hydroxyethyl)-1-quinol-4-ylmethyl-3-(4-trifluoromethanesulfonylphenyl)imidazolidine-2,4-dione trifluoroacetate;
4-quinol-4-ylmethyl-6-(4-trifluoromethylsulfanylphenyl)-4,6-diazaspiro[2.4]heptane-5,7-dione trifluoroacetate;
4-quinol-4-ylmethyl-6-(4-trifluoromethanesulfonylphenyl)-4,6-diazaspiro[2.4]heptane-5,7-dione trifluoroacetate;
4-pyrid-4-ylmethyl-6-(4-trifluoromethylsulfanylphenyl)-4,6-diazaspiro[2.4]heptane-5,7-dione trifluoroacetate;
4-pyrid-4-ylmethyl-6-(4-trifluoromethanesulfonylphenyl)-4,6-diazaspiro[2.4]heptane-5,7-dione trifluoroacetate;
(R)-1-(3-hydroxypyrid-4-ylmethyl)-5-methyl-3-(4-trifluoromethylsulfanylphenyl)imidazolidine-2,4-dione trifluoroacetate;
5,5-dimethyl-1-quinol-4-ylmethyl-3-(4-trifluoromethoxyphenyl)imidazolidine-2,4-dione trifluoroacetate;
5,5-dimethyl-1-quinol-4-ylmethyl-3-(4-trifluoromethylsulfanylphenyl)imidazolidine-2,4-dione trifluoroacetate;
5,5-dimethyl-1-(3-methylpyrid-4-ylmethyl)-3-(4-trifluoromethoxyphenyl)imidazolidine-2,4-dione trifluoroacetate;
5,5-dimethyl-1-(3-methylpyrid-4-ylmethyl)-3-(4-trifluoromethylsulfanylphenyl)imidazolidine-2,4-dione trifluoroacetate;
5,5-dimethyl-1-(3-methylpyrid-4-ylmethyl)-3-(4-trifluoromethanesulfonylphenyl)imidazolidine-2,4-dione trifluoroacetate;
1-(3-hydroxypyrid-4-ylmethyl)-5,5-dimethyl-3-(4-trifluoromethoxyphenyl)imidazolidine-2,4-dione trifluoroacetate;
1-(3-hydroxypyrid-4-ylmethyl)-5,5-dimethyl-3-(4-trifluoromethylsulfanylphenyl)imidazolidine-2,4-dione trifluoroacetate;
1-(3-hydroxypyrid-4-ylmethyl)-5,5-dimethyl-3-(4-trifluoromethanesulfonylphenyl)imidazolidine-2,4-dione trifluoroacetate;
4-quinol-4-ylmethyl-6-(4-trifluoromethoxyphenyl)-4,6-diazaspiro[2.4]heptane-5,7-dione trifluoroacetate;
4-(3-methylpyrid-4-ylmethyl)-6-(4-trifluoromethylsulfanylphenyl)-4,6-diazaspiro[2.4]heptane-5,7-dione trifluoroacetate;
4-(3-hydroxypyrid-4-ylmethyl)-6-(4-trifluoromethoxyphenyl)-4,6-diazaspiro[2.4]heptane-5,7-dione trifluoroacetate;
4-(3-hydroxypyrid-4-ylmethyl)-6-(4-trifluoromethylsulfanylphenyl)-4,6-diazaspiro[2.4]heptane-5,7-dione trifluoroacetate;
4-(3-hydroxypyrid-4-ylmethyl)-6-(4-trifluoromethanesulfonylphenyl)-4,6-diazaspiro[2.4]heptane-5,7-dione trifluoroacetate, said compound of formula I being in any possible racemic, enantiomeric or diastereoisomeric isomer form, and also the addition salts of said compound of formula I with pharmaceutically acceptable mineral and organic acids or with pharmaceutically acceptable mineral and organic bases.

A subject of the invention is particularly the use, as medicinal products, of the products whose names are given below:
{4-[5,5-dimethyl-2,4-dioxo-3-(4-trifluoromethylsulfanylphenyl)imidazolidin-1-ylmethyl]pyrid-2-yl}cyclopropanecarboxamide trifluoroacetate;
5,5-dimethyl-1-[2-(pyrid-2-ylamino)pyrid-4-ylmethyl]-3-(4-trifluoromethylsulfanylphenyl)imidazolidine-2,4-dione; compound with trifluoroacetic acid;
N-{4-[5,5-dimethyl-2,4-dioxo-3-(4-trifluoromethylsulfanylphenyl)imidazolidin-1-ylmethyl]pyrid-2-yl}isobutyramide; compound with trifluoroacetic acid;
N-{4-[5,5-dimethyl-2,4-dioxo-3-(4-trifluoromethylsulfanylphenyl)imidazolidin-1-ylmethyl]pyrid-2-yl}propionamide; compound with trifluoroacetic acid;
1-(2-aminopyrid-4-ylmethyl)-5,5-dimethyl-3-(4-trifluoromethylsulfanylphenyl)-imidazolidine-2,4-dione hydrochloride;
{4-[5,5-dimethyl-2,4-dioxo-3-(4-trifluoromethylsulfanylphenyl)imidazolidin-1-ylmethyl]pyrid-2-yl}pyridine-2-carboxamide trifluoroacetate;
N-{4-[5,5-dimethyl-2,4-dioxo-3-(4-trifluoromethylsulfanylphenyl)imidazolidin-1-ylmethyl]pyrid-2-yl}-3-piperid-1-ylpropionamide trifluoroacetate;
N-{4-[5,5-dimethyl-2,4-dioxo-3-(4-trifluoromethylsulfanylphenyl)imidazolidin-1-ylmethyl]pyrid-2-yl}-3-[4-(2-hydroxyethyl)piperazin-1-yl]propionamide trifluoroacetate;
N-{4-[5,5-dimethyl-2,4-dioxo-3-(4-trifluoromethylsulfanylphenyl)imidazolidin-1-ylmethyl]pyrid-2-yl}-3-morpholin-4-ylpropionamide trifluoroacetate;
N-{4-[5,5-dimethyl-2,4-dioxo-3-(4-trifluoromethylsulfanylphenyl)imidazolidin-1-ylmethyl]pyrid-2-yl}-3-pyrrolidin-1-ylpropionamide trifluoroacetate;
N-{4-[5,5-dimethyl-2,4-dioxo-3-(4-trifluoromethylsulfanylphenyl)imidazolidin-1-ylmethyl]pyrid-2-yl}-3-(4-methylpiperazin-1-yl)propionamide trifluoroacetate;

1-{4-[5,5-dimethyl-2,4-dioxo-3-(4-trifluoromethylsulfanylphenyl)imidazolidin-1-ylmethyl]pyrid-2-yl}-3-phenylurea;

1-[2-(6-ethylpyrid-2-ylamino)pyrid-4-ylmethyl]-5,5-dimethyl-3-(4-trifluoromethylsulfanylphenyl)imidazolidine-2,4-dione;

5,5-dimethyl-1-[2-(4-methylpyrid-2-ylamino)pyridin-4-ylmethyl]-3-(4-trifluoromethylsulfanylphenyl)imidazolidine-2,4-dione;

5,5-dimethyl-1-[2-(6-methylpyrid-2-ylamino)pyridin-4-ylmethyl]-3-(4-trifluoromethylsulfanylphenyl)imidazolidine-2,4-dione;

1-[2-(4,6-dimethylpyrid-2-ylamino)pyrid-4-ylmethyl]-5,5-dimethyl-3-(4-trifluoromethylsulfanylphenyl)imidazolidine-2,4-dione;

1-[2-(3,5-dichloropyrid-2-ylamino)pyrid-4-ylmethyl]-5,5-dimethyl-3-(4-trifluoromethylsulfanylphenyl)imidazolidine-2,4-dione;

5,5-dimethyl-1-[2-(pyrid-4-ylamino)pyrid-4-ylmethyl]-3-(4-trifluoromethylsulfanylphenyl)imidazolidine-2,4-dione;

5,5-dimethyl-1-[2-(pyrid-3-ylamino)pyrid-4-ylmethyl]-3-(4-trifluoromethylsulfanylphenyl)-imidazolidine-2,4-dione;

N-{4-[5,5-dimethyl-2,4-dioxo-3-(4-trifluoromethylsulfanylphenyl)imidazolidin-1-ylmethyl]pyrid-2-yl}-3-(2-oxoazepan-1-yl)propionamide;

3-(benzylmethylamino)-N-{4-[5,5-dimethyl-2,4-di-oxo-3-(4-trifluoromethylsulfanylphenyl)imidazolidin-1-ylmethyl]pyrid-2-yl} propionamide;

4,5-diacetoxy-6-acetoxymethyl-2-(3-{4-[5,5-dimethyl-2,4-dioxo-3-(4-trifluoromethylsulfanylphenyl)imidazolidin-1-ylmethyl]pyrid-2-yl}thioureidoacetic acid;

5,5-dimethyl-1-[2-(5-methylpyrid-2-ylamino)pyridin-4-ylmethyl]-3-(4-trifluoromethylsulfanylphenyl)imidazolidine-2,4-dione;

N-{4-[5,5-dimethyl-2,4-dioxo-3-(4-trifluoromethylsulfanylphenyl)imidazolidin-1-ylmethyl]pyrid-2-yl}-3,5-dimethoxybenzamide trifluoroacetate;

5,5-dimethyl-1-[2-(pyrazin-2-ylamino)pyrid-4-ylmethyl]-3-(4-trifluoromethylsulfanylphenyl)imidazolidine-2,4-dione trifluoroacetate;

N-{4-[5,5-dimethyl-2,4-dioxo-3-(4-trifluoromethylsulfanylphenyl)imidazolidin-1-ylmethyl]pyrid-2-yl}-3-(3-methylpiperid-1-yl)propionamide trifluoroacetate;

N-{4-[5,5-dimethyl-2,4-dioxo-3-(4-trifluoromethylsulfanylphenyl)imidazolidin-1-ylmethyl]pyrid-2-yl}-3-(3,5-dimethylpiperid-1-yl)propionamide trifluoroacetate;

N-{4-[5,5-dimethyl-2,4-dioxo-3-(4-trifluoromethylsulfanylphenyl)imidazolidin-1-ylmethyl]pyrid-2-yl}-3-methoxybenzamide trifluoroacetate;

{4-[5,5-dimethyl-2,4-dioxo-3-(4-trifluoromethylsulfanylphenyl)imidazolidin-1-ylmethyl]pyrid-2-yl}pyrazine-2-carboxamide trifluoroacetate;

{4-[5,5-dimethyl-2,4-dioxo-3-(4-trifluoromethylsulfanylphenyl)imidazolidin-1-ylmethyl]pyrid-2-yl}thiophene-2-carboxamide trifluoroacetate;

N-{4-[5,5-dimethyl-2,4-dioxo-3-(4-trifluoromethylsulfanylphenyl)imidazolidin-1-ylmethyl]pyrid-2-yl}-4-methylbenzamide; compound with trifluoroacetic acid;

1-isoquinolin-5-yl-5,5-dimethyl-3-(4-trifluoro-methylsulfanylphenyl)imidazolidine-2,4-dione;

3-(4-acetylpiperazin-1-yl)-N-{4-[5,5-dimethyl-2,4-dioxo-3-(4-trifluoromethylsulfanylphenyl)imidazolidin-1-ylmethyl]pyrid-2-yl} propionamide;

3-[4-(2-diethylaminoethyl)piperazin-1-yl]-N-{4-[5,5-dimethyl-2,4-dioxo-3-(4-trifluoromethylsulfanylphenyl)imidazolidin-1-ylmethyl]pyrid-2-yl}propionamide;

N-{4-[5,5-dimethyl-2,4-dioxo-3-(4-trifluoromethylsulfanylphenyl)imidazolidin-1-ylmethyl]pyrid-2-yl}-3-(2,6-dimethylmorpholin-4-yl)propionamide;

N-{4-[5,5-dimethyl-2,4-dioxo-3-(4-trifluoromethylsulfanylphenyl)imidazolidin-1-ylmethyl]pyrid-2-yl}-3-(4-pyrrolidin-1-ylpiperid-1-yl)propionamide;

N-{4-[5,5-dimethyl-2,4-dioxo-3-(4-trifluoromethylsulfanylphenyl)imidazolidin-1-ylmethyl]pyrid-2-yl}-2-(4-pyrrolidin-1-ylpiperid-1-yl)acetamide;

5,5-dimethyl-1-[2-(4-methylpyrid-3-ylamino)pyridin-4-ylmethyl]-3-(4-trifluoromethylsulfanylphenyl)imidazolidine-2,4-dione;

5,5-dimethyl-1-[2-(6-morpholin-4-ylpyrid-3-ylamino)pyrid-4-ylmethyl]-3-(4-trifluoromethylsulfanylphenyl)imidazolidine-2,4-dione;

1-[2-(2,6-dimethylpyrid-3-ylamino)pyrid-4-ylmethyl]-5,5-dimethyl-3-(4-trifluoromethylsulfanylphenyl)imidazolidine-2,4-dione;

methyl 5-{4-[5,5-dimethyl-2,4-dioxo-3-(4-trifluoromethylsulfanylphenyl)imidazolidin-1-ylmethyl]pyrid-2-ylamino}pyridine-2-carboxylate;

1-[2-(2,6-dimethoxypyrid-3-ylamino)pyrid-4-ylmethyl]-5,5-dimethyl-3-(4-trifluoromethylsulfanylphenyl)imidazolidine-2,4-dione;

1-[2-(6-fluoropyrid-3-ylamino)pyrid-4-ylmethyl]-5,5-dimethyl-3-(4-trifluoromethylsulfanylphenyl)imidazolidine-2,4-dione;

1-[2-(6-methoxypyrid-3-ylamino)pyrid-4-ylmethyl]-5,5-dimethyl-3-(4-trifluoromethylsulfanylphenyl)imidazolidine-2,4-dione, said compound of formula I being in any possible racemic, enantiomeric or diastereoisomeric isomer form, and also the addition salts of said compound of formula I with pharmaceutically acceptable mineral and organic acids or with pharmaceutically acceptable mineral and organic bases.

The products may be administered via the parenteral, oral, perlingual, rectal or topical route. A subject of the invention is also pharmaceutical compositions, characterized in that they contain, as active principle, at least one of the medicinal compound of formula I.

These compositions may be in the form of injectable solutions or suspensions, tablets, coated tablets, capsules, syrups, suppositories, creams, ointments and lotions. These pharmaceutical forms are prepared according to the usual methods. The active principle may be incorporated into excipients usually used in these compositions, such as aqueous or nonaqueous vehicles, talc, gum arabic, lactose, starch, magnesium stearate, cocoa butter, fatty substances of animal or plant origin, paraffin derivatives, glycols, various wetting, dispersing or emulsifying agents, and preserving agents.

The usual dose, which varies according to the individual treated and the complaint under consideration, may be, for example, from 10 mg to 500 mg per day orally in man.

The present invention thus relates to the use of compound of formula I as defined above or of pharmaceutically acceptable salts of said compound of formula I for the preparation of medicinal products for inhibiting the activity of protein kinases and especially of a protein kinase.

The present invention thus relates to the use of compound of formula I as defined above or of pharmaceutically acceptable salts of said compound of formula I in which the protein kinase is a protein tyrosine kinase.

The present invention thus relates to the use of compound of formula I as defined above or of pharmaceutically acceptable salts of said compound of formula I in which the protein kinase is chosen from the following group: EGFR, Fak, FLK-1, FGFR1, FGFR2, FGFR3, FGFR4, FGFR5, flt-1, IGF-1R, KDR, PDGFR, tie2, VEGFR, AKT, Raf.

The present invention thus relates particularly to the use of compound of formula I as defined above or of pharmaceutically acceptable salts of said compound of formula I in which the protein kinase is IGF1R.

The present invention also relates to the use of compound of formula I as defined above or of pharmaceutically acceptable salts of said compound of formula I in which the protein kinase is FAK.

The present invention also relates to the use of compound of formula I as defined above or of pharmaceutically acceptable salts of said compound of formula I in which the protein kinase is AKT.

The present invention also relates to the use of compound of formula I as defined above or of pharmaceutically acceptable salts of said compound of formula I in which the protein kinase is in a cell culture, and also to this use in a mammal.

The present invention thus relates to the use of compound of formula I as defined above or of pharmaceutically acceptable salts of said compound of formula I for the preparation of a medicinal product for preventing or treating a disease characterized by deregulation of the activity of a protein kinase and especially such a disease in a mammal.

The present invention relates to the use of compound of formula I as defined above or of pharmaceutically acceptable salts of said compound of formula I for the preparation of a medicinal product for preventing or treating a disease belonging to the following group: disorders of blood vessel proliferation, fibrotic disorders, disorders of mesangial cell proliferation, metabolic disorders, allergies, asthma, thrombosis, diseases of the nervous system, retinopathy, psoriasis, rheumatoid arthritis, diabetes, muscle degeneration, oncology diseases and cancer.

The present invention thus relates to the use of compound of formula I as defined above or of pharmaceutically acceptable salts of said compound of formula I for the preparation of a medicinal product for treating oncology diseases.

The present invention relates particularly to the use of compound of formula I as defined above or of pharmaceutically acceptable salts of said compound of formula I for the preparation of a medicinal product for treating cancers.

Among these cancers, the present invention is most particularly of interest in the treatment of solid tumors and the treatment of cancers that are resistant to cytotoxic agents.

Among these cancers, the present invention relates most particularly to the treatment of breast cancer, stomach cancer, cancer of the colon, lung cancer, cancer of the ovaries, cancer of the uterus, brain cancer, cancer of the kidney, cancer of the larynx, cancer of the lymphatic system, cancer of the thyroid, cancer of the urogenital tract, cancer of the tract including the seminal vesicle and prostate, bone cancer, cancer of the pancreas and melanomas.

The present invention is even more particularly of interest in treating breast cancer, cancer of the colon and lung cancer.

The protein kinase IGF1-R (Insulin Growth Factor-1 Receptor) is particularly indicated.

The protein kinase FAK is also indicated.

The protein kinase AKT is also indicated.

The present invention thus relates particularly to novel inhibitors of the IGF-1R receptor that may be used for oncology treatments.

The present invention also relates to novel FAK receptor inhibitors that may be used for oncology treatments.

The present invention also relates to novel AKT receptor inhibitors that may be used for oncology treatments.

Among the kinases for which a modulation of the activity is desired, FAK (Focal Adhesion Kinase) is also a preferred kinase.

The present invention also relates to the use of compound of formula I as defined above or of pharmaceutically acceptable salts of said compound of formula I for the preparation of a medicinal product for cancer chemotherapy.

As medicinal products according to the present invention for cancer chemotherapy, the compound of formula I according to the present invention may be used alone or in combination with chemotherapy or radiotherapy or in combination with other therapeutic agents.

The present invention thus relates especially to the pharmaceutical compositions as defined above, also containing active principles of other chemotherapy medicinal products for combating cancer.

Such therapeutic agents may be commonly used antitumor agents.

As examples of known inhibitors of protein kinases, mention may be made especially of butyrolactone, flavopiridol, 2-(2-hydroxyethylamino)-6-benzylamino-9-methylpurine, olomucine, Glivec and Iressa.

The compound of formula I according to the present invention may thus also be advantageously used in combination with antiproliferative agents: as examples of such antiproliferative agents, but without, however, being limited to this list, mention may be made of aromatase inhibitors, antiestrogens, the topoisomerase I inhibitors, the topoisomerase II inhibitors, microtubule-active agents, alkylating agents, histone deacetylase inhibitors, farnesyl transferase inhibitors, COX-2 inhibitors, MMP inhibitors, mTOR inhibitors, antineoplastic antimetabolites, platinum compounds, compounds that reduce the activity of protein kinases and also anti-angiogenic compounds, gonadorelin agonists, antiandrogens, bengamides, biphosphonates and trastuzumab.

Examples that may thus be mentioned include anti-microtubule agents, for instance taxoids, vinca alkaloids, alkylating agents such as cyclophosphamide, DNA-intercalating agents, for instance cis-platinum, agents that are interactive on topoisomerase, for instance camptothecin and derivatives, anthracyclines, for instance adriamycin, antimetabolites, for instance 5-fluorouracil and derivatives, and the like.

The present invention thus relates to compound of formula I as protein kinase inhibitors, said compound of formula I being in any possible racemic, enantiomeric or diastereoisomeric isomer form, and also the addition salts of said compound of formula I with pharmaceutically acceptable mineral and organic acids or with pharmaceutically acceptable mineral and organic bases, and also the prodrugs thereof.

The present invention relates particularly to compound of formula I as defined above as IGF1R inhibitors.

The present invention also relates to compound of formula I as defined above as FAK inhibitors.

The present invention also relates to compound of formula I as defined above as AKT inhibitors.

The present invention relates more particularly to the products of formula (IA) as defined above as IGF1R inhibitors.

The compound of formula I according to the present invention may be prepared by application or adaptation of known methods and especially of the methods described in the literature such as, for example, those described by R. C. Larock in: Comprehensive Organic Transformations, VCH publishers, 1989.

In the reactions described below, it may be necessary to protect reactive functional groups such as, for example, hydroxyl, amino, imino, thio or carboxyl groups, when these groups are desired in the final product but when their participation is not desired in the reactions for synthesizing the compound of formula I. Conventional protecting groups may be used in accordance with the usual standard practices, for instance those described, for example, by T. W. Greene and P. G. M. Wuts in "Protective Groups in Organic Chemistry" John Wiley and Sons, 1991.

The products of formula (II) used at the start of the invention may be obtained by the action of phosgene when X is an oxygen atom, or of thiophosgene when X is a sulfur atom, on the corresponding amine of formula (A), i.e., the aminophenyl derivative bearing the substituents Y and Y1' as defined above.

A product of this type is also described in French patent 2 329 276.

The products of formula (III) or (III') are known or may be prepared from the corresponding cyanohydrin according to the process described in the publication: J. Am. Chem. Soc. (1953), 75, 4841.

The products of formula (III) may be obtained by the action of a product of formula Y2-B2-A2-Hal on 2-cyano-2-aminopropane under the conditions stated above for the action of Y2-B2-A2-Hal on the products of formula (IV). An example of a preparation of this type is described in the reference:
Jilek et al. Collect. Czech. Chem. Comm. 54(8) 2248 (1989).

The products of formula (IV') are described in French patent 2 329 276.

The starting materials of formulae (V) and (VI), on which a process that is the subject of the invention is performed, to obtain the compound of formula I, are known and commercially available or may be prepared according to methods known to those skilled in the art.

The preparation of products of formula (VI) is described especially in the following publications:
Zhur. Préklad. Khim. 28, 969-75 (1955) (CA 50, 4881a, 1956);
Tetrahedron 43, 1753 (1987);
J. Org. Chem. 52, 2407 (1987);
Zh. Org. Khim. 21, 2006 (1985);
J. Fluor. Chem. 17, 345 (1981)
or in:
German patent DRP 637 318 (1935);
European patent EP 0 130 875;
Japanese patent JP 81 121 524.

The products of formula (VI) that are hydantoin derivatives are widely used and cited in the literature, for instance in the following articles:
J. Pharm. Pharmacol., 67, Vol. 19(4), p. 209-16 (1967);
Khim. Farm. Zh., 67, Vol. 1 (5) p. 51-2;
German patent 2 217 914;
European patent 0 091 596;
J. Chem. Soc. Perkin. Trans. 1, p. 219-21 (1974).

The compound of formula I of the present patent application as defined above, for which p is 0 and which thus constitute hydantoin derivatives, may be synthesized according to the process indicated above and especially according to the general scheme below which describes this synthesis on a solid support. The protocol that follows this scheme gives the operating conditions for such a synthesis of the compound of formula I of the present patent application on a solid support.

The experimental section below more particularly gives an illustration of such a synthesis on a solid support according to the above protocol with the preparation of Examples 1 to 56 of the present patent application.

Such a synthesis may be performed according to the general protocol below. Rink resin, protected with an Fmoc group, is deprotected with a 20% solution of piperidine in DMF. The resulting amine resin is coupled with an amino acid protected with an Fmoc group, in the presence of diisopropylaminecarbodiimide (DIC) and hydroxybenzotriazole (HOBt). The supported N-Fmoc amino acid is then deprotected with a 20% solution of piperidine in DMF. The free amine is reacted with an aldehyde dissolved in a 50/50 mixture of THF and triethyl orthoformate (TEOF) to give a Schiff's base, which is reduced with sodium cyanoborohydride. The resulting amine is coupled with an isocyanate or an isothiocyanate to give the corresponding urea or thiourea. When the isocyanate is not commercially available, it may be prepared from the corresponding amine by reaction with ⅓ equivalent of triphosgene in the presence of 2 equivalents of pyridine. The product is then cleaved with a 95% trifluoroacetic acid/water mixture. The urea thus released cyclizes to give the expected hydantoinine. In certain cases, the cleavage solution must be heated to 80° C. to obtain complete cyclization.

The compound of formula I of the present patent application as defined above, for which p is 1 and which thus constitute dihydrouracil derivatives, may be synthesized according to the process indicated above and especially according to the general scheme below which describes this synthesis on a solid support. The protocol that follows this scheme gives the operating conditions for such a synthesis of the compound of formula I of the present patent application on a solid support.

The experimental section below more particularly gives an illustration of such a synthesis on a solid support according to the above protocol with the preparation of Example 5 of the present patent application.

For the synthesis of the dihydrouracils on a solid support, the protocol that follows may be used.

Wang polystyrene resin (1.7 mmol/g) is used, for example, which resin is treated with a mixture of β-amino acid, 2,6-dichlorobenzoyl chloride and pyridine in DMF. After washing, the resin is treated with a 10% solution of piperidine in DMF. The resulting free amine is reacted with an aldehyde in a mixture of THF/trimethyl orthoformate (TMOF). The resulting Schiff's base is reduced with sodium cyanoborohydride in a mixture of methanol, THF and acetic acid. The secondary amine obtained is acylated with phosgene and the resulting carbamoyl chloride is treated with a primary amine to give the corresponding urea.

Cyclization to the dihydrouracil and cleavage of the final product are performed by treating with a strong base such as diazabicycloundecene (DBU).

The compound of formula I of the present patent application may thus be synthesized on a solid support as described above or in liquid phase according to the process indicated below: the experimental section of the present patent application gives an illustration of such a liquid-phase synthesis with the preparation of Examples 57 to 62.

For this liquid-phase synthetic process, two routes A and B may be performed, each involving two steps.

Route A:

step a: the alkylation of the amino ester may be performed by reductive amination with an aromatic or heterocyclic aldehyde according to the general process described in Advanced Organic Reaction, March, third edition, page 798-800. In particular, the formation of the Schiff's base (intermediate) may be performed using an amino ester optionally in salt form, an aldehyde and optionally a dehydrating agent (for example magnesium sulfate) in a solvent, for instance dichloromethane or dichloroethane, at a temperature of between 0° C. and the reflux point of the solvent. The imine formed may be isolated. The imine formed is reduced with a metal hydride, for instance sodium borohydride, in a solvent, for instance an alcohol (for example ethanol or methanol), at a temperature of between 0° C. and the reflux point of the solvent.

step b: the amino ester obtained is coupled with an isocyanate in a solvent, for instance THF or dichloromethane, with or without the presence of a base (for example triethylamine) or an acid (for example trifluoroacetic acid), at a temperature of between 0° C. and the reflux point of the solvent. When the isocyanates are not commercially available, they are prepared from the corresponding amines and triphosgene or diphosgene or phosgene in the presence of a base (for example pyridine or triethylamine) according to the general procedure described in Advanced Organic Reaction, March, third edition, page 370.

Route B:

step a: the formation of the isocyanate may be performed by coupling an aromatic or heterocyclic amine with diphosgene in the presence of activated plant charcoal, in a solvent, for instance toluene, at a temperature of between −40° C. and the reflux point of the solvent. The isocyanate formed is not isolated, and may react with the amino ester or its salt in the same solvent in the presence of a base, for instance triethylamine, at a temperature of between 0° C. and the reflux point of the solvent, to give the 3-arylimidazolidine-2,4-dione derivative.

step b: the coupling of this derivative with an alkyl halide is performed in the presence of a base, for instance potassium tert-butoxide or sodium hydride, in a solvent, for instance THF or DMF, at a temperature of between 0° C. and the reflux point of the solvent.

The compound of formula I of the present patent application which constitute Examples 201 to 207 of the present patent application were prepared as indicated below in the experimental section and as indicated in the following schemes: in these schemes, Example I is Example 201, Example II is Example 202, Example III is Example 203, Example IV is Example 204, Example V is Example 205, Example VI is Example 206 and Example VII is Example 207.

EXAMPLES I AND II

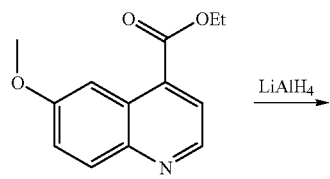

EXAMPLES III AND IV

-continued
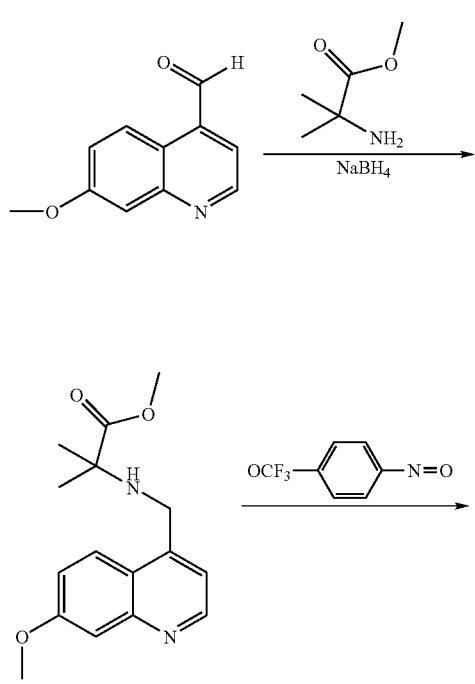
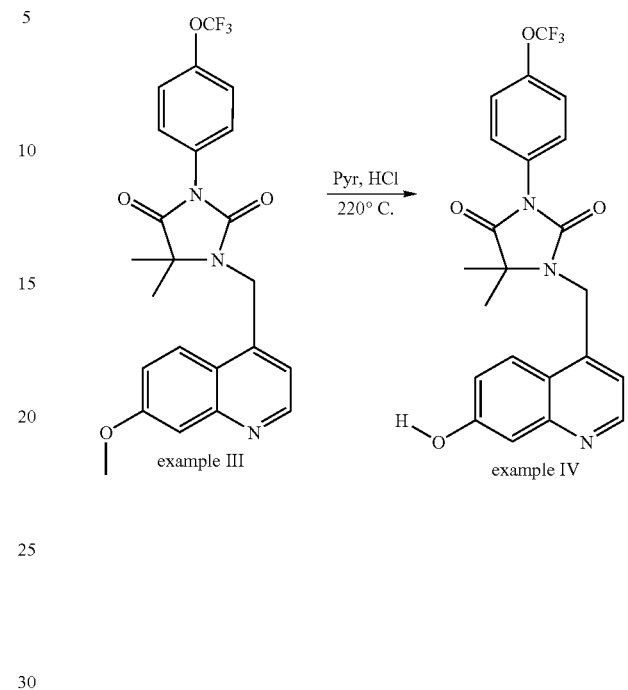
example III
example IV
EXAMPLES V, VI AND VII
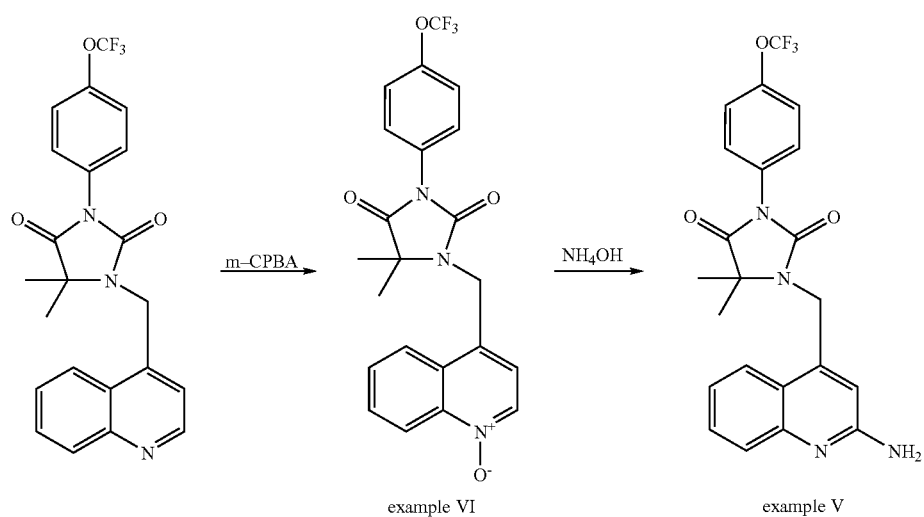
example VI
example V

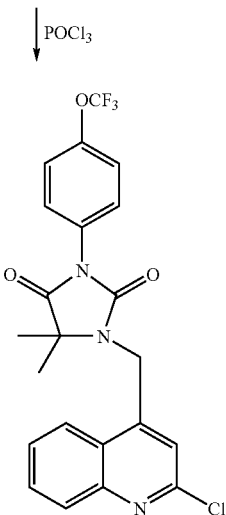
example VII
The synthesis of the compound of formula I of the present patent application which constitute the products of Examples 208 to 243 were performed using route B. The alkyl halide may be prepared from the corresponding carboxylic acids.
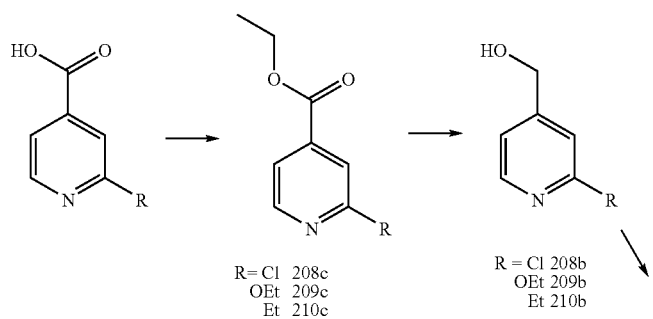
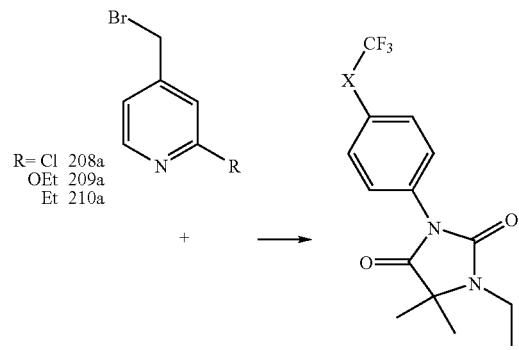

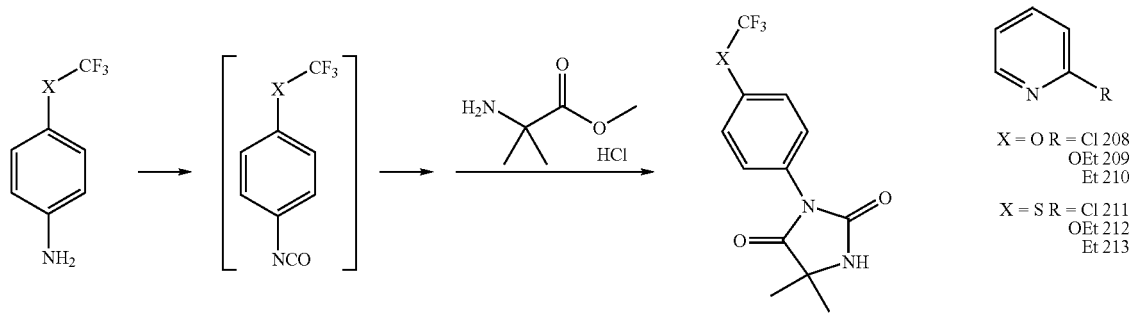

The ethyl carboxylates were prepared by esterification of the carboxylic acids in ethanol in the presence of sulfuric acid, adopting the conditions described in Synthesis 2000, 1138.

The reduction of the ethyl carboxylates in alcohol was performed in ethanol in the presence of sodium borohydride, adopting the conditions described in Synthesis 2000, 1665.

The conversion of the alcohols thus obtained into alkyl halides was performed using dibromotriphenylphosphorane as halogenating agent, adopting the conditions described in J. Heterocyclic Chem., 30, 631 (1993).

The alkyl halides may also be prepared by free-radical bromination of the corresponding methylenes in the presence of N-bromosuccinimide and benzoyl peroxide in carbon tetrachloride, adopting the conditions described in J. Heterocyclic Chem., 30, 631 (1993).

Thus, we functionalized the pyridine nucleus in position −2 with a bromine or fluorine atom or with a nitrile group.

The latter compound will also allow us to prepare various carbonyl compounds.

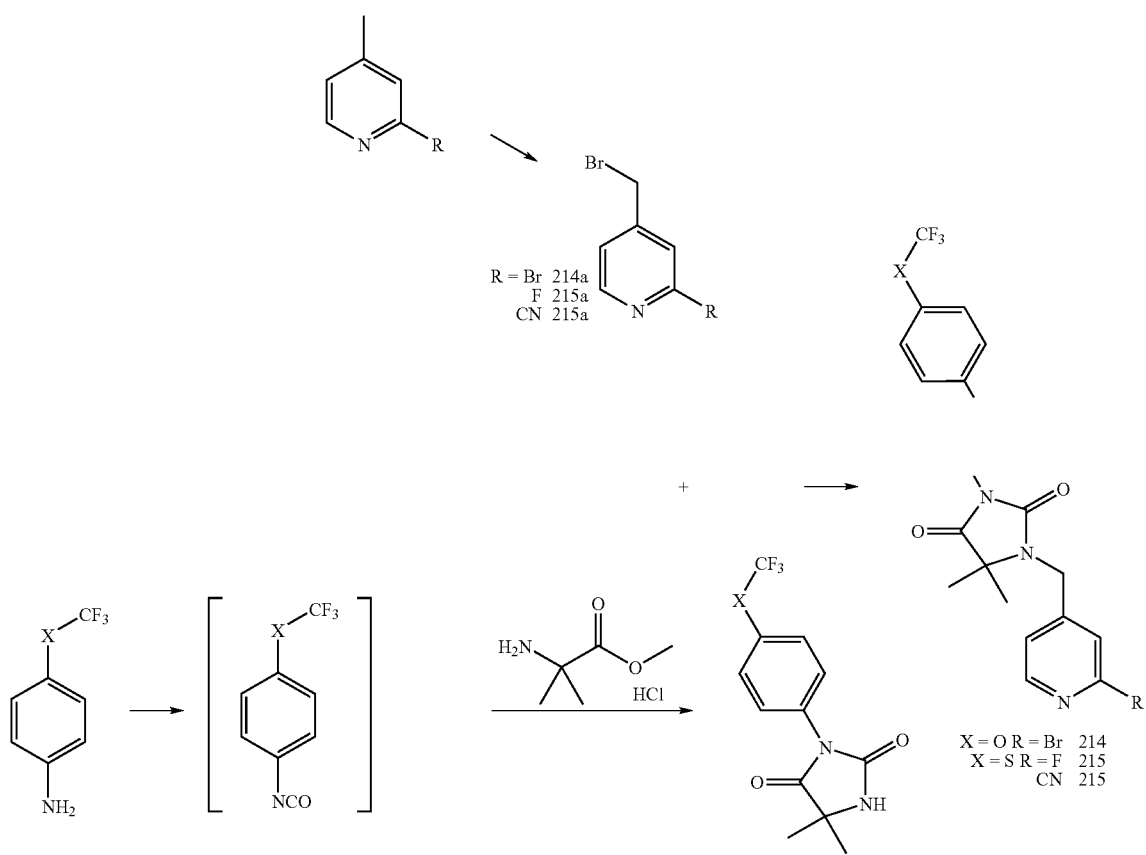

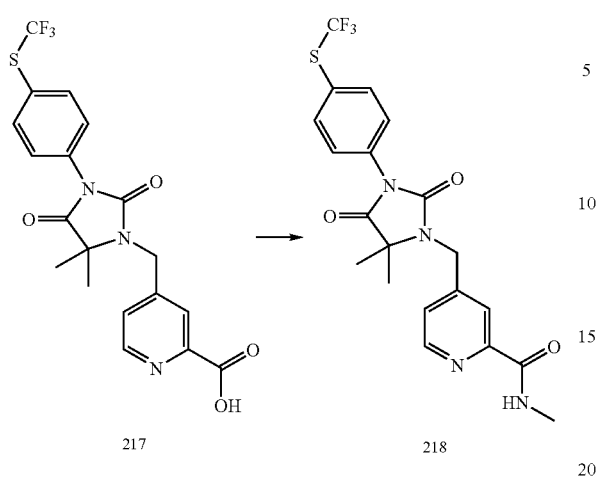

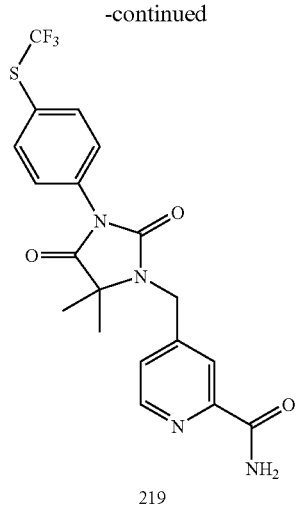

Acidic hydrolysis of the nitrile in the presence of sulfuric acid, adopting the conditions described in J. Med. Chem. 1991, 34, 281-290, led to the carboxamide in dimeric form. Hydrolysis of the nitrile under milder conditions allowed the expected carboxamide to be obtained.

Acidic hydrolysis of the nitrile in the presence of 5N hydrochloric acid, adopting the conditions described in J. Heterocyclic Chem., 30, 631 (1993), gave the corresponding carboxylic acid.

The amide could be obtained from the carboxylic acid using 1-(3-dimethylaminopropyl)-3-ethylcarbodiimide hydrochloride as coupling agent in dichloromethane, adopting the conditions described in J. Am. Chem. Soc., 95, 875, (1973). Various amino analogs were obtained by nucleophilic substitution of the chloro intermediate with amines under irradiation in a microwave oven, inspired by the conditions described in Tetrahedron 2002, 58, 1125.

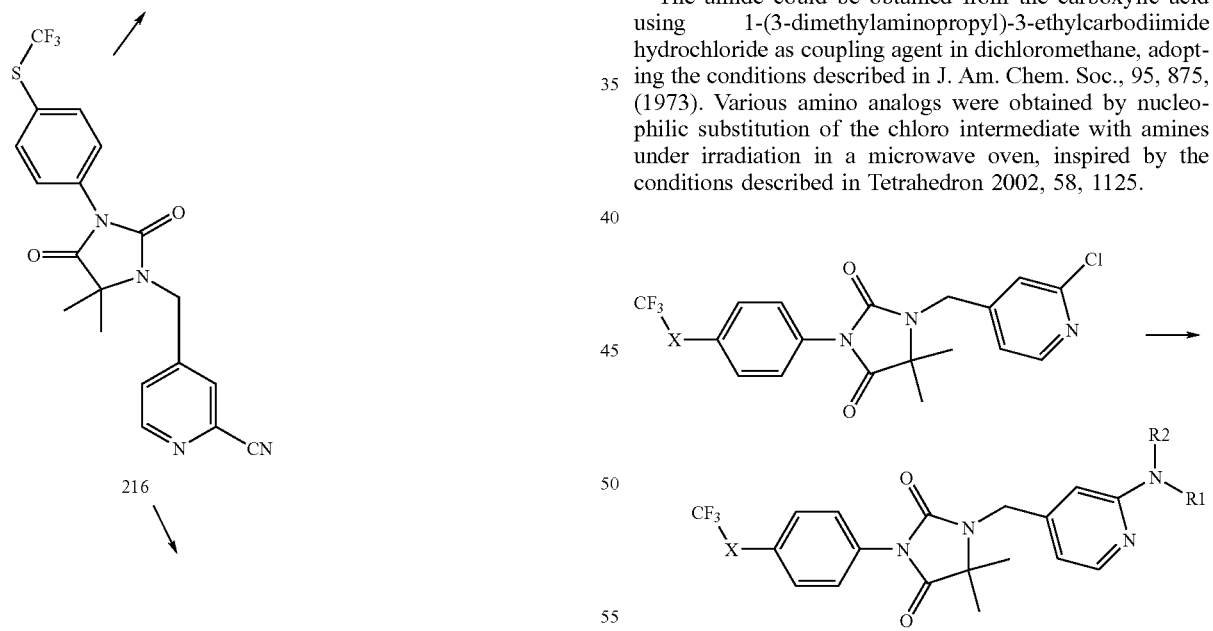

-continued

| X | NR1R2 | | NR1R2 | | NR1R2 | |
|---|---|---|---|---|---|---|
| S | morpholine | 221 | isopropylamine | 225 | piperazine | 229 |
| | dimethylamine | 222 | piperidine | 226 | ethylamine | 230 |
| | methylamine | 223 | N-methylpiperazine | 227 | benzylamine | 231 |
| | cyclohexylamine | 224 | aniline | 228 | 4-methoxybenzylamine | 232 |

The amino analog was obtained by deprotection of the p-methoxybenzylamine group in the presence of trifluoroacetic acid, inspired by the conditions described in J. Chem. Soc., Perkin Trans. 1, 2002, 428-433.

This amino derivative allowed access to other chemical functions, for instance the amide function, the carbamate function or the sulfonamide function.

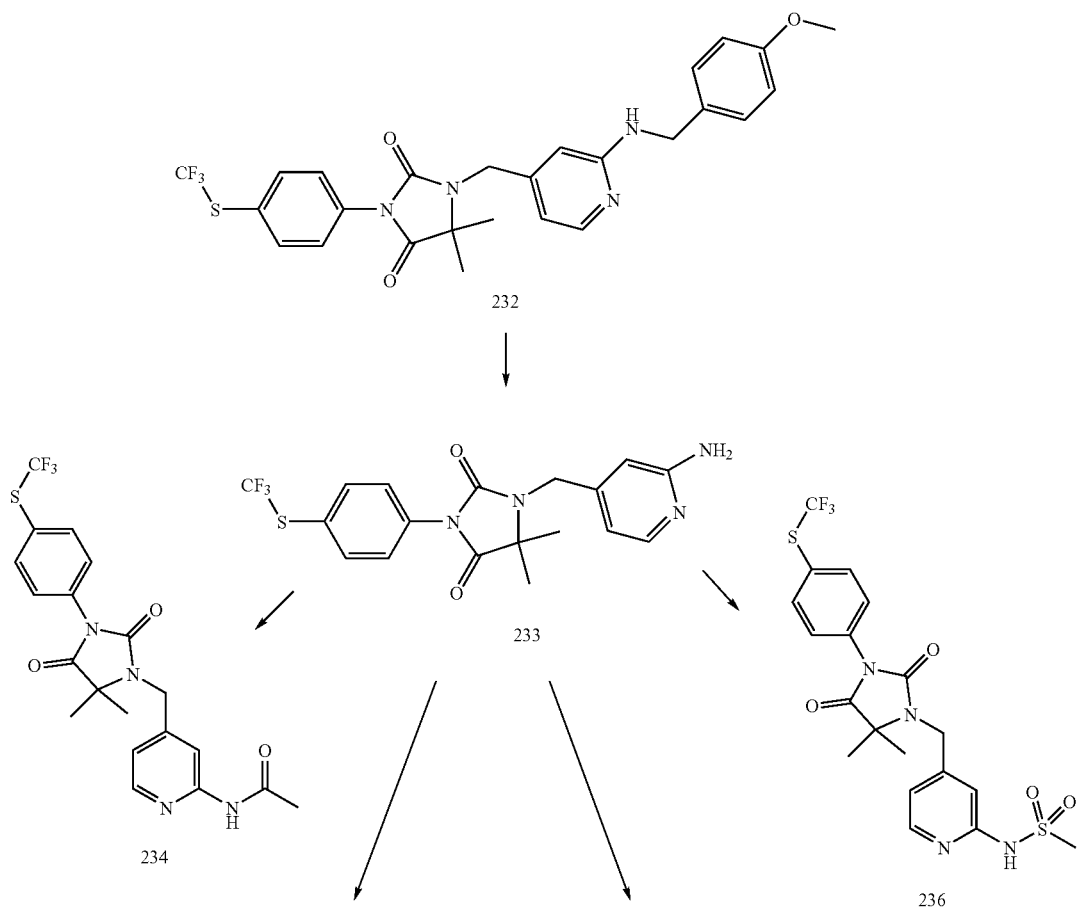

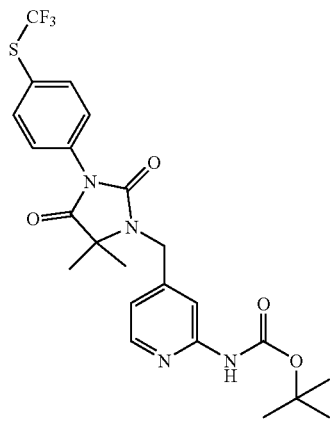
235

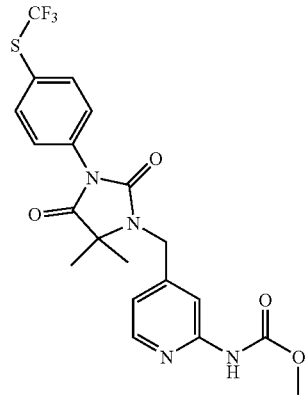
237

The acetamido derivative was obtained by acylation of the amino derivative in the presence of acetic anhydride, inspired by the conditions described in Tetrahedron Lett. 2002, 43, 3121. We also prepared the methyl and tert-butyl carbamates inspired by the conditions described in J. Heterocyclic Chem., 22, 313 (1985) and in J. Org. Chem. 2002, 67, 4965. The amino derivative was also sulfonylated with mesyl chloride, inspired by the conditions described in J. Med. Chem., 1985, 28, 824.

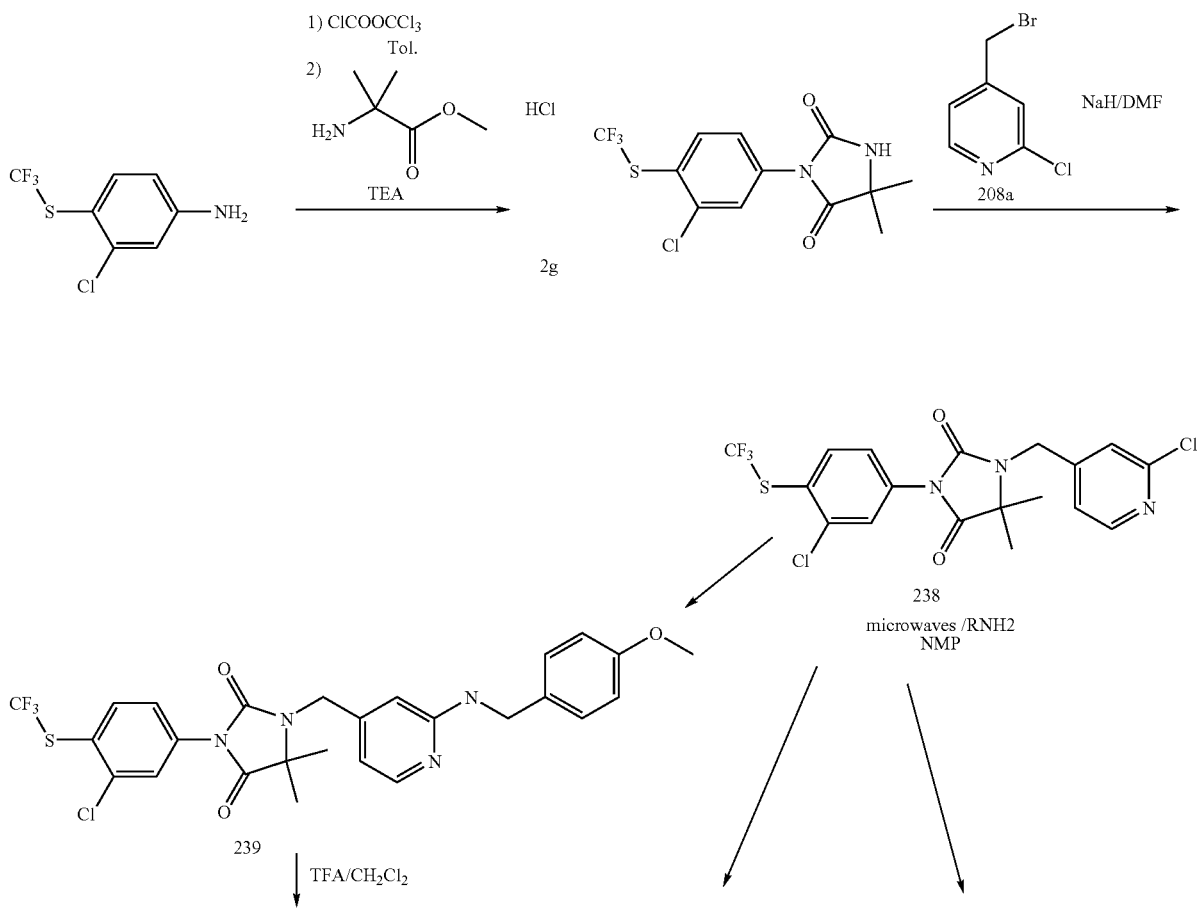

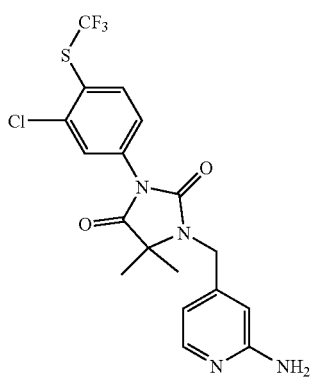
242

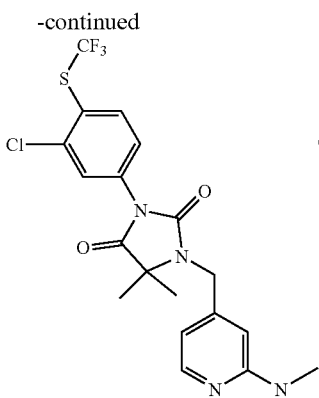
241

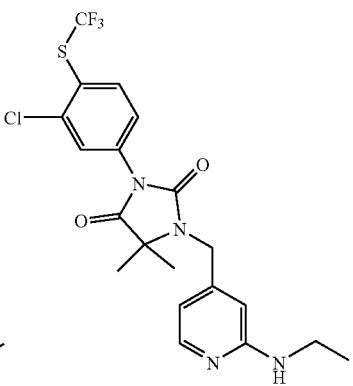
240

The above conditions were also used for the synthesis of the compounds containing a disubstituted phenyl group.

The hydantoin containing a pyridine nucleus disubstituted in position –2.6 with a bromine atom was prepared using the above conditions, starting with 2,6-dibromo-4-(hydroxymethyl)pyridine described in Synthesis 2000, 1665.

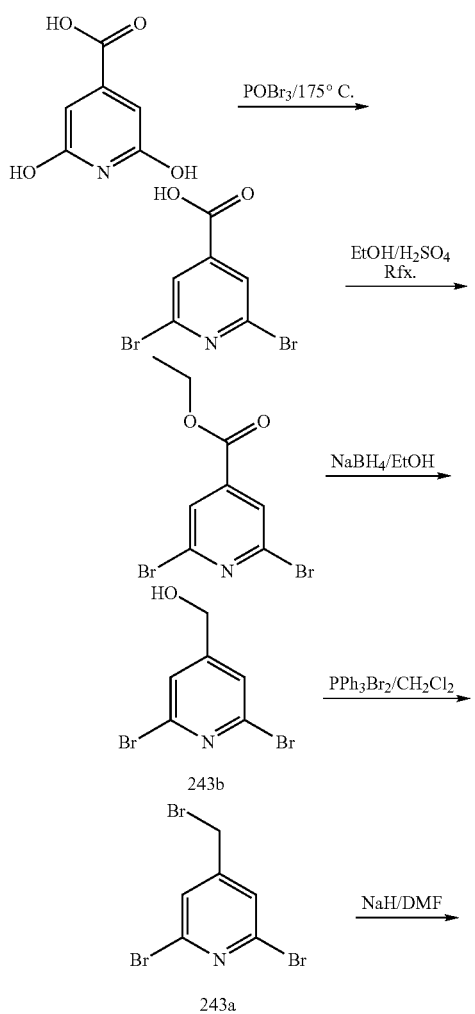

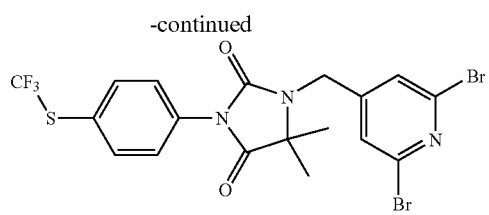
243

The products may be purified as follows:

Purification by LC/MS

The products may be purified by LC/MS using a Waters FractionLynx system composed of a Waters model 600 gradient pump, a Waters model 515 regeneration pump, a Waters Reagent Manager dilution pump, a Waters model 2700 autoinjector, two Rheodyne LabPro model valves, a Waters model 996 diode array detector, a Waters model ZMD mass spectrometer and a Gilson model 204 fraction collector. The system was controlled by the Waters FractionLynx software. The separation was performed alternately on two Waters Symmetry columns ($C_{18}$, 5 µM, 19×50 mm, catalog reference 186000210), one column undergoing regeneration with a 95/5 (v/v) water/acetonitrile mixture containing 0.07% (v/v) trifluoroacetic acid, while the other column was performing separation. The columns were eluted using a linear gradient of from 5% to 95% of acetonitrile containing 0.07% (v/v) of trifluoroacetic acid in water containing 0.07% (v/v) trifluoroacetic acid, at a flow rate of 10 ml/minute. At the separation column outlet, one-thousandth of the effluent is separated by an LC Packing Accurate, diluted with methyl alcohol, at a flow rate of 0.5 ml/minute, and sent to the detectors, in a proportion of 75% to the diode array detector and the remaining 25% to the mass spectrometer. The rest of the effluent (999/1000) is sent to the fraction collector, where the flow is discarded as long as the mass of the expected product has not been detected by the FractionLynx software. The molecular formulae of the expected products are supplied to the FractionLynx software, which initiates the collection of the product when the mass signal detected corresponds to the ion $[M+H]^+$ and/or to $[M+Na]^+$. In certain cases, depending on the analytical LC/MS results, when an intense ion corresponding to $[M+2H]^{++}$ was detected, the value corresponding to half the calculated molecular mass (MW/2) is also supplied to the FractionLynx software. Under these conditions, collection is also initiated when the mass signal of the ion [M+2H]⁺⁺ and/or [M+Na+H]⁺⁺ is detected. The products were collected in tared glass tubes. After collection, the solvents were evaporated off, in a Savant AES 2000 or Genevac HT8 centrifuge evaporator and the product masses were determined by weighing the tubes after evaporating off the solvents.

The LC/MS analyses were performed on a Micromass LCT model machine connected to an HP 1100 machine. The abundance of the products was measured using an HP G1315A diode array detector over a wavelength range from 200-600 nm and a Sedex 65 light scattering detector. The acquisition of the mass spectra was performed over a range from 180 to 800. The data were analyzed using the Micromass MassLynx software. The separation was performed on a Hypersil BDS C18, 3 µm column (50×4.6 mm), eluting with a linear gradient of from 5% to 90% of acetonitrile containing 0.05% (v/v) trifluoroacetic acid (TFA) in water containing 0.05% (v/v) TFA over 3.5 minutes at a flow rate of 1 ml/minute. The total analysis time, including the column reequilibration time, is 7 minutes.

The products of Examples 244 to 255 of the present invention were prepared as indicated in the experimental section and according to the general synthetic route of the scheme below:

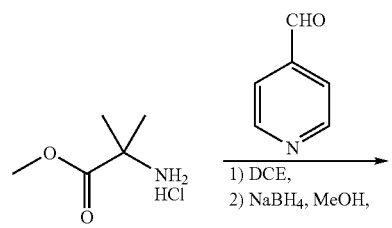

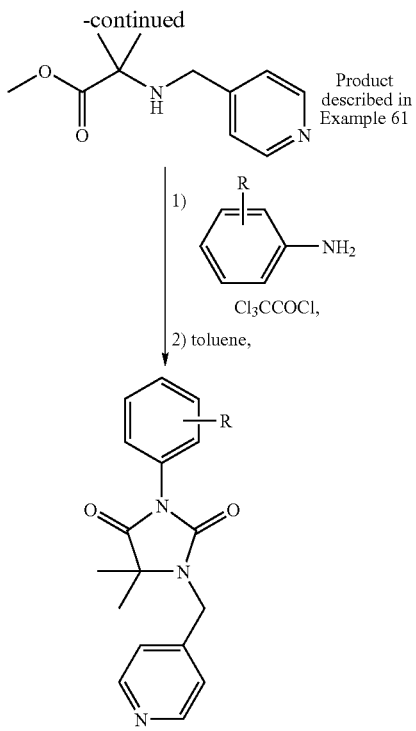

The products of Examples 256 to 263 of the present invention were prepared according to reaction Schemes 1 and 2 indicated below, in which the FIGS. 1 to 8 correspond, respectively, to Examples 256 to 263: the products of Examples 256 to 261 (i.e. products 1 to 6) were prepared according to Scheme 1 and the two thiohydantoin compounds of Examples 262 and 263 (i.e. products 7 and 8) were prepared according to Scheme 2.

SCHEME 1

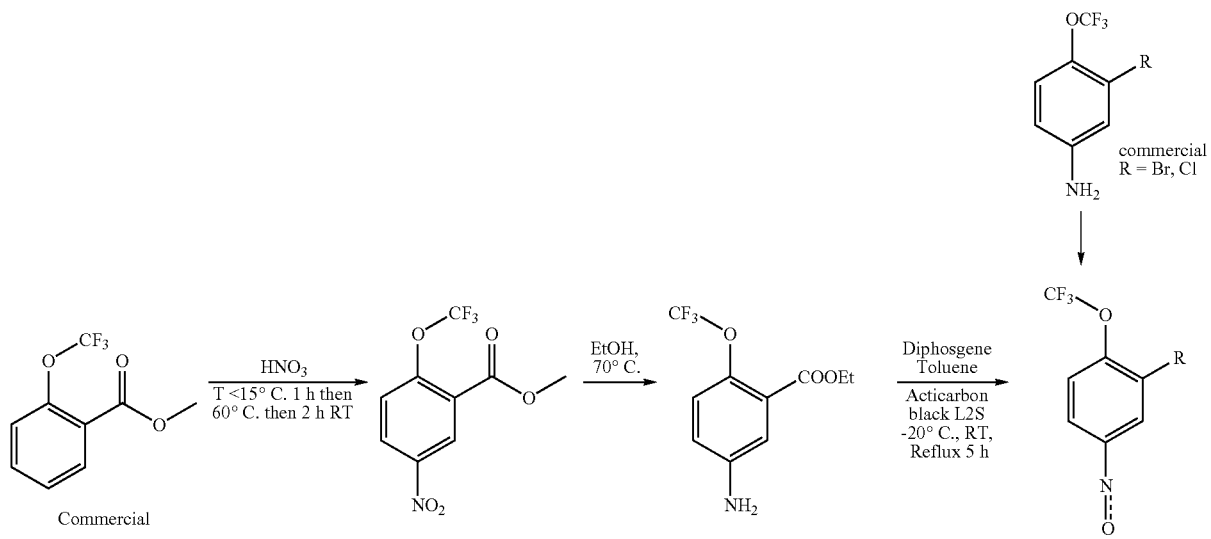

R = C(O)OCH₃, Br, Cl

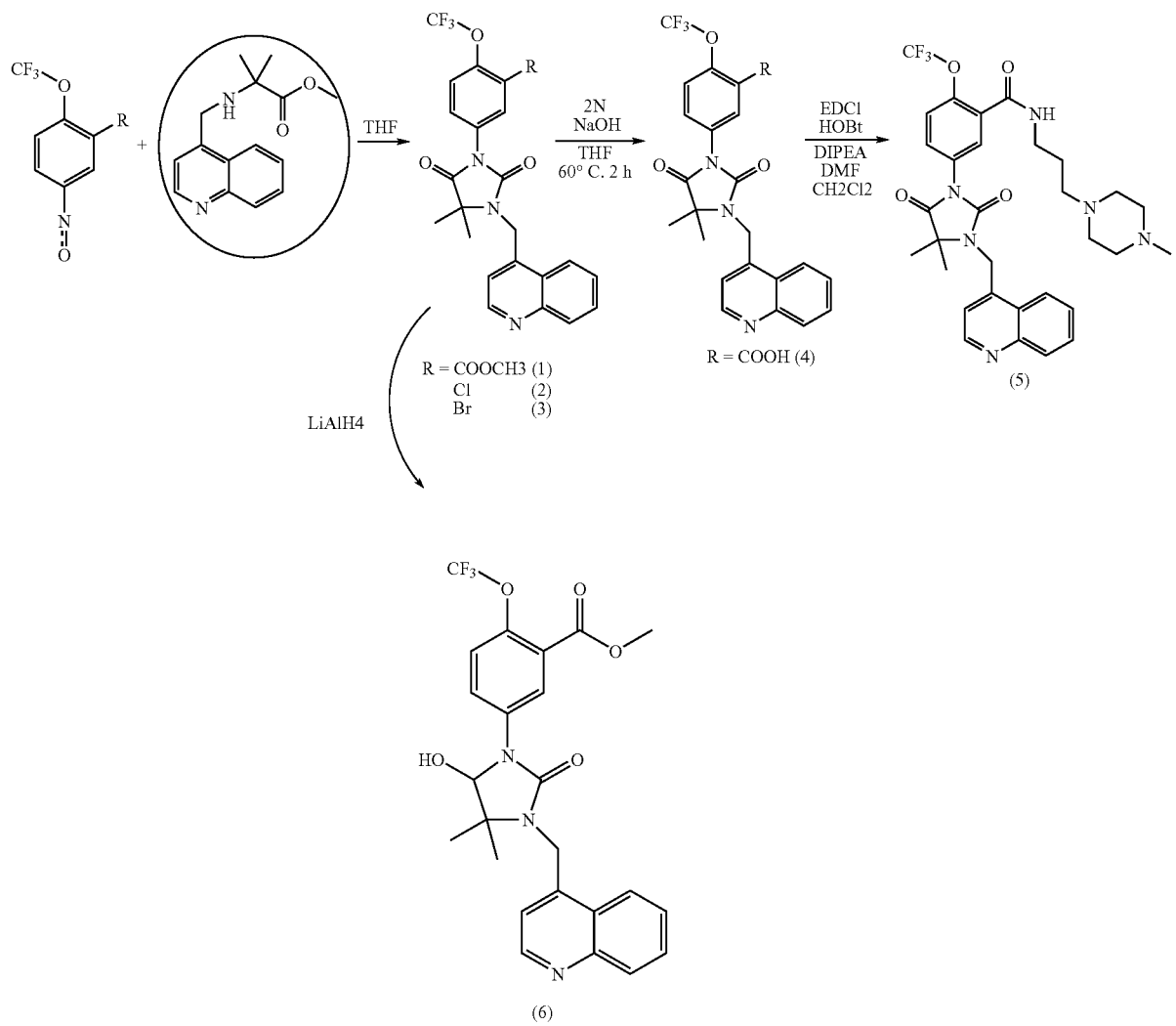

The nitro compound is prepared by nitration of methyl 2-trifluoromethoxybenzoate by nitration (fuming nitric acid) by controlling the temperature.

According to the conditions described in patent PCT Int. Appl. (2000), 564: WO 0069810.

The corresponding amine is prepared by reduction of the nitro function in the presence of $SnCl_2$ in ethanol, according to the same patent.

The isocyanate is prepared by reacting diphosgene dissolved in toluene at −20° C. under the usual known conditions. The isocyanate is reacted with the quinoline derivative prepared according to the known methods, in order to prepare the desired hydantoin.

The acid is obtained by saponification using 2N sodium hydroxide in THF at 60° C.

The amide is prepared by coupling the desired amine using EDCI as coupling agent (standard coupling conditions).

The alcohol is obtained by reducing the ester in THF in the presence of $LiAlH_4$.

The halo derivatives R=Cl and R=Br are prepared from the commercial anilines according to the same synthetic scheme.

SCHEME 2

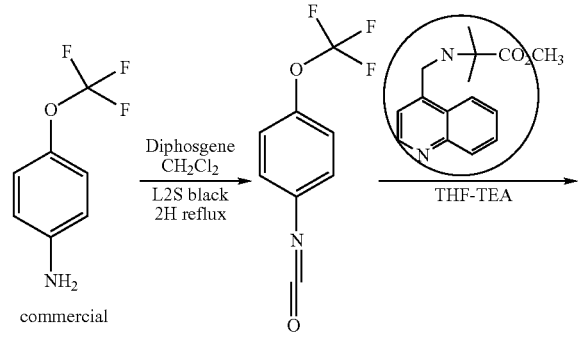

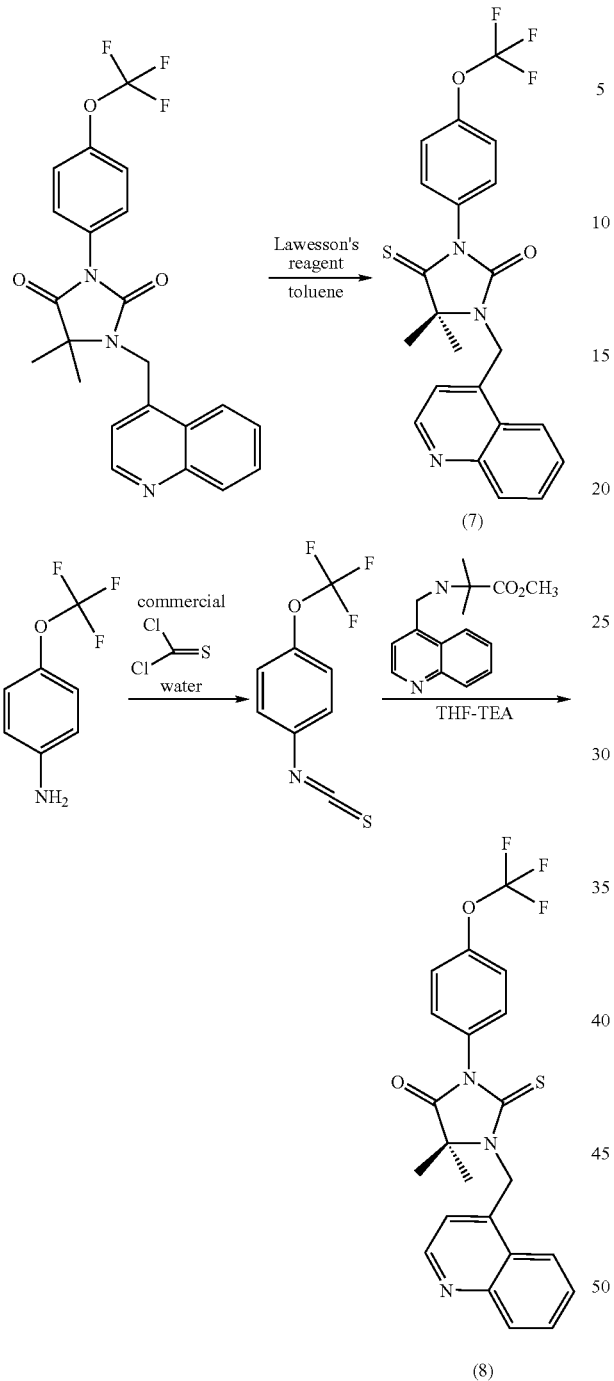

DMF is filtered and replaced with 10 ml of a 20% solution of piperidine in DMF. After agitation for one hour at room temperature, the solution is filtered and the resin washed successively with 3×10 ml of DMF, 2×10 ml of methanol and 3×10 ml of DMF. A solution of 0.94 g of Fmoc-Ala(OH) (3 mmol), 0.41 g of HOBt (3 mmol) and 0.48 ml of DIC (3 mmol) in 10 ml of DMF is added to the resin. The syringe is agitated overnight at room temperature and the resin is then washed successively with 5×10 ml of DMF, 3×10 ml of MeOH and 5×10 ml of DCM. Next, 10 ml of a 20% solution of piperidine in DMF are introduced into the syringe. After agitation for 1 hour, the solution is filtered and the resin washed with 5×10 ml of DMF, 2×10 ml of MeOH, 3×10 ml of DCM and 3×10 ml of THF. Next, a solution of 0.79 g of quinoline-4-carboxaldehyde (5.1 mmol) in 10 ml of a 50/50 THF/TEOF mixture is added to the resin. After agitation overnight at room temperature, the solution is filtered and the resin washed with 10×10 ml of THF. 0.63 g of sodium cyanoborohydride in a mixture of 1.5 ml of MeOH, 3.5 ml of dichloroethane and 0.1 ml of acetic acid is then added to the resin. The resin is agitated overnight and then, after filtration, washed with 10×10 ml of DCM, 3×10 ml of MeOH and 5×10 ml of DCM.

In parallel, a solution of 0.563 g of 4-(trifluoromethanesulfonyl)aniline (2.5 mmol) is treated with 0.25 g of triphosgene (0.83 mmol), followed by 0.23 ml of pyridine (2.5 mmol) at 0° C. under nitrogen. After the temperature has warmed gradually to room temperature, the reaction is stirred for 2 hours and a further 0.23 ml of pyridine in 1 ml of DMF is added to the mixture. The solution obtained is transferred into the syringe, which is agitated for 2 hours. The solution is then filtered and the resin washed with 5×10 ml of DCM, 3×10 ml of MeOH and 5×10 ml of DCM. Finally, the resin is treated with 5 ml of a 95% solution of trifluoroacetic acid in water. The mixture is agitated for 2 hours and then filtered. The resin is washed with 2 ml of MeOH, followed by 2 ml of DCM. The combined filtrates are evaporated under vacuum. 280 mg of crude product are thus obtained. After purification by preparative LC-MS, 240 mg (overall yield=41%) of expected product are isolated in the form of a white solid.

EIMS ([M+H]$^+$: 464

Retention time (RT)=3.12 min (YMC basic S5 column; 2-85% ACN/H2O gradient over 7 min)

1H NMR (300 MHz) (CDCl3): 1.59 (d, 3H); 4.11 (t, 1H); 5.01 and 5.55 (AB, 2H); 7.70 (d, 1H); 7.89 (m, 1H); 7.99 (m, 3H); 8.15 (m, 2H); 8.30 (d, 1H); 8.50 (d, 1H); 9.22 (d, 1H).

EXAMPLE 2

Preparation of (S)-4-methyl-3-quinol-4-ylmethyl-5-thioxo-1-(4-trifluoromethanesulfonylphenyl)imidazolidin-2-one trifluoroacetate Resin 3, 0.036 mmol, prepared according to Example 1, is used for the preparation of the compound.

33 mg of thiocarbonyldiimidazole (0.18 mmol) are added to a solution of 41 mg of 4-(trifluoromethanesulfonyl)aniline (0.18 mmol) in 3 ml of DCM. The reaction mixture is stirred for 2 hours at room temperature and then added directly to the resin. After stirring for 2 hours, the solution is filtered and the resin is then washed with 5×2 ml of DCM, 3×5 ml of MeOH and 5×2 ml of DCM.

Finally, 2 ml of a 95% solution of TFA in water are added to the resin. After stirring for 2 hours, the mixture is filtered and the resin washed with 1 ml of MeOH and 1 ml of DCM. The combined filtrates are heated at 60° C. for 2 hours and The examples whose preparation follows illustrate the present invention without, however, limiting it.

EXAMPLE 1

Preparation of (S)-5-methyl-1-quinolin-4-ylmethyl-3-(4-trifluoromethanesulfonylphenyl)imidazolidine-2,4-dione trifluoroacetate 2 g (1.02 mmol) of Polystyrene AM RAM (Rink resin) (0.51 mmol/g) are suspended in 20 ml of DMF in a 50 ml syringe fitted with a sinter. After agitation for 10 minutes, the

EXAMPLE 3

Preparation of (S)-5-methyl-1-pyrid-4-ylmethyl-3-(4-trifluoromethanesulfonylphenyl)imidazolidine-2,4-dione trifluoroacetate The compound is prepared from 0.025 mmol of resin, 0.075 mmol of N-Fmoc-L-Ala(OH), 0.125 mmol of 4-pyridinecarboxaldehyde and 0.0625 mmol of 4-(trifluoromethanesulfonyl)aniline, in the same way as in Example 1. After purification by preparative LC-MS, 5.6 mg of expected product are obtained.

EIMS ([M+H]+): 414
RT=2.72 min

EXAMPLE 4

Preparation of (S)-5-methyl-1-pyrid-4-ylmethyl-3-(4-trifluoromethylsulfanylphenyl)imidazolidine-2,4-dione trifluoroacetate The compound is prepared from 0.025 mmol of resin, 0.075 mmol of N-Fmoc-L-Ala(OH), 0.125 mmol of 4-pyridinecarboxaldehyde and 0.0625 mmol of 4-(trifluoromethanethio)aniline, in the same way as in Example 1. After purification by preparative LC-MS, 1.3 mg of expected product are obtained.

EIMS ([M+H]+): 382
RT=2.83 min

EXAMPLE 5

Preparation of (S)-5-methyl-1-quinol-4-ylmethyl-3-(4-trifluoromethylsulfanylphenyl)imidazolidine-2,4-dione trifluoroacetate The compound is prepared from 0.025 mmol of resin, 0.075 mmol of N-Fmoc-L-Ala(OH), 0.125 mmol of 4-quinolinecarboxaldehyde and 0.0625 mmol of 4-(trifluoromethanethio)aniline, in the same way as in Example 1. After purification by preparative LC-MS, 0.6 mg of expected product is obtained.

EIMS ([M+H]+): 432
RT=3.14 min

EXAMPLE 6

Preparation of 1-quinol-4-ylmethyl-3-(4-trifluoromethanesulfonylphenyl)imidazolidine-2,4-dione trifluoroacetate The compound is prepared from 4 mmol of resin, 12 mmol of N-Fmoc-Gly(OH), 20 mmol of 4-quinolinecarboxaldehyde, and 10 mmol of 4-(trifluoromethanesulfonyl)aniline in the same way as in Example 1. After purification by preparative LC-MS, 1 g of expected product is obtained.

EIMS ([M+H]+): 450
RT=3.20 min

EXAMPLE 7

Preparation of 5,5-dimethyl-1-quinol-4-ylmethyl-3-(4-trifluoromethanesulfonylphenyl)imidazolidine-2,4-dione trifluoroacetate The compound is prepared from 0.25 mmol of resin, 0.75 mmol of Fmoc-AIB-(OH), 1.25 mmol of 4-quinolinecarboxaldehyde and 0.625 mmol of 4-(trifluoromethanesulfonyl)aniline, in the same way as in Example 1. After purification by preparative LC-MS, 22 mg of expected product are obtained.

EIMS ([M+H]+): 478
RT=4.26 min

EXAMPLE 8

Preparation of (R)-5-methyl-1-quinol-4-ylmethyl-3-(4-trifluoromethanesulfonylphenyl)imidazolidine-2,4-dione trifluoroacetate The compound is prepared from 0.04 mmol of resin, 0.12 mmol of N-Fmoc-D-Ala(OH), 0.20 mmol of 4-quinolinecarboxaldehyde and 0.10 mmol of 4-(trifluoromethanesulfonyl)aniline, in the same way as in Example 1. After purification by preparative LC-MS, 10 mg of expected product are obtained.

EIMS ([M+H]+): 464
RT=4.36 min

EXAMPLE 9

Preparation of (R)-5-methyl-1-quinol-4-ylmethyl-3-(4-trifluoromethylsulfanylphenyl)imidazolidine-2,4-dione trifluoroacetate The compound is prepared from 0.04 mmol of resin, 0.12 mmol of N-Fmoc-D-Ala(OH), 0.20 mmol of 4-quinolinecarboxaldehyde and 0.10 mmol of 4-(trifluoromethanethio)aniline, in the same way as in Example 1. After purification by preparative LC-MS, 11 mg of expected product are obtained.

EIMS ([M+H]+): 432
RT=4.50 min

EXAMPLE 10

Preparation of (R)-5-methyl-1-pyrid-4-ylmethyl-3-(4-trifluoromethanesulfonylphenyl)imidazolidine-2,4-dione trifluoroacetate The compound is prepared from 0.28 mmol of resin, 0.84 mmol of N-Fmoc-D-Ala(OH), 1.4 mmol of 4-pyridinecarboxaldehyde and 0.70 mmol of 4-(trifluoromethanesulfonyl)aniline, in the same way as in Example 1. After purification by preparative LC-MS, 105 mg of expected product are obtained.

EIMS ([M+H]+): 414
RT=2.40 min

EXAMPLE 11

Preparation of (R)-5-methyl-1-pyrid-4-ylmethyl-3-(4-trifluoromethylsulfanylphenyl)imidazolidine-2,4-dione trifluoroacetate The compound is prepared from 0.28 mmol of resin, 0.84 mmol of N-Fmoc-D-Ala(OH), 1.4 mmol of 4-pyridinecarboxaldehyde and 0.70 mmol of 4-(trifluoromethanethio)

EXAMPLE 12

Preparation of (S)-5-methyl-1-(3-methylpyrid-4-ylmethyl)-3-(4-trifluoromethylsulfanylphenyl)imidazolidine-2,4-dione trifluoroacetate The compound is prepared from 0.04 mmol of resin, 0.12 mmol of N-Fmoc-L-Ala(OH), 0.20 mmol of 3-methyl-4-pyridinecarboxaldehyde and 0.10 mmol of 4-(trifluoromethanethio)aniline, in the same way as in Example 1. After purification by preparative LC-MS, 17 mg of expected product are obtained.

EIMS ([M+H]+): 396
RT=4.20 min

EXAMPLE 13

Preparation of (S)-5-methyl-1-(3-methylpyrid-4-ylmethyl)-3-(4-trifluoromethanesulfonylphenyl)imidazolidine-2,4-dione trifluoroacetate The compound is prepared from 0.04 mmol of resin, 0.12 mmol of N-Fmoc-L-Ala(OH), 0.20 mmol of 3-methyl-4-pyridinecarboxaldehyde, and 0.10 mmol of 4-(trifluoromethanesulfonyl)aniline, in the same way as in Example 1. After purification by preparative LC-MS, 16 mg of expected product are obtained.

EIMS ([M+H]+): 428
RT=4.07 min

EXAMPLE 14

Preparation of (S)-4-methyl-3-pyrid-4-ylmethyl-5-thioxo-1-(4-trifluoromethylsulfanylphenyl)imidazolidin-2-one trifluoroacetate The compound is prepared from 0.04 mmol of resin, 0.12 mmol of N-Fmoc-L-Ala(OH), 0.20 mmol of 4-pyridinecarboxaldehyde and 0.10 mmol of 4-(trifluoromethanethio)aniline, in the same way as in Example 2. After purification by preparative LC-MS, 1.7 mg of expected product are obtained.

EIMS ([M+H]+): 398
RT=4.51 min

EXAMPLE 15

Preparation of (S)-4-methyl-3-pyrid-4-ylmethyl-5-thioxo-1-(4-trifluoromethanesulfonylphenyl)imidazolidin-2-one trifluoroacetate The compound is prepared from 0.04 mmol of resin, 0.12 mmol of N-Fmoc-L-Ala(OH), 0.20 mmol of 4-pyridinecarboxaldehyde and 0.10 mmol of 4-(trifluoromethanesulfonyl)aniline, in the same way as in Example 2. After purification by preparative LC-MS, 2.2 mg of expected product are obtained.

EIMS ([M+H]+): 430
RT=4.34 min

EXAMPLE 16

Preparation of (R)-4-methyl-3-(3-methylpyrid-4-ylmethyl)-5-thioxo-1-(4-trifluoromethylsulfanylphenyl)imidazolidin-2-one trifluoroacetate The compound is prepared from 0.04 mmol of resin, 0.12 mmol of N-Fmoc-D-Ala(OH), 0.20 mmol of 3-methyl-4-pyridinecarboxaldehyde and 0.10 mmol of 4-(trifluoromethanethio)aniline, in the same way as in Example 2. After purification by preparative LC-MS, 1.9 mg of expected product are obtained.

EIMS ([M+H]+): 412
RT=4.60 min

EXAMPLE 17

Preparation of (R)-4-methyl-3-(3-methylpyrid-4-ylmethyl)-5-thioxo-1-(4-trifluoromethylsulfonylphenyl)imidazolidin-2-one trifluoroacetate The compound is prepared from 0.04 mmol of resin, 0.12 mmol of N-Fmoc-D-Ala(OH), 0.20 mmol of 3-methyl-4-pyridinecarboxaldehyde and 0.10 mmol of 4-(trifluoromethanesulfonyl)aniline, in the same way as in Example 2. After purification by preparative LC-MS, 4.5 mg of expected product are obtained.

EIMS ([M+H]+): 444
RT=4.41 min

EXAMPLE 18

Preparation of (R)-5-methyl-1-(3-methylpyrid-4-ylmethyl)-3-(4-trifluoromethylsulfanylphenyl)imidazolidine-2,4-dione trifluoroacetate The compound is prepared from 0.04 mmol of resin, 0.12 mmol of N-Fmoc-D-Ala(OH), 0.20 mmol of 3-methyl-4-pyridinecarboxaldehyde and 0.10 mmol of 4-(trifluoromethanethio)aniline, in the same way as in Example 1. After purification by preparative LC-MS, 14 mg of expected product are obtained.

EIMS ([M+H]+): 396
RT=4.22 min

EXAMPLE 19

Preparation of (R)-5-methyl-1-(3-methylpyrid-4-ylmethyl)-3-(4-trifluoromethanesulfonylphenyl)imidazolidine-2,4-dione trifluoroacetate The compound is prepared from 0.04 mmol of resin, 0.12 mmol of N-Fmoc-D-Ala(OH), 0.20 mmol of 3-methyl-4-pyridinecarboxaldehyde and 0.10 mmol of 4-(trifluoromethanesulfonyl)aniline, in the same way as in Example 1. After purification by preparative LC-MS, 6.3 mg of expected product are obtained.

EIMS ([M+H]+): 428
RT=4.10 min aniline, in the same way as in Example 1. After purification by preparative LC-MS, 91 mg of expected product are obtained.

EIMS ([M+H]+): 382
RT=2.52 min

EXAMPLE 20

Preparation of (R)-4-methyl-3-quinol-4-ylmethyl-5-thioxo-1-(4-trifluoromethylsulfanylphenyl)imidazolidin-2-one trifluoroacetate The compound is prepared from 0.04 mmol of resin, 0.12 mmol of N-Fmoc-D-Ala(OH), 0.20 mmol of 4-qinolinecarboxaldehyde and 0.10 mmol of 4-(trifluoromethanethio)aniline, in the same way as in Example 2. After purification by preparative LC-MS, 0.4 mg of expected product is obtained.
EIMS ([M+H]+): 448
RT=4.89 min

EXAMPLE 21

Preparation of (R)-5-isopropyl-1-quinol-4-ylmethyl-3-(4-trifluoromethylsulfanylphenyl)imidazolidine-2,4-dione trifluoroacetate The compound is prepared from 0.05 mmol of resin, 0.15 mmol of N-Fmoc-D-Val(OH), 0.25 mmol of 4-quinolinecarboxaldehyde and 0.125 mmol of 4-(trifluoromethanethio)aniline, in the same way as in Example 1. After purification by preparative LC-MS, 0.3 mg of expected product is obtained.
RT=4.01 min
EIMS ([M+H]+): 460

EXAMPLE 22

Preparation of (R)-5-isopropyl-1-quinol-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-Val(OH), 0.25 mmol of 4-quinolinecarboxaldehyde and 0.125 mmol of 4-(trifluoromethanesulfonyl)aniline, in the same way as in Example 1. After purification by preparative LC-MS, 1 mg of expected product is obtained.
EIMS ([M+H]+): 492
RT=3.91 min

EXAMPLE 23

Preparation of (R)-5-Benzyl-1-quinol-4-ylmethyl-3-(4-trifluoromethylsulfanylphenyl)imidazolidine-2,4-dione trifluoroacetate The compound is prepared from 0.05 mmol of resin, 0.15 mmol of N-Fmoc-D-Phe(OH), 0.25 mmol of 4-quinolinecarboxaldehyde and 0.125 mmol of 4-(trifluoromethanethio)aniline, in the same way as in Example 1. After purification by preparative LC-MS, 8.9 mg of expected product are obtained.
EIMS ([M+H]+): 508
RT=4.11 min

EXAMPLE 24

Preparation of (R)-5-Benzyl-1-quinol-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-Phe(OH), 0.25 mmol of 4-quinolinecarboxaldehyde and 0.125 mmol of 4-(trifluoromethanesulfonyl)aniline, in the same way as in Example 1. After purification by preparative LC-MS, 5.9 mg of expected product are obtained.
EIMS ([M+H]+): 540
RT=4.01 min

EXAMPLE 25

Preparation of (R)-5-Benzyl-1-pyrid-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-Phe(OH), 0.25 mmol of 4-pyridinecarboxaldehyde and 0.125 mmol of 4-(trifluoromethanesulfonyl)aniline, in the same way as in Example 1. After purification by preparative LC-MS, 11.1 mg of expected product are obtained.
EIMS ([M+H]+): 490
RT=3.76 min

EXAMPLE 26

Preparation of (R)-5-isobutyl-1-quinol-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-Leu(OH), 0.25 mmol of 4-quinolinecarboxaldehyde and 0.125 mmol of 4-(trifluoromethanesulfonyl)aniline, in the same way as in Example 1. After purification by preparative LC-MS, 5.9 mg of expected product are obtained.
RT=4.02 min
EIMS ([M+H]+): 506

EXAMPLE 27

Preparation of (R)-5-(4-hydroxybenzyl)-1-quinol-4-ylmethyl-3-(4-trifluoromethylsulfanylphenyl)imidazolidine-2,4-dione trifluoroacetate The compound is prepared from 0.05 mmol of resin, 0.15 mmol of N-Fmoc-D-Tyr(OH), 0.25 mmol of 4-quinolinecarboxaldehyde and 0.125 mmol of 4-(trifluoromethanethio)aniline, in the same way as in Example 1. After purification by preparative LC-MS, 5.1 mg of expected product are obtained.
EIMS ([M+H]+): 524
RT=3.75 min

EXAMPLE 28

Preparation of (R)-5-(4-hydroxybenzyl)-1-quinol-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-Tyr(OH), 0.25 mmol of 4-quinolinecarboxaldehyde and 0.125 mmol of 4-(trifluoromethanesulfonyl)aniline, in the same way as in Example 1. After purification by preparative LC-MS, 1.8 mg of expected product are obtained.
EIMS ([M+H]+): 556
RT=3.66 min

EXAMPLE 29

Preparation of (R)-5-(4-hydroxybenzyl)-1-pyrid-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-Tyr(OH), 0.25 mmol of 4-pyridinecarboxaldehyde and 0.125 mmol of 4-(trifluoromethanesulfonyl)aniline, in the same way as in Example 1. After purification by preparative LC-MS, 0.7 mg of expected product is obtained.
EIMS ([M+H]+): 506
RT=3.48 min

EXAMPLE 30

Preparation of (R)-5-(1-hydroxyethyl)-1-quinol-4-ylmethyl-3-(4-trifluoromethylsulfanylphenyl)imidazolidine-2,4-dione trifluoroacetate The compound is prepared from 0.05 mmol of resin, 0.15 mmol of N-Fmoc-D-Thr(OH), 0.25 mmol of 4-quinolinecarboxaldehyde and 0.125 mmol of 4-(trifluoromethanethio)aniline, in the same way as in Example 1. After purification by preparative LC-MS, 4.2 mg of expected product are obtained.
EIMS ([M+H]+): 462
RT=3.52 min

EXAMPLE 31

Preparation of (R)-5-(1-hydroxyethyl)-1-quinol-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-Thr(OH), 0.25 mmol of 4-quinolinecarboxaldehyde and 0.125 mmol of 4-trifluoromethanesulfonyl)aniline, in the same way as in Example 1. After purification by preparative LC-MS, 3.4 mg of expected product are obtained.
EIMS ([M+H]+): 494
RT=3.43 min

EXAMPLE 32

Preparation of 4-quinol-4-ylmethyl-6-(4-trifluoromethylsulfanylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 4-quinolinecarboxaldehyde and 0.125 mmol of 4-(trifluoromethanethio)aniline, in the same way as in Example 1. After purification by preparative LC-MS, 7.5 mg of expected product are obtained.
EIMS ([M+H]+): 444
RT=3.68 min

EXAMPLE 33

Preparation of 4-quinol-4-ylmethyl-6-(4-trifluoromethanesulfonylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 4-quinolinecarboxaldehyde and 0.125 mmol of 4-(trifluoromethanesulfonyl)aniline, in the same way as in Example 1. After purification by preparative LC-MS, 3.8 mg of expected product are obtained.
EIMS ([M+H]+): 476
RT=3.60 min

EXAMPLE 34

Preparation of 4-pyrid-4-ylmethyl-6-(4-trifluoromethylsulfanylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 4-pyridinecarboxaldehyde and 0.125 mmol of 4-(trifluoromethanethio)aniline, in the same way as in Example 1. After purification by preparative LC-MS, 1.7 mg of expected product are obtained.
EIMS ([M+H]+): 394
RT=3.43 min

EXAMPLE 35

Preparation of 4-pyrid-4-ylmethyl-6-(4-trifluoromethanesulfonylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 4-pyridinecarboxaldehyde, and 0.125 mmol of 4-(trifluoromethanesulfonyl)aniline, in the same way as in Example 1. After purification by preparative LC-MS, 1.4 mg of expected product are obtained.
EIMS ([M+H]+): 426
RT=3.35 min

EXAMPLE 36

Preparation of (R)-5-benzo[b]thiophen-3-ylmethyl-1-quinol-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-benzothienyl Ala(OH), 0.25 mmol of 4-quinolinecarboxaldehyde and 0.125 mmol of 4-(trifluoromethanesulfonyl)aniline, in the same way as in Example 1. After purification by preparative LC-MS, 5 mg of expected product are obtained.
EIMS ([M+H]+): 596
RT=4.12 min

EXAMPLE 37

Preparation of (R)-5-benzo[b]thiophen-3-ylmethyl-1-pyrid-4-ylmethyl-3-(4-trifluoromethylsulfanylphenyl)imidazolidine-2,4-dione trifluoroacetate The compound is prepared from 0.05 mmol of resin, 0.15 mmol of N-Fmoc-D-benzothienyl Ala(OH), 0.25 mmol of 4-pyridinecarboxaldehyde and 0.125 mmol of 4-(trifluoromethanethio)aniline, in the same way as in Example 1.

After purification by preparative LC-MS, 1.4 mg of expected product are obtained.

EIMS ([M+H]+): 514
RT=3.35 min

EXAMPLE 38

Preparation of (R)-5-benzo[b]thiophen-3-ylmethyl-1-pyrid-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-benzothienyl Ala(OH), 0.25 mmol of 4-pyridinecarboxaldehyde and 0.125 mmol of 4-(trifluoromethanesulfonyl)aniline, in the same way as in Example 1. After purification by preparative LC-MS, 8.5 mg of expected product are obtained.

EIMS ([M+H]+): 546
RT=3.90 min

EXAMPLE 39

Preparation of (S)-5-pyrid-2-ylmethyl-1-quinol-4-ylmethyl-3-(4-trifluoromethylsulfanylphenyl)imidazolidine-2,4-dione trifluoroacetate The compound is prepared from 0.05 mmol of resin, 0.15 mmol of N-Fmoc-D-2-pyridine-Ala(OH), 0.25 mmol of 4-quinolinecarboxaldehyde and 0.125 mmol of 4-(trifluoromethanethio)aniline, in the same way as in Example 1. After purification by preparative LC-MS, 7.5 mg of expected product are obtained.

EIMS ([M+H]+): 509
RT=3.47 min

EXAMPLE 40

Preparation of (S)-5-pyrid-2-ylmethyl-1-quinol-4-ylmethyl-3-(4-trifluoromethanesulfonylphenyl)imidazolidine-2,4-dione trifluoroacetate The compound is prepared from 0.05 mmol of resin, 0.15 mmol of N-Fmoc-D-2-pyridine-Ala(OH), 0.25 mmol of 4-quinolinecarboxaldehyde and 0.125 mmol of 4-(trifluoromethanesulfonyl)aniline, in the same way as in Example 1. After purification by preparative LC-MS, 1.6 mg of expected product are obtained.

EIMS ([M+H]+): 541
RT=3.41 min

EXAMPLE 41

Preparation of (R)-1-(3-hydroxypyrid-4-ylmethyl)-5-methyl-3-(4-trifluoromethylsulfanylphenyl)imidazolidine-2,4-dione trifluoroacetate The compound is prepared from 0.05 mmol of resin, 0.15 mmol of N-Fmoc-D-Ala(OH), 0.25 mmol of 3-hydroxy-4-pyridinecarboxaldehyde and 0.125 mmol of 4-(trifluoromethanethio)aniline, in the same way as in Example 1. After purification by preparative LC-MS, 8.3 mg of expected product are obtained.

EIMS ([M+H]+): 398
RT=4.26 min

EXAMPLE 42

Preparation of 5,5-dimethyl-1-quinol-4-ylmethyl-3-(4-trifluoromethoxyphenyl)imidazolidine-2,4-dione trifluoroacetate The compound is prepared from 0.05 mmol of resin, 0.15 mmol of Fmoc-AIB-(OH), 0.25 mmol of 4-quinolinecarboxaldehyde and 0.125 mmol of 4-(trifluoromethoxy)aniline, in the same way as in Example 1. After purification by preparative LC-MS, 5.5 mg of expected product are obtained.

EIMS ([M+H]+): 430
RT=4.33 min

EXAMPLE 43

Preparation of 5,5-dimethyl-1-quinol-4-ylmethyl-3-(4-trifluoromethylsulfanylphenyl)imidazolidine-2,4-dione trifluoroacetate The compound is prepared from 0.05 mmol of resin, 0.15 mmol of Fmoc-AIB-(OH), 0.25 mmol of 4-quinolinecarboxaldehyde, and 0.125 mmol of 4-(trifluoromethanethio)aniline, in the same way as in Example 1. After purification by preparative LC-MS, 9.4 mg of expected product are obtained.

EIMS ([M+H]+): 446
RT=4.58 min

EXAMPLE 44

Preparation of 5,5-dimethyl-1-(3-methylpyrid-4-ylmethyl)-3-(4-trifluoromethoxyphenyl)imidazolidine-2,4-dione trifluoroacetate The compound is prepared from 0.05 mmol of resin, 0.15 mmol of Fmoc-AIB-(OH), 0.25 mmol of 3-methyl-4-pyridinecarboxaldehyde and 0.125 mmol of 4-(trifluoromethoxy)aniline, in the same way as in Example 1. After purification by preparative LC-MS, 5.5 mg of expected product are obtained.

EIMS ([M+H]+): 394
RT=4.06 min

EXAMPLE 45

Preparation of 5,5-dimethyl-1-(3-methylpyrid-4-ylmethyl)-3-(4-trifluoromethylsulfanylphenyl)imidazolidine-2,4-dione trifluoroacetate The compound is prepared from 0.05 mmol of resin, 0.15 mmol of Fmoc-AIB-(OH), 0.25 mmol of 3-methyl-4-pyridinecarboxaldehyde and 0.125 mmol of 4-(trifluoromethanethio)aniline, in the same way as in Example 1. After purification by preparative LC-MS, 13.1 mg of expected product are obtained.

EIMS ([M+H]+): 410
RT=4.30 min

EXAMPLE 46

Preparation of 5,5-dimethyl-1-(3-methylpyrid-4-ylmethyl)-3-(4-trifluoromethanesulfonylphenyl)imidazolidine-2,4-dione trifluoroacetate The compound is prepared from 0.05 mmol of resin, 0.15 mmol of Fmoc-AIB-(OH), 0.25 mmol of 3-methyl-4-pyridinecarboxaldehyde and 0.125 mmol of 4-(trifluoromethanesulfonyl)aniline, in the same way as in Example 1. After purification by preparative LC-MS, 9.6 mg of expected product are obtained.
EIMS ([M+H]+): 442
RT=4.18 min

EXAMPLE 47

Preparation of 1-(3-hydroxypyrid-4-ylmethyl)-5,5-dimethyl-3-(4-trifluoromethoxyphenyl)imidazolidine-2,4-dione trifluoroacetate The compound is prepared from 0.05 mmol of resin, 0.15 mmol of Fmoc-AIB-(OH), 0.25 mmol of 3-hydroxy-4-pyridinecarboxaldehyde and 0.125 mmol of 4-(trifluoromethoxy)aniline, in the same way as in Example 1. After purification by preparative LC-MS, 6.9 mg of expected product are obtained.
EIMS ([M+H]+): 394
RT=4.15 min

EXAMPLE 48

Preparation of 1-(3-hydroxypyrid-4-ylmethyl)-5,5-dimethyl-3-(4-trifluoromethylsulfanylphenyl)imidazolidine-2,4-dione trifluoroacetate The compound is prepared from 0.05 mmol of resin, 0.15 mmol of Fmoc-AIB-(OH), 0.25 mmol of 3-hydroxy-4-pyridinecarboxaldehyde and 0.125 mmol of 4-(trifluoromethanethio)aniline, in the same way as in Example 1. After purification by preparative LC-MS, 9.7 mg of expected product are obtained.
EIMS ([M+H]+): 412
RT=4.39 min

EXAMPLE 49

Preparation of 1-(3-hydroxypyrid-4-ylmethyl)-5,5-dimethyl-3-(4-trifluoromethanesulfonylphenyl)imidazolidine-2,4-dione trifluoroacetate The compound is prepared from 0.05 mmol of resin, 0.15 mmol of Fmoc-AIB-(OH), 0.25 mmol of 3-hydroxy-4-pyridinecarboxaldehyde and 0.125 mmol of 4-(trifluoromethanesulfonyl)aniline, in the same way as in Example 1. After purification by preparative LC-MS, 15.2 mg of expected product are obtained.
EIMS ([M+H]+): 444
RT=4.30 min

EXAMPLE 50

Preparation of 4-quinol-4-ylmethyl-6-(4-trifluoromethoxyphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 4-quinolinecarboxaldehyde and 0.125 mmol of 4-(trifluoromethoxy)aniline, in the same way as in Example 1. After purification by preparative LC-MS, 4.1 mg of expected product are obtained.
EIMS ([M+H]+): 428
RT=4.24 min

EXAMPLE 51

Preparation of 4-(3-methylpyrid-4-ylmethyl)-6-(4-trifluoromethoxyphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 4-pyridinecarboxaldehyde and 0.125 mmol of 4-(trifluoromethoxy)aniline, in the same way as in Example 1. After purification by preparative LC-MS, 3 mg of expected product are obtained.
EIMS ([M+H]+): 392
RT=3.95 min

EXAMPLE 52

Preparation of 4-(3-methylpyrid-4-ylmethyl)-6-(4-trifluoromethylsulfanylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 3-methyl-4-pyridinecarboxaldehyde and 0.125 mmol of 4-(trifluoromethanethio)aniline, in the same way as in Example 1. After purification by preparative LC-MS, 5 mg of expected product are obtained.
EIMS ([M+H]+): 408
RT=4.24 min

EXAMPLE 53

Preparation of 4-(3-methylpyrid-4-ylmethyl)-6-(4-trifluoromethanesulfonylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 3-methyl-4-pyridinecarboxaldehyde and 0.125 mmol of 4-(trifluoromethanesulfonyl)aniline, in the same way as in Example 1. After purification by preparative LC-MS, 1.9 mg of expected product are obtained.
EIMS ([M+H]+): 440
RT=4.11 min

EXAMPLE 54

Preparation of 4-(3-hydroxypyrid-4-ylmethyl)-6-(4-trifluoromethoxyphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 3-hydroxy-4-pyridinecarboxaldehyde and 0.125 mmol of 4-(trifluoromethoxy)aniline, in the same way as in Example 1. After purification by preparative LC-MS, 5.5 mg of expected product are obtained.
EIMS ([M+H]+): 394
RT=4.04 min

EXAMPLE 55

Preparation of 4-(3-hydroxypyrid-4-ylmethyl)-6-(4-trifluoromethylsulfanylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 3-hydroxy-4- pyridinecarboxaldehyde and 0.125 mmol of 4-(trifluoromethanethio)aniline, in the same way as in Example 1. After purification by preparative LC-MS, 0.7 mg of expected product is obtained.

EIMS ([M+H]+): 410
RT=4.34 min

EXAMPLE 56

Preparation of 4-(3-hydroxypyrid-4-ylmethyl)-6-(4-trifluoromethanesulfonylphenyl)-4,6-diazaspiro[2.4]heptane-5,7-dione trifluoroacetate The compound is prepared from 0.05 mmol of resin, 0.15 mmol of Fmoc-ACPC-(OH), 0.25 mmol of 3-hydroxy-4-pyridinecarboxaldehyde and 0.125 mmol of 4-(trifluoromethanesulfonyl)aniline, in the same way as in Example 1. After purification by preparative LC-MS, 2.5 mg of expected product are obtained.

EIMS ([M+H]+): 442
RT=4.17 min

EXAMPLE 57

Preparation of 5-methyl-1-quinol-4-ylmethyl-3-(4-trifluoromethanesulfonylphenyl)dihydropyrimidine-2,4-dione 588 mg (1 mmol) of Wang polystyrene resin (1.7 mmol/g) are washed with 2×5 ml of DMF, 1×5 ml of DCM and then treated with a solution of 0.49 g of N-Fmoc-3-amino-2-(R,S)-methylpropionic acid (1.5 mmol), 0.24 g of pyridine (3 mmol) in 5 ml of DMF, immediately followed by 0.31 g of 2,6-dichlorobenzoyl chloride (dropwise addition to control the exothermicity). The reaction mixture is stirred overnight at room temperature. The mixture is filtered and the resin is then washed with 1×5 ml of DMF, 1×5 ml of DCM and 2×5 ml of DMF and then treated with 5 ml of a 10% solution of piperidine in DMF. The resin is then washed with 2×5 ml of DMF, 1×5 ml of DCM, 1×5 ml of DMF, 1×5 ml of DMF, 4×5 ml of DCM, 4×5 ml of MeOH and dried under vacuum. 0.94 g of 4-quinolinecarboxaldehyde (6 mol) in 16 ml of a 50/50 mixture of THF/TMOF is added to the resin, which is stirred overnight. The resin is then washed 3 times with 5 ml of the same THF/TMOF mixture and then treated with 12 ml of a 1M solution of sodium cyanoborohydride in THF (12 mmol) in the presence of 1.2 ml of MeOH and 0.12 ml of acetic acid. After stirring overnight at room temperature, the resin is washed with 1×5 ml of THF, 4×5 ml of a 30% solution of acetic acid in DMF, 1×5 ml of MeOH, 1×5 ml of THF, 1×5 ml of DMF, 1×5 ml of THF, 1×5 ml of MeOH and dried under vacuum. In parallel, 0.121 g of triphosgene (0.41 mmol) in 1 ml of DCM is added dropwise to a solution of 0.281 g of 4-(trifluoromethanesulfonyl)aniline (1.25 mmol) and 0.1 g of pyridine (1.25 mmol) in 2 ml of DCM. After stirring for 15 minutes at room temperature, the same amount of pyridine is added, followed by the resin previously prepared. The mixture is stirred overnight and then filtered. The resin is washed with 1×5 ml of MeOH, 1×5 ml of THF, 1×5 ml of MeOH, 1×5 ml of DMF, 1×5 ml of THF, 1×5 ml of MeOH and 3×5 ml of THF and dried under vacuum. The resin is then treated with 154 mg of DBU (1 mmol) in 5 ml of DCM and stirred overnight. Finally, the dihydrouracil is obtained by treating the resin with 5 ml of 2% solution of acetic acid in THF. After purification by preparative HPLC, 90 mg of expected product are isolated.

EIMS ([M+H]+): 477
RT=1.83 min (20-100% ACN/H2O gradient over 5 minutes)

EXAMPLE 58

(S)-5-Methyl-1-quinol-4-ylmethyl-3-(4-trifluoromethanesulfanylphenyl)imidazolidine-2,4-dione This example describes a novel preparation of Example 5 above.

A mixture of 0.71 g of ethyl (S)-2-[(quinol-4-ylmethyl)amino]propanoate and 1.42 g of 4-(trifluoromethanesulfanylphenyl) isocyanate in 15 ml of THF is stirred for 15 hours at room temperature under an argon atmosphere. After evaporating off the solvent under reduced pressure, 20 ml of dichloromethane are added. The precipitate is filtered off. The filtrate is concentrated under reduced pressure and the residue is purified by flash chromatography (SiO2, CH2Cl2 and then CH2Cl2/MeOH, 95/5 by volume as eluent, Ar). 0.69 g of (S)-5-methyl-1-quinol-4-ylmethyl-3-(4-trifluoromethanesulfanylphenyl)imidazolidine-2,4-dione is isolated in the form of a white powder.

[α]D=−33.1°+/−0.8° (MeOH)
Mass: EI m/z=431 M+. base peak
m/z=143 [C10H9N]+.
1H NMR spectrum (400 MHz, (CD3)2SO d6, δ in ppm): 1.42 (d, J=5.5 Hz: 3H); 4.35 (q, J=5.5 Hz: 1H); 5.08 (d, J=17 Hz: 1H); 5.25 (d, J=17 Hz: 1H); 7.65 (d, J=5 Hz: 1H); from 7.65 to 7.75 (mt: 1H); 7.70 (d, J=8.5 Hz: 2H); 7.83 (broad t, J=8 Hz: 1H); 7.89 (d, J=8.5 Hz: 2H); 8.10 (broad d, J=8.5 Hz: 1H); 8.25 (broad d, J=8.5 Hz: 1H); 8.90 (d, J=5 Hz: 1H).

Ethyl (S)-2-[(quinol-4-ylmethyl)amino]propanoate (P-31397-073-1)

A mixture of 2 g of L-alanine ethyl ester in hydrochloride form and 1.83 ml of triethylamine in 30 ml of dichloromethane is stirred at room temperature for 10 minutes. Next, 2.05 g of quinoline-4-carbaldehyde are added. The reaction medium is stirred at room temperature for 15 hours and then concentrated under reduced pressure. 35 ml of ethanol are then added; the solution is cooled to 0° C. and 0.49 g of sodium borohydride is then added portionwise. Stirring is continued for 15 hours at room temperature. The precipitate formed is filtered off; the filtrate is concentrated under reduced pressure. The residue is purified by flash chromatography on a column (SiO2, CH2Cl2/MeOH, 95/5 by volume as eluent, Ar). 0.71 g of ethyl (S)-2-[(quinol-4-ylmethyl)amino]propanoate is obtained in the form of a pink oil.

Mass: EI m/z=258 M+.
m/z=185 [M−COOCH2CH3]+ base peak
m/z=142 [C10H8N]+
1H NMR spectrum (300 MHz, (CD3)2SO d6, δ in ppm): 1.22 (t, J=7 Hz: 3H); 1.28 (d, J=7 Hz: 3H); 2.72 (unresolved peak: 1H); 3.42 (mt: 1H); from 4.00 to 4.20 (mt: 1H); 4.13 (q, J=7 Hz: 2H); 4.27 (broad d, J=16 Hz: 1H); 7.55 (broad d, J=5 Hz: 1H); 7.64 (ddd, J=8.5-7.5 and 1 Hz: 1H); 7.77 (ddd, J=8.5-7.5 and 1 Hz: 1H); 8.04 (broad d, J=8.5 Hz: 1H); 8.22 (broad d, J=8.5 Hz: 1H); 8.86 (d, J=5 Hz: 1H).

EXAMPLE 59

5,5-Dimethyl-1-quinol-4-ylmethyl-3-(4-trifluoromethoxyphenyl)imidazolidine-2,4-dione This example describes a novel preparation of Example 42 above.

The product is prepared according to the procedure described in Example 58 with 600 mg of methyl 2-methyl- 2-[(quinol-4-ylmethyl)amino]propanoate instead of ethyl (S)-2-[(quinol-4-ylmethyl)amino]propanoate used in Example 58 and 1.114 g of 4-(trifluoromethoxyphenyl) isocyanate instead of 4-(trifluoromethanesulfanylphenyl) isocyanate used in Example 58. After purification by flash chromatography on a column (SiO2, CH2Cl2 as eluent, Ar) and then a second purification by flash chromatography on a column (SiO2, 60/40 cyclohexane/EtOAc by volume as eluent, Ar), 710 mg of the desired product are obtained.

Mass: EI m/z=429 M+. base peak
m/z=414 [M−CH3]+
m/z=359 [M−C4H6O]+.

1H NMR spectrum (300 MHz, (CD3)2SO d6, δ in ppm): 1.46 (s: 6H); 5.16 (s: 2H); 7.55 (broad d, J=8.5 Hz: 2H); 7.65 (d, J=5 Hz: 1H); 7.69 (d, J=8.5 Hz: 2H); 7.70 (mt: 1H); 7.83 (ddd, J=8-7.5 and 1.5 Hz: 1H); 8.09 (broad d, J=8.5 Hz: 1H); 8.27 (broad d, J=8.5 Hz: 1H); 8.88 (d, J=5 Hz: 1H).

Preparation of methyl 2-((quinol-4-ylmethyl)amino)propanoate

A mixture of 1.5 g of methyl α-aminoisobutyrate hydrochloride and 1.4 ml of triethylamine in 30 ml of dichloromethane is stirred at 0° C. for 20 minutes. Next, 1 g of magnesium sulfate and 1.5 g of quinoline-4-carbaldehyde are added. Stirring is continued for 15 hours at room temperature and the mixture is then concentrated under reduced pressure. The residue is taken up in 35 ml of methanol and the solution obtained is cooled to 0° C. 0.4 g of sodium borohydride is added portionwise and stirring is continued at room temperature for 15 hours. The precipitate formed is filtered and the filtrate is concentrated under reduced pressure. The residue obtained is purified by recrystallization from diisopropyl ether. 600 mg of the expected product are obtained in the form of a pink oil.

Mass: DCI m/z=259 [M+H]+
m/z=199 [M+H−HCOOCH3]+

1H NMR spectrum (300 MHz, (CD3)2SO d6, δ in ppm): 1.36 (s: 6H); 2.68 (broad t, J=7 Hz: 1H); 3.69 (s: 3H); 4.11 (d, J=7 Hz: 2H); 7.60 (broad d, J=5 Hz: 1H); 7.63 (ddd, J=9-8.5 and 1 Hz: 1H); 7.76 (ddd, J=9-8.5 and 1 Hz: 1H); 8.03 (broad d, J=8.5 Hz: 1H); 8.20 (broad d, J=8.5 Hz: 1H); 8.85 (d, J=5 Hz: 1H).

EXAMPLE 60

5,5-dimethyl-1-(3-chloro-6-methoxyquinol-4-ylmethyl)-3-(4-trifluoromethoxyphenyl)imidazolidine-2,4-dione The product is prepared according to the procedure described in Example 59, starting with 180 mg of methyl 2-methyl-2-[(3-chloro-6-methoxyquinol-4-ylmethyl)amino]propanoate instead of methyl 2-methyl-2-[(quinol-4-ylmethyl)amino]propanoate used in Example 59 and 267 mg of 4-(trifluoromethoxy)phenyl isocyanate. After purification by flash chromatography on a column (SiO2, 80/20 cyclohexane/EtOAc by volume as eluent, Ar), 137 mg of the expected product are obtained.

Mass: EI m/z=493 M+. isotopic band of the peak monochloro m/z=458 [M−Cl]+ base peak 1H NMR spectrum (300 MHz, (CD3)2SO d6, δ in ppm): 1.27 (s: 6H); 3.89 (s: 3H); 5.27 (s: 2H); 7.48 (dd, J=9 and 3 Hz: 1H); 7.56 (broad d, J=8.5 Hz: 2H); 7.68 (dt, J=8.5 and 2 Hz: 2H); 7.79 (d, J=3 Hz: 1H); 8.01 (d, J=9 Hz: 1H); 8.80 (s: 1H).

Preparation of methyl 2-methyl-2-[(3-chloro-6-methoxyquinol-4-ylmethyl)amino]propanoate (P-31397-099-1)

The product is prepared according to the procedure described in Example 59, starting with 1 g of methyl α-aminoisobutyrate hydrochloride, 1.25 g of (3-chloro-6-methoxy)quinoline-4-carbaldehyde instead of quinoline-4-carbaldehyde used in Example 59, 0.66 g of triethylamine and 250 mg of sodium borohydride. After purification by flash chromatography (SiO2, 70/30 cyclohexane/EtOAc by volume as eluent, Ar), 180 mg of the expected product are obtained.

Mass: EI m/z=322 M+. isotopic band of the peak monochloro m/z=263 [M−COOCH3]+ base peak
isotopic band of the monochloro peak m/z=206 [M−C5H10O2N]+
isotopic band of the monochloro peak 1H NMR spectrum (300 MHz, (CD3)2SO d6, ∇ in ppm): 1.39 (s: 6H); 2.47 (broad t, J=7.5 Hz: 1H); 3.74 (s: 3H); 3.98 (s: 3H); 4.04 (d, J=7.5 Hz: 2H); 7.46 (dd, J=9 and 3 Hz: 1H); 7.66 (d, J=3 Hz: 1H); 7.97 (d, J=9 Hz: 1H); 8.71 (s: 1H).

Preparation of (3-chloro-6-methoxyquinoline)-4-carbaldehyde (P-31397-097-1)

A solution of 2 g of 4-bromo-3-chloro-6-methoxyquinoline in 50 ml of THF is cooled to −78° C. 6.9 ml of a 1.6 M solution of nBuLi in dioxane are added. The solution is stirred for 2 hours at this temperature and 1.7 ml of DMF are then added. The mixture is stirred at −60° C. for 2 hours 30 minutes and the reaction medium is then allowed to warm to room temperature. 200 ml of water are then added. The organic phase is extracted with 200 ml of ethyl acetate, washed with 5×200 ml of water, dried over magnesium sulfate and concentrated under reduced pressure. The residue obtained is purified by flash chromatography on a column (SiO2, 80/20 cyclohexane/EtOAc by volume as eluent, Ar).

1.2 g of the expected product are obtained in the form of a yellow powder.

Mass: EI m/z=221 M+. base peak, isotopic band of the monochloro
m/z=193 [M−CO]+. isotopic band of the monochloro peak
m/z=150 [M—C3H3O2]+ isotopic band of the monochloro peak 1H NMR spectrum (300 MHz, (CD3)2SO d6, □ in ppm): 3.96 (s: 3H); 7.56 (dd, J=9 and 3 Hz: 1H); 8.07 (d, J=9 Hz: 1H); 8.22 (d, J=3 Hz: 1H); 8.93 (s: 1H); 10.77 (s: 1H).

Preparation of 4-bromo-3-chloro-6-methoxyquinoline is described in French patent FR 2 816 618 in Example 1.

EXAMPLE 61

5,5-Dimethyl-1-pyrid-4-ylmethyl-3-(4-trifluoromethanesulfanylphenyl)imidazolidine-2,4-dione 0.764 g of 4-(trifluoromethanesulfanylphenyl) isocyanate is added to a solution of 0.726 g of methyl 2-methyl-2-[(pyrid-4-ylmethyl)amino]propanoate in 10 ml of tetrahydrofuran. The reaction medium is stirred under an argon atmosphere for about 3 days at a temperature in the region of 20° C. The reaction mixture is taken up in ethyl acetate, washed successively with water and then with saturated sodium chloride solution. The organic phase is dried over magnesium sulfate and then concentrated under reduced pressure. The residue thus obtained is purified by flash chromatography on an AIT cartridge of reference FC-50SI filled with 50 g of silica conditioned and eluted with dichloromethane at a flow rate of 10 ml per minute. The fractions between 100 and 280 ml are concentrated under reduced pressure, the residue obtained is taken up in ethyl ether and the insoluble material is filtered off. 700 mg of 5,5-dimethyl-1-pyrid-4-ylmethyl-3-(4-trifluoromethanesulfanylphenyl)imidazolidine-2,4-dione are thus obtained in the form of a white powder, the characteristics of which are as follows:

1H NMR spectrum (300 MHz, (CD3)2SO d6, δ in ppm): 1.43 (s: 6H); 4.66 (s: 2H); 7.44 (broad d, J=6 Hz: 2H); 7.69 (d t, J=8.5 and 2.5 Hz: 2H); 7.87 (broad d, J=8.5 Hz: 2H); 8.55 (dd, J=6 and 1.5 Hz: 2H).

Mass IE m/z=395 M+. base peak
m/z=380 (M−CH3)+
m/z=219 C8H4NOSF3+.
m/z=92 C6H6N+

Preparation of methyl 2-methyl-2-[(pyrid-4-ylmethyl)amino]propanoate (P-31402-151-1)

1.04 ml of triethylamine and then 0.659 g of pyridine-4-carbaldehyde are successively added to a solution of 0.945 g of methyl α-aminoisobutyrate hydrochloride in 28 ml of dichloroethane. The reaction mixture is stirred overnight at a temperature in the region of 20° C. The mixture is purified by filtration on Merck Lichroprep aminopropyl-grafted silica. The filtrate is concentrated under reduced pressure and the residue thus obtained is taken up in 25 ml of methanol, 0.372 g of sodium borohydride is added. The reaction mixture is stirred for 48 hours at a temperature in the region of 20° C. and then poured into a mixture of a normal solution of sodium hydroxide/ice. The mixture obtained is extracted three times with ethyl acetate. The organic phase is dried over magnesium sulfate and then concentrated under reduced pressure. 0.726 g of methyl 2-methyl-2-[(pyrid-4-ylmethyl)amino]propanoate is thus obtained in the form of an oil, the characteristics of which are as follows:

1H NMR spectrum (300 MHz, (CD3)2SO d6, δ in ppm): 1.27 (s: 6H); 2.69 (broad t, J=5 Hz: 1H); 3.64 (s: 3H); 3.65 (d, J=5 Hz: 2H); 7.35 (broad d, J=6 Hz: 2H); 8.47 (dd, J=6 and 1.5 Hz: 2H).

Mass IC m/z=209 MH+ base peak
m/z=149 (M−C2H4O2)+

EXAMPLE 62

1-Pyrid-4-ylmethyl-3-(4-trifluoromethanesulfanylphenyl)imidazolidine-2,4-dione 0.087 g sodium hydride is added to a solution of 0.300 g of 3-(4-trifluoromethylsulfanylphenyl)imidazolidine-2,4-dione in 6 ml of anhydrous dimethylformamide, under an inert atmosphere of argon at a temperature in the region of 20° C., stirring is continued at this temperature for 30 minutes, 0.152 ml of triethylamine and 0.274 g of 4-(bromomethyl) pyridine hydrobromide are successively added, followed by addition of ice-cold water 10 minutes later. The reaction mixture is placed on a cartridge 37 mm in diameter packed with 50 g of Amicon 50 μm octadecyl-grafted silica of ref. conditioned successively with a water/acetonitrile mixture (5/95, v/v) and then a water/acetonitrile mixture (95/5, v/v). The elution was performed with a water/acetonitrile mixture (95/5, v/v) over 20 minutes, followed by a linear gradient from 5% to 95% of acetonitrile over 60 minutes, at a flow rate of 10 ml/minute. The fractions between 580 and 630 ml are concentrated under reduced pressure. 0.220 g of 1-pyrid-4-ylmethyl-3-(4-trifluoromethylsulfanylphenyl)imidazolidine-2,4-dione is thus obtained in the form of a white powder, the characteristics of which are as follows:

1H NMR spectrum (300 MHz, (CD3)2SO d6, δ in ppm): 4.16 (s: 2H); 4.65 (s: 2H); 7.42 (broad d, J=6 Hz: 2H); 7.64 (broad d, J=8.5 Hz: 2H); 7.87 (broad d, J=8.5 Hz: 2H); 8.57 (broad d, J=6 Hz: 2H).

Mass IE m/z=367 M+. base peak
m/z=219 C8H4NOSF3+.
m/z=92 C6H6N+

The compound 3-(4-trifluoromethylsulfanylphenyl)imidazolidine-2,4-dione is described in U.S. Pat. No. 4,496,575.

EXAMPLE 63

5,5-Dimethyl-1-pyrid-4-ylmethyl-3-(4-trifluoromethoxyphenyl)imidazolidine-2,4-dione 0.042 g of sodium hydride is added to a solution of 0.150 g of 5,5-dimethyl-3-(4-trifluoromethoxyphenyl)imidazolidine-2,4-dione in 3 ml of anhydrous dimethylformamide, under an inert atmosphere of argon and at a temperature in the region of 20° C., stirring is continued at this temperature for 30 minutes, 0.094 ml of triethylamine and 0.132 g of 4-(bromomethyl)pyridine hydrobromide are successively added, followed by addition of ice-cold water 10 minutes later. The reaction mixture is placed on a cartridge 27 mm in diameter packed with 30 g of Amicon 50 μm octadecyl-grafted silica conditioned successively with a water/acetonitrile mixture (5/95, v/v) and then a water/acetonitrile mixture (95/5, v/v). The elution was performed with a water/acetonitrile mixture (95/5, v/v) over 20 minutes, followed by a linear gradient from 5% to 95% of acetonitrile over 60 minutes, at a flow rate of 10 ml/minute. The fractions between 300 and 450 ml are concentrated under reduced pressure. 0.1 g of mixture is thus obtained, which is repurified on a cartridge of 37 mm in diameter packed with 50 g of Amicon 50 μm octadecyl-grafted silica of ref. conditioned successively with a water/acetonitrile mixture (5/95, v/v) and then a water/acetonitrile mixture (95/5, v/v). The elution was performed with a water/acetonitrile mixture (95/5, v/v) over 20 minutes, followed by a linear gradient from 5% to 95% of acetonitrile over 60 minutes, at a flow rate of 10 ml/minute. The fractions between 550 and 750 ml are concentrated under reduced pressure. 0.060 g of 5,5-dimethyl-1-pyrid-4-ylmethyl-3-(4-trifluoromethoxyphenyl) imidazolidine-2,4-dione is thus obtained, the characteristics of which are as follows:

1H NMR spectrum (300 MHz, (CD3)2SO d6, δ in ppm): 1.42 (s: 6H); 4.65 (s: 2H); 7.44 (broad d, J=6 Hz: 2H); 7.53 (broad d, J=8.5 Hz: 2H); 7.64 (dt, J=8.5 and 2.5 Hz: 2H); 8.54 (broad d, J=6 Hz: 2H).

Mass IE m/z=379 M+. base peak
m/z=364 (M−CH3)+
m/z=203 C8H4NO2F3+.
m/z=92 C6H6N+

Preparation of 5,5-dimethyl-3-(4-trifluoromethoxyphenyl)imidazolidine-2,4-dione

A solution of 7.08 g of 4-trifluoromethoxyaniline in 50 ml of toluene is added over 15 minutes to a suspension of 8.7 g of diphosgene and 1 g of plant charcoal in 100 ml of toluene, at a temperature in the region of −20° C. The mixture is stirred until the temperature is in the region of 20° C., and then refluxed for 3 hours. The mixture is cooled to a temperature in the region of 20° C. and then filtered through Celite, 5 g of methyl α-aminoisobutyrate hydrochloride, 50 ml of toluene and 10 ml of triethylamine are added to the filtrate. The mixture thus obtained is refluxed for 16 hours and then cooled to a temperature in the region of 20° C. The precipitate is filtered off and the filtrate is concentrated under reduced pressure, the residue obtained is purified by flash chromatography on a column packed with silica, conditioned and then eluted with a cyclohexane/ethyl acetate mixture (50/50, v/v). The fractions containing the expected product are concentrated under reduced pressure, and 3.4 g of 5,5-dimethyl-3-(4-trifluoromethoxyphenyl)imidazolidine-2,4-dione are thus obtained, the characteristics of which are as follows:

Mass IE m/z=288 M+. base peak
m/z=273 (M−CH3)+
m/z=203 C8H4NO2F3+.

1H NMR spectrum (300 MHz, (CD3)2SO d6, δ in ppm): 1.42 (s: 6H); 7.49 (d, J=9 Hz: 2H); 7.55 (d, J=9 Hz: 2H); 8.63 (unresolved peak: 1H).

EXAMPLE 64

Preparation of 3-[4-(pentafluorothio)phenyl]-5,5-dimethyl-1-quinolin-4-ylmethylimidazolidine-2,4-dione trifluoroacetate The compound is prepared from 0.16 mmol of resin, 0.48 mmol of Fmoc-AIB-(OH), 1.12 mmol of 4-quinolinecarboxaldehyde and 0.4 mmol of 4-(pentafluorothio)aniline, in the same manner as in Example 1. After purification by preparative LC-MS chromatography, 5 mg of the desired product are obtained.

EIMS ([M+H]+): 472

EXAMPLE 65

Preparation of 3-[4-(pentafluorothio)phenyl]-5,5-dimethyl-1-pyrid-4-ylmethylimidazolidine-2,4-dione trifluoroacetate The compound is prepared from 0.16 mmol of resin, 0.48 mmol of Fmoc-AIB-(OH), 1.12 mmol of 4-pyridinecarboxaldehyde and 0.4 mmol of 4-(pentafluorothio)aniline, in the same manner as in Example 1. After purification by preparative LC-MS chromatography, 13.2 mg of the desired product are obtained.

EIMS ([M+H]+): 422

EXAMPLE 66

Preparation of 3-[4-(pentafluorothio)phenyl]-1-quinolin-4-ylmethylimidazolidine-2,4-dione trifluoroacetate The compound is prepared from 0.1 mmol of resin, 0.3 mmol of N-Fmoc-Gly-(OH), 0.5 mmol of 4-quinolinecarboxaldehyde and 0.25 mmol of 4-(pentafluorothio)aniline, in the same manner as in Example 1. After purification by preparative LC-MS chromatography, 18 mg of the desired product are obtained.

EIMS ([M+H]+): 444

EXAMPLE 67

Preparation of 3-[4-(pentafluorothio)phenyl]-1-pyrid-4-ylmethylimidazolidine-2,4-dione trifluoroacetate The compound is prepared from 0.1 mmol of resin, 0.3 mmol of N-Fmoc-Gly-(OH), 0.5 mmol of 4-quinolinecarboxaldehyde and 0.25 mmol of 4-(pentafluorothio)aniline, in the same manner as in Example 1. After purification by preparative LC-MS chromatography, 18 mg of the desired product are obtained.

EIMS ([M+H]+): 394

EXAMPLE 68

Preparation of 3-[4-(pentafluorothio)phenyl]-1-pyrid-2-ylmethylimidazolidine-2,4-dione trifluoroacetate The compound is prepared from 0.1 mmol of resin, 0.3 mmol of N-Fmoc-Gly-(OH), 0.5 mmol of 4-quinolinecarboxaldehyde and 0.25 mmol of 4-(pentafluorothio)aniline, in the same manner as in Example 1. After purification by preparative LC-MS chromatography, 9 mg of the desired product are obtained.

EIMS ([M+H]+): 394

EXAMPLE 69

Preparation of 3-[4-(pentafluorothio)phenyl]-1-pyrid-3-ylmethylimidazolidine-2,4-dione trifluoroacetate The compound is prepared from 0.2 mmol of resin, 0.6 mmol of N-Fmoc-Gly-(OH), 1 mmol of 4-quinolinecarboxaldehyde and 0.5 mmol of 4-(pentafluorothio)aniline, in the same manner as in Example 1. After purification by preparative LC-MS chromatography, 42 mg of the desired product are obtained.

EIMS ([M+H]+): 394

The 6 reaction schemes below describe the preparation of compound of formula I according to the present invention, especially among the products of Examples 70 to 178 below.

Scheme 1 describes the preparation of hydantoin derivatives with amino substituents in the two positions of the pyridine ring (B2).

Scheme 1:
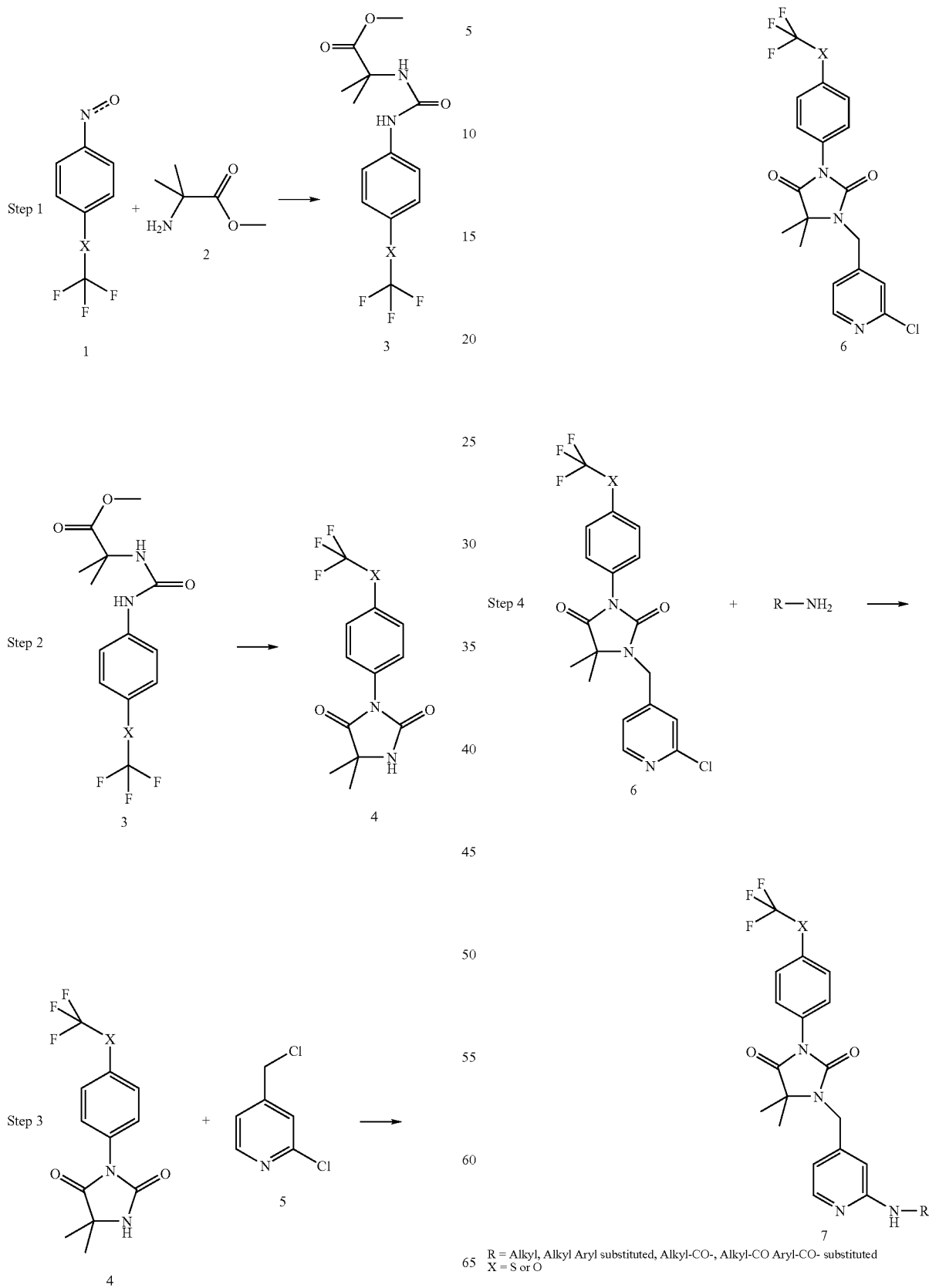
R = Alkyl, Alkyl Aryl substituted, Alkyl-CO-, Alkyl-CO Aryl-CO- substituted
X = S or O Procedures for Scheme 1

Step 1

(Syntheses described for X=S, analogous scheme for X=O).

1-Isocyanato-4-trifluoromethylsulfanylbenzene (14.27 g, 65 mmol) is dissolved in 30 ml of dry $CH_2Cl_2$ and is cooled to 0° C. 7.5 g (65 mmol) of N-ethylmorpholine are added, followed by addition of 10 g (65 mmol) of methyl 2-amino-2-methylpropionate. The reaction mixture is left to reach 25° C. over a period of 6 hours, washed with water and, after removing the solvent, 21.8 g of methyl 2-methyl-2-[3-(4-trifluoromethylsulfanylphenyl)-ureido]propionate 3 are isolated.

Step 2

30 g of 2-methyl-2-[3-(4-trifluoromethylsulfanylphenyl)ureido]propionate 3 are dissolved in a mixture of 225 ml of 3 N HCl and 230 ml of dioxane, refluxed for 6 hours and, after cooling to 4° C., the product 5,5-dimethyl-3-(4-trifluoromethylsulfanylphenyl)-imidazolidine-2,4-dione is isolated in the form of white crystals (24.14 g).

Step 3

5,5-Dimethyl-3-(4-trifluoromethylsulfanylphenyl)imidazolidine-2,4-dione 3 (1 g, 3.29 mmol) is dissolved in 10 ml of DMF, 1.36 g of $K_2CO_3$ (3 eq, 9.87 mmol) and 909 mg of 2-chloro-4-chloromethylpyridine (3.95 mmol, 1.2 eq) are added, and the mixture is refluxed for 20 hours. The solvent is removed under vacuum and the residue is dissolved in $CH_2Cl_2$ and treated three times with active charcoal. After removing the solvent, the product 1-(2-chloropyrid-4-ylmethyl)-5,5-dimethyl-3-(4-trifluoromethylsulfanylphenyl)imidazolidine-2,4-dione is obtained (3.2 g; 56%).

Analytical data:
MS (LC-MS): 429.05; retention time: 2.49 min.
NMR: 1.4: s, 6H, 4.7: s, 2H, 7.45: m, 1H, 7.6: s, 1H, 7.7: d, 2H, 7.9: d, 2H, 8.4: m, 1H.

Preparation of 2-chloro-4-chloromethylpyridine 10 g of 2-chloro-4-methylpyridine are dissolved in 30 ml of $CH_3CN$ and a mixture of AIBN (3 g) and NCS (30 g) is added. The resulting mixture is refluxed for 4 hours. After removing the solvent, the crude product is further purified by distillation (boiling point: 70° C., 20 mtorr).

Step 4: General Procedure for the Palladium-Catalyzed Amination of the Pyridine Ring System in 1-(2-chloropyrid-4-ylmethyl)-5,5-dimethyl-3-(4-trifluoromethylsulfanylphenyl)imidazolidine-2,4-dione 100 mg (0.23 mmol) of 1-(2-chloropyrid-4-ylmethyl)-5,5-dimethyl-3-(4-trifluoromethylsulfanylphenyl)imidazolidine-2,4-dione, 20 mg of $Pd(OAc)_2$, 60 mg of XANTPHOS and 300 mg of $Cs_2CO_3$ are transferred into a reaction tube with a screw stopper equipped with a rubber seal, and an argon atmosphere is generated in the tube. 1.5 equivalents (0.35 mmol) of the appropriate amine or amide are dissolved in 10 ml of toluene, the solution is transferred into the reaction tube mentioned above and the resulting mixture is heated at 95° C. for 6 to 10 hours depending on the reaction progress, monitored by LCMS.

After filtration, the solvent is removed under vacuum and the crude product is further purified by chromatography on an HPLC system.

Scheme 2 describes the preparation of urea and thiourea derivatives.

Scheme 2:

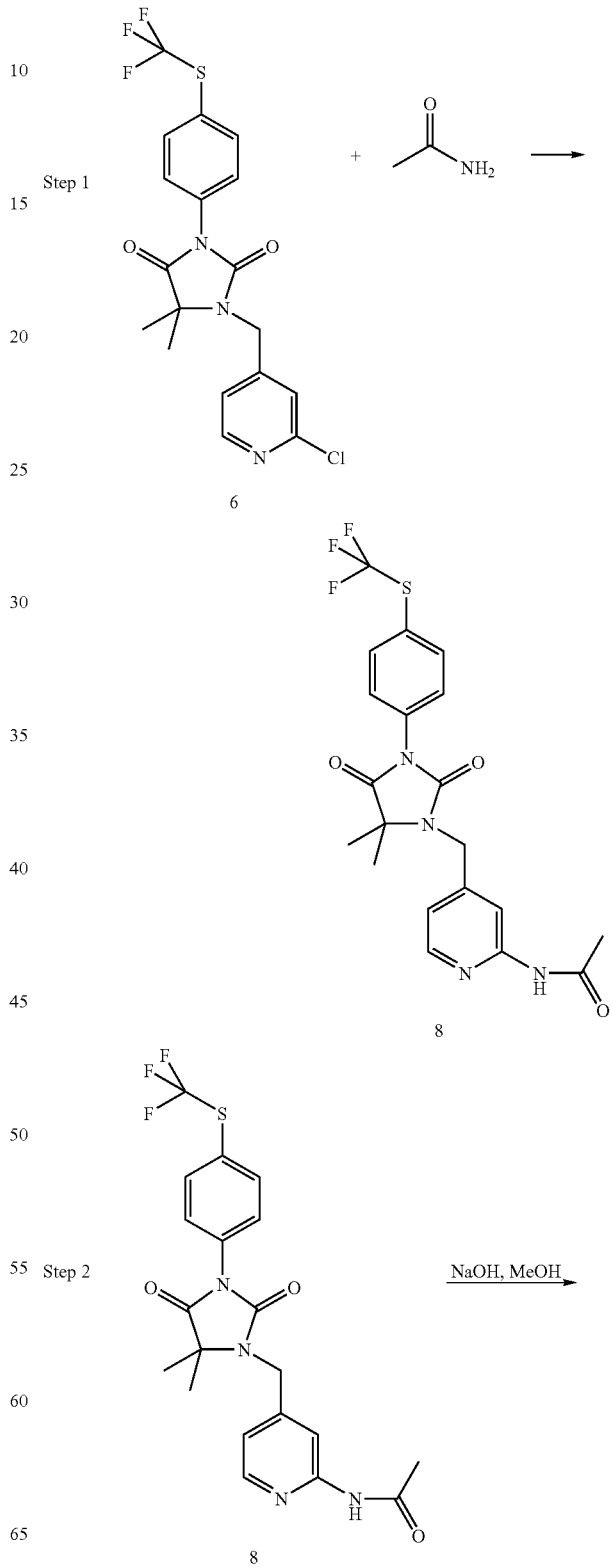

Step 1

Step 2

NaOH, MeOH

-continued

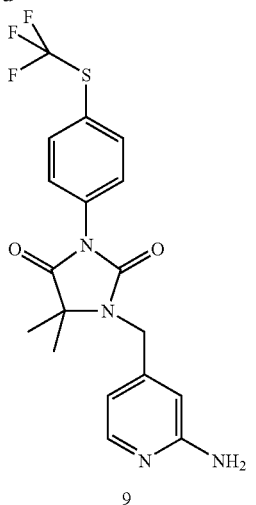

Step 3

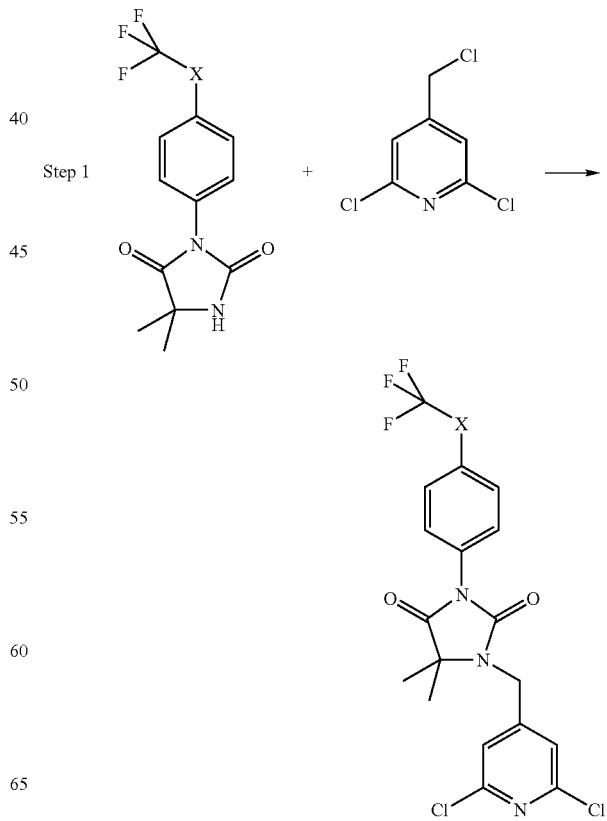

Procedures for Scheme 2:

Step 1:
This step is identical to step 4 of Scheme 1, with acetamide as reagent in the catalytic reaction.

Analytical data for N-{4-[5,5-dimethyl-2,4-dioxo-3-(4-trifluoromethylsulfanylphenyl)imidazolidin-1-ylmethyl]pyrid-2-yl}acetamide:

MS (LC-MS): 452.11; retention time: 1.82 min.
NMR: 1.4: s, 6H, 2.05: s, 3H, 4.65: s, 2H, 7.1: m, 1H; 7.65: d, 2H, 7.85: d, 2H, 8.15: m, 1H, 8.25: m, 1H.

Step 2:
500 mg (1.11 mmol) of N-{4-[5,5-dimethyl-2,4-dioxo-3-(4-trifluoromethylsulfanylphenyl)imidazolidin-1-ylmethyl]pyrid-2-yl}acetamide are dissolved in MeOH, 1.5 mmol of NaOMe are added and the resulting mixture is refluxed for 4 hours. The solvent is removed, the residue is taken up in $CH_2Cl_2$ and washed twice with 10% $NaHCO_3$ solution and with water, and the organic phase is evaporated off. 340 mg (75%) of 1-(2-aminopyrid-4-ylmethyl)-5,5-dimethyl-3-(4-trifluoromethylsulfanylphenyl)imidazolidine-2,4-dione are isolated in this manner.

MS (LC-MS): 410.10; retention time: 1.57.
NMR: 1.4: s, 6H, 4.4: s, 2H, 6.35: s, 2H, 6.4: m, 1H, 6.5: m, 1H, 7.65: d, 2H, 7.9: m, 3H.

Step 3: General Procedure, All the Urea and Thiourea Derivatives are Prepared in this Manner.

100 mg of 1-(2-aminopyrid-4-ylmethyl)-5,5-dimethyl-3-(4-trifluoromethylsulfanylphenyl)imidazolidine-2,4-dione are dissolved in 5 ml of dioxane and 1.5 equivalents of the corresponding isocyanate or isothiocyanate are added. The reaction mixture is stirred at slightly elevated temperature up to the end, which is monitored by LCMS. The solvent is removed and further purification is performed by chromatography on an HPLC system.

Scheme 3

-continued

Step 2 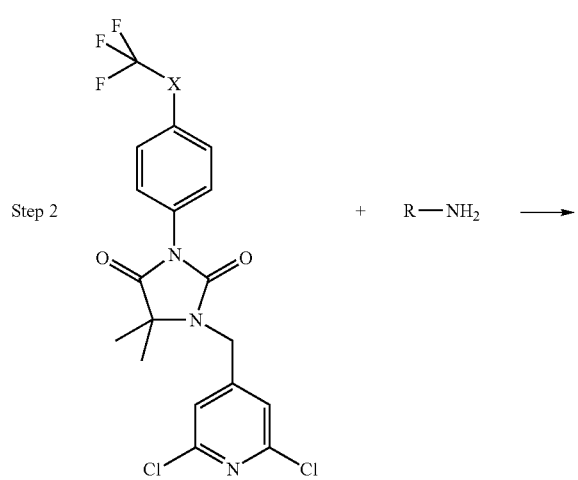 + R—NH₂ ⟶ 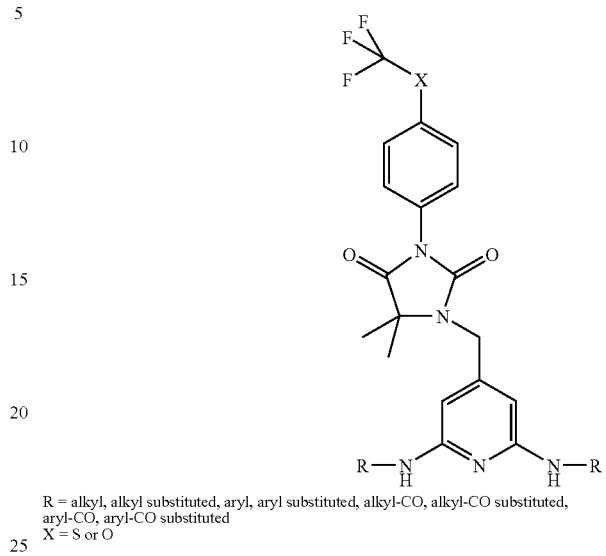

R = alkyl, alkyl substituted, aryl, aryl substituted, alkyl-CO, alkyl-CO substituted, aryl-CO, aryl-CO substituted
X = S or O

Step 1

(Syntheses described for X=S, analogous scheme for X=O)

5,5-Dimethyl-3-(4-trifluoromethylsulfanylphenyl)imidazolidine-2,4-dione (1 000 mg/3.29 mmol) is dissolved in 20 ml of DMF, Cs₂CO₃ (3.21 g/9.9 mmol) and 2,6-dichloro-4-chloromethylpyridine (774 g/3.9 mmol) are added and the resulting mixture is heated at 80° C. for 6 hours. The solvent is removed and the residue is dissolved in CH₂Cl₂ and washed three times with water. After evaporating off the solvent, the crude material is further purified by chromatography on an HPLC system.

Step 2: General Procedure for the Pd-catalyzed Monoamination of 1-(2,6-dichloropyrid-4-ylmethyl)-5,5-dimethyl-3-(4-trifluoromethylsulfanylphenyl)imidazolidine-2,4-dione This step is identical to step 4 of Scheme 1, but only 1 equivalent of the corresponding amine or amide is used.

Step 3: General Procedure for the Pd-catalyzed Bisamination of 1-(2,6-dichloropyrid-4-ylmethyl)-5,5-dimethyl-3-(4-trifluoromethylsulfanylphenyl)imidazolidine-2,4-dione This step is identical to step 4 of Scheme 1, but in this case 2.2 equivalents of the corresponding amine or amide are used.

Step 3 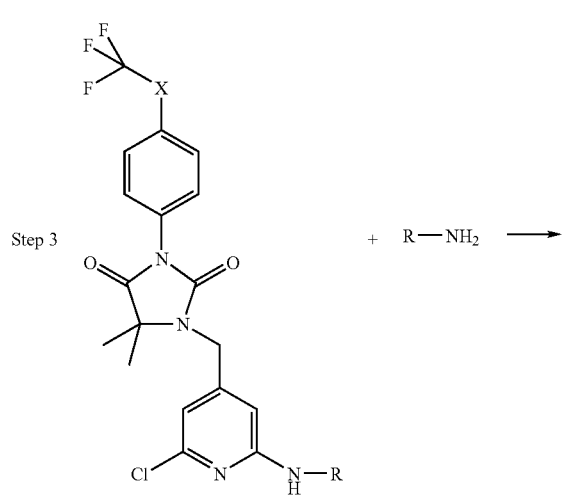 + R—NH₂ ⟶

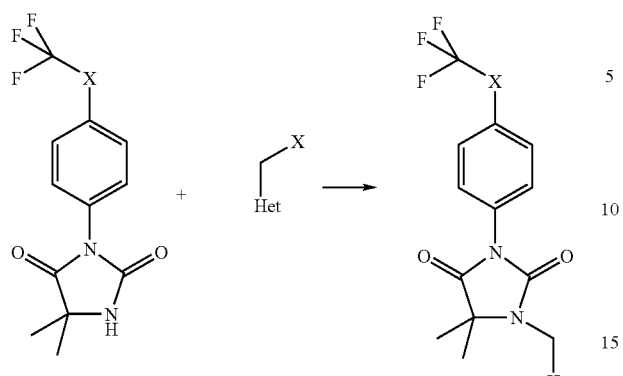

Het = aromatic or aliphatic heterocycle
X = Cl or Br

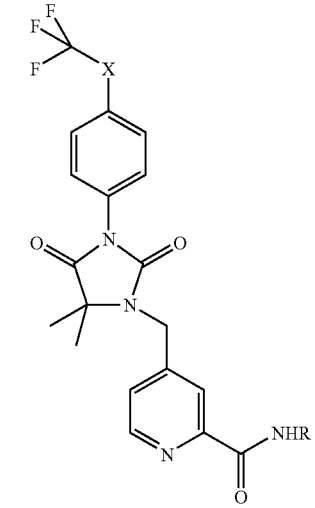

Scheme 4: General Procedure for the Alkylation of 5,5-dimethyl-3-(4-trifluoromethylsulfanylphenyl) imidazolidine-2,4-dione with Aromatic or Aliphatic Heterocycles Bearing a Chloromethyl or Bromomethyl Substituent 5,5-Dimethyl-3-(4-trifluoromethylsulfanylphenyl)imidazolidine-2,4-dione (100 mg/0.33 mmol) is dissolved in 10 ml of DMF, $Cs_2CO_3$ (321 mg/0.99 mmol) and 0.49 mmol (1.5 equivalents) of the aromatic or aliphatic heterocycle substituted with a corresponding chloromethyl or bromomethyl group are added and the resulting mixture is heated at 80° C. for 6 hours. The solvent is removed and the crude material obtained is further purified by chromatography on an HPLC system.

SYNTHESES OF EXAMPLES 175, 176 AND 177

100 mg (0.23 mmol) of 1-(2-chloropyrid-4-ylmethyl)-5,5-dimethyl-3-(4-trifluoromethylsulfanylphenyl)imidazolidine-2,4-dione, 20 mg of $Pd(OAc)_2$, 60 mg of XANTPHOS, 300 mg of $Cs_2CO_3$ and 124 mg of $Mo(CO)_6$ (2 eq) are transferred into a reaction tube with a screw stopper, equipped with a rubber seal, and an argon atmosphere is generated in the tube.

1.5 equivalents (0.35 mmol) of the appropriate amine and 212 mg of DBU are dissolved in 10 ml of toluene, this solution is transferred into the reaction tube mentioned above and the resulting mixture is heated at 95° C. for 6 to 10 hours depending on the reaction progress, which is monitored by LCMS.

After filtration, the solvent is removed under vacuum and the crude product is further purified by chromatography on an HPLC system.

SYNTHESIS OF EXAMPLE 178

Scheme 5

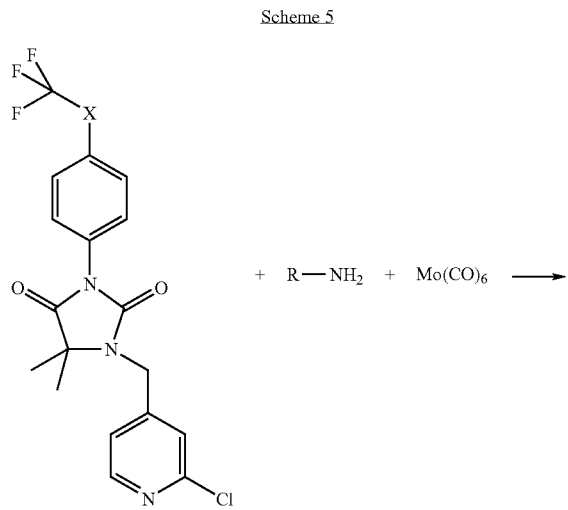

Scheme 6

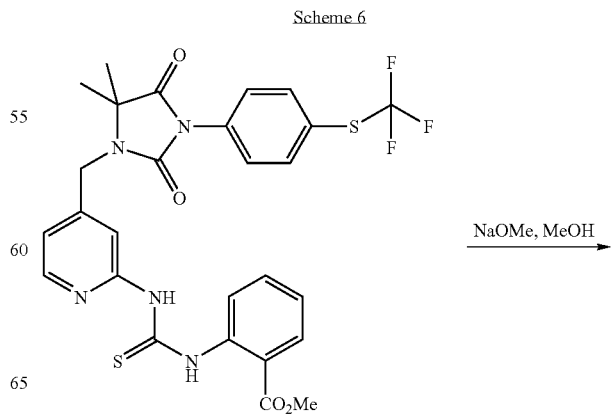

-continued

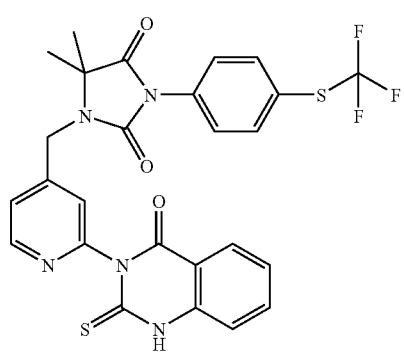

30 mg (0.05 mmol) of methyl 2-(3-{4-[5,5-dimethyl-2,4-dioxo-3-(4-trifluoromethylsulfanylphenyl)imidazolidin-1-ylmethyl]pyrid-2-yl}thioureido)benzoate are dissolved in 2 ml of MeOH, 0.1 mmol of NaOMe is added and the resulting mixture is stirred overnight at room temperature. After evaporating off the solvent, the crude 5,5-dimethyl-1-[2-(4-oxo-2-thioxo-1,4-dihydro-2H-quinazolin-3-yl)pyrid-4-ylmethyl]-3-(4-trifluoromethylsulfanylphenyl)imidazolidine-2,4-dione is further purified by chromatography on an HPLC system.

EXAMPLE 70

N-{4-[5,5-dimethyl-2,4-dioxo-3-(4-trifluoromethyl-sulfanylphenyl)imidazolidin-1-ylmethyl]pyrid-2-yl}propionamide; Compound with Trifluoroacetic Acid

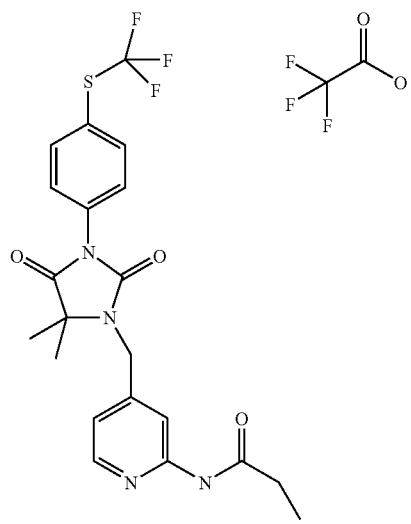

MS (LC-MS): 466.13, Retention time: 1.83 min.

NMR: 1.05: t, 3H, 1.40: s, 6H, 2.35: q, 2H, 4.65: s, 2H, 7.1: d, 1H, 7.65: d, 2H, 7.85: d, 2H, 8.15: s, 1H, 8.25: d, 1H.

The synthesis is described in Scheme 1.

EXAMPLE 71

N-{4-[5,5-dimethyl-2,4-dioxo-3-(4-trifluoromethyl-sulfanylphenyl)imidazolidin-1-ylmethyl]pyrid-2-yl}isobutyramide; Compound with Trifluoroacetic Acid

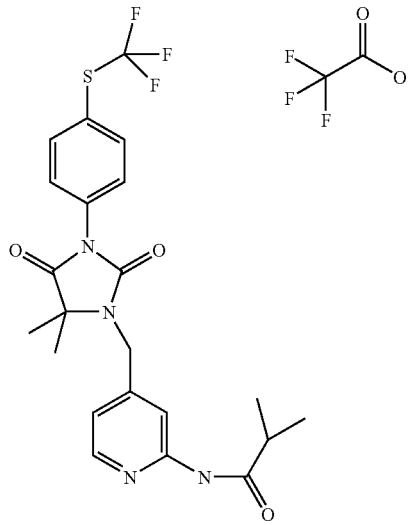

MS (LC-MS): 480.14, Retention time: 1.93 min.
NMR: 1.10: d, 6H, 1.40: s, 6H, 2.75: s, 1H, 4.65: s, 2H, 7.15: d, 1H, 7.65: d, 2H, 7.85: d, 2H, 8.15: s, 1H, 8.25: d, 1H.
The synthesis is described in Scheme 1.

EXAMPLE 72

N-{4-[5,5-dimethyl-2,4-dioxo-3-(4-trifluoromethyl-sulfanylphenyl)imidazolidin-1-ylmethyl]pyrid-2-yl}-3-morpholin-4-ylpropionamide; Compound with Trifluoroacetic Acid

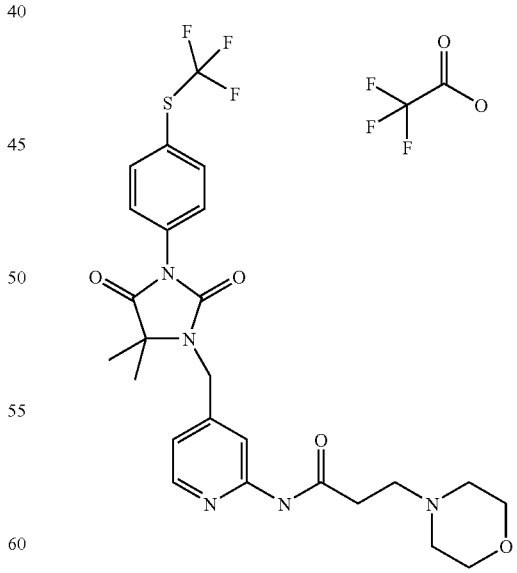

MS (LC-MS): 551.18, Retention time: 1.54 min.
NMR: 1.40: s, 6H, 2.85: m, 2H, 3.1: m, 2H, 3.4: m, 2H, 3.95: m, 2H, 4.65: s, 2H, 7.15: d, 1H, 7.65: d, 2H, 7.85: d, 2H, 8.15: s, 1H, 8.25: d, 1H.
The synthesis is described in Scheme 1.

EXAMPLE 73

N-{4-[5,5-dimethyl-2,4-dioxo-3-(4-trifluoromethyl-sulfanylphenyl)imidazolidin-1-ylmethyl]pyrid-2-yl}-3-[4-(2-hydroxyethyl)piperazin-1-yl]propionamide

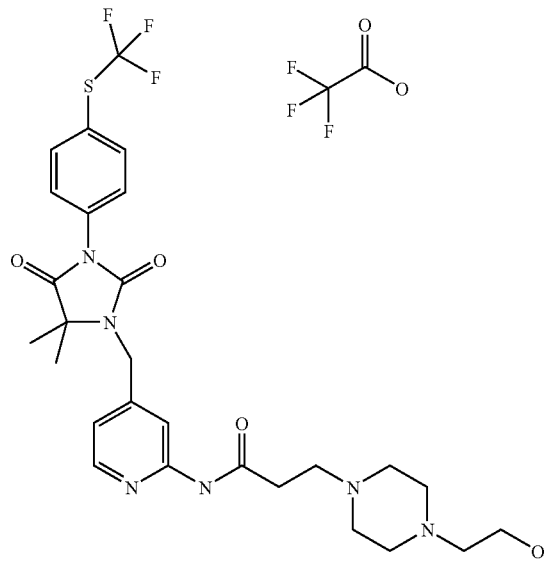

MS (LC-MS): 594.22, Retention time: 1.40 min.
NMR: 1.40: s, 6H, 2.55 to 3.50: m, 12H, 4.65: s, 2H, 7.15: m, 1H, 7.65: d, 2H, 7.85: d, 2H, 8.15: s, 1H, 8.25: d, 1H.
The synthesis is described in Scheme 1.

EXAMPLE 74

N-{4-[5,5-dimethyl-2,4-dioxo-3-(4-trifluoromethyl-sulfanylphenyl)imidazolidin-1-ylmethyl]pyrid-2-yl}-3-(4-methylpiperazin-1-yl)propionamide

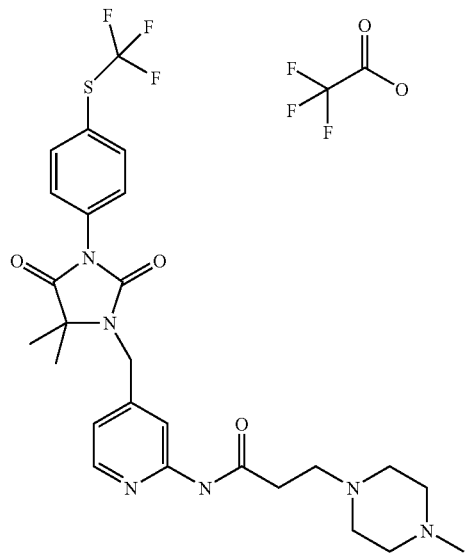

MS (LC-MS): 564.21, Retention time: 1.41 min.
NMR: 1.40: s, 6H, 2.55 to 3.50: m, 12H, 2.75: s, 3H, 4.65: s, 2H, 7.15: m, 1H, 7.65: d, 2H, 7.85: d, 2H, 8.15: s, 1H, 8.25: d, 1H.
The synthesis is described in Scheme 1.

EXAMPLE 75

{4-[5,5-dimethyl-2,4-dioxo-3-(4-trifluoromethylsul-fanylphenyl)imidazolidin-1-ylmethyl]pyrid-2-yl}-cyclopropanecarboxamide

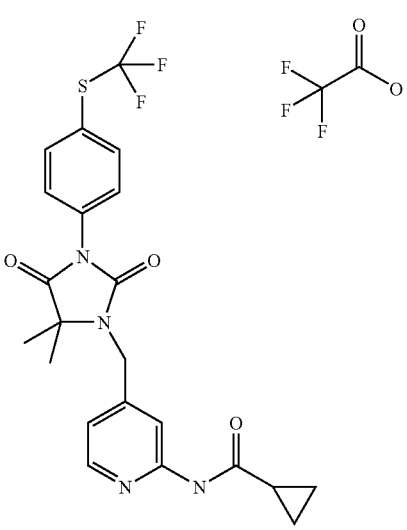

MS (LC-MS): 478.13, Retention time: 1.99 min.
NMR: 0.80: m, 4H, 1.15: t, 1H, 1.40: s, 6H, 4.65: s, 2H, 7.15: m, 1H, 7.65: d, 2H, 7.85: d, 2H, 8.15: s, 1H, 8.25: d, 1H.
The synthesis is described in Scheme 1.

EXAMPLE 76

5,5-dimethyl-1-[2-(pyrid-2-ylamino)pyrid-4-ylm-ethyl]-3-(4-trifluoromethylsulfanylphenyl)imidazoli-dine-2,4-dione

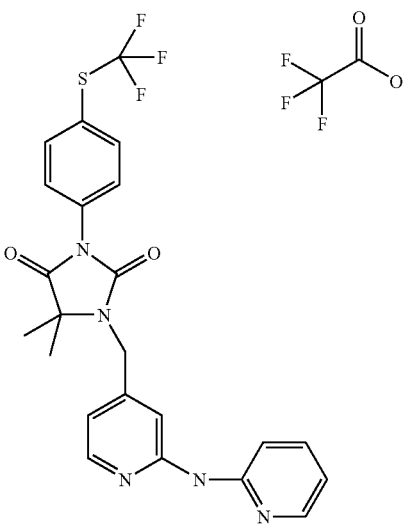

MS (LC-MS): 487.13, Retention time: 1.85 min.
NMR: 1.40: s, 6H, 4.65: s, 2H, 7.3: m, 4H, 7.65: d, 2H, 7.85: d, 2H, 8.05: s, 1H, 8.35: m, 1H.
The synthesis is described in Scheme 1.

EXAMPLE 77

N-{4-[5,5-dimethyl-2,4-dioxo-3-(4-trifluoromethyl-sulfanylphenyl)imidazolidin-1-ylmethyl]pyrid-2-yl}-3-pyrrolidin-1-ylpropionamide

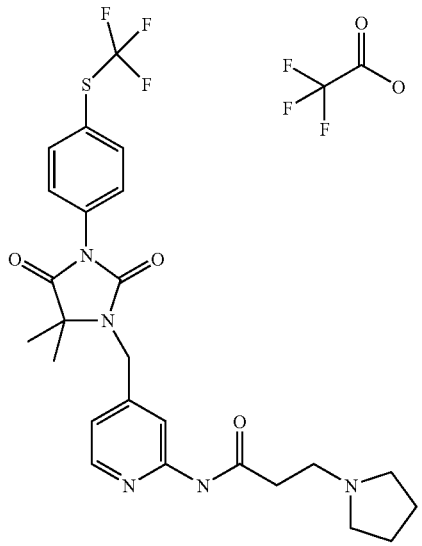

MS (LC-MS): 535.19, Retention time: 1.52 min.
NMR: 1.40: s, 6H, 1.8: m, 2H, 2.0: m, 2H, 2.85: m, 2H, 3.0: m, 2H, 3.4: m, 2H, 3.5: m, 2H, 4.65: s, 2H, 7.2: m, 1H, 7.65: d, 2H, 7.85: d, 2H, 8.15: s, 1H, 8.40: m, 1H.
The synthesis is described in Scheme 1.

EXAMPLE 78

5,5-dimethyl-1-{2-[3-(4-methylpiperazin-1-yl)pro-pylamino]pyrid-4-ylmethyl}-3-(4-trifluoromethyl-sulfanylphenyl)imidazolidine-2,4-dione

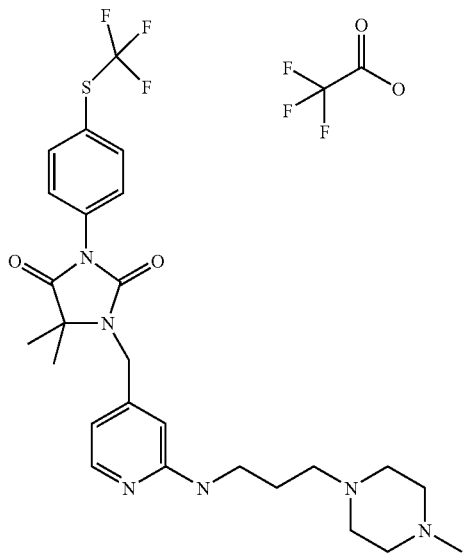

MS (LC-MS): 550.23, Retention time: 1.52 min.
NMR: 1.40: s, 6H, 2.6 to 3.5: m, 14H, 2.75: s, 3H, 4.65: s, 2H, 6.85: m, 1H, 6.95: m, 1H, 7.65: d, 2H, 7.9: m, 3H.
The synthesis is described in Scheme 1.

EXAMPLE 79

5,5-dimethyl-1-{2-[3-(4-ethylpiperazin-1-yl)propy-lamino]pyrid-4-ylmethyl}-3-(4-trifluoromethylsulfa-nylphenyl)imidazolidine-2,4-dione

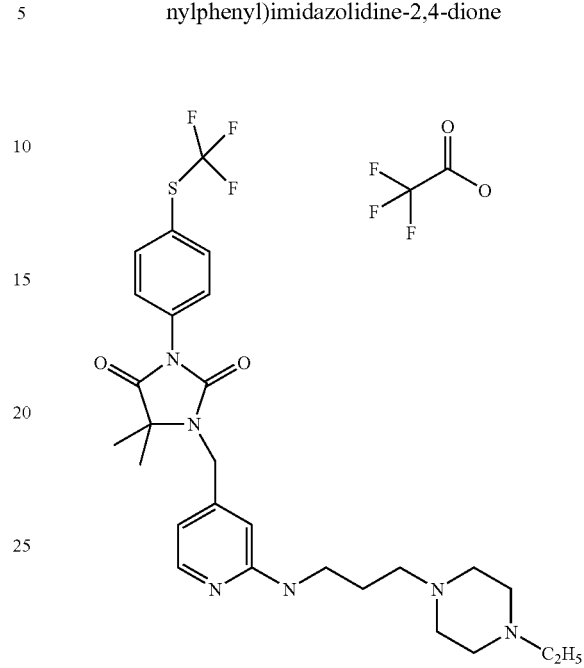

The synthesis is described in Scheme 1.

EXAMPLE 80

1-[2-(3-methoxyphenylamino)pyrid-4-ylmethyl]-5,5-dimethyl-3-(4-trifluoromethylsulfanylphenyl)imida-zolidine-2,4-dione

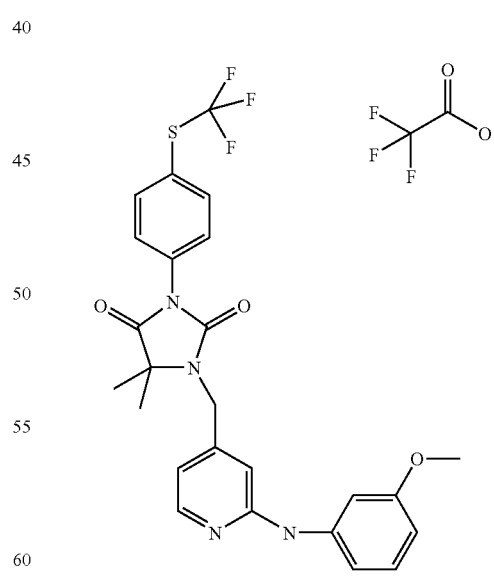

MS (LC-MS): 516.14, Retention time: 1.90 min.
NMR: 1.40: s, 6H, 3.7: s, 3H, 4.65: s, 2H, 6.6: m, 1H, 6.9: m, 2H, 7.15: m, 1H, 7.2: m, 1H, 7.25: m, 1H, 7.65: d, 2H, 7.85: d, 2H, 8.05: s, 1H.
The synthesis is described in Scheme 1.

EXAMPLE 81

N-{4-[5,5-dimethyl-2,4-dioxo-3-(4-trifluoromethyl-sulfanylphenyl)imidazolidin-1-ylmethyl]pyrid-2-yl}-3-(4-ethylpiperazin-1-yl)propionamide

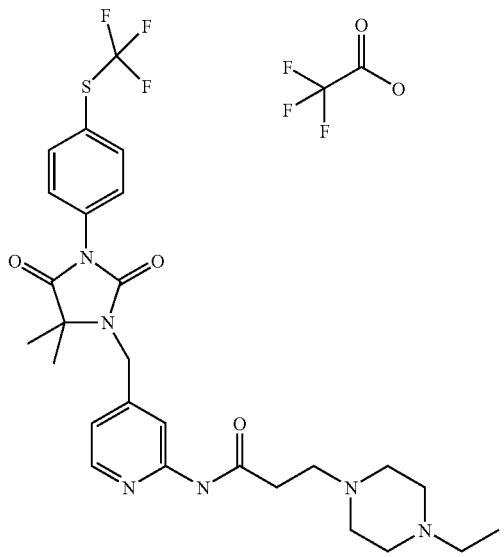

MS (LC-MS): 516.14, Retention time: 1.90 min.
NMR: 1.15: t, 3H, 1.40: s, 6H, 2.5 to 3.7: m, 14H, 4.65: s, 2H, 7.15: m, 1H, 7.65: d, 2H, 7.85: d, 2H, 8.15: s, 1H, 8.25: m, 1H.
The synthesis is described in Scheme 1.

EXAMPLE 82

5,5-dimethyl-1-[2-(3-methyl-2-oxopyrrolidin-1-yl)pyrid-4-ylmethyl]-3-(4-trifluoromethylsulfanylphenyl)imidazolidine-2,4-dione; Compound with Trifluoroacetic Acid

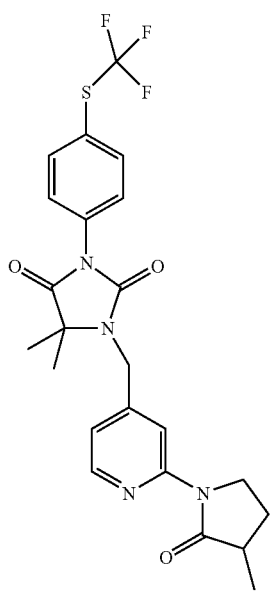

MS (LC-MS): 492.14; Retention time: 2.23 min.
NMR: 1.15: d, 3H, 1.40: s, 6H, 1.60: m, 1H, 2.30: m, 1H, 2.70: m, 1H, 3.80: m, 1H, 4.0: m, 1H; 4.65: s, 2H, 7.15: m, 1H; 7.65: d, 2H, 7.85: d, 2H, 8.35: m, 2H.
The synthesis is described in Scheme 1.

EXAMPLE 83

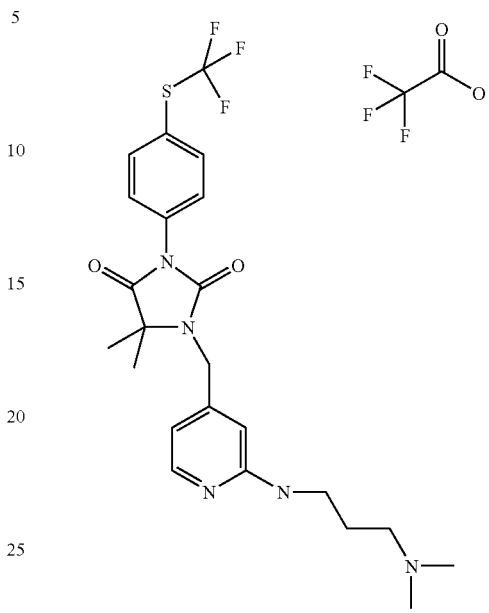

MS (LC-MS): 495.19; Retention time: 1.43 min.
The synthesis is described in Scheme 1.

EXAMPLE 84

5,5-dimethyl-1-[2-(4-pyrid-2-ylpiperazin-1-yl)pyrid-4-ylmethyl]-3-(4-trifluoromethylsulfanylphenyl)imidazolidine-2,4-dione; Compound with Trifluoroacetic Acid

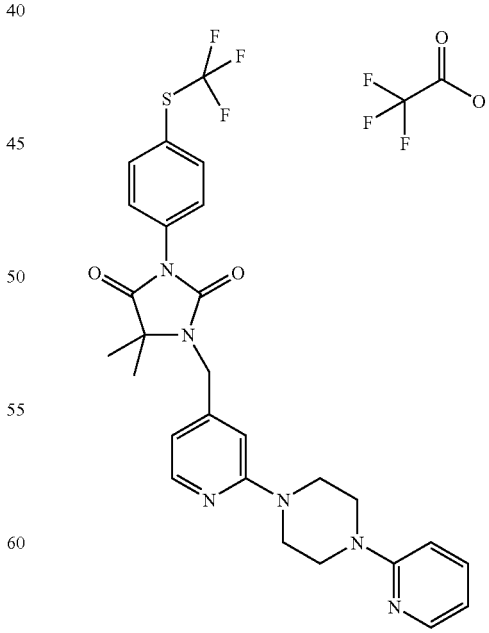

MS (LC-MS): 556.19; Retention time: 1.56 min.
The synthesis is described in Scheme 1.

EXAMPLE 85

N-{4-[5,5-dimethyl-2,4-dioxo-3-(4-trifluoromethyl-sulfanylphenyl)imidazolidin-1-ylmethyl]pyrid-2-yl}-3-piperid-1-ylpropionamide; Compound with Trifluoroacetic Acid

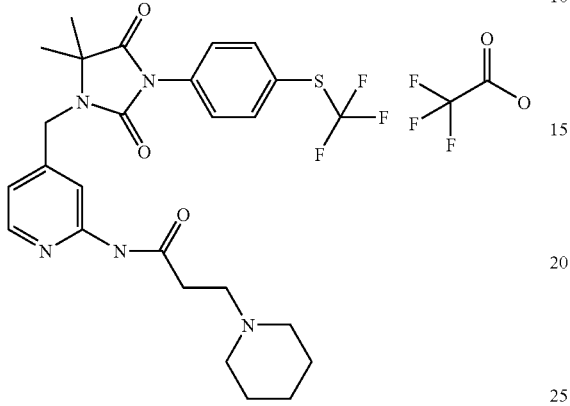

MS (LC-MS): 549.22; Retention time: 1.62 min.
NMR: 1.45: s, 6H, 1.55: m, 3H, 1.80: m, 2H, 2.80: m, 4H, 3.3 to 3.5: m, 7H, 4.65: s, 2H, 7.15: m, 1H, 7.65: d, 2H, 7.85: m, 2H, 8.15: m, 1H, 8.3: m, 1H, 9.0: m, 1H.
The synthesis is described in Scheme 1.

EXAMPLE 86

1-[2-(3-imidazol-1-ylpropylamino)pyrid-4-ylmethyl]-5,5-dimethyl-3-(4-trifluoromethylsulfanylphenyl)imidazolidine-2,4-dione; Compound with Trifluoroacetic Acid

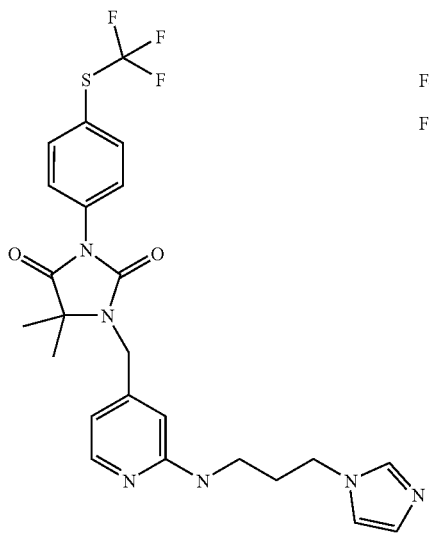

MS (LC-MS): 518.17; Retention time: 1.57 min.
The synthesis is described in Scheme 1.

EXAMPLE 87

1-[2-(4-ethylpyrid-2-ylamino)pyrid-4-ylmethyl]-5,5-dimethyl-3-(4-trifluoromethylsulfanylphenyl)imidazolidine-2,4-dione

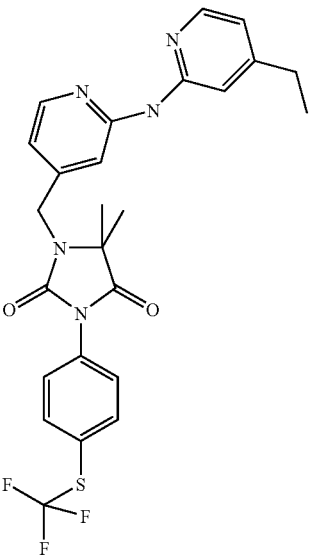

MS (LC-MS): 515.16; Retention time: 1.85 min.
NMR: 1.15: t, 3H, 1.45: s, 6H, 2.7: q, 2H, 4.75: s, 2H, 7.1: broad s, 2H, 7.3: broad s 2HM; 7.65: d, 2H, 7.85: d, 2H, 8.25: s, 1H, 8.45: s, 1H.
The synthesis is described in Scheme 1.

EXAMPLE 88

1-[2-(6-ethylpyrid-2-ylamino)pyrid-4-ylmethyl]-5,5-dimethyl-3-(4-trifluoromethylsulfanylphenyl)imidazolidine-2,4-dione

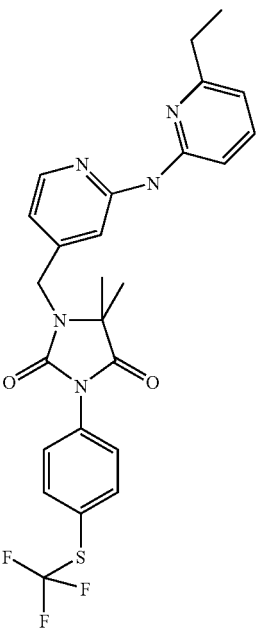

MS (LC-MS): 515.16; Retention time: 1.95 min.
NMR: 1.15: t, 3H, 1.45: s, 6H, 2.7: q, 2H, 4.75: s, 2H, 7.1: broad s, 2H, 7.3: broad s 2HM; 7.65: d, 2H, 7.85: d, 2H, 8.25: s, 1H, 8.45: s, 1H.
The synthesis is described in Scheme 1.

EXAMPLE 89

5,5-dimethyl-1-[2-(quinolin-2-ylamino)pyrid-4-ylmethyl]-3-(4-trifluoromethylsulfanylphenyl)imidazolidine-2,4-dione

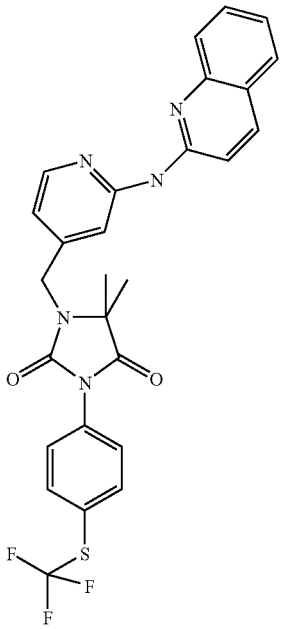

MS (LC-MS): 537.14; Retention time: 1.95 min.
NMR: 1.45: s, 6H, 4.75: s, 2H, 7.4 to 7.6: m, 6H, 7.65: d, 2H, 7.85: d, 2H, 8.00: broad s, 1H, 8.50: broad s, 2H.
The synthesis is described in Scheme 1.

EXAMPLE 90

5,5-dimethyl-1-[2-(4-methylpyrid-2-ylamino)pyrid-4-ylmethyl]-3-(4-trifluoromethylsulfanylphenyl)imidazolidine-2,4-dione

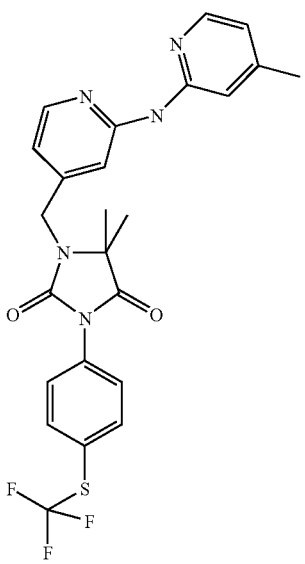

MS (LC-MS): 501.14; Retention time: 1.80 min.
NMR: 1.45: s, 6H, 2.4: s, 3H, 4.75: s, 2H, 7.1: m, 2H, 7.25: m, 2H, 7.65: d, 2H, 7.85: d, 2H, 8.20: broad s, 1H, 8.45: broad s, 1H.

The synthesis is described in Scheme 1.

EXAMPLE 91

5,5-dimethyl-1-[2-(6-methylpyrid-2-ylamino)pyrid-4-ylmethyl]-3-(4-trifluoromethylsulfanylphenyl)imidazolidine-2,4-dione

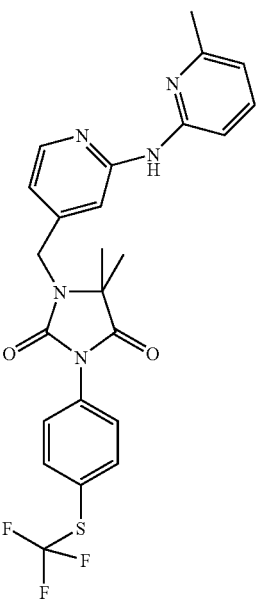

MS (LC-MS): 501.14; Retention time: 1.85 min.
NMR: 1.45: s, 6H; 2.55: s, 3H, 4.75: s, 2H, 7.1: m, 1H, 7.25: m, 2H, 7.4: s, 1H, 7.65: d, 2H, 7.85: m, 3H, 8.45: broad s, 1H.
The synthesis is described in Scheme 1.

EXAMPLE 92

1-[2-(3,5-dichloropyrid-2-ylamino)pyrid-4-ylmethyl]-5,5-dimethyl-3-(4-trifluoromethylsulfanylphenyl)imidazolidine-2,4-dione

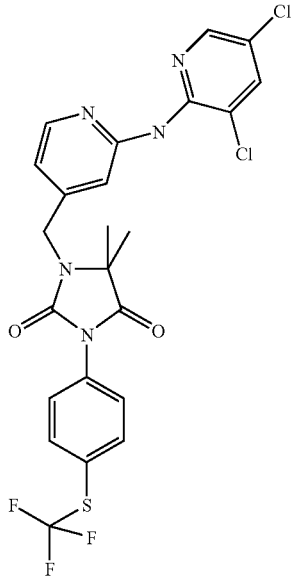

MS (LC-MS): 555.05; Retention time: 1.96 min.
NMR: 1.45: s, 6H, 4.70: s, 2H, 7.1: m, 1H, 7.20: m, 1H, 7.65: d, 2H, 7.85: m, 3H, 8.30: m, 3H.
The synthesis is described in Scheme 1.

EXAMPLE 93

1-[2-(4,6-dimethylpyrid-2-ylamino)pyrid-4-ylmethyl]-5,5-dimethyl-3-(4-trifluoromethylsulfanylphenyl)imidazolidine-2,4-dione

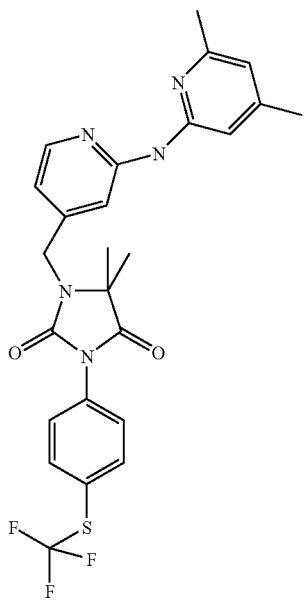

MS (LC-MS): 515.16; Retention time: 2.00 min.
NMR: 1.45: s; 2.35: s, 3H, 2.6: s, 3H; 6H, 4.75: s, 2H, 7.0: m, 2H, 7.35: m, 2H, 7.70: d, 2H, 7.9: d, 2H, 8.40: broad s, 1H.
The synthesis is described in Scheme 1.

EXAMPLE 94

5,5-dimethyl-1-[2-(methylpyrid-2-ylamino)pyrid-4-ylmethyl]-3-(4-trifluoromethylsulfanylphenyl)imidazolidine-2,4-dione

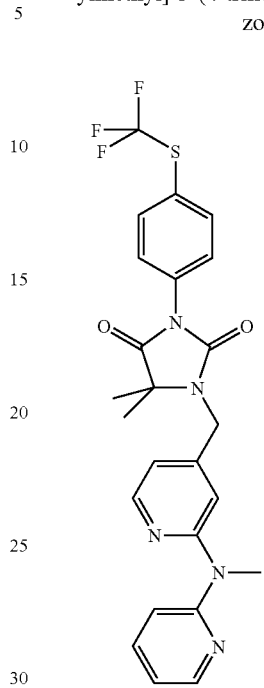

MS (LC-MS): 501.14; Retention time: 1.74 min.
The synthesis is described in Scheme 1.

EXAMPLE 95

5,5-dimethyl-1-[2-(pyrid-4-ylamino)pyrid-4-ylmethyl]-3-(4-trifluoromethylsulfanylphenyl)imidazolidine-2,4-dione

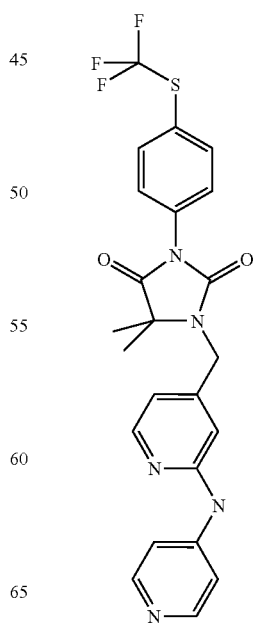

MS (LC-MS): 487.13; Retention time: 1.69 min.
NMR: 1.45: s; 4.70: s, 2H, 7.15: m, 1H, 7.25: m, 1H, 7.65: d, 2H, 7.9: d, 2H, 8.10: broad s, 2H, 8.40: s, 1H, 8.50: m, 2H.
The synthesis is described in Scheme 1.

EXAMPLE 96

5,5-dimethyl-1-[2-(pyrid-3-ylamino)pyrid-4-ylmethyl]-3-(4-trifluoromethylsulfanylphenyl)imidazolidine-2,4-dione

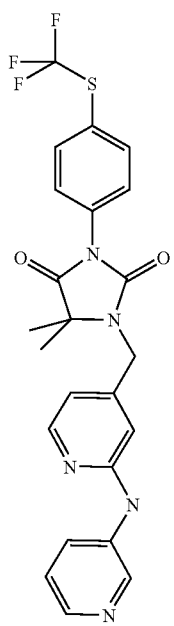

EXAMPLE 97

N-{4-[5,5-dimethyl-2,4-dioxo-3-(4-trifluoromethylsulfanylphenyl)imidazolidin-1-ylmethyl]pyrid-2-yl}-3-(2-oxoazepan-1-yl)propionamide

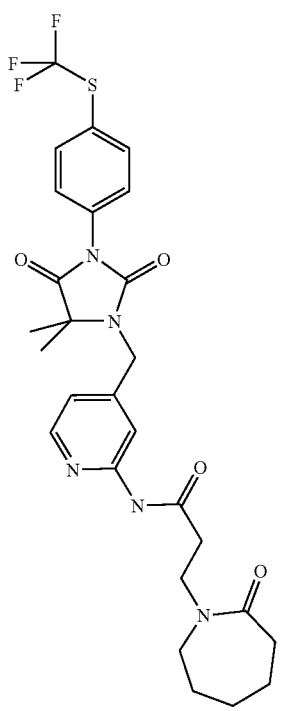

MS (LC-MS): 487.13; Retention time: 1.69 min.
NMR: 1.45: s; 4.60: s, 2H, 6.95: s, 1H, 7.05: s, 1H, 7.7: d, 2H, 7.8: m, 1H, 7.85: d, 2H, 8.25: s, 1H, 8.35: s, 1H, 8.45: m, 1H, 9.4: s, 1H.
The synthesis is described in Scheme 1.

MS (LC-MS): 577.20; Retention time: 2.00 min.
NMR: 1.45: s, 6H, 1.5: m, 4H, 1.55: m, 2H, 2.35: m, 2H, 2.6: m, 4H, 3.3 m, 2H, 4.65: s, 2H, 7.15: s, 1H, 7.65: d, 2H, 7.85: d, 2H, 8.1: s, 1H, 8.35: s, 1H.
The synthesis is described in Scheme 1.

EXAMPLE 98

3-(benzylmethylamino)-N-{4-[5,5-dimethyl-2,4-dioxo-3-(4-trifluoromethylsulfanylphenyl)imidazolidin-1-ylmethyl]pyrid-2-yl}propionamide

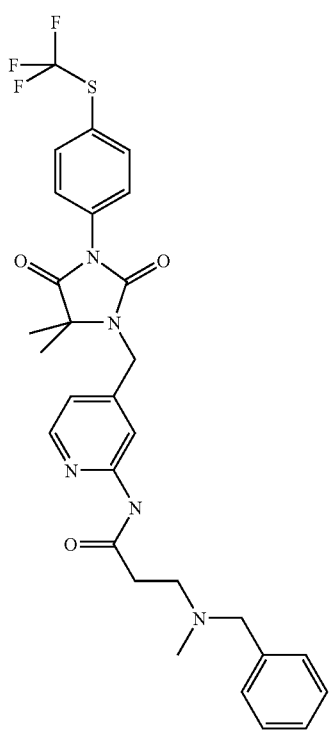

MS (LC-MS): 585.20, Retention time: 1.73 min.
NMR: 1.45: s, 6H, 2.2: s, 3H, 2.95: m, 2H, 3.3: m, 1H, 4.3: m, 1H, 4.4: m, 1H, 4.65: s, 2H, 7.2: s, 1H, 7.45: m, 2H, 7.50: m, 2H, 7.65: d, 2H, 7.85: d, 2H, 8.1: m, 1H, 8.3: m, 1H.
The synthesis is described in Scheme 1.

EXAMPLE 99

N-{4-[5,5-dimethyl-2,4-dioxo-3-(4-trifluoromethylsulfanylphenyl)imidazolidin-1-ylmethyl]pyrid-2-yl}-2-pyrrolidin-1-ylacetamide

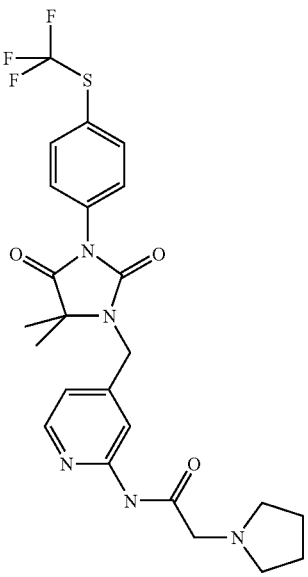

MS (LC-MS): 521.17, Retention time: 1.68 min.
NMR: 1.45: s, 6H, 1.85: m, 2H, 2.00: m, 2H, 3.1: m, 2H, 4.25: m, 2H, 4.7: s, 2H, 7.25: m, 1H, 7.65: d, 2H, 7.85: d, 2H, 8.1: broad s, 1H, 8.3: s, 1H.
The synthesis is described in Scheme 1.

EXAMPLE 100

N-{4-[5,5-dimethyl-2,4-dioxo-3-(4-trifluoromethylsulfanylphenyl)imidazolidin-1-ylmethyl]pyrid-2-yl}-2-(4-pyrid-2-ylpiperazin-1-yl)acetamide

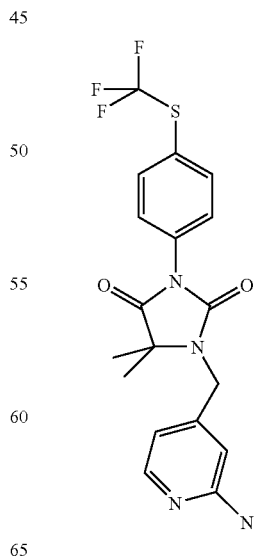

MS (LC-MS): 613.21, Retention time: 1.60 min.
NMR: 1.45: s, 6H, 3.3: broad m, 4H, 4.35: broad m, 4H, 4.65: s, 2H, 6.7: m, 1H, 6.9: m, 1H, 7.25: s, 1H, 7.65, m+d: 3H, 7.85: d, 2H, 8.15: m, 2H, 8.35: s, 1H.
The synthesis is described in Scheme 1.

EXAMPLE 101

2-[(2-dimethylaminoethyl)methylamino]-N-{4-[5,5-dimethyl-2,4-dioxo-3-(4-trifluoromethylsulfanylphenyl)imidazolidin-1-ylmethyl]pyrid-2-yl}acetamide

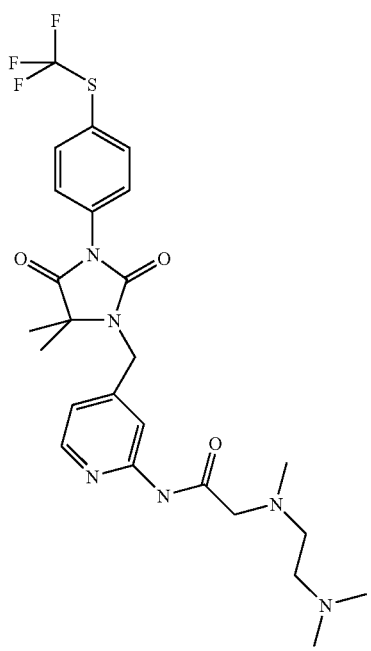

MS (LC-MS): 552.21, Retention time: 1.52 min.
NMR: 1.45: s, 6H, 2.75: s, 6H, 4.65: s, 2H, 7.20: m, 1H, 7.65: d, 2H, 7.85: d, 2H, 8.15: s, 1H, 8.30: m, 1H.
The synthesis is described in Scheme 1.

EXAMPLE 102

3-[(2-dimethylaminoethyl)methylamino]-N-{4-[5,5-dimethyl-2,4-dioxo-3-(4-trifluoromethylsulfanylphenyl)imidazolidin-1-ylmethyl]pyrid-2-yl}propionamide

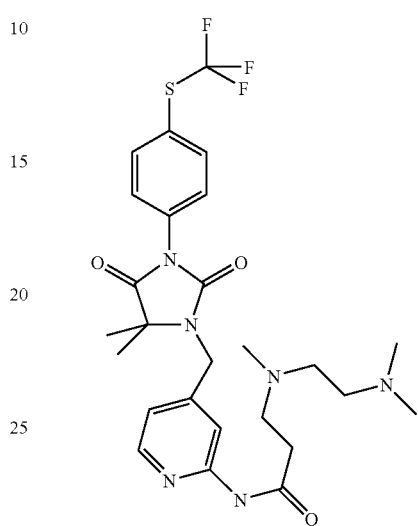

MS (LC-MS): 566.23, Retention time: 1.37 min.
NMR: 1.45: s, 6H, 2.75: s, 6H, 2.8 to 3.4: broad m, 8H, 7.20: m, 1H, 7.65: d, 2H, 7.85: d, 2H, 8.15: s, 1H, 8.30: m, 1H.
The synthesis is described in Scheme 1.

EXAMPLE 103

5,5-dimethyl-1-[2-(5-methylpyrid-2-ylamino)pyrid-4-ylmethyl]-3-(4-trifluoromethylsulfanylphenyl)imidazolidine-2,4-dione

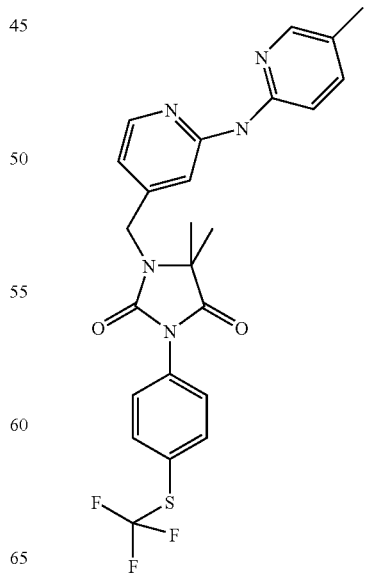

MS (LC-MS): 501.14, Retention time: 1.83 min.
NMR: 1.45: s, 6H, 2.3: s, 3H, 4.7: s, 2H, 7.3: m, 3H, 7.7: d, 2H, 7.9: d, 2H, 8.2: m, 1H, 8.35: m, 1H.
The synthesis is described in Scheme 1.

EXAMPLE 104

N-{4-[5,5-dimethyl-2,4-dioxo-3-(4-trifluoromethyl-sulfanylphenyl)imidazolidin-1-ylmethyl]pyrid-2-yl}-3,5-dimethoxybenzamide; Compound with Trifluoroacetic Acid

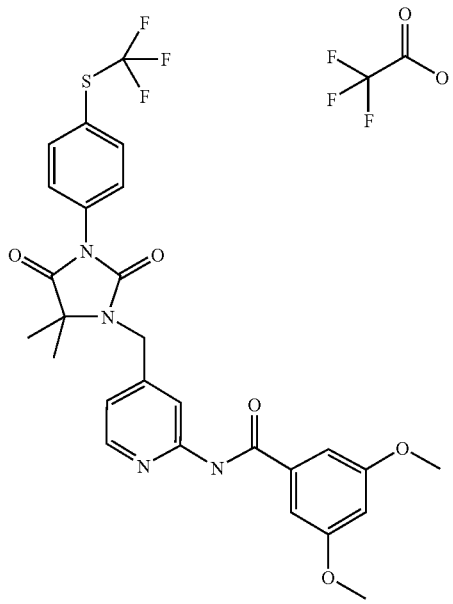

MS (LC-MS): 574.78, Retention time: 2.34 min.
NMR: 1.45: s, 6H, 2.3: s, 3H, 4.7: s, 2H, 6.7: s, 2H, 7.2: m, 2H, 7.25: m, 1H, 7.7: d, 2H, 7.9: d, 2H, 8.2: m, 1H, 8.3: m, 1H.
The synthesis is described in Scheme 1.

EXAMPLE 105

2-(benzylmethylamino)-N-{4-[5,5-dimethyl-2,4-dioxo-3-(4-trifluoromethylsulfanylphenyl)imidazolidin-1-ylmethyl]pyrid-2-yl}acetamide; Compound with Trifluoroacetic Acid

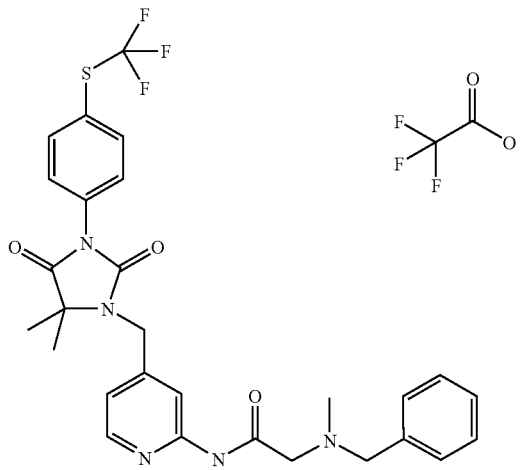

MS (LC-MS): 574.78, Retention time: 2.34 min.
NMR: 1.45: s, 6H, 2.8: s, 4.0 to 4.4: m, 4H, 4.7: s, 2H, 7.2: m, 1H, 7.4: m, 2H, 7.5: m, 2H, 7.7: d, 2H, 7.9: d, 2H, 8.1: m, 1H, 8.3: m, 1H.
The synthesis is described in Scheme 1.

EXAMPLE 106

5,5-dimethyl-1-[2-(pyrazin-2-ylamino)pyrid-4-ylmethyl]-3-(4-trifluoromethylsulfanylphenyl)imidazolidine-2,4-dione; Compound with Trifluoroacetic Acid

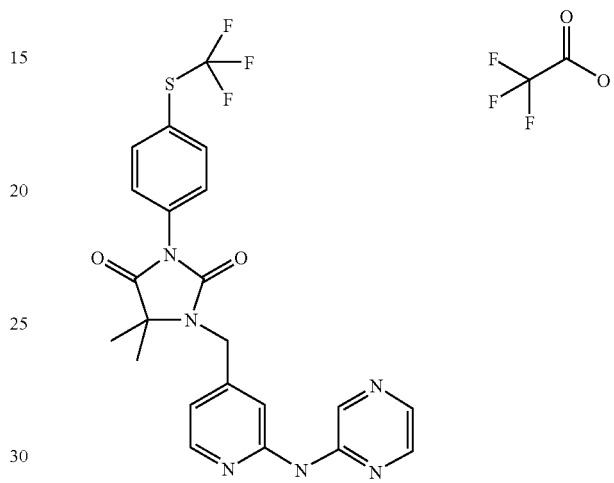

MS (LC-MS): 488.12, Retention time: 1.63.
NMR: 1.45: s, 6H, 4.7: s, 2H, 7.1: m, 1H, 7.6: m, 1H, 7.65: d, 2H, 7.9: d, 2H, 8.2: s, 1H; 8.3: m, 2H, 9.0: s, 1H.
The synthesis is described in Scheme 1.

EXAMPLE 107

N-{4-[5,5-dimethyl-2,4-dioxo-3-(4-trifluoromethylsulfanylphenyl)imidazolidin-1-ylmethyl]pyrid-2-yl}-2-phenylbutyramide; Compound with Trifluoroacetic Acid

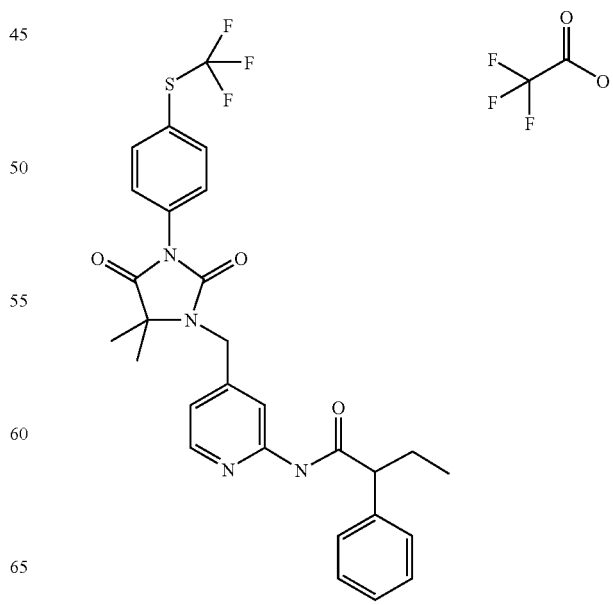

MS (LC-MS): 566.18, Retention time: 2.43.
NMR: 0.7: t, 3H, 1.4: s, 6H, 1.7: m, 1H, 2.05: m, 1H, 4.6: s, 2H, 7.1: s, 1H, 7.25: m, 1H, 7.3: m, 1H, 7.4: m, 2H, 7.65: d, 2H, 7.85: d, 2H, 8.15: s, 1H, 8.25: m, 1H.
The synthesis is described in Scheme 1.

EXAMPLE 108

N-{4-[5,5-dimethyl-2,4-dioxo-3-(4-trifluoromethyl-sulfanylphenyl)imidazolidin-1-ylmethyl]pyrid-2-yl}-3-(3-methylpiperid-1-yl)propionamide; Compound with Trifluoroacetic Acid

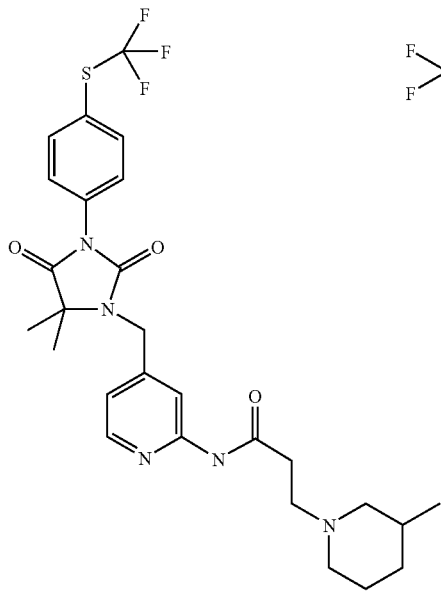

MS (LC-MS): 563.22, Retention time: 1.62.
The synthesis is described in Scheme 1.

EXAMPLE 109

1-[2-(4-methoxyphenylamino)pyrid-4-ylmethyl]-5,5-dimethyl-3-(4-trifluoromethylsulfanylphenyl)imidazolidine-2,4-dione

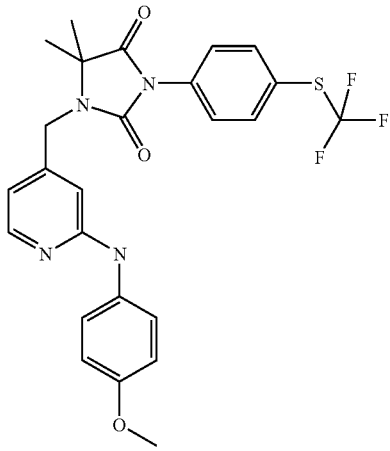

MS (LC-MS): 517.1; Retention time: 1.74.
NMR: 1.4: s, 6H, 4.6: s, 2H, 6.85: broad s, 1H, 7.0: m, 1H, 7.4: m, 2H, 7.6: d, 2H, 7.9: d, 2H, 8.95: s, 1H.
The synthesis is described in Scheme 1.

EXAMPLE 110

5,5-dimethyl-1-[2-(2-oxopyrrolidin-1-yl)pyrid-4-ylmethyl]-3-(4-trifluoromethylsulfanylphenyl)imidazolidine-2,4-dione

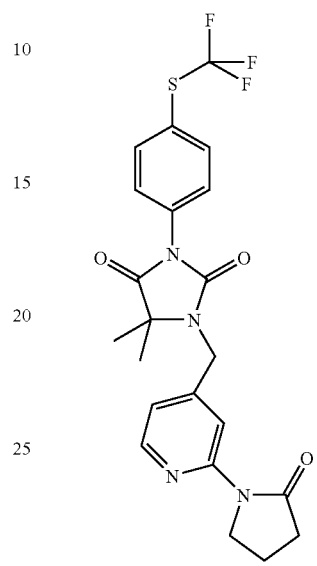

MS (LC-MS): 478.13; Retention time: 1.83.
The synthesis is described in Scheme 1.

EXAMPLE 111

{4-[5,5-dimethyl-2,4-dioxo-3-(4-trifluoromethylsulfanylphenyl)imidazolidin-1-ylmethyl]pyrid-2-yl}-pyrazine-2-carboxamide; Compound with Trifluoroacetic Acid

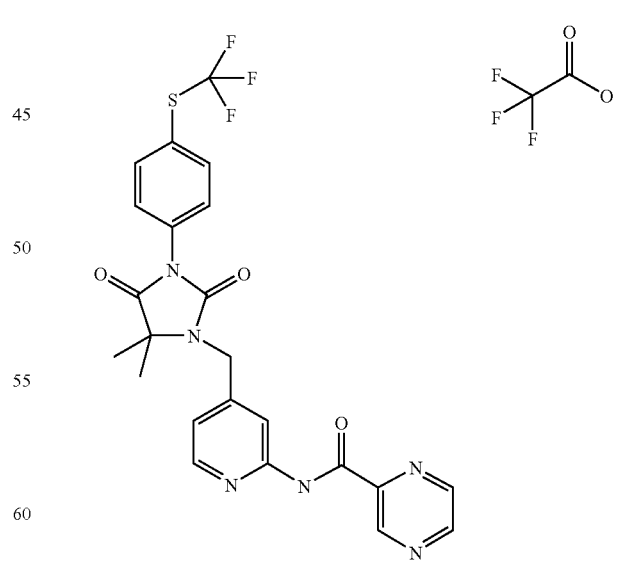

MS (LC-MS): 516.12; Retention time: 2.42.
NMR: 1.4: s, 6H, 4.7: s, 2H, 7.3: m, 1H, 7.65: d, 2H, 7.95: d, 2H, 8.3: s, 1H, 8.4: s, 1H, 8.7: s, 1H, 9.0: s, 1H, 9.4: s, 1H.
The synthesis is described in Scheme 1.

EXAMPLE 112

N-{4-[5,5-dimethyl-2,4-dioxo-3-(4-trifluoromethyl-sulfanylphenyl)imidazolidin-1-ylmethyl]pyrid-2-yl}-2,2-dimethylpropionamide; Compound with Trifluoroacetic Acid

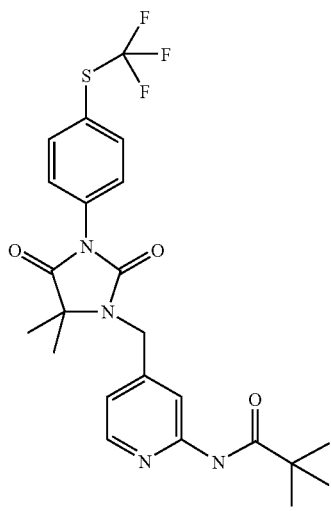

MS (LC-MS): 494.16; Retention time: 2.48.

NMR: 1.2: s, 9H, 1.4: s, 6H, 4.7: s, 2H, 7.2: m, 1H, 7.65: d, 2H, 7.90: d, 2H, 8.1: s, 1H, 8.3: s, 1H.

The synthesis is described in Scheme 1.

EXAMPLE 113

{4-[5,5-dimethyl-2,4-dioxo-3-(4-trifluoromethylsulfanylphenyl)imidazolidin-1-ylmethyl]pyrid-2-yl}-thiophene-2-carboxamide; Compound with Trifluoroacetic Acid

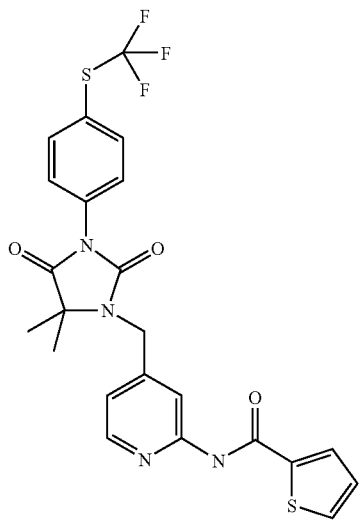

MS (LC-MS): 520.09; Retention time: 2.14.

NMR: 1.4: s, 6H, 4.7: s, 2H, 7.2: m, 2H, 7.65: d, 2H, 7.8: m, 3H, 8.2: s, 1H, 8.25: s, 1H, 8.4: m, 1H.

The synthesis is described in Scheme 1.

EXAMPLE 114

N-{4-[5,5-dimethyl-2,4-dioxo-3-(4-trifluoromethyl-sulfanylphenyl)imidazolidin-1-ylmethyl]pyrid-2-yl}-4-methylbenzamide; Compound with Trifluoroacetic Acid

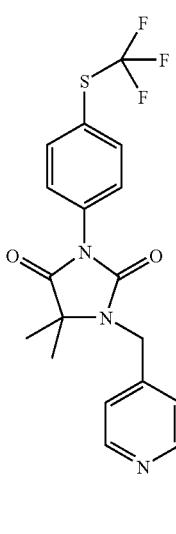

MS (LC-MS): 528.16; Retention time: 2.23.

NMR: 1.4: s, 6H, 4.7: s, 2H, 7.2: m, 1H, 7.3: d, 2H, 7.7: d, 2H, 7.85: d, 2H, 7.95: d, 2H, 8.2: s, 1H, 8.3: s, 1H.

The synthesis is described in Scheme 1.

EXAMPLE 115

N-{4-[5,5-dimethyl-2,4-dioxo-3-(4-trifluoromethyl-sulfanylphenyl)imidazolidin-1-ylmethyl]pyrid-2-yl}-3-(3,5-dimethylpiperid-1-yl)propionamide; Compound with Trifluoroacetic Acid

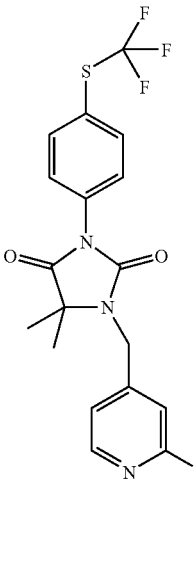

MS (LC-MS): 577.23; Retention time: 1.72.
The synthesis is described in Scheme 1.

EXAMPLE 116

N-{4-[5,5-dimethyl-2,4-dioxo-3-(4-trifluoromethyl-sulfanylphenyl)imidazolidin-1-ylmethyl]pyrid-2-yl}-3-(4-pyrid-2-ylpiperazin-1-yl)propionamide; Compound with Trifluoroacetic Acid

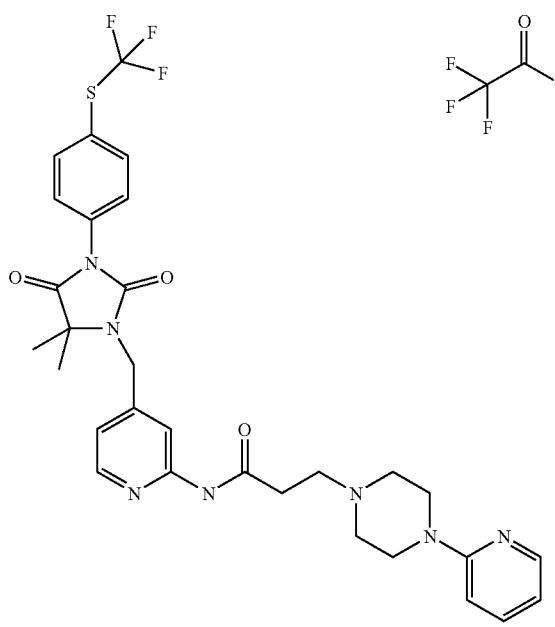

MS (LC-MS): 627.22; Retention time: 1.50.

NMR: 1.4: s, 6H, 2.9: m, 2H, 3.1: m, 2H, 3.4: m, 2H, 3.6: m, 2H, 4.4: m, 2H, 4.65: s, 2H, 6.7: m, 1H, 6.95: d, 1H, 7.2: m, 1H, 7.7: d, 2H, 7.9: d, 2H, 8.15: m, 2H, 8.3: m, 1H.

The synthesis is described in Scheme 1.

EXAMPLE 117

5,5-dimethyl-1-[2-(5-trifluoromethylpyrid-2-ylamino)pyrid-4-ylmethyl]-3-(4-trifluoromethylsulfanylphenyl)imidazolidine-2,4-dione

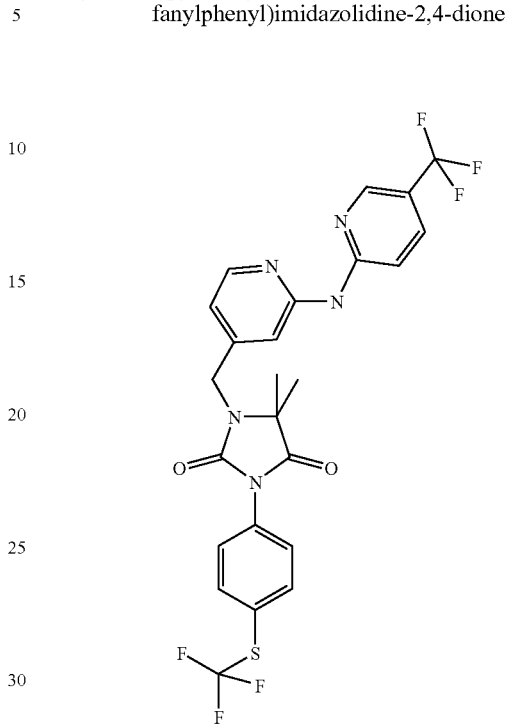

MS (LC-MS): 555.51; Retention time: 1.78.
The synthesis is described in Scheme 1.

EXAMPLE 118

N-{4-[5,5-dimethyl-2,4-dioxo-3-(4-trifluoromethyl-sulfanylphenyl)imidazolidin-1-ylmethyl]pyrid-2-yl}-3-methoxybenzamide; Compound with Trifluoroacetic Acid

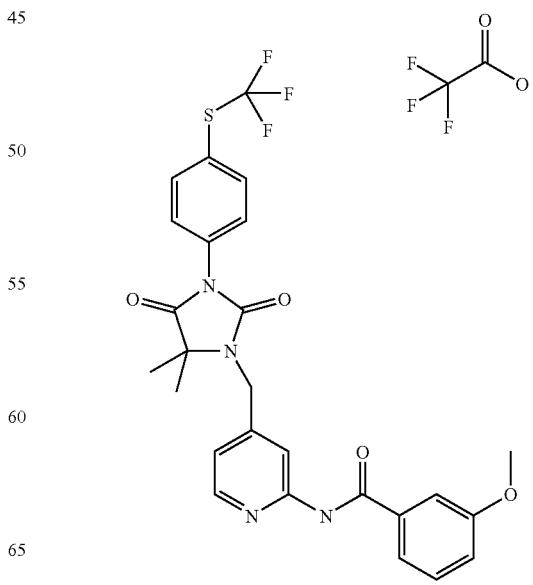

MS (LC-MS): 544.14; Retention time: 2.15.
The synthesis is described in Scheme 1.

EXAMPLE 119

1-(3,5-dichlorophenyl)-3-{4-[5,5-dimethyl-2,4-di-oxo-3-(4-trifluoromethylsulfanylphenyl)imidazoli-din-1-ylmethyl]pyrid-2-yl}urea

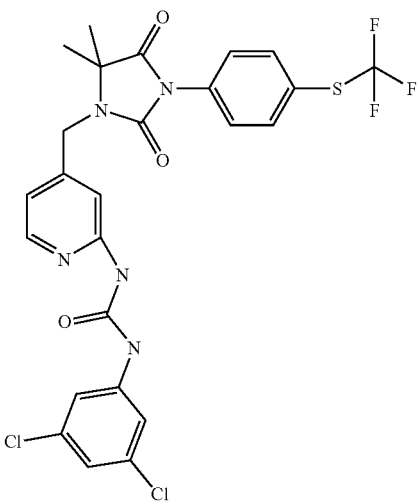

MS (LC-MS): 597.06; Retention time: 2.15 min.
The synthesis is described in Scheme 2.

EXAMPLE 120

Methyl 3-(3-{4-[5,5-dimethyl-2,4-dioxo-3-(4-trif-luoromethylsulfanylphenyl)imidazolidin-1-ylmethyl]pyrid-2-yl}thioureido)benzoate

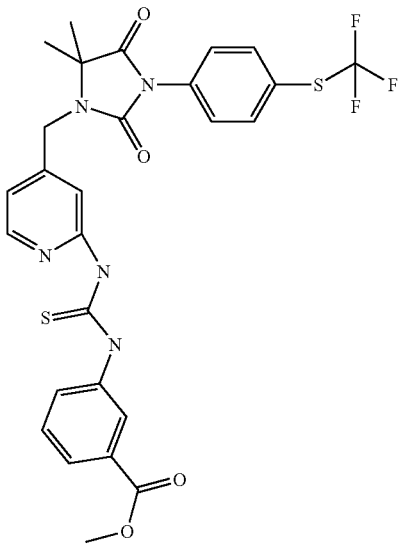

MS (LC-MS): 603.12; Retention time: 2.81 min.
The synthesis is described in Scheme 2.

EXAMPLE 121

1-{4-[5,5-dimethyl-2,4-dioxo-3-(4-trifluoromethyl-sulfanylphenyl)imidazolidin-1-ylmethyl]pyrid-2-yl}-3-phenylurea

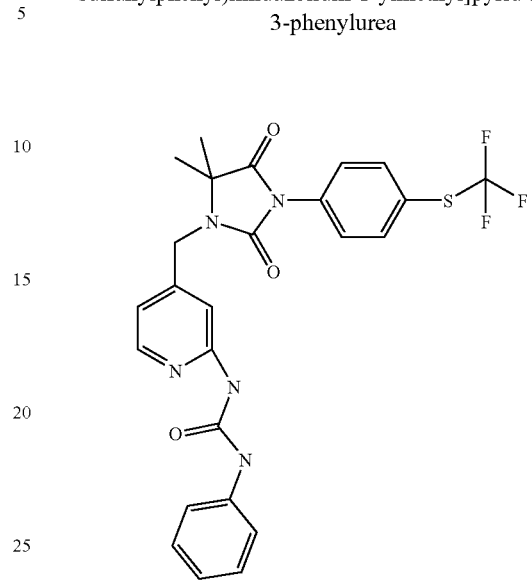

MS (LC-MS): 529.14; Retention time: 2.33 min.
NMR: 1.50: s, 6H, 4.65: s, 1H; 7.0: m, 2H, 7.30: m, 2H, 7.5: m, 3H, 7.65: d, 2H, 7.85: d, 2H, 8.25: d, 1H, 9.4: s, 1H.
The synthesis is described in Scheme 2.

EXAMPLE 122

1-(2,4-dichlorophenyl)-3-{4-[5,5-dimethyl-2,4-di-oxo-3-(4-trifluoromethylsulfanylphenyl)imidazoli-din-1-ylmethyl]pyrid-2-yl}urea

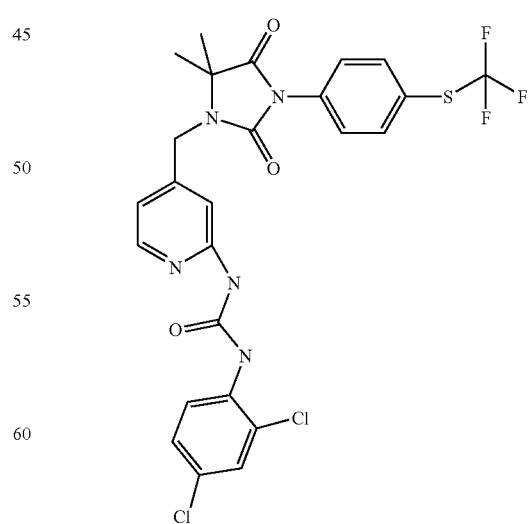

MS (LC-MS): 597.06; Retention time: 3.00 min.
The synthesis is described in Scheme 2.

EXAMPLE 123

1-(3-chlorophenyl)-3-{4-[5,5-dimethyl-2,4-dioxo-3-(4-trifluoromethylsulfanylphenyl)imidazolidin-1-ylmethyl]pyrid-2-yl}thiourea

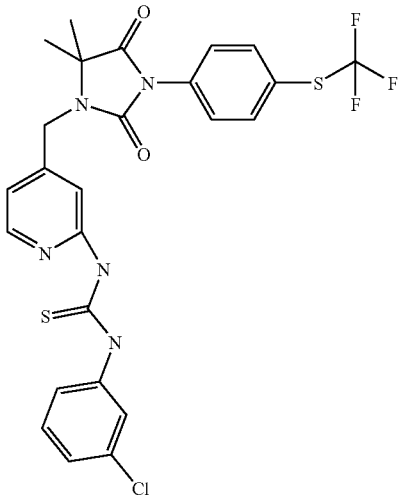

MS (LC-MS): 579.08; Retention time: 3.05 min.

The synthesis is described in Scheme 2.

EXAMPLE 124

Methyl 2-(3-{4-[5,5-dimethyl-2,4-dioxo-3-(4-trifluoromethylsulfanylphenyl)imidazolidin-1-ylmethyl]pyrid-2-yl}thioureido)benzoate

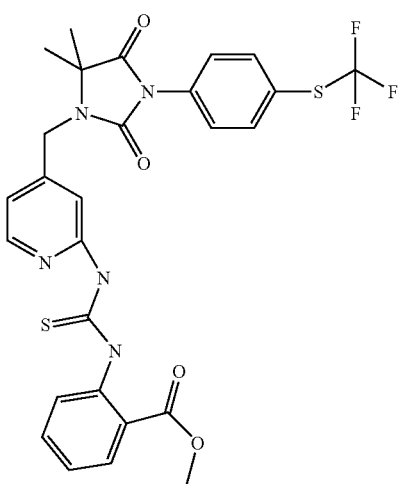

MS (LC-MS): 603.12; Retention time: 2.85 min.

The synthesis is described in Scheme 2.

EXAMPLE 125

3,5-diacetoxy-2-acetoxymethyl-6-(3-{4-[5,5-dimethyl-2,4-dioxo-3-(4-trifluoromethylsulfanylphenyl)imidazolidin-1-ylmethyl]pyrid-2-yl}thioureido)tetrahydropyran-4-yl acetate

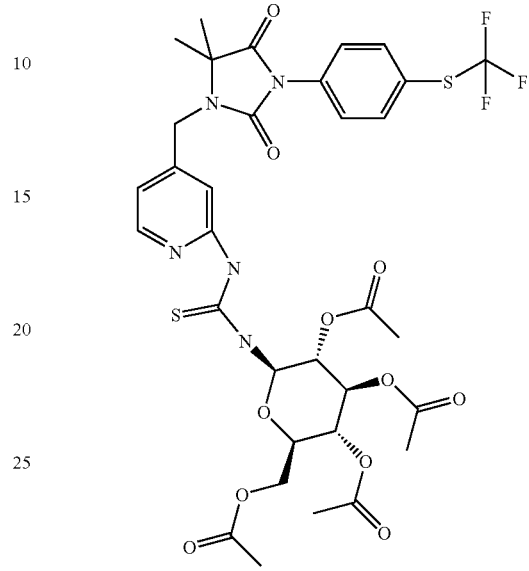

MS (LC-MS): 799.18, Retention time: 2.60 min.

The synthesis is described in Scheme 2.

EXAMPLE 126

1-(4-dimethylaminophenyl)-3-{4-[5,5-dimethyl-2,4-dioxo-3-(4-trifluoromethylsulfanylphenyl)imidazolidin-1-ylmethyl]pyrid-2-yl}thiourea

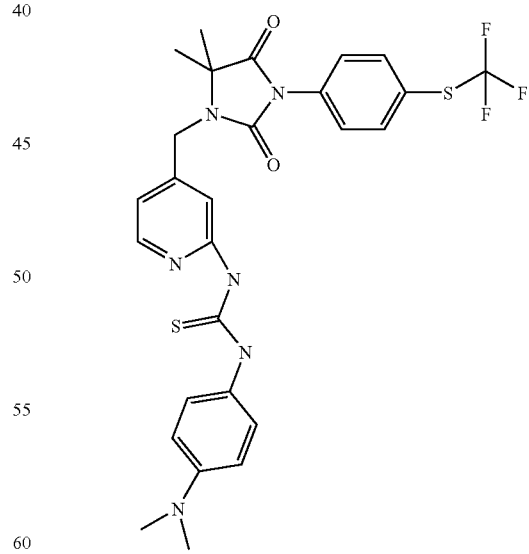

MS (LC-MS): 588.16; Retention time: 1.99.

NMR: 1.4: s, 6H, 2.9: s, 6H, 4.7: s, 2H, 6.7: d, 2H, 7.1: m, 1H, 7.25: s, 1H, 7.4: d, 2H, 7.7: d, 2H, 7.9: d, 2H, 8.25: m, 1H.

The synthesis is described in Scheme 2.

EXAMPLE 127

1-(2,4-dimethoxyphenyl)-3-{4-[5,5-dimethyl-2,4-dioxo-3-(4-trifluoromethylsulfanylphenyl)imidazolidin-1-ylmethyl]pyrid-2-yl}urea

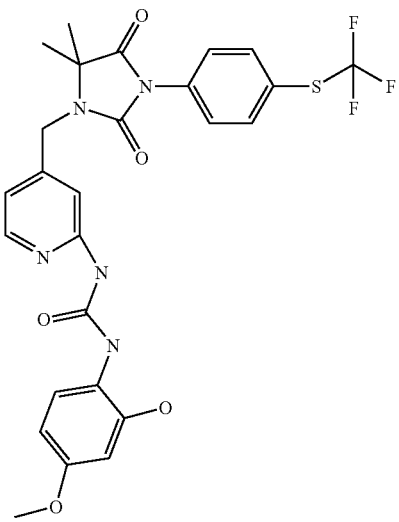

MS (LC-MS): 589.60; Retention time: 1.98.
The synthesis is described in Scheme 2.

EXAMPLE 128

3-(3-{4-[5,5-dimethyl-2,4-dioxo-3-(4-trifluoromethylsulfanylphenyl)imidazolidin-1-ylmethyl]pyrid-2-yl}thioureido)benzoic acid

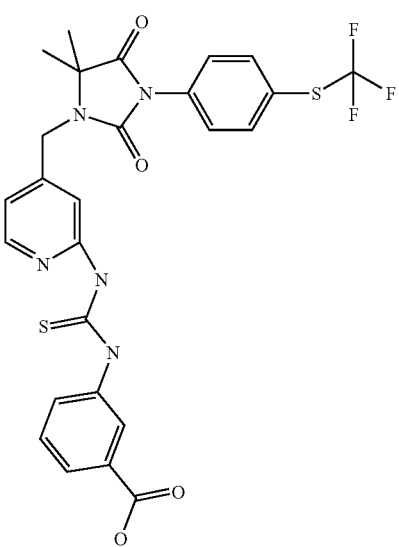

MS (LC-MS): 589.11; Retention time: 2.30.
The synthesis is described in Scheme 2.

EXAMPLE 129

1-{4-[5,5-dimethyl-2,4-dioxo-3-(4-trifluoromethylsulfanylphenyl)imidazolidin-1-ylmethyl]pyrid-2-yl}-3-(2-methoxyphenyl)urea

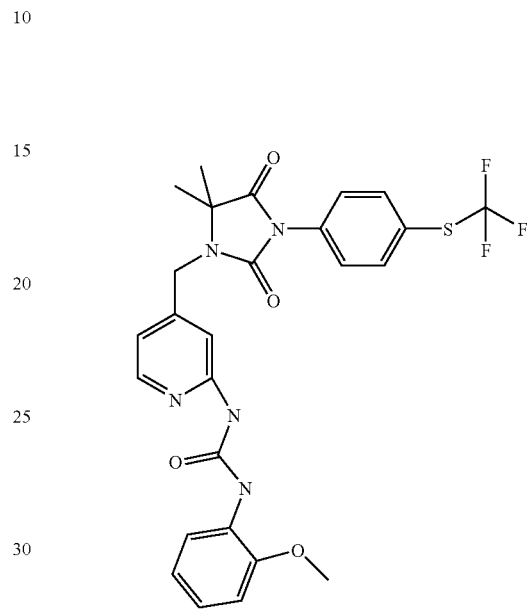

MS (LC-MS): 559.15; Retention time: 1.88.
The synthesis is described in Scheme 2.

EXAMPLE 130

1-(2-aminopyrid-4-ylmethyl)-5,5-dimethyl-3-(4-trifluoromethylsulfanylphenyl)imidazolidine-2,4-dione

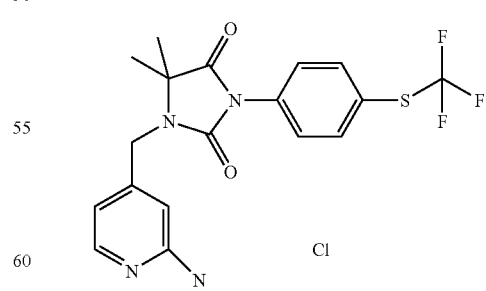

MS (LC-MS): 410.10; Retention time: 1.57.
NMR: 1.4: s, 6H, 4.6: s, 2H, 6.9: d, 1H, 7.0: s, 1H, 7.7: d, 2H, 7.85: d, 2H, 7.95: d, 1H, 8.0: broad s, 1H.
The synthesis is described in Scheme 2.

EXAMPLE 131

1-(2,6-dichloropyrid-4-yl)-3-{4-[5,5-dimethyl-2,4-dioxo-3-(4-trifluoromethylsulfanylphenyl)imidazolidin-1-ylmethyl]pyrid-2-yl}urea

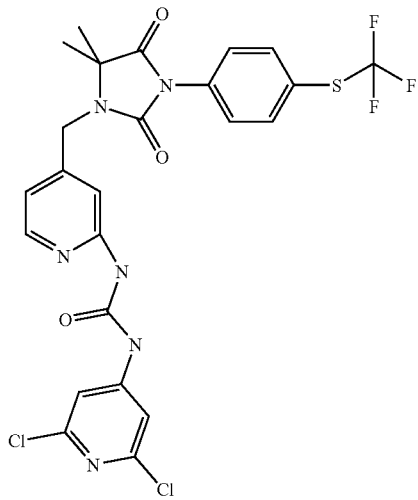

MS (LC-MS): 599.42; Retention time: 2.73 min.
NMR: 1.40, s, 6H, 4.65 s, 2H, 7.15: m, 1H, 7.65: d, 2H, 7.85: d, 2H, 8.15: s, 1H, 8.25: m, 1H.
The synthesis is described in Scheme 2.

EXAMPLE 132

1-(2,6-dichlorophenyl)-3-{4-[5,5-dimethyl-2,4-dioxo-3-(4-trifluoromethylsulfanylphenyl)imidazolidin-1-ylmethyl]pyrid-2-yl}urea

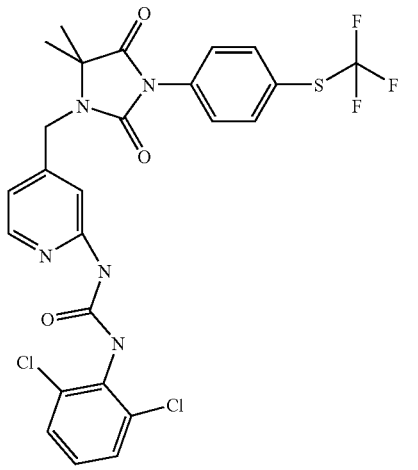

MS (LC-MS): 597.06; Retention time: 2.44 min.
The synthesis is described in Scheme 2.

EXAMPLE 133

1-(2,3-dichlorophenyl)-3-{4-[5,5-dimethyl-2,4-dioxo-3-(4-trifluoromethylsulfanylphenyl)imidazolidin-1-ylmethyl]pyrid-2-yl}urea

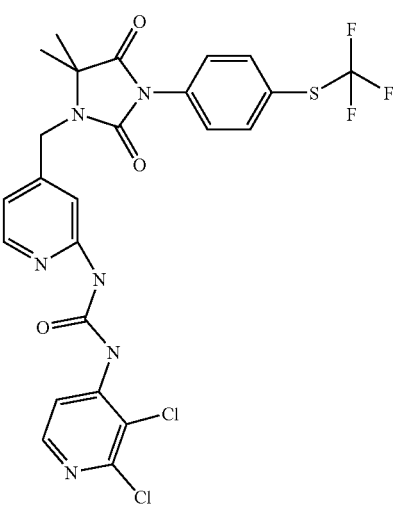

MS (LC-MS): 597.06; Retention time: 2.08 min.
The synthesis is described in Scheme 2.

EXAMPLE 134

1-{4-[5,5-dimethyl-2,4-dioxo-3-(4-trifluoromethylsulfanylphenyl)imidazolidin-1-ylmethyl]pyrid-2-yl}-3-pyrid-3-ylthiourea

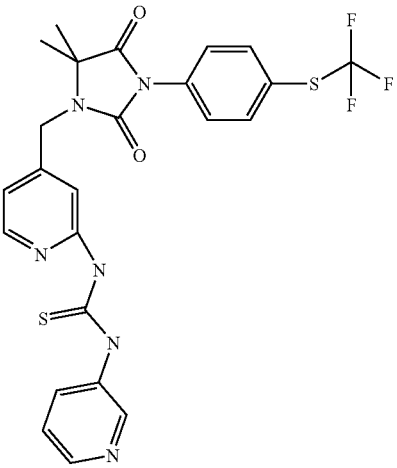

MS (LC-MS): 546.11; Retention time: 1.89 min.
The synthesis is described in Scheme 2.

EXAMPLE 135

1-[2-chloro-6-(4-methylthiazol-2-ylamino)pyrid-4-ylmethyl]-5,5-dimethyl-3-(4-trifluoromethylsulfanylphenyl)imidazolidine-2,4-dione

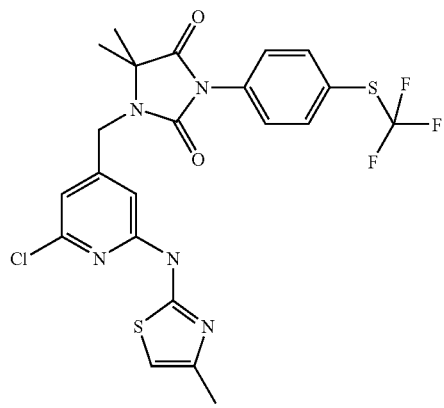

MS (LC-MS): 541.06; Retention time: 2.49 min.
The synthesis is described in Scheme 3.

EXAMPLE 136

N-{6-chloro-4-[5,5-dimethyl-2,4-dioxo-3-(4-trifluoromethylsulfanylphenyl)imidazolidin-1-ylmethyl]pyrid-2-yl}-2-phenylbutyramide

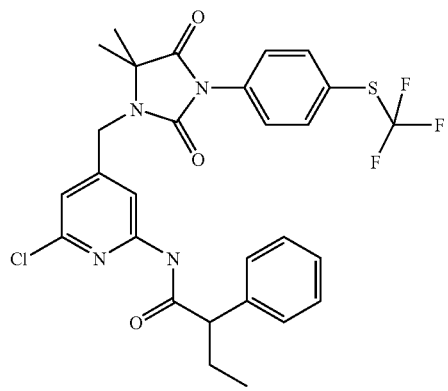

MS (LC-MS): 541.06; Retention time: 2.49 min.
The synthesis is described in Scheme 3.

EXAMPLE 137

N-{6-acetylamino-4-[5,5-dimethyl-2,4-dioxo-3-(4-trifluoromethylsulfanylphenyl)imidazolidin-1-ylmethyl]pyrid-2-yl}acetamide

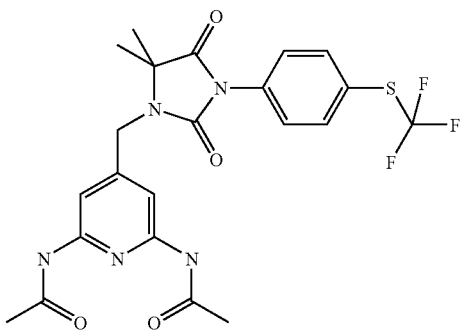

MS (LC-MS): 509.13; Retention time: 1.73 min.
The synthesis is described in Scheme 3.

EXAMPLE 138

1-[2-chloro-6-(4-methylpyrid-2-ylamino)pyrid-4-ylmethyl]-5,5-dimethyl-3-(4-trifluoromethylsulfanylphenyl)imidazolidine-2,4-dione

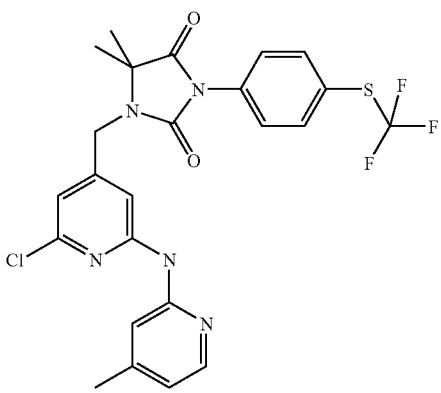

MS (LC-MS): 535.11; Retention time: 1.90 min.
The synthesis is described in Scheme 3.

EXAMPLE 139

1-[2,6-bis(3-methoxyphenylamino)pyrid-4-ylmethyl]-5,5-dimethyl-3-(4-trifluoromethoxyphenyl)imidazolidine-2,4-dione; Compound with Trifluoroacetic Acid

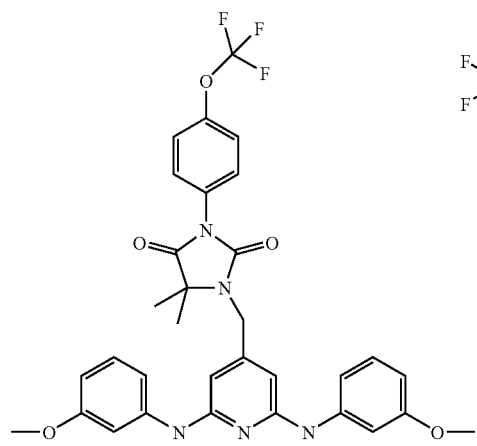

MS (LC-MS): 621.22; Retention time: 1.95 min.
The synthesis is described in Scheme 3.

EXAMPLE 140

1-[2,6-bis(2,4-dimethoxyphenylamino)pyrid-4-ylmethyl]-5,5-dimethyl-3-(4-trifluoromethoxyphenyl)imidazolidine-2,4-dione; Compound with Trifluoroacetic Acid

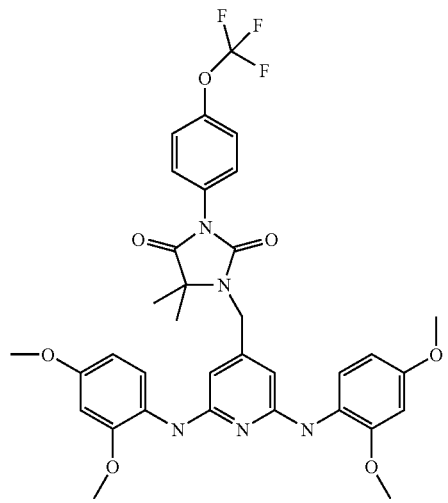

MS (LC-MS): 681.24; Retention time: 1.83 min.
The synthesis is described in Scheme 3.

EXAMPLE 141

1-[2,6-bis(4-methoxyphenylamino)pyrid-4-ylmethyl]-5,5-dimethyl-3-(4-trifluoromethoxyphenyl)imida-zolidine-2,4-dione; Compound with Trifluoroacetic Acid

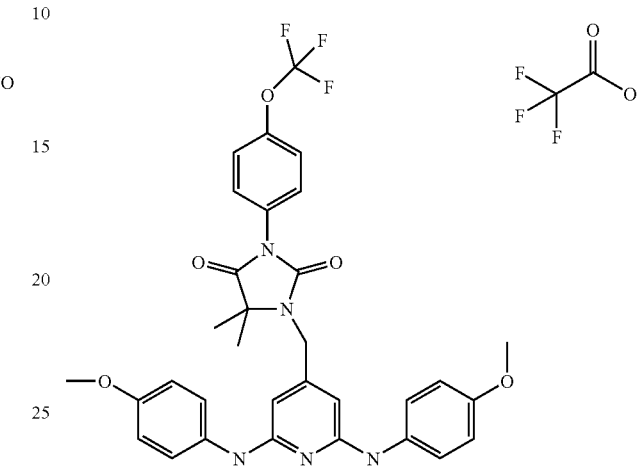

MS (LC-MS): 621.22; Retention time: 1.63 min.
The synthesis is described in Scheme 3.

EXAMPLE 142

N-{4-[5,5-dimethyl-2,4-dioxo-3-(4-trifluoromethoxyphenyl)imidazolidin 1-ylmethyl]-6-estobutyrylaminopyrid-2-yl}isobutyramide; Compound with Trifluoroacetic Acid

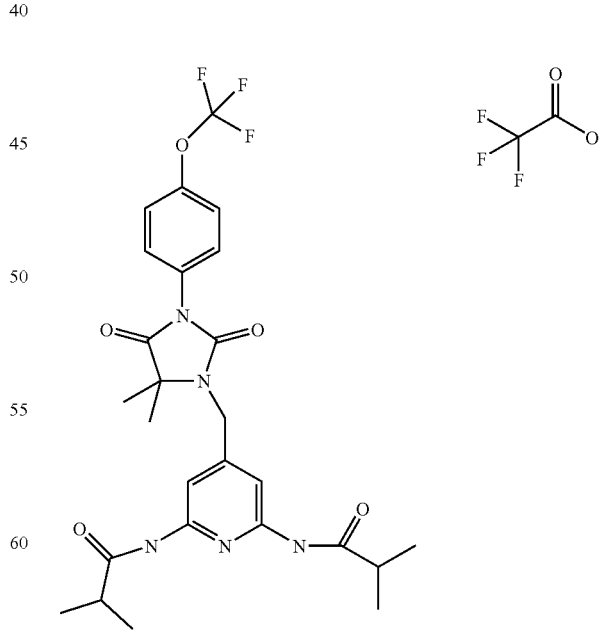

MS (LC-MS): 549.22; Retention time: 1.83 min.
The synthesis is described in Scheme 3.

EXAMPLE 143

1-[2-chloro-6-(pyrid-4-ylamino)pyrid-4-ylmethyl]-5,5-dimethyl-3-(4-trifluoromethoxyphenyl)imidazolidine-2,4-dione; Compound with Trifluoroacetic Acid

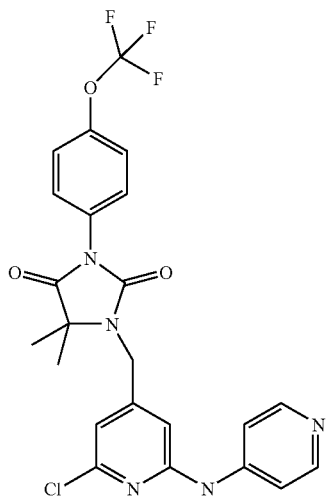

MS (LC-MS): 563.19; Retention time: 2.61 min.
The synthesis is described in Scheme 3.

EXAMPLE 144

1-[2-chloro-6-(pyrid-4-ylamino)pyrid-4-ylmethyl]-5,5-dimethyl-3-(4-trifluoromethylsulfanylphenyl)imidazolidine-2,4-dione

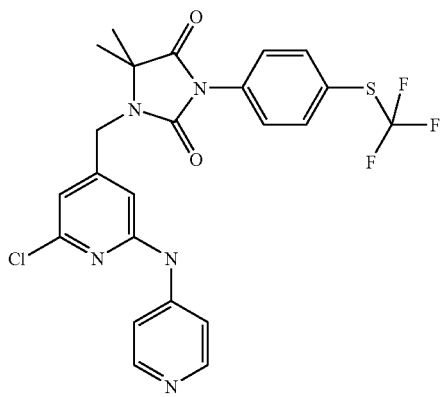

MS (LC-MS): 521.09; Retention time: 1.91 min.
The synthesis is described in Scheme 3.

EXAMPLE 145

N-{6-chloro-4-[5,5-dimethyl-2,4-dioxo-3-(4-trifluoromethylsulfanylphenyl)imidazolidin-1-ylmethyl]pyridin-2-yl}propionamide

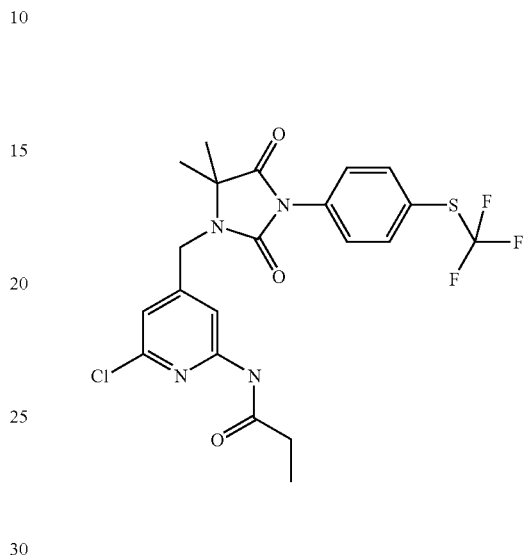

MS (LC-MS): 500.09; Retention time: 2.46.
The synthesis is described in Scheme 3.

EXAMPLE 146

N-{6-chloro-4-[5,5-dimethyl-2,4-dioxo-3-(4-trifluoromethylsulfanylphenyl)imidazolidin-1-ylmethyl]pyrid-2-yl}acetamide

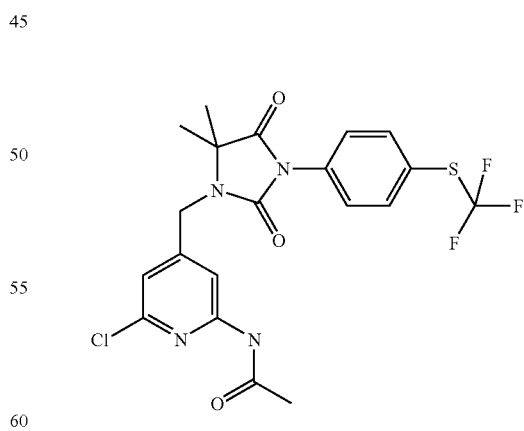

MS (LC-MS): 486.90; Retention time: 2.15.
The synthesis is described in Scheme 3.

EXAMPLE 147

1-[2-chloro-6-(pyrid-3-ylamino)pyrid-4-ylmethyl]-5,5-dimethyl-3-(4-trifluoromethoxyphenyl)imidazolidine-2,4-dione; Compound with Trifluoroacetic Acid

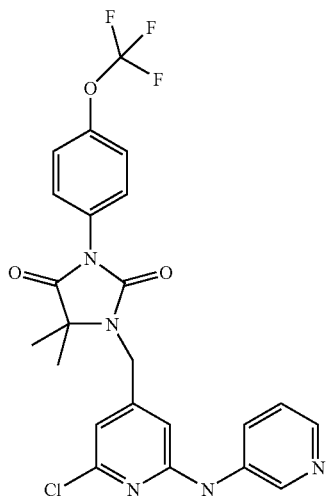
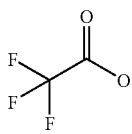

MS (LC-MS): 505.11; Retention time: 2.27.
The synthesis is described in Scheme 3.

EXAMPLE 148

{6-chloro-4-[5,5-dimethyl-2,4-dioxo-3-(4-trifluoromethylsulfanylphenyl)imidazolidin-1-ylmethyl]pyrid-2-yl}cyclopropanecarboxamide

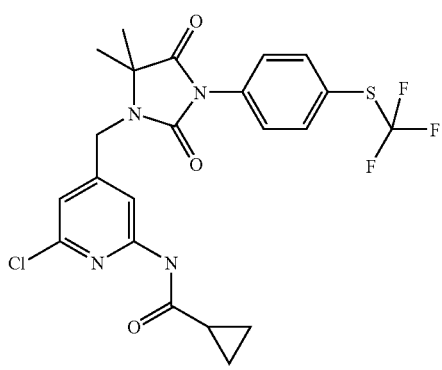

MS (LC-MS): 512.09; Retention time: 2.32.
The synthesis is described in Scheme 3.

EXAMPLE 149

N-{6-chloro-4-[5,5-dimethyl-2,4-dioxo-3-(4-trifluoromethylsulfanylphenyl)imidazolidin-1-ylmethyl]pyrid-2-yl}isobutyramide

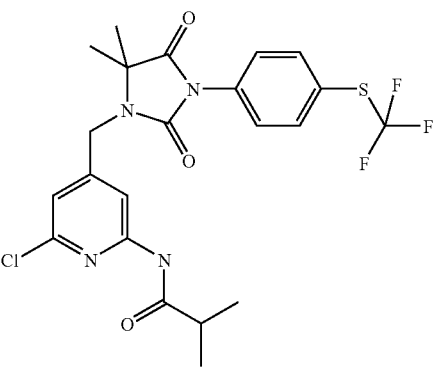

MS (LC-MS): 514.11; Retention time: 1.63.
The synthesis is described in Scheme 3.

EXAMPLE 150

1-[2,6-bis(pyrid-2-ylamino)pyrid-4-ylmethyl]-5,5-dimethyl-3-(4-trifluoromethoxyphenyl)imidazolidine-2,4-dione; Compound with Trifluoroacetic Acid

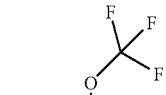
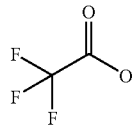
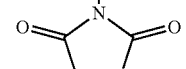
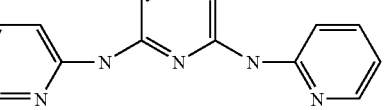

MS (LC-MS): 563.15; Retention time: 1.70 min.
The synthesis is described in Scheme 3.

EXAMPLE 151

1-[2-chloro-6-(pyrid-2-ylamino)pyrid-4-ylmethyl]-5,5-dimethyl-3-(4-trifluoromethylsulfanylphenyl)imidazolidine-2,4-dione

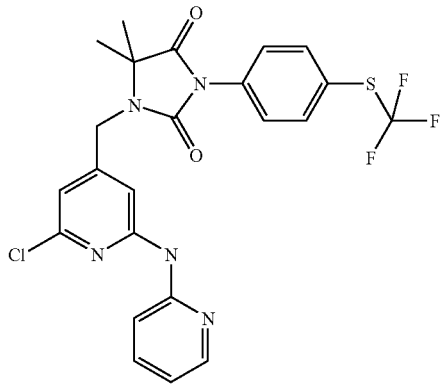

MS (LC-MS): 521.09; Retention time: 1.78 min.
The synthesis is described in Scheme 3.

EXAMPLE 152

5,5-dimethyl-1-(5-phenyl[1,2,4]oxadiazol-3-ylmethyl)-3-(4-trifluoromethylsulfanylphenyl)imidazolidine-2,4-dione

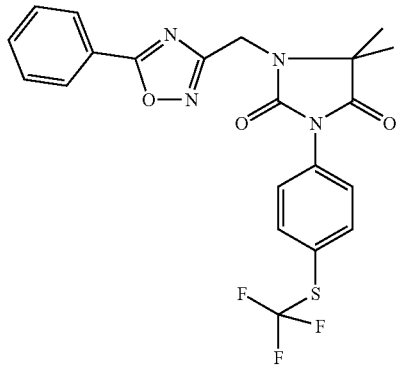

MS (LC-MS): 462.10; Retention time: 2.77 min.
The synthesis is described in Scheme 4.

EXAMPLE 153

1-(2-imidazol-1-ylethyl)-5,5-dimethyl-3-(4-trifluoromethylsulfanylphenyl)imidazolidine-2,4-dione

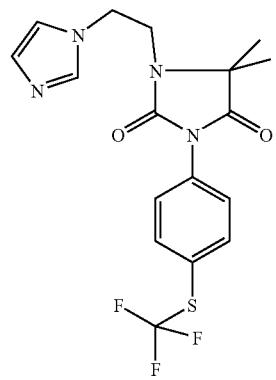

MS (LC-MS): 398.10; Retention time: 1.49 min.
The synthesis is described in Scheme 4.

EXAMPLE 154

1-[2-(4-chlorophenyl)oxazol-5-ylmethyl]-5,5-dimethyl-3-(4-trifluoromethylsulfanylphenyl)imidazolidine-2,4-dione

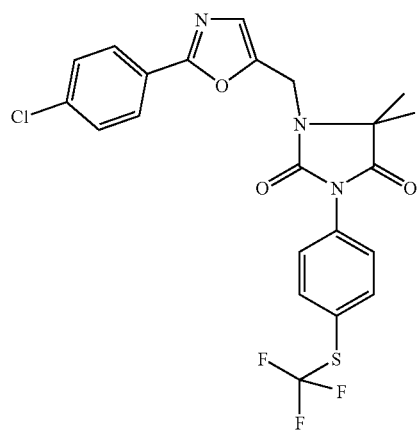

MS (LC-MS): 495.06; Retention time: 2.99 min.
The synthesis is described in Scheme 4.

EXAMPLE 155

Preparation of 1-isoquinolin-5-yl-5,5-dimethyl-3-(4-trifluoromethylsulfanylphenyl)imidazolidine-2,4-dione 500 mg (2.4 mmol) of 2-(isoquinolin-5-ylamino)-2-methylpropionitrile, 1.6 mg (0.013 mmol) of benzoic acid and 526 mg (2.4 mmol) of 4-(trifluoromethylthio)phenyl isocyanate in 4 ml of chlorobenzene were refluxed for 2 days. The resulting mixture was filtered and the filtrate was evaporated to dryness. The intermediate imine was separated out by preparative HPLC chromatography (RP 18, acetonitrile, water, 0.01% TFA). 60 mg of the resulting product were stirred for 1 hour at 40° C. with 1N hydrochloric acid. The solvent was evaporated off and the residue was taken up in sodium hydrogen carbonate solution and extracted with ethyl acetate. The combined organic phases were dried and the residue remaining after evaporation was purified by flash chromatography (SiO$_2$, methylene chloride/methanol=98/2), to give 38 mg of the desired product.

M+H$^+$=432.

LC/MS Retention time=1.245.

EXAMPLE 156

5,5-dimethyl-1-(5-phenyloxazol-4-ylmethyl)-3-(4-trifluoromethylsulfanylphenyl)imidazolidine-2,4-dione

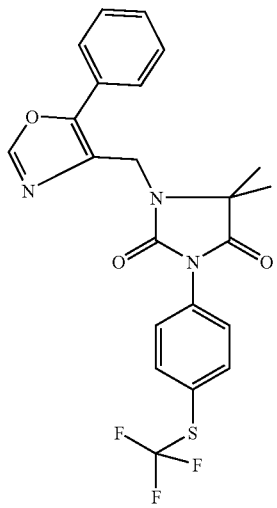

MS (LC-MS): 461.10, Retention time: 2.63 min.
The synthesis is described in Scheme 4.

EXAMPLE 157

5,5-dimethyl-1-(1-methylpiperid-3-ylmethyl)-3-(4-trifluoromethylsulfanylphenyl)imidazolidine-2,4-dione

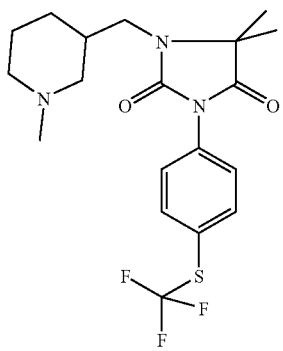

MS (LC-MS): 415.15; Retention time: 1.63.
The synthesis is described in Scheme 4.

EXAMPLE 158

5,5-dimethyl-1-(1-methylpiperid-3-ylmethyl)-3-(4-trifluoromethoxyphenyl)imidazolidine-2,4-dione

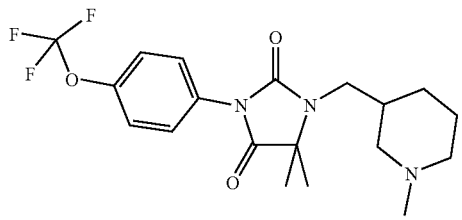

MS (LC-MS): 499.18; Retention time: 1.39.
The synthesis is described in Scheme 4.

EXAMPLE 159

1-[2-(4-chlorophenyl)thiazol-4-ylmethyl]-5,5-dimethyl-3-(4-trifluoromethylsulfanylphenyl)imidazolidine-2,4-dione

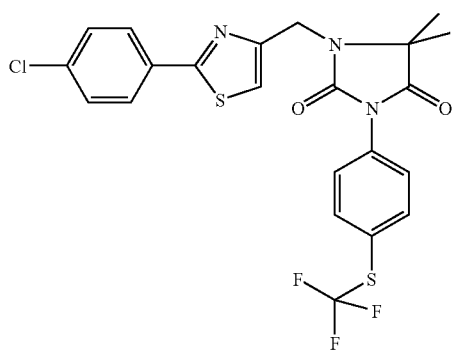

MS (LC-MS): 511.04; Retention time: 3.12.
The synthesis is described in Scheme 4.

EXAMPLE 160

5,5-dimethyl-1-(1-methyl-1H-imidazol-2-ylmethyl)-3-(4-trifluoromethylsulfanylphenyl)imidazolidine-2,4-dione

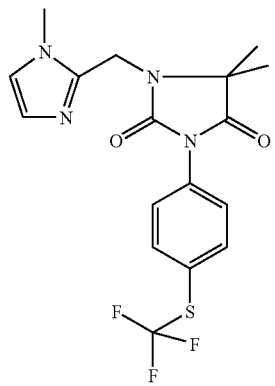

MS (LC-MS): 398.10; Retention time: 1.53.
The synthesis is described in Scheme 4.

EXAMPLE 161

1-(7-methoxy-2-oxo-2H-chromen-4-ylmethyl)-5,5-dimethyl-3-(4-trifluoromethylsulfanylphenyl)imidazolidine-2,4-dione

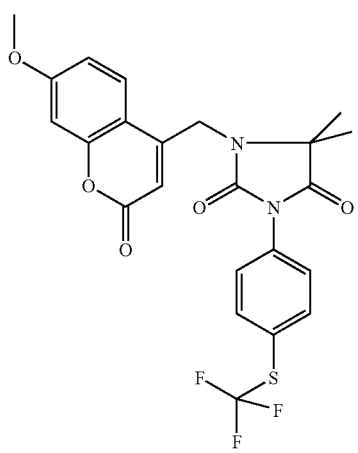

MS (LC-MS): 492.48; Retention time: 1.84.
The synthesis is described in Scheme 4.

EXAMPLE 162

5,5-dimethyl-1-(5-methylestoxazol-3-ylmethyl)-3-(4-trifluoromethylsulfanylphenyl)imidazolidine-2,4-dione

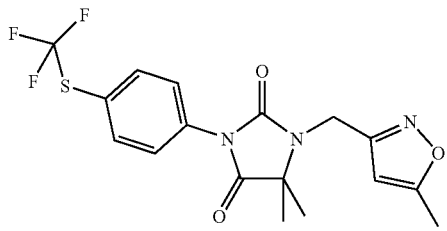

MS (LC-MS): 500.09; Retention time: 2.52.
The synthesis is described in Scheme 4.

EXAMPLE 163

1-[5-(4-methoxyphenyl)[1,2,4]oxadiazol-3-ylmethyl]-5,5-dimethyl-3-(4-trifluoromethylsulfanylphenyl)imidazolidine-2,4-dione

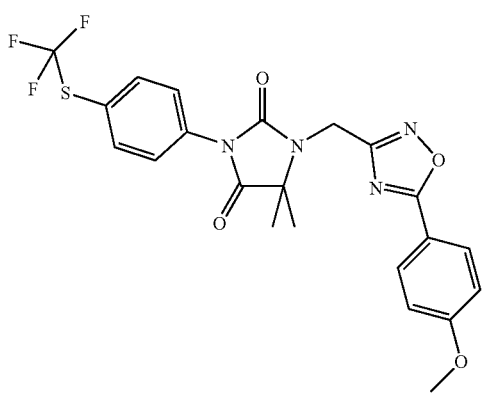

MS (LC-MS): 492.11; Retention time: 1.87.
The synthesis is described in Scheme 4.

EXAMPLE 164

1-[5-(4-methoxyphenyl)[1,2,4]oxadiazol-3-ylmethyl]-5,5-dimethyl-3-(4-trifluoromethoxyphenyl)imidazolidine-2,4-dione

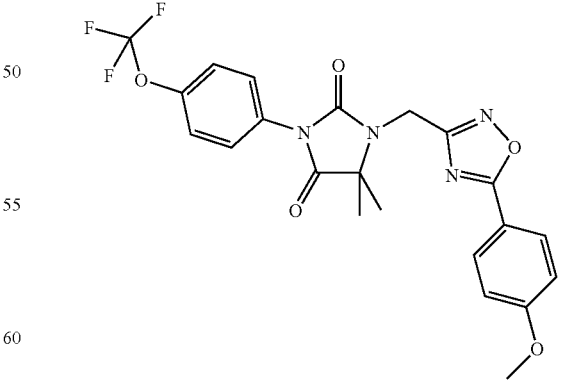

MS (LC-MS): 476.13; Retention time: 2.03.
The synthesis is described in Scheme 4.

EXAMPLE 165

Methyl 5-[5,5-dimethyl-2,4-dioxo-3-(4-trifluoromethylsulfanylphenyl)imidazolidin-1-ylmethyl]-furan-2-carboxylate

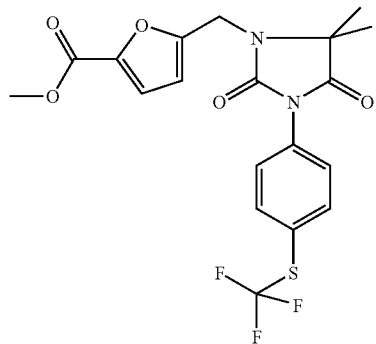

MS (LC-MS): 442.42; Retention time: 1.74.
The synthesis is described in Scheme 4.

EXAMPLE 166

1-(1-benzyl-1H-imidazol-2-ylmethyl)-5,5-dimethyl-3-(4-trifluoromethylsulfanylphenyl)imidazolidine-2,4-dione

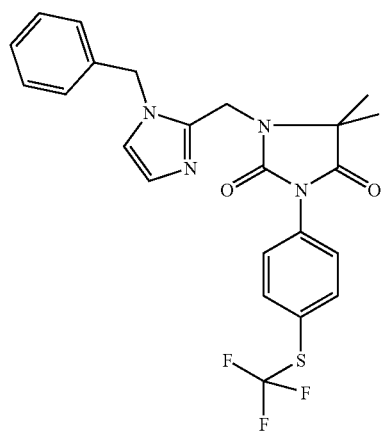

MS (LC-MS): 474.13; Retention time: 2.02.
The synthesis is described in Scheme 4.

EXAMPLE 167

1-(4-dimethylaminopyrimidin-2-ylmethyl)-5,5-dimethyl-3-(4-trifluoromethylsulfanylphenyl)imidazolidine-2,4-dione

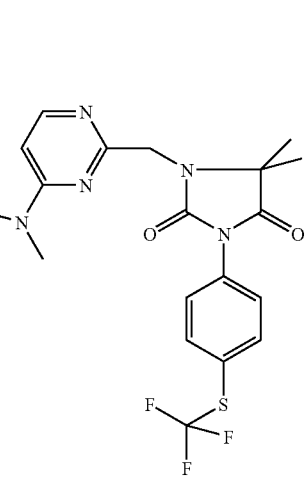

MS (LC-MS): 439.46; Retention time: 1.91.
The synthesis is described in Scheme 4.

EXAMPLE 168

1-[1-(4-methoxybenzyl)-1H-imidazol-2-ylmethyl]-5,5-dimethyl-3-(4-trifluoromethylsulfanylphenyl)imidazolidine-2,4-dione

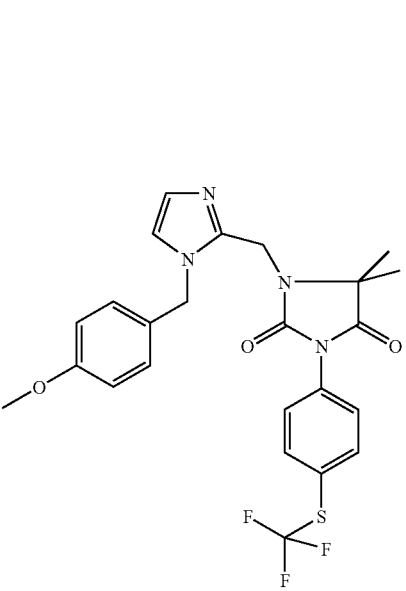

MS (LC-MS): 504.14; Retention time: 2.24.
The synthesis is described in Scheme 4.

EXAMPLE 169

5,5-dimethyl-1-[2-(1-methylpyrrolidin-2-yl)-ethyl]-3-(4-trifluoromethylsulfanylphenyl)imidazolidine-2,4-dione

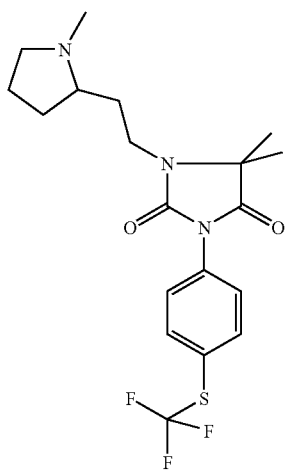

MS (LC-MS): 415.15; Retention time: 1.66 min.
The synthesis is described in Scheme 4.

EXAMPLE 170

5,5-dimethyl-1-(2-morpholin-4-ylethyl)-3-(4-trifluoromethylsulfanylphenyl)imidazolidine-2,4-dione

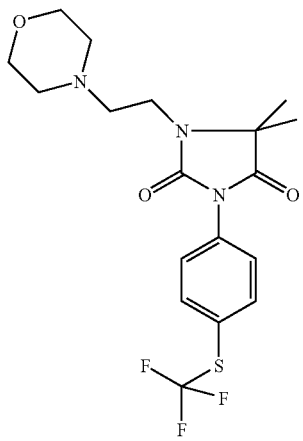

MS (LC-MS): 417.13; Retention time: 1.62 min.
The synthesis is described in Scheme 4.

EXAMPLE 171

1-[5-(2-methoxyphenyl)[1,2,4]oxadiazol-3-ylmethyl]-5,5-dimethyl-3-(4-trifluoromethylsulfanylphenyl)imidazolidine-2,4-dione

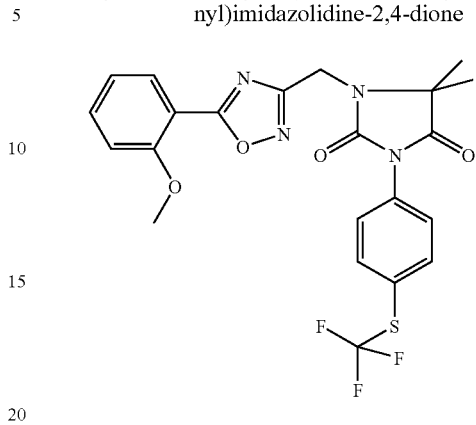

MS (LC-MS): 492.11; Retention time: 2.67 min.
The synthesis is described in Scheme 4.

EXAMPLE 172

5,5-dimethyl-1-(5-methylestoxazol-3-ylmethyl)-3-(4-trifluoromethoxyphenyl)imidazolidine-2,4-dione

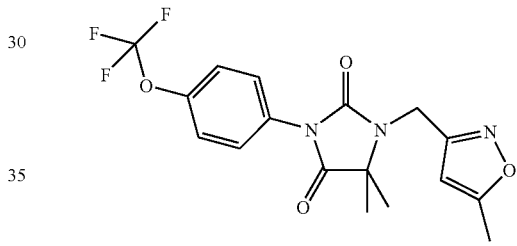

MS (LC-MS): 383.33; Retention time: 1.95 min.
The synthesis is described in Scheme 4.

EXAMPLE 173

1-(5-tert-butyl[1,2,4]oxadiazol-3-ylmethyl)-5,5-dimethyl-3-(4-trifluoromethylsulfanylphenyl)imidazolidine-2,4-dione

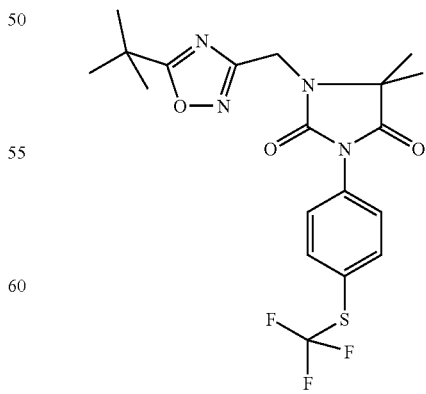

MS (LC-MS): 442.16; Retention time: 2.64 min.
The synthesis is described in Scheme 4.

EXAMPLE 174

4-[5,5-dimethyl-2,4-dioxo-3-(4-trifluoromethylsulfanylphenyl)imidazolidin-1-ylmethyl]pyridine-2-carboxylic acid 4-methylbenzylamide; Compound with Trifluoroacetic Acid

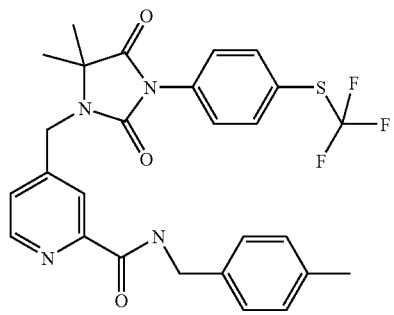

MS (LC-MS): 542.16; Retention time: 2.80 min.
The synthesis is described in Scheme 5.

EXAMPLE 175

4-[5,5-dimethyl-2,4-dioxo-3-(4-trifluoromethylsulfanylphenyl)imidazolidin-1-ylmethyl]pyridine-2-carboxylic acid (2-p-tolylethyl)amide

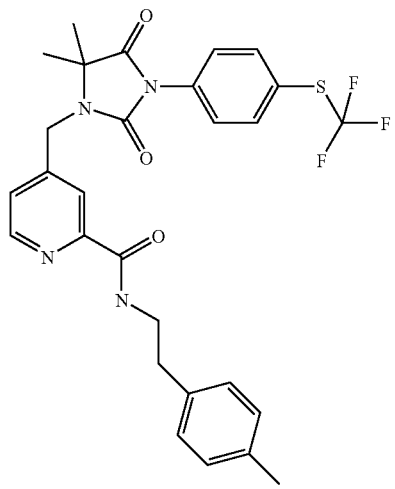

MS (LC-MS): 556.18; Retention time: 2.31.
The synthesis is described in Scheme 5.

EXAMPLE 176

4-[5,5-dimethyl-2,4-dioxo-3-(4-trifluoromethylsulfanylphenyl)imidazolidin-1-ylmethyl]pyridine-2-carboxylic acid 3,4-dimethoxybenzylamide

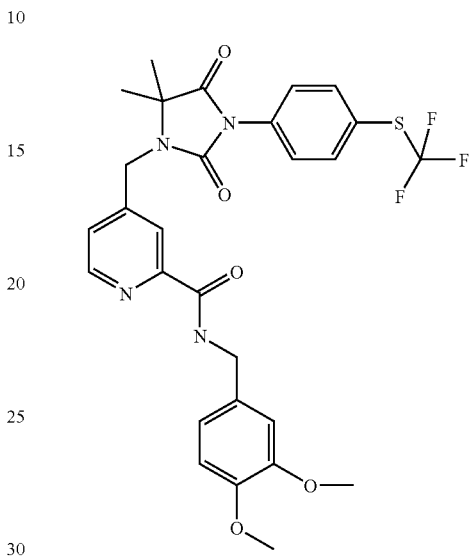

MS (LC-MS): 588.16; Retention time: 1.58.
The synthesis is described in Scheme 5.

EXAMPLE 177

4-[5,5-dimethyl-2,4-dioxo-3-(4-trifluoromethylsulfanylphenyl)imidazolidin-1-ylmethyl]pyridine-2-carboxylic acid benzylamide

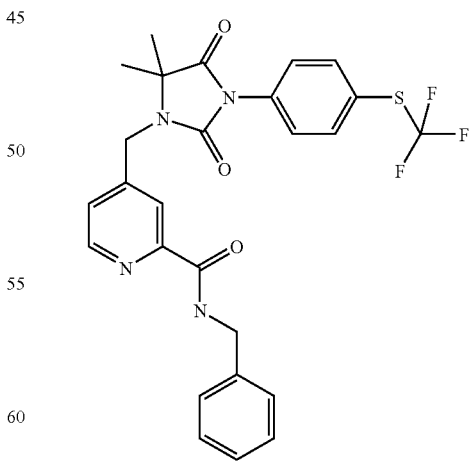

MS (LC-MS): 528.14; Retention time: 1.77.
The synthesis is described in Scheme 5.

EXAMPLE 178

5,5-dimethyl-1-[2-(4-oxo-2-thioxo-1,4-dihydro-2H-quinazolin-3-yl)pyrid-4-ylmethyl]-3-(4-trifluoromethylsulfanylphenyl)imidazolidine-2,4-dione

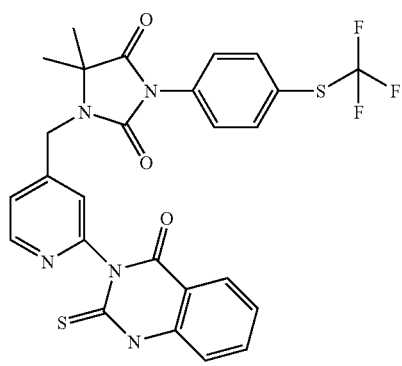

MS (LC-MS): 571.10; Retention time: 2.3.

The synthesis is described in Scheme 6

The two reaction schemes below describe the synthesis of compound of formula I according to the present invention, especially among the products of Examples 178 to 200 below.

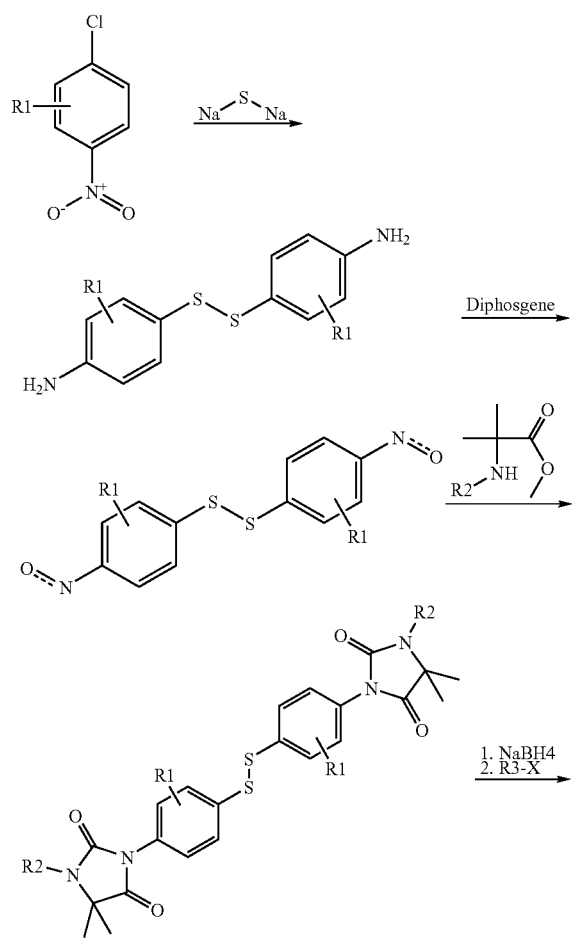

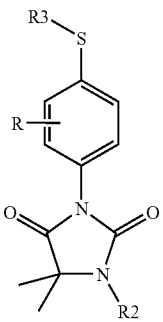

Scheme 2

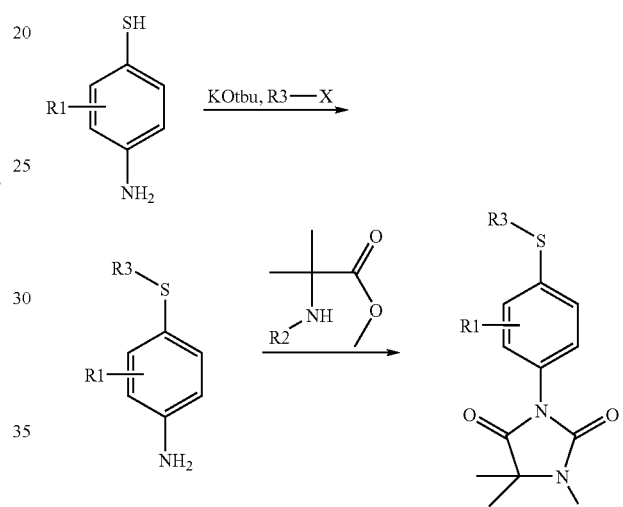

Bis(4-amino-2-chlorophenyl)disulfide 76.8 g (0.4 mol) of 1,2-dichloro-4-nitrobenzene, suspended in 120 ml of water, were heated to 90° C. and treated with a solution of 62.4 g (0.8 mol) of sodium sulfide and 12.8 g (0.4 mol) of sulfur in 200 ml of water.

After refluxing the mixture for 5 hours, 6 g of carbon dioxide were bubbled through the solution, followed by a regular stream of air. The pH was adjusted to 5.5, the mixture was cooled to room temperature and the resulting precipitate was collected by filtration.

The crude material was recrystallized from isopropanol to give 45 g (71%) of the desired product.

$M+H^+=318$.

LC/MS retention time=1.526.

Bis[(2-chloro-4-(4,4-dimethyl-2,5-dioxo-3-pyrid-4-ylmethylimidazolidin-1-yl)]phenyl disulfide A solution of 13.7 g (69.5 mmol) of diphosgene in 100 ml of toluene was cooled to −20° C. and treated with a solution of 5.0 g (15.8 mmol) of bis(4-amino-2-chlorophenyl)disulfide. The resulting mixture was stirred for 30 minutes at room temperature, refluxed for 1 hour and then evaporated to dryness.

2.53 g (about 6.86 mmol) of this material were dissolved in THF and treated with 2.0 g (9.5 mmol) of methyl 2-methyl-2-[(pyrid-4-ylmethyl)amino]propionate. The mixture was stirred for 3 hours at room temperature and evaporated to dryness, and the resulting solid was purified by flash chromatography (SiO$_2$, methylene chloride:methanol=97:3) to give 1.8 g (37%) of the desired product.
M+H$^+$=722.
LC/MS retention time=1.176.

EXAMPLE 179

Preparation of 3-(4-tert-butylsulfanyl-3-chlorophenyl)-5,5-dimethyl-1-pyrid-4-ylmethylimidazolidine-2,4-dione trifluoroacetate 200 mg (0.28 mol) of bis[(2-chloro-4-(4,4-dimethyl-2,5-dioxo-3-pyrid-4-ylmethylimidazolidin-1-yl)]phenyl disulfide were dissolved in 10 ml of methanol and treated with 22 mg (0.56 mmol) of sodium borohydride. After stirring for 30 minutes at room temperature, the mixture was evaporated to dryness. The residue was dissolved in 10 ml of sulfuric acid (75%) and added to 20 ml of sulfuric acid (75%) saturated with isobutylene. The mixture was stirred for 20 minutes at room temperature and then added cautiously to a cooled solution of sodium hydroxide in water. The alkaline aqueous phase was extracted three times with ethyl acetate, the combined organic phases were dried with sodium sulfate and the material remaining after evaporation was filtered off on silica gel (methylene chloride/methanol=95/5). The resulting crude product was purified by preparative HPLC chromatography (RP 18, acetonitrile, water, 0.01% TFA) to give 120 mg (81%) of the desired product.
M+H$^+$=418.
LC/MS retention time=1.249.

General Procedure 1A: Preparation of 3-(3-chloro-4-alkylsulfanylphenyl)-5,5-dimethyl-1-pyrid-4-ylmethylimidazolidine-2,4-diones 445 mg (0.62 mol) of bis[(2-chloro-4-(4,4-dimethyl-2,5-dioxo-3-pyrid-4-ylmethylimidazolidin-1-yl)]phenyl disulfide were dissolved in 15 ml of methanol and treated with 49 mg (1.24 mmol) of sodium borohydride. After stirring for 30 minutes at room temperature, 1.24 mmol of the respective alkyl halide were added and the resulting mixture was refluxed for 1 hour. The solvent was removed by evaporation and the remaining crude materials were purified by preparative HPLC chromatography (RP 18, acetonitrile, water, 0.01% TFA).

EXAMPLE 180

Preparation of 3-(3-chloro-4-isopropylsulfanylphenyl)-5,5-dimethyl-1-pyrid-4-ylmethylimidazolidine-2,4-dione Synthesis according to the general procedure 1A.
M+H$^+$=404.
LC/MS retention time=1.196.

EXAMPLE 181

Preparation of 3-(3-chloro-4-isobutylsulfanylphenyl)-5,5-dimethyl-1-pyrid-4-ylmethylimidazolidine-2,4-dione trifluoroacetate Prepared according to the general procedure 1A.
M+H$^+$=418.
LC/MS retention time=1.272.

EXAMPLE 182

Preparation of 3-(3-chloro-4-methylsulfanylphenyl)-5,5-dimethyl-1-pyrid-4-ylmethylimidazolidine-2,4-dione Prepared according to the general procedure 1A.
M+H$^+$=376.
LC/MS retention time=1.054.

EXAMPLE 183

Preparation of 3-[3-chloro-4-(3-methoxypropylsulfanyl)phenyl]-5,5-dimethyl-1-pyrid-4-ylmethylimidazolidine-2,4-dione trifluoroacetate Prepared according to the general procedure 1A.
M+H$^+$=434.
LC/MS retention time=1.096.

EXAMPLE 184

Preparation of 3-[3-chloro-4-(2-morpholin-4-ylethylsulfanyl)phenyl]-5,5-dimethyl-1-pyrid-4-ylmethylimidazolidine-2,4-dione trifluoroacetate Prepared according to the general procedure 1A.
M+H$^+$=475.
LC/MS retention time=0.792

EXAMPLE 185

Preparation of 3-{3-chloro-4-[2-(1-methylpyrrolidin-2-yl)ethylsulfanyl]phenyl}-5,5-dimethyl-1-pyrid-4-ylmethylimidazolidine-2,4-dione trifluoroacetate Prepared according to the general procedure 1A.
M+H$^+$=473.
LC/MS retention time=0.865.

EXAMPLE 186

Preparation of 3-{3-chloro-4-[3-(4-methylpiperazin-1-yl)propylsulfanyl]-phenyl}-5,5-dimethyl-1-pyrid-4-ylmethylimidazolidine-2,4-dione trifluoroacetate Prepared according to the general procedure 1A.
M+H$^+$=502.
LC/MS retention time=0.795.

EXAMPLE 187

Preparation of 3-[3-chloro-4-(3-hydroxypropylsulfanyl)phenyl]-5,5-dimethyl-1-pyrid-4-ylmethylimidazolidine-2,4-dione trifluoroacetate Prepared according to the general procedure 1A.
M+H$^+$=420.
LC/MS retention time=0.968.

EXAMPLE 188

Preparation of 3-[3-chloro-4-(2-hydroxyethylsulfanyl)phenyl]-5,5-dimethyl-1-pyrid-4-ylmethylimidazolidine-2,4-dione trifluoroacetate Prepared according to the general procedure 1A.
M+H$^+$=406.
LC/MS retention time=0.921.

EXAMPLE 189

Preparation of [2-chloro-4-(4,4-dimethyl-2,5-dioxo-3-pyrid-4-ylmethylimidazolidin-1-yl)phenylsulfanyl] acetonitrile trifluoroacetate Prepared according to the general procedure 1A.
M+H$^+$=401.
LC/MS retention time=0.999.

3-nitro-4-trifluoromethoxyaniline 20 g (112.9 mmol) of 4-trifluoromethoxyaniline were dissolved in 50 ml of concentrated sulfuric acid at a temperature of 0 to 5° C., treated with 30 ml of a 4/1 mixture of sulfuric acid and nitric acid. The mixture was stirred for 5 hours at 0° C. and then poured into an ice-cold water mixture and made alkaline with 200 ml of concentrated aqueous ammonia solution. Extraction with EE, drying with sodium sulfate, evaporation to dryness and recrystallization from ethyl acetate/heptane gave 15.5 g (63%) of the desired product.
M+H$^+$=223.
LC/MS retention time=1.378.

EXAMPLE 190

Preparation of Trifluoroacetic Acid; 5,5-dimethyl-3-(3-nitro-4-trifluoromethoxyphenyl)-1-pyrid-4-ylmethylimidazolidine-2,4-dione 2.27 g (11.5 mmol) of diphosgene in 1,2-dichloroethane were added at −20° C. to 1.0 g (4.5 mmol) of 3-nitro-4-trifluoromethoxyaniline, dissolved in 20 ml of 1,2-dichloroethane. The mixture was stirred for 1 hour while warming to room temperature and was then heated at 50° C. for 2 hours. After leaving to stand overnight, the solvent was evaporated off and the residue was taken up in dry THF and treated with 937 mg (4.5 mmol) of methyl 2-methyl-2-[(pyrid-4-ylmethyl)amino]propionate. The mixture was stirred for 2 hours at room temperature and for 1 hour at 40° C., and then evaporated to dryness and the remaining residue was purified (RP 18, acetonitrile, water, 0.01% TFA) to give 1.15 g (61%) of the desired product.
M+H$^+$=425.
LC/MS retention time=1.324.

EXAMPLE 191

Preparation of 3-(3-amino-4-trifluoro-methoxyphenyl)-5,5-dimethyl-1-pyrid-4-ylmethylimidazolidine-2,4-dione 9.63 g (22.7 mmol) of 5,5-dimethyl-3-(3-nitro-4-trifluoromethoxyphenyl)-1-pyrid-4-ylmethylimidazolidine-2,4-dione trifluoroacetate were dissolved in semi-concentrated hydrochloric acid, heated to reflux and treated with 30 g of zinc powder. After 1.5 hours, the mixture was cooled, filtered and extracted twice with methyl tert-butyl ether. The aqueous phase was made alkaline with 6 N sodium hydroxide and extracted with methyl tert-butyl ether, and the combined organic phases were dried over sodium sulfate. Evaporation of the solvent gave 5.0 g (56%) of the desired product.
M+H$^+$=395.
LC/MS retention time=0.948.

EXAMPLE 192

Preparation of 5,5-dimethyl-1-pyrid-4-ylmethyl-3-[4-(2,2,2-trifluoroethoxy)phenyl]imidazolidine-2,4-dione 688 mg (3.6 mmol) of 2,2,2-trifluoroethoxyaniline in 30 ml of methylene chloride were added at 0° C. to 356 mg (3.6 mmol) of triethylamine and a solution of 356 mg (1.2 mmol) of triphosgene in 30 ml of methylene chloride. The mixture was stirred overnight while warming to room temperature. Next, the solvent was evaporated off, the residue was taken up in 15 ml of THF and treated with 100 mg (0.48 mmol) of methyl 2-methyl-2-[(pyrid-4-ylmethyl)amino]propionate and 48.5 mg (0.48 mmol) of triethylamine. The mixture was stirred for 4 hours at room temperature and for 1 hour at 50° C., and then evaporated to dryness, and the remaining residue was purified by preparative HPLC chromatography (RP 18, acetonitrile, water, 0.01% TFA) to give 67 g (36%) of the desired product.
M+H$^+$=394.
LC/MS retention time=1.032.

EXAMPLE 193

Preparation of 3-(8-chloro-3,4,4-trimethylthiochroman-6-yl)-5,5-dimethyl-1-pyrid-4-ylmethylimidazolidine-2,4-dione 200 mg (0.28 mol) of bis[(2-chloro-4-(4,4-dimethyl-2,5-dioxo-3-pyrid-4-ylmethylimidazolidin-1-yl)]phenyl disulfide were dissolved in 10 ml of methanol and treated with 22 mg (0.56 mmol) of sodium borohydride. After stirring for 30 minutes at room temperature, the mixture was evaporated to dryness. The residue was dissolved in 10 ml of sulfuric acid (75%) and added to 20 ml of sulfuric acid (75%) saturated with isobutylene. The mixture was stirred for 30 minutes at 40° C., while a regular airstream of isobutylene was bubbled through the solution. After leaving to stand overnight, the mixture was added cautiously to a cooled solution of sodium hydroxide in water. The alkaline aqueous phase was extracted three times with ethyl acetate, the combined organic phases were dried over sodium sulfate and the material remaining after evaporation was filtered on silica gel (methylene chloride/methanol=95/5). The resulting crude product was purified by preparative HPLC chromatography (RP 18, acetonitrile, water, 0.01% TFA) to give 70 mg (56%) of the desired product.
M+H$^+$=444.
LC/MS retention time=1.240.

EXAMPLE 194

Preparation of 1-(2-chlorothiazol-5-ylmethyl)-5,5-dimethyl-3-(4-trifluoromethylsulfanylphenyl)imidazolidine-2,4-dione trifluoroacetate 200 mg (0.65 mmol) of 5,5-dimethyl-3-(4-trifluoro-methylsulfanylphenyl)imidazolidine-2,4-dione, 115 mg (0.82 mmol) of potassium carbonate and 276 mg (1.64 mmol) of 2-chloro-5-chloromethylthiazole were dissolved in 2 ml of DMF and stirred at room temperature for 2 days. The mixture was poured into water, extracted three times with ethyl acetate, the combined organic phases were dried over sodium sulfate and the material remaining after evaporation was purified by preparative HPLC chromatography (RP 18, acetonitrile, water, 0.01% TFA) to give 143 mg (50%) of the desired product.
M+H$^+$=436.
LC/MS retention time=1.784.

EXAMPLE 195

Preparation of 3-[3-chloro-4-(propane-2-sulfonyl)phenyl]-5,5-dimethyl-1-pyrid-4-ylmethylimidazolidine-2,4-dione 40 mg (0.1 mmol) of 3-(3-chloro-4-isopropylsulfanylphenyl)-5,5-dimethyl-1-pyrid-4-ylmethylimidazolidine-2,4-dione were dissolved in 2 ml of methylene chloride and treated with a solution of 37 mg (0.15 mmol) of m-chloroperbenzoic acid in 2 ml of methylene chloride. The reaction was monitored by TLC and stopped when the sulfoxide and the sulfone were formed in equal amounts. The mixture was evaporated to dryness and purified by flash chromatography (SiO$_2$, methylene chloride/methanol=98/2) to give 4 mg of 3-[3-chloro-4-(propane-2-sulfonyl)phenyl]-5,5-dimethyl-1-pyrid-4-ylmethylimidazolidine-2,4-dione and 7 mg of 3-[3-chloro-4-(propane-2-sulfinyl)phenyl]-5,5-dimethyl-1-pyrid-4-ylmethylimidazolidine-2,4-dione.
M+H$^+$=436.
LC/MS retention time=0.970.

EXAMPLE 196

Preparation of 3-[3-chloro-4-(propane-2-sulfinyl)phenyl]-5,5-dimethyl-1-pyrid-4-ylmethylimidazolidine-2,4-dione Prepared as described above.
M+H$^+$=420.
LC/MS retention time=0.932.

2-(Isoquinolin-5-ylamino)-2-methylpropionitrile 5.0 g (34.7 mmol) of 5-aminoisoquinolin, 5.1 ml (69.4 mmol) of acetone and 945 mg (6.94 mmol) of zinc chloride were dissolved in 100 ml of acetonitrile and treated at 0° C. with 6.9 g (69.4 mmol) of trimethylsilyl cyanide. The mixture was refluxed for 3 hours, the solvent was then evaporated off and the residue was taken up in 200 ml of sodium hydrogen carbonate and extracted three times with ethyl acetate. The combined organic phases were dried and the residue remaining after evaporation was purified by flash chromatography (SiO$_2$, methylene chloride/methanol=95/5) to give 6.0 g (82%) of the desired product.
M+H$^+$=212.
LC/MS retention time=0.696.

General Procedure 2: Synthesis of Alkylsulfanylanilines 1.1 g (8 mmol) of 4-aminothiophenol and 896 mg (8 mmol) of potassium tert-butoxide were dissolved in 10 ml of DMF and stirred for 45 minutes under an argon atmosphere. Next, 8.8 mmol of the corresponding alkyl bromide were added and the mixture was stirred for 3 hours at room temperature, poured into water and extracted with ethyl acetate. The combined organic phases were dried and evaporated. The residual product was essentially pure and could be used without further purification.

4-(3-Methoxypropylsulfanyl)phenylamine

Prepared according to the general procedure 2.
M+H$^+$=197.
LC/MS retention time=0.777.

4-Isopropylsulfanylphenylamine

Prepared according to the general procedure 2.
M+H$^+$=266.
LC/MS retention time=0.173.

4-[3-(4-Methylpiperazin-1-yl)propylsulfanyl]phenylamine

Prepared according to the general procedure 2.
M+H$^+$=168.
LC/MS retention time=0.894.

General Procedure 3: Preparation of 3-(3-chloro-4-alkylsulfanylphenyl)-5,5-dimethyl-1-pyrid-4-ylmethylimidazolidine-2,4-diones 371 mg (2.3 mmol) of carbonyldiimidazole, 41 mg (0.5 mmol) of imidazole and 1.9 mmol of the respective alkylsulfanylaniline were dissolved at 0° C. in 10 ml of THF and stirred for 1 hour. Next, 280 mg (1.35 mmol) of methyl 2-methyl-2-[(pyrid-4-ylmethyl)amino]propionate dissolved in 5 ml of THF were added and the mixture was refluxed for 5 hours. Next, the solvent was evaporated off and the material remaining after evaporation was purified by preparative HPLC chromatography (RP 18, acetonitrile, water, 0.01% TFA).

EXAMPLE 197

Preparation of 5,5-dimethyl-3-(4-methylsulfanylphenyl)-1-pyrid-4-ylmethylimidazolidine-2,4-dione trifluoroacetate Prepared according to the general procedure 3.
M+H$^+$=342.
LC/MS retention time=0.942.

EXAMPLE 198

Preparation of 3-[4-(3-methoxypropylsulfanyl)phenyl]-5,5-dimethyl-1-pyrid-4-ylmethylimidazolidine-2,4-dione trifluoroacetate Prepared according to the general procedure 3.
M+H$^+$=400.
LC/MS retention time=1.007.

EXAMPLE 199

Preparation of 3-(4-isopropylsulfanylphenyl)-5,5-dimethyl-1-pyrid-4-ylmethylimidazolidine-2,4-dione trifluoroacetate Prepared according to the general procedure 3.
M+H$^+$=370.
LC/MS retention time=1.096.

EXAMPLE 200

Preparation of 5,5-dimethyl-3-{4-[3-(4-methylpiperazin-1-yl)propylsulfanyl]phenyl}-1-pyrid-4-ylmethylimidazolidine-2,4-dione trifluoroacetate Prepared according to the general procedure 3.
M+H$^+$=468.
LC/MS retention time=0.689

EXAMPLE 201

5,5-Dimethyl-1-(6-methoxyquinolin-4-ylmethyl)-3-(4-trifluoromethoxyphenyl)imidazolidine-2,4-dione

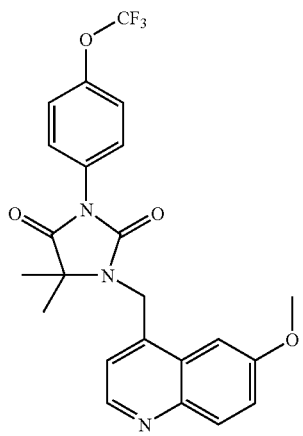

0.1 g of sodium hydride (at 60%) is added to a solution of 0.65 g of 5,5-dimethyl-3-(4-trifluoromethoxyphenyl)imidazolidine-2,4-dione in 40 ml of anhydrous THF, under an inert atmosphere of argon at a temperature in the region of 20° C. Stirring is maintained at this temperature for 30 minutes. 0.47 g of 4-chloromethyl-6-methoxyquinoline dissolved in 10 ml of THF is added. The reaction medium is refluxed for 16 hours. After cooling, 100 ml of water and 75 ml of ethyl acetate are added. After separation of the phases by settling, the organic phase is dried over sodium sulfate, filtered and then concentrated under reduced pressure. The brown oil obtained is purified by flash chromatography (SiO$_2$, EtOAc/cyclohexane, 50/50 by volume, as eluent, Ar). The fractions containing the product are concentrated under reduced pressure. 0.36 g of 5,5-dimethyl-1-(6-methoxyquinolin-4-ylmethyl)-3-(4-trifluoromethoxyphenyl)imidazolidine-2,4-dione is thus obtained, the characteristics of which product are as follows:

$^1$H NMR spectrum (300 MHz, (CD$_3$)$_2$SO d6, δ in ppm): 1.45 (s: 6H); 3.96 (s: 3H); 5.10 (broad s: 2H); 7.46 (dd, J=9 and 3 Hz: 1H); 7.54 (d, J=3 Hz: 1H); 7.56 (broad d, J=9 Hz: 2H); 7.61 (d, J=4.5 Hz: 1H); 7.68 (broad d, J=9 Hz: 2H); 8.00 (d, J=9 Hz: 1H); 8.72 (d, J=4.5 Hz: 1H).

Mass IE m/z=459 M+. base peak
m/z=213 C$_{12}$H$_9$N$_2$O$_2$$^+$
m/z=172 C$_{11}$H$_{10}$NO$^+$ The compound 5,5-dimethyl-3-(4-trifluoromethoxyphenyl)imidazolidine-2,4-dione is prepared according to the process described in Example 63.

Preparation of 4-chloromethyl-6-methoxyquinoline 1.16 ml of triethylamine and 0.64 ml of methanesulfonyl chloride are successively added to a solution of 1.2 g of 4-hydroxymethyl-6-methoxyquinoline in 45 ml of dichloromethane, under an inert atmosphere of argon at a temperature in the region of 20° C. Stirring is maintained at this temperature for 3 hours. The reaction medium is concentrated under reduced pressure to give a brown residue. The product is used without further purification in the following step.

$^1$H NMR spectrum (300 MHz, (CD$_3$)$_2$SO d6, δ in ppm): 3.97 (s: 3H); 5.30 (s: 2H); 7.48 (dd, J=9 and 3 Hz: 1H); 7.52 (d, J=3 Hz: 1H); 7.62 (d, J=4.5 Hz: 1H); 8.00 (d, J=9 Hz: 1H); 8.75 (d, J=4.5 Hz: 1H).

Mass E m/z=207 M$^+$.
m/z=172 (M−Cl)$^+$ base peak
m/z=157 (m/z=172−CH$_3$)$^+$
m/z=129 (m/z=157−CO)$^+$ Preparation of 4-hydroxymethyl-6-methoxyquinoline 17 ml of a 1M solution of LiAlH$_4$ in THF are added dropwise to a solution of 4 g of 4-ethoxycarbonyl-6-methoxyquinoline in 100 ml of anhydrous THF, under an inert atmosphere of argon at a temperature in the region of 5° C. The reaction medium is maintained with stirring for 16 hours at a temperature in the region of 20° C. 50 ml of water and 50 ml of ethyl acetate are added. After separation of the phases by settling, the organic phase is dried over sodium sulfate, filtered and then concentrated under reduced pressure. The foam obtained is purified by flash chromatography (SiO$_2$, EtOAc as eluent, Ar). The fractions containing the product are concentrated under reduced pressure. 0.86 g of 4-hydroxymethyl-6-methoxyquinoline is thus obtained, the characteristics of which product are as follows:

$^1$H NMR spectrum (300 MHz, (CD$_3$)$_2$SO d6, δ in ppm): 3.93 (s: 3H); 5.02 (d, J=5.5 Hz: 2H); 5.57 (t, J=5.5 Hz: 1H); 7.30 (d, J=3 Hz: 1H); 7.38 (dd, J=9 and 3 Hz: 1H); 7.50 (d, J=4.5 Hz: 1H); 7.92 (d, J=9 Hz: 1H); 8.69 (d, J=4.5 Hz: 1H).

Mass IE, m/z=189 M$^+$. base peak
m/z=174 (M−CH$_3$)$^+$
m/z=160 (M−CHO)$^+$
m/z=146 (m/z=174−CO)$^+$
m/z=117 (m/z=146−CHO)$^+$.

EXAMPLE 202

5,5-Dimethyl-1-(6-hydroxyquinoline-4-ylmethyl)-3-(4-trifluoromethoxyphenyl)imidazolidine-2,4-dione

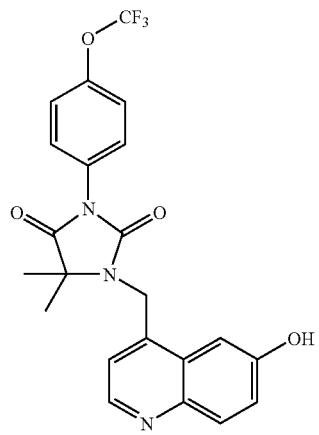

6 ml of a 1M solution of boron tribromide in $CH_2Cl_2$ are added to a solution of 0.26 g of 5,5-dimethyl-1-(6-methoxyquinolin-4-ylmethyl)-3-(4-trifluoromethoxyphenyl)imidazolidine-2,4-dione in 40 ml of dichloromethane, under an inert atmosphere of argon at a temperature in the region of 0° C. The reaction medium is stirred at a temperature in the region of 20° C. for 16 hours. 5 ml of methanol are added dropwise. After stirring for 30 minutes at this temperature, 50 ml of water, 30 ml of $CH_2Cl_2$ and 10 ml of saturated $NaHCO_3$ are added. After separation of the phases by settling, the organic phase is dried over sodium sulfate, filtered and then concentrated under reduced pressure. The beige-colored foam obtained is purified by flash chromatography ($SiO_2$, EtOAc as eluent, Ar). The fractions containing the product are concentrated under reduced pressure. 0.17 g of 5,5-dimethyl-1-(6-hydroxyquinoline-4-ylmethyl)-3-(4-trifluoromethoxyphenyl)imidazolidine-2,4-dione is thus obtained, the characteristics of which product are as follows:

$^1$H NMR spectrum (300 MHz, $(CD_3)_2SO$ d6, δ in ppm): 1.46 (s: 6H); 5.00 (broad s: 2H); 7.30 to 7.40 (mt: 2H); 7.51 (d, J=4.5 Hz: 1H); 7.55 (broad d, J=8.5 Hz: 2H); 7.69 (d, J=8.5 Hz: 2H); 7.94 (d, J=9 Hz: 1H); 8.64 (d, J=4.5 Hz: 1H); 10.12 (unresolved complex: 1H).

Mass IE m/z=445 M$^+$.

m/z=199 $C_{11}H_7N_2O_2^+$ m/z=158 $C_{10}H_8NO^+$ base peak

EXAMPLE 203

5,5-Dimethyl-1-(7-methoxyquinolin-4-ylmethyl)-3-(4-trifluoromethoxyphenyl)imidazolidine-2,4-dione

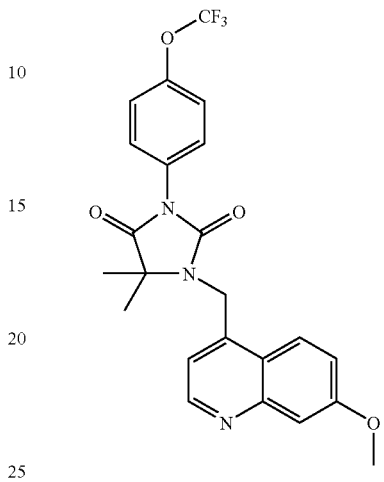

The product is prepared according to the procedure described in Example 59, starting with 0.94 g of methyl 2-methyl-2-[(7-methoxyquinolin-4-ylmethyl)amino]propanoate instead of methyl 2-methyl-2-[(quinolin-4-ylmethyl)amino]propanoate used in Example 59, and 1.7 g of 4-(trifluoromethoxyphenyl) isocyanate. After purification by flash chromatography on a column ($SiO_2$, cyclohexane/ethyl acetate 70/30 by volume and then $CH_2Cl_2$/MeOH 90/10 by volume as eluents, Ar), 1.45 g of the expected product are obtained.

$^1$H NMR spectrum (300 MHz, $(CD_3)_2SO$ d6, δ in ppm): 1.44 (s: 6H); 3.96 (s: 3H); 5.12 (broad s: 2H); 7.35 (dd, J=9 and 3 Hz: 1H); 7.47 (d, J=3 Hz: 1H); 7.49 (d, J=4.5 Hz: 1H); 7.55 (broad d, J=9 Hz: 2H); 7.68 (broad d, J=9 Hz: 2H); 8.19 (d, J=9 Hz: 1H); 8.80 (d, J=4.5 Hz: 1H).

Mass IE m/z=459 M$^+$. base peak m/z=444 (M–CH$_3$)$^+$ m/z=213 $C_{12}H_9N_2O_2^+$ m/z=172 $C_{11}H_{10}NO^+$ Preparation of methyl 2-((7-methoxyquinolin-4-ylmethyl)amino)propanoate A mixture of 1.23 g of methyl α-aminoisobutyrate hydrochloride and 1.12 ml of triethylamine in 30 ml of dichloromethane is stirred at 0° C. for 20 minutes. Next, 1 g of magnesium sulfate and 1.5 g of 7-methoxyquinoline-4-carbaldehyde are added. Stirring is continued for 15 hours at room temperature and the mixture is then concentrated under reduced pressure. The residue is taken up in 35 ml of methanol, the solution obtained is cooled to 0° C. and 0.31 g of sodium borohydride is then added portionwise. The reaction medium is stirred at a temperature in the region of 20° C. for 15 hours. The reaction medium is concentrated under reduced pressure. The residue obtained is taken up in 100 ml of EtOAc. The precipitate formed is filtered off and the filtrate is concentrated under reduced pressure and then purified by flash chromatography on a column ($SiO_2$, EtOAc as eluent, Ar), and 0.95 g of the expected product is obtained.

$^1$H NMR spectrum (300 MHz, (CD$_3$)$_2$SO d6, δ in ppm): 1.35 (s: 6H); 2.63 (t, J=7.5 Hz: 1H); 3.70 (s: 3H); 3.93 (s: 3H); 4.05 (d, J=7.5 Hz: 2H); 7.28 (dd, J=9 and 3 Hz: 1H); 7.41 (d, J=3 Hz: 1H); 7.43 (d, J=4.5 Hz: 1H); 8.12 (d, J=9 Hz: 1H); 8.76 (d, J=4.5 Hz: 1H).

Mass IC m/z=289 MH$^+$ base peak
m/z=229 (M–C$_2$H$_4$O$_2$)$^+$

Preparation of 7-methoxyquinoline-4-carbaldehyde

A mixture of 1.9 g of selenium oxide dissolved in 35 ml of dioxane is added dropwise to a solution of 2.7 g of 4-methyl-7-methoxyquinoline in 35 ml of dioxane preheated to 65° C. At the end of the addition, the brown suspension is heated to a temperature in the region of 80° C. for 5 hours. The reaction medium is stirred for 16 hours at a temperature in the region of 20° C. The greenish suspension is suction-filtered and then washed with EtOAc. The filtrate is concentrated under reduced pressure. The suspension obtained is crystallized from isopropyl ether to give 1.54 g of 7-methoxyquinoline-4-carbaldehyde.

$^1$H NMR spectrum (300 MHz, (CD$_3$)$_2$SO d6, δ in ppm): 3.99 (s: 3H); 7.48 (dd, J=9 and 3 Hz: 1H); 7.57 (d, J=3 Hz: 1H); 7.90 (d, J=4.5 Hz: 1H); 8.89 (d, J=9 Hz: 1H); 9.19 (d, J=4.5 Hz: 1H); 10.52 (s: 1H).

Mass IC m/z=188 MH$^+$ base peak

Preparation of 4-methyl-7-methoxyquinoline 4 g of triphenylphosphine, 5.3 g of lithium chloride, 14 ml of tetramethyltin and 2.1 g of bis(triphenylphosphine)palladium(II) chloride are added to a solution of 6 g of 4-bromo-7-methoxyquinoline in 100 ml of DMF, under an inert atmosphere of argon at a temperature in the region of 20° C. The reaction medium is heated at a temperature in the region of 120° C. for 16 hours. After cooling, the insoluble material is filtered off. The filtrate is concentrated under reduced pressure. The residue obtained is taken up in 300 ml of EtOAc and 300 ml of water. After separation of the phases by settling, the organic phase is dried over magnesium sulfate, filtered and then concentrated under reduced pressure. The oil obtained is taken up in 300 ml of EtOAc and 300 ml of water and then acidified with hydrochloric acid to pH 1. The aqueous phase is basified with sodium hydroxide to pH 10 and then extracted with 300 ml of EtOAc. After separation of the phases by settling, the organic phase is dried over magnesium sulfate, filtered and then concentrated under reduced pressure to give 2.7 g of 4-methyl-7-methoxyquinoline, the characteristics of which product are as follows:

$^1$H NMR spectrum (300 z, (CD$_3$)$_2$SO d6, δ in ppm): 2.65 (s: 3H); 3.94 (s: 3H); 7.23 (broad d, J=4.5 Hz: 1H); 7.28 (dd, J=9 and 3 Hz: 1H); 7.40 (d, J=3 Hz: 1H); 8.01 (d, J=9 Hz: 1H); 8.58 (d, J=4.5 Hz: 1H).

Mass IE m/z=173 M$^+$. base peak
m/z=158 (M–CH$_3$)$^+$
m/z=143 (M–CH$_2$O)$^+$.
m/z=130 (m/z=158–CO)$^+$ Preparation of 4-bromo-7-methoxyquinoline 22.74 g of 4-hydroxy-7-methoxyquinoline are added to 200 g of phosphorus oxybromide preheated to a temperature in the region of 110° C. The reaction medium is heated at this same temperature for 3 hours. The reaction medium is poured, while hot, into a mixture of 500 ml of EtOAc and 500 ml of ice-cold water. The medium is neutralized with potassium carbonate to pH 7. After separation of the phases by settling, the organic phase is dried over magnesium sulfate, evaporated under reduced pressure and then purified by column chromatography (SiO$_2$, EtOAc/cyclohexane 50/50 by volume as eluents, Ar), and 14.6 g of the expected product are obtained.

$^1$H NMR spectrum (300 MHz, (CD$_3$)$_2$SO d6, δ in ppm): 3.97 (s: 3H); 7.43 (dd, J=9 and 3 Hz: 1H); 7.49 (d, J=3 Hz: 1H); 7.79 (d, J=4.5 Hz: 1H); 8.06 (d, J=9 Hz: 1H); 8.67 (d, J=4.5 Hz: 1H).

Mass IE m/z=237 M$^+$. base peak

4-Hydroxy-7-methoxyquinoline is prepared according to the process described in: J. Am. Chem. Soc., 68, 1268, 1946.

EXAMPLE 204

5,5-Dimethyl-1-(7-hydroxyquinoline-4-ylmethyl)-3-(4-trifluoromethoxyphenyl)imidazolidine-2,4-dione

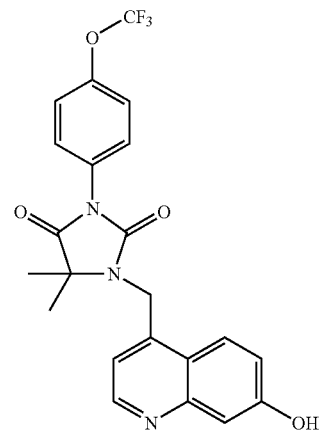

A mixture of 0.89 g of 5,5-dimethyl-1-(7-methoxyquinolin-4-ylmethyl)-3-(4-trifluoromethoxyphenyl)imidazolidine-2,4-dione and 5.5 g of pyridine hydrochloride is heated at a temperature in the region of 220° C. for 4 hours. After cooling, 200 ml of water and 100 ml of CH$_2$Cl$_2$ are added. After separation of the phases by settling, the organic phase is dried over sodium sulfate, filtered and then concentrated under reduced pressure. The solid obtained is purified by flash chromatography (SiO$_2$, EtOAc/CH$_2$Cl$_2$ 40/60 by volume as eluent, Ar). The fractions containing the product are concentrated under reduced pressure. 85 mg of 5,5-dimethyl-1-(7-hydroxyquinoline-4-ylmethyl)-3-(4-trifluoromethoxyphenyl)imidazolidine-2,4-dione are thus obtained, the characteristics of which product are as follows:

$^1$H NMR spectrum (300 MHz, (CD$_3$)$_2$SO d6, δ in ppm): 1.45 (s: 6H); 5.08 (broad s: 2H); 7.24 (dd, J=9 and 3 Hz: 1H); 7.30 (d, J=3 Hz: 1H); 7.38 (d, J=4.5 Hz: 1H); 7.55 (broad d, J=9 Hz: 2H); 7.68 (broad d, J=9 Hz: 2H); 8.10 (d, J=9 Hz: 1H); 8.71 (d, J=4.5 Hz: 1H); from 9.90 to 10.50 (broad unresolved complex: 1H).

Mass IE m/z=445 M$^+$. base peak
m/z=430 (M–CH$_3$)$^+$
m/z=199 C$_{11}$H$_7$N$_2$O$_2$$^+$
m/z=158 C$_{10}$H$_8$NO$^+$

EXAMPLE 205

5,5-Dimethyl-1-(2-aminoquinoline-4-ylmethyl)-3-(4-trifluoromethoxyphenyl)-imidazolidine-2,4-dione

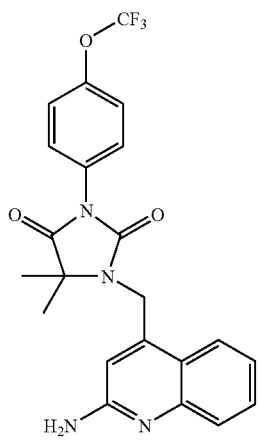

0.44 g of tosyl chloride is added to a solution of 0.8 g of 5,5-dimethyl-1-(N-oxyquinoline-4-ylmethyl)-3-(4-trifluoromethoxyphenyl)imidazolidine-2,4-dione in 10 ml of chloroform, under an inert atmosphere of argon at a temperature in the region of 5° C. After stirring for 30 minutes at this same temperature, 1.5 ml of 32% aqueous ammonia are added. The temperature is allowed to rise to 20° C. The reaction medium is stirred at a temperature in the region of 20° C. for 16 hours. 100 ml of water are added. After separation of the phases by settling, the organic phase is dried over sodium sulfate, filtered and then concentrated under reduced pressure. The solid obtained is purified by flash chromatography (SiO$_2$, EtOAc as eluent, Ar). The fractions containing the product are concentrated under reduced pressure. 200 mg of 5,5-dimethyl-1-(2-aminoquinoline-4-ylmethyl)-3-(4-trifluoromethoxyphenyl)-imidazolidine-2,4-dione are thus obtained, the characteristics of which product are as follows:

$^1$H NMR spectrum (300 MHz, (CD$_3$)$_2$SO d6, δ in ppm): 1.49 (s: 6H); 4.96 (broad s: 2H); 6.36 (broad s: 2H); 6.81 (s: 1H); 7.23 (mt: 1H); 7.51 (mt: 2H); 7.58 (broad d, J=9 Hz: 2H); 7.68 (broad d, J=9 Hz: 2H); 7.91 (d, J=8.5 Hz: 1H).

Mass IE m/z=444M$^+$. base peak
m/z=429 (M−CH$_3$)$^+$
m/z=198 C$_{11}$H$_8$N$_3$O$^+$
m/z=158 C$_{10}$H$_{10}$N$_2$$^+$

EXAMPLE 206

5,5-Dimethyl-1-(N-oxyquinoline-4-ylmethyl)-3-(4-trifluoromethoxyphenyl)-imidazolidine-2,4-dione

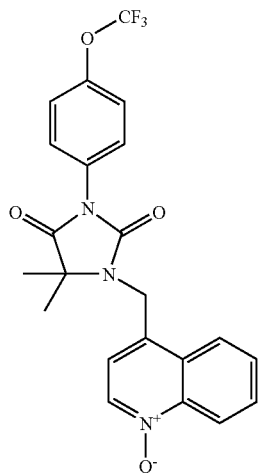

0.78 g of m-chloroperbenzoic acid is added to a solution of 1.95 g of 5,5-dimethyl-1-(quinolin-4-ylmethyl)-3-(4-trifluoromethoxyphenyl)imidazolidine-2,4-dione in 200 ml of chloroform and 10 ml of methanol, under an inert atmosphere of argon, at a temperature in the region of 20° C. The reaction medium is stirred at a temperature in the region of 20° C. for 4 hours. A further 0.8 g of m-chloroperbenzoic acid is added. The reaction medium is concentrated under reduced pressure. The product is crystallized from isopropyl ether to give 1.76 g of 5,5-dimethyl-1-(N-oxyquinoline-4-ylmethyl)-3-(4-trifluoromethoxyphenyl)-imidazolidine-2,4-dione, the characteristics of which product are as follows:

$^1$H NMR spectrum (300 MHz, (CD$_3$)$_2$SO d6, δ in ppm): 1.45 (s: 6H); 5.09 (broad s: 2H); 7.55 (broad d, J=8.5 Hz: 2H); 7.63 (d, J=4.5 Hz: 1H); 7.68 (broad d, J=8.5 Hz: 2H); 7.85 (broad t, J=8.5 Hz: 1H); 7.91 (broad t, J=8.5 Hz: 1H); 8.35 (broad d, J=8.5 Hz: 1H); 8.56 (d, J=4.5 Hz: 1H); 8.64 (broad d, J=8.5 Hz: 1H).

Mass ES m/z=446 MH$^+$ base peak

EXAMPLE 207

5,5-Dimethyl-1-(2-chloroquinoline-4-ylmethyl)-3-(4-trifluoromethoxyphenyl)-imidazolidine-2,4-dione

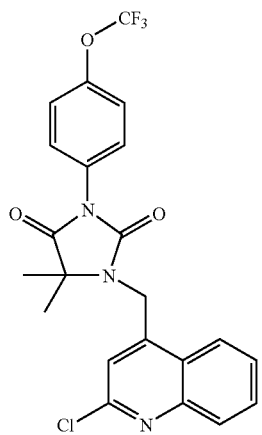

0.17 ml of phosphorus oxychloride is added to a solution of 4 ml of DMF and 2 ml of toluene, under an inert atmosphere of argon at a temperature in the region of 5° C. After stirring for 30 minutes at this same temperature, 0.4 g of 5,5-dimethyl-1-(N-oxyquinolin-4-ylmethyl)-3-(4-trifluoromethoxyphenyl)imidazolidine-2,4-dione in 10 ml of toluene is added. The reaction medium is stirred at a temperature in the region of 5° C. for 2 and a half hours. The temperature is allowed to return to 20° C. The reaction medium is concentrated under reduced pressure. The residue obtained is taken up in 50 ml of EtOAc and washed with saturated NaHCO$_3$ solution. After separation of the phases by settling, the organic phase is dried over sodium sulfate, filtered and then concentrated under reduced pressure. The product is crystallized from isopropyl ether to give 0.37 g of 5,5-dimethyl-1-(2-chloroquinolin-4-ylmethyl)-3-(4-trifluoromethoxyphenyl)imidazolidine-2,4-dione, the characteristics of which product are as follows:

$^1$H NMR spectrum (300 MHz, (CD$_3$)$_2$SO d6, δ in ppm): 1.50 (s: 6H); 5.17 (broad s: 2H); 7.56 (broad d, J=8.5 Hz: 2H); 7.71 (broad d, J=8.5 Hz: 2H); 7.76 (s: 1H); 7.76 (split t, J=8 and 1.5 Hz: 1H); 7.89 (split t, J=8 and 1.5 Hz: 1H); 8.03 (broad d, J=8 Hz: 1H); 8.31 (broad d, J=8 Hz: 1H).

Mass IE m/z=463 M$^+$. base peak
m/z=448 (M−CH$_3$)$^+$
m/z=428 (M−Cl)$^+$
m/z=358 (m/z=428−C$_4$H$_6$O)$^+$
m/z=217 C$_{11}$H$_6$N$_2$OCl$^+$
m/z=176 C$_{10}$H$_7$NCl$^+$

EXAMPLE 208

5,5-Dimethyl-1-(2-chloropyrid-4-ylmethyl)-3-(4-trifluoromethoxyphenyl)-imidazolidine-2,4-dione 0.028 g of sodium hydride is added to a solution of 0.1 g of 5,5-dimethyl-3-(4-trifluoromethoxyphenyl)imidazolidine-2,4-dione in 2 ml of anhydrous dimethylformamide, under an inert atmosphere of argon at a temperature in the region of 20° C. Stirring is continued at this temperature for 30 minutes. A solution of 0.1 g of 2-chloro-4-(bromomethyl)pyridine in 2 ml of dimethylformamide is added, followed by addition of ice-cold water after reaction for 10 minutes. The reaction medium is placed on a cartridge 20 mm in diameter packed with 17 g of octadecyl-grafted 50 μm silica conditioned successively with acetonitrile and then with water. The elution is performed by gradient using the mixture (water/acetonitrile) of from 0 to 100% acetonitrile. The fractions containing the expected product are concentrated under reduced pressure. 0.130 g of crude product is thus obtained, which product is purified by a double chromatography using a cartridge packed with 10 g of 20-40 μm of conditioned silica, and then eluted with a mixture (cyclohexane/ethyl acetate), (8/2) (v/v) at a flow rate of 5 ml/minute. The fractions between 30 and 75 ml are concentrated under reduced pressure. 0.1 g of 5,5-dimethyl-1-(2-chloropyrid-4-ylmethyl)-3-(4-trifluoromethoxyphenyl)imidazolidine-2,4-dione is thus obtained in the form of a white powder, the characteristics of which product are as follows:

m.p. 134° C.
Mass IE m/z=413 M$^+$. base peak
m/z=398 (M−CH$_3$)$^+$
m/z=203 C$_8$H$_4$NO$_2$F$_3$$^+$.
m/z=167 C$_7$H$_4$N$_2$OCl$^+$
m/z=126 C$_6$H$_5$NCl$^+$ $^1$H NMR spectrum (300 MHz, (CD$_3$)$_2$SO d6, δ in ppm): 1.44 (s: 6H); 4.67 (s: 2H); 7.50 (broad d, J=5.5 Hz: 1H); 7.54 (broad d, J=9 Hz: 2H); 7.61 (broad s: 1H); 7.66 (broad d, J=9 Hz: 2H); 8.40 (d, J=5.5 Hz: 1H).

The compound 5,5-dimethyl-3-(4-trifluoromethoxyphenyl)imidazolidine-2,4-dione is described in Example 63.

EXAMPLE 209

5,5-Dimethyl-1-(2-ethoxypyrid-4-ylmethyl)-3-(4-trifluoromethoxyphenyl)-imidazolidine-2,4-dione 0.015 g of sodium hydride is added to a solution of 0.175 g of 5,5-dimethyl-3-(4-trifluoromethoxyphenyl)imidazolidine-2,4-dione in 2 ml of anhydrous dimethylformamide, under an inert atmosphere of argon at a temperature in the region of 20° C. Stirring is maintained at this temperature for 30 minutes. A solution of 0.185 g of 2-ethoxy-4-(bromomethyl)pyridine in 2 ml of anhydrous dimethylformamide is added, followed by addition of ice-cold water after reaction for 10 minutes. The reaction mixture is placed on a cartridge 37 mm in diameter packed with 65 g of octadecyl-grafted 40-60 μm silica conditioned successively with the mixture (water/acetonitrile) (5/95) (v/v) and then with the mixture (water/acetonitrile) (95/5) (v/v). The elution is performed with a mixture (water/acetonitrile) (95/5) (v/v) over 20 minutes, followed by a linear gradient of from 5% to 95% acetonitrile over 60 minutes, at a flow rate of 10 ml/minute. The fractions between 700 and 760 ml are concentrated under reduced pressure. 0.145 g of 5,5-dimethyl-1-(2-ethoxypyrid-4-ylmethyl)-3-(4-trifluoromethoxyphenyl)imidazolidine-2,4-dione is thus obtained, the characteristics of which product are as follows:

Mass IE m/z=423 M$^+$.
m/z=408 (M−CH$_3$)$^+$ base peak
m/z=395 (M−C$_2$H$_4$)$^+$.
m/z=203 C$_8$H$_4$NO$_2$F$_3$$^+$.

$^1$H NMR spectrum (300 MHz, (CD$_3$)$_2$SO d6, δ in ppm): 1.32 (t, J=7 Hz: 3H); 1.42 (s: 6H); 4.30 (q, J=7 Hz: 2H); 4.58 (broad s: 2H); 6.85 (broad s: 1H); 7.01 (broad d, J=5.5 Hz: 1H); 7.52 (broad d, J=8.5 Hz: 2H); 7.63 (broad d, J=8.5 Hz: 2H); 8.10 (d, J=5.5 Hz: 1H).

The compound 5,5-dimethyl-3-(4-trifluoromethoxyphenyl)imidazolidine-2,4-dione is described in Example 63.

EXAMPLE 210

5,5-Dimethyl-1-(2-ethylpyrid-4-ylmethyl)-3-(4-trifluoromethoxyphenyl)-imidazolidine-2,4-dione 0.009 g of sodium hydride is added to a solution of 0.064 g of 5,5-dimethyl-3-(4-trifluoromethoxyphenyl)imidazolidine-2,4-dione in 1 ml of anhydrous dimethylformamide, under an inert atmosphere of argon, at a temperature in the region of 20° C. Stirring is continued at this temperature for 30 minutes. A solution of 0.062 g of 2-ethyl-4-(bromomethyl)pyridine in 0.5 ml of anhydrous dimethylformamide is added, followed by addition of ice-cold water after reaction for 10 minutes. The reaction mixture is placed on a cartridge 27 mm in diameter packed with 25 g of octadecyl-grafted 40-60 μm silica conditioned successively with the mixture (water/acetonitrile) (5/95) (v/v) and then with the mixture (water/acetonitrile) (95/5) (v/v). The elution is performed with a mixture (water/acetonitrile) (95/5) (v/v) over 20 minutes, followed by a linear gradient of from 5% to 95% acetonitrile over 60 minutes, at a flow rate of 10 ml/minute. The fractions between 750 and 790 ml are concentrated under reduced pressure. 0.06 g of 5,5-dimethyl-1-(2-ethylpyrid-4-ylmethyl)-3-(4-trifluoromethoxyphenyl)imidazolidine-2,4-dione is thus obtained, the characteristics of which product are as follows:
Mass IE m/z=407 M+. base peak
m/z=392 (M−CH₃)+
m/z=203 C₈H₄NO₂F₃+.
m/z=120 C₈H₁₀N+
¹H NMR spectrum (400 MHz, (CD₃)₂SO d6, δ in ppm): 1.27 (t, J=7.5 Hz: 3H); 1.44 (s: 6H); 2.75 (q, J=7.5 Hz: 2H); 4.54 (s: 2H); 7.10 (broad d, J=5.5 Hz: 1H); 7.15 (broad s: 1H); 7.39 (broad d, J=8.5 Hz: 2H); 7.49 (d, J=8.5 Hz: 2H); 8.26 (d, J=5.5 Hz: 1H).

The compound 5,5-dimethyl-3-(4-trifluoromethoxy-phenyl)imidazolidine-2,4-dione is described in Example 63.

EXAMPLE 211

5,5-Dimethyl-1-(2-chloropyrid-4-ylmethyl)-3-(4-trifluoromethanesulfanylphenyl)imidazolidine-2,4-dione 0.046 g of sodium hydride is added to a solution of 0.175 g of 5,5-dimethyl-3-(4-trifluoromethylsulfanylphenyl)imidazolidine-2,4-dione in 3 ml of anhydrous dimethylformamide, under an inert atmosphere of argon, at a temperature in the region of 20° C. Stirring is continued at this temperature for 30 minutes. A solution of 0.166 g of 2-chloro-4-(bromomethyl)pyridine in 2 ml of anhydrous dimethylformamide is added, followed by addition of ice-cold water after reaction for 10 minutes. The reaction mixture is placed on a cartridge 37 mm in diameter packed with 65 g of octadecyl-grafted 40-60 μm silica conditioned successively with the mixture (water/acetonitrile) (5/95) (v/v) and then with the mixture (water/acetonitrile) (95/5) (v/v). The elution is performed with a mixture (water/acetonitrile) (95/5) (v/v) over 20 minutes, followed by a linear gradient of from 5 to 95% acetonitrile over 60 minutes, at a flow rate of 10 ml/minute. The fractions between 740 and 780 ml are concentrated under reduced pressure. 0.03 g of 5,5-dimethyl-1-(2-chloropyrid-4-ylmethyl)-3-(4-trifluoromethanesulfanylphenyl)imidazolidine-2,4-dione is thus obtained in the form of a white powder, the characteristics of which product are as follows:
m.p. 111° C.
Mass IC
m/z=447 MNH₄+
m/z=430 MH+ base peak
¹H NMR spectrum (300 MHz, (CD₃)₂SO d6, δ in ppm): 1.44 (s: 6H); 4.67 (broad s: 2H); 7.49 (broad d, J=5.5 Hz: 1H); 7.61 (broad s: 1H); 7.70 (broad d, J=8.5 Hz: 2H); 7.88 (broad d, J=8.5 Hz: 2H); 8.38 (d, J=5.5 Hz: 1H).

Preparation of 5,5-dimethyl-3-(4-trifluoromethylsulfanylphenyl)imidazolidine-2,4-dione 5.12 ml of triethylamine and 2.8 g of methyl α-aminoisobutyrate hydrochloride are added to a solution of 4 g of 4-trifluoromethylsulfanylphenyl isocyanate in 40 ml of toluene, under an inert atmosphere of argon at a temperature in the region of 20° C. The mixture thus obtained is refluxed for 24 hours and then cooled to a temperature in the region of 20° C. The reaction mixture is concentrated to dryness under reduced pressure and the residue obtained is taken up in ethyl ether and filtered. 5.3 g of 5,5-dimethyl-3-(4-trifluoromethylsulfanylphenyl)-imidazolidine-2,4-dione are thus obtained, the characteristics of which product are as follows:
Mass IC
m/z=322 MNH₄+
m/z=102 triethylamine H+ base peak ¹H NMR spectrum (300 MHz, (CD₃)₂SO d6, δ in ppm): 1.44 (s: 6H); 7.62 (broad d, J=8.5 Hz: 2H); 7.85 (broad d, J=8.5 Hz: 2H); 8.72 (unresolved complex: 1H).

The insoluble material thus obtained is taken up in dichloromethane and then washed with water. 2.76 g of 5,5-dimethyl-3-(4-trifluoromethylsulfanylphenyl)imidazolidine-2,4-dione are thus obtained, which product is used for the subsequent synthesis.

EXAMPLE 212

5,5-Dimethyl-1-(2-ethoxypyrid-4-ylmethyl)-3-(4-trifluoromethanesulfanylphenyl)imidazolidine-2,4-dione 0.049 g of sodium hydride is added to a solution of 0.185 g of 5,5-dimethyl-3-(4-trifluoromethylsulfanylphenyl)imidazolidine-2,4-dione in 3.2 ml of anhydrous dimethylformamide, under an inert atmosphere of argon at a temperature in the region of 20° C. Stirring is continued at this temperature for 30 minutes. A solution of 0.184 g of 2-ethoxy-4-(bromomethyl)pyridine in 2 ml of dimethylformamide is added, followed by addition of ice-cold water after reaction for 10 minutes. The reaction mixture is placed on a cartridge 37 mm in diameter packed with 65 g of octadecyl-grafted 40-60 μm silica conditioned successively with the mixture (water/acetonitrile) (5/95) (v/v) and then the mixture (water/acetonitrile) (95/5) (v/v). The elution was performed with a mixture (water/acetonitrile) (95/5) (v/v) over 20 minutes, followed by a linear gradient of from 5% to 95% of acetonitrile over 60 minutes, at a flow rate of 10 ml/minute. The fractions between 520 and 700 ml are concentrated under reduced pressure. The residue thus obtained is purified by flash chromatography using a cartridge packed with 2 g of conditioned 15-35 μm silica, and then eluted with a mixture (cyclohexane/ethyl acetate) (9/1) (v/v). The fractions containing the expected product are concentrated under reduced pressure. 0.01 g of 5,5-dimethyl-1-(2-ethoxypyrid-4-ylmethyl)-3-(4-trifluoromethanesulfanylphenyl)imidazolidine-2,4-dione is thus obtained, the characteristics of which product are as follows:
Mass IE
m/z=439 M+.
m/z=424 (M−CH₃)+ base peak
m/z=411 (M−C₂H₄)+.
m/z=219 C₈H₄NOSF₃+.
¹H NMR spectrum (300 MHz, (CD₃)₂SO d6, δ in ppm): 1.32 (t, J=7 Hz: 3H); 1.42 (s: 6H); 4.30 (q, J=7 Hz: 2H); 4.58 (broad s: 2H); 6.86 (broad s: 1H); 7.01 (broad d, J=5.5 Hz: 1H); 7.69 (broad d, J=8.5 Hz: 2H); 7.88 (broad d, J=8.5 Hz: 2H); 8.10 (broad d, J=5.5 Hz: 1H).

The compound 5,5-dimethyl-3-(4-trifluoromethylsulfanylphenyl)imidazolidine-2,4-dione is described in Example 211.

EXAMPLE 213

5,5-Dimethyl-1-(2-ethylpyrid-4-ylmethyl)-3-(4-trifluoromethanesulfanylphenyl)imidazolidine-2,4-dione 0.021 g of sodium hydride is added to a solution of 0.135 g of 5,5-dimethyl-3-(4-trifluoromethylsulfanylphenyl)imidazolidine-2,4-dione in 2 ml of anhydrous dimethylformamide, under an inert atmosphere of argon at a temperature in the region of 20° C. Stirring is continued at this temperature for 30 minutes. A solution of 0.126 g of 2-ethyl-4-(bromomethyl)pyridine in 1 ml of anhydrous dimethylformamide is added, followed by addition of ice-cold water after reaction for 10 minutes. The reaction mixture is placed on a cartridge 37 mm in diameter packed with 65 g of octadecyl-grafted 40-60 μm silica conditioned successively with the mixture (water/acetonitrile) (5/95) (v/v) and then the mixture (water/acetonitrile) (95/5) (v/v). The elution was performed with a mixture (water/acetonitrile) (95/5) (v/v) over 20 minutes, followed by a linear gradient of from 5% to 95% of acetonitrile over 60 minutes and by an elution with 100% acetonitrile for 10 minutes, at a flow rate of 10 ml/minute. The fractions between 800 and 880 ml are concentrated under reduced pressure. 0.120 g of 5,5-dimethyl-1-(2-ethylpyrid-4-ylmethyl)-3-(4-trifluoromethanesulfanylphenyl) imidazolidine-2,4-dione is thus obtained, the characteristics of which product are as follows:

Mass IE
m/z=423 M$^+$. base peak
m/z=408 (M−CH$_3$)$^+$
m/z=219 C$_8$H$_4$NOSF$_3$$^+$.
m/z=120 C$_8$H$_{10}$N$^+$
$^1$H NMR spectrum (400 MHz, (CD$_3$)$_2$SO d6, δ in ppm): 1.23 (t, J=7.5 Hz: 3H); 1.42 (s: 6H); 2.75 (q, J=7.5 Hz: 2H); 4.62 (broad s: 2H); 7.25 (broad d, J=5.5 Hz: 1H); 7.30 (broad s: 1H); 7.70 (d, J=8.5 Hz: 2H); 7.88 (d, J=8.5 Hz: 2H); 8.43 (d, J=5.5 Hz: 1H).

The compound 5,5-dimethyl-3-(4-trifluoromethylsulfanylphenyl)imidazolidine-2,4-dione is described in Example 211.

EXAMPLE 214

5,5-Dimethyl-1-(2-bromopyrid-4-ylmethyl)-3-(4-trifluoromethoxyphenyl)-imidazolidine-2,4-dione 0.023 g of sodium hydride is added to a solution of 0.081 g of 5,5-dimethyl-3-(4-trifluoromethoxyphenyl)imidazolidine-2,4-dione in 2 ml of anhydrous dimethylformamide, under an inert atmosphere of argon at a temperature in the region of 20° C. Stirring is continued at this temperature for 35 minutes. A solution of 0.071 g of 2-bromo-4-(bromomethyl)pyridine in 1 ml of anhydrous dimethylformamide is added, followed by addition of ice-cold water after reaction for 15 minutes. The reaction mixture is placed on a cartridge 16 mm in diameter packed with 5 g of octadecyl-grafted 40-60 μm silica conditioned successively with the mixture (water/acetonitrile) (5/95) (v/v) and then the mixture (water/acetonitrile) (95/5) (v/v). The elution was performed with a linear gradient of from 5% to 95% of acetonitrile over 30 minutes then with a mixture (water/acetonitrile) (5/95) (v/v) over 10 minutes, at a flow rate of 5 ml/minute. The fractions between 90 and 100 ml are concentrated under reduced pressure. 0.015 g of 5,5-dimethyl-1-(2-bromopyrid-4-ylmethyl)-3-(4-trifluoromethoxyphenyl)-imidazolidine-2,4-dione is thus obtained in the form of a white foam, the characteristics of which product are as follows:

Mass IE
m/z=457 M$^+$. base peak
m/z=442 (M−CH$_3$)$^+$
m/z=211 C$_7$H$_4$N$_2$OBr$^+$
m/z=203 C$_8$H$_4$NO$_2$F$_3$$^+$.
m/z=170 C$_6$H$_5$Br$^+$
$^1$H NMR spectrum (300 MHz, (CD$_3$)$_2$SO d6, δ in ppm): 1.44 (s: 6H); 4.67 (broad s: 2H); 7.52 (broad d, J=5.5 Hz: 1H); 7.54 (broad d, J=9 Hz: 2H); 7.66 (broad d, J=9 Hz: 2H); 7.75 (broad s: 1H); 8.37 (d, J=5.5 Hz: 1H).

The compound 5,5-dimethyl-3-(4-trifluoromethoxyphenyl)imidazolidine-2,4-dione is described in Example 63.

EXAMPLE 215

5,5-Dimethyl-1-(2-fluoropyrid-4-ylmethyl)-3-(4-trifluoromethanesulfanylphenyl)imidazolidine-2,4-dione 0.025 g of sodium hydride is added to a solution of 0.096 g of 5,5-dimethyl-3-(4-trifluoromethylsulfanylphenyl)imidazolidine-2,4-dione in 2 ml of anhydrous dimethylformamide, under an inert atmosphere of argon at a temperature in the region of 20° C. Stirring is continued at this temperature for 25 minutes. A solution of 0.060 g of 2-fluoro-4-(bromomethyl)pyridine in 1 ml of anhydrous dimethylformamide is added, followed by addition of ice-cold water after reaction for 15 minutes. The reaction mixture is placed on a cartridge 16 mm in diameter packed with 5 g of octadecyl-grafted 40-60 μm silica conditioned successively with the mixture (water/acetonitrile) (5/95) (v/v) and then the mixture (water/acetonitrile) (95/5) (v/v). The elution was performed with a linear gradient of from 5% to 95% of acetonitrile over 30 minutes then with a mixture (water/acetonitrile) (5/95) (v/v) over 10 minutes, at a flow rate of 5 ml/minute. The fractions between 105 and 125 ml are concentrated under reduced pressure. 0.069 g of 5,5-dimethyl-1-(2-fluoropyrid-4-ylmethyl)-3-(4-trifluoromethanesulfanylphenyl)imidazolidine-2,4-dione is thus obtained in the form of a white solid, the characteristics of which are as follows:

m.p.: 82° C.
Mass IE
m/z=413 M$^+$. base peak
m/z=398 (M−CH$_3$)$^+$
m/z=219 C$_8$H$_4$NOSF$_3$$^+$.
m/z=151 C$_7$H$_4$N$_2$OF$^+$
m/z=110 C$_6$H$_5$NF$^+$
$^1$H NMR spectrum (300 MHz, (CD$_3$)$_2$SO d6, δ in ppm): 1.45 (s: 6H); 4.72 (broad s: 2H); 7.29 (broad s: 1H); 7.43 (broad d, J=5.5 Hz: 1H); 7.71 (broad d, J=8.5 Hz: 2H); 7.89 (broad d, J=8.5 Hz: 2H); 8.23 (d, J=5.5 Hz: 1H).

The compound 5,5-dimethyl-3-(4-trifluoromethylsulfanylphenyl)imidazolidine-2,4-dione is described in Example 211.

EXAMPLE 216

5,5-Dimethyl-1-(2-cyanopyrid-4-ylmethyl)-3-(4-trifluoromethanesulfanylphenyl)imidazolidine-2,4-dione 0.037 g of sodium hydride is added to a solution of 0.139 g of 5,5-dimethyl-3-(4-trifluoromethylsulfanylphenyl)imidazolidine-2,4-dione in 4 ml of anhydrous dimethylformamide, under an inert atmosphere of argon at a temperature in the region of 20° C. Stirring is continued at this temperature for 30 minutes. A solution of 0.090 g of 2-cyano-4-(bromomethyl)pyridine in 1 ml of anhydrous dimethylformamide is added, followed by addition of ice-cold water after reaction for 15 minutes. The reaction mixture is placed on a cartridge 20 mm in diameter packed with 10 g of octadecyl-grafted 40-60 μm silica conditioned successively with the mixture (water/acetonitrile) (5/95) (v/v) and then the mixture (water/acetonitrile) (95/5) (v/v). The elution was performed with a linear gradient of from 5% to 95% of acetonitrile over 30 minutes then with a mixture (water-acetonitrile) (5/95) (v/v) over 10 minutes, at a flow rate of 5 ml/minute. The fractions between 210 and 230 ml are concentrated under reduced pressure. 0.1 g of 5,5-dimethyl-1-(2-cyanopyrid-4-ylmethyl)-3-(4-trifluoromethanesulfanylphenyl)imidazolidine-2,4-dione is thus obtained in the form of a solid, the characteristics of which are as follows:

m.p.: 148° C.

Mass IE m/z=420 M$^+$. base peak m/z=405 (M–CH$_3$)$^+$ m/z=219 C$_8$H$_4$NOSF$_3{}^+$.

m/z=158 C$_8$H$_4$N$_3$O$^+$ m/z=117 C$_7$H$_5$N$_2{}^+$ $^1$H NMR spectrum (300 MHz, (CD$_3$)$_2$SO d6, δ in ppm): 1.44 (s: 6H); 4.74 (broad s: 2H); 7.72 (broad d, J=9 Hz: 2H); 7.81 (dd, J=5.5 and 2 Hz: 1H); 7.89 (broad d, J=9 Hz: 2H); 8.15 (broad s: 1H); 8.72 (broad d, J=5.5 Hz: 1H).

The compound 5,5-dimethyl-3-(4-trifluoromethylsulfanylphenyl)imidazolidine-2,4-dione is described in Example 211.

EXAMPLE 217

5,5-Dimethyl-1-(2-hydroxycarbonylpyrid-4-ylmethyl)-3-(4-trifluoromethanesulfanylphenyl)imidazolidine-2,4-dione A solution of 0.09 g of 5,5-dimethyl-1-(2-cyanopyrid-4-ylmethyl)-3-(4-trifluoromethanesulfanylphenyl)imidazolidine-2,4-dione in 5 ml of 5N hydrochloric acid is refluxed for about 16 hours. The reaction mixture is concentrated under reduced pressure and the crude product thus obtained is purified by flash chromatography using a cartridge 20 mm in diameter packed with 10 g of conditioned 20-40 μm silica, and then eluted with a mixture (dichloromethane/methanol) (9/1) (v/v) at a flow rate of 8 ml/minute. The fractions between 40 and 200 ml are concentrated under reduced pressure. 0.06 g of 5,5-dimethyl-1-(2-hydroxycarbonylpyrid-4-ylmethyl)-3-(4-trifluoromethanesulfanylphenyl)imidazolidine-2,4-dione is thus obtained, the characteristics of which product are as follows:

Mass IE m/z=439 M$^+$.

m/z=395 (M–CONH$_2$)$^+$ base peak m/z=219 C$_8$H$_4$NOSF$_3{}^+$.

m/z=185 C$_7$H$_9$N$_2$O$_2$S$^+$ $^1$H NMR spectrum (300 MHz, (CD$_3$)$_2$SO d6, δ in ppm): 1.45 (s: 6H); 4.76 (broad s: 2H); 7.70 (d, J=8.5 Hz: 2H); 7.72 (mt: 1H); 7.89 (d, J=8.5 Hz: 2H); 8.12 (broad s: 1H); 8.68 (d, J=5.5 Hz: 1H).

EXAMPLE 218

5,5-Dimethyl-1-[2-(methylamino)carbonylpyrid-4-ylmethyl]-3-(4-trifluoromethanesulfanylphenyl)imidazolidine-2,4-dione 0.025 g of methylamine hydrochloride, 0.005 g of hydroxybenzotriazole hydrate, 0.105 ml of triethylamine and 72 mg of 1-(3-dimethylaminopropyl)-3-ethylcarbodiimide hydrochloride are successively added to a solution of 0.055 g of 5,5-dimethyl-1-(2-hydroxycarbonylpyrid-4-ylmethyl)-3-(4-trifluoromethanesulfanylphenyl)imidazolidine-2,4-dione in 2 ml of dichloromethane, under an inert atmosphere of argon, at a temperature in the region of 20° C. Stirring is continued at this temperature for about 16 hours. The reaction mixture is washed with water and the organic phase is dried over magnesium sulfate, filtered and then concentrated under reduced pressure. The crude product thus obtained is purified by flash chromatography using a cartridge 16 mm in diameter packed with 5 g of conditioned 20-40 μm silica, and then eluted with a mixture (dichloromethane/methanol) (95/05) (v/v) at a flow rate of 10 ml/minute. The fractions containing the expected product are concentrated under reduced pressure. 0.013 g of 5,5-dimethyl-1-[2-(methylamino)carbonylpyrid-4-ylmethyl]-3-(4-trifluoromethanesulfanylphenyl)imidazolidine-2,4-dione is thus obtained in the form of a white powder, the characteristics of which are as follows:

Mass IE m/z=452 M$^+$.

m/z=395 (M–C$_2$H$_3$ON)$^+$ base peak m/z=219 C$_8$H$_4$NOSF$_3{}^+$.

m/z=148 C$_8$H$_8$N$_2$O$^+$ $^1$H NMR spectrum (300 MHz, (CD$_3$)$_2$SO d6, δ in ppm): 1.44 (s: 6H); 2.85 (d, J=5 Hz: 3H); 4.76 (broad s: 2H); 7.67 (dd, J=5 and 2 Hz: 1H); 7.70 (broad d, J=8.5 Hz: 2H); 7.89 (broad d, J=8.5 Hz: 2H); 8.10 (broad s: 1H); 8.60 (d, J=5 Hz: 1H); 8.75 (broad q, J=5 Hz: 1H).

EXAMPLE 219

5,5-Dimethyl-1-(2-aminocarbonylpyrid-4-ylmethyl)-3-(4-trifluoromethanesulfanylphenyl)imidazolidine-2,4-dione A solution of 0.04 g of 5,5-dimethyl-1-(2-cyanopyrid-4-ylmethyl)-3-(4-trifluoromethanesulfanylphenyl)imidazolidine-2,4-dione in 1 ml of 98% sulfuric acid is maintained at 40° C. for 30 minutes. The mixture is taken up in 15 ml of ice-cold water and then neutralized with normal sodium hydroxide solution. The solution thus obtained is extracted with 100 ml of ethyl acetate. The organic phase is dried over magnesium sulfate, filtered and then concentrated under reduced pressure. The crude product thus obtained is purified by flash chromatography using a cartridge 16 mm in diameter packed with 5 g of conditioned 20-40 μm silica, and then eluted with dichloromethane at a flow rate of 10 ml/minute. The fractions containing the expected product are concentrated under reduced pressure. 0.017 g of 5,5-dimethyl-1-(2-aminocarbonylpyrid-4-ylmethyl)-3-(4-trifluoromethanesulfanylphenyl)-imidazolidine-2,4-dione is thus obtained in the form of an amorphous white powder, the characteristics of which product are as follows:

Mass IE m/z=438 M$^+$. base peak m/z=423 (M–CH$_3$)$^+$ m/z=393 (M–CH$_3$NO)$^+$ m/z=219 C$_8$H$_4$NOSF$_3{}^+$.

m/z=135 C$_7$H$_7$N$_2$O$^+$ $^1$H NMR spectrum (300 MHz, (CD$_3$)$_2$SO d6, δ in ppm): 1.44 (s: 6H); 4.76 (broad s: 2H); from 7.60 to 7.70 (mt: 2H); 7.71 (broad d, J=8.5 Hz: 2H); 7.89 (broad d, J=8.5 Hz: 2H); 8.11 (broad s: 2H); 8.60 (d, J=5.5 Hz: 1H).

EXAMPLE 220

5,5-Dimethyl-1-(2-morpholinopyrid-4-ylmethyl)-3-(4-trifluoromethoxyphenyl)imidazolidine-2,4-dione A sealed 2.5 ml tube containing 0.05 g of 5,5-dimethyl-1-(2-chloropyrid-4-ylmethyl)-3-(4-trifluoromethoxyphenyl)imidazolidine-2,4-dione, 0.5 ml of dimethylformamide, 0.034 g of potassium carbonate and 0.021 ml of morpholine is placed in a Personal Chemistry Emrys Optimiser microwave oven. The mixture is irradiated with magnetic stirring at 210° C. for about 50 minutes. The reaction mixture is placed on a Bond Elut Varian cartridge of reference 1225-6053 containing 2 g of SCX phase conditioned with dimethylformamide. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 µm silica, and then eluted with a mixture (cyclohexane/ethyl acetate) (8/2) (v/v) at a flow rate of 10 ml/minute. The fractions between 160 and 260 ml are concentrated to dryness under reduced pressure. 0.01 g of 5,5-dimethyl-1-(2-morpholinopyrid-4-ylmethyl)-3-(4-trifluoromethoxyphenyl)imidazolidine-2,4-dione is thus obtained in the form of a powder, the characteristics of which product are as follows:

Mass IE
m/z=464 M$^+$.
m/z=433 (M–CH$_3$O)$^+$ base peak
m/z=419 (M–C$_2$H$_5$O)$^+$
m/z=407 (M–C$_3$H$_5$O)$^+$
m/z=379 (M–C$_4$H$_5$NO)$^+$
m/z=203 C$_8$H$_4$NO$_2$F$_3$$^+$.
m/z=176 C$_{10}$H$_{12}$N$_2$O$^+$.
$^1$H NMR spectrum (300 MHz, (CD$_3$)$_2$SO d6, δ in ppm): 1.42 (s: 6H); 3.44 (broad t, J=5 Hz: 4H); 3.72 (broad t, J=5 Hz: 4H); 4.53 (broad s: 2H); 6.75 (broad d, J=5.5 Hz: 1H); 6.85 (broad s: 1H); 7.54 (broad d, J=8.5 Hz: 2H); 7.64 (d, J=8.5 Hz: 2H); 8.10 (d, J=5.5 Hz: 1H).

EXAMPLE 221

5,5-Dimethyl-1-(2-morpholinopyrid-4-ylmethyl)-3-(4-trifluoromethanesulfanylphenyl)imidazolidine-2,4-dione A sealed 2.5 ml tube containing 0.05 g of 5,5-dimethyl-1-(2-chloropyrid-4-ylmethyl)-3-(4-trifluoromethanesulfanylphenyl)imidazolidine-2,4-dione and 0.5 ml of morpholine is placed in a Personal Chemistry Emrys Optimiser microwave oven. The mixture is irradiated with magnetic stirring at 160° C. for about 70 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6053 containing 2 g of SCX phase conditioned with methanol. The cartridge is washed with methanol and then eluted with 2M ammoniacal methanol. The ammoniacal fractions are concentrated to dryness under reduced pressure. 0.03 g of 5,5-dimethyl-1-(2-morpholinopyrid-4-ylmethyl)-3-(4-trifluoromethanesulfanylphenyl)imidazolidine-2,4-dione is thus obtained in the form of a powder, the characteristics of which are as follows:

Mass IE
m/z=480 M$^+$.
m/z=449 (M–CH$_3$O)$^+$ base peak
m/z=435 (M–C$_2$H$_5$O)$^+$
m/z=423 (M–C$_3$H$_5$O)$^+$
m/z=219 C$_8$H$_4$NOSF$_3$$^+$.
m/z=176 C$_{10}$H$_{12}$N$_2$O$^+$.
$^1$H NMR spectrum (300 MHz, (CD$_3$)$_2$SO d6, δ in ppm): 1.42 (s: 6H); 3.45 (broad t, J=5 Hz: 4H); 3.71 (broad t, J=5 Hz: 4H); 4.54 (broad s: 2H); 6.75 (broad d, J=5.5 Hz: 1H); 6.84 (broad s: 1H); 7.68 (broad d, J=8.5 Hz: 2H); 7.88 (d, J=8.5 Hz: 2H); 8.09 (d, J=5.5 Hz: 1H).

EXAMPLE 222

5,5-Dimethyl-1-(2-dimethylaminopyrid-4-ylmethyl)-3-(4-trifluoromethanesulfanylphenyl)imidazolidine-2,4-dione A sealed 2.5 ml tube containing 0.05 g of 5,5-dimethyl-1-(2-chloropyrid-4-ylmethyl)-3-(4-trifluoromethanesulfanylphenyl)imidazolidine-2,4-dione, 0.4 ml of isopropylamine and 0.1 ml of dimethylformamide is placed in a Personal Chemistry Emrys Optimiser microwave oven. The mixture is irradiated with magnetic stirring at 140° C. for about 130 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6053 containing 2 g of SCX phase conditioned with methanol. The cartridge is washed with methanol and then eluted with 2M ammoniacal methanol. The ammoniacal fractions are concentrated to dryness under reduced pressure. 0.013 g of 5,5-dimethyl-1-(2-dimethylaminopyrid-4-ylmethyl)-3-(4-trifluoromethanesulfanylphenyl)imidazolidine-2,4-dione is thus obtained in the form of a powder, the characteristics of which are as follows:

Mass IC
m/z=439 MH$^+$ base peak
$^1$H NMR spectrum (300 MHz, (CD$_3$)$_2$SO d6, δ in ppm): 1.42 (s: 6H); 3.03 (s: 6H); 4.53 (broad s: 2H); 6.62 (broad d, J=5.5 Hz: 1H); 6.65 (broad s: 1H); 7.68 (broad d, J=8.5 Hz: 2H); 7.87 (d, J=8.5 Hz: 2H); 8.03 (d, J=5.5 Hz: 1H).

EXAMPLE 223

5,5-Dimethyl-1-(2-methylaminopyrid-4-ylmethyl)-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.5 ml of N-methyl-2-pyrrolidone, 0.016 mg of methylamine hydrochloride and 0.064 ml of triethylamine is placed in a Personal Chemistry Emrys Optimiser microwave oven. The mixture is irradiated with magnetic stirring at 180° C. for about 80 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6054 containing 3 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 µm silica, and then eluted with dichloromethane, at a flow rate of 5 ml/minute. The fractions containing the expected product are concentrated to dryness under reduced pressure. 0.021 g of 5,5-dimethyl-1-(2-methylaminopyrid-4-ylmethyl)-3-(4-trifluoromethanesulfanylphenyl)imidazolidine-2,4-dione is thus obtained in the form of an amorphous white powder, the characteristics of which are as follows:

Mass IE
m/z=424 M$^+$. base peak
m/z=396 (M–CH$_2$N)$^+$ m/z=219 $C_8H_4NOSF_3^+$.
m/z=120 $C_7H_8N_2^+$.
$^1$H NMR spectrum (300 MHz, $(CD_3)_2SO$ d6, δ in ppm): 1.42 (s: 6H); 2.77 (d, J=5 Hz: 3H); 4.48 (broad s: 2H); 6.42 (mt: 1H); 6.46 (broad s: 1H); 6.52 (broad d, J=5.5 Hz: 1H); 7.69 (broad d, J=8.5 Hz: 2H); 7.89 (broad d, J=8.5 Hz: 2H); 7.94 (d, J=5.5 Hz: 1H).

EXAMPLE 224

5,5-Dimethyl-1-(2-cyclohexylaminopyrid-4-ylmethyl)-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.2 ml of N-methyl-2-pyrrolidone and 0.4 ml of cyclohexylamine is placed in a Personal Chemistry Emrys Optimiser microwave oven. The mixture is irradiated with magnetic stirring at 200° C. for about 50 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6054 containing 3 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 μm silica, and then eluted with dichloromethane, at a flow rate of 5 ml/minute. The fractions between 15 and 45 ml are concentrated to dryness under reduced pressure. 0.017 g of 5,5-dimethyl-1-(2-cyclohexylaminopyrid-4-ylmethyl)-3-(4-trifluoromethanesulfanylphenyl)imidazolidine-2,4-dione is thus obtained in the form of an amorphous powder, the characteristics of which product are as follows:
Mass IE
m/z=492 M$^+$.
m/z=449 (M–$C_3H_7$)$^+$
m/z=435 (M–$C_3H_7$)$^+$
m/z=410 (M–$C_6H_{10}$)$^+$. base peak
m/z=219 $C_8H_4NOSF_3^+$.
m/z=175 $C_{11}H_{15}N_2^+$
m/z=98 $C_6H_{12}N^+$
$^1$H NMR spectrum (400 MHz, $(CD_3)_2SO$ d6, δ in ppm): from 1.10 to 1.40 (mt: 5H); 1.43 (s: 6H); from 1.55 to 2.00 (mt: 5H); 3.67 (mt: 1H); 4.45 (s: 2H); 6.28 (d, J=8 Hz: 1H); 6.44 (broad s: 1H); 6.46 (broad d, J=5.5 Hz: 1H); 7.68 (broad d, J=9 Hz: 2H); from 7.85 to 7.95 (mt: 3H).

EXAMPLE 225

5,5-Dimethyl-1-(2-isopropylaminopyrid-4-ylmethyl)-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.2 ml of N-methyl-2-pyrrolidone and 0.4 ml of isopropylamine is placed in a Personal Chemistry Emrys Optimiser microwave oven. The mixture is irradiated with magnetic stirring at 200° C. for about 70 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 μm silica, and then eluted with dichloromethane, at a flow rate of 5 ml/minute. The fractions between 10 and 35 ml are concentrated to dryness under reduced pressure. 0.008 g of 5,5-dimethyl-1-(2-isopropylaminopyrid-4-ylmethyl)-3-(4-trifluoromethanesulfanylphenyl)-imidazolidine-2,4-dione is thus obtained in the form of an amorphous powder, the characteristics of which product are as follows:
Mass IE
m/z=452 M$^+$.
m/z=437 (M–$CH_3$)$^+$ base peak
m/z=410 (M–$C_3H_6$)$^+$.
m/z=219 $C_9H_4NOSF_3^+$.
m/z=134 $C_8H_{10}N_2^+$.
m/z=58 $C_3H^8N^+$
$^1$H NMR spectrum (300 MHz, $(CD_3)_2SO$ d6, δ in ppm): 1.13 (d, J=6.5 Hz: 6H); 1.42 (s: 6H); 3.98 (mt: 1H); 4.45 (broad s: 2H); 6.27 (broad d, J=7.5 Hz: 1H); 6.42 (broad s: 1H); 6.46 (broad d, J=5.5 Hz: 1H); 7.68 (broad d, J=8 Hz: 2H); 7.88 (broad d, J=8 Hz: 2H); 7.90 (d, J=5.5 Hz: 1H).

EXAMPLE 226

5,5-Dimethyl-1-(2-piperidinopyrid-4-ylmethyl)-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.2 ml of N-methyl-2-pyrrolidone and 0.4 ml of piperidine is placed in a Personal Chemistry Emrys Optimiser microwave oven. The mixture is irradiated with magnetic stirring at 200° C. for about 30 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 μm silica, and then eluted with dichloromethane, at a flow rate of 5 ml/minute. The fractions between 10 and 30 ml are concentrated to dryness under reduced pressure. 0.07 g of 5,5-dimethyl-1-(2-piperidinopyrid-4-ylmethyl)-3-(4-trifluoromethanesulfanylphenyl)imidazolidine-2,4-dione is thus obtained in the form of an amorphous powder, the characteristics of which product are as follows:
Mass IE
m/z=478 M$^+$. base peak
m/z=449 (M–$C_2H_5$)$^+$
m/z=422 (M–$C_4H_5$)$^+$.
m/z=395 (M–$C_5H_9N$)$^+$
m/z=219 $C_8H_4NOSF_3^+$.
m/z=161 $C_{10}H_{13}N_2^+$
m/z=84 $C_5H_{10}N^+$ ¹H NMR spectrum (300 MHz, (CD₃)₂SO d6, δ in ppm): 1.42 (s: 6H); from 1.45 to 1.65 (mt: 6H); 3.52 (broad t, J=5 Hz: 4H); 4.52 (broad s: 2H); 6.64 (broad d, J=5.5 Hz: 1H); 6.83 (broad s: 1H); 7.68 (d, J=8.5 Hz: 2H); 7.88 (d, J=8.5 Hz: 2H); 8.04 (d, J=5.5 Hz: 1H).

EXAMPLE 227

5,5-Dimethyl-1-[2-(4-methylpiperazino)pyrid-4-ylmethyl]-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.2 ml of N-methyl-2-pyrrolidone and 0.4 ml of N-methylpiperazine is placed in a Personal Chemistry Emrys Optimiser microwave oven. The mixture is irradiated with magnetic stirring at 200° C. for about 30 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 µm silica, and then eluted with dichloromethane, at a flow rate of 5 ml/minute. The fractions between 105 and 135 ml are concentrated to dryness under reduced pressure. 0.028 g of 5,5-dimethyl-1-[2-(4-methylpiperazino)pyrid-4-ylmethyl]-3-(4-trifluoromethanesulfanylphenyl)imidazolidine-2,4-dione is thus obtained in the form of an amorphous powder, the characteristics of which product are as follows:

Mass IE
m/z=493 M⁺.
m/z=423 (M–C₄H₈N)⁺. base peak
m/z=219 C₈H₄NOSF₃⁺.
m/z=176 C₁₀H₁₄N₃⁺

¹H NMR spectrum (300 MHz, (CD₃)₂SO d6, δ in ppm): 1.42 (s: 6H); 2.23 (s: 3H); 2.40 (broad t, J=5 Hz: 4H); 3.50 (broad t, J=5 Hz: 4H); 4.53 (broad s: 2H); 6.70 (broad d, J=5.5 Hz: 1H); 6.85 (broad s: 1H); 7.69 (d, J=8.5 Hz: 2H); 7.88 (d, J=8.5 Hz: 2H); 8.07 (d, J=5.5 Hz: 1H).

EXAMPLE 228

5,5-Dimethyl-1-(2-phenylaminopyrid-4-ylmethyl)-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.2 ml of N-methyl-2-pyrrolidone and 0.4 ml of aniline is placed in a Personal Chemistry Emrys Optimiser microwave oven. The mixture is irradiated with magnetic stirring at 200° C. for about 30 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 µm silica, and then eluted with dichloromethane, at a flow rate of 5 ml/minute. The fractions between 40 and 85 ml are concentrated to dryness under reduced pressure. 0.082 g of 5,5-dimethyl-1-(2-phenylaminopyrid-4-ylmethyl)-3-(4-trifluoromethanesulfanylphenyl)-imidazolidine-2,4-dione is thus obtained in the form of an amorphous powder, the characteristics of which product are as follows:

Mass IE
m/z=486 M⁺.
m/z=485 (M–H)⁺ base peak
m/z=417 (M–—CF₃)⁺
m/z=182 C₁₂H₁₀N₂⁺.

¹H NMR spectrum (300 MHz, (CD₃)₂SO d6, δ in ppm): 1.46 (s: 6H); 4.55 (broad s: 2H); 6.80 (broad d, J=5.5 Hz: 1H); 6.84 (broad s: 1H); 6.88 (broad t, J=7.5 Hz: 1H); 7.25 (dd, J=8 and 7.5 Hz: 2H); 7.67 (broad d, J=8 Hz: 2H); 7.69 (d, J=8.5 Hz: 2H); 7.88 (broad d, J=8.5 Hz: 2H); 8.01 (d, J=5.5 Hz: 1H); 9.01 (broad s: 1H).

EXAMPLE 229

5,5-Dimethyl-1-[2-(4-piperazino)pyrid-4-ylmethyl]-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.6 ml of N-methyl-2-pyrrolidone and 0.123 g of piperazine is placed in a Personal Chemistry Emrys Optimiser microwave oven. The mixture is irradiated with magnetic stirring at 200° C. for about 30 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 µm silica, and then eluted with dichloromethane, at a flow rate of 5 ml/minute. The fractions between 45 and 110 ml are concentrated to dryness under reduced pressure. 0.042 g of 5,5-dimethyl-1-[2-(4-piperazino)pyrid-4-ylmethyl]-3-(4-trifluoromethanesulfanylphenyl)-imidazolidine-2,4-dione is thus obtained in the form of an amorphous powder, the characteristics of which product are as follows:

Mass IC
m/z=480 MH⁺ base peak

¹H NMR spectrum (300 MHz, (CD₃)₂SO d6, δ in ppm): 1.43 (s: 6H); 2.79 (broad t, J=5 Hz: 4H); 3.41 (broad t, J=5 Hz: 4H); 4.52 (broad s: 2H); 6.69 (broad d, J=5.5 Hz: 1H); 6.82 (broad s: 1H); 7.69 (broad d, J=8.5 Hz: 2H); 7.88 (d, J=8.5 Hz: 2H); 8.06 (d, J=5.5 Hz: 1H).

EXAMPLE 230

5,5-Dimethyl-1-(2-ethylaminopyrid-4-ylmethyl)-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.5 ml of N-methyl-2-pyrrolidone, 0.019 g of ethylamine hydrochloride and 0.064 ml of triethylamine is placed in a Personal Chemistry Emrys Optimiser microwave oven. The mixture is irradiated with magnetic stirring at 200° C. for about 120 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 μm silica, and then eluted with dichloromethane, at a flow rate of 5 ml/minute. The fractions between 280 and 300 ml are concentrated to dryness under reduced pressure. 0.033 g of 5,5-dimethyl-1-(2-ethylaminopyrid-4-ylmethyl)-3-(4-trifluoromethanesulfanylphenyl)imidazolidine-2,4-dione is thus obtained in the form of an amorphous powder, the characteristics of which product are as follows:

m.p.=136° C.
Mass IE
m/z=438 M$^+$.
m/z=423 (M–CH$_3$)$^+$ base peak
m/z=395 (M–C$_2$H$_5$N)$^+$
m/z=369 (M–CF$_3$)$^+$
m/z=121 C$_7$H$_9$N$_2^+$.
m/z=44 C$_2$H$_6$N$^+$ $^1$H NMR spectrum (300 MHz, (CD$_3$)$_2$SO d6, δ in ppm): 1.14 (t, J=7 Hz: 3H); 1.44 (s: 6H); 3.26 (mt: 2H); 4.47 (broad s: 2H); 6.40 (broad t, J=5.5 Hz: 1H); 6.45 (broad s: 1H); 6.50 (broad d, J=5.5 Hz: 1H); 7.69 (broad d, J=8.5 Hz: 2H); 7.89 (broad d, J=8.5 Hz: 2H); 7.92 (d, J=5.5 Hz: 1H).

EXAMPLE 231

5,5-Dimethyl-1-(2-benzylaminopyrid-4-ylmethyl)-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.2 ml of N-methyl-2-pyrrolidone and 0.4 ml of benzylamine is placed in a Personal Chemistry Emrys Optimiser microwave oven. The mixture is irradiated with magnetic stirring at 200° C. for about 30 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 μm silica, and then eluted with dichloromethane, at a flow rate of 5 ml/minute. The fractions between 10 and 50 ml are concentrated to dryness under reduced pressure. 0.035 g of 5,5-dimethyl-1-(2-benzylaminopyrid-4-ylmethyl)-3-(4-trifluoromethanesulfanylphenyl)imidazolidine-2,4-dione is thus obtained in the form of an amorphous powder, the characteristics of which are as follows:

m.p. 144° C.
Mass IE
m/z=500 M$^+$. base peak
m/z=431 (M–CF$_3$)$^+$
m/z=196 C$_{13}$H$_{12}$N$_2^+$.
m/z=106 C$_7$H$_8$N$^+$
m/z=91 C$_7$H$_7^+$ $^1$H NMR spectrum (300 MHz, (CD$_3$)$_2$SO d6, δ in ppm): 1.39 (s: 6H); 4.47 (broad s: 2H); 4.48 (d, J=6 Hz: 2H); 6.51 (broad s: 1H); 6.54 (broad d, J=5.5 Hz: 1H); 7.02 (broad t, J=6 Hz: 1H); from 7.15 to 7.35 (mt: 5H); 7.68 (broad d, J=8.5 Hz: 2H); 7.89 (d, J=8.5 Hz: 2H); 7.92 (d, J=5.5 Hz: 1H).

EXAMPLE 232

5,5-Dimethyl-1-[2-(4-methoxybenzylamino)pyrid-4-ylmethyl]-3-(4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(4-trifluoromethanesulfanylphenyl)imidazolidine-2,4-dione, 0.2 ml of N-methyl-2-pyrrolidone and 0.4 ml of para-methoxybenzylamine is placed in a Personal Chemistry Emrys Optimiser microwave oven. The mixture is irradiated with magnetic stirring at 200° C. for about 30 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 16 mm in diameter packed with 2 g of conditioned 15-35 μm silica, and then eluted with dichloromethane, at a flow rate of 5 ml/minute. The fractions between 5 and 55 ml are concentrated to dryness under reduced pressure. 0.035 g of 5,5-dimethyl-1-[2-(4-methoxybenzylamino)pyrid-4-ylmethyl]-3-(4-trifluoromethanesulfanylphenyl)imidazolidine-2,4-dione is thus obtained in the form of an amorphous powder, the characteristics of which product are as follows:

Mass IE
m/z=530 M$^+$.
m/z=461 (M–CF$_3$)$^+$
m/z=136 C$_8$H$_{10}$NO$^+$
m/z=121 C$_8$H$_9$O$^+$ base peak $^1$H NMR spectrum (300 MHz, (CD$_3$)$_2$SO d6, δ in ppm): 1.39 (s: 6H); 3.72 (s: 3H); 4.39 (d, J=5.5 Hz: 2H); 4.46 (broad s: 2H); 6.48 (broad s: 1H); 6.53 (broad d, J=5.5 Hz: 1H); 6.87 (broad d, J=8.5 Hz: 2H); 6.93 (t, J=5.5 Hz: 1H); 7.25 (broad d, J=8.5 Hz: 2H); 7.68 (broad d, J=8.5 Hz: 2H); 7.89 (broad d, J=8.5 Hz: 2H); 7.92 (d, J=5.5 Hz: 1H).

EXAMPLE 233

5,5-Dimethyl-1-(2-aminopyrid-4-ylmethyl)-3-(4-trifluoromethanesulfanylphenyl)imidazolidine-2,4-dione 0.5 ml of trifluoroacetic acid is added to a solution of 0.035 g of 5,5-dimethyl-1-[2-(4-methoxybenzylamino)pyrid-4-ylmethyl]-3-(4-trifluoromethanesulfanylphenyl)imidazolidine-2,4-dione in 0.5 ml of dichloromethane, at a temperature in the region of 20° C. Stirring is continued at this temperature for 5 hours. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. 0.015 g of 5,5-dimethyl-1-(2-aminopyrid-4-ylmethyl)-3-(4-trifluoromethanesulfanylphenyl)-imidazolidine-2,4-dione is thus obtained in the form of a powder, the characteristics of which product are as follows:

m.p.: 161° C.
Mass IE
m/z=410 M$^+$ base peak
m/z=395 (M−CH$_3$)$^+$
m/z=219 C$_8$H$_4$NOSF$_3$$^+$.
m/z=148 C$_7$H$_6$N$_3$O$^+$
m/z=107 C$_6$H$_7$N$_2$$^+$ $^1$H NMR spectrum (300 MHz, (CD$_3$)$_2$SO d6, δ in ppm): 1.43 (s: 6H); 4.46 (broad s: 2H); 5.86 (broad s: 2H); 6.46 (broad s: 1H); 6.53 (broad d, J=5.5 Hz: 1H); 7.69 (broad d, J=8.5 Hz: 2H); 7.84 (d, J=5.5 Hz: 1H); 7.89 (broad d, J=8.5 Hz: 2H).

EXAMPLE 234

5,5-Dimethyl-1-(2-acetamidopyrid-4-ylmethyl)-3-(4-trifluoromethanesulfanylphenyl)imidazolidine-2,4-dione A solution of 0.050 g of 5,5-dimethyl-1-(2-aminopyrid-4-ylmethyl)-3-(4-trifluoromethanesulfanylphenyl)imidazolidine-2,4-dione in 5 ml of acetic anhydride is stirred under an inert atmosphere of argon for 24 hours at a temperature in the region of 80° C. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. 0.006 g of 5,5-dimethyl-1-(2-acetamidopyrid-4-ylmethyl)-3-(4-trifluoromethanesulfanylphenyl)imidazolidine-2,4-dione is thus obtained in the form of a powder, the characteristics of which product are as follows:

Mass IE
m/z=452 M$^+$.
m/z=410 (M−C$_2$H$_2$O)$^+$. base peak
m/z=395 (m/z=410−CH$_3$)$^+$
m/z=219 C$_8$H$_4$NOSF$_3$$^+$.
m/z=150 C$_8$H$_{10}$N$_2$O$^+$.
m/z=107 C$_6$H$_7$N$_2$$^+$
m/z=43 C$_2$H$_3$O$^+$ $^1$H NMR spectrum (300 MHz, (CD$_3$)$_2$SO d6, δ in ppm): 1.44 (broad s: 6H); 2.11 (s: 3H); 4.65 (broad s: 2H); 7.15 (broad d, J=5.5 Hz: 1H); 7.68 (broad d, J=8.5 Hz: 2H); 7.89 (broad d, J=8.5 Hz: 2H); 8.14 (broad s: 1H); 8.27 (d, J=5.5 Hz: 1H); 10.49 (unresolved complex: 1H).

EXAMPLE 235

5,5-Dimethyl-1-(2-tert-butoxycarbonylaminopyrid-4-ylmethyl)-3-(4-trifluoromethanesulfanylphenyl)imidazolidine-2,4-dione 0.05 g of 5,5-dimethyl-1-(2-aminopyrid-4-ylmethyl)-3-(4-trifluoromethanesulfanylphenyl)-imidazolidine-2,4-dione is added portionwise to a solution of 0.029 g of di-tert-butyl dicarbonate in 0.65 ml of tert-butyl alcohol, under an inert atmosphere of argon at a temperature in the region of 20° C. Stirring is continued at this temperature for 24 hours. The reaction mixture is concentrated to dryness under reduced pressure. The residue thus obtained is purified by flash chromatography using a cartridge 16 mm in diameter packed with 5 g of conditioned 20-40 μm silica, and then eluted with a mixture (cyclohexane/ethyl acetate) (8/2) (v/v). The fractions between 260 and 400 ml are concentrated under reduced pressure. 0.035 g of 5,5-dimethyl-1-(2-tert-butoxycarbonylaminopyrid-4-ylmethyl)-3-(4-trifluoromethanesulfanylphenyl)imidazolidine-2,4-dione is thus obtained, the characteristics of which product are as follows:

Mass IC
m/z=511 MH$^+$ base peak $^1$H NMR spectrum (300 MHz, (CD$_3$)$_2$SO d6, δ in ppm): 1.43 (s: 6H); 1.49 (s: 9H); 4.63 (broad s: 2H); 7.08 (broad dd, J=5.5 and 1.5 Hz: 1H); 7.68 (broad d, J=9 Hz: 2H); 7.84 (broad s: 1H); 7.87 (broad d, J=9 Hz: 2H); 8.19 (d, J=5.5 Hz: 1H); 9.73 (broad s: 1H).

EXAMPLE 236

5,5-Dimethyl-1-(2-methylsulfonylaminopyrid-4-ylmethyl)-3-(4-trifluoromethanesulfanylphenyl)imidazolidine-2,4-dione 0.010 ml of methanesulfonyl chloride is added to a solution of 0.050 g of 5,5-dimethyl-1-(2-aminopyrid-4-ylmethyl)-3-(4-trifluoromethanesulfanylphenyl)imidazolidine-2,4-dione in 0.4 ml of pyridine, under an inert atmosphere of argon at a temperature in the region of 20° C. Stirring is continued at this temperature for 2 hours. The reaction mixture is poured into 50 ml of saturated sodium bicarbonate solution and then extracted with 2×50 ml of ethyl acetate. The organic phase is dried over magnesium sulfate, filtered and then concentrated to dryness under reduced pressure. 0.020 g of 5,5-dimethyl-1-(2-methylsulfonylaminopyrid-4-ylmethyl)-3-(4-trifluoromethanesulfanylphenyl)imidazolidine-2,4-dione is thus obtained in the form of a white powder, the characteristics of which product are as follows:

m.p.: 208° C.
Mass IE
m/z=488 M$^+$. base peak
m/z=473 (M−CH$_3$)$^+$
m/z=409 (M−SO$_2$CH$_3$)$^+$
m/z=219 C$_8$H$_4$NOSF$_3$$^+$.
m/z=185 C$_7$H$_9$N$_2$O$_2$S.$^+$ $^1$H NMR spectrum (300 MHz, (CD$_3$)$_2$SO d6, δ in ppm): 1.45 (s: 6H); 3.27 (unresolved complex: 3H); 4.63 (broad s:

2H); from 6.95 to 7.10 (unresolved complex: 2H); 7.68 (broad d, J=8.5 Hz: 2H); 7.89 (broad d, J=8.5 Hz: 2H); 8.17 (unresolved complex: 1H).

EXAMPLE 237

5,5-Dimethyl-1-(2-methoxycarbonylaminopyrid-4-ylmethyl)-3-(4-trifluoromethanesulfanylphenyl)imidazolidine-2,4-dione 0.056 ml of methyl chloroformate is added to a solution of 0.100 g of 5,5-dimethyl-1-(2-aminopyrid-4-ylmethyl)-3-(4-trifluoromethanesulfanylphenyl)imidazolidine-2,4-dione in 1.5 ml of pyridine, under an inert atmosphere of argon at a temperature in the region of 20° C. Stirring is continued at this temperature for 20 hours. A further 0.56 ml of methyl chloroformate is added. Stirring is continued at this temperature for 20 hours. The reaction mixture is taken up in 5 ml of ethyl acetate, and then washed successively with 5 ml of water, ml of saturated sodium chloride solution and then 5 ml of water. The organic phase is dried over magnesium sulfate, filtered and then concentrated to dryness under reduced pressure. The residue obtained is purified on a Kromasil C18, 5 μm column (100×20 mm), eluting with a linear gradient of from 5% to 95% acetonitrile containing 0.07% (v/v) of trifluoroacetic acid (TFA) in water containing 0.07% (v/v) TFA, at a flow rate of ml/minute. The fractions containing the expected product are concentrated to dryness under reduced pressure. The residue obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. 0.024 g of 5,5-dimethyl-1-(2-methoxycarbonylaminopyrid-4-ylmethyl)-3-(4-trifluoromethanesulfanylphenyl)imidazolidine-2,4-dione is thus obtained in the form of a white solid, the characteristics of which product are as follows:
Mass IE
m/z=468 M$^+$. base peak
m/z=453 (M–CH$_3$)$^+$
m/z=410 (M–C$_2$H$_2$O$_2$)$^+$.
m/z=219 C$_8$H4NOSF$_3$$^+$.
m/z=166 C$_8$H$_{10}$N$_2$O$_2$$^+$.
$^1$H NMR spectrum (300 MHz, (CD$_3$)$_2$SO d6, δ in ppm): 1.44 (s: 6H); 3.70 (s: 3H); 4.65 (broad s: 2H); 7.12 (dd, J=5.5 and 2 Hz: 1H); 7.69 (broad d, J=9 Hz: 2H); 7.89 (broad d, J=9 Hz: 2H); 7.90 (broad s: 1H); 8.23 (d, J=5.5 Hz: 1H); 10.18 (broad s: 1H).

EXAMPLE 238

5,5-Dimethyl-1-(2-chloropyrid-4-ylmethyl)-3-(3-chloro-4-trifluoromethanesulfanylphenyl)imidazolidine-2,4-dione 0.1 g of sodium hydride is added to a solution of 0.417 g of 5,5-dimethyl-3-(3-chloro-4-trifluoromethylsulfanylphenyl)imidazolidine-2,4-dione in 20 ml of anhydrous dimethylformamide, under an inert atmosphere of argon at a temperature in the region of 0° C. Stirring is continued at this temperature for 30 minutes. A solution of 0.380 g of 2-chloro-4-(bromomethyl)pyridine in 20 ml of anhydrous dimethylformamide is added, followed by addition of ice-cold water after reaction for 10 minutes. The reaction mixture is taken up in 400 ml of ethyl acetate and then washed with 400 ml of water. The organic phase is dried over magnesium sulfate, filtered and then concentrated to dryness under reduced pressure. The residue thus obtained is purified by flash chromatography using a cartridge 27 mm in diameter packed with 25 g of conditioned 20-40 μm silica, and then eluted with a mixture (cyclohexane/ethyl acetate) (8/2) (v/v). The fractions between 150 and 350 ml are concentrated to dryness under reduced pressure. 0.3 g of 5,5-dimethyl-1-(2-chloropyrid-4-ylmethyl)-3-(3-chloro-4-trifluoromethanesulfanylphenyl)imidazolidine-2,4-dione is thus obtained, the characteristics of which product are as follows:
Mass IE
m/z=463 M$^+$. base peak
m/z=448 (M–CH$_3$)$^+$
m/z=253 C$_8$H$_3$NOSClF$_3$$^+$.
m/z=167 C$_7$H$_4$N$_2$OCl$^+$
m/z=126 C$_6$H$_5$NCl$^+$
$^1$H NMR spectrum (300 MHz, (CD$_3$)$_2$SO d6, δ in ppm): 1.43 (s: 6H); 4.68 (broad s: 2H); 7.49 (broad d, J=5.5 Hz: 1H); 7.63 (broad s: 1H); 7.71 (dd, J=9 and 3 Hz: 1H); 7.97 (d, J=3 Hz: 1H); 8.05 (d, J=9 Hz: 1H); 8.38 (d, J=5.5 Hz: 1H).

Preparation of 5,5-dimethyl-3-(3-chloro-4-trifluoromethylsulfanylphenyl)imidazolidine-2,4-dione A solution of 2 g of 3-chloro-4-trifluoromethylsulfanylaniline in 22 ml of toluene is added over 30 minutes to a suspension of 1.97 g of diphosgene and 0.03 g of vegetable charcoal in 22 ml of toluene, at a temperature in the region of –20° C. The mixture is stirred to a temperature in the region of 20° C. and is then refluxed for 3 hours. The mixture is cooled to a temperature in the region of 20° C. and then filtered through Celite. 1.35 g of methyl α-aminoisobutyrate hydrochloride, 15 ml of toluene and 2.23 ml of triethylamine are added to the filtrate. The mixture thus obtained is refluxed for 24 hours and then cooled to a temperature in the region of 20° C. The reaction mixture is concentrated under reduced pressure. The residue obtained is purified by flash chromatography on a cartridge 37 mm in diameter packed with conditioned 20-40 μm silica and then eluted with a mixture (cyclohexane/ethyl acetate) (5/5) (v/v). The fractions between 110 and 250 ml are concentrated under reduced pressure, and 2 g of 5,5-dimethyl-3-(3-chloro-4-trifluoromethylsulfanylphenyl)imidazolidine-2,4-dione are thus obtained, the characteristics of which product are as follows:
Mass IE
m/z=338 M$^+$. base peak
m/z=253 C$_8$H$_3$NOSClF$_3$$^+$.
m/z=184 (m/z=253—CF$_3$)$^+$
m/z=84 C$_4$H$_6$NO$^+$
$^1$H NMR spectrum (300 MHz, (CD$_3$)$_2$SO d6, δ in ppm): 1.42 (s: 6H); 7.63 (dd, J=8.5 and 2.5 Hz: 1H); 7.90 (d, J=2.5 Hz: 1H); 8.02 (d, J=8.5 Hz: 1H); 8.75 (unresolved complex: 1H).

EXAMPLE 239

5,5-Dimethyl-1-[2-(4-methoxybenzylamino)pyrid-4-ylmethyl]-3-(3-chloro-4-trifluoromethanesulfanylphenyl)imidazolidine-2,4-dione A sealed 2.5 ml tube containing 0.3 g of 5,5-dimethyl-1-(2-chloropyrid-4-ylmethyl)-3-(3-chloro-4-trifluoromethanesulfanylphenyl)imidazolidine-2,4-dione, 0.2 ml of N-methyl-2-pyrrolidone and 0.4 ml of para-methoxybenzylamine is placed in a Personal Chemistry Emrys Optimiser microwave oven. The mixture is irradiated with magnetic stirring at 200° C. for about 70 minutes. The reaction mixture is purified by flash chromatography using a cartridge 37 mm in diameter packed with 50 g of 20-40 μm conditioned silica, and then eluted with a mixture (cyclohexane/ethyl acetate) (8/2) (v/v). The fractions between 470 and 640 ml are concentrated to dryness under reduced pressure. 0.091 g of 5,5-dimethyl-1-[2-(4-methoxybenzylamino)pyrid-4-ylmethyl]-3-(3-chloro-4-trifluoromethanesulfanylphenyl)-imidazolidine-2,4-dione is thus obtained, the characteristics of which are as follows:

Mass IE m/z=564 $M^+$.

m/z=495 $(M-CF_3)^+$ m/z=136 $C_8H_{10}NO^+$ m/z=121 $C_8H_9O^+$ base peak $^1$H NMR spectrum (300 MHz, $(CD_3)_2SO$ d6, δ in ppm): 1.38 (s: 6H); 3.71 (s: 3H); 4.39 (d, J=5.5 Hz: 2H); 4.45 (broad s: 2H); 6.48 (broad s: 1H); 6.53 (broad d, J=5.5 Hz: 1H); 6.85 (d, J=8.5 Hz: 2H); 6.89 (t, J=5.5 Hz: 1H); 7.24 (d, J=8.5 Hz: 2H); 7.69 (dd, J=8.5 and 2.5 Hz: 1H); 7.92 (d, J=5.5 Hz: 1H); 7.95 (d, J=2.5 Hz: 1H); 8.06 (d, J=8.5 Hz: 1H).

EXAMPLE 240

5,5-Dimethyl-1-(2-ethylaminopyrid-4-ylmethyl)-3-(3-chloro-4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(3-chloro-4-trifluoromethanesulfanylphenyl)imidazolidine-2,4-dione, 0.4 ml of N-methyl-2-pyrrolidone, 0.044 g of ethylamine hydrochloride and 0.120 ml of triethylamine is placed in a Personal Chemistry Emrys Optimiser microwave oven. The mixture is irradiated with magnetic stirring at 200° C. for about 70 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. 0.029 g of 5,5-dimethyl-1-(2-ethylaminopyrid-4-ylmethyl)-3-(3-chloro-4-trifluoromethanesulfanylphenyl)imidazolidine-2,4-dione is thus obtained, the characteristics of which are as follows:

Mass IE m/z=472 $M^+$.

m/z=457 $(M-CH_3)^+$ base peak m/z=429 $(M-C_2H_5N)^+$ m/z=403 $(M-CF_3)^+$ m/z=121 $C_7H_9N_2^+$.

m/z=44 $C_2H_6N^+$ $^1$H NMR spectrum (300 MHz, $(CD_3)_2SO$ d6, δ in ppm): 1.14 (t, J=7 Hz: 3H); 1.43 (s: 6H); 3.27 (mt: 2H); 4.46 (broad s: 2H); 6.38 (broad t, J=5.5 Hz: 1H); 6.45 (broad s: 1H); 6.51 (broad d, J=5.5 Hz: 1H); 7.70 (dd, J=8.5 and 2.5 Hz: 1H); 7.92 (d, J=5.5 Hz: 1H); 7.96 (d, J=2.5 Hz: 1H); 8.06 (d, J=8.5 Hz: 1H).

EXAMPLE 241

5,5-Dimethyl-1-(2-methylaminopyrid-4-ylmethyl)-3-(3-chloro-4-trifluoromethanesulfanylphenyl)imidazolidine-2,4-dione A sealed 2.5 ml tube containing 0.1 g of 5,5-dimethyl-1-(2-chloropyrid-4-ylmethyl)-3-(3-chloro-4-trifluoromethanesulfanylphenyl)imidazolidine-2,4-dione, 0.5 ml of N-methyl-2-pyrrolidone, 0.030 g of methylamine hydrochloride and 0.120 ml of triethylamine is placed in a Personal Chemistry Emrys Optimiser microwave oven. The mixture is irradiated with magnetic stirring at 200° C. for about 70 minutes. The reaction mixture is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. The residue thus obtained is purified by flash chromatography using a cartridge 20 mm in diameter packed with 10 g of 20-40 μm conditioned silica, and then eluted with dichloromethane at a flow rate of 8 ml/minute. The fractions between 70 and 100 ml are concentrated to dryness under reduced pressure. 0.015 g of 5,5-dimethyl-1-(2-methylaminopyrid-4-ylmethyl)-3-(3-chloro-4-trifluoromethanesulfanylphenyl)imidazolidine-2,4-dione is thus obtained in the form of an amorphous white powder, the characteristics of which are as follows:

$^1$H NMR spectrum (300 MHz, $(CD_3)_2SO$ d6, δ in ppm): 1.43 (s: 6H); 2.77 (d, J=5 Hz: 3H); 4.48 (broad s: 2H); 6.40 (broad q, J=5 Hz: 1H); 6.46 (broad s: 1H); 6.54 (broad d, J=5.5 Hz: 1H); 7.70 (dd, J=8.5 and 3 Hz: 1H); 7.94 (d, J=5.5 Hz: 1H); 7.97 (d, J=3 Hz: 1H); 8.06 (d, J=8.5 Hz: 1H).

EXAMPLE 242

5,5-Dimethyl-1-(2-aminopyrid-4-ylmethyl)-3-(3-chloro-4-trifluoromethanesulfanylphenyl)imidazolidine-2,4-dione 3 ml of trifluoroacetic acid are added to a solution of 0.080 g of 5,5-dimethyl-1-[2-(4-methoxybenzylamino)pyrid-4-ylmethyl]-3-(3-chloro-4-trifluoromethanesulfanylphenyl)-imidazolidine-2,4-dione in 1 ml of dichloromethane, at a temperature in the region of 20° C. Stirring is continued at this temperature for about 16 hours. The reaction mixture is concentrated to dryness under reduced pressure. The residue obtained is purified by preparative LC/MS. The fractions containing the expected product are concentrated to dryness under reduced pressure. The residue thus obtained is taken up in methanol and then placed on a Bond Elut Varian cartridge of reference 1225-6027 containing 5 g of SCX phase conditioned with methanol. The cartridge is washed with methanol and then eluted with 2M ammoniacal methanol. The ammoniacal fractions are concentrated to dryness under reduced pressure. 0.027 g of 5,5-dimethyl-1-(2-aminopyrid-4-ylmethyl)-3-(3-chloro-4-trifluoromethanesulfanylphenyl)imidazolidine-2,4-dione is thus obtained in the form of a powder, the characteristics of which are as follows:

Mass IE m/z=444 $M^+$. base peak m/z=429 $(M-CH_3)^+$ m/z=148 $C_7H_6N_3O^+$ m/z=107 $C_6H_7N_2^+$ $^1$H NMR spectrum (300 MHz, (CD$_3$)$_2$SO d6, δ in ppm): 1.43 (s: 6H); 4.46 (broad s: 2H); 5.86 (broad s: 2H); 6.46 (broad s: 1H); 6.54 (broad dd, J=5.5 and 1.5 Hz: 1H); 7.70 (dd, J=8.5 and 2.5 Hz: 1H); 7.86 (d, J=5.5 Hz: 1H); 7.97 (d, J=2.5 Hz: 1H); 8.06 (d, J=8.5 Hz: 1H).

EXAMPLE 243

5,5-Dimethyl-1-(2,6-dibromopyrid-4-ylmethyl)-3†-trifluoromethoxyphenyl)-imidazolidine-2,4-dione 0.036 g of sodium hydride is added to a solution of 0.230 g of 5,5-dimethyl-3-(4-trifluoromethylsulfanylphenyl)imidazolidine-2,4-dione in 2 ml of anhydrous dimethylformamide, under an inert atmosphere of argon at a temperature in the region of 20° C. Stirring is continued at this temperature for 30 minutes. A solution of 0.349 g of 2,6-dibromo-4-(bromomethyl)pyridine in 3 ml of anhydrous dimethylformamide is added, followed by addition of ice-cold water after reaction for 20 minutes. The reaction mixture is taken up in ethyl acetate and then washed with water. The organic phase is dried over magnesium sulfate, filtered and then concentrated to dryness under reduced pressure. The residue thus obtained is purified by flash chromatography using a cartridge 27 mm in diameter packed with 25 g of 20-40 μm conditioned silica, and then eluted with dichloromethane. The fractions between 65 and 135 ml are concentrated under reduced pressure. 0.25 g of 5,5-dimethyl-1-(2,6-dibromopyrid-4-ylmethyl)-3-(4-trifluoromethoxyphenyl)imidazolidine-2,4-dione is thus obtained, the characteristics of which product are as follows:

Mass IC
m/z=569 MNH$_4^+$ base peak
m/z=552 MH$^+$
m/z=474 (M−Br+2H)$^+$
m/z=396 (m/z=474−Br+H)$^+$
$^1$H NMR spectrum (300 MHz, (CD$_3$)$_2$SO d6, δ in ppm): 1.45 (s: 6H); 4.67 (broad s: 2H); 7.72 (broad d, J=8 Hz: 2H); 7.83 (s: 2H); 7.89 (broad d, J=8 Hz: 2H).

The compound 5,5-dimethyl-3-(4-trifluoromethylsulfanylphenyl)imidazolidine-2,4-dione is described in Example 211.

Synthesis of the Reagents

REFERENCE EXAMPLE 208a

2-Chloro-4-(bromomethyl)pyridine

A solution of 0.2 g of 2-chloro-4-(hydroxymethyl)pyridine in 2.5 ml of dichloromethane is added dropwise to a solution of 0.706 g of dibromotriphenylphosphorane in 9.5 ml of dichloromethane, under an inert atmosphere of argon at a temperature in the region of 20° C. Stirring is continued at this temperature for about 1 hour. The reaction medium is taken up in 50 ml of dichloromethane and then washed with 3×50 ml of water. The organic phase is dried over magnesium sulfate, filtered and then concentrated to dryness under reduced pressure. The residue thus obtained is purified by flash chromatography using a cartridge 20 mm in diameter packed with 10 g of 20-40 μm conditioned silica, and then eluted with a mixture (cyclohexane/ethyl acetate) (8/2) (v/v) at a flow rate of 8 ml/minute. The fractions between 8 and 24 ml are concentrated under reduced pressure. 0.1 g of 2-chloro-4-(bromomethyl)-pyridine is thus obtained.

REFERENCE EXAMPLE 208b 2-chloro-4-(hydroxymethyl)pyridine 2.04 g of sodium borohydride are added portionwise to a solution of 1.7 g of ethyl 2-chloropyridine-4-carboxylate in 20 ml of ethanol, under an inert atmosphere of argon at a temperature in the region of 0° C. The reaction mixture is refluxed with stirring for 3 hours and then concentrated to dryness under reduced pressure. The residue thus obtained is taken up in dichloromethane and then washed with water. The organic phase is dried over magnesium sulfate, filtered and then concentrated to dryness under reduced pressure. 1 g of 2-chloro-4-(hydroxymethyl)pyridine is thus obtained.

REFERENCE EXAMPLE 208c

Ethyl 2-chloropyridine-4-carboxylate 1 ml of concentrated sulfuric acid is added to a solution of 2.2 g of 2-chloropyridine-4-carboxylic acid in 30 ml of ethanol. The reaction mixture is refluxed with stirring for 16 hours and then concentrated to dryness under reduced pressure. The residue thus obtained is taken up in 30 ml of water and then extracted with 3×30 ml of dichloromethane. The organic phase is dried over magnesium sulfate, filtered and then concentrated to dryness under reduced pressure. The oil thus obtained is purified by filtration through 13 g of silica, eluting with dichloromethane. The fractions containing the expected product are concentrated to dryness under reduced pressure. 2.1 g of ethyl 2-chloropyridine-4-carboxylate are thus obtained.

REFERENCE EXAMPLE 209a 2-ethoxy-4-(bromomethyl)pyridine

A solution of 0.31 g of 2-ethoxy-4-(hydroxymethyl)pyridine in 6 ml of dichloromethane is added dropwise to a solution of 1.025 g of dibromotriphenylphosphorane in 12 ml of dichloromethane, under an inert atmosphere of argon at a temperature in the region of 20° C. Stirring is continued at this temperature for about 1 hour. The reaction medium is taken up in 100 ml of dichloromethane and then washed with 3×100 ml of water. The organic phase is dried over magnesium sulfate, filtered and then concentrated to dryness under reduced pressure. The residue thus obtained is purified by flash chromatography, using a cartridge 27 mm in diameter packed with 20 g of 20-40 μm conditioned silica, and then eluted with a mixture (cyclohexane/ethyl acetate) (9/1) (v/v) at a flow rate of 8 ml/minute. The fractions between 80 and 180 ml are concentrated under reduced pressure. 0.37 g of 2-ethoxy-4-(bromomethyl)pyridine is thus obtained.

REFERENCE EXAMPLE 209b 2-ethoxy-4-(hydroxymethyl)pyridine 0.508 g of sodium borohydride is added portionwise to a solution of 0.524 g of ethyl 2-ethoxypyridine-4-carboxylate in 5.2 ml of ethanol, under an inert atmosphere of argon at a temperature in the region of 0° C. The reaction mixture is refluxed with stirring for 3 hours and then concentrated to dryness under reduced pressure. The residue thus obtained is taken up in 50 ml of dichloromethane and then washed with 50 ml of water. The organic phase is dried over magnesium sulfate, filtered and then concentrated to dryness under reduced pressure. 0.310 g of 2-ethoxy-4-(hydroxymethyl) pyridine is thus obtained.

REFERENCE EXAMPLE 209c

Ethyl 2-ethoxypyridine-4-carboxylate 0.5 ml of concentrated sulfuric acid is added to a solution of 1 g of 2-fluoropyridine-4-carboxylic acid in 15 ml of ethanol. The reaction mixture is refluxed with stirring for 48 hours and then concentrated to dryness under reduced pressure. The residue thus obtained is taken up in 100 ml of water and then extracted with 3×100 ml of dichloromethane. The organic phase is dried over magnesium sulfate, filtered and then concentrated to dryness under reduced pressure. The crude product thus obtained is purified by flash chromatography using a cartridge 37 mm in diameter packed with 50 g of 20-40 μm conditioned silica, and then eluted with a mixture (dichloromethane/methanol) (90/10) (v/v), at a flow rate of 8 ml par minute. The fractions between 350 ml and 390 ml are concentrated under reduced pressure. 0.524 g of ethyl 2-ethoxypyridine-4-carboxylate is thus obtained in the form of an oil.

REFERENCE EXAMPLE 210a

2-Ethyl-4-(bromomethyl)pyridine

A solution of 0.3 g of 2-ethyl-4-(hydroxymethyl)pyridine in 3.5 ml of dichloromethane is added dropwise to a solution of 1.25 g of dibromotriphenylphosphorane in 4 ml of dichloromethane, under an inert atmosphere of argon at a temperature in the region of 0° C. The mixture is stirred to a temperature in the region of 20° C. over about 1 hour. The reaction medium is taken up in 50 ml of dichloromethane and then washed with 3×50 ml of water. The organic phase is dried over magnesium sulfate, filtered and then concentrated to dryness under reduced pressure. The residue thus obtained is purified by flash chromatography using a cartridge 20 mm in diameter packed with 10 g of 20-40 μm conditioned silica, and then eluted with a mixture (cyclohexane/ethyl acetate) (9/1) (v/v), at a flow rate of 8 ml/minute. The fractions between 80 and 120 ml are concentrated under reduced pressure. 0.062 g of 2-ethyl-4-(bromomethyl)pyridine is thus obtained.

REFERENCE EXAMPLE 210b 2-ethyl-4-(hydroxymethyl)pyridine 5.36 g of sodium borohydride are added portionwise to a solution of 5.08 g of ethyl 2-ethylpyridine-4-carboxylate in 53 ml of ethanol, under an inert atmosphere of argon at a temperature in the region of 0° C. The reaction mixture is refluxed with stirring for 3 hours and then concentrated to dryness under reduced pressure. The residue thus obtained is taken up in 500 ml of dichloromethane and then washed with 500 ml of water. The organic phase is dried over magnesium sulfate, filtered and then concentrated to dryness under reduced pressure. 3.16 g of 2-ethyl-4-(hydroxymethyl)pyridine are thus obtained.

REFERENCE EXAMPLE 210c

Ethyl 2-ethylpyridine-4-carboxylate 2.35 ml of concentrated sulfuric acid are added to a solution of 5 g of 2-ethylpyridine-4-carboxylic acid in 75 ml of ethanol. The reaction mixture is refluxed with stirring for about 64 hours and then concentrated to dryness under reduced pressure. The residue thus obtained is taken up in 500 ml of water and then extracted with 500 ml of dichloromethane. The organic phase is dried over magnesium sulfate, filtered and then concentrated to dryness under reduced pressure. 5.08 g of ethyl 2-ethylpyridine-4-carboxylate are thus obtained in the form of an oil.

REFERENCE EXAMPLE 214a 2-bromo-4-(bromomethyl)pyridine 0.073 ml of acetic acid is added to a solution of 0.172 g of 2-bromo-4-methylpyridine in 2.5 ml of carbon tetrachloride, under an inert atmosphere of argon at a temperature in the region of 20° C. The mixture brought, with stirring, to a temperature of 50° C. 0.356 g of N-bromosuccinimide and 0.048 g of benzoyl peroxide are added successively at this temperature. The mixture is maintained at 80° C. for about 18 hours. After cooling, the reaction medium is placed on a cartridge 20 mm in diameter packed with 10 g of 20-40 μm silica not conditioned beforehand, and then eluted with dichloromethane at a flow rate of 5 ml/minute. The fractions between 30 and 40 ml are concentrated to dryness under reduced pressure. 0.071 g of 2-bromo-4-(bromomethyl)pyridine is thus obtained.

REFERENCE EXAMPLE 215a

2-Fluoro-4-(bromomethyl)pyridine 0.073 ml of acetic acid is added to a solution of 0.111 g of 2-fluoro-4-methylpyridine in 2.5 ml of carbon tetrachloride, under an inert atmosphere of argon at a temperature in the region of 20° C. The mixture is brought, with stirring, to a temperature of 50° C. 0.356 g of N-bromosuccinimide and 0.048 g of benzoyl peroxide are successively added at this temperature. The mixture is brought to 80° C. over about 16 hours. After cooling, the reaction medium is placed on a cartridge 20 mm in diameter packed with 10 g of 20-40 μm silica not conditioned beforehand, and then eluted with dichloromethane at a flow rate of 5 ml/minute. The fractions between 28 and 38 ml are concentrated to dryness under reduced pressure. 0.063 g of 2-fluoro-4-(bromomethyl)pyridine is thus obtained.

REFERENCE EXAMPLE 216a

2-Cyano-4-(bromomethyl)pyridine 0.146 ml of acetic acid is added to a solution of 0.236 g of 2-cyano-4-methylpyridine in 5 ml of carbon tetrachloride, under an inert atmosphere of argon at a temperature in the region of 20° C. The mixture is brought, with stirring, to a temperature of 50° C. 0.712 g of N-bromosuccinimide and 0.096 g of benzoyl peroxide are successively added at this temperature. The mixture is maintained at 80° C. for about 18 hours. After cooling, the reaction medium is placed on a cartridge 27 mm in diameter packed with 25 g of 20-40 μm silica not conditioned beforehand, and then eluted with dichloromethane at a flow rate of 10 ml/minute. The fractions between 140 and 175 ml are concentrated to dryness under reduced pressure. 0.097 g of 2-cyano-4(bromomethyl) pyridine is thus obtained.

REFERENCE EXAMPLE 243a

2,6-dibromo-4-(bromomethyl)pyridine

A solution of 0.5 g of 2,6-dibromo-4-(hydroxymethyl)pyridine in 7 ml of dichloromethane is added dropwise to a solution of 0.95 g of dibromotriphenylphosphorane in 5 ml of dichloromethane, under an inert atmosphere of argon at a temperature in the region of 0° C. The mixture is stirred to a temperature in the region of 20° C. over about 2 hours. The reaction medium is taken up in 100 ml of dichloromethane and then washed with 100 ml of water. The organic phase is dried over magnesium sulfate, filtered and then concentrated to dryness under reduced pressure. The residue thus obtained is purified by flash chromatography using a cartridge 37 mm in diameter packed with 50 g of 20-40 μm conditioned silica, and then eluted with a mixture (cyclohexane/ethyl acetate) (9/1) (v/v), at a flow rate of 8 ml/minute. The fractions between 135 and 200 ml are concentrated under reduced pressure. 0.349 g of 2,6-dibromo-4-(bromomethyl)pyridine is thus obtained.

GENERAL PROCEDURE FOR THE PRODUCTS OF EXAMPLES 244 TO 255

A solution of 0.481 mM of anilino derivative in 0.6 ml of toluene is added to a suspension of 0.064 ml of diphosgene (0.53 mM) and 20 mg of vegetable charcoal in 1 ml of toluene, at a temperature in the region of −20° C. The mixture is stirred to a temperature in the region of 20° C., and then refluxed for 3 hours. The mixture is cooled to a temperature in the region of 20° C. and then filtered through Celite. A solution of 100 mg of methyl 2-methyl-2-[(pyrid-4-ylmethyl)amino]propanoate (0.48 mM) in 0.6 ml of toluene is added to the filtrate. The mixture thus obtained is refluxed for 16 hours and then cooled to a temperature in the region of 20° C. The precipitate is filtered off and the filtrate is concentrated under reduced pressure. The residue obtained is purified by preparative LC/MS.

Summary table of the starting anilino derivatives and of the products prepared

| Example No | Name of the starting anilino derivative | Amount of the anilino derivative used (mg) | Structure of the product obtained | Name of the product obtained | Empirical formula of the product obtained | Molecular weight of the product obtained | Amount obtained (mg) |
|---|---|---|---|---|---|---|---|
| 244 | 2-NITRO-4-(TRI-FLUORO-METHOXY)-ANILINE | 106.7 | 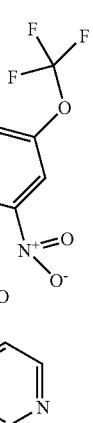 | 5,5-Dimethyl-3-(2-nitro-4-trifluoromethoxyphenyl)-1-pyrid-4-yl-methylimidazolidine-2,4-dione 2 | C18 H15 F3 N4 O5 | 424.34 | 54.2 |
| 245 | 4-(1,1,2,2-TETRAFLUORO-ETHOXY)-ANILINE | 100.4 | 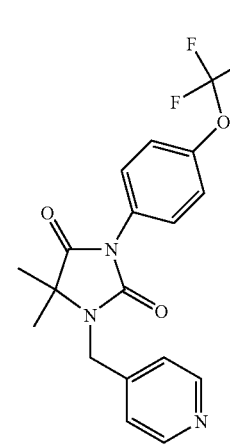 | 5,5-Dimethyl-1-pyrid-4-ylmethyl-3-[4-(1,1,2,2-tetrafluoroethoxy)phenyl]-imidazolidine-2,4-dione 2 | C19 H17 F4 N3 O3 | 411.36 | 32.1 |

-continued

| Example No | Name of the starting anilino derivative | Amount of the anilino derivative used (mg) | Structure of the product obtained | Name of the product obtained | Empirical formula of the product obtained | Molecular weight of the product obtained | Amount obtained (mg) |
|---|---|---|---|---|---|---|---|
| 246 | 4-(DIFLUORO-METHOXY)-ANILINE | 76.4 | | 3-(4-Difluoromethoxy-phenyl)-5,5-dimethyl-1-pyrid-4-yl-methylimidazolidine-2,4-dione 2 | C18 H17 F2 N3 O3 | 361.35 | 3.9 |
| 247 | 3-CHLORO-4-(TRIFLUORO-METHOXY)-ANILINE | 101.6 | | 3-(3-Chloro-4-trifluoro-methyoxyphenyl)-5,5-dimethyl-1-pyrid-4-yl-methylimidazolidine-2,4-dione 2 | C18 H15 Cl F3 N3 O3 | 413.79 | 46.2 |
| 248 | 3-BROMO-4-(TRIFLUORO-METHOXY)-ANILINE | 122.9 | | 3-(3-Bromo-4-trifluoro-methyoxyphenyl)-5,5-dimethyl-1-pyrid-4-yl-methylimidazolidine-2,4-dione 2 | C18 H15 Br F3 N3 O3 | 458.24 | 43.2 |

-continued

| Example No | Name of the starting anilino derivative | Amount of the anilino derivative used (mg) | Structure of the product obtained | Name of the product obtained | Empirical formula of the product obtained | Molecular weight of the product obtained | Amount obtained (mg) |
|---|---|---|---|---|---|---|---|
| 249 | 2,6-DICHLORO-4-(TRIFLUORO-METHOXY)-ANILINE | 118.1 | | 3-(2,6-Dichloro-4-methyloxyphenyl)-5,5-dimethyl-1-pyrid-4-yl-methylimidazolidine-2,4-dione 2 | C18 H14 C12 F3 N3 O3 | 448.23 | 19.9 |
| 250 | 3-CHLORO-4-(TRIFLUORO-METHYLTHIO)-ANILINE | 109.3 | | 3-(3-Chloro-4-trifluoro-methylsulfanylphenyl)-5,5-dimethyl-1-pyrid-4-yl-methylimidazolidine-2,4-dione 2 | C18 H15 C1 F3 N3 O2 S | 429.85 | 33 |
| 251 | 2,2-DIFLUORO-5-AMINO-BENZODIOXOLE | 83.1 | | 3-(2,2-Difluoro-1,3-benzodioxol-5-yl)-5,5-dimethyl-1-pyrid-4-yl-methylimidazolidine-2,4-dione 2 | C18 H15 F2 N3 O4 | 375.33 | 7.4 |

-continued

| Example No | Name of the starting anilino derivative | Amount of the anilino derivative used (mg) | Structure of the product obtained | Name of the product obtained | Empirical formula of the product obtained | Molecular weight of the product obtained | Amount obtained (mg) |
|---|---|---|---|---|---|---|---|
| 252 | 2-BROMO-4-(TRIFLUORO-METHOXY)-ANILINE | 122.9 | 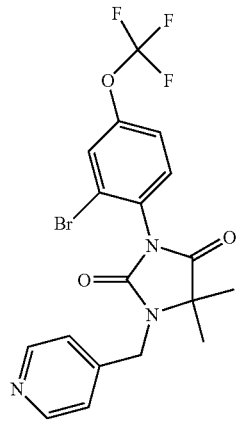 | 3-(2-Bromo-4-trifluoro-methoxyphenyl)-5,5-dimethyl-1-pyrid-4-yl-methylimidazolidine-2,4-dione 2 | C18 H15 Br F3 N3 O3 | 458.24 | 21.9 |
| 253 | 4-(HEPTA-FLUOROPROPYL-THIO)ANILINE | 140.8 | 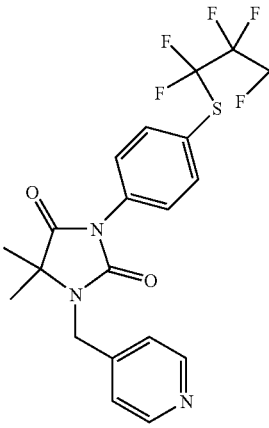 | 3-(4-Heptafluoropropylsulfanyl-phenyl)-5,5-dimethyl-1-pyrid-4-yl-methylimidazolidine-2,4-dione 2 | C20 H16 F7 N3 O2 S | 495.42 | 38.5 |
| 254 | 2-METHYL-4-(TRIFLUORO-METHOXY)-ANILINE | 91.8 | 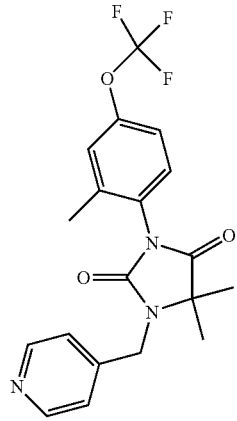 | 5,5-Dimethyl-3-(2-methyl-4-trifluoro-methoxyphenyl)-1-pyrid-4-ylmethylimidazolidine-2,4-dione 2 | C19 H18 F3 N3 O3 | 393.37 | 68.8 |

-continued

| Example No | Name of the starting anilino derivative | Amount of the anilino derivative used (mg) | Structure of the product obtained | Name of the product obtained | Empirical formula of the product obtained | Molecular weight of the product obtained | Amount obtained (mg) |
|---|---|---|---|---|---|---|---|
| 255 | 2-CHLORO-4-(TRIFLUORO-METHOXY)-ANILINE | 101.6 | | 3-(2-Chloro-4-trifluoro-methoxyphenyl)-5,5-dimethyl-1-pyrid-4-yl-methylimidazolidine-2,4-dione 2 | C19 H15 Cl F3 N3 O3 | 413.79 | 77.6 |

Summary table of the physicochemical characteristics of the products obtained

| Example N° | Name of the product obtained | Empirical formula of the product obtained | Molecular weight of the product obtained | Description of the mass spectrum (electron impact) | Description of the mass spectrum (analytical LC/MS) retention time, m/z | Description of the NMR spectrum (1H NMR spectrum (300 MHz, (CD3)2SO-d6, in ppm) |
|---|---|---|---|---|---|---|
| 244 | 5,5-Dimethyl-3-(2-nitro-4-trifluoromethoxyphenyl)-1-pyrid-4-yl-methylimidazolidine-2,4-dione 2 | C18 H15 F3 N4 O5 | 424.34 | m/z = 424 M+. m/z = 409 (M − CH3)+ m/z = 407 (M − OH)+ m/z = 378 (M − NO2)+. m/z = 147 C9H11N2+ m/z = 133 C7H5N2O+ m/z = 92 C6H6N+ base peak | | 1.44(broad s: 6H); 4.69(broad s: 2H); 7.41(broad d, J=5.5Hz: 2H); 7.98(d, J=8.5Hz: 1H); 8.07(broad d, J=8.5Hz: 1H); 8.29(d, J=2.5Hz: 1H); 8.56(broad d, J=5.5Hz: 2H) |
| 245 | 5,5-Dimethyl-1-pyrid-4-ylmethyl-3-[4-(1,1,2,2-tetrafluoroethoxy)phenyl]-imidazolidine-2,4-dione 2 | C19 H17 F4 N3 O3 | 411.36 | m/z = 411 M+. base peak m/z = 396 (M − CH3)+ m/z = 294 (m/z = 396 − C2H2F4)+ m/z = 235 C9H5NO2F4+. m/z = 147 C9H11N2+ m/z = 133 C7H5N2O+ m/z = 92 C6H6N+ | | 1.43(s: 6H); 4.65(s: 2H); 6.85(tt, J=51 and 3Hz: 1H); 7.46(mt: 4H); 7.62(dt, J=8.5 and 2.5Hz: 2H); 8.56(dd, J=6 and 1.5Hz: 2H) |
| 246 | 3-(4-Difluoromethoxy-phenyl)-5,5-dimethyl-1-pyrid-4-yl-methylimidazolidine-2,4-dione 2 | C18 H17 F2 N3 O3 | 361.35 | | t = 2.64 min m/z = 362 (M + 1) | |
| 247 | 3-(3-Chloro-4-trifluoro-methoxyphenyl)-5,5- | C18 H15 Cl F3 N3 | 413.79 | m/z = 413 M+. m/z = 398 (M − | | 1.43(s: 6H); 4.66(s: 2H); 7.46(d, J=6Hz: |

| Example N° | Name of the product obtained | Empirical formula of the product obtained | Molecular weight of the product obtained | Description of the mass spectrum (electron impact) | Description of the mass spectrum (analytical LC/MS) retention time, m/z | Description of the NMR spectrum (1H NMR spectrum (300 MHz, (CD3)2SO-d6, in ppm) |
|---|---|---|---|---|---|---|
| | dimethyl-1-pyrid-4-yl-methylimidazolidine-2,4-dione 2 | O3 | | CH3)+<br>m/z = 237 C8H3NO2ClF3+.<br>m/z = 147 C9H11N2+<br>m/z = 133 C7H5N2O+<br>m/z = 92 C6H6N+ base peak | | 2H); 7.66(dd, J=8.5 and 2.5Hz: 1H); 7.77(broad dd, J=8.5 and 1Hz: 1H); 7.93(d, J=2.5Hz: 1H); 8.55(broad d, J=6Hz: 2H) |
| 248 | 3-(3-Bromo-4-trifluoromethoxyphenyl)-5,5-dimethyl-1-pyrid-4-yl-methylimidazolidine-2,4-dione 2 | C18 H15 Br F3 N3 O3 | 458.24 | m/z = 457 M+.<br>m/z = 422 (M − CH3)+<br>m/z = 281 C8H3NO2BrF3+.<br>m/z = 147 C9H11N2+<br>m/z = 133 C7H5N2O+<br>m/z = 92 C6H6N+ base peak | | 1.43(s: 6H); 4.65(s: 2H); 7.46(broad d, J=6Hz: 2H); 7.68(dd, J=8.5 and 2.5Hz: 1H); 7.74(broad d, J=8.5Hz: 1H); 8.05(d, J=2.5Hz: 1H); 8.55(dd, J=6 and 1.5Hz: 2H) |
| 249 | 3-(2,6-Dichloro-4-trifluoromethoxyphenyl)-5,5-dimethyl-1-pyrid-4-yl-methylimidazolidine-2,4-dione 2 | C18 H14 Cl2 F3 N3 O3 | 448.23 | m/z = 447 M+.<br>m/z = 432 (M − CH3)+<br>m/z = 412 (M − Cl)+<br>m/z = 271 C8H2NO2Cl2F3+.<br>m/z = 147 C9H11N2+<br>m/z = 133 C7H5N2O+<br>m/z = 92 C6H6N+ base peak | | 1.47(s: 6H); 4.73(s: 2H); 7.47(broad d, J=6Hz: 2H); 8.00(broad s: 2H); 8.58(dd, J=6 and 1.5Hz: 2H) |
| 250 | 3-(3-Chloro-4-trifluoromethylsulfanylphenyl)-5,5-dimethyl-1-pyrid-4-yl-methylimidazolidine-2,4-dione 2 | C18 H15 Cl F3 N3 O2 S | 429.85 | m/z = 429 M+. base peak<br>m/z = 414 (M − CH3)+<br>m/z = 253 C8H3NOSClF3+.<br>m/z = 147 C9H11N2+<br>m/z = 133 C7H5N2O+<br>m/z = 92 C6H6N+ | | 1.43(s: 6H); 4.66(s: 2H); 7.46(broad d, J=6Hz: 2H); 7.70(dd, J=8.5 and 2Hz: 1H); 7.97(d, J=2Hz: 1H); 8.05(d, J=8.5Hz: 1H); 8.54(dd, J=6 and 1.5Hz: 2H) |
| 251 | 3-(2,2-Difluoro-1,3-benzodioxol-5-yl)-5,5-dimethyl-1-pyrid-4-yl-methylimidazolidine-2,4-dione 2 | C18 H15 F2 N3 O4 | 375.33 | | t = 2.80 min<br>m/z = 376 (M + 1) | |
| 252 | 3-(2-Bromo-4-trifluoromethoxyphenyl)-5,5-dimethyl-1-pyrid-4-yl-methylimidazolidine-2,4-dione 2 | C18 H15 Br F3 N3 O3 | 458.24 | m/z = 457 M+.<br>m/z = 414 (M − CH3)+<br>m/z = 378 (M − Br)+ base peak<br>m/z = 350 (m/z = 378 − CO)+<br>m/z = 281 C8H3NO2BrF3+.<br>m/z = 244 (m/z = 378 − C7H6N2O)+<br>m/z = 147 C9H11N2+<br>m/z = 133 C7H5N2O+<br>m/z = 92 C6H6N+ | | 1.43(s: 3H); 1.48(s: 3H); 4.68(limit AB, J=17Hz: 2H); 7.42(broad d, J=6Hz: 2H); 7.66(broad dd, J=8.5 and 2Hz: 1H); 7.83(d, J=8.5Hz: 1H); 8.07(broad d, J=2Hz: 1H); 8.56(dd, J=6 and 1.5Hz: 2H) |
| 253 | 3-(4-Heptafluoropropylsulfanylphenyl)-5,5-dimethyl-1-pyrid-4-yl- | C20 H16 F7 N3 O2 S | 495.42 | m/z = 495 M+. base peak<br>m/z = 480 (M − CH3)+ | | 1.43(s: 6H); 4.66(s: 2H); 7.46(broad d, J=6Hz: 2H); 7.71(broad d, J=8.5Hz: |

-continued

| Example N° | Name of the product obtained | Empirical formula of the product obtained | Molecular weight of the product obtained | Description of the mass spectrum (electron impact) | Description of the mass spectrum (analytical LC/MS) retention time, m/z | Description of the NMR spectrum (1H NMR spectrum (300 MHz, (CD3)2SO-d6, in ppm) |
|---|---|---|---|---|---|---|
| | methylimidazolidine-2,4-dione 2 | | | | m/z = 319 C10H4NOSF7+. m/z = 150 (m/z = 319 − C3F7)+ m/z = 147 C9H11N2+ m/z = 133 C7H5N2O+ m/z = 92 C6H6N+ | 2H); 7.89(broad d, J=8.5Hz: 2H); 8.55(dd, J=6 and 1.5Hz: 2H) |
| 254 | 5,5-Dimethyl-3-(2-methyl-4-trifluoro-methoxyphenyl)-1-pyrid-4-ylmethylimidazolidine-2,4-dione 2 | C19 H18 F3 N3 O3 | 393.37 | m/z = 393 M+. base peak m/z = 378 (M − CH3)+ m/z = 217 C9H6NO2F3+. m/z = 147 C9H11N2+ m/z = 133 C7H5N2O+ m/z = 92 C6H6N+ | | 1.43 and 1.44(2 s: 6H in total); 2.21(s: 3H); 4.65(broad s: 2H); 7.36(broad d, J=8.5Hz: 1H); 7.42(broad d, J=6Hz: 2H); 7.45(broad s: 1H); 7.55(d, J=8.5Hz: 1H); 8.55(dd, J=6 and 1.5Hz: 2H) |
| 255 | 3-(2-Chloro-4-trifluoro-methoxyphenyl)-5,5-dimethyl-1-pyrid-4-yl-methylimidazolidine-2,4-dione 2 | C18 H15 Cl F3 N3 O3 | 413.79 | m/z = 413 M+. m/z = 398 (M − CH3)+ m/z = 378 (M − Cl)+ base peak m/z = 350 (m/z = 378 − CO)+ m/z = 237 C8H3NO2Cl F3+. m/z = 147 C9H11N2+ m/z = 133 C7H5N2O+ m/z = 92 C6H6N+ | | 1.43(s: 3H); 1.48(s: 3H); 4.67(broad s: 2H); 7.42(broad d, J=6Hz: 2H); 7.62(ddd, J=8.5-2.5 and 1Hz: 1H); 7.85(d, J=8.5Hz: 1H); 7.88(broad d, J=2.5Hz: 1H); 8.57(dd, J=6 and 1.5Hz: 2H) |

The products of Examples 256 to 263 were obtained according to the procedure described above.

EXAMPLE 256

Methyl 5-(5-hydroxy-4,4-dimethyl-2-oxo-3-quinolin-4-ylmethylimidazolidin-1-yl)-2-trifluoromethoxybenzoate 1H NMR (DMSO)
(P-31800-112-1): 1.47 ppm (s, 6H); 3.89 ppm (s, 3H); 5.15 ppm (s, 2H); from 7.65 to 7.73 ppm (m, 3H); 7.82 ppm (bt, J=8.5 Hz, 1H); 7.92 ppm (dd, J=2.5-8.5 Hz, 1H); 8.07 ppm (bd, J=8.5 Hz, 1H); 8.17 ppm (d, J=2.5 Hz, 1H); 8.26 ppm (bd, J=8.5 Hz, 1H); 8.86 ppm (d, J=4.5 Hz, 1H)
LC/MS: MH+=488

EXAMPLE 257

3-(3-Bromo-4-trifluoromethoxyphenyl)-5,5-dimethyl-1-quinolin-4-ylmethylimidazolidine-2,4-dione 1H NMR (DMSO)
(P-31800-101-1): 1.45 ppm (s, 6H); 5.15 ppm (s, 2H); from 7.62 to 7.72 ppm (m, 4H); 7.80 ppm (bt, J=8.5 Hz, 1H); 8.08 ppm (m, 2H); 8.26 ppm (bd, J=8.5 Hz, 1H); 8.86 ppm (d, J=4.5 Hz).
LC/SM: MH+=508

EXAMPLE 258

3-(3-Chloro-4-trifluoromethoxyphenyl)-5,5-dimethyl-1-quinolin-4-ylmethylimidazoline-2,4-dione 1H NMR (DMSO):
P-31800-105-1 NMR No. 6354R: 1.44 ppm (s, 6H); 5.14 ppm (s, 2H); from 7.61 to 7.84 ppm (m, 5H); 7.94 ppm (d, J=2.5 Hz, 1H); 8.07 ppm (bd, J=8.5 Hz, 1H); 8.24 ppm (bd, J=8.5 Hz, 1H); 8.83 ppm (d, J=4.5 Hz, 1H).
LC/MS: MH+=464

EXAMPLE 259

5-(4,4-Dimethyl-2,5-dioxo-3-quinolin-4-ylmethylimidazolidin-1-yl)-2-trifluoromethyl-benzoic acid 1H NMR (DMSO)
(P-29798-111-1): 1.47 ppm (s, 6H); 5.15 ppm (s, 2H); from 7.62 to 7.72 ppm (m, 3H); 7.81 ppm (bt, J=8.5 Hz, 1H); 7.88 ppm (dd, J=2.5-8.5, 1H); 8.08 ppm (bt, J=8.5 Hz, 1H); 8.15 ppm (d, J=2.5 Hz, 1H); 8.26 ppm (bd, J=8.5 Hz, 1H); 8.87 ppm (d, J=4.5 Hz, 1H); 13.5 ppm (bs, 1H).
LC/MS: MH+=474

EXAMPLE 260

5,5-Dimethyl-3-{3-[4-(4-methylpiperazin-1-yl)bu-tyryl]-4-trifluoromethoxyphenyl}-1-quinolin-4-ylm-ethylimidazolidine-2,4-dione 1H NMR (DMSO)
(P-29798-112-1): 1.51 ppm (s, 6H); 1.97 ppm (m, 2H); 2.82 ppm (s, 3H); from 3.0 to 4.0 ppm (broad multiplet, 12H); 5.35 ppm (s, 2H); 7.63 ppm (dq, J=1.5-8.5 Hz, 1H); 7.75 ppm (dd, J=2.5-8.5 Hz, 1H); 7.82 ppm (d, J=2.5 Hz, 1H); 7.94 ppm (bt, J=8.5 Hz, 1H); 8.10 ppm (m, 2H); 8.39 ppm (bd, J=8.5 Hz, 1H); 8.51 ppm (bd, J=8.5 Hz, 1H); 8.72 ppm (bt, J=5.5 Hz, 1H); 9.15 ppm (d, J=5 Hz, 1H); 11.97 ppm (bs, 1H).
MS/EI: M+=612+

EXAMPLE 261

5-(5-Hydroxy-4,4-dimethyl-2-oxo-3-quinolin-4-ylmethylimidazolidin-1-yl)-2-trifluoromethoxybenzoic acid The following are introduced into a 30 ml round-bottomed flask equipped with a magnetic stirrer and a septum on which is mounted a nitrogen inlet:

−200 mg (0.41 mmol) of ester in 2 ml of ether;

−8 mg (0.205 mmol) of LiAlH$_4$, i.e., 8 ml of a 1M solution in 2 ml of THF.

The reaction medium is stirred at room temperature for 24 hours.

By TLC; 8/2 CH$_2$Cl$_2$/EtOAc: a product more polar than the starting material is formed, but starting material remains.

A further 0.5 equivalent of LiAlH$_4$ is added and the mixture is stirred for 5 hours. A small amount of starting material still remains, but the reaction mixture is worked up.

The reaction medium is hydrolyzed by adding water thereto, and is extracted with 3 times 10 ml of ethyl acetate. The organic fractions are combined and dried over magnesium sulfate, and the EtOAc is evaporated off.

The crude reaction product is purified using a CH$_2$Cl$_2$/EtOAc eluent mixture (9/1).

60 mg of alcohol are thus obtained.

$^1$H NMR (DMSO): 1.19 ppm (s, 3H); 1.24 ppm (s, 3H); 3.86 ppm (s, 3H); 4.92 ppm (AB system, J=18 Hz, 2H); 5.36 ppm (s, 1H); 7.51 ppm (dm, J=9.0 Hz, 1H); 7.58 ppm (d, J=4.5 Hz, 1H); 7.66 ppm (m, 1H); 7.80 ppm (m, 1H); 8.00 ppm (dd, J=2.5-9.0 Hz, 1H); 8.06 ppm (dd, J=1.5-8.5 Hz, 1H); 8.28 ppm (dd, J=1.5-8.5 Hz, 1H); 8.33 ppm (d, J=2.5 Hz, 1H); 8.84 ppm (df, J=4.5 Hz, 1H).
LC/MS: MH+=489

EXAMPLE 262

4,4-dimethyl-3-quinolin-4-ylmethyl-5-thioxo-1-(4-trifluoromethoxyphenyl)imidazolidin-2-one The following reaction mixture:

317 mg (0.739×10$^{-3}$ mol) of hydantoin SB 31051-139

78 mg (0.19×10$^{-3}$ mol) of Lawesson's reagent 1 cm$^3$ of toluene is refluxed for 9 hours and then cooled, filtered and concentrated under reduced pressure. A yellow foam is recovered, and is purified by chromatography several times on silica, with chloroform/acetone eluent (97/3). 231 mg of pure yellow resin are obtained: Rf=0.38 Th=329 mg Yield=70%

1H NMR (DMSO) ppm
(P-31051-146-2): 1.57 ppm (s, 6H); 5.24 ppm (s, 2H); 7.57 ppm (m, 2H); 7.63 ppm (d, J=4.5 Hz, 1H); 7.70 ppm (m, 3H); 7.81 ppm (bt, J=8.5 Hz, 1H); 8.08 ppm (dd, J=1.5-8.5 Hz, 1H); 8.26 ppm (dd, J=1.5-8.5 Hz, 1H); 8.86 ppm (d, J=4.5 Hz, 1H).
LC/SM: MH$_+$=446

EXAMPLE 263

5,5-dimethyl-1-quinolin-4-ylmethyl-2-thioxo-3-(4-trifluoromethoxyphenyl)imidazolidin-4-one The following reaction mixture:

0.6 g (mmol) of quinoline derivative 0.918 g (mmol) of thioisocyanate 12 cm$^3$ of anhydrous THF 0.2 cm$^3$ of TEA is stirred at room temperature for 20 hours.

The mixture is concentrated under reduced pressure and then purified on a 25 g AIT column, eluent 95/5 DCM/acetone.

The product of Rf=0.12 is recovered, i.e., 266 mg
Yield=26%
1H NMR (DMSO)
(P-31051-160-2): 1.55 ppm (s, 6H); 5.56 ppm (s, 2H); 7.55 ppm (m, 3H); 7.69 ppm (m, 3H); 7.82 ppm (bt, J=8.5 Hz, 1H); 8.08 ppm (dd, J=1.5-8.5, 1H); 8.28 ppm (dd, J=1.5-8.5, 1H); 8.83 ppm (d, J=4.5 Hz, 1H).
MS: M$^+$=445$^+$ The products of Examples 264 to 332 are described in Table 1 below: these products are prepared as indicated in the experimental section of the present patent application and especially as indicated for the products of Examples 70 to 200, and thus constitute Examples 264 to 332 of the present invention.

EXAMPLE 333

Pharmaceutical Composition

Tablets were prepared corresponding to the following formula:

Product of Example 9 . . . 0.2 g

Excipient for a finished tablet weighing . . . 1 g (details of the excipient: lactose, talc, starch, magnesium stearate).

EXAMPLE 334

Pharmaceutical Composition

Tablets were prepared corresponding to the following formula:

Product of Example 52 . . . 0.2 g

Excipient for a finished tablet weighing . . . 1 g (details of the excipient: lactose, talc, starch, magnesium stearate).

Pharmaceutical Composition Examples 333 and 334 above illustrate the present invention, it being understood that the same preparations can be made with other preferred products of the present invention, and form part of the present invention.

The present invention also comprises as examples the compound of formula I below: the list below gives the names of compound of formula I as defined above for which B2 is a pyridyl radical or a quinolyl radical: these products form part of the present invention and may be synthesized according to the processes described above for obtaining the compound of formula I, and especially according to the operating conditions described for the preparation of Examples 61 to 63:

5,5-dimethyl-1-(2-methylpyrid-4-ylmethyl)-3-(4-trifluoromethoxyphenyl)imidazolidine-2,4-dione;
5,5-dimethyl-1-(2-ethylpyrid-4-ylmethyl)-3-(4-trifluoromethoxyphenyl)imidazolidine-2,4-dione;
5,5-dimethyl-1-(2-isopropylpyrid-4-ylmethyl)-3-(4-trifluoromethoxyphenyl)imidazolidine-2,4-dione;
5,5-dimethyl-1-(2-tert-butylpyrid-4-ylmethyl)-3-(4-trifluoromethoxyphenyl)imidazolidine-2,4-dione;
5,5-dimethyl-1-(2-isobutylpyrid-4-ylmethyl)-3-(4-trifluoromethoxyphenyl)imidazolidine-2,4-dione;
5,5-dimethyl-1-(2-cyclohexylpyrid-4-ylmethyl)-3-(4-trifluoromethoxyphenyl)imidazolidine-2,4-dione;
5,5-dimethyl-1-(2-phenylpyrid-4-ylmethyl)-3-(4-trifluoromethoxyphenyl)imidazolidine-2,4-dione;
5,5-dimethyl-1-[2-(4-chlorophenyl)pyrid-4-ylmethyl]-3-(4-trifluoromethoxyphenyl)imidazolidine-2,4-dione;
5,5-dimethyl-1-[2-(3-chlorophenyl)pyrid-4-ylmethyl]-3-(4-trifluoromethoxyphenyl)imidazolidine-2,4-dione;
5,5-dimethyl-1-[2-(2-chlorophenyl)pyrid-4-ylmethyl]-3-(4-trifluoromethoxyphenyl)imidazolidine-2,4-dione;
5,5-dimethyl-1-[2-(4-fluorophenyl)pyrid-4-ylmethyl]-3-(4-trifluoromethoxyphenyl)imidazolidine-2,4-dione;
5,5-dimethyl-1-[2-(4-methoxyphenyl)pyrid-4-ylmethyl]-3-(4-trifluoromethoxyphenyl)imidazolidine-2,4-dione;
5,5-dimethyl-1-(2-benzylpyrid-4-ylmethyl)-3-(4-trifluoromethoxyphenyl)imidazolidine-2,4-dione;
5,5-dimethyl-1-(2,2'-bipyrid-4-ylmethyl)-3-(4-trifluoromethoxyphenyl)imidazolidine-2,4-dione;
5,5-dimethyl-1-(2-hydroxymethylpyrid-4-ylmethyl)-3-(4-trifluoromethoxyphenyl)imidazolidine-2,4-dione;
5,5-dimethyl-1-(2-chloropyrid-4-ylmethyl)-3-(4-trifluoromethoxyphenyl)imidazolidine-2,4-dione;
5,5-dimethyl-1-(2-fluoropyrid-4-ylmethyl)-3-(4-trifluoromethoxyphenyl)imidazolidine-2,4-dione;
5,5-dimethyl-1-(2-bromopyrid-4-ylmethyl)-3-(4-trifluoromethoxyphenyl)imidazolidine-2,4-dione;
5,5-dimethyl-1-(2-aminopyrid-4-ylmethyl)-3-(4-trifluoromethoxyphenyl)imidazolidine-2,4-dione;
5,5-dimethyl-1-(2-methylaminopyrid-4-ylmethyl)-3-(4-trifluoromethoxyphenyl)imidazolidine-2,4-dione;
5,5-dimethyl-1-(2-ethylaminopyrid-4-ylmethyl)-3-(4-trifluoromethoxyphenyl)imidazolidine-2,4-dione;
5,5-dimethyl-1-(2-isopropylaminopyrid-4-ylmethyl)-3-(4-trifluoromethoxyphenyl)imidazolidine-2,4-dione;
5,5-dimethyl-1-(2-phenylaminopyrid-4-ylmethyl)-3-(4-trifluoromethoxyphenyl)imidazolidine-2,4-dione;
5,5-dimethyl-1-(2-cyclohexylaminopyrid-4-ylmethyl)-3-(4-trifluoromethoxyphenyl)imidazolidine-2,4-dione;
5,5-dimethyl-1-(2-diethylaminopyrid-4-ylmethyl)-3-(4-trifluoromethoxyphenyl)imidazolidine-2,4-dione;
5,5-dimethyl-1-(2-N-cyclohexyl-N-methylaminopyrid-4-ylmethyl)-3-(4-trifluoromethoxyphenyl)imidazolidine-2,4-dione;
5,5-dimethyl-1-(2-piperidinopyrid-4-ylmethyl)-3-(4-trifluoromethoxyphenyl)imidazolidine-2,4-dione;
5,5-dimethyl-1-(2-morpholinopyrid-4-ylmethyl)-3-(4-trifluoromethoxyphenyl)imidazolidine-2,4-dione;
5,5-dimethyl-1-[2-(4-methylpiperazino)pyrid-4-ylmethyl]-3-(4-trifluoromethoxyphenyl)imidazolidine-2,4-dione;
5,5-dimethyl-1-[2-(1H-pyrazol-1-yl)pyrid-4-ylmethyl]-3-(4-trifluoromethoxyphenyl)imidazolidine-2,4-dione;
5,5-dimethyl-1-[2-(2-benzoylhydrazino)pyrid-4-ylmethyl]-3-(4-trifluoromethoxyphenyl)imidazolidine-2,4-dione;
5,5-dimethyl-1-(2-benzoylaminopyrid-4-ylmethyl)-3-(4-trifluoromethoxyphenyl)imidazolidine-2,4-dione;
5,5-dimethyl-1-[2-(4-chlorobenzoylamino)pyrid-4-ylmethyl]-3-(4-trifluoromethoxyphenyl)imidazolidine-2,4-dione;
5,5-dimethyl-1-[2-(3-chlorobenzoylamino)pyrid-4-ylmethyl]-3-(4-trifluoromethoxyphenyl)imidazolidine-2,4-dione;
5,5-dimethyl-1-[2-(2-chlorobenzoylamino)pyrid-4-ylmethyl]-3-(4-trifluoromethoxyphenyl)imidazolidine-2,4-dione;
5,5-dimethyl-1-[2-(4-fluorobenzoylamino)pyrid-4-ylmethyl]-3-(4-trifluoromethoxyphenyl)imidazolidine-2,4-dione;
5,5-dimethyl-1-[2-(4-methoxybenzoylamino)pyrid-4-ylmethyl]-3-(4-trifluoromethoxyphenyl)imidazolidine-2,4-dione;
5,5-dimethyl-1-(2-acetamidopyrid-4-ylmethyl)-3-(4-trifluoromethoxyphenyl)imidazolidine-2,4-dione;
5,5-dimethyl-1-(2-phenylacetamidopyrid-4-ylmethyl)-3-(4-trifluoromethoxyphenyl)imidazolidine-2,4-dione;
5,5-dimethyl-1-[2-(4-methylpiperazino)acetamidopyrid-4-ylmethyl]-3-(4-trifluoromethoxyphenyl)imidazolidine-2,4-dione;
5,5-dimethyl-1-(2-cyclohexanylcarboxamidopyrid-4-ylmethyl)-3-(4-trifluoromethoxyphenyl)imidazolidine-2,4-dione;
5,5-dimethyl-1-[2-(1-methyl-4-piperidinyl)carbonylaminopyrid-4-ylmethyl]-3-(4-trifluoromethoxyphenyl)imidazolidine-2,4-dione;
5,5-dimethyl-1-[2-(2-furanylcarbonyl)aminopyrid-4-ylmethyl]-3-(4-trifluoromethoxyphenyl)imidazolidine-2,4-dione;
5,5-dimethyl-1-(2-ethoxycarbonylaminopyrid-4-ylmethyl)-3-(4-trifluoromethoxyphenyl)imidazolidine-2,4-dione;
5,5-dimethyl-1-(2-isopropoxycarbonylaminopyrid-4-ylmethyl)-3-(4-trifluoromethoxyphenyl)imidazolidine-2,4-dione;
5,5-dimethyl-1-(2-butoxycarbonylaminopyrid-4-ylmethyl)-3-(4-trifluoromethoxyphenyl)imidazolidine-2,4-dione;
5,5-dimethyl-1-[2-(2-diethylaminoethoxycarbonylamino)pyrid-4-ylmethyl]-3-(4-trifluoromethoxyphenyl)imidazolidine-2,4-dione;
5,5-dimethyl-1-(2-phenoxycarbonylaminopyrid-4-ylmethyl)-3-(4-trifluoromethoxyphenyl)imidazolidine-2,4-dione;
5,5-dimethyl-1-[2-(4-chloroanilino)carbonylaminopyrid-4-ylmethyl]-3-(4-trifluoromethoxyphenyl)imidazolidine-2,4-dione;
5,5-dimethyl-1-(2-anilinocarbonylaminopyrid-4-ylmethyl)-3-(4-trifluoromethoxyphenyl)imidazolidine-2,4-dione;
5,5-dimethyl-1-(2-benzylaminocarbonylaminopyrid-4-ylmethyl)-3-(4-trifluoromethoxyphenyl)imidazolidine-2,4-dione;
5,5-dimethyl-1-[2-(2-pyridylamino)carbonylaminopyrid-4-ylmethyl]-3-(4-trifluoromethoxyphenyl)imidazolidine-2,4-dione;

5,5-dimethyl-1-(2-ureidopyrid-4-ylmethyl)-3-(4-trifluoromethoxyphenyl)imidazolidine-2,4-dione;

5,5-dimethyl-1-(2-benzylaminosulfonylaminopyrid-4-ylmethyl)-3-(4-trifluoromethoxyphenyl)imidazolidine-2,4-dione;

5,5-dimethyl-1-(2-methylaminosulfonylaminopyrid-4-ylmethyl)-3-(4-trifluoromethoxyphenyl)imidazolidine-2,4-dione;

5,5-dimethyl-1-(2-aminosulfonylaminopyrid-4-ylmethyl)-3-(4-trifluoromethoxyphenyl)imidazolidine-2,4-dione;

5,5-dimethyl-1-(2-morpholinosulfonylaminopyrid-4-ylmethyl)-3-(4-trifluoromethoxyphenyl)imidazolidine-2,4-dione;

5,5-dimethyl-1-(2-dimethylaminosulfonylaminopyrid-4-ylmethyl)-3-(4-trifluoromethoxyphenyl)imidazolidine-2,4-dione;

5,5-dimethyl-1-(2-anilinosulfonylaminopyrid-4-ylmethyl)-3-(4-trifluoromethoxyphenyl)imidazolidine-2,4-dione;

5,5-dimethyl-1-(2-phenylsulfonylaminopyrid-4-ylmethyl)-3-(4-trifluoromethoxyphenyl)imidazolidine-2,4-dione;

5,5-dimethyl-1-[2-(2-thienyl)sulfonylaminopyrid-4-ylmethyl]-3-(4-trifluoromethoxyphenyl)imidazolidine-2,4-dione;

5,5-dimethyl-1-(2-methylsulfonylaminopyrid-4-ylmethyl)-3-(4-trifluoromethoxyphenyl)imidazolidine-2,4-dione;

5,5-dimethyl-1-[2-(4-chlorophenyl)sulfonylaminopyrid-4-ylmethyl]-3-(4-trifluoromethoxyphenyl)imidazolidine-2,4-dione;

5,5-dimethyl-1-(2-benzylsulfonylaminopyrid-4-ylmethyl)-3-(4-trifluoromethoxyphenyl)imidazolidine-2,4-dione;

5,5-dimethyl-(2-hydroxycarbonylpyrid-4-ylmethyl)-3-(4-trifluoromethoxyphenyl)imidazolidine-2,4-dione;

5,5-dimethyl-1-(2-ethoxycarbonylpyrid-4-ylmethyl)-3-(4-trifluoromethoxyphenyl)imidazolidine-2,4-dione;

5,5-dimethyl-1-(2-tert-butoxycarbonylpyrid-4-ylmethyl)-3-(4-trifluoromethoxyphenyl)imidazolidine-2,4-dione;

5,5-dimethyl-1-(2-phenoxycarbonylpyrid-4-ylmethyl)-3-(4-trifluoromethoxyphenyl)imidazolidine-2,4-dione;

5,5-dimethyl-1-[2-(4-methylpiperazinocarbonyl)pyrid-4-ylmethyl]-3-(4-trifluoromethoxyphenyl)imidazolidine-2,4-dione;

5,5-dimethyl-1-[2-(methylamino)carbonylpyrid-4-ylmethyl]-3-(4-trifluoromethoxyphenyl)imidazolidine-2,4-dione;

5,5-dimethyl-1-[2-(dimethylamino)carbonylpyrid-4-ylmethyl]-3-(4-trifluoromethoxyphenyl)imidazolidine-2,4-dione;

5,5-dimethyl-1-(2-piperidinocarbonylpyrid-4-ylmethyl)-3-(4-trifluoromethoxyphenyl)imidazolidine-2,4-dione;

5,5-dimethyl-1-(2-morpholinocarbonylpyrid-4-ylmethyl)-3-(4-trifluoromethoxyphenyl)imidazolidine-2,4-dione;

5,5-dimethyl-1-[2-(4-phenylpiperazinocarbonyl)pyrid-4-ylmethyl]-3-(4-trifluoromethoxyphenyl)imidazolidine-2,4-dione;

5,5-dimethyl-1-(2-phenylaminocarbonylpyrid-4-ylmethyl)-3-(4-trifluoromethoxyphenyl)imidazolidine-2,4-dione;

5,5-dimethyl-1-[2-(methylphenylamino)carbonylpyrid-4-ylmethyl]-3-(4-trifluoromethoxyphenyl)imidazolidine-2,4-dione;

5,5-dimethyl-1-[2-(4-methoxyphenyl)methylaminocarbonylpyrid-4-ylmethyl]-3-(4-trifluoromethoxyphenyl)imidazolidine-2,4-dione;

5,5-dimethyl-1-[2-(4-chlorophenyl)methylaminocarbonylpyrid-4-ylmethyl]-3-(4-trifluoromethoxyphenyl)imidazolidine-2,4-dione;

5,5-dimethyl-1-[2-(4-morpholinylamino)carbonylpyrid-4-ylmethyl]-3-(4-trifluoromethoxyphenyl)imidazolidine-2,4-dione;

5,5-dimethyl-1-(2-aminocarbonylpyrid-4-ylmethyl)-3-(4-trifluoromethoxyphenyl)imidazolidine-2,4-dione;

5,5-dimethyl-1-(2-phenoxypyrid-4-ylmethyl)-3-(4-trifluoromethoxyphenyl)imidazolidine-2,4-dione;

5,5-dimethyl-1-(2-methoxypyrid-4-ylmethyl)-3-(4-trifluoromethoxyphenyl)imidazolidine-2,4-dione;

5,5-dimethyl-1-(2-ethoxypyrid-4-ylmethyl)-3-(4-trifluoromethoxyphenyl)imidazolidine-2,4-dione;

5,5-dimethyl-1-[2-(1-pyrrolidinyl)ethoxypyrid-4-ylmethyl]-3-(4-trifluoromethoxyphenyl)imidazolidine-2,4-dione;

5,5-dimethyl-1-(2-benzyloxypyrid-4-ylmethyl)-3-(4-trifluoromethoxyphenyl)imidazolidine-2,4-dione;

5,5-dimethyl-1-(2-benzoyloxypyrid-4-ylmethyl)-3-(4-trifluoromethoxyphenyl)imidazolidine-2,4-dione;

5,5-dimethyl-1-[2-(4,5-dihydro-1H-imidazol-2-yl)pyrid-4-ylmethyl]-3-(4-trifluoromethoxyphenyl)imidazolidine-2,4-dione;

5,5-dimethyl-1-[2-(1H-imidazol-2-yl)pyrid-4-ylmethyl]-3-(4-trifluoromethoxyphenyl)imidazolidine-2,4-dione;

5,5-dimethyl-1-[2-(1H-tetrazol-5-yl)pyrid-4-ylmethyl]-3-(4-trifluoromethoxyphenyl)imidazolidine-2,4-dione;

5,5-dimethyl-1-(2-amidinopyrid-4-ylmethyl)-3-(4-trifluoromethoxyphenyl)imidazolidine-2,4-dione;

5,5-dimethyl-1-(2-dimethylaminomethylpyrid-4-ylmethyl)-3-(4-trifluoromethoxyphenyl)imidazolidine-2,4-dione;

5,5-dimethyl-1-(2-aminomethylpyrid-4-ylmethyl)-3-(4-trifluoromethoxyphenyl)imidazolidine-2,4-dione;

5,5-dimethyl-1-(3-methylpyrid-4-ylmethyl)-3-(4-trifluoromethoxyphenyl)imidazolidine-2,4-dione;

5,5-dimethyl-1-(3-ethylpyrid-4-ylmethyl)-3-(4-trifluoromethoxyphenyl)imidazolidine-2,4-dione;

5,5-dimethyl-1-(3-isopropylpyrid-4-ylmethyl)-3-(4-trifluoromethoxyphenyl)imidazolidine-2,4-dione;

5,5-dimethyl-1-(3-tert-butylpyrid-4-ylmethyl)-3-(4-trifluoromethoxyphenyl)imidazolidine-2,4-dione;

5,5-dimethyl-1-(3-isobutylpyrid-4-ylmethyl)-3-(4-trifluoromethoxyphenyl)imidazolidine-2,4-dione;

5,5-dimethyl-1-(3-cyclohexylpyrid-4-ylmethyl)-3-(4-trifluoromethoxyphenyl)imidazolidine-2,4-dione;

5,5-dimethyl-1-(3-phenylpyrid-4-ylmethyl)-3-(4-trifluoromethoxyphenyl)imidazolidine-2,4-dione;

5,5-dimethyl-1-[3-(4-chlorophenyl)pyrid-4-ylmethyl]-3-(4-trifluoromethoxyphenyl)imidazolidine-2,4-dione;

5,5-dimethyl-1-[3-(3-chlorophenyl)pyrid-4-ylmethyl]-3-(4-trifluoromethoxyphenyl)imidazolidine-2,4-dione;

5,5-dimethyl-1-[3-(2-chlorophenyl)pyrid-4-ylmethyl]-3-(4-trifluoromethoxyphenyl)imidazolidine-2,4-dione;

5,5-dimethyl-1-[3-(4-fluorophenyl)pyrid-4-ylmethyl]-3-(4-trifluoromethoxyphenyl)imidazolidine-2,4-dione;

5,5-dimethyl-1-[3-(4-methoxyphenyl)pyrid-4-ylmethyl]-3-(4-trifluoromethoxyphenyl)imidazolidine-2,4-dione;

5,5-dimethyl-1-(3-benzylpyrid-4-ylmethyl)-3-(4-trifluoromethoxyphenyl)imidazolidine-2,4-dione;

5,5-dimethyl-1-(3,2'-bipyrid-4-ylmethyl)-3-(4-trifluoromethoxyphenyl)imidazolidine-2,4-dione;

5,5-dimethyl-1-(3-hydroxymethylpyrid-4-ylmethyl)-3-(4-trifluoromethoxyphenyl)imidazolidine-2,4-dione;

5,5-dimethyl-1-(3-chloropyrid-4-ylmethyl)-3-(4-trifluoromethoxyphenyl)imidazolidine-2,4-dione;

5,5-dimethyl-1-(3-fluoropyrid-4-ylmethyl)-3-(4-trifluoromethoxyphenyl)imidazolidine-2,4-dione;

5,5-dimethyl-1-(3-bromopyrid-4-ylmethyl)-3-(4-trifluoromethoxyphenyl)imidazolidine-2,4-dione;

5,5-dimethyl-1-(3-aminopyrid-4-ylmethyl)-3-(4-trifluoromethoxyphenyl)imidazolidine-2,4-dione;
5,5-dimethyl-1-(3-methylaminopyrid-4-ylmethyl)-3-(4-trifluoromethoxyphenyl)imidazolidine-2,4-dione;
5,5-dimethyl-1-(3-ethylaminopyrid-4-ylmethyl)-3-(4-trifluoromethoxyphenyl)imidazolidine-2,4-dione;
5,5-dimethyl-1-(3-isopropylaminopyrid-4-ylmethyl)-3-(4-trifluoromethoxyphenyl)imidazolidine-2,4-dione;
5,5-dimethyl-1-(3-phenylaminopyrid-4-ylmethyl)-3-(4-trifluoromethoxyphenyl)imidazolidine-2,4-dione;
5,5-dimethyl-1-(3-cyclohexylaminopyrid-4-ylmethyl)-3-(4-trifluoromethoxyphenyl)imidazolidine-2,4-dione;
5,5-dimethyl-1-(3-diethylaminopyrid-4-ylmethyl)-3-(4-trifluoromethoxyphenyl)imidazolidine-2,4-dione;
5,5-dimethyl-1-(3-N-cyclohexyl-N-methylaminopyrid-4-ylmethyl)-3-(4-trifluoromethoxyphenyl)imidazolidine-2,4-dione;
5,5-dimethyl-1-(3-piperidinopyrid-4-ylmethyl)-3-(4-trifluoromethoxyphenyl)imidazolidine-2,4-dione;
5,5-dimethyl-1-(3-morpholinopyrid-4-ylmethyl)-3-(4-trifluoromethoxyphenyl)imidazolidine-2,4-dione;
5,5-dimethyl-1-[3-(4-methylpiperazino)pyrid-4-ylmethyl]-3-(4-trifluoromethoxyphenyl)imidazolidine-2,4-dione;
5,5-dimethyl-1-[3-(1H-pyrazol-1-yl)pyrid-4-ylmethyl]-3-(4-trifluoromethoxyphenyl)imidazolidine-2,4-dione;
5,5-dimethyl-1-[3-(2-benzoylhydrazino)pyrid-4-ylmethyl]-3-(4-trifluoromethoxyphenyl)imidazolidine-2,4-dione;
5,5-dimethyl-1-(3-benzoylaminopyrid-4-ylmethyl)-3-(4-trifluoromethoxyphenyl)imidazolidine-2,4-dione;
5,5-dimethyl-1-[3-(4-chlorobenzoylamino)pyrid-4-ylmethyl]-3-(4-trifluoromethoxyphenyl)imidazolidine-2,4-dione;
5,5-dimethyl-1-[3-(3-chlorobenzoylamino)pyrid-4-ylmethyl]-3-(4-trifluoromethoxyphenyl)imidazolidine-2,4-dione;
5,5-dimethyl-1-[3-(2-chlorobenzoylamino)pyrid-4-ylmethyl]-3-(4-trifluoromethoxyphenyl)imidazolidine-2,4-dione;
5,5-dimethyl-1-[3-(4-fluorobenzoylamino)pyrid-4-ylmethyl]-3-(4-trifluoromethoxyphenyl)imidazolidine-2,4-dione;
5,5-dimethyl-1-[3-(4-methoxybenzoylamino)pyrid-4-ylmethyl]-3-(4-trifluoromethoxyphenyl)imidazolidine-2,4-dione;
5,5-dimethyl-1-(3-acetamidopyrid-4-ylmethyl)-3-(4-trifluoromethoxyphenyl)imidazolidine-2,4-dione;
5,5-dimethyl-1-(3-phenylacetamidopyrid-4-ylmethyl)-3-(4-trifluoromethoxyphenyl)imidazolidine-2,4-dione;
5,5-dimethyl-1-[3-(4-methylpiperazino)acetamidopyrid-4-ylmethyl]-3-(4-trifluoromethoxyphenyl)imidazolidine-2,4-dione;
5,5-dimethyl-1-(3-cyclohexanylcarboxamidopyrid-4-ylmethyl)-3-(4-trifluoromethoxyphenyl)imidazolidine-2,4-dione;
5,5-dimethyl-1-[3-(1-methyl-4-piperidinyl)carbonylaminopyrid-4-ylmethyl]-3-(4-trifluoromethoxyphenyl)imidazolidine-2,4-dione;
5,5-dimethyl-1-[3-(2-furanylcarbonyl)aminopyrid-4-ylmethyl]-3-(4-trifluoromethoxyphenyl)imidazolidine-2,4-dione;
5,5-dimethyl-1-(3-ethoxycarbonylaminopyrid-4-ylmethyl)-3-(4-trifluoromethoxyphenyl)imidazolidine-2,4-dione;
5,5-dimethyl-1-(3-isopropoxycarbonylaminopyrid-4-ylmethyl)-3-(4-trifluoromethoxyphenyl)imidazolidine-2,4-dione;
5,5-dimethyl-1-(3-butoxycarbonylaminopyrid-4-ylmethyl)-3-(4-trifluoromethoxyphenyl)imidazolidine-2,4-dione;
5,5-dimethyl-1-[3-(2-diethylaminoethoxycarbonylamino)pyrid-4-ylmethyl]-3-(4-trifluoromethoxyphenyl)imidazolidine-2,4-dione;
5,5-dimethyl-1-(3-phenoxycarbonylaminopyrid-4-ylmethyl)-3-(4-trifluoromethoxyphenyl)imidazolidine-2,4-dione;
5,5-dimethyl-1-[3-(4-chloroanilino)carbonylaminopyrid-4-ylmethyl]-3-(4-trifluoromethoxyphenyl)imidazolidine-2,4-dione;
5,5-dimethyl-1-(3-anilinocarbonylaminopyrid-4-ylmethyl)-3-(4-trifluoromethoxyphenyl)imidazolidine-2,4-dione;
5,5-dimethyl-1-(3-benzylaminocarbonylaminopyrid-4-ylmethyl)-3-(4-trifluoromethoxyphenyl)imidazolidine-2,4-dione;
5,5-dimethyl-1-[3-(2-pyridylamino)carbonylaminopyrid-4-ylmethyl]-3-(4-trifluoromethoxyphenyl)imidazolidine-2,4-dione;
5,5-dimethyl-1-(3-ureidopyrid-4-ylmethyl)-3-(4-trifluoromethoxyphenyl)imidazolidine-2,4-dione;
5,5-dimethyl-1-(3-benzylaminosulfonylaminopyrid-4-ylmethyl)-3-(4-trifluoromethoxyphenyl)imidazolidine-2,4-dione;
5,5-dimethyl-1-(3-methylaminosulfonylaminopyrid-4-ylmethyl)-3-(4-trifluoromethoxyphenyl)imidazolidine-2,4-dione;
5,5-dimethyl-1-(3-aminosulfonylaminopyrid-4-ylmethyl)-3-(4-trifluoromethoxyphenyl)imidazolidine-2,4-dione;
5,5-dimethyl-1-(3-morpholinosulfonylaminopyrid-4-ylmethyl)-3-(4-trifluoromethoxyphenyl)imidazolidine-2,4-dione;
5,5-dimethyl-1-(3-dimethylaminosulfonylaminopyrid-4-ylmethyl)-3-(4-trifluoromethoxyphenyl)imidazolidine-2,4-dione;
5,5-dimethyl-1-(3-anilinosulfonylaminopyrid-4-ylmethyl)-3-(4-trifluoromethoxyphenyl)imidazolidine-2,4-dione;
5,5-dimethyl-1-(3-phenylsulfonylaminopyrid-4-ylmethyl)-3-(4-trifluoromethoxyphenyl)imidazolidine-2,4-dione;
5,5-dimethyl-1-[3-(2-thienyl)sulfonylaminopyrid-4-ylmethyl]-3-(4-trifluoromethoxyphenyl)imidazolidine-2,4-dione;
5,5-dimethyl-1-(3-methylsulfonylaminopyrid-4-ylmethyl)-3-(4-trifluoromethoxyphenyl)imidazolidine-2,4-dione;
5,5-dimethyl-1-[3-(4-chlorophenyl)sulfonylaminopyrid-4-ylmethyl]-3-(4-trifluoromethoxyphenyl)imidazolidine-2,4-dione;
5,5-dimethyl-1-(3-benzylsulfonylaminopyrid-4-ylmethyl)-3-(4-trifluoromethoxyphenyl)imidazolidine-2,4-dione;
5,5-dimethyl-1-(3-hydroxycarbonylpyrid-4-ylmethyl)-3-(4-trifluoromethoxyphenyl)imidazolidine-2,4-dione;
5,5-dimethyl-1-(3-ethoxycarbonylpyrid-4-ylmethyl)-3-(4-trifluoromethoxyphenyl)imidazolidine-2,4-dione;
5,5-dimethyl-1-(3-tert-butoxycarbonylpyrid-4-ylmethyl)-3-(4-trifluoromethoxyphenyl)imidazolidine-2,4-dione;
5,5-dimethyl-1-(3-phenoxycarbonylpyrid-4-ylmethyl)-3-(4-trifluoromethoxyphenyl)imidazolidine-2,4-dione;
5,5-dimethyl-1-[3-(4-methylpiperazinocarbonyl)pyrid-4-ylmethyl]-3-(4-trifluoromethoxyphenyl)imidazolidine-2,4-dione;
5,5-dimethyl-1-[3-(methylamino)carbonylpyrid-4-ylmethyl]-3-(4-trifluoromethoxyphenyl)imidazolidine-2,4-dione;
5,5-dimethyl-1-[3-(dimethylamino)carbonylpyrid-4-ylmethyl]-3-(4-trifluoromethoxyphenyl)imidazolidine-2,4-dione;
5,5-dimethyl-1-(3-piperidinocarbonylpyrid-4-ylmethyl)-3-(4-trifluoromethoxyphenyl)imidazolidine-2,4-dione;

5,5-dimethyl-1-(3-morpholinocarbonylpyrid-4-ylmethyl)-3-(4-trifluoromethoxyphenyl)imidazolidine-2,4-dione;

5,5-dimethyl-1-[3-(4-phenylpiperazinocarbonyl)pyrid-4-ylmethyl]-3-(4-trifluoromethoxyphenyl)imidazolidine-2,4-dione;

5,5-dimethyl-1-(3-phenylaminocarbonylpyrid-4-ylmethyl)-3-(4-trifluoromethoxyphenyl)imidazolidine-2,4-dione;

5,5-dimethyl-1-[3-(methylphenylamino)carbonylpyrid-4-ylmethyl]-3-(4-trifluoromethoxyphenyl)imidazolidine-2,4-dione;

5,5-dimethyl-1-[3-(4-methoxyphenyl)methylaminocarbonylpyrid-4-ylmethyl]-3-(4-trifluoromethoxyphenyl)imidazolidine-2,4-dione;

5,5-dimethyl-1-[3-(4-chlorophenyl)methylaminocarbonylpyrid-4-ylmethyl]-3-(4-trifluoromethoxyphenyl)imidazolidine-2,4-dione;

5,5-dimethyl-1-[3-(4-morpholinylamino)carbonylpyrid-4-ylmethyl]-3-(4-trifluoromethoxyphenyl)imidazolidine-2,4-dione;

5,5-dimethyl-1-(3-aminocarbonylpyrid-4-ylmethyl)-3-(4-trifluoromethoxyphenyl)imidazolidine-2,4-dione;

5,5-dimethyl-1-(3-phenoxypyrid-4-ylmethyl)-3-(4-trifluoromethoxyphenyl)imidazolidine-2,4-dione;

5,5-dimethyl-1-(3-methoxypyrid-4-ylmethyl)-3-(4-trifluoromethoxyphenyl)imidazolidine-2,4-dione;

5,5-dimethyl-1-(3-ethoxypyrid-4-ylmethyl)-3-(4-trifluoromethoxyphenyl)imidazolidine-2,4-dione;

5,5-dimethyl-1-[3-(1-pyrrolidinyl)ethoxypyrid-4-ylmethyl]-3-(4-trifluoromethoxyphenyl)imidazolidine-2,4-dione;

5,5-dimethyl-1-(3-benzyloxypyrid-4-ylmethyl)-3-(4-trifluoromethoxyphenyl)imidazolidine-2,4-dione;

5,5-dimethyl-1-(3-benzoyloxypyrid-4-ylmethyl)-3-(4-trifluoromethoxyphenyl)imidazolidine-2,4-dione;

5,5-dimethyl-1-[3-(4,5-dihydro-1H-imidazol-2-yl)pyrid-4-ylmethyl]-3-(4-trifluoromethoxyphenyl)imidazolidine-2,4-dione;

5,5-dimethyl-1-[3-(1H-imidazol-2-yl)pyrid-4-ylmethyl]-3-(4-trifluoromethoxyphenyl)imidazolidine-2,4-dione;

5,5-dimethyl-1-[3-(1H-tetrazol-5-yl)pyrid-4-ylmethyl]-3-(4-trifluoromethoxyphenyl)imidazolidine-2,4-dione;

5,5-dimethyl-1-(3-amidinopyrid-4-ylmethyl)-3-(4-trifluoromethoxyphenyl)imidazolidine-2,4-dione;

5,5-dimethyl-1-(3-dimethylaminomethylpyrid-4-ylmethyl)-3-(4-trifluoromethoxyphenyl)imidazolidine-2,4-dione;

5,5-dimethyl-1-(3-aminomethylpyrid-4-ylmethyl)-3-(4-trifluoromethoxyphenyl)imidazolidine-2,4-dione;

4-(2-methylpyridin)-4-ylmethyl-6-(4-trifluoromethoxyphenyl)-4,6-diazaspiro[2.4]heptane-5,7-dione;

4-(2-ethylpyridin)-4-ylmethyl-6-(4-trifluoromethoxyphenyl)-4,6-diazaspiro[2.4]heptane-5,7-dione;

4-(2-isopropylpyridin)-4-ylmethyl-6-(4-trifluoromethoxyphenyl)-4,6-diazaspiro[2.4]heptane-5,7-dione;

4-(2-tert-butylpyridine)-4-ylmethyl-6-(4-trifluoromethoxyphenyl)-4,6-diazaspiro[2.4]heptane-5,7-dione;

4-(2-isobutylpyridin)-4-ylmethyl-6-(4-trifluoromethoxyphenyl)-4,6-diazaspiro[2.4]heptane-5,7-dione;

4-(2-cyclohexylpyridin)-4-ylmethyl-6-(4-trifluoromethoxyphenyl)-4,6-diazaspiro[2.4]heptane-5,7-dione;

4-(2-phenylpyridin)-4-ylmethyl-6-(4-trifluoromethoxyphenyl)-4,6-diazaspiro[2.4]heptane-5,7-dione;

4-[2-(4-chlorophenyl)pyridin]-4-ylmethyl-6-(4-trifluoromethoxyphenyl)-4,6-diazaspiro[2.4]heptane-5,7-dione;

4-[2-(3-chlorophenyl)pyridin]-4-ylmethyl-6-(4-trifluoromethoxyphenyl)-4,6-diazaspiro[2.4]heptane-5,7-dione;

4-[2-(2-chlorophenyl)pyridin]-4-ylmethyl-6-(4-trifluoromethoxyphenyl)-4,6-diazaspiro[2.4]heptane-5,7-dione;

4-[2-(4-fluorophenyl)pyridin]-4-ylmethyl-6-(4-trifluoromethoxyphenyl)-4,6-diazaspiro[2.4]heptane-5,7-dione;

4-[2-(4-methoxyphenyl)pyridin]-4-ylmethyl-6-(4-trifluoromethoxyphenyl)-4,6-diazaspiro[2.4]heptane-5,7-dione;

4-(2-benzylpyridin)-4-ylmethyl-6-(4-trifluoromethoxyphenyl)-4,6-diazaspiro[2.4]heptane-5,7-dione;

4-(2,2'-bipyridin)-4-ylmethyl-6-(4-trifluoromethoxyphenyl)-4,6-diazaspiro[2.4]heptane-5,7-dione;

4-(2-hydroxymethylpyridine)-4-ylmethyl-6-(4-trifluoromethoxyphenyl)-4,6-diazaspiro[2.4]heptane-5,7-dione;

4-(2-chloropyridin)-4-ylmethyl-6-(4-trifluoromethoxyphenyl)-4,6-diazaspiro[2.4]heptane-5,7-dione;

4-(2-fluoropyridin)-4-ylmethyl-6-(4-trifluoromethoxyphenyl)-4,6-diazaspiro[2.4]heptane-5,7-dione;

4-(2-bromopyridin)-4-ylmethyl-6-(4-trifluoromethoxyphenyl)-4,6-diazaspiro[2.4]heptane-5,7-dione;

4-(2-aminopyridine)-4-ylmethyl-6-(4-trifluoromethoxyphenyl)-4,6-diazaspiro[2.4]heptane-5,7-dione;

4-(2-methylaminopyridin)-4-ylmethyl-6-(4-trifluoromethoxyphenyl)-4,6-diazaspiro[2.4]heptane-5,7-dione;

4-(2-ethylaminopyridin)-4-ylmethyl-6-(4-trifluoromethoxyphenyl)-4,6-diazaspiro[2.4]heptane-5,7-dione;

4-(2-isopropylaminopyridin)-4-ylmethyl-6-(4-trifluoromethoxyphenyl)-4,6-diazaspiro[2.4]heptane-5,7-dione;

4-(2-phenylaminopyridin)-4-ylmethyl-6-(4-trifluoromethoxyphenyl)-4,6-diazaspiro[2.4]heptane-5,7-dione;

4-(2-cyclohexylaminopyridin)-4-ylmethyl-6-(4-trifluoromethoxyphenyl)-4,6-diazaspiro[2.4]heptane-5,7-dione;

4-(2-diethylaminopyridine)-4-ylmethyl-6-(4-trifluoromethoxyphenyl)-4,6-diazaspiro[2.4]heptane-5,7-dione;

4-(2-N-cyclohexyl-N-methylaminopyridin)-4-ylmethyl-6-(4-trifluoromethoxyphenyl)-4,6-diazaspiro[2.4]heptane-5,7-dione;

4-(2-piperidinopyridine)-4-ylmethyl-6-(4-trifluoromethoxyphenyl)-4,6-diazaspiro[2.4]heptane-5,7-dione;

4-(2-morpholinopyridin)-4-ylmethyl-6-(4-trifluoromethoxyphenyl)-4,6-diazaspiro[2.4]heptane-5,7-dione;

4-[2-(4-methylpiperazino)pyridin]-4-ylmethyl-6-(4-trifluoromethoxyphenyl)-4,6-diazaspiro[2.4]heptane-5,7-dione;

4-[2-(1H-pyrazol-1-yl)pyridin]-4-ylmethyl-6-(4-trifluoromethoxyphenyl)-4,6-diazaspiro[2.4]heptane-5,7-dione;

4-(2-(2-benzoylhydrazino)pyridin)-4-ylmethyl-6-(4-trifluoromethoxyphenyl)-4,6-diazaspiro[2.4]heptane-5,7-dione;

4-(2-benzoylaminopyridin)-4-ylmethyl-6-(4-trifluoromethoxyphenyl)-4,6-diazaspiro[2.4]heptane-5,7-dione;

4-[2-(4-chlorobenzoylamino)pyridin]-4-ylmethyl-6-(4-trifluoromethoxyphenyl)-4,6-diazaspiro[2.4]heptane-5,7-dione;

4-[2-(3-chlorobenzoylamino)pyridin]-4-ylmethyl-6-(4-trifluoromethoxyphenyl)-4,6-diazaspiro[2.4]heptane-5,7-dione;

4-[2-(2-chlorobenzoylamino)pyridin]-4-ylmethyl-6-(4-trifluoromethoxyphenyl)-4,6-diazaspiro[2.4]heptane-5,7-dione;

4-[2-(4-fluorobenzoylamino)pyridin]-4-ylmethyl-6-(4-trifluoromethoxyphenyl)-4,6-diazaspiro[2.4]heptane-5,7-dione;

4-[2-(4-methoxybenzoylamino)pyridin]-4-ylmethyl-6-(4-trifluoromethoxyphenyl)-4,6-diazaspiro[2.4]heptane-5,7-dione;

4-(2-acetamidopyridin)-4-ylmethyl-6-(4-trifluoromethoxyphenyl)-4,6-diazaspiro[2.4]heptane-5,7-dione;

4-(2-phenylacetamidopyridin)-4-ylmethyl-6-(4-trifluoromethoxyphenyl)-4,6-diazaspiro[2.4]heptane-5,7-dione;

4-[2-(4-methylpiperazino)acetamidopyridin]-4-ylmethyl-6-(4-trifluoromethoxyphenyl)-4,6-diazaspiro[2.4]heptane-5,7-dione;

4-(2-cyclohexanylcarboxamidopyridin)-4-ylmethyl-6-(4-trifluoromethoxyphenyl)-4,6-diazaspiro[2.4]heptane-5,7-dione;
4-[2-(1-methyl-4-piperidinyl)carbonylaminopyridin]-4-ylmethyl-6-(4-trifluoromethoxyphenyl)-4,6-diazaspiro[2.4]heptane-5,7-dione;
4-[2-(2-furanylcarbonyl)aminopyridin]-4-ylmethyl-6-(4-trifluoromethoxyphenyl)-4,6-diazaspiro[2.4]heptane-5,7-dione;
4-(2-ethoxycarbonylaminopyridin)-4-ylmethyl-6-(4-trifluoromethoxyphenyl)-4,6-diazaspiro[2.4]heptane-5,7-dione;
4-(2-isopropoxycarbonylaminopyridin)-4-ylmethyl-6-(4-trifluoromethoxyphenyl)-4,6-diazaspiro[2.4]heptane-5,7-dione;
4-(2-butoxycarbonylaminopyridin)-4-ylmethyl-6-(4-trifluoromethoxyphenyl)-4,6-diazaspiro[2.4]heptane-5,7-dione;
4-[2-(2-diethylaminoethoxycarbonylamino)pyridin]-4-ylmethyl-6-(4-trifluoromethoxyphenyl)-4,6-diazaspiro[2.4]heptane-5,7-dione;
4-(2-phenoxycarbonylaminopyridin)-4-ylmethyl-6-(4-trifluoromethoxyphenyl)-4,6-diazaspiro[2.4]heptane-5,7-dione;
4-[2-(4-chloroanilino)carbonylaminopyridin]-4-ylmethyl)-6-(4-trifluoromethoxyphenyl)-4,6-diazaspiro[2.4]heptane-5,7-dione;
4-(2-anilinocarbonylaminopyridin)-4-ylmethyl-6-(4-trifluoromethoxyphenyl)-4,6-diazaspiro[2.4]heptane-5,7-dione;
4-(2-benzylaminocarbonylaminopyridin)-4-ylmethyl-6-(4-trifluoromethoxyphenyl)-4,6-diazaspiro[2.4]heptane-5,7-dione;
4-[2-(2-pyridylamino)carbonylaminopyridin]-4-ylmethyl-6-(4-trifluoromethoxyphenyl)-4,6-diazaspiro[2.4]heptane-5,7-dione;
4-(2-ureidopyridin)-4-ylmethyl-6-(4-trifluoromethoxyphenyl)-4,6-diazaspiro[2.4]heptane-5,7-dione;
4-(2-benzylaminosulfonylaminopyridin)-4-ylmethyl-6-(4-trifluoromethoxyphenyl)-4,6-diazaspiro[2.4]heptane-5,7-dione;
4-(2-methylaminosulfonylaminopyridin)-4-ylmethyl-6-(4-trifluoromethoxyphenyl)-4,6-diazaspiro[2.4]heptane-5,7-dione;
4-(2-aminosulfonylaminopyridin)-4-ylmethyl-6-(4-trifluoromethoxyphenyl)-4,6-diazaspiro[2.4]heptane-5,7-dione;
4-(2-morpholinosulfonylaminopyridin)-4-ylmethyl-6-(4-trifluoromethoxyphenyl)-4,6-diazaspiro[2.4]heptane-5,7-dione;
4-(2-dimethylaminosulfonylaminopyridin)-4-ylmethyl-6-(4-trifluoromethoxyphenyl)-4,6-diazaspiro[2.4]heptane-5,7-dione;
4-(2-anilinosulfonylaminopyridin)-4-ylmethyl-6-(4-trifluoromethoxyphenyl)-4,6-diazaspiro[2.4]heptane-5,7-dione;
4-(2-phenylsulfonylaminopyridin)-4-ylmethyl-6-(4-trifluoromethoxyphenyl)-4,6-diazaspiro[2.4]heptane-5,7-dione;
4-[2-(2-thienyl)sulfonylaminopyridin]-4-ylmethyl-6-(4-trifluoromethoxyphenyl)-4,6-diazaspiro[2.4]heptane-5,7-dione;
4-(2-methylsulfonylaminopyridin)-4-ylmethyl-6-(4-trifluoromethoxyphenyl)-4,6-diazaspiro[2.4]heptane-5,7-dione;
4-[2-(4-chlorophenyl)sulfonylaminopyridin]-4-ylmethyl-6-(4-trifluoromethoxyphenyl)-4,6-diazaspiro[2.4]heptane-5,7-dione;
4-(2-benzylsulfonylaminopyridin)-4-ylmethyl-6-(4-trifluoromethoxyphenyl)-4,6-diazaspiro[2.4]heptane-5,7-dione;
4-(2-hydroxycarbonylpyridin)-4-ylmethyl-6-(4-trifluoromethoxyphenyl)-4,6-diazaspiro[2.4]heptane-5,7-dione;
4-(2-ethoxycarbonylpyridin)-4-ylmethyl-6-(4-trifluoromethoxyphenyl)-4,6-diazaspiro[2.4]heptane-5,7-dione;
4-(2-tert-butoxycarbonylpyridin)-4-ylmethyl-6-(4-trifluoromethoxyphenyl)-4,6-diazaspiro[2.4]heptane-5,7-dione;
4-(2-phenoxycarbonylpyridin)-4-ylmethyl-6-(4-trifluoromethoxyphenyl)-4,6-diazaspiro[2.4]heptane-5,7-dione;
4-[2-(4-methylpiperazinocarbonyl)pyridin]-4-ylmethyl-6-(4-trifluoromethoxyphenyl)-4,6-diazaspiro[2.4]heptane-5,7-dione;
4-[2-(methylamino)carbonylpyridin]-4-ylmethyl-6-(4-trifluoromethoxyphenyl)-4,6-diazaspiro[2.4]heptane-5,7-dione;
4-[2-(dimethylamino)carbonylpyridin]-4-ylmethyl-6-(4-trifluoromethoxyphenyl)-4,6-diazaspiro[2.4]heptane-5,7-dione;
4-(2-piperidinocarbonylpyridin)-4-ylmethyl-6-(4-trifluoromethoxyphenyl)-4,6-diazaspiro[2.4]heptane-5,7-dione;
4-(2-morpholinocarbonylpyridin)-4-ylmethyl-6-(4-trifluoromethoxyphenyl)-4,6-diazaspiro[2.4]heptane-5,7-dione;
4-[2-(4-phenylpiperazinocarbonyl)pyridin]-4-ylmethyl-6-(4-trifluoromethoxyphenyl)-4,6-diazaspiro[2.4]heptane-5,7-dione;
4-(2-phenylaminocarbonylpyridin)-4-ylmethyl-6-(4-trifluoromethoxyphenyl)-4,6-diazaspiro[2.4]heptane-5,7-dione;
4-[2-(methylphenylamino)carbonylpyridin]-4-ylmethyl-6-(4-trifluoromethoxyphenyl)-4,6-diazaspiro[2.4]heptane-5,7-dione;
4-[2-(4-methoxyphenyl)methylaminocarbonylpyridin]-4-ylmethyl-6-(4-trifluoromethoxyphenyl)-4,6-diazaspiro[2.4]heptane-5,7-dione;
4-[2-(4-chlorophenyl)methylaminocarbonylpyridin]-4-ylmethyl-6-(4-trifluoromethoxyphenyl)-4,6-diazaspiro[2.4]heptane-5,7-dione;
4-[2-(4-morpholinylamino)carbonylpyridin]-4-ylmethyl-6-(4-trifluoromethoxyphenyl)-4,6-diazaspiro[2.4]heptane-5,7-dione;
4-(2-aminocarbonylpyridin)-4-ylmethyl-6-(4-trifluoromethoxyphenyl)-4,6-diazaspiro[2.4]heptane-5,7-dione;
4-(2-phenoxypyridin)-4-ylmethyl-6-(4-trifluoromethoxyphenyl)-4,6-diazaspiro[2.4]heptane-5,7-dione;
4-(2-methoxypyridin)-4-ylmethyl-6-(4-trifluoromethoxyphenyl)-4,6-diazaspiro[2.4]heptane-5,7-dione;
4-(2-ethoxypyridin)-4-ylmethyl-6-(4-trifluoromethoxyphenyl)-4,6-diazaspiro[2.4]heptane-5,7-dione;
4-[2-(1-pyrrolidinyl)ethoxypyridin]-4-ylmethyl-6-(4-trifluoromethoxyphenyl)-4,6-diazaspiro[2.4]heptane-5,7-dione;
4-(2-benzyloxypyridin)-4-ylmethyl-6-(4-trifluoromethoxyphenyl)-4,6-diazaspiro[2.4]heptane-5,7-dione;
4-(2-benzoyloxypyridin)-4-ylmethyl-6-(4-trifluoromethoxyphenyl)-4,6-diazaspiro[2.4]heptane-5,7-dione;
4-[2-(4,5-dihydro-1H-imidazol-2-yl)pyridin]-4-ylmethyl-6-(4-trifluoromethoxyphenyl)-4,6-diazaspiro[2.4]heptane-5,7-dione;
4-[2-(1H-imidazol-2-yl)pyridin]-4-ylmethyl-6-(4-trifluoromethoxyphenyl)-4,6-diazaspiro[2.4]heptane-5,7-dione;
4-[2-(1H-tetrazol-5-yl)pyridin]-4-ylmethyl-6-(4-trifluoromethoxyphenyl)-4,6-diazaspiro[2.4]heptane-5,7-dione;
4-(2-amidinopyridin)-4-ylmethyl-6-(4-trifluoromethoxyphenyl)-4,6-diazaspiro[2.4]heptane-5,7-dione;
4-(2-dimethylaminomethylpyridin)-4-ylmethyl-6-(4-trifluoromethoxyphenyl)-4,6-diazaspiro[2.4]heptane-5,7-dione;
4-(2-aminomethylpyridin)-4-ylmethyl-6-(4-trifluoromethoxyphenyl)-4,6-diazaspiro[2.4]heptane-5,7-dione;
4-(3-methylpyridin)-4-ylmethyl-6-(4-trifluoromethoxyphenyl)-4,6-diazaspiro[2.4]heptane-5,7-dione;
4-(3-ethylpyridin)-4-ylmethyl-6-(4-trifluoromethoxyphenyl)-4,6-diazaspiro[2.4]heptane-5,7-dione;

4-(3-isopropylpyridin)-4-ylmethyl-6-(4-trifluoromethoxyphenyl)-4,6-diazaspiro[2.4]heptane-5,7-dione;
4-(3-tert-butylpyridin)-4-ylmethyl-6-(4-trifluoromethoxyphenyl)-4,6-diazaspiro[2.4]heptane-5,7-dione;
4-(3-isobutylpyridin)-4-ylmethyl-6-(4-trifluoromethoxyphenyl)-4,6-diazaspiro[2.4]heptane-5,7-dione;
4-(3-cyclohexylpyridin)-4-ylmethyl-6-(4-trifluoromethoxyphenyl)-4,6-diazaspiro[2.4]heptane-5,7-dione;
4-(3-phenylpyridin)-4-ylmethyl-6-(4-trifluoromethoxyphenyl)-4,6-diazaspiro[2.4]heptane-5,7-dione;
4-[3-(4-chlorophenyl)pyridin]-4-ylmethyl-6-(4-trifluoromethoxyphenyl)-4,6-diazaspiro[2.4]heptane-5,7-dione;
4-[3-(3-chlorophenyl)pyridin]-4-ylmethyl-6-(4-trifluoromethoxyphenyl)-4,6-diazaspiro[2.4]heptane-5,7-dione;
4-[3-(2-chlorophenyl)pyridin]-4-ylmethyl-6-(4-trifluoromethoxyphenyl)-4,6-diazaspiro[2.4]heptane-5,7-dione;
4-[3-(4-fluorophenyl)pyridin]-4-ylmethyl-6-(4-trifluoromethoxyphenyl)-4,6-diazaspiro[2.4]heptane-5,7-dione;
4-[3-(4-methoxyphenyl)pyridin]-4-ylmethyl-6-(4-trifluoromethoxyphenyl)-4,6-diazaspiro[2.4]heptane-5,7-dione;
4-(3-benzylpyridin)-4-ylmethyl-6-(4-trifluoromethoxyphenyl)-4,6-diazaspiro[2.4]heptane-5,7-dione;
4-(3,2'-bipyridin)-4-ylmethyl-6-(4-trifluoromethoxyphenyl)-4,6-diazaspiro[2.4]heptane-5,7-dione;
4-(3-hydroxymethylpyridine)-4-ylmethyl-6-(4-trifluoromethoxyphenyl)-4,6-diazaspiro[2.4]heptane-5,7-dione;
4-(3-chloropyridin)-4-ylmethyl-6-(4-trifluoromethoxyphenyl)-4,6-diazaspiro[2.4]heptane-5,7-dione;
4-(3-fluoropyridin)-4-ylmethyl-6-(4-trifluoromethoxyphenyl)-4,6-diazaspiro[2.4]heptane-5,7-dione;
4-(3-bromopyridin)-4-ylmethyl-6-(4-trifluoromethoxyphenyl)-4,6-diazaspiro[2.4]heptane-5,7-dione;
4-(3-aminopyridine)-4-ylmethyl-6-(4-trifluoromethoxyphenyl)-4,6-diazaspiro[2.4]heptane-5,7-dione;
4-(3-methylaminopyridin)-4-ylmethyl-6-(4-trifluoromethoxyphenyl)-4,6-diazaspiro[2.4]heptane-5,7-dione;
4-(3-ethylaminopyridin)-4-ylmethyl-6-(4-trifluoromethoxyphenyl)-4,6-diazaspiro[2.4]heptane-5,7-dione;
4-(3-isopropylaminopyridin)-4-ylmethyl-6-(4-trifluoromethoxyphenyl)-4,6-diazaspiro[2.4]heptane-5,7-dione;
4-(3-phenylaminopyridin)-4-ylmethyl-6-(4-trifluoromethoxyphenyl)-4,6-diazaspiro[2.4]heptane-5,7-dione;
4-(3-cyclohexylaminopyridin)-4-ylmethyl-6-(4-trifluoromethoxyphenyl)-4,6-diazaspiro[2.4]heptane-5,7-dione;
4-(3-diethylaminopyridine)-4-ylmethyl-6-(4-trifluoromethoxyphenyl)-4,6-diazaspiro[2.4]heptane-5,7-dione;
4-(3-N-cyclohexyl-N-methylaminopyridin)-4-ylmethyl-6-(4-trifluoromethoxyphenyl)-4,6-diazaspiro[2.4]heptane-5,7-dione;
4-(3-piperidinopyridine)-4-ylmethyl-6-(4-trifluoromethoxyphenyl)-4,6-diazaspiro[2.4]heptane-5,7-dione;
4-(3-morpholinopyridin)-4-ylmethyl-6-(4-trifluoromethoxyphenyl)-4,6-diazaspiro[2.4]heptane-5,7-dione;
4-[3-(4-methylpiperazino)pyridin]-4-ylmethyl-6-(4-trifluoromethoxyphenyl)-4,6-diazaspiro[2.4]heptane-5,7-dione;
4-[3-(1H-pyrazol-1-yl)pyridin]-4-ylmethyl-6-(4-trifluoromethoxyphenyl)-4,6-diazaspiro[2.4]heptane-5,7-dione;
4-[3-(2-benzoylhydrazino)pyridin]-4-ylmethyl-6-(4-trifluoromethoxyphenyl)-4,6-diazaspiro[2.4]heptane-5,7-dione;
4-(3-benzoylaminopyridin)-4-ylmethyl-6-(4-trifluoromethoxyphenyl)-4,6-diazaspiro[2.4]heptane-5,7-dione;
4-[3-(4-chlorobenzoylamino)pyridin]-4-ylmethyl-6-(4-trifluoromethoxyphenyl)-4,6-diazaspiro[2.4]heptane-5,7-dione;
4-[3-(3-chlorobenzoylamino)pyridin]-4-ylmethyl-6-(4-trifluoromethoxyphenyl)-4,6-diazaspiro[2.4]heptane-5,7-dione;
4-[3-(2-chlorobenzoylamino)pyridin]-4-ylmethyl-6-(4-trifluoromethoxyphenyl)-4,6-diazaspiro[2.4]heptane-5,7-dione;
4-[3-(4-fluorobenzoylamino)pyridin]-4-ylmethyl-6-(4-trifluoromethoxyphenyl)-4,6-diazaspiro[2.4]heptane-5,7-dione;
4-[3-(4-methoxybenzoylamino)pyridin]-4-ylmethyl-6-(4-trifluoromethoxyphenyl)-4,6-diazaspiro[2.4]heptane-5,7-dione;
4-(3-acetamidopyridin)-4-ylmethyl-6-(4-trifluoromethoxyphenyl)-4,6-diazaspiro[2.4]heptane-5,7-dione;
4-(3-phenylacetamidopyridin)-4-ylmethyl-6-(4-trifluoromethoxyphenyl)-4,6-diazaspiro[2.4]heptane-5,7-dione;
4-[3-(4-methylpiperazino)acetamidopyridin]-4-ylmethyl-6-(4-trifluoromethoxyphenyl)-4,6-diazaspiro[2.4]heptane-5,7-dione;
4-(3-cyclohexanylcarboxamidopyridin)-4-ylmethyl-6-(4-trifluoromethoxyphenyl)-4,6-diazaspiro[2.4]heptane-5,7-dione;
4-[3-(1-methyl-4-piperidinyl)carbonylaminopyridin]-4-ylmethyl-6-(4-trifluoromethoxyphenyl)-4,6-diazaspiro[2.4]heptane-5,7-dione;
4-[3-(2-furanylcarbonyl)aminopyridin]-4-ylmethyl-6-(4-trifluoromethoxyphenyl)-4,6-diazaspiro[2.4]heptane-5,7-dione;
4-(3-ethoxycarbonylaminopyridin)-4-ylmethyl-6-(4-trifluoromethoxyphenyl)-4,6-diazaspiro[2.4]heptane-5,7-dione;
4-(3-isopropoxycarbonylaminopyridin)-4-ylmethyl-6-(4-trifluoromethoxyphenyl)-4,6-diazaspiro[2.4]heptane-5,7-dione;
4-(3-butoxycarbonylaminopyridin)-4-ylmethyl-6-(4-trifluoromethoxyphenyl)-4,6-diazaspiro[2.4]heptane-5,7-dione;
4-[3-(2-diethylaminoethoxycarbonylamino)pyridin]-4-ylmethyl-6-(4-trifluoromethoxyphenyl)-4,6-diazaspiro[2.4]heptane-5,7-dione;
4-(3-phenoxycarbonylaminopyridin)-4-ylmethyl-6-(4-trifluoromethoxyphenyl)-4,6-diazaspiro[2.4]heptane-5,7-dione;
4-[3-(4-chloroanilino)carbonylaminopyridin]-4-ylmethyl-6-(4-trifluoromethoxyphenyl)-4,6-diazaspiro[2.4]heptane-5,7-dione;
4-(3-anilinocarbonylaminopyridin)-4-ylmethyl-6-(4-trifluoromethoxyphenyl)-4,6-diazaspiro[2.4]heptane-5,7-dione;
4-(3-benzylaminocarbonylaminopyridin)-4-ylmethyl-6-(4-trifluoromethoxyphenyl)-4,6-diazaspiro[2.4]heptane-5,7-dione;
4-[3-(2-pyridylamino)carbonylaminopyridin]-4-ylmethyl-6-(4-trifluoromethoxyphenyl)-4,6-diazaspiro[2.4]heptane-5,7-dione;
4-(3-ureidopyridin)-4-ylmethyl-6-(4-trifluoromethoxyphenyl)-4,6-diazaspiro[2.4]heptane-5,7-dione;
4-(3-benzylaminosulfonylaminopyridin)-4-ylmethyl-6-(4-trifluoromethoxyphenyl)-4,6-diazaspiro[2.4]heptane-5,7-dione;
4-(3-methylaminosulfonylaminopyridin)-4-ylmethyl-6-(4-trifluoromethoxyphenyl)-4,6-diazaspiro[2.4]heptane-5,7-dione;
4-(3-aminosulfonylaminopyridin)-4-ylmethyl-6-(4-trifluoromethoxyphenyl)-4,6-diazaspiro[2.4]heptane-5,7-dione;
4-(3-morpholinosulfonylaminopyridin)-4-ylmethyl-6-(4-trifluoromethoxyphenyl)-4,6-diazaspiro[2.4]heptane-5,7-dione;
4-(3-dimethylaminosulfonylaminopyridin)-4-ylmethyl-6-(4-trifluoromethoxyphenyl)-4,6-diazaspiro[2.4]heptane-5,7-dione;
4-(3-anilinosulfonylaminopyridin)-4-ylmethyl-6-(4-trifluoromethoxyphenyl)-4,6-diazaspiro[2.4]heptane-5,7-dione;

4-(3-phenylsulfonylaminopyridin)-4-ylmethyl-6-(4-trifluoromethoxyphenyl)-4,6-diazaspiro[2.4]heptane-5,7-dione;

4-[3-(2-thienyl)sulfonylaminopyridin]-4-ylmethyl-6-(4-trifluoromethoxyphenyl)-4,6-diazaspiro[2.4]heptane-5,7-dione;

4-(3-methylsulfonylaminopyridin)-4-ylmethyl-6-(4-trifluoromethoxyphenyl)-4,6-diazaspiro[2.4]heptane-5,7-dione;

4-[3-(4-chlorophenyl)sulfonylaminopyridin]-4-ylmethyl-6-(4-trifluoromethoxyphenyl)-4,6-diazaspiro[2.4]heptane-5,7-dione;

4-(3-benzylsulfonylaminopyridin)-4-ylmethyl-6-(4-trifluoromethoxyphenyl)-4,6-diazaspiro[2.4]heptane-5,7-dione;

4-(3-hydroxycarbonylpyridin)-4-ylmethyl-6-(4-trifluoromethoxyphenyl)-4,6-diazaspiro[2.4]heptane-5,7-dione;

4-(3-ethoxycarbonylpyridin)-4-ylmethyl-6-(4-trifluoromethoxyphenyl)-4,6-diazaspiro[2.4]heptane-5,7-dione;

4-(3-tert-butoxycarbonylpyridin)-4-ylmethyl-6-(4-trifluoromethoxyphenyl)-4,6-diazaspiro[2.4]heptane-5,7-dione;

4-(3-phenoxycarbonylpyridin)-4-ylmethyl-6-(4-trifluoromethoxyphenyl)-4,6-diazaspiro[2.4]heptane-5,7-dione;

4-[3-(4-methylpiperazinocarbonyl)pyridin]-4-ylmethyl-6-(4-trifluoromethoxyphenyl)-4,6-diazaspiro[2.4]heptane-5,7-dione;

4-[3-(methylamino)carbonylpyridin]-4-ylmethyl-6-(4-trifluoromethoxyphenyl)-4,6-diazaspiro[2.4]heptane-5,7-dione;

4-[3-(dimethylamino)carbonylpyridin]-4-ylmethyl-6-(4-trifluoromethoxyphenyl)-4,6-diazaspiro[2.4]heptane-5,7-dione;

4-(3-piperidinocarbonylpyridin)-4-ylmethyl-6-(4-trifluoromethoxyphenyl)-4,6-diazaspiro[2.4]heptane-5,7-dione;

4-(3-morpholinocarbonylpyridin)-4-ylmethyl-6-(4-trifluoromethoxyphenyl)-4,6-diazaspiro[2.4]heptane-5,7-dione;

4-[3-(4-phenylpiperazinocarbonyl)pyridin]-4-ylmethyl-6-(4-trifluoromethoxyphenyl)-4,6-diazaspiro[2.4]heptane-5,7-dione;

4-(3-phenylaminocarbonylpyridin)-4-ylmethyl-6-(4-trifluoromethoxyphenyl)-4,6-diazaspiro[2.4]heptane-5,7-dione;

4-[3-(methylphenylamino)carbonylpyridin]-4-ylmethyl-6-(4-trifluoromethoxyphenyl)-4,6-diazaspiro[2.4]heptane-5,7-dione;

4-[3-(4-methoxyphenyl)methylaminocarbonylpyridin]-4-ylmethyl-6-(4-trifluoromethoxyphenyl)-4,6-diazaspiro[2.4]heptane-5,7-dione;

4-[3-(4-chlorophenyl)methylaminocarbonylpyridin]-4-ylmethyl-6-(4-trifluoromethoxyphenyl)-4,6-diazaspiro[2.4]heptane-5,7-dione;

4-[3-(4-morpholinylamino)carbonylpyridin]-4-ylmethyl-6-(4-trifluoromethoxyphenyl)-4,6-diazaspiro[2.4]heptane-5,7-dione;

4-(3-aminocarbonylpyridin)-4-ylmethyl-6-(4-trifluoromethoxyphenyl)-4,6-diazaspiro[2.4]heptane-5,7-dione;

4-(3-phenoxypyridin)-4-ylmethyl-6-(4-trifluoromethoxyphenyl)-4,6-diazaspiro[2.4]heptane-5,7-dione;

4-(3-methoxypyridin)-4-ylmethyl-6-(4-trifluoromethoxyphenyl)-4,6-diazaspiro[2.4]heptane-5,7-dione;

4-(3-ethoxypyridin)-4-ylmethyl-6-(4-trifluoromethoxyphenyl)-4,6-diazaspiro[2.4]heptane-5,7-dione;

4-[3-(1-pyrrolidinyl)ethoxypyridin]-4-ylmethyl-6-(4-trifluoromethoxyphenyl)-4,6-diazaspiro[2.4]heptane-5,7-dione;

4-(3-benzyloxypyridin)-4-ylmethyl-6-(4-trifluoromethoxyphenyl)-4,6-diazaspiro[2.4]heptane-5,7-dione;

4-(3-benzoyloxypyridin)-4-ylmethyl-6-(4-trifluoromethoxyphenyl)-4,6-diazaspiro[2.4]heptane-5,7-dione;

4-[3-(4,5-dihydro-1H-imidazol-2-yl)pyridin]-4-ylmethyl-6-(4-trifluoromethoxyphenyl)-4,6-diazaspiro[2.4]heptane-5,7-dione;

4-[3-(1H-imidazol-2-yl)pyridin]-4-ylmethyl-6-(4-trifluoromethoxyphenyl)-4,6-diazaspiro[2.4]heptane-5,7-dione;

4-[3-(1H-tetrazol-5-yl)pyridin]-4-ylmethyl-6-(4-trifluoromethoxyphenyl)-4,6-diazaspiro[2.4]heptane-5,7-dione;

4-(3-amidinopyridin)-4-ylmethyl-6-(4-trifluoromethoxyphenyl)-4,6-diazaspiro[2.4]heptane-5,7-dione;

4-(3-dimethylaminomethylpyridin)-4-ylmethyl-6-(4-trifluoromethoxyphenyl)-4,6-diazaspiro[2.4]heptane-5,7-dione;

4-(3-aminomethylpyridin)-4-ylmethyl-6-(4-trifluoromethoxyphenyl)-4,6-diazaspiro[2.4]heptane-5,7-dione;

5-methyl-1-(2-methylpyrid-4-ylmethyl)-3-(4-trifluoromethoxyphenyl)imidazolidine-2,4-dione;

5-methyl-1-(2-ethylpyrid-4-ylmethyl)-3-(4-trifluoromethoxyphenyl)imidazolidine-2,4-dione;

5-methyl-1-(2-isopropylpyrid-4-ylmethyl)-3-(4-trifluoromethoxyphenyl)imidazolidine-2,4-dione;

5-methyl-1-(2-tert-butylpyrid-4-ylmethyl)-3-(4-trifluoromethoxyphenyl)imidazolidine-2,4-dione;

5-methyl-1-(2-isobutylpyrid-4-ylmethyl)-3-(4-trifluoromethoxyphenyl)imidazolidine-2,4-dione;

5-methyl-1-(2-cyclohexylpyrid-4-ylmethyl)-3-(4-trifluoromethoxyphenyl)imidazolidine-2,4-dione;

5-methyl-1-(2-phenylpyrid-4-ylmethyl)-3-(4-trifluoromethoxyphenyl)imidazolidine-2,4-dione;

5-methyl-1-[2-(4-chlorophenyl)pyrid-4-ylmethyl]-3-(4-trifluoromethoxyphenyl)imidazolidine-2,4-dione;

5-methyl-1-[2-(3-chlorophenyl)pyrid-4-ylmethyl]-3-(4-trifluoromethoxyphenyl)imidazolidine-2,4-dione;

5-methyl-1-[2-(2-chlorophenyl)pyrid-4-ylmethyl]-3-(4-trifluoromethoxyphenyl)imidazolidine-2,4-dione;

5-methyl-1-[2-(4-fluorophenyl)pyrid-4-ylmethyl]-3-(4-trifluoromethoxyphenyl)imidazolidine-2,4-dione;

5-methyl-1-[2-(4-methoxyphenyl)pyrid-4-ylmethyl]-3-(4-trifluoromethoxyphenyl)imidazolidine-2,4-dione;

5-methyl-1-(2-benzylpyrid-4-ylmethyl)-3-(4-trifluoromethoxyphenyl)imidazolidine-2,4-dione;

5-methyl-1-(2,2'-bipyrid-4-ylmethyl)-3-(4-trifluoromethoxyphenyl)imidazolidine-2,4-dione;

5-methyl-1-(2-hydroxymethylpyrid-4-ylmethyl)-3-(4-trifluoromethoxyphenyl)imidazolidine-2,4-dione;

5-methyl-1-(2-chloropyrid-4-ylmethyl)-3-(4-trifluoromethoxyphenyl)imidazolidine-2,4-dione;

5-methyl-1-(2-fluoropyrid-4-ylmethyl)-3-(4-trifluoromethoxyphenyl)imidazolidine-2,4-dione;

5-methyl-1-(2-bromopyrid-4-ylmethyl)-3-(4-trifluoromethoxyphenyl)imidazolidine-2,4-dione;

5-methyl-1-(2-aminopyrid-4-ylmethyl)-3-(4-trifluoromethoxyphenyl)imidazolidine-2,4-dione;

5-methyl-1-(2-methylaminopyrid-4-ylmethyl)-3-(4-trifluoromethoxyphenyl)imidazolidine-2,4-dione;

5-methyl-1-(2-ethylaminopyrid-4-ylmethyl)-3-(4-trifluoromethoxyphenyl)imidazolidine-2,4-dione;

5-methyl-1-(2-isopropylaminopyrid-4-ylmethyl)-3-(4-trifluoromethoxyphenyl)imidazolidine-2,4-dione;

5-methyl-1-(2-phenylaminopyrid-4-ylmethyl)-3-(4-trifluoromethoxyphenyl)imidazolidine-2,4-dione;

5-methyl-1-(2-cyclohexylaminopyrid-4-ylmethyl)-3-(4-trifluoromethoxyphenyl)imidazolidine-2,4-dione;

5-methyl-1-(2-diethylaminopyrid-4-ylmethyl)-3-(4-trifluoromethoxyphenyl)imidazolidine-2,4-dione;

5-methyl-1-(2-N-cyclohexyl-N-methylaminopyrid-4-ylmethyl)-3-(4-trifluoromethoxyphenyl)imidazolidine-2,4-dione;

5-methyl-1-(2-piperidinopyrid-4-ylmethyl)-3-(4-trifluoromethoxyphenyl)imidazolidine-2,4-dione;
5-methyl-1-(2-morpholinopyrid-4-ylmethyl)-3-(4-trifluoromethoxyphenyl)imidazolidine-2,4-dione;
5-methyl-1-[2-(4-methylpiperazino)pyrid-4-ylmethyl]-3-(4-trifluoromethoxyphenyl)imidazolidine-2,4-dione;
5-methyl-1-[2-(1H-pyrazol-1-yl)pyrid-4-ylmethyl]-3-(4-trifluoromethoxyphenyl)imidazolidine-2,4-dione;
5-methyl-1-[2-(2-benzoylhydrazino)pyrid-4-ylmethyl]-3-(4-trifluoromethoxyphenyl)imidazolidine-2,4-dione;
5-methyl-1-(2-benzoylaminopyrid-4-ylmethyl)-3-(4-trifluoromethoxyphenyl)imidazolidine-2,4-dione;
5-methyl-1-[2-(4-chlorobenzoylamino)pyrid-4-ylmethyl]-3-(4-trifluoromethoxyphenyl)imidazolidine-2,4-dione;
5-methyl-1-[2-(3-chlorobenzoylamino)pyrid-4-ylmethyl]-3-(4-trifluoromethoxyphenyl)imidazolidine-2,4-dione;
5-methyl-1-[2-(2-chlorobenzoylamino)pyrid-4-ylmethyl]-3-(4-trifluoromethoxyphenyl)imidazolidine-2,4-dione;
5-methyl-1-[2-(4-fluorobenzoylamino)pyrid-4-ylmethyl]-3-(4-trifluoromethoxyphenyl)imidazolidine-2,4-dione;
5-methyl-1-[2-(4-methoxybenzoylamino)pyrid-4-ylmethyl]-3-(4-trifluoromethoxyphenyl)imidazolidine-2,4-dione;
5-methyl-1-(2-acetamidopyrid-4-ylmethyl)-3-(4-trifluoromethoxyphenyl)imidazolidine-2,4-dione;
5-methyl-1-(2-phenylacetamidopyrid-4-ylmethyl)-3-(4-trifluoromethoxyphenyl)imidazolidine-2,4-dione;
5-methyl-1-[2-(4-methylpiperazino)acetamidopyrid-4-ylmethyl]-3-(4-trifluoromethoxyphenyl)imidazolidine-2,4-dione;
5-methyl-1-(2-cyclohexanylcarboxamidopyrid-4-ylmethyl)-3-(4-trifluoromethoxyphenyl)imidazolidine-2,4-dione;
5-methyl-1-[2-(1-methyl-4-piperidinyl)carbonylaminopyrid-4-ylmethyl]-3-(4-trifluoromethoxyphenyl)imidazolidine-2,4-dione;
5-methyl-1-[2-(2-furanylcarbonyl)aminopyrid-4-ylmethyl]-3-(4-trifluoromethoxyphenyl)imidazolidine-2,4-dione;
5-methyl-1-(2-ethoxycarbonylaminopyrid-4-ylmethyl)-3-(4-trifluoromethoxyphenyl)imidazolidine-2,4-dione;
5-methyl-1-(2-isopropoxycarbonylaminopyrid-4-ylmethyl)-3-(4-trifluoromethoxyphenyl)imidazolidine-2,4-dione;
5-methyl-1-(2-butoxycarbonylaminopyrid-4-ylmethyl)-3-(4-trifluoromethoxyphenyl)imidazolidine-2,4-dione;
5-methyl-1-[2-(2-diethylaminoethoxycarbonylamino)pyrid-4-ylmethyl]-3-(4-trifluoromethoxyphenyl)imidazolidine-2,4-dione;
5-methyl-1-(2-phenoxycarbonylaminopyrid-4-ylmethyl)-3-(4-trifluoromethoxyphenyl)imidazolidine-2,4-dione;
5-methyl-1-[2-(4-chloroanilino)carbonylaminopyrid-4-ylmethyl]-3-(4-trifluoromethoxyphenyl)imidazolidine-2,4-dione;
5-methyl-1-(2-anilinocarbonylaminopyrid-4-ylmethyl)-3-(4-trifluoromethoxyphenyl)imidazolidine-2,4-dione;
5-methyl-1-(2-benzylaminocarbonylaminopyrid-4-ylmethyl)-3-(4-trifluoromethoxyphenyl)imidazolidine-2,4-dione;
5-methyl-1-[2-(2-pyridylamino)carbonylaminopyrid-4-ylmethyl]-3-(4-trifluoromethoxyphenyl)imidazolidine-2,4-dione;
5-methyl-1-(2-ureidopyrid-4-ylmethyl)-3-(4-trifluoromethoxyphenyl)imidazolidine-2,4-dione;
5-methyl-1-(2-benzylaminosulfonylaminopyrid-4-ylmethyl)-3-(4-trifluoromethoxyphenyl)imidazolidine-2,4-dione;
5-methyl-1-(2-methylaminosulfonylaminopyrid-4-ylmethyl)-3-(4-trifluoromethoxyphenyl)imidazolidine-2,4-dione;
5-methyl-1-(2-aminosulfonylaminopyrid-4-ylmethyl)-3-(4-trifluoromethoxyphenyl)imidazolidine-2,4-dione;
5-methyl-1-(2-morpholinosulfonylaminopyrid-4-ylmethyl)-3-(4-trifluoromethoxyphenyl)imidazolidine-2,4-dione;
5-methyl-1-(2-dimethylaminosulfonylaminopyrid-4-ylmethyl)-3-(4-trifluoromethoxyphenyl)imidazolidine-2,4-dione;
5-methyl-1-(2-anilinosulfonylaminopyrid-4-ylmethyl)-3-(4-trifluoromethoxyphenyl)imidazolidine-2,4-dione;
5-methyl-1-(2-phenylsulfonylaminopyrid-4-ylmethyl)-3-(4-trifluoromethoxyphenyl)imidazolidine-2,4-dione;
5-methyl-1-[2-(2-thienyl)sulfonylaminopyrid-4-ylmethyl]-3-(4-trifluoromethoxyphenyl)imidazolidine-2,4-dione;
5-methyl-1-(2-methylsulfonylaminopyrid-4-ylmethyl)-3-(4-trifluoromethoxyphenyl)imidazolidine-2,4-dione;
5-methyl-1-[2-(4-chlorophenyl)sulfonylaminopyrid-4-ylmethyl]-3-(4-trifluoromethoxyphenyl)imidazolidine-2,4-dione;
5-methyl-1-(2-benzylsulfonylaminopyrid-4-ylmethyl)-3-(4-trifluoromethoxyphenyl)imidazolidine-2,4-dione;
5-methyl-1-(2-hydroxycarbonylpyrid-4-ylmethyl)-3-(4-trifluoromethoxyphenyl)imidazolidine-2,4-dione;
5-methyl-1-(2-ethoxycarbonylpyrid-4-ylmethyl)-3-(4-trifluoromethoxyphenyl)imidazolidine-2,4-dione;
5-methyl-1-(2-tert-butoxycarbonylpyrid-4-ylmethyl)-3-(4-trifluoromethoxyphenyl)imidazolidine-2,4-dione;
5-methyl-1-(2-phenoxycarbonylpyrid-4-ylmethyl)-3-(4-trifluoromethoxyphenyl)imidazolidine-2,4-dione;
5-methyl-1-[2-(4-methylpiperazinocarbonyl)pyrid-4-ylmethyl]-3-(4-trifluoromethoxyphenyl)imidazolidine-2,4-dione;
5-methyl-1-[2-(methylamino)carbonylpyrid-4-ylmethyl]-3-(4-trifluoromethoxyphenyl)imidazolidine-2,4-dione;
5-methyl-1-[2-(dimethylamino)carbonylpyrid-4-ylmethyl]-3-(4-trifluoromethoxyphenyl)imidazolidine-2,4-dione;
5-methyl-1-(2-piperidinocarbonylpyrid-4-ylmethyl)-3-(4-trifluoromethoxyphenyl)imidazolidine-2,4-dione;
5-methyl-1-(2-morpholinocarbonylpyrid-4-ylmethyl)-3-(4-trifluoromethoxyphenyl)imidazolidine-2,4-dione;
5-methyl-1-[2-(4-phenylpiperazinocarbonyl)pyrid-4-ylmethyl]-3-(4-trifluoromethoxyphenyl)imidazolidine-2,4-dione;
5-methyl-1-(2-phenylaminocarbonylpyrid-4-ylmethyl)-3-(4-trifluoromethoxyphenyl)imidazolidine-2,4-dione;
5-methyl-1-[2-(methylphenylamino)carbonylpyrid-4-ylmethyl]-3-(4-trifluoromethoxyphenyl)imidazolidine-2,4-dione;
5-methyl-1-[2-(4-methoxyphenyl)methylaminocarbonylpyrid-4-ylmethyl]-3-(4-trifluoromethoxyphenyl)imidazolidine-2,4-dione;
5-methyl-1-[2-(4-chlorophenyl)methylaminocarbonylpyrid-4-ylmethyl]-3-(4-trifluoromethoxyphenyl)imidazolidine-2,4-dione;
5-methyl-1-[2-(4-morpholinylamino)carbonylpyrid-4-ylmethyl]-3-(4-trifluoromethoxyphenyl)imidazolidine-2,4-dione;
5-methyl-1-(2-aminocarbonylpyrid-4-ylmethyl)-3-(4-trifluoromethoxyphenyl)imidazolidine-2,4-dione;
5-methyl-1-(2-phenoxypyrid-4-ylmethyl)-3-(4-trifluoromethoxyphenyl)imidazolidine-2,4-dione;
5-methyl-1-(2-methoxypyrid-4-ylmethyl)-3-(4-trifluoromethoxyphenyl)imidazolidine-2,4-dione;
5-methyl-1-(2-ethoxypyrid-4-ylmethyl)-3-(4-trifluoromethoxyphenyl)imidazolidine-2,4-dione;
5-methyl-1-[2-(1-pyrrolidinyl)ethoxypyrid-4-ylmethyl]-3-(4-trifluoromethoxyphenyl)imidazolidine-2,4-dione;

5-methyl-1-(2-benzyloxypyrid-4-ylmethyl)-3-(4-trifluoromethoxyphenyl)imidazolidine-2,4-dione;

5-methyl-1-(2-benzoyloxypyrid-4-ylmethyl)-3-(4-trifluoromethoxyphenyl)imidazolidine-2,4-dione;

5-methyl-1-[2-(4,5-dihydro-1H-imidazol-2-yl)pyrid-4-ylmethyl]-3-(4-trifluoromethoxyphenyl)imidazolidine-2,4-dione;

5-methyl-1-[2-(1H-imidazol-2-yl)pyrid-4-ylmethyl]-3-(4-trifluoromethoxyphenyl)imidazolidine-2,4-dione;

5-methyl-1-[2-(1H-tetrazol-5-yl)pyrid-4-ylmethyl]-3-(4-trifluoromethoxyphenyl)imidazolidine-2,4-dione;

5-methyl-1-(2-amidinopyrid-4-ylmethyl)-3-(4-trifluoromethoxyphenyl)imidazolidine-2,4-dione;

5-methyl-1-(2-dimethylaminomethylpyrid-4-ylmethyl)-3-(4-trifluoromethoxyphenyl)imidazolidine-2,4-dione;

5-methyl-1-(2-aminomethylpyrid-4-ylmethyl)-3-(4-trifluoromethoxyphenyl)imidazolidine-2,4-dione;

5-methyl-1-(3-methylpyrid-4-ylmethyl)-3-(4-trifluoromethoxyphenyl)imidazolidine-2,4-dione;

5-methyl-1-(3-ethylpyrid-4-ylmethyl)-3-(4-trifluoromethoxyphenyl)imidazolidine-2,4-dione;

5-methyl-1-(3-isopropylpyrid-4-ylmethyl)-3-(4-trifluoromethoxyphenyl)imidazolidine-2,4-dione;

5-methyl-1-(3-tert-butylpyrid-4-ylmethyl)-3-(4-trifluoromethoxyphenyl)imidazolidine-2,4-dione;

5-methyl-1-(3-isobutylpyrid-4-ylmethyl)-3-(4-trifluoromethoxyphenyl)imidazolidine-2,4-dione;

5-methyl-1-(3-cyclohexylpyrid-4-ylmethyl)-3-(4-trifluoromethoxyphenyl)imidazolidine-2,4-dione;

5-methyl-1-(3-phenylpyrid-4-ylmethyl)-3-(4-trifluoromethoxyphenyl)imidazolidine-2,4-dione;

5-methyl-1-[3-(4-chlorophenyl)pyrid-4-ylmethyl]-3-(4-trifluoromethoxyphenyl)imidazolidine-2,4-dione;

5-methyl-1-[3-(3-chlorophenyl)pyrid-4-ylmethyl]-3-(4-trifluoromethoxyphenyl)imidazolidine-2,4-dione;

5-methyl-1-[3-(2-chlorophenyl)pyrid-4-ylmethyl]-3-(4-trifluoromethoxyphenyl)imidazolidine-2,4-dione;

5-methyl-1-[3-(4-fluorophenyl)pyrid-4-ylmethyl]-3-(4-trifluoromethoxyphenyl)imidazolidine-2,4-dione;

5-methyl-1-[3-(4-methoxyphenyl)pyrid-4-ylmethyl]-3-(4-trifluoromethoxyphenyl)imidazolidine-2,4-dione;

5-methyl-1-(3-benzylpyrid-4-ylmethyl)-3-(4-trifluoromethoxyphenyl)imidazolidine-2,4-dione;

5-methyl-1-(3,2'-bipyrid-4-ylmethyl)-3-(4-trifluoromethoxyphenyl)imidazolidine-2,4-dione;

5-methyl-1-(3-hydroxymethylpyrid-4-ylmethyl)-3-(4-trifluoromethoxyphenyl)imidazolidine-2,4-dione;

5-methyl-1-(3-chloropyrid-4-ylmethyl)-3-(4-trifluoromethoxyphenyl)imidazolidine-2,4-dione;

5-methyl-1-(3-fluoropyrid-4-ylmethyl)-3-(4-trifluoromethoxyphenyl)imidazolidine-2,4-dione;

5-methyl-1-(3-bromopyrid-4-ylmethyl)-3-(4-trifluoromethoxyphenyl)imidazolidine-2,4-dione;

5-methyl-1-(3-aminopyrid-4-ylmethyl)-3-(4-trifluoromethoxyphenyl)imidazolidine-2,4-dione;

5-methyl-1-(3-methylaminopyrid-4-ylmethyl)-3-(4-trifluoromethoxyphenyl)imidazolidine-2,4-dione;

5-methyl-1-(3-ethylaminopyrid-4-ylmethyl)-3-(4-trifluoromethoxyphenyl)imidazolidine-2,4-dione;

5-methyl-1-(3-isopropylaminopyrid-4-ylmethyl)-3-(4-trifluoromethoxyphenyl)imidazolidine-2,4-dione;

5-methyl-1-(3-phenylaminopyrid-4-ylmethyl)-3-(4-trifluoromethoxyphenyl)imidazolidine-2,4-dione;

5-methyl-1-(3-cyclohexylaminopyrid-4-ylmethyl)-3-(4-trifluoromethoxyphenyl)imidazolidine-2,4-dione;

5-methyl-1-(3-diethylaminopyrid-4-ylmethyl)-3-(4-trifluoromethoxyphenyl)imidazolidine-2,4-dione;

5-methyl-1-(3-N-cyclohexyl-N-methylaminopyrid-4-ylmethyl)-3-(4-trifluoromethoxyphenyl)imidazolidine-2,4-dione;

5-methyl-1-(3-piperidinopyrid-4-ylmethyl)-3-(4-trifluoromethoxyphenyl)imidazolidine-2,4-dione;

5-methyl-1-(3-morpholinopyrid-4-ylmethyl)-3-(4-trifluoromethoxyphenyl)imidazolidine-2,4-dione;

5-methyl-1-[3-(4-methylpiperazino)pyrid-4-ylmethyl]-3-(4-trifluoromethoxyphenyl)imidazolidine-2,4-dione;

5-methyl-1-[3-(1H-pyrazol-1-yl)pyrid-4-ylmethyl]-3-(4-trifluoromethoxyphenyl)imidazolidine-2,4-dione;

5-methyl-1-[3-(2-benzoylhydrazino)pyrid-4-ylmethyl]-3-(4-trifluoromethoxyphenyl)imidazolidine-2,4-dione;

5-methyl-1-(3-benzoylaminopyrid-4-ylmethyl)-3-(4-trifluoromethoxyphenyl)imidazolidine-2,4-dione;

5-methyl-1-[3-(4-chlorobenzoylamino)pyrid-4-ylmethyl]-3-(4-trifluoromethoxyphenyl)imidazolidine-2,4-dione;

5-methyl-1-[3-(3-chlorobenzoylamino)pyrid-4-ylmethyl]-3-(4-trifluoromethoxyphenyl)imidazolidine-2,4-dione;

5-methyl-1-[3-(2-chlorobenzoylamino)pyrid-4-ylmethyl]-3-(4-trifluoromethoxyphenyl)imidazolidine-2,4-dione;

5-methyl-1-[3-(4-fluorobenzoylamino)pyrid-4-ylmethyl]-3-(4-trifluoromethoxyphenyl)imidazolidine-2,4-dione;

5-methyl-1-[3-(4-methoxybenzoylamino)pyrid-4-ylmethyl]-3-(4-trifluoromethoxyphenyl)imidazolidine-2,4-dione;

5-methyl-1-(3-acetamidopyrid-4-ylmethyl)-3-(4-trifluoromethoxyphenyl)imidazolidine-2,4-dione;

5-methyl-1-(3-phenylacetamidopyrid-4-ylmethyl)-3-(4-trifluoromethoxyphenyl)imidazolidine-2,4-dione;

5-methyl-1-[3-(4-methylpiperazino)acetamidopyrid-4-ylmethyl]-3-(4-trifluoromethoxyphenyl)imidazolidine-2,4-dione;

5-methyl-1-(3-cyclohexanylcarboxamidopyrid-4-ylmethyl)-3-(4-trifluoromethoxyphenyl)imidazolidine-2,4-dione;

5-methyl-1-[3-(1-methyl-4-piperidinyl)carbonylaminopyrid-4-ylmethyl]-3-(4-trifluoromethoxyphenyl)imidazolidine-2,4-dione;

5-methyl-1-[3-(2-furanylcarbonyl)aminopyrid-4-ylmethyl]-3-(4-trifluoromethoxyphenyl)imidazolidine-2,4-dione;

5-methyl-1-(3-ethoxycarbonylaminopyrid-4-ylmethyl)-3-(4-trifluoromethoxyphenyl)imidazolidine-2,4-dione;

5-methyl-1-(3-isopropoxycarbonylaminopyrid-4-ylmethyl)-3-(4-trifluoromethoxyphenyl)imidazolidine-2,4-dione;

5-methyl-1-(3-butoxycarbonylaminopyrid-4-ylmethyl)-3-(4-trifluoromethoxyphenyl)imidazolidine-2,4-dione;

5-methyl-1-[3-(2-diethylaminoethoxycarbonylamino)pyrid-4-ylmethyl]-3-(4-trifluoromethoxyphenyl)imidazolidine-2,4-dione;

5-methyl-1-(3-phenoxycarbonylaminopyrid-4-ylmethyl)-3-(4-trifluoromethoxyphenyl)imidazolidine-2,4-dione;

5-methyl-1-[3-(4-chloroanilino)carbonylaminopyrid-4-ylmethyl]-3-(4-trifluoromethoxyphenyl)imidazolidine-2,4-dione;

5-methyl-1-(3-anilinocarbonylaminopyrid-4-ylmethyl)-3-(4-trifluoromethoxyphenyl)imidazolidine-2,4-dione;

5-methyl-1-(3-benzylaminocarbonylaminopyrid-4-ylmethyl)-3-(4-trifluoromethoxyphenyl)imidazolidine-2,4-dione;

5-methyl-1-[3-(2-pyridylamino)carbonylaminopyrid-4-ylmethyl]-3-(4-trifluoromethoxyphenyl)imidazolidine-2,4-dione;

5-methyl-1-(3-ureidopyrid-4-ylmethyl)-3-(4-trifluoromethoxyphenyl)imidazolidine-2,4-dione;

5-methyl-1-(3-benzylaminosulfonylaminopyrid-4-ylmethyl)-3-(4-trifluoromethoxyphenyl)imidazolidine-2,4-dione;

5-methyl-1-(3-methylaminosulfonylaminopyrid-4-ylmethyl)-3-(4-trifluoromethoxyphenyl)imidazolidine-2,4-dione;
5-methyl-1-(3-aminosulfonylaminopyrid-4-ylmethyl)-3-(4-trifluoromethoxyphenyl)imidazolidine-2,4-dione;
5-methyl-1-(3-morpholinosulfonylaminopyrid-4-ylmethyl)-3-(4-trifluoromethoxyphenyl)imidazolidine-2,4-dione;
5-methyl-1-(3-dimethylaminosulfonylaminopyrid-4-ylmethyl)-3-(4-trifluoromethoxyphenyl)imidazolidine-2,4-dione;
5-methyl-1-(3-anilinosulfonylaminopyrid-4-ylmethyl)-3-(4-trifluoromethoxyphenyl)imidazolidine-2,4-dione;
5-methyl-1-(3-phenylsulfonylaminopyrid-4-ylmethyl)-3-(4-trifluoromethoxyphenyl)imidazolidine-2,4-dione;
5-methyl-1-[3-(2-thienyl)sulfonylaminopyrid-4-ylmethyl]-3-(4-trifluoromethoxyphenyl)imidazolidine-2,4-dione;
5-methyl-1-(3-methylsulfonylaminopyrid-4-ylmethyl)-3-(4-trifluoromethoxyphenyl)imidazolidine-2,4-dione;
5-methyl-1-[3-(4-chlorophenyl)sulfonylaminopyrid-4-ylmethyl]-3-(4-trifluoromethoxyphenyl)imidazolidine-2,4-dione;
5-methyl-1-(3-benzylsulfonylaminopyrid-4-ylmethyl)-3-(4-trifluoromethoxyphenyl)imidazolidine-2,4-dione;
5-methyl-1-(3-hydroxycarbonylpyrid-4-ylmethyl)-3-(4-trifluoromethoxyphenyl)imidazolidine-2,4-dione;
5-methyl-1-(3-ethoxycarbonylpyrid-4-ylmethyl)-3-(4-trifluoromethoxyphenyl)imidazolidine-2,4-dione;
5-methyl-1-(3-tert-butoxycarbonylpyrid-4-ylmethyl)-3-(4-trifluoromethoxyphenyl)imidazolidine-2,4-dione;
5-methyl-1-(3-phenoxycarbonylpyrid-4-ylmethyl)-3-(4-trifluoromethoxyphenyl)imidazolidine-2,4-dione;
5-methyl-1-[3-(4-methylpiperazinocarbonyl)pyrid-4-ylmethyl]-3-(4-trifluoromethoxyphenyl)imidazolidine-2,4-dione;
5-methyl-1-[3-(methylamino)carbonylpyrid-4-ylmethyl]-3-(4-trifluoromethoxyphenyl)imidazolidine-2,4-dione;
5-methyl-1-[3-(dimethylamino)carbonylpyrid-4-ylmethyl]-3-(4-trifluoromethoxyphenyl)imidazolidine-2,4-dione;
5-methyl-1-(3-piperidinocarbonylpyrid-4-ylmethyl)-3-(4-trifluoromethoxyphenyl)imidazolidine-2,4-dione;
5-methyl-1-(3-morpholinocarbonylpyrid-4-ylmethyl)-3-(4-trifluoromethoxyphenyl)imidazolidine-2,4-dione;
5-methyl-1-[3-(4-phenylpiperazinocarbonyl)pyrid-4-ylmethyl]-3-(4-trifluoromethoxyphenyl)imidazolidine-2,4-dione;
5-methyl-1-(3-phenylaminocarbonylpyrid-4-ylmethyl)-3-(4-trifluoromethoxyphenyl)imidazolidine-2,4-dione;
5-methyl-1-[3-(methylphenylamino)carbonylpyrid-4-ylmethyl]-3-(4-trifluoromethoxyphenyl)imidazolidine-2,4-dione;
5-methyl-1-[3-(4-methoxyphenyl)methylaminocarbonylpyrid-4-ylmethyl]-3-(4-trifluoromethoxyphenyl)imidazolidine-2,4-dione;
5-methyl-1-[3-(4-chlorophenyl)methylaminocarbonylpyrid-4-ylmethyl]-3-(4-trifluoromethoxyphenyl)imidazolidine-2,4-dione;
5-methyl-1-[3-(4-morpholinylamino)carbonylpyrid-4-ylmethyl]-3-(4-trifluoromethoxyphenyl)imidazolidine-2,4-dione;
5-methyl-1-(3-aminocarbonylpyrid-4-ylmethyl)-3-(4-trifluoromethoxyphenyl)imidazolidine-2,4-dione;
5-methyl-1-(3-phenoxypyrid-4-ylmethyl)-3-(4-trifluoromethoxyphenyl)imidazolidine-2,4-dione;
5-methyl-1-(3-methoxypyrid-4-ylmethyl)-3-(4-trifluoromethoxyphenyl)imidazolidine-2,4-dione;
5-methyl-1-(3-ethoxypyrid-4-ylmethyl)-3-(4-trifluoromethoxyphenyl)imidazolidine-2,4-dione;
5-methyl-1-[3-(1-pyrrolidinyl)ethoxypyrid-4-ylmethyl]-3-(4-trifluoromethoxyphenyl)imidazolidine-2,4-dione;
5-methyl-1-(3-benzyloxypyrid-4-ylmethyl)-3-(4-trifluoromethoxyphenyl)imidazolidine-2,4-dione;
5-methyl-1-(3-benzoyloxypyrid-4-ylmethyl)-3-(4-trifluoromethoxyphenyl)imidazolidine-2,4-dione;
5-methyl-1-[3-(4,5-dihydro-1H-imidazol-2-yl)pyrid-4-ylmethyl]-3-(4-trifluoromethoxyphenyl)imidazolidine-2,4-dione;
5-methyl-1-[3-(1H-imidazol-2-yl)pyrid-4-ylmethyl]-3-(4-trifluoromethoxyphenyl)imidazolidine-2,4-dione;
5-methyl-1-[3-(1H-tetrazol-5-yl)pyrid-4-ylmethyl]-3-(4-trifluoromethoxyphenyl)imidazolidine-2,4-dione;
5-methyl-1-(3-amidinopyrid-4-ylmethyl)-3-(4-trifluoromethoxyphenyl)imidazolidine-2,4-dione;
5-methyl-1-(3-dimethylaminomethylpyrid-4-ylmethyl)-3-(4-trifluoromethoxyphenyl)imidazolidine-2,4-dione;
5-methyl-1-(3-aminomethylpyrid-4-ylmethyl)-3-(4-trifluoromethoxyphenyl)imidazolidine-2,4-dione;
1-(2-methylpyrid-4-ylmethyl)-3-(4-trifluoromethoxyphenyl)imidazolidine-2,4-dione;
1-(2-ethylpyrid-4-ylmethyl)-3-(4-trifluoromethoxyphenyl)imidazolidine-2,4-dione;
1-(2-isopropylpyrid-4-ylmethyl)-3-(4-trifluoromethoxyphenyl)imidazolidine-2,4-dione;
1-(2-tert-butylpyrid-4-ylmethyl)-3-(4-trifluoromethoxyphenyl)imidazolidine-2,4-dione;
1-(2-isobutylpyrid-4-ylmethyl)-3-(4-trifluoromethoxyphenyl)imidazolidine-2,4-dione;
1-(2-cyclohexylpyrid-4-ylmethyl)-3-(4-trifluoromethoxyphenyl)imidazolidine-2,4-dione;
1-(2-phenylpyrid-4-ylmethyl)-3-(4-trifluoromethoxyphenyl)imidazolidine-2,4-dione;
1-[2-(4-chlorophenyl)pyrid-4-ylmethyl]-3-(4-trifluoromethoxyphenyl)imidazolidine-2,4-dione;
1-[2-(3-chlorophenyl)pyrid-4-ylmethyl]-3-(4-trifluoromethoxyphenyl)imidazolidine-2,4-dione;
1-[2-(2-chlorophenyl)pyrid-4-ylmethyl]-3-(4-trifluoromethoxyphenyl)imidazolidine-2,4-dione;
1-[2-(4-fluorophenyl)pyrid-4-ylmethyl]-3-(4-trifluoromethoxyphenyl)imidazolidine-2,4-dione;
1-[2-(4-methoxyphenyl)pyrid-4-ylmethyl]-3-(4-trifluoromethoxyphenyl)imidazolidine-2,4-dione;
1-(2-benzylpyrid-4-ylmethyl)-3-(4-trifluoromethoxyphenyl)imidazolidine-2,4-dione;
1-(2,2'-bipyrid-4-ylmethyl)-3-(4-trifluoromethoxyphenyl)imidazolidine-2,4-dione;
1-(2-hydroxymethylpyrid-4-ylmethyl)-3-(4-trifluoromethoxyphenyl)imidazolidine-2,4-dione;
1-(2-chloropyrid-4-ylmethyl)-3-(4-trifluoromethoxyphenyl)imidazolidine-2,4-dione;
1-(2-fluoropyrid-4-ylmethyl)-3-(4-trifluoromethoxyphenyl)imidazolidine-2,4-dione;
1-(2-bromopyrid-4-ylmethyl)-3-(4-trifluoromethoxyphenyl)imidazolidine-2,4-dione;
1-(2-aminopyrid-4-ylmethyl)-3-(4-trifluoromethoxyphenyl)imidazolidine-2,4-dione;
1-(2-methylaminopyrid-4-ylmethyl)-3-(4-trifluoromethoxyphenyl)imidazolidine-2,4-dione;
1-(2-ethylaminopyrid-4-ylmethyl)-3-(4-trifluoromethoxyphenyl)imidazolidine-2,4-dione;
1-(2-isopropylaminopyrid-4-ylmethyl)-3-(4-trifluoromethoxyphenyl)imidazolidine-2,4-dione;
1-(2-phenylaminopyrid-4-ylmethyl)-3-(4-trifluoromethoxyphenyl)imidazolidine-2,4-dione;
1-(2-cyclohexylaminopyrid-4-ylmethyl)-3-(4-trifluoromethoxyphenyl)imidazolidine-2,4-dione;

1-(2-diethylaminopyrid-4-ylmethyl)-3-(4-trifluoromethoxyphenyl)imidazolidine-2,4-dione;
1-(2-N-cyclohexyl-N-methylaminopyrid-4-ylmethyl)-3-(4-trifluoromethoxyphenyl)imidazolidine-2,4-dione;
1-(2-piperidinopyrid-4-ylmethyl)-3-(4-trifluoromethoxyphenyl)imidazolidine-2,4-dione;
1-(2-morpholinopyrid-4-ylmethyl)-3-(4-trifluoromethoxyphenyl)imidazolidine-2,4-dione;
1-[2-(4-methylpiperazino)pyrid-4-ylmethyl]-3-(4-trifluoromethoxyphenyl)imidazolidine-2,4-dione;
1-[2-(1H-pyrazol-1-yl)pyrid-4-ylmethyl]-3-(4-trifluoromethoxyphenyl)imidazolidine-2,4-dione;
1-[2-(2-benzoylhydrazino)pyrid-4-ylmethyl]-3-(4-trifluoromethoxyphenyl)imidazolidine-2,4-dione;
1-(2-benzoylaminopyrid-4-ylmethyl)-3-(4-trifluoromethoxyphenyl)imidazolidine-2,4-dione;
1-[2-(4-chlorobenzoylamino)pyrid-4-ylmethyl]-3-(4-trifluoromethoxyphenyl)imidazolidine-2,4-dione;
1-[2-(3-chlorobenzoylamino)pyrid-4-ylmethyl]-3-(4-trifluoromethoxyphenyl)imidazolidine-2,4-dione;
1-[2-(2-chlorobenzoylamino)pyrid-4-ylmethyl]-3-(4-trifluoromethoxyphenyl)imidazolidine-2,4-dione;
1-[2-(4-fluorobenzoylamino)pyrid-4-ylmethyl]-3-(4-trifluoromethoxyphenyl)imidazolidine-2,4-dione;
1-[2-(4-methoxybenzoylamino)pyrid-4-ylmethyl]-3-(4-trifluoromethoxyphenyl)imidazolidine-2,4-dione;
1-(2-acetamidopyrid-4-ylmethyl)-3-(4-trifluoromethoxyphenyl)imidazolidine-2,4-dione;
1-(2-phenylacetamidopyrid-4-ylmethyl)-3-(4-trifluoromethoxyphenyl)imidazolidine-2,4-dione;
1-[2-(4-methylpiperazino)acetamidopyrid-4-ylmethyl]-3-(4-trifluoromethoxyphenyl)imidazolidine-2,4-dione;
1-(2-cyclohexanylcarboxamidopyrid-4-ylmethyl)-3-(4-trifluoromethoxyphenyl)imidazolidine-2,4-dione;
1-[2-(1-methyl-4-piperidinyl)carbonylaminopyrid-4-ylmethyl]-3-(4-trifluoromethoxyphenyl)imidazolidine-2,4-dione;
1-[2-(2-furanylcarbonyl)aminopyrid-4-ylmethyl]-3-(4-trifluoromethoxyphenyl)imidazolidine-2,4-dione;
1-(2-ethoxycarbonylaminopyrid-4-ylmethyl)-3-(4-trifluoromethoxyphenyl)imidazolidine-2,4-dione;
1-(2-isopropoxycarbonylaminopyrid-4-ylmethyl)-3-(4-trifluoromethoxyphenyl)imidazolidine-2,4-dione;
1-(2-butoxycarbonylaminopyrid-4-ylmethyl)-3-(4-trifluoromethoxyphenyl)imidazolidine-2,4-dione;
1-[2-(2-diethylaminoethoxycarbonylamino)pyrid-4-ylmethyl]-3-(4-trifluoromethoxyphenyl)imidazolidine-2,4-dione;
1-(2-phenoxycarbonylaminopyrid-4-ylmethyl)-3-(4-trifluoromethoxyphenyl)imidazolidine-2,4-dione;
1-[2-(4-chloroanilino)carbonylaminopyrid-4-ylmethyl]-3-(4-trifluoromethoxyphenyl)imidazolidine-2,4-dione;
1-(2-anilinocarbonylaminopyrid-4-ylmethyl)-3-(4-trifluoromethoxyphenyl)imidazolidine-2,4-dione;
1-(2-benzylaminocarbonylaminopyrid-4-ylmethyl)-3-(4-trifluoromethoxyphenyl)imidazolidine-2,4-dione;
1-[2-(2-pyridylamino)carbonylaminopyrid-4-ylmethyl]-3-(4-trifluoromethoxyphenyl)imidazolidine-2,4-dione;
1-(2-ureidopyrid-4-ylmethyl)-3-(4-trifluoromethoxyphenyl)imidazolidine-2,4-dione;
1-(2-benzylaminosulfonylaminopyrid-4-ylmethyl)-3-(4-trifluoromethoxyphenyl)imidazolidine-2,4-dione;
1-(2-methylaminosulfonylaminopyrid-4-ylmethyl)-3-(4-trifluoromethoxyphenyl)imidazolidine-2,4-dione;
1-(2-aminosulfonylaminopyrid-4-ylmethyl)-3-(4-trifluoromethoxyphenyl)imidazolidine-2,4-dione;
1-(2-morpholinosulfonylaminopyrid-4-ylmethyl)-3-(4-trifluoromethoxyphenyl)imidazolidine-2,4-dione;
1-(2-dimethylaminosulfonylaminopyrid-4-ylmethyl)-3-(4-trifluoromethoxyphenyl)imidazolidine-2,4-dione;
1-(2-anilinosulfonylaminopyrid-4-ylmethyl)-3-(4-trifluoromethoxyphenyl)imidazolidine-2,4-dione;
1-(2-phenylsulfonylaminopyrid-4-ylmethyl)-3-(4-trifluoromethoxyphenyl)imidazolidine-2,4-dione;
1-[2-(2-thienyl)sulfonylaminopyrid-4-ylmethyl]-3-(4-trifluoromethoxyphenyl)imidazolidine-2,4-dione;
1-(2-methylsulfonylaminopyrid-4-ylmethyl)-3-(4-trifluoromethoxyphenyl)imidazolidine-2,4-dione;
1-[2-(4-chlorophenyl)sulfonylaminopyrid-4-ylmethyl]-3-(4-trifluoromethoxyphenyl)imidazolidine-2,4-dione;
1-(2-benzylsulfonylaminopyrid-4-ylmethyl)-3-(4-trifluoromethoxyphenyl)imidazolidine-2,4-dione;
1-(2-hydroxycarbonylpyrid-4-ylmethyl)-3-(4-trifluoromethoxyphenyl)imidazolidine-2,4-dione;
1-(2-ethoxycarbonylpyrid-4-ylmethyl)-3-(4-trifluoromethoxyphenyl)imidazolidine-2,4-dione;
1-(2-tert-butoxycarbonylpyrid-4-ylmethyl)-3-(4-trifluoromethoxyphenyl)imidazolidine-2,4-dione;
1-(2-phenoxycarbonylpyrid-4-ylmethyl)-3-(4-trifluoromethoxyphenyl)imidazolidine-2,4-dione;
1-[2-(4-methylpiperazinocarbonyl)pyrid-4-ylmethyl]-3-(4-trifluoromethoxyphenyl)imidazolidine-2,4-dione;
1-[2-(methylamino)carbonylpyrid-4-ylmethyl]-3-(4-trifluoromethoxyphenyl)imidazolidine-2,4-dione;
1-[2-(dimethylamino)carbonylpyrid-4-ylmethyl]-3-(4-trifluoromethoxyphenyl)imidazolidine-2,4-dione;
1-(2-piperidinocarbonylpyrid-4-ylmethyl)-3-(4-trifluoromethoxyphenyl)imidazolidine-2,4-dione;
1-(2-morpholinocarbonylpyrid-4-ylmethyl)-3-(4-trifluoromethoxyphenyl)imidazolidine-2,4-dione;
1-[2-(4-phenylpiperazinocarbonyl)pyrid-4-ylmethyl]-3-(4-trifluoromethoxyphenyl)imidazolidine-2,4-dione;
1-(2-phenylaminocarbonylpyrid-4-ylmethyl)-3-(4-trifluoromethoxyphenyl)imidazolidine-2,4-dione;
1-[2-(methylphenylamino)carbonylpyrid-4-ylmethyl]-3-(4-trifluoromethoxyphenyl)imidazolidine-2,4-dione;
1-[2-(4-methoxyphenyl)methylaminocarbonylpyrid-4-ylmethyl]-3-(4-trifluoromethoxyphenyl)imidazolidine-2,4-dione;
1-[2-(4-chlorophenyl)methylaminocarbonylpyrid-4-ylmethyl]-3-(4-trifluoromethoxyphenyl)imidazolidine-2,4-dione;
1-[2-(4-morpholinylamino)carbonylpyrid-4-ylmethyl]-3-(4-trifluoromethoxyphenyl)imidazolidine-2,4-dione;
1-(2-aminocarbonylpyrid-4-ylmethyl)-3-(4-trifluoromethoxyphenyl)imidazolidine-2,4-dione;
1-(2-phenoxypyrid-4-ylmethyl)-3-(4-trifluoromethoxyphenyl)imidazolidine-2,4-dione;
1-(2-methoxypyrid-4-ylmethyl)-3-(4-trifluoromethoxyphenyl)imidazolidine-2,4-dione;
1-(2-ethoxypyrid-4-ylmethyl)-3-(4-trifluoromethoxyphenyl)imidazolidine-2,4-dione;
1-[2-(1-pyrrolidinyl)ethoxypyrid-4-ylmethyl]-3-(4-trifluoromethoxyphenyl)imidazolidine-2,4-dione;
1-(2-benzyloxypyrid-4-ylmethyl)-3-(4-trifluoromethoxyphenyl)imidazolidine-2,4-dione;
1-(2-benzoyloxypyrid-4-ylmethyl)-3-(4-trifluoromethoxyphenyl)imidazolidine-2,4-dione;
1-[2-(4,5-dihydro-1H-imidazol-2-yl)pyrid-4-ylmethyl]-3-(4-trifluoromethoxyphenyl)imidazolidine-2,4-dione;
1-[2-(1H-imidazol-2-yl)pyrid-4-ylmethyl]-3-(4-trifluoromethoxyphenyl)imidazolidine-2,4-dione;

1-[2-(1H-tetrazol-5-yl)pyrid-4-ylmethyl]-3-(4-trifluoromethoxyphenyl)imidazolidine-2,4-dione;
1-(2-amidinopyrid-4-ylmethyl)-3-(4-trifluoromethoxyphenyl)imidazolidine-2,4-dione;
1-(2-dimethylaminomethylpyrid-4-ylmethyl)-3-(4-trifluoromethoxyphenyl)imidazolidine-2,4-dione;
1-(2-aminomethylpyrid-4-ylmethyl)-3-(4-trifluoromethoxyphenyl)imidazolidine-2,4-dione;
1-(3-methylpyrid-4-ylmethyl)-3-(4-trifluoromethoxyphenyl)imidazolidine-2,4-dione;
1-(3-ethylpyrid-4-ylmethyl)-3-(4-trifluoromethoxyphenyl)imidazolidine-2,4-dione;
1-(3-isopropylpyrid-4-ylmethyl)-3-(4-trifluoromethoxyphenyl)imidazolidine-2,4-dione;
1-(3-tert-butylpyrid-4-ylmethyl)-3-(4-trifluoromethoxyphenyl)imidazolidine-2,4-dione;
1-(3-isobutylpyrid-4-ylmethyl)-3-(4-trifluoromethoxyphenyl)imidazolidine-2,4-dione;
1-(3-cyclohexylpyrid-4-ylmethyl)-3-(4-trifluoromethoxyphenyl)imidazolidine-2,4-dione;
1-(3-phenylpyrid-4-ylmethyl)-3-(4-trifluoromethoxyphenyl)imidazolidine-2,4-dione;
1-[3-(4-chlorophenyl)pyrid-4-ylmethyl]-3-(4-trifluoromethoxyphenyl)imidazolidine-2,4-dione;
1-[3-(3-chlorophenyl)pyrid-4-ylmethyl]-3-(4-trifluoromethoxyphenyl)imidazolidine-2,4-dione;
1-[3-(2-chlorophenyl)pyrid-4-ylmethyl]-3-(4-trifluoromethoxyphenyl)imidazolidine-2,4-dione;
1-[3-(4-fluorophenyl)pyrid-4-ylmethyl]-3-(4-trifluoromethoxyphenyl)imidazolidine-2,4-dione;
1-[3-(4-methoxyphenyl)pyrid-4-ylmethyl]-3-(4-trifluoromethoxyphenyl)imidazolidine-2,4-dione;
1-(3-benzylpyrid-4-ylmethyl)-3-(4-trifluoromethoxyphenyl)imidazolidine-2,4-dione;
1-(3,2'-bipyrid-4-ylmethyl)-3-(4-trifluoromethoxyphenyl)imidazolidine-2,4-dione;
1-(3-hydroxymethylpyrid-4-ylmethyl)-3-(4-trifluoromethoxyphenyl)imidazolidine-2,4-dione;
1-(3-chloropyrid-4-ylmethyl)-3-(4-trifluoromethoxyphenyl)imidazolidine-2,4-dione;
1-(3-fluoropyrid-4-ylmethyl)-3-(4-trifluoromethoxyphenyl)imidazolidine-2,4-dione;
1-(3-bromopyrid-4-ylmethyl)-3-(4-trifluoromethoxyphenyl)imidazolidine-2,4-dione;
1-(3-aminopyrid-4-ylmethyl)-3-(4-trifluoromethoxyphenyl)imidazolidine-2,4-dione;
1-(3-methylaminopyrid-4-ylmethyl)-3-(4-trifluoromethoxyphenyl)imidazolidine-2,4-dione;
1-(3-ethylaminopyrid-4-ylmethyl)-3-(4-trifluoromethoxyphenyl)imidazolidine-2,4-dione;
1-(3-isopropylaminopyrid-4-ylmethyl)-3-(4-trifluoromethoxyphenyl)imidazolidine-2,4-dione;
1-(3-phenylaminopyrid-4-ylmethyl)-3-(4-trifluoromethoxyphenyl)imidazolidine-2,4-dione;
1-(3-cyclohexylaminopyrid-4-ylmethyl)-3-(4-trifluoromethoxyphenyl)imidazolidine-2,4-dione;
1-(3-diethylaminopyrid-4-ylmethyl)-3-(4-trifluoromethoxyphenyl)imidazolidine-2,4-dione;
1-(3-N-cyclohexyl-N-methylaminopyrid-4-ylmethyl)-3-(4-trifluoromethoxyphenyl)imidazolidine-2,4-dione;
1-(3-piperidinopyrid-4-ylmethyl)-3-(4-trifluoromethoxyphenyl)imidazolidine-2,4-dione;
1-(3-morpholinopyrid-4-ylmethyl)-3-(4-trifluoromethoxyphenyl)imidazolidine-2,4-dione;
1-[3-(4-methylpiperazino)pyrid-4-ylmethyl]-3-(4-trifluoromethoxyphenyl)imidazolidine-2,4-dione;
1-[3-(1H-pyrazol-1-yl)pyrid-4-ylmethyl]-3-(4-trifluoromethoxyphenyl)imidazolidine-2,4-dione;
1-[3-(2-benzoylhydrazino)pyrid-4-ylmethyl]-3-(4-trifluoromethoxyphenyl)imidazolidine-2,4-dione;
1-(3-benzoylaminopyrid-4-ylmethyl)-3-(4-trifluoromethoxyphenyl)imidazolidine-2,4-dione;
1-[3-(4-chlorobenzoylamino)pyrid-4-ylmethyl]-3-(4-trifluoromethoxyphenyl)imidazolidine-2,4-dione;
1-[3-(3-chlorobenzoylamino)pyrid-4-ylmethyl]-3-(4-trifluoromethoxyphenyl)imidazolidine-2,4-dione;
1-[3-(2-chlorobenzoylamino)pyrid-4-ylmethyl]-3-(4-trifluoromethoxyphenyl)imidazolidine-2,4-dione;
1-[3-(4-fluorobenzoylamino)pyrid-4-ylmethyl]-3-(4-trifluoromethoxyphenyl)imidazolidine-2,4-dione;
1-[3-(4-methoxybenzoylamino)pyrid-4-ylmethyl]-3-(4-trifluoromethoxyphenyl)imidazolidine-2,4-dione;
1-(3-acetamidopyrid-4-ylmethyl)-3-(4-trifluoromethoxyphenyl)imidazolidine-2,4-dione;
1-(3-phenylacetamidopyrid-4-ylmethyl)-3-(4-trifluoromethoxyphenyl)imidazolidine-2,4-dione;
1-[3-(4-methylpiperazino)acetamidopyrid-4-ylmethyl]-3-(4-trifluoromethoxyphenyl)imidazolidine-2,4-dione;
1-(3-cyclohexanylcarboxamidopyrid-4-ylmethyl)-3-(4-trifluoromethoxyphenyl)imidazolidine-2,4-dione;
1-[3-(1-methyl-4-piperidinyl)carbonylaminopyrid-4-ylmethyl]-3-(4-trifluoromethoxyphenyl)imidazolidine-2,4-dione;
1-[3-(2-furanylcarbonyl)aminopyrid-4-ylmethyl]-3-(4-trifluoromethoxyphenyl)imidazolidine-2,4-dione;
1-(3-ethoxycarbonylaminopyrid-4-ylmethyl)-3-(4-trifluoromethoxyphenyl)imidazolidine-2,4-dione;
1-(3-isopropoxycarbonylaminopyrid-4-ylmethyl)-3-(4-trifluoromethoxyphenyl)imidazolidine-2,4-dione;
1-(3-butoxycarbonylaminopyrid-4-ylmethyl)-3-(4-trifluoromethoxyphenyl)imidazolidine-2,4-dione;
1-[3-(2-diethylaminoethoxycarbonylamino)pyrid-4-ylmethyl]-3-(4-trifluoromethoxyphenyl)imidazolidine-2,4-dione;
1-(3-phenoxycarbonylaminopyrid-4-ylmethyl)-3-(4-trifluoromethoxyphenyl)imidazolidine-2,4-dione;
1-[3-(4-chloroanilino)carbonylaminopyrid-4-ylmethyl]-3-(4-trifluoromethoxyphenyl)imidazolidine-2,4-dione;
1-(3-anilinocarbonylaminopyrid-4-ylmethyl)-3-(4-trifluoromethoxyphenyl)imidazolidine-2,4-dione;
1-(3-benzylaminocarbonylaminopyrid-4-ylmethyl)-3-(4-trifluoromethoxyphenyl)imidazolidine-2,4-dione;
1-[3-(2-pyridylamino)carbonylaminopyrid-4-ylmethyl]-3-(4-trifluoromethoxyphenyl)imidazolidine-2,4-dione;
1-(3-ureidopyrid-4-ylmethyl)-3-(4-trifluoromethoxyphenyl)imidazolidine-2,4-dione;
1-(3-benzylaminosulfonylaminopyrid-4-ylmethyl)-3-(4-trifluoromethoxyphenyl)imidazolidine-2,4-dione;
1-(3-methylaminosulfonylaminopyrid-4-ylmethyl)-3-(4-trifluoromethoxyphenyl)imidazolidine-2,4-dione;
1-(3-aminosulfonylaminopyrid-4-ylmethyl)-3-(4-trifluoromethoxyphenyl)imidazolidine-2,4-dione;
1-(3-morpholinosulfonylaminopyrid-4-ylmethyl)-3-(4-trifluoromethoxyphenyl)imidazolidine-2,4-dione;
1-(3-dimethylaminosulfonylaminopyrid-4-ylmethyl)-3-(4-trifluoromethoxyphenyl)imidazolidine-2,4-dione;
1-(3-anilinosulfonylaminopyrid-4-ylmethyl)-3-(4-trifluoromethoxyphenyl)imidazolidine-2,4-dione;
1-(3-phenylsulfonylaminopyrid-4-ylmethyl)-3-(4-trifluoromethoxyphenyl)imidazolidine-2,4-dione;
1-[3-(2-thienyl)sulfonylaminopyrid-4-ylmethyl]-3-(4-trifluoromethoxyphenyl)imidazolidine-2,4-dione;

1-(3-methylsulfonylaminopyrid-4-ylmethyl)-3-(4-trifluoromethoxyphenyl)imidazolidine-2,4-dione;
1-[3-(4-chlorophenyl)sulfonylaminopyrid-4-ylmethyl]-3-(4-trifluoromethoxyphenyl)imidazolidine-2,4-dione;
1-(3-benzylsulfonylaminopyrid-4-ylmethyl)-3-(4-trifluoromethoxyphenyl)imidazolidine-2,4-dione;
1-(3-hydroxycarbonylpyrid-4-ylmethyl)-3-(4-trifluoromethoxyphenyl)imidazolidine-2,4-dione;
1-(3-ethoxycarbonylpyrid-4-ylmethyl)-3-(4-trifluoromethoxyphenyl)imidazolidine-2,4-dione;
1-(3-tert-butoxycarbonylpyrid-4-ylmethyl)-3-(4-trifluoromethoxyphenyl)imidazolidine-2,4-dione;
1-(3-phenoxycarbonylpyrid-4-ylmethyl)-3-(4-trifluoromethoxyphenyl)imidazolidine-2,4-dione;
1-[3-(4-methylpiperazinocarbonyl)pyrid-4-ylmethyl]-3-(4-trifluoromethoxyphenyl)imidazolidine-2,4-dione;
1-[3-(methylamino)carbonylpyrid-4-ylmethyl]-3-(4-trifluoromethoxyphenyl)imidazolidine-2,4-dione;
1-[3-(dimethylamino)carbonylpyrid-4-ylmethyl]-3-(4-trifluoromethoxyphenyl)imidazolidine-2,4-dione;
1-(3-piperidinocarbonylpyrid-4-ylmethyl)-3-(4-trifluoromethoxyphenyl)imidazolidine-2,4-dione;
1-(3-morpholinocarbonylpyrid-4-ylmethyl)-3-(4-trifluoromethoxyphenyl)imidazolidine-2,4-dione;
1-[3-(4-phenylpiperazinocarbonyl)pyrid-4-ylmethyl]-3-(4-trifluoromethoxyphenyl)imidazolidine-2,4-dione;
1-(3-phenylaminocarbonylpyrid-4-ylmethyl)-3-(4-trifluoromethoxyphenyl)imidazolidine-2,4-dione;
1-[3-(methylphenylamino)carbonylpyrid-4-ylmethyl]-3-(4-trifluoromethoxyphenyl)imidazolidine-2,4-dione;
1-[3-(4-methoxyphenyl)methylaminocarbonylpyrid-4-ylmethyl]-3-(4-trifluoromethoxyphenyl)imidazolidine-2,4-dione;
1-[3-(4-chlorophenyl)methylaminocarbonylpyrid-4-ylmethyl]-3-(4-trifluoromethoxyphenyl)imidazolidine-2,4-dione;
1-[3-(4-morpholinylamino)carbonylpyrid-4-ylmethyl]-3-(4-trifluoromethoxyphenyl)imidazolidine-2,4-dione;
1-(3-aminocarbonylpyrid-4-ylmethyl)-3-(4-trifluoromethoxyphenyl)imidazolidine-2,4-dione;
1-(3-phenoxypyrid-4-ylmethyl)-3-(4-trifluoromethoxyphenyl)imidazolidine-2,4-dione;
1-(3-methoxypyrid-4-ylmethyl)-3-(4-trifluoromethoxyphenyl)imidazolidine-2,4-dione;
1-(3-ethoxypyrid-4-ylmethyl)-3-(4-trifluoromethoxyphenyl)imidazolidine-2,4-dione;
1-[3-(1-pyrrolidinyl)ethoxypyrid-4-ylmethyl]-3-(4-trifluoromethoxyphenyl)imidazolidine-2,4-dione;
1-(3-benzyloxypyrid-4-ylmethyl)-3-(4-trifluoromethoxyphenyl)imidazolidine-2,4-dione;
1-(3-benzoyloxypyrid-4-ylmethyl)-3-(4-trifluoromethoxyphenyl)imidazolidine-2,4-dione;
1-[3-(4,5-dihydro-1H-imidazol-2-yl)pyrid-4-ylmethyl]-3-(4-trifluoromethoxyphenyl)imidazolidine-2,4-dione;
1-[3-(1H-imidazol-2-yl)pyrid-4-ylmethyl]-3-(4-trifluoromethoxyphenyl)imidazolidine-2,4-dione;
1-[3-(1H-tetrazol-5-yl)pyrid-4-ylmethyl]-3-(4-trifluoromethoxyphenyl)imidazolidine-2,4-dione;
1-(3-amidinopyrid-4-ylmethyl)-3-(4-trifluoromethoxyphenyl)imidazolidine-2,4-dione;
1-(3-dimethylaminomethylpyridin)-4-ylmethyl]-3-(4-trifluoromethoxyphenyl)imidazolidine-2,4-dione;
1-(3-aminomethylpyrid-4-ylmethyl)-3-(4-trifluoromethoxyphenyl)imidazolidine-2,4-dione;
5,5-dimethyl-1-(2-methylpyrid-4-ylmethyl)3-(4-trifluoromethanesulfanylphenyl)imidazolidine-2,4-dione;
5,5-dimethyl-1-(2-ethylpyrid-4-ylmethyl)-3-(4-trifluoromethanesulfanylphenyl)imidazolidine-2,4-dione;
5,5-dimethyl-1-(2-isopropylpyrid-4-ylmethyl)-3-(4-trifluoromethanesulfanylphenyl)imidazolidine-2,4-dione;
5,5-dimethyl-1-(2-tert-butylpyrid-4-ylmethyl)-3-(4-trifluoromethanesulfanylphenyl)imidazolidine-2,4-dione;
5,5-dimethyl-1-(2-isobutylpyrid-4-ylmethyl)-3-(4-trifluoromethanesulfanylphenyl)imidazolidine-2,4-dione;
5,5-dimethyl-1-(2-cyclohexylpyrid-4-ylmethyl)-3-(4-trifluoromethanesulfanylphenyl)imidazolidine-2,4-dione;
5,5-dimethyl-1-(2-phenylpyrid-4-ylmethyl)-3-(4-trifluoromethanesulfanylphenyl)imidazolidine-2,4-dione;
5,5-dimethyl-1-[2-(4-chlorophenyl)pyrid-4-ylmethyl]-3-(4-trifluoromethanesulfanylphenyl)imidazolidine-2,4-dione;
5,5-dimethyl-1-[2-(3-chlorophenyl)pyrid-4-ylmethyl]-3-(4-trifluoromethanesulfanylphenyl)imidazolidine-2,4-dione;
5,5-dimethyl-1-[2-(2-chlorophenyl)pyrid-4-ylmethyl]-3-(4-trifluoromethanesulfanylphenyl)imidazolidine-2,4-dione;
5,5-dimethyl-1-[2-(4-fluorophenyl)pyrid-4-ylmethyl]-3-(4-trifluoromethanesulfanylphenyl)imidazolidine-2,4-dione;
5,5-dimethyl-1-[2-(4-methoxyphenyl)pyrid-4-ylmethyl]-3-(4-trifluoromethanesulfanylphenyl)imidazolidine-2,4-dione;
5,5-dimethyl-1-(2-benzylpyrid-4-ylmethyl)-3-(4-trifluoromethanesulfanylphenyl)imidazolidine-2,4-dione;
5,5-dimethyl-1-(2,2'-bipyrid-4-ylmethyl)-3-(4-trifluoromethanesulfanylphenyl)imidazolidine-2,4-dione;
5,5-dimethyl-1-(2-hydroxymethylpyrid-4-ylmethyl)-3-(4-trifluoromethanesulfanylphenyl)imidazolidine-2,4-dione;
5,5-dimethyl-1-(2-chloropyrid-4-ylmethyl)-3-(4-trifluoromethanesulfanylphenyl)imidazolidine-2,4-dione;
5,5-dimethyl-1-(2-fluoropyrid-4-ylmethyl)-3-(4-trifluoromethanesulfanylphenyl)imidazolidine-2,4-dione;
5,5-dimethyl-1-(2-bromopyrid-4-ylmethyl)-3-(4-trifluoromethanesulfanylphenyl)imidazolidine-2,4-dione;
5,5-dimethyl-1-(2-aminopyrid-4-ylmethyl)-3-(4-trifluoromethanesulfanylphenyl)imidazolidine-2,4-dione;
5,5-dimethyl-1-(2-methylaminopyrid-4-ylmethyl)-3-(4-trifluoromethanesulfanylphenyl)imidazolidine-2,4-dione;
5,5-dimethyl-1-(2-ethylaminopyrid-4-ylmethyl)-3-(4-trifluoromethanesulfanylphenyl)imidazolidine-2,4-dione;
5,5-dimethyl-1-(2-isopropylaminopyrid-4-ylmethyl)-3-(4-trifluoromethanesulfanylphenyl)imidazolidine-2,4-dione;
5,5-dimethyl-1-(2-phenylaminopyrid-4-ylmethyl)-3-(4-trifluoromethanesulfanylphenyl)imidazolidine-2,4-dione;
5,5-dimethyl-1-(2-cyclohexylaminopyrid-4-ylmethyl)-3-(4-trifluoromethanesulfanylphenyl)imidazolidine-2,4-dione;
5,5-dimethyl-1-(2-diethylaminopyrid-4-ylmethyl)-3-(4-trifluoromethanesulfanylphenyl)imidazolidine-2,4-dione;
5,5-dimethyl-1-(2-N-cyclohexyl-N-methylaminopyrid-4-ylmethyl)-3-(4-trifluoromethanesulfanylphenyl)imidazolidine-2,4-dione;
5,5-dimethyl-1-(2-piperidinopyrid-4-ylmethyl)-3-(4-trifluoromethanesulfanylphenyl)imidazolidine-2,4-dione;
5,5-dimethyl-1-(2-morpholinopyrid-4-ylmethyl)-3-(4-trifluoromethanesulfanylphenyl)imidazolidine-2,4-dione;
5,5-dimethyl-1-[2-(4-methylpiperazino)pyrid-4-ylmethyl]-3-(4-trifluoromethanesulfanylphenyl)imidazolidine-2,4-dione;
5,5-dimethyl-1-[2-(1H-pyrazol-1-yl)pyrid-4-ylmethyl]-3-(4-trifluoromethanesulfanylphenyl)imidazolidine-2,4-dione;
5,5-dimethyl-1-[2-(2-benzoylhydrazino)pyrid-4-ylmethyl]-3-(4-trifluoromethanesulfanylphenyl)imidazolidine-2,4-dione;
5,5-dimethyl-1-(2-benzoylaminopyrid-4-ylmethyl)-3-(4-trifluoromethanesulfanylphenyl)imidazolidine-2,4-dione;

5,5-dimethyl-1-[2-(4-chlorobenzoylamino)pyrid-4-ylmethyl]-3-(4-trifluoromethanesulfanylphenyl)imidazolidine-2,4-dione;
5,5-dimethyl-1-[2-(3-chlorobenzoylamino)pyrid-4-ylmethyl]-3-(4-trifluoromethanesulfanylphenyl)imidazolidine-2,4-dione;
5,5-dimethyl-1-[2-(2-chlorobenzoylamino)pyrid-4-ylmethyl]-3-(4-trifluoromethanesulfanylphenyl)imidazolidine-2,4-dione;
5,5-dimethyl-1-[2-(4-fluorobenzoylamino)pyrid-4-ylmethyl]-3-(4-trifluoromethanesulfanylphenyl)imidazolidine-2,4-dione;
5,5-dimethyl-1-[2-(4-methoxybenzoylamino)pyrid-4-ylmethyl]-3-(4-trifluoromethanesulfanylphenyl)imidazolidine-2,4-dione;
5,5-dimethyl-1-(2-acetamidopyrid-4-ylmethyl)-3-(4-trifluoromethanesulfanylphenyl)imidazolidine-2,4-dione;
5,5-dimethyl-1-(2-phenylacetamidopyrid-4-ylmethyl)-3-(4-trifluoromethanesulfanylphenyl)imidazolidine-2,4-dione;
5,5-dimethyl-1-[2-(4-methylpiperazino)acetamidopyrid-4-ylmethyl]-3-(4-trifluoromethanesulfanylphenyl)imidazolidine-2,4-dione;
5,5-dimethyl-1-(2-cyclohexanylcarboxamidopyrid-4-ylmethyl)-3-(4-trifluoromethanesulfanylphenyl)imidazolidine-2,4-dione;
5,5-dimethyl-1-[2-(1-methyl-4-piperidinyl)carbonylaminopyrid-4-ylmethyl]-3-(4-trifluoromethanesulfanylphenyl)imidazolidine-2,4-dione;
5,5-dimethyl-1-[2-(2-furanylcarbonyl)aminopyrid-4-ylmethyl]-3-(4-trifluoromethanesulfanylphenyl)imidazolidine-2,4-dione;
5,5-dimethyl-1-(2-ethoxycarbonylaminopyrid-4-ylmethyl)-3-(4-trifluoromethanesulfanylphenyl)imidazolidine-2,4-dione;
5,5-dimethyl-1-(2-isopropoxycarbonylaminopyrid-4-ylmethyl)-3-(4-trifluoromethanesulfanylphenyl)imidazolidine-2,4-dione;
5,5-dimethyl-1-(2-butoxycarbonylaminopyrid-4-ylmethyl)-3-(4-trifluoromethanesulfanylphenyl)imidazolidine-2,4-dione;
5,5-dimethyl-1-[2-(2-diethylaminoethoxycarbonylamino)pyrid-4-ylmethyl]-3-(4-trifluoromethanesulfanylphenyl)imidazolidine-2,4-dione;
5,5-dimethyl-1-(2-phenoxycarbonylaminopyrid-4-ylmethyl)-3-(4-trifluoromethanesulfanylphenyl)imidazolidine-2,4-dione;
5,5-dimethyl-1-[2-(4-chloroanilino)carbonylaminopyrid-4-ylmethyl]-3-(4-trifluoromethanesulfanylphenyl)imidazolidine-2,4-dione;
5,5-dimethyl-1-(2-anilinocarbonylaminopyrid-4-ylmethyl)-3-(4-trifluoromethanesulfanylphenyl)imidazolidine-2,4-dione;
5,5-dimethyl-1-(2-benzylaminocarbonylaminopyrid-4-ylmethyl)-3-(4-trifluoromethanesulfanylphenyl)imidazolidine-2,4-dione;
5,5-dimethyl-1-[2-(2-pyridylamino)carbonylaminopyrid-4-ylmethyl]-3-(4-trifluoromethanesulfanylphenyl)imidazolidine-2,4-dione;
5,5-dimethyl-1-(2-ureidopyrid-4-ylmethyl)-3-(4-trifluoromethanesulfanylphenyl)imidazolidine-2,4-dione;
5,5-dimethyl-1-(2-benzylaminosulfonylaminopyrid-4-ylmethyl)-3-(4-trifluoromethanesulfanylphenyl)imidazolidine-2,4-dione;
5,5-dimethyl-1-(2-methylaminosulfonylaminopyrid-4-ylmethyl)-3-(4-trifluoromethanesulfanylphenyl)imidazolidine-2,4-dione;
5,5-dimethyl-1-(2-aminosulfonylaminopyrid-4-ylmethyl)-3-(4-trifluoromethanesulfanylphenyl)imidazolidine-2,4-dione;
5,5-dimethyl-1-(2-morpholinosulfonylaminopyrid-4-ylmethyl)-3-(4-trifluoromethanesulfanylphenyl)imidazolidine-2,4-dione;
5,5-dimethyl-1-(2-dimethylaminosulfonylaminopyrid-4-ylmethyl)-3-(4-trifluoromethanesulfanylphenyl)imidazolidine-2,4-dione;
5,5-dimethyl-1-(2-anilinosulfonylaminopyrid-4-ylmethyl)-3-(4-trifluoromethanesulfanylphenyl)imidazolidine-2,4-dione;
5,5-dimethyl-1-(2-phenylsulfonylaminopyrid-4-ylmethyl)-3-(4-trifluoromethanesulfanylphenyl)imidazolidine-2,4-dione;
5,5-dimethyl-1-[2-(2-thienyl)sulfonylaminopyrid-4-ylmethyl]-3-(4-trifluoromethanesulfanylphenyl)imidazolidine-2,4-dione;
5,5-dimethyl-1-(2-methylsulfonylaminopyrid-4-ylmethyl)-3-(4-trifluoromethanesulfanylphenyl)imidazolidine-2,4-dione;
5,5-dimethyl-1-[2-(4-chlorophenyl)sulfonylaminopyrid-4-ylmethyl]-3-(4-trifluoromethanesulfanylphenyl)imidazolidine-2,4-dione;
5,5-dimethyl-1-(2-benzylsulfonylaminopyrid-4-ylmethyl)-3-(4-trifluoromethanesulfanylphenyl)imidazolidine-2,4-dione;
5,5-dimethyl-1-(2-hydroxycarbonylpyrid-4-ylmethyl)-3-(4-trifluoromethanesulfanylphenyl)imidazolidine-2,4-dione;
5,5-dimethyl-1-(2-ethoxycarbonylpyrid-4-ylmethyl)-3-(4-trifluoromethanesulfanylphenyl)imidazolidine-2,4-dione;
5,5-dimethyl-1-(2-tert-butoxycarbonylpyrid-4-ylmethyl)-3-(4-trifluoromethanesulfanylphenyl)imidazolidine-2,4-dione;
5,5-dimethyl-1-(2-phenoxycarbonylpyrid-4-ylmethyl)-3-(4-trifluoromethanesulfanylphenyl)imidazolidine-2,4-dione;
5,5-dimethyl-1-[2-(4-methylpiperazinocarbonyl)pyrid-4-ylmethyl]-3-(4-trifluoromethanesulfanylphenyl)imidazolidine-2,4-dione;
5,5-dimethyl-1-[2-(methylamino)carbonylpyrid-4-ylmethyl]-3-(4-trifluoromethanesulfanylphenyl)imidazolidine-2,4-dione;
5,5-dimethyl-1-[2-(dimethylamino)carbonylpyrid-4-ylmethyl]-3-(4-trifluoromethanesulfanylphenyl)imidazolidine-2,4-dione;
5,5-dimethyl-1-(2-piperidinocarbonylpyrid-4-ylmethyl)-3-(4-trifluoromethanesulfanylphenyl)imidazolidine-2,4-dione;
5,5-dimethyl-1-(2-morpholinocarbonylpyrid-4-ylmethyl)-3-(4-trifluoromethanesulfanylphenyl)imidazolidine-2,4-dione;
5,5-dimethyl-1-[2-(4-phenylpiperazinocarbonyl)pyrid-4-ylmethyl]-3-(4-trifluoromethanesulfanylphenyl)imidazolidine-2,4-dione;
5,5-dimethyl-1-(2-phenylaminocarbonylpyrid-4-ylmethyl)-3-(4-trifluoromethanesulfanylphenyl)imidazolidine-2,4-dione;
5,5-dimethyl-1-[2-methylphenylamino)carbonylpyrid-4-ylmethyl]-3-(4-trifluoromethanesulfanylphenyl)imidazolidine-2,4-dione;
5,5-dimethyl-1-[2-(4-methoxyphenyl)methylaminocarbonylpyrid-4-ylmethyl]-3-(4-trifluoromethanesulfanylphenyl)imidazolidine-2,4-dione;
5,5-dimethyl-1-[2-(4-chlorophenyl)methylaminocarbonylpyrid-4-ylmethyl]-3-(4-trifluoromethanesulfanylphenyl)imidazolidine-2,4-dione;

5,5-dimethyl-1-[2-(4-morpholinylamino)carbonylpyrid-4-ylmethyl]-3-(4-trifluoromethanesulfanylphenyl)imidazolidine-2,4-dione;

5,5-dimethyl-1-(2-aminocarbonylpyrid-4-ylmethyl)-3-(4-trifluoromethanesulfanylphenyl)imidazolidine-2,4-dione;

5,5-dimethyl-1-(2-phenoxypyrid-4-ylmethyl)-3-(4-trifluoromethanesulfanylphenyl)imidazolidine-2,4-dione;

5,5-dimethyl-1-(2-methoxypyrid-4-ylmethyl)-3-(4-trifluoromethanesulfanylphenyl)imidazolidine-2,4-dione;

5,5-dimethyl-1-(2-ethoxypyrid-4-ylmethyl)-3-(4-trifluoromethanesulfanylphenyl)imidazolidine-2,4-dione;

5,5-dimethyl-1-[2-(1-pyrrolidinyl)ethoxypyrid-4-ylmethyl]-3-(4-trifluoromethanesulfanylphenyl)imidazolidine-2,4-dione;

5,5-dimethyl-1-(2-benzyloxypyrid-4-ylmethyl)-3-(4-trifluoromethanesulfanylphenyl)imidazolidine-2,4-dione;

5,5-dimethyl-1-(2-benzoyloxypyrid-4-ylmethyl)-3-(4-trifluoromethanesulfanylphenyl)imidazolidine-2,4-dione;

5,5-dimethyl-1-[2-(4,5-dihydro-1H-imidazol-2-yl)pyrid-4-ylmethyl]-3-(4-trifluoromethanesulfanylphenyl)imidazolidine-2,4-dione;

5,5-dimethyl-1-[2-(1H-imidazol-2-yl)pyrid-4-ylmethyl]-3-(4-trifluoromethanesulfanylphenyl)imidazolidine-2,4-dione;

5,5-dimethyl-1-[2-(1H-tetrazol-5-yl)pyrid-4-ylmethyl]-3-(4-trifluoromethanesulfanylphenyl)imidazolidine-2,4-dione;

5,5-dimethyl-1-(2-amidinopyrid-4-ylmethyl)-3-(4-trifluoromethanesulfanylphenyl)imidazolidine-2,4-dione;

5,5-dimethyl-1-(2-dimethylaminomethylpyrid-4-ylmethyl)-3-(4-trifluoromethanesulfanylphenyl)imidazolidine-2,4-dione;

5,5-dimethyl-1-(2-aminomethylpyrid-4-ylmethyl)-3-(4-trifluoromethanesulfanylphenyl)imidazolidine-2,4-dione;

5,5-dimethyl-1-(3-methylpyrid-4-ylmethyl)-3-(4-trifluoromethanesulfanylphenyl)imidazolidine-2,4-dione;

5,5-dimethyl-1-(3-ethylpyrid-4-ylmethyl)-3-(4-trifluoromethanesulfanylphenyl)imidazolidine-2,4-dione;

5,5-dimethyl-1-(3-isopropylpyrid-4-ylmethyl)-3-(4-trifluoromethanesulfanylphenyl)imidazolidine-2,4-dione;

5,5-dimethyl-1-(3-tert-butylpyrid-4-ylmethyl)-3-(4-trifluoromethanesulfanylphenyl)imidazolidine-2,4-dione;

5,5-dimethyl-1-(3-isobutylpyrid-4-ylmethyl)-3-(4-trifluoromethanesulfanylphenyl)imidazolidine-2,4-dione;

5,5-dimethyl-1-(3-cyclohexylpyrid-4-ylmethyl)-3-(4-trifluoromethanesulfanylphenyl)imidazolidine-2,4-dione;

5,5-dimethyl-1-(3-phenylpyrid-4-ylmethyl)-3-(4-trifluoromethanesulfanylphenyl)imidazolidine-2,4-dione;

5,5-dimethyl-1-[3-(4-chlorophenyl)pyrid-4-ylmethyl]-3-(4-trifluoromethanesulfanylphenyl)imidazolidine-2,4-dione;

5,5-dimethyl-1-[3-(3-chlorophenyl)pyrid-4-ylmethyl]-3-(4-trifluoromethanesulfanylphenyl)imidazolidine-2,4-dione;

5,5-dimethyl-1-[3-(2-chlorophenyl)pyrid-4-ylmethyl]-3-(4-trifluoromethanesulfanylphenyl)imidazolidine-2,4-dione;

5,5-dimethyl-1-[3-(4-fluorophenyl)pyrid-4-ylmethyl]-3-(4-trifluoromethanesulfanylphenyl)imidazolidine-2,4-dione;

5,5-dimethyl-1-[3-(4-methoxyphenyl)pyrid-4-ylmethyl]-3-(4-trifluoromethanesulfanylphenyl)imidazolidine-2,4-dione;

5,5-dimethyl-1-(3-benzylpyrid-4-ylmethyl)-3-(4-trifluoromethanesulfanylphenyl)imidazolidine-2,4-dione;

5,5-dimethyl-1-(3,2'-bipyrid-4-ylmethyl)-3-(4-trifluoromethanesulfanylphenyl)imidazolidine-2,4-dione;

5,5-dimethyl-1-(3-hydroxymethylpyrid-4-ylmethyl)-3-(4-trifluoromethanesulfanylphenyl)imidazolidine-2,4-dione;

5,5-dimethyl-1-(3-chloropyrid-4-ylmethyl)-3-(4-trifluoromethanesulfanylphenyl)imidazolidine-2,4-dione;

5,5-dimethyl-1-(3-fluoropyrid-4-ylmethyl)-3-(4-trifluoromethanesulfanylphenyl)imidazolidine-2,4-dione;

5,5-dimethyl-1-(3-bromopyrid-4-ylmethyl)-3-(4-trifluoromethanesulfanylphenyl)imidazolidine-2,4-dione;

5,5-dimethyl-1-(3-aminopyrid-4-ylmethyl)-3-(4-trifluoromethanesulfanylphenyl)imidazolidine-2,4-dione;

5,5-dimethyl-1-(3-methylaminopyrid-4-ylmethyl)-3-(4-trifluoromethanesulfanylphenyl)imidazolidine-2,4-dione;

5,5-dimethyl-1-(3-ethylaminopyrid-4-ylmethyl)-3-(4-trifluoromethanesulfanylphenyl)imidazolidine-2,4-dione;

5,5-dimethyl-1-(3-isopropylaminopyrid-4-ylmethyl)-3-(4-trifluoromethanesulfanylphenyl)imidazolidine-2,4-dione;

5,5-dimethyl-1-(3-phenylaminopyrid-4-ylmethyl)-3-(4-trifluoromethanesulfanylphenyl)imidazolidine-2,4-dione;

5,5-dimethyl-1-(3-cyclohexylaminopyrid-4-ylmethyl)-3-(4-trifluoromethanesulfanylphenyl)imidazolidine-2,4-dione;

5,5-dimethyl-1-(3-diethylaminopyrid-4-ylmethyl)-3-(4-trifluoromethanesulfanylphenyl)imidazolidine-2,4-dione;

5,5-dimethyl-1-(3-N-cyclohexyl-N-methylaminopyrid-4-ylmethyl)-3-(4-trifluoromethanesulfanylphenyl)imidazolidine-2,4-dione;

5,5-dimethyl-1-(3-piperidinopyrid-4-ylmethyl)-3-(4-trifluoromethanesulfanylphenyl)imidazolidine-2,4-dione;

5,5-dimethyl-1-(3-morpholinopyrid-4-ylmethyl)-3-(4-trifluoromethanesulfanylphenyl)imidazolidine-2,4-dione;

5,5-dimethyl-1-[3-(4-methylpiperazino)pyrid-4-ylmethyl]-3-(4-trifluoromethanesulfanylphenyl)imidazolidine-2,4-dione;

5,5-dimethyl-1-[3-(1H-pyrazol-1-yl)pyrid-4-ylmethyl]-3-(4-trifluoromethanesulfanylphenyl)imidazolidine-2,4-dione;

5,5-dimethyl-1-[3-(2-benzoylhydrazino)pyrid-4-ylmethyl]-3-(4-trifluoromethanesulfanylphenyl)imidazolidine-2,4-dione;

5,5-dimethyl-1-(3-benzoylaminopyrid-4-ylmethyl)-3-(4-trifluoromethanesulfanylphenyl)imidazolidine-2,4-dione;

5,5-dimethyl-1-[3-(4-chlorobenzoylamino)pyrid-4-ylmethyl]-3-(4-trifluoromethanesulfanylphenyl)imidazolidine-2,4-dione;

5,5-dimethyl-1-[3-(3-chlorobenzoylamino)pyrid-4-ylmethyl]-3-(4-trifluoromethanesulfanylphenyl)imidazolidine-2,4-dione;

5,5-dimethyl-1-[3-(2-chlorobenzoylamino)pyrid-4-ylmethyl]-3-(4-trifluoromethanesulfanylphenyl)imidazolidine-2,4-dione;

5,5-dimethyl-1-[3-(4-fluorobenzoylamino)pyrid-4-ylmethyl]-3-(4-trifluoromethanesulfanylphenyl)imidazolidine-2,4-dione;

5,5-dimethyl-1-[3-(4-methoxybenzoylamino)pyrid-4-ylmethyl]-3-(4-trifluoromethanesulfanylphenyl)imidazolidine-2,4-dione;

5,5-dimethyl-1-(3-acetamidopyrid-4-ylmethyl)-3-(4-trifluoromethanesulfanylphenyl)imidazolidine-2,4-dione;

5,5-dimethyl-1-(3-phenylacetamidopyrid-4-ylmethyl)-3-(4-trifluoromethanesulfanylphenyl)imidazolidine-2,4-dione;

5,5-dimethyl-1-[3-(4-methylpiperazino)acetamidopyrid-4-ylmethyl]-3-(4-trifluoromethanesulfanylphenyl)imidazolidine-2,4-dione;

5,5-dimethyl-1-(3-cyclohexanylcarboxamidopyrid-4-ylmethyl)-3-(4-trifluoromethanesulfanylphenyl)imidazolidine-2,4-dione;

5,5-dimethyl-1-[3-(1-methyl-4-piperidinyl)carbonylaminopyrid-4-ylmethyl]-3-(4-trifluoromethanesulfanylphenyl)imidazolidine-2,4-dione;

5,5-dimethyl-1-[3-(2-furanylcarbonyl)aminopyrid-4-ylmethyl]-3-(4-trifluoromethanesulfanylphenyl)imidazolidine-2,4-dione;

5,5-dimethyl-1-(3-ethoxycarbonylaminopyrid-4-ylmethyl)-3-(4-trifluoromethanesulfanylphenyl)imidazolidine-2,4-dione;
5,5-dimethyl-1-(3-isopropoxycarbonylaminopyrid-4-ylmethyl)-3-(4-trifluoromethanesulfanylphenyl)imidazolidine-2,4-dione;
5,5-dimethyl-1-(3-butoxycarbonylaminopyrid-4-ylmethyl)-3-(4-trifluoromethanesulfanylphenyl)imidazolidine-2,4-dione;
5,5-dimethyl-1-[3-(2-diethylaminoethoxycarbonylamino)pyrid-4-ylmethyl]-3-(4-trifluoromethanesulfanylphenyl)imidazolidine-2,4-dione;
5,5-dimethyl-1-(3-phenoxycarbonylaminopyrid-4-ylmethyl)-3-(4-trifluoromethanesulfanylphenyl)imidazolidine-2,4-dione;
5,5-dimethyl-1-[3-(4-chloroanilino)carbonylaminopyrid-4-ylmethyl]-3-(4-trifluoromethanesulfanylphenyl)imidazolidine-2,4-dione;
5,5-dimethyl-1-(3-anilinocarbonylaminopyrid-4-ylmethyl)-3-(4-trifluoromethanesulfanylphenyl)imidazolidine-2,4-dione;
5,5-dimethyl-1-(3-benzylaminocarbonylaminopyrid-4-ylmethyl)-3-(4-trifluoromethanesulfanylphenyl)imidazolidine-2,4-dione;
5,5-dimethyl-1-[3-(2-pyridylamino)carbonylaminopyrid-4-ylmethyl]-3-(4-trifluoromethanesulfanylphenyl)imidazolidine-2,4-dione;
5,5-dimethyl-1-(3-ureidopyrid-4-ylmethyl)-3-(4-trifluoromethanesulfanylphenyl)imidazolidine-2,4-dione;
5,5-dimethyl-1-(3-benzylaminosulfonylaminopyrid-4-ylmethyl)-3-(4-trifluoromethanesulfanylphenyl)imidazolidine-2,4-dione;
5,5-dimethyl-1-(3-methylaminosulfonylaminopyrid-4-ylmethyl)-3-(4-trifluoromethanesulfanylphenyl)imidazolidine-2,4-dione;
5,5-dimethyl-1-(3-aminosulfonylaminopyrid-4-ylmethyl)-3-(4-trifluoromethanesulfanylphenyl)imidazolidine-2,4-dione;
5,5-dimethyl-1-(3-morpholinosulfonylaminopyrid-4-ylmethyl)-3-(4-trifluoromethanesulfanylphenyl)imidazolidine-2,4-dione;
5,5-dimethyl-1-(3-dimethylaminosulfonylaminopyrid-4-ylmethyl)-3-(4-trifluoromethanesulfanylphenyl)imidazolidine-2,4-dione;
5,5-dimethyl-1-(3-anilinosulfonylaminopyrid-4-ylmethyl)-3-(4-trifluoromethanesulfanylphenyl)imidazolidine-2,4-dione;
5,5-dimethyl-1-(3-phenylsulfonylaminopyrid-4-ylmethyl)-3-(4-trifluoromethanesulfanylphenyl)imidazolidine-2,4-dione;
5,5-dimethyl-1-[3-(2-thienyl)sulfonylaminopyrid-4-ylmethyl]-3-(4-trifluoromethanesulfanylphenyl)imidazolidine-2,4-dione;
5,5-dimethyl-1-(3-methylsulfonylaminopyrid-4-ylmethyl)-3-(4-trifluoromethanesulfanylphenyl)imidazolidine-2,4-dione;
5,5-dimethyl-1-[3-(4-chlorophenyl)sulfonylaminopyrid-4-ylmethyl]-3-(4-trifluoromethanesulfanylphenyl)imidazolidine-2,4-dione;
5,5-dimethyl-1-(3-benzylsulfonylaminopyrid-4-ylmethyl)-3-(4-trifluoromethanesulfanylphenyl)imidazolidine-2,4-dione;
5,5-dimethyl-1-(3-hydroxycarbonylpyrid-4-ylmethyl)-3-(4-trifluoromethanesulfanylphenyl)imidazolidine-2,4-dione;
5,5-dimethyl-1-(3-ethoxycarbonylpyrid-4-ylmethyl)-3-(4-trifluoromethanesulfanylphenyl)imidazolidine-2,4-dione;
5,5-dimethyl-1-(3-tert-butoxycarbonylpyrid-4-ylmethyl)-3-(4-trifluoromethanesulfanylphenyl)imidazolidine-2,4-dione;
5,5-dimethyl-1-(3-phenoxycarbonylpyrid-4-ylmethyl)-3-(4-trifluoromethanesulfanylphenyl)imidazolidine-2,4-dione;
5,5-dimethyl-1-[3-(4-methylpiperazinocarbonyl)pyrid-4-ylmethyl]-3-(4-trifluoromethanesulfanylphenyl)imidazolidine-2,4-dione;
5,5-dimethyl-1-[3-(methylamino)carbonylpyrid-4-ylmethyl]-3-(4-trifluoromethanesulfanylphenyl)imidazolidine-2,4-dione;
5,5-dimethyl-1-[3-(dimethylamino)carbonylpyrid-4-ylmethyl]-3-(4-trifluoromethanesulfanylphenyl)imidazolidine-2,4-dione;
5,5-dimethyl-1-(3-piperidinocarbonylpyrid-4-ylmethyl)-3-(4-trifluoromethanesulfanylphenyl)imidazolidine-2,4-dione;
5,5-dimethyl-1-(3-morpholinocarbonylpyrid-4-ylmethyl)-3-(4-trifluoromethanesulfanylphenyl)imidazolidine-2,4-dione;
5,5-dimethyl-1-[3-(4-phenylpiperazinocarbonyl)pyrid-4-ylmethyl]-3-(4-trifluoromethanesulfanylphenyl)imidazolidine-2,4-dione;
5,5-dimethyl-1-(3-phenylaminocarbonylpyrid-4-ylmethyl)-3-(4-trifluoromethanesulfanylphenyl)imidazolidine-2,4-dione;
5,5-dimethyl-1-[3-(methylphenylamino)carbonylpyrid-4-ylmethyl]-3-(4-trifluoromethanesulfanylphenyl)imidazolidine-2,4-dione;
5,5-dimethyl-1-[3-(4-methoxyphenyl)methylaminocarbonylpyrid-4-ylmethyl]-3-(4-trifluoromethanesulfanylphenyl)imidazolidine-2,4-dione;
5,5-dimethyl-1-[3-(4-chlorophenyl)methylaminocarbonylpyrid-4-ylmethyl]-3-(4-trifluoromethanesulfanylphenyl)imidazolidine-2,4-dione;
5,5-dimethyl-1-[3-(4-morpholinylamino)carbonylpyrid-4-ylmethyl]-3-(4-trifluoromethanesulfanylphenyl)imidazolidine-2,4-dione;
5,5-dimethyl-1-(3-aminocarbonylpyrid-4-ylmethyl)-3-(4-trifluoromethanesulfanylphenyl)imidazolidine-2,4-dione;
5,5-dimethyl-1-(3-phenoxypyrid-4-ylmethyl)-3-(4-trifluoromethanesulfanylphenyl)imidazolidine-2,4-dione;
5,5-dimethyl-1-(3-methoxypyrid-4-ylmethyl)-3-(4-trifluoromethanesulfanylphenyl)imidazolidine-2,4-dione;
5,5-dimethyl-1-(3-ethoxypyrid-4-ylmethyl)-3-(4-trifluoromethanesulfanylphenyl)imidazolidine-2,4-dione;
5,5-dimethyl-1-[3-(1-pyrrolidinyl)ethoxypyrid-4-ylmethyl]-3-(4-trifluoromethanesulfanylphenyl)imidazolidine-2,4-dione;
5,5-dimethyl-1-(3-benzyloxypyrid-4-ylmethyl)-3-(4-trifluoromethanesulfanylphenyl)imidazolidine-2,4-dione;
5,5-dimethyl-1-(3-benzoyloxypyrid-4-ylmethyl)-3-(4-trifluoromethanesulfanylphenyl)imidazolidine-2,4-dione;
5,5-dimethyl-1-[3-(4,5-dihydro-1H-imidazol-2-yl)pyrid-4-ylmethyl]-3-(4-trifluoromethanesulfanylphenyl)imidazolidine-2,4-dione;
5,5-dimethyl-1-[3-(1H-imidazol-2-yl)pyrid-4-ylmethyl]-3-(4-trifluoromethanesulfanylphenyl)imidazolidine-2,4-dione;
5,5-dimethyl-1-[3-(1H-tetrazol-5-yl)pyrid-4-ylmethyl]-3-(4-trifluoromethanesulfanylphenyl)imidazolidine-2,4-dione;
5,5-dimethyl-1-(3-amidinopyrid-4-ylmethyl)-3-(4-trifluoromethanesulfanylphenyl)imidazolidine-2,4-dione;
5,5-dimethyl-1-(3-dimethylaminomethylpyrid-4-ylmethyl)-3-(4-trifluoromethanesulfanylphenyl)imidazolidine-2,4-dione;

5,5-dimethyl-1-(3-aminomethylpyrid-4-ylmethyl)-3-(4-trifluoromethanesulfanylphenyl)imidazolidine-2,4-dione;
4-(2-methylpyridin)-4-ylmethyl-6-(4-trifluoromethanesulfanylphenyl)-4,6-diazaspiro[2.4]heptane-5,7-dione;
4-(2-ethylpyridin)-4-ylmethyl-6-(4-trifluoromethanesulfanylphenyl)-4,6-diazaspiro[2.4]heptane-5,7-dione;
4-(2-isopropylpyridin)-4-ylmethyl-6-(4-trifluoromethanesulfanylphenyl)-4,6-diazaspiro[2.4]heptane-5,7-dione;
4-(2-tert-butylpyridin)-4-ylmethyl-6-(4-trifluoromethanesulfanylphenyl)-4,6-diazaspiro[2.4]heptane-5,7-dione;
4-(2-isobutylpyridin)-4-ylmethyl-6-(4-trifluoromethanesulfanylphenyl)-4,6-diazaspiro[2.4]heptane-5,7-dione;
4-(2-cyclohexylpyridin)-4-ylmethyl-6-(4-trifluoromethanesulfanylphenyl)-4,6-diazaspiro[2.4]heptane-5,7-dione;
4-(2-phenylpyridin)-4-ylmethyl-6-(4-trifluoromethanesulfanylphenyl)-4,6-diazaspiro[2.4]heptane-5,7-dione;
4-[2-(4-chlorophenyl)pyridin]-4-ylmethyl-6-(4-trifluoromethanesulfanylphenyl)-4,6-diazaspiro[2.4]heptane-5,7-dione;
4-[2-(3-chlorophenyl)pyridin]-4-ylmethyl-6-(4-trifluoromethanesulfanylphenyl)-4,6-diazaspiro[2.4]heptane-5,7-dione;
4-[2-(2-chlorophenyl)pyridin]-4-ylmethyl-6-(4-trifluoromethanesulfanylphenyl)-4,6-diazaspiro[2.4]heptane-5,7-dione;
4-[2-(4-fluorophenyl)pyridin]-4-ylmethyl-6-(4-trifluoromethanesulfanylphenyl)-4,6-diazaspiro[2.4]heptane-5,7-dione;
4-[2-(4-methoxyphenyl)pyridin]-4-ylmethyl-6-(4-trifluoromethanesulfanylphenyl)-4,6-diazaspiro[2.4]heptane-5,7-dione;
4-(2-benzylpyridin)-4-ylmethyl-6-(4-trifluoromethanesulfanylphenyl)-4,6-diazaspiro[2.4]heptane-5,7-dione;
4-(2,2'-bipyridin)-4-ylmethyl-6-(4-trifluoromethanesulfanylphenyl)-4,6-diazaspiro[2.4]heptane-5,7-dione;
4-(2-hydroxymethylpyridine)-4-ylmethyl-6-(4-trifluoromethanesulfanylphenyl)-4,6-diazaspiro[2.4]heptane-5,7-dione;
4-(2-chloropyridin)-4-ylmethyl-6-(4-trifluoromethanesulfanylphenyl)-4,6-diazaspiro[2.4]heptane-5,7-dione;
4-(2-fluoropyridin)-4-ylmethyl-6-(4-trifluoromethanesulfanylphenyl)-4,6-diazaspiro[2.4]heptane-5,7-dione;
4-(2-bromopyridin)-4-ylmethyl-6-(4-trifluoromethanesulfanylphenyl)-4,6-diazaspiro[2.4]heptane-5,7-dione;
4-(2-aminopyridine)-4-ylmethyl-6-(4-trifluoromethanesulfanylphenyl)-4,6-diazaspiro[2.4]heptane-5,7-dione;
4-(2-methylaminopyridin)-4-ylmethyl-6-(4-trifluoromethanesulfanylphenyl)-4,6-diazaspiro[2.4]heptane-5,7-dione;
4-(2-ethylaminopyridin)-4-ylmethyl-6-(4-trifluoromethanesulfanylphenyl)-4,6-diazaspiro[2.4]heptane-5,7-dione;
4-(2-isopropylaminopyridin)-4-ylmethyl-6-(4-trifluoromethanesulfanylphenyl)-4,6-diazaspiro[2.4]heptane-5,7-dione;
4-(2-phenylaminopyridin)-4-ylmethyl-6-(4-trifluoromethanesulfanylphenyl)-4,6-diazaspiro[2.4]heptane-5,7-dione;
4-(2-cyclohexylaminopyridin)-4-ylmethyl-6-(4-trifluoromethanesulfanylphenyl)-4,6-diazaspiro[2.4]heptane-5,7-dione;
4-(2-diethylaminopyridine)-4-ylmethyl-6-(4-trifluoromethanesulfanylphenyl)-4,6-diazaspiro[2.4]heptane-5,7-dione;
4-(2-N-cyclohexyl-N-methylaminopyridin)-4-ylmethyl-6-(4-trifluoromethanesulfanylphenyl)-4,6-diazaspiro[2.4]heptane-5,7-dione;
4-(2-piperidinopyridine)-4-ylmethyl-6-(4-trifluoromethanesulfanylphenyl)-4,6-diazaspiro[2.4]heptane-5,7-dione;
4-(2-morpholinopyridin)-4-ylmethyl-6-(4-trifluoromethanesulfanylphenyl)-4,6-diazaspiro[2.4]heptane-5,7-dione;
4-[2-(4-methylpiperazino)pyridin]-4-ylmethyl-6-(4-trifluoromethanesulfanylphenyl)-4,6-diazaspiro[2.4]heptane-5,7-dione;
4-[2-(1H-pyrazol-1-yl)pyridin]-4-ylmethyl-6-(4-trifluoromethanesulfanylphenyl)-4,6-diazaspiro[2.4]heptane-5,7-dione;
4-[2-(2-benzoylhydrazino)pyridin]-4-ylmethyl-6-(4-trifluoromethanesulfanylphenyl)-4,6-diazaspiro[2.4]heptane-5,7-dione;
4-(2-benzoylaminopyridin)-4-ylmethyl-6-(4-trifluoromethanesulfanylphenyl)-4,6-diazaspiro[2.4]heptane-5,7-dione;
4-[2-(4-chlorobenzoylamino)pyridin]-4-ylmethyl-6-(4-trifluoromethanesulfanylphenyl)-4,6-diazaspiro[2.4]heptane-5,7-dione;
4-[2-(3-chlorobenzoylamino)pyridin]-4-ylmethyl-6-(4-trifluoromethanesulfanylphenyl)-4,6-diazaspiro[2.4]heptane-5,7-dione;
4-[2-(2-chlorobenzoylamino)pyridin]-4-ylmethyl-6-(4-trifluoromethanesulfanylphenyl)-4,6-diazaspiro[2.4]heptane-5,7-dione;
4-[2-(4-fluorobenzoylamino)pyridin]-4-ylmethyl-6-(4-trifluoromethanesulfanylphenyl)-4,6-diazaspiro[2.4]heptane-5,7-dione;
4-[2-(4-methoxybenzoylamino)pyridin]-4-ylmethyl-6-(4-trifluoromethanesulfanylphenyl)-4,6-diazaspiro[2.4]heptane-5,7-dione;
4-(2-acetamidopyridin)-4-ylmethyl-6-(4-trifluoromethanesulfanylphenyl)-4,6-diazaspiro[2.4]heptane-5,7-dione;
4-(2-phenylacetamidopyridin)-4-ylmethyl-6-(4-trifluoromethanesulfanylphenyl)-4,6-diazaspiro[2.4]heptane-5,7-dione;
4-[2-(4-methylpiperazino)acetamidopyridin]-4-ylmethyl-6-(4-trifluoromethanesulfanylphenyl)-4,6-diazaspiro[2.4]heptane-5,7-dione;
4-(2-cyclohexanylcarboxamidopyridin)-4-ylmethyl-6-(4-trifluoromethanesulfanylphenyl)-4,6-diazaspiro[2.4]heptane-5,7-dione;
4-[2-(1-methyl-4-piperidinyl)carbonylaminopyridin]-4-ylmethyl-6-(4-trifluoromethanesulfanylphenyl)-4,6-diazaspiro[2.4]heptane-5,7-dione;
4-[2-(2-furanylcarbonyl)aminopyridin]-4-ylmethyl-6-(4-trifluoromethanesulfanylphenyl)-4,6-diazaspiro[2.4]heptane-5,7-dione;
4-(2-ethoxycarbonylaminopyridin)-4-ylmethyl-6-(4-trifluoromethanesulfanylphenyl)-4,6-diazaspiro[2.4]heptane-5,7-dione;
4-(2-isopropoxycarbonylaminopyridin)-4-ylmethyl-6-(4-trifluoromethanesulfanylphenyl)-4,6-diazaspiro[2.4]heptane-5,7-dione;
4-(2-butoxycarbonylaminopyridin)-4-ylmethyl-6-(4-trifluoromethanesulfanylphenyl)-4,6-diazaspiro[2.4]heptane-5,7-dione;
4-[2-(2-diethylaminoethoxycarbonylamino)pyridin]-4-ylmethyl-6-(4-trifluoromethanesulfanylphenyl)-4,6-diazaspiro[2.4]heptane-5,7-dione;
4-(2-phenoxycarbonylaminopyridin)-4-ylmethyl-6-(4-trifluoromethanesulfanylphenyl)-4,6-diazaspiro[2.4]heptane-5,7-dione;
4-[2-(4-chloroanilino)carbonylaminopyridin]-4-ylmethyl-6-(4-trifluoromethanesulfanylphenyl)-4,6-diazaspiro[2.4]heptane-5,7-dione;

4-(2-anilinocarbonylaminopyridin)-4-ylmethyl-6-(4-trifluoromethanesulfanylphenyl)-4,6-diazaspiro[2.4]heptane-5,7-dione;

4-(2-benzylaminocarbonylaminopyridin)-4-ylmethyl-6-(4-trifluoromethanesulfanylphenyl)-4,6-diazaspiro[2.4]heptane-5,7-dione;

4-[2-(2-pyridylamino)carbonylaminopyridin]-4-ylmethyl-6-(4-trifluoromethanesulfanylphenyl)-4,6-diazaspiro[2.4]heptane-5,7-dione;

4-(2-ureidopyridin)-4-ylmethyl-6-(4-trifluoromethanesulfanylphenyl)-4,6-diazaspiro[2.4]heptane-5,7-dione;

4-(2-benzylaminosulfonylaminopyridin)-4-ylmethyl-6-(4-trifluoromethanesulfanylphenyl)-4,6-diazaspiro[2.4]heptane-5,7-dione;

4-(2-methylaminosulfonylaminopyridin)-4-ylmethyl-6-(4-trifluoromethanesulfanylphenyl)-4,6-diazaspiro[2.4]heptane-5,7-dione;

4-(2-aminosulfonylaminopyridin)-4-ylmethyl-6-(4-trifluoromethanesulfanylphenyl)-4,6-diazaspiro[2.4]heptane-5,7-dione;

4-(2-morpholinosulfonylaminopyridin)-4-ylmethyl-6-(4-trifluoromethanesulfanylphenyl)-4,6-diazaspiro[2.4]heptane-5,7-dione;

4-(2-dimethylaminosulfonylaminopyridin)-4-ylmethyl-6-(4-trifluoromethanesulfanylphenyl)-4,6-diazaspiro[2.4]heptane-5,7-dione;

4-(2-aniliosulfonylaminopyridin)-4-ylmethyl-6-(4-trifluoromethanesulfanylphenyl)-4,6-diazaspiro[2.4]heptane-5,7-dione;

4-(2-phenylsulfonylaminopyridin)-4-ylmethyl-6-(4-trifluoromethanesulfanylphenyl)-4,6-diazaspiro[2.4]heptane-5,7-dione;

4-[2-(2-thienyl)sulfonylaminopyridin]-4-ylmethyl-6-(4-trifluoromethanesulfanylphenyl)-4,6-diazaspiro[2.4]heptane-5,7-dione;

4-(2-methylsulfonylaminopyridin)-4-ylmethyl-6-(4-trifluoromethanesulfanylphenyl)-4,6-diazaspiro[2.4]heptane-5,7-dione;

4-[2-(4-chlorophenyl)sulfonylaminopyridin]-4-ylmethyl-6-(4-trifluoromethanesulfanylphenyl)-4,6-diazaspiro[2.4]heptane-5,7-dione;

4-(2-benzylsulfonylaminopyridin)-4-ylmethyl-6-(4-trifluoromethanesulfanylphenyl)-4,6-diazaspiro[2.4]heptane-5,7-dione;

4-(2-hydroxycarbonylpyridin)-4-ylmethyl-6-(4-trifluoromethanesulfanylphenyl)-4,6-diazaspiro[2.4]heptane-5,7-dione;

4-(2-ethoxycarbonylpyridin)-4-ylmethyl-6-(4-trifluoromethanesulfanylphenyl)-4,6-diazaspiro[2.4]heptane-5,7-dione;

4-(2-tert-butoxycarbonylpyridin)-4-ylmethyl-6-(4-trifluoromethanesulfanylphenyl)-4,6-diazaspiro[2.4]heptane-5,7-dione;

4-(2-phenoxycarbonylpyridin)-4-ylmethyl-6-(4-trifluoromethanesulfanylphenyl)-4,6-diazaspiro[2.4]heptane-5,7-dione;

4-[2-(4-methylpiperazinocarbonyl)pyridin]-4-ylmethyl-6-(4-trifluoromethanesulfanylphenyl)-4,6-diazaspiro[2.4]heptane-5,7-dione;

4-[2-(methylamino)carbonylpyridin]-4-ylmethyl-6-(4-trifluoromethanesulfanylphenyl)-4,6-diazaspiro[2.4]heptane-5,7-dione;

4-[2-dimethylamino)carbonylpyridin]-4-ylmethyl-6-(4-trifluoromethanesulfanylphenyl)-4,6-diazaspiro[2.4]heptane-5,7-dione;

4-(2-piperidinocarbonylpyridin)-4-ylmethyl-6-(4-trifluoromethanesulfanylphenyl)-4,6-diazaspiro[2.4]heptane-5,7-dione;

4-(2-morpholinocarbonylpyridin)-4-ylmethyl-6-(4-trifluoromethanesulfanylphenyl)-4,6-diazaspiro[2.4]heptane-5,7-dione;

4-[2-(4-phenylpiperazinocarbonyl)pyridin]-4-ylmethyl-6-(4-trifluoromethanesulfanylphenyl)-4,6-diazaspiro[2.4]heptane-5,7-dione;

4-(2-phenylaminocarbonylpyridin)-4-ylmethyl-6-(4-trifluoromethanesulfanylphenyl)-4,6-diazaspiro[2.4]heptane-5,7-dione;

4-[2-(methylphenylamino)carbonylpyridin]-4-ylmethyl-6-(4-trifluoromethanesulfanylphenyl)-4,6-diazaspiro[2.4]heptane-5,7-dione;

4-[2-(4-methoxyphenyl)methylaminocarbonylpyridin]-4-ylmethyl-6-(4-trifluoromethanesulfanylphenyl)-4,6-diazaspiro[2.4]heptane-5,7-dione;

4-[2-(4-chlorophenyl)methylaminocarbonylpyridin]-4-ylmethyl-6-(4-trifluoromethanesulfanylphenyl)-4,6-diazaspiro[2.4]heptane-5,7-dione;

4-[2-(4-morpholinylamino)carbonylpyridin]-4-ylmethyl-6-(4-trifluoromethanesulfanylphenyl)-4,6-diazaspiro[2.4]heptane-5,7-dione;

4-(2-aminocarbonylpyridin)-4-ylmethyl-6-(4-trifluoromethanesulfanylphenyl)-4,6-diazaspiro[2.4]heptane-5,7-dione;

4-(2-phenoxypyridin)-4-ylmethyl-6-(4-trifluoromethanesulfanylphenyl)-4,6-diazaspiro[2.4]heptane-5,7-dione;

4-(2-methoxypyridin)-4-ylmethyl-6-(4-trifluoromethanesulfanylphenyl)-4,6-diazaspiro[2.4]heptane-5,7-dione;

4-(2-ethoxypyridin)-4-ylmethyl-6-(4-trifluoromethanesulfanylphenyl)-4,6-diazaspiro[2.4]heptane-5,7-dione;

4-[2-(1-pyrrolidinyl)ethoxypyridin]-4-ylmethyl-6-(4-trifluoromethanesulfanylphenyl)-4,6-diazaspiro[2.4]heptane-5,7-dione;

4-(2-benzyloxypyridin)-4-ylmethyl-6-(4-trifluoromethanesulfanylphenyl)-4,6-diazaspiro[2.4]heptane-5,7-dione;

4-(2-benzoyloxypyridin)-4-ylmethyl-6-(4-trifluoromethanesulfanylphenyl)-4,6-diazaspiro[2.4]heptane-5,7-dione;

4-[2-(4,5-dihydro-1H-imidazol-2-yl)pyridin]-4-ylmethyl-6-(4-trifluoromethanesulfanylphenyl)-4,6-diazaspiro[2.4]heptane-5,7-dione;

4-[2-(1H-imidazol-2-yl)pyridin]-4-ylmethyl-6-(4-trifluoromethanesulfanylphenyl)-4,6-diazaspiro[2.4]heptane-5,7-dione;

4-[2-(1H-tetrazol-5-yl)pyridin]-4-ylmethyl-6-(4-trifluoromethanesulfanylphenyl)-4,6-diazaspiro[2.4]heptane-5,7-dione;

4-(2-amidinopyridin)-4-ylmethyl-6-(4-trifluoromethanesulfanylphenyl)-4,6-diazaspiro[2.4]heptane-5,7-dione;

4-(2-dimethylaminomethylpyridin)-4-ylmethyl-6-(4-trifluoromethanesulfanylphenyl)-4,6-diazaspiro[2.4]heptane-5,7-dione;

4-(2-aminomethylpyridin)-4-ylmethyl-6-(4-trifluoromethanesulfanylphenyl)-4,6-diazaspiro[2.4]heptane-5,7-dione;

4-(3-methylpyridin)-4-ylmethyl-6-(4-trifluoromethanesulfanylphenyl)-4,6-diazaspiro[2.4]heptane-5,7-dione;

4-(3-ethylpyridin)-4-ylmethyl-6-(4-trifluoromethanesulfanylphenyl)-4,6-diazaspiro[2.4]heptane-5,7-dione;

4-(3-isopropylpyridin)-4-ylmethyl-6-(4-trifluoromethanesulfanylphenyl)-4,6-diazaspiro[2.4]heptane-5,7-dione;

4-(3-tert-butylpyridin)-4-ylmethyl-6-(4-trifluoromethanesulfanylphenyl)-4,6-diazaspiro[2.4]heptane-5,7-dione;

4-(3-isobutylpyridin)-4-ylmethyl-6-(4-trifluoromethanesulfanylphenyl)-4,6-diazaspiro[2.4]heptane-5,7-dione;

4-(3-cyclohexylpyridin)-4-ylmethyl-6-(4-trifluoromethanesulfanylphenyl)-4,6-diazaspiro[2.4]heptane-5,7-dione;
4-(3-phenylpyridin)-4-ylmethyl-6-(4-trifluoromethanesulfanylphenyl)-4,6-diazaspiro[2.4]heptane-5,7-dione;
4-[3-(4-chlorophenyl)pyridin]-4-ylmethyl-6-(4-trifluoromethanesulfanylphenyl)-4,6-diazaspiro[2.4]heptane-5,7-dione;
4-[3-(3-chlorophenyl)pyridin]-4-ylmethyl-6-(4-trifluoromethanesulfanylphenyl)-4,6-diazaspiro[2.4]heptane-5,7-dione;
4-[3-(2-chlorophenyl)pyridin]-4-ylmethyl-6-(4-trifluoromethanesulfanylphenyl)-4,6-diazaspiro[2.4]heptane-5,7-dione;
4-[3-(4-fluorophenyl)pyridin]-4-ylmethyl-6-(4-trifluoromethanesulfanylphenyl)-4,6-diazaspiro[2.4]heptane-5,7-dione;
4-[3-(4-methoxyphenyl)pyridin]-4-ylmethyl-6-(4-trifluoromethanesulfanylphenyl)-4,6-diazaspiro[2.4]heptane-5,7-dione;
4-(3-benzylpyridin)-4-ylmethyl-6-(4-trifluoromethanesulfanylphenyl)-4,6-diazaspiro[2.4]heptane-5,7-dione;
4-(3,2'-bipyridin)-4-ylmethyl-6-(4-trifluoromethanesulfanylphenyl)-4,6-diazaspiro[2.4]heptane-5,7-dione;
4-(3-hydroxymethylpyridine)-4-ylmethyl-6-(4-trifluoromethanesulfanylphenyl)-4,6-diazaspiro[2.4]heptane-5,7-dione;
4-(3-chloropyridin)-4-ylmethyl-6-(4-trifluoromethanesulfanylphenyl)-4,6-diazaspiro[2.4]heptane-5,7-dione;
4-(3-fluoropyridin)-4-ylmethyl-6-(4-trifluoromethanesulfanylphenyl)-4,6-diazaspiro[2.4]heptane-5,7-dione;
4-(3-bromopyridin)-4-ylmethyl-6-(4-trifluoromethanesulfanylphenyl)-4,6-diazaspiro[2.4]heptane-5,7-dione;
4-(3-aminopyridine)-4-ylmethyl-6-(4-trifluoromethanesulfanylphenyl)-4,6-diazaspiro[2.4]heptane-5,7-dione;
4-(3-methylaminopyridin)-4-ylmethyl-6-(4-trifluoromethanesulfanylphenyl)-4,6-diazaspiro[2.4]heptane-5,7-dione;
4-(3-ethylaminopyridin)-4-ylmethyl-6-(4-trifluoromethanesulfanylphenyl)-4,6-diazaspiro[2.4]heptane-5,7-dione;
4-(3-isopropylaminopyridin)-4-ylmethyl-6-(4-trifluoromethanesulfanylphenyl)-4,6-diazaspiro[2.4]heptane-5,7-dione;
4-(3-phenylaminopyridin)-4-ylmethyl-6-(4-trifluoromethanesulfanylphenyl)-4,6-diazaspiro[2.4]heptane-5,7-dione;
4-(3-cyclohexylaminopyridin)-4-ylmethyl-6-(4-trifluoromethanesulfanylphenyl)-4,6-diazaspiro[2.4]heptane-5,7-dione;
4-(3-diethylaminopyridine)-4-ylmethyl-6-(4-trifluoromethanesulfanylphenyl)-4,6-diazaspiro[2.4]heptane-5,7-dione;
4-(3-N-cyclohexyl-N-methylaminopyridin)-4-ylmethyl-6-(4-trifluoromethanesulfanylphenyl)-4,6-diazaspiro[2.4]heptane-5,7-dione;
4-(3-piperidinopyridine)-4-ylmethyl-6-(4-trifluoromethanesulfanylphenyl)-4,6-diazaspiro[2.4]heptane-5,7-dione;
4-(3-morpholinopyridin)-4-ylmethyl-6-(4-trifluoromethanesulfanylphenyl)-4,6-diazaspiro[2.4]heptane-5,7-dione;
4-[3-(4-methylpiperazino)pyridin]-4-ylmethyl-6-(4-trifluoromethanesulfanylphenyl)-4,6-diazaspiro[2.4]heptane-5,7-dione;
4-[3-(1H-pyrazol-1-yl)pyridin]-4-ylmethyl-6-(4-trifluoromethanesulfanylphenyl)-4,6-diazaspiro[2.4]heptane-5,7-dione;
4-[3-(2-benzoylhydrazino)pyridin]-4-ylmethyl-6-(4-trifluoromethanesulfanylphenyl)-4,6-diazaspiro[2.4]heptane-5,7-dione;
4-(3-benzoylaminopyridin)-4-ylmethyl-6-(4-trifluoromethanesulfanylphenyl)-4,6-diazaspiro[2.4]heptane-5,7-dione;
4-[3-(4-chlorobenzoylamino)pyridin]-4-ylmethyl-6-(4-trifluoromethanesulfanylphenyl)-4,6-diazaspiro[2.4]heptane-5,7-dione;
4-[3-(3-chlorobenzoylamino)pyridin]-4-ylmethyl-6-(4-trifluoromethanesulfanylphenyl)-4,6-diazaspiro[2.4]heptane-5,7-dione;
4-[3-(2-chlorobenzoylamino)pyridin]-4-ylmethyl-6-(4-trifluoromethanesulfanylphenyl)-4,6-diazaspiro[2.4]heptane-5,7-dione;
4-[3-(4-fluorobenzoylamino)pyridin]-4-ylmethyl-6-(4-trifluoromethanesulfanylphenyl)-4,6-diazaspiro[2.4]heptane-5,7-dione;
4-[3-(4-methoxybenzoylamino)pyridin]-4-ylmethyl-6-(4-trifluoromethanesulfanylphenyl)-4,6-diazaspiro[2.4]heptane-5,7-dione;
4-(3-acetamidopyridin)-4-ylmethyl-6-(4-trifluoromethanesulfanylphenyl)-4,6-diazaspiro[2.4]heptane-5,7-dione;
4-(3-phenylacetamidopyridin)-4-ylmethyl-6-(4-trifluoromethanesulfanylphenyl)-4,6-diazaspiro[2.4]heptane-5,7-dione;
4-[3-(4-methylpiperazino)acetamidopyridin]-4-ylmethyl-6-(4-trifluoromethanesulfanylphenyl)-4,6-diazaspiro[2.4]heptane-5,7-dione;
4-(3-cyclohexanylcarboxamidopyridin)-4-ylmethyl-6-(4-trifluoromethanesulfanylphenyl)-4,6-diazaspiro[2.4]heptane-5,7-dione;
4-[3-(1-methyl-4-piperidinyl)carbonylaminopyridin]-4-ylmethyl-6-(4-trifluoromethanesulfanylphenyl)-4,6-diazaspiro[2.4]heptane-5,7-dione;
4-[3-(2-furanylcarbonyl)aminopyridin]-4-ylmethyl-6-(4-trifluoromethanesulfanylphenyl)-4,6-diazaspiro[2.4]heptane-5,7-dione;
4-(3-ethoxycarbonylaminopyridin)-4-ylmethyl-6-(4-trifluoromethanesulfanylphenyl)-4,6-diazaspiro[2.4]heptane-5,7-dione;
4-(3-isopropoxycarbonylaminopyridin)-4-ylmethyl-6-(4-trifluoromethanesulfanylphenyl)-4,6-diazaspiro[2.4]heptane-5,7-dione;
4-(3-butoxycarbonylaminopyridin)-4-ylmethyl-6-(4-trifluoromethanesulfanylphenyl)-4,6-diazaspiro[2.4]heptane-5,7-dione;
4-[3-(2-diethylaminoethoxycarbonylamino)pyridin]-4-ylmethyl-6-(4-trifluoromethanesulfanylphenyl)-4,6-diazaspiro[2.4]heptane-5,7-dione;
4-(3-phenoxycarbonylaminopyridin)-4-ylmethyl-6-(4-trifluoromethanesulfanylphenyl)-4,6-diazaspiro[2.4]heptane-5,7-dione;
4-[3-(4-chloroanilino)carbonylaminopyridin]-4-ylmethyl-6-(4-trifluoromethanesulfanylphenyl)-4,6-diazaspiro[2.4]heptane-5,7-dione;
4-(3-anilinocarbonylaminopyridin)-4-ylmethyl-6-(4-trifluoromethanesulfanylphenyl)-4,6-diazaspiro[2.4]heptane-5,7-dione;
4-(3-benzylaminocarbonylaminopyridin)-4-ylmethyl-6-(4-trifluoromethanesulfanylphenyl)-4,6-diazaspiro[2.4]heptane-5,7-dione;
4-[3-(2-pyridylamino)carbonylaminopyridin]-4-ylmethyl-6-(4-trifluoromethanesulfanylphenyl)-4,6-diazaspiro[2.4]heptane-5,7-dione;
4-(3-ureidopyridin)-4-ylmethyl-6-(4-trifluoromethanesulfanylphenyl)-4,6-diazaspiro[2.4]heptane-5,7-dione;
4-(3-benzylaminosulfonylaminopyridin)-4-ylmethyl-6-(4-trifluoromethanesulfanylphenyl)-4,6-diazaspiro[2.4]heptane-5,7-dione;

4-(3-methylaminosulfonylaminopyridin)-4-ylmethyl-6-(4-trifluoromethanesulfanylphenyl)-4,6-diazaspiro[2.4]heptane-5,7-dione;

4-(3-aminosulfonylaminopyridin)-4-ylmethyl-6-(4-trifluoromethanesulfanylphenyl)-4,6-diazaspiro[2.4]heptane-5,7-dione;

4-(3-morpholinosulfonylaminopyridin)-4-ylmethyl-6-(4-trifluoromethanesulfanylphenyl)-4,6-diazaspiro[2.4]heptane-5,7-dione;

4-(3-dimethylaminosulfonylaminopyridin)-4-ylmethyl-6-(4-trifluoromethanesulfanylphenyl)-4,6-diazaspiro[2.4]heptane-5,7-dione;

4-(3-anilinosulfonylaminopyridin)-4-ylmethyl-6-(4-trifluoromethanesulfanylphenyl)-4,6-diazaspiro[2.4]heptane-5,7-dione;

4-(3-phenylsulfonylaminopyridin)-4-ylmethyl-6-(4-trifluoromethanesulfanylphenyl)-4,6-diazaspiro[2.4]heptane-5,7-dione;

4-[3-(2-thienyl)sulfonylaminopyridin]-4-ylmethyl-6-(4-trifluoromethanesulfanylphenyl)-4,6-diazaspiro[2.4]heptane-5,7-dione;

4-(3-methylsulfonylaminopyridin)-4-ylmethyl-6-(4-trifluoromethanesulfanylphenyl)-4,6-diazaspiro[2.4]heptane-5,7-dione;

4-[3-(4-chlorophenyl)sulfonylaminopyridin]-4-ylmethyl-6-(4-trifluoromethanesulfanylphenyl)-4,6-diazaspiro[2.4]heptane-5,7-dione;

4-(3-benzylsulfonylaminopyridin)-4-ylmethyl-6-(4-trifluoromethanesulfanylphenyl)-4,6-diazaspiro[2.4]heptane-5,7-dione;

4-(3-hydroxycarbonylpyridin)-4-ylmethyl-6-(4-trifluoromethanesutfanylphenyl)-4,6-diazaspiro[2.4]heptane-5,7-dione;

4-(3-ethoxycarbonylpyridin)-4-ylmethyl-6-(4-trifluoromethanesulfanylphenyl)-4,6-diazaspiro[2.4]heptane-5,7-dione;

4-(3-tert-butoxycarbonylpyridin)-4-ylmethyl-6-(4-trifluoromethanesulfanylphenyl)-4,6-diazaspiro[2.4]heptane-5,7-dione;

4-(3-phenoxycarbonylpyridin)-4-ylmethyl-6-(4-trifluoromethanesulfanylphenyl)-4,6-diazaspiro[2.4]heptane-5,7-dione;

4-[3-(4-methylpiperazinocarbonyl)pyridin]-4-ylmethyl-6-(4-trifluoromethanesulfanylphenyl)-4,6-diazaspiro[2.4]heptane-5,7-dione;

4-[3-(methylamino)carbonylpyridin]-4-ylmethyl-6-(4-trifluoromethanesulfanylphenyl)-4,6-diazaspiro[2.4]heptane-5,7-dione;

4-[3-(dimethylamino)carbonylpyridin]-4-ylmethyl-6-(4-trifluoromethanesulfanylphenyl)-4,6-diazaspiro[2.4]heptane-5,7-dione;

4-(3-piperidinocarbonylpyridin)-4-ylmethyl-6-(4-trifluoromethanesulfanylphenyl)-4,6-diazaspiro[2.4]heptane-5,7-dione;

4-(3-morpholinocarbonylpyridin)-4-ylmethyl-6-(4-trifluoromethanesulfanylphenyl)-4,6-diazaspiro[2.4]heptane-5,7-dione;

4-[3-(4-phenylpiperazinocarbonyl)pyridin]-4-ylmethyl-6-(4-trifluoromethanesulfanylphenyl)-4,6-diazaspiro[2.4]heptane-5,7-dione;

4-(3-phenylaminocarbonylpyridin)-4-ylmethyl-6-(4-trifluoromethanesulfanylphenyl)-4,6-diazaspiro[2.4]heptane-5,7-dione;

4-[3-(methylphenylamino)carbonylpyridin]-4-ylmethyl-6-(4-trifluoromethanesulfanylphenyl)-4,6-diazaspiro[2.4]heptane-5,7-dione;

4-[3-(4-methoxyphenyl)methylaminocarbonylpyridin]-4-ylmethyl-6-(4-trifluoromethanesulfanylphenyl)-4,6-diazaspiro[2.4]heptane-5,7-dione;

4-[3-(4-chlorophenyl)methylaminocarbonylpyridin]-4-ylmethyl-6-(4-trifluoromethanesulfanylphenyl)-4,6-diazaspiro[2.4]heptane-5,7-dione;

4-[3-(4-morpholinylamino)carbonylpyridin]-4-ylmethyl-6-(4-trifluoromethanesulfanylphenyl)-4,6-diazaspiro[2.4]heptane-5,7-dione;

4-(3-aminocarbonylpyridin)-4-ylmethyl-6-(4-trifluoromethanesulfanylphenyl)-4,6-diazaspiro[2.4]heptane-5,7-dione;

4-(3-phenoxypyridin)-4-ylmethyl-6-(4-trifluoromethanesulfanylphenyl)-4,6-diazaspiro[2.4]heptane-5,7-dione;

4-(3-methoxypyridin)-4-ylmethyl-6-(4-trifluoromethanesulfanylphenyl)-4,6-diazaspiro[2.4]heptane-5,7-dione;

4-(3-ethoxypyridin)-4-ylmethyl-6-(4-trifluoromethanesulfanylphenyl)-4,6-diazaspiro[2.4]heptane-5,7-dione;

4-[3-(1-pyrrolidinyl)ethoxypyridin]-4-ylmethyl-6-(4-trifluoromethanesulfanylphenyl)-4,6-diazaspiro[2.4]heptane-5,7-dione;

4-(3-benzyloxypyridin)-4-ylmethyl-6-(4-trifluoromethanesulfanylphenyl)-4,6-diazaspiro[2.4]heptane-5,7-dione;

4-(3-benzoyloxypyridin)-4-ylmethyl-6-(4-trifluoromethanesulfanylphenyl)-4,6-diazaspiro[2.4]heptane-5,7-dione;

4-[3-(4,5-dihydro-1H-imidazol-2-yl)pyridin]-4-ylmethyl-6-(4-trifluoromethanesulfanylphenyl)-4,6-diazaspiro[2.4]heptane-5,7-dione;

4-[3-(1H-imidazol-2-yl)pyridin]-4-ylmethyl-6-(4-trifluoromethanesulfanylphenyl)-4,6-diazaspiro[2.4]heptane-5,7-dione;

4-[3-(1H-tetrazol-5-yl)pyridin]-4-ylmethyl-6-(4-trifluoromethanesulfanylphenyl)-4,6-diazaspiro[2.4]heptane-5,7-dione;

4-(3-amidinopyridin)-4-ylmethyl-6-(4-trifluoromethanesulfanylphenyl)-4,6-diazaspiro[2.4]heptane-5,7-dione;

4-(3-dimethylaminomethylpyridin)-4-ylmethyl-6-(4-trifluoromethanesulfanylphenyl)-4,6-diazaspiro[2.4]heptane-5,7-dione;

4-(3-aminomethylpyridin)-4-ylmethyl-6-(4-trifluoromethanesulfanylphenyl)-4,6-diazaspiro[2.4]heptane-5,7-dione;

5-methyl-1-(2-methylpyrid-4-ylmethyl)-3-(4-trifluoromethanesulfanylphenyl)imidazolidine-2,4-dione;

5-methyl-1-(2-ethylpyrid-4-ylmethyl)-3-(4-trifluoromethanesulfanylphenyl)imidazolidine-2,4-dione;

5-methyl-1-(2-isopropylpyrid-4-ylmethyl)-3-(4-trifluoromethanesulfanylphenyl)imidazolidine-2,4-dione;

5-methyl-1-(2-tert-butylpyrid-4-ylmethyl)-3-(4-trifluoromethanesulfanylphenyl)imidazolidine-2,4-dione;

5-methyl-1-(2-isobutylpyrid-4-ylmethyl)-3-(4-trifluoromethanesulfanylphenyl)imidazolidine-2,4-dione;

5-methyl-1-(2-cyclohexylpyrid-4-ylmethyl)-3-(4-trifluoromethanesulfanylphenyl)imidazolidine-2,4-dione;

5-methyl-1-(2-phenylpyrid-4-ylmethyl)-3-(4-trifluoromethanesulfanylphenyl)imidazolidine-2,4-dione;

5-methyl-1-[2-(4-chlorophenyl)pyrid-4-ylmethyl]-3-(4-trifluoromethanesulfanylphenyl)imidazolidine-2,4-dione;

5-methyl-1-[2-(3-chlorophenyl)pyrid-4-ylmethyl]-3-(4-trifluoromethanesulfanylphenyl)imidazolidine-2,4-dione;

5-methyl-1-[2-(2-chlorophenyl)pyrid-4-ylmethyl]-3-(4-trifluoromethanesulfanylphenyl)imidazolidine-2,4-dione;

5-methyl-1-[2-(4-fluorophenyl)pyrid-4-ylmethyl]-3-(4-trifluoromethanesulfanylphenyl)imidazolidine-2,4-dione;

5-methyl-1-[2-(4-methoxyphenyl)pyrid-4-ylmethyl]-3-(4-trifluoromethanesulfanylphenyl)imidazolidine-2,4-dione;

5-methyl-1-(2-benzylpyrid-4-ylmethyl)-3-(4-trifluoromethanesulfanylphenyl)imidazolidine-2,4-dione;
5-methyl-1-(2,2'-bipyrid-4-ylmethyl)-3-(4-trifluoromethanesulfanylphenyl)imidazolidine-2,4-dione;
5-methyl-1-(2-hydroxymethylpyrid-4-ylmethyl)-3-(4-trifluoromethanesulfanylphenyl)imidazolidine-2,4-dione;
5-methyl-1-(2-chloropyrid-4-ylmethyl)-3-(4-trifluoromethanesulfanylphenyl)imidazolidine-2,4-dione;
5-methyl-1-(2-fluoropyrid-4-ylmethyl)-3-(4-trifluoromethanesulfanylphenyl)imidazolidine-2,4-dione;
5-methyl-1-(2-bromopyrid-4-ylmethyl)-3-(4-trifluoromethanesulfanylphenyl)imidazolidine-2,4-dione;
5-methyl-1-(2-aminopyrid-4-ylmethyl)-3-(4-trifluoromethanesulfanylphenyl)imidazolidine-2,4-dione;
5-methyl-1-(2-methylaminopyrid-4-ylmethyl)-3-(4-trifluoromethanesulfanylphenyl)imidazolidine-2,4-dione;
5-methyl-1-(2-ethylaminopyrid-4-ylmethyl)-3-(4-trifluoromethanesulfanylphenyl)imidazolidine-2,4-dione;
5-methyl-1-(2-isopropylaminopyrid-4-ylmethyl)-3-(4-trifluoromethanesulfanylphenyl)imidazolidine-2,4-dione;
5-methyl-1-(2-phenylaminopyrid-4-ylmethyl)-3-(4-trifluoromethanesulfanylphenyl)imidazolidine-2,4-dione;
5-methyl-1-(2-cyclohexylaminopyrid-4-ylmethyl)-3-(4-trifluoromethanesulfanylphenyl)imidazolidine-2,4-dione;
5-methyl-1-(2-diethylaminopyrid-4-ylmethyl)-3-(4-trifluoromethanesulfanylphenyl)imidazolidine-2,4-dione;
5-methyl-1-(2-N-cyclohexyl-N-methylaminopyrid-4-ylmethyl)-3-(4-trifluoromethanesulfanylphenyl)imidazolidine-2,4-dione;
5-methyl-1-(2-piperidinopyrid-4-ylmethyl)-3-(4-trifluoromethanesulfanylphenyl)imidazolidine-2,4-dione;
5-methyl-1-(2-morpholinopyrid-4-ylmethyl)-3-(4-trifluoromethanesulfanylphenyl)imidazolidine-2,4-dione;
5-methyl-1-[2-(4-methylpiperazino)pyrid-4-ylmethyl]-3-(4-trifluoromethanesulfanylphenyl)imidazolidine-2,4-dione;
5-methyl-1-[2-(1H-pyrazol-1-yl)pyrid-4-ylmethyl]-3-(4-trifluoromethanesulfanylphenyl)imidazolidine-2,4-dione;
5-methyl-1-[2-(2-benzoylhydrazino)pyrid-4-ylmethyl]-3-(4-trifluoromethanesulfanylphenyl)imidazolidine-2,4-dione;
5-methyl-1-(2-benzoylaminopyrid-4-ylmethyl)-3-(4-trifluoromethanesulfanylphenyl)imidazolidine-2,4-dione;
5-methyl-1-[2-(4-chlorobenzoylamino)pyrid-4-ylmethyl]-3-(4-trifluoromethanesulfanylphenyl)imidazolidine-2,4-dione;
5-methyl-1-[2-(3-chlorobenzoylamino)pyrid-4-ylmethyl]-3-(4-trifluoromethanesulfanylphenyl)imidazolidine-2,4-dione;
5-methyl-1-[2-(2-chlorobenzoylamino)pyrid-4-ylmethyl]-3-(4-trifluoromethanesulfanylphenyl)imidazolidine-2,4-dione;
5-methyl-1-[2-(4-fluorobenzoylamino)pyrid-4-ylmethyl]-3-(4-trifluoromethanesulfanylphenyl)imidazolidine-2,4-dione;
5-methyl-1-[2-(4-methoxybenzoylamino)pyrid-4-ylmethyl]-3-(4-trifluoromethanesulfanylphenyl)imidazolidine-2,4-dione;
5-methyl-1-(2-acetamidopyrid-4-ylmethyl)-3-(4-trifluoromethanesulfanylphenyl)imidazolidine-2,4-dione;
5-methyl-1-(2-phenylacetamidopyrid-4-ylmethyl)-3-(4-trifluoromethanesulfanylphenyl)imidazolidine-2,4-dione;
5-methyl-1-[2-(4-methylpiperazino)acetamidopyrid-4-ylmethyl]-3-(4-trifluoromethanesulfanylphenyl)imidazolidine-2,4-dione;
5-methyl-1-(2-cyclohexanylcarboxamidopyrid-4-ylmethyl)-3-(4-trifluoromethanesulfanylphenyl)imidazolidine-2,4-dione;
5-methyl-1-[2-(1-methyl-4-piperidinyl)carbonylaminopyrid-4-ylmethyl]-3-(4-trifluoromethanesulfanylphenyl)imidazolidine-2,4-dione;
5-methyl-1-[2-(2-furanylcarbonyl)aminopyrid-4-ylmethyl]-3-(4-trifluoromethanesulfanylphenyl)imidazolidine-2,4-dione;
5-methyl-1-(2-ethoxycarbonylaminopyrid-4-ylmethyl)-3-(4-trifluoromethanesulfanylphenyl)imidazolidine-2,4-dione;
5-methyl-1-(2-isopropoxycarbonylaminopyrid-4-ylmethyl)-3-(4-trifluoromethanesulfanylphenyl)imidazolidine-2,4-dione;
5-methyl-1-(2-butoxycarbonylaminopyrid-4-ylmethyl)-3-(4-trifluoromethanesulfanylphenyl)imidazolidine-2,4-dione;
5-methyl-1-[2-(2-diethylaminoethoxycarbonylamino)pyrid-4-ylmethyl]-3-(4-trifluoromethanesulfanylphenyl)imidazolidine-2,4-dione;
5-methyl-1-(2-phenoxycarbonylaminopyrid-4-ylmethyl)-3-(4-trifluoromethanesulfanylphenyl)imidazolidine-2,4-dione;
5-methyl-1-[2-(4-chloroanilino)carbonylaminopyrid-4-ylmethyl]-3-(4-trifluoromethanesulfanylphenyl)imidazolidine-2,4-dione;
5-methyl-1-(2-anilinocarbonylaminopyrid-4-ylmethyl)-3-(4-trifluoromethanesulfanylphenyl)imidazolidine-2,4-dione;
5-methyl-1-(2-benzylaminocarbonylaminopyrid-4-ylmethyl)-3-(4-trifluoromethanesulfanylphenyl)imidazolidine-2,4-dione;
5-methyl-1-[2-(2-pyridylamino)carbonylaminopyrid-4-ylmethyl]-3-(4-trifluoromethanesulfanylphenyl)imidazolidine-2,4-dione;
5-methyl-1-(2-ureidopyrid-4-ylmethyl)-3-(4-trifluoromethanesulfanylphenyl)imidazolidine-2,4-dione;
5-methyl-1-(2-benzylaminosulfonylaminopyrid-4-ylmethyl)-3-(4-trifluoromethanesulfanylphenyl)imidazolidine-2,4-dione;
5-methyl-1-(2-methylaminosulfonylaminopyrid-4-ylmethyl)-3-(4-trifluoromethanesulfanylphenyl)imidazolidine-2,4-dione;
5-methyl-1-(2-aminosulfonylaminopyrid-4-ylmethyl)-3-(4-trifluoromethanesulfanylphenyl)imidazolidine-2,4-dione;
5-methyl-1-(2-morpholinosulfonylaminopyrid-4-ylmethyl)-3-(4-trifluoromethanesulfanylphenyl)imidazolidine-2,4-dione;
5-methyl-1-(2-dimethylaminosulfonylaminopyrid-4-ylmethyl)-3-(4-trifluoromethanesulfanylphenyl)imidazolidine-2,4-dione;
5-methyl-1-(2-anilinosulfonylaminopyrid-4-ylmethyl)-3-(4-trifluoromethanesulfanylphenyl)imidazolidine-2,4-dione;
5-methyl-1-(2-phenylsulfonylaminopyrid-4-ylmethyl)-3-(4-trifluoromethanesulfanylphenyl)imidazolidine-2,4-dione;
5-methyl-1-[2-(2-thienyl)sulfonylaminopyrid-4-ylmethyl]-3-(4-trifluoromethanesulfanylphenyl)imidazolidine-2,4-dione;
5-methyl-1-(2-methylsulfonylaminopyrid-4-ylmethyl)-3-(4-trifluoromethanesulfanylphenyl)imidazolidine-2,4-dione;
5-methyl-1-[2-(4-chlorophenyl)sulfonylaminopyrid-4-ylmethyl]-3-(4-trifluoromethanesulfanylphenyl)imidazolidine-2,4-dione;
5-methyl-1-(2-benzylsulfonylaminopyrid-4-ylmethyl)-3-(4-trifluoromethanesulfanylphenyl)imidazolidine-2,4-dione;
5-methyl-1-(2-hydroxycarbonylpyrid-4-ylmethyl)-3-(4-trifluoromethanesulfanylphenyl)imidazolidine-2,4-dione;
5-methyl-1-(2-ethoxycarbonylpyrid-4-ylmethyl)-3-(4-trifluoromethanesulfanylphenyl)imidazolidine-2,4-dione;

5-methyl-1-(2-tert-butoxycarbonylpyrid-4-ylmethyl)-3-(4-trifluoromethanesulfanylphenyl)imidazolidine-2,4-dione;
5-methyl-1-(2-phenoxycarbonylpyrid-4-ylmethyl)-3-(4-trifluoromethanesulfanylphenyl)imidazolidine-2,4-dione;
5-methyl-1-[2-(4-methylpiperazinocarbonyl)pyrid-4-ylmethyl]-3-(4-trifluoromethanesulfanylphenyl)imidazolidine-2,4-dione;
5-methyl-1-[2-(methylamino)carbonylpyrid-4-ylmethyl]-3-(4-trifluoromethanesulfanylphenyl)imidazolidine-2,4-dione;
5-methyl-1-[2-dimethylamino)carbonylpyrid-4-ylmethyl]-3-(4-trifluoromethanesulfanylphenyl)imidazolidine-2,4-dione;
5-methyl-1-(2-piperidinocarbonylpyrid-4-ylmethyl)-3-(4-trifluoromethanesulfanylphenyl)imidazolidine-2,4-dione;
5-methyl-1-(2-morpholinocarbonylpyrid-4-ylmethyl)-3-(4-trifluoromethanesulfanylphenyl)imidazolidine-2,4-dione;
5-methyl-1-[2-(4-phenylpiperazinocarbonyl)pyrid-4-ylmethyl]-3-(4-trifluoromethanesulfanylphenyl)imidazolidine-2,4-dione;
5-methyl-1-(2-phenylaminocarbonylpyrid-4-ylmethyl)-3-(4-trifluoromethanesulfanylphenyl)imidazolidine-2,4-dione;
5-methyl-1-[2-(methylphenylamino)carbonylpyrid-4-ylmethyl]-3-(4-trifluoromethanesulfanylphenyl)imidazolidine-2,4-dione;
5-methyl-1-[2-(4-methoxyphenyl)methylaminocarbonylpyrid-4-ylmethyl]-3-(4-trifluoromethanesulfanylphenyl)imidazolidine-2,4-dione;
5-methyl-1-[2-(4-chlorophenyl)methylaminocarbonylpyrid-4-ylmethyl]-3-(4-trifluoromethanesulfanylphenyl)imidazolidine-2,4-dione;
5-methyl-1-[2-(4-morpholinylamino)carbonylpyrid-4-ylmethyl]-3-(4-trifluoromethanesulfanylphenyl)imidazolidine-2,4-dione;
5-methyl-1-(2-aminocarbonylpyrid-4-ylmethyl)-3-(4-trifluoromethanesulfanylphenyl)imidazolidine-2,4-dione;
5-methyl-1-(2-phenoxypyrid-4-ylmethyl)-3-(4-trifluoromethanesulfanylphenyl)imidazolidine-2,4-dione;
5-methyl-1-(2-methoxypyrid-4-ylmethyl)-3-(4-trifluoromethanesulfanylphenyl)imidazolidine-2,4-dione;
5-methyl-1-(2-ethoxypyrid-4-ylmethyl)-3-(4-trifluoromethanesulfanylphenyl)imidazolidine-2,4-dione;
5-methyl-1-[2-(1-pyrrolidinyl)ethoxypyrid-4-ylmethyl]-3-(4-trifluoromethanesulfanylphenyl)imidazolidine-2,4-dione;
5-methyl-1-(2-benzyloxypyrid-4-ylmethyl)-3-(4-trifluoromethanesulfanylphenyl)imidazolidine-2,4-dione;
5-methyl-1-(2-benzoyloxypyrid-4-ylmethyl)-3-(4-trifluoromethanesulfanylphenyl)imidazolidine-2,4-dione;
5-methyl-1-[2-(4,5-dihydro-1H-imidazol-2-yl)pyrid-4-ylmethyl]-3-(4-trifluoromethanesulfanylphenyl)imidazolidine-2,4-dione;
5-methyl-1-[2-(1H-imidazol-2-yl)pyrid-4-ylmethyl]-3-(4-trifluoromethanesulfanylphenyl)imidazolidine-2,4-dione;
5-methyl-1-[2-(1H-tetrazol-5-yl)pyrid-4-ylmethyl]-3-(4-trifluoromethanesulfanylphenyl)imidazolidine-2,4-dione;
5-methyl-1-(2-amidinopyrid-4-ylmethyl)-3-(4-trifluoromethanesulfanylphenyl)imidazolidine-2,4-dione;
5-methyl-1-(2-dimethylaminomethylpyrid-4-ylmethyl)-3-(4-trifluoromethanesulfanylphenyl)imidazolidine-2,4-dione;
5-methyl-1-(2-aminomethylpyrid-4-ylmethyl)-3-(4-trifluoromethanesulfanylphenyl)imidazolidine-2,4-dione;
5-methyl-1-(3-methylpyrid-4-ylmethyl)-3-(4-trifluoromethanesulfanylphenyl)imidazolidine-2,4-dione;
5-methyl-1-(3-ethylpyrid-4-ylmethyl)-3-(4-trifluoromethanesulfanylphenyl)imidazolidine-2,4-dione;
5-methyl-1-(3-isopropylpyrid-4-ylmethyl)-3-(4-trifluoromethanesulfanylphenyl)imidazolidine-2,4-dione;
5-methyl-1-(3-tert-butylpyrid-4-ylmethyl)-3-(4-trifluoromethanesulfanylphenyl)imidazolidine-2,4-dione;
5-methyl-1-(3-isobutylpyrid-4-ylmethyl)-3-(4-trifluoromethanesulfanylphenyl)imidazolidine-2,4-dione;
5-methyl-1-(3-cyclohexylpyrid-4-ylmethyl)-3-(4-trifluoromethanesulfanylphenyl)imidazolidine-2,4-dione;
5-methyl-1-(3-phenylpyrid-4-ylmethyl)-3-(4-trifluoromethanesulfanylphenyl)imidazolidine-2,4-dione;
5-methyl-1-[3-(4-chlorophenyl)pyrid-4-ylmethyl]-3-(4-trifluoromethanesulfanylphenyl)imidazolidine-2,4-dione;
5-methyl-1-[3-(3-chlorophenyl)pyrid-4-ylmethyl]-3-(4-trifluoromethanesulfanylphenyl)imidazolidine-2,4-dione;
5-methyl-1-[3-(2-chlorophenyl)pyrid-4-ylmethyl]-3-(4-trifluoromethanesulfanylphenyl)imidazolidine-2,4-dione;
5-methyl-1-[3-(4-fluorophenyl)pyrid-4-ylmethyl]-3-(4-trifluoromethanesulfanylphenyl)imidazolidine-2,4-dione;
5-methyl-1-[3-(4-methoxyphenyl)pyrid-4-ylmethyl]-3-(4-trifluoromethanesulfanylphenyl)imidazolidine-2,4-dione;
5-methyl-1-(3-benzylpyrid-4-ylmethyl)-3-(4-trifluoromethanesulfanylphenyl)imidazolidine-2,4-dione;
5-methyl-1-(3,2'-bipyrid-4-ylmethyl)-3-(4-trifluoromethanesulfanylphenyl)imidazolidine-2,4-dione;
5-methyl-1-(3-hydroxymethylpyrid-4-ylmethyl)-3-(4-trifluoromethanesulfanylphenyl)imidazolidine-2,4-dione;
5-methyl-1-(3-chloropyrid-4-ylmethyl)-3-(4-trifluoromethanesulfanylphenyl)imidazolidine-2,4-dione;
5-methyl-1-(3-fluoropyrid-4-ylmethyl)-3-(4-trifluoromethanesulfanylphenyl)imidazolidine-2,4-dione;
5-methyl-1-(3-bromopyrid-4-ylmethyl)-3-(4-trifluoromethanesulfanylphenyl)imidazolidine-2,4-dione;
5-methyl-1-(3-aminopyrid-4-ylmethyl)-3-(4-trifluoromethanesulfanylphenyl)imidazolidine-2,4-dione;
5-methyl-1-(3-methylaminopyrid-4-ylmethyl)-3-(4-trifluoromethanesulfanylphenyl)imidazolidine-2,4-dione;
5-methyl-1-(3-ethylaminopyrid-4-ylmethyl)-3-(4-trifluoromethanesulfanylphenyl)imidazolidine-2,4-dione;
5-methyl-1-(3-isopropylaminopyrid-4-ylmethyl)-3-(4-trifluoromethanesulfanylphenyl)imidazolidine-2,4-dione;
5-methyl-1-(3-phenylaminopyrid-4-ylmethyl)-3-(4-trifluoromethanesulfanylphenyl)imidazolidine-2,4-dione;
5-methyl-1-(3-cyclohexylaminopyrid-4-ylmethyl)-3-(4-trifluoromethanesulfanylphenyl)imidazolidine-2,4-dione;
5-methyl-1-(3-diethylaminopyrid-4-ylmethyl)-3-(4-trifluoromethanesulfanylphenyl)imidazolidine-2,4-dione;
5-methyl-1-(3-N-cyclohexyl-N-methylaminopyrid-4-ylmethyl)-3-(4-trifluoromethanesulfanylphenyl)imidazolidine-2,4-dione;
5-methyl-1-(3-piperidinopyrid-4-ylmethyl)-3-(4-trifluoromethanesulfanylphenyl)imidazolidine-2,4-dione;
5-methyl-1-(3-morpholinopyrid-4-ylmethyl)-3-(4-trifluoromethanesulfanylphenyl)imidazolidine-2,4-dione;
5-methyl-1-[3-(4-methylpiperazino)pyrid-4-ylmethyl]-3-(4-trifluoromethanesulfanylphenyl)imidazolidine-2,4-dione;
5-methyl-1-[3-(1H-pyrazol-1-yl)pyrid-4-ylmethyl]-3-(4-trifluoromethanesulfanylphenyl)imidazolidine-2,4-dione;
5-methyl-1-[3-(2-benzoylhydrazino)pyrid-4-ylmethyl]-3-(4-trifluoromethanesulfanylphenyl)imidazolidine-2,4-dione;
5-methyl-1-(3-benzoylaminopyrid-4-ylmethyl)-3-(4-trifluoromethanesulfanylphenyl)imidazolidine-2,4-dione;
5-methyl-1-[3-(4-chlorobenzoylamino)pyrid-4-ylmethyl]-3-(4-trifluoromethanesulfanylphenyl)imidazolidine-2,4-dione;

5-methyl-1-[3-(3-chlorobenzoylamino)pyrid-4-ylmethyl]-3-(4-trifluoromethanesulfanylphenyl)imidazolidine-2,4-dione;

5-methyl-1-[3-(2-chlorobenzoylamino)pyrid-4-ylmethyl]-3-(4-trifluoromethanesulfanylphenyl)imidazolidine-2,4-dione;

5-methyl-1-[3-(4-fluorobenzoylamino)pyrid-4-ylmethyl]-3-(4-trifluoromethanesulfanylphenyl)imidazolidine-2,4-dione;

5-methyl-1-[3-(4-methoxybenzoylamino)pyrid-4-ylmethyl]-3-(4-trifluoromethanesulfanylphenyl)imidazolidine-2,4-dione;

5-methyl-1-(3-acetamidopyrid-4-ylmethyl)-3-(4-trifluoromethanesulfanylphenyl)imidazolidine-2,4-dione;

5-methyl-1-(3-phenylacetamidopyrid-4-ylmethyl)-3-(4-trifluoromethanesulfanylphenyl)imidazolidine-2,4-dione;

5-methyl-1-[3-(4-methylpiperazino)acetamidopyrid-4-ylmethyl]-3-(4-trifluoromethanesulfanylphenyl)imidazolidine-2,4-dione;

5-methyl-1-(3-cyclohexanylcarboxamidopyrid-4-ylmethyl)-3-(4-trifluoromethanesulfanylphenyl)imidazolidine-2,4-dione;

5-methyl-1-[3-(1-methyl-4-piperidinyl)carbonylaminopyrid-4-ylmethyl]-3-(4-trifluoromethanesulfanylphenyl)imidazolidine-2,4-dione;

5-methyl-1-[3-(2-furanylcarbonyl)aminopyrid-4-ylmethyl]-3-(4-trifluoromethanesulfanylphenyl)imidazolidine-2,4-dione;

5-methyl-1-(3-ethoxycarbonylaminopyrid-4-ylmethyl)-3-(4-trifluoromethanesulfanylphenyl)imidazolidine-2,4-dione;

5-methyl-1-(3-isopropoxycarbonylaminopyrid-4-ylmethyl)-3-(4-trifluoromethanesulfanylphenyl)imidazolidine-2,4-dione;

5-methyl-1-(3-butoxycarbonylaminopyrid-4-ylmethyl)-3-(4-trifluoromethanesulfanylphenyl)imidazolidine-2,4-dione;

5-methyl-1-[3-(2-diethylaminoethoxycarbonylamino)pyrid-4-ylmethyl]-3-(4-trifluoromethanesulfanylphenyl)imidazolidine-2,4-dione;

5-methyl-1-(3-phenoxycarbonylaminopyrid-4-ylmethyl)-3-(4-trifluoromethanesulfanylphenyl)imidazolidine-2,4-dione;

5-methyl-1-[3-(4-chloroanilino)carbonylaminopyrid-4-ylmethyl]-3-(4-trifluoromethanesulfanylphenyl)imidazolidine-2,4-dione;

5-methyl-1-(3-anilinocarbonylaminopyrid-4-ylmethyl)-3-(4-trifluoromethanesulfanylphenyl)imidazolidine-2,4-dione;

5-methyl-1-(3-benzylaminocarbonylaminopyrid-4-ylmethyl)-3-(4-trifluoromethanesulfanylphenyl)imidazolidine-2,4-dione;

5-methyl-1-[3-(2-pyridylamino)carbonylaminopyrid-4-ylmethyl]-3-(4-trifluoromethanesulfanylphenyl)imidazolidine-2,4-dione;

5-methyl-1-(3-ureidopyrid-4-ylmethyl)-3-(4-trifluoromethanesulfanylphenyl)imidazolidine-2,4-dione;

5-methyl-1-(3-benzylaminosulfonylaminopyrid-4-ylmethyl)-3-(4-trifluoromethanesulfanylphenyl)imidazolidine-2,4-dione;

5-methyl-1-(3-methylaminosulfonylaminopyrid-4-ylmethyl)-3-(4-trifluoromethanesulfanylphenyl)imidazolidine-2,4-dione;

5-methyl-1-(3-aminosulfonylaminopyrid-4-ylmethyl)-3-(4-trifluoromethanesulfanylphenyl)imidazolidine-2,4-dione;

5-methyl-1-(3-morpholinosulfonylaminopyrid-4-ylmethyl)-3-(4-trifluoromethanesulfanylphenyl)imidazolidine-2,4-dione;

5-methyl-1-(3-dimethylaminosulfonylaminopyrid-4-ylmethyl)-3-(4-trifluoromethanesulfanylphenyl)imidazolidine-2,4-dione;

5-methyl-1-(3-anilinosulfonylaminopyrid-4-ylmethyl)-3-(4-trifluoromethanesulfanylphenyl)imidazolidine-2,4-dione;

5-methyl-1-(3-phenylsulfonylaminopyrid-4-ylmethyl)-3-(4-trifluoromethanesulfanylphenyl)imidazolidine-2,4-dione;

5-methyl-1-[3-(2-thienyl)sulfonylaminopyrid-4-ylmethyl]-3-(4-trifluoromethanesulfanylphenyl)imidazolidine-2,4-dione;

5-methyl-1-(3-methylsulfonylaminopyrid-4-ylmethyl)-3-(4-trifluoromethanesulfanylphenyl)imidazolidine-2,4-dione;

5-methyl-1-[3-(4-chlorophenyl)sulfonylaminopyrid-4-ylmethyl]-3-(4-trifluoromethanesulfanylphenyl)imidazolidine-2,4-dione;

5-methyl-1-(3-benzylsulfonylaminopyrid-4-ylmethyl)-3-(4-trifluoromethanesulfanylphenyl)imidazolidine-2,4-dione;

5-methyl-1-(3-hydroxycarbonylpyrid-4-ylmethyl)-3-(4-trifluoromethanesulfanylphenyl)imidazolidine-2,4-dione;

5-methyl-1-(3-ethoxycarbonylpyrid-4-ylmethyl)-3-(4-trifluoromethanesulfanylphenyl)imidazolidine-2,4-dione;

5-methyl-1-(3-tert-butoxycarbonylpyrid-4-ylmethyl)-3-(4-trifluoromethanesulfanylphenyl)imidazolidine-2,4-dione;

5-methyl-1-(3-phenoxycarbonylpyrid-4-ylmethyl)-3-(4-trifluoromethanesulfanylphenyl)imidazolidine-2,4-dione;

5-methyl-1-[3-(4-methylpiperazinocarbonyl)pyrid-4-ylmethyl]-3-(4-trifluoromethanesulfanylphenyl)imidazolidine-2,4-dione;

5-methyl-1-[3-(methylamino)carbonylpyrid-4-ylmethyl]-3-(4-trifluoromethanesulfanylphenyl)imidazolidine-2,4-dione;

5-methyl-1-[3-(dimethylamino)carbonylpyrid-4-ylmethyl]-3-(4-trifluoromethanesulfanylphenyl)imidazolidine-2,4-dione;

5-methyl-1-(3-piperidinocarbonylpyrid-4-ylmethyl)-3-(4-trifluoromethanesulfanylphenyl)imidazolidine-2,4-dione;

5-methyl-1-(3-morpholinocarbonylpyrid-4-ylmethyl)-3-(4-trifluoromethanesulfanylphenyl)imidazolidine-2,4-dione;

5-methyl-1-[3-(4-phenylpiperazinocarbonyl)pyrid-4-ylmethyl]-3-(4-trifluoromethanesulfanylphenyl)imidazolidine-2,4-dione;

5-methyl-1-[3-(phenylaminocarbonyl)pyrid-4-ylmethyl]-3-(4-trifluoromethanesulfanylphenyl)imidazolidine-2,4-dione;

5-methyl-1-[3-(methylphenylamino)carbonylpyrid-4-ylmethyl]-3-(4-trifluoromethanesulfanylphenyl)imidazolidine-2,4-dione;

5-methyl-1-[3-(4-methoxyphenyl)methylaminocarbonylpyrid-4-ylmethyl]-3-(4-trifluoromethanesulfanylphenyl)imidazolidine-2,4-dione;

5-methyl-1-[3-(4-chlorophenyl)methylaminocarbonylpyrid-4-ylmethyl]-3-(4-trifluoromethanesulfanylphenyl)imidazolidine-2,4-dione;

5-methyl-1-[3-(4-morpholinylamino)carbonylpyrid-4-ylmethyl]-3-(4-trifluoromethanesulfanylphenyl)imidazolidine-2,4-dione;

5-methyl-1-(3-aminocarbonylpyrid-4-ylmethyl)-3-(4-trifluoromethanesulfanylphenyl)imidazolidine-2,4-dione;

5-methyl-1-(3-phenoxypyrid-4-ylmethyl)-3-(4-trifluoromethanesulfanylphenyl)imidazolidine-2,4-dione;

5-methyl-1-(3-methoxypyrid-4-ylmethyl)-3-(4-trifluoromethanesulfanylphenyl)imidazolidine-2,4-dione;

5-methyl-1-(3-ethoxypyrid-4-ylmethyl)-3-(4-trifluoromethanesulfanylphenyl)imidazolidine-2,4-dione;

5-methyl-1-[3-(1-pyrrolidinyl)ethoxypyrid-4-ylmethyl]-3-(4-trifluoromethanesulfanylphenyl)imidazolidine-2,4-dione;
5-methyl-1-(3-benzyloxypyrid-4-ylmethyl)-3-(4-trifluoromethanesulfanylphenyl)imidazolidine-2,4-dione;
5-methyl-1-(3-benzoyloxypyrid-4-ylmethyl)-3-(4-trifluoromethanesulfanylphenyl)imidazolidine-2,4-dione;
5-methyl-1-[3-(4,5-dihydro-1H-imidazol-2-yl)pyrid-4-ylmethyl]-3-(4-trifluoromethanesulfanylphenyl)imidazolidine-2,4-dione;
5-methyl-1-[3-(1H-imidazol-2-yl)pyrid-4-ylmethyl]-3-(4-trifluoromethanesulfanylphenyl)imidazolidine-2,4-dione;
5-methyl-1-[3-(1H-tetrazol-5-yl)pyrid-4-ylmethyl]-3-(4-trifluoromethanesulfanylphenyl)imidazolidine-2,4-dione;
5-methyl-1-(3-amidinopyrid-4-ylmethyl)-3-(4-trifluoromethanesulfanylphenyl)imidazolidine-2,4-dione;
5-methyl-1-(3-dimethylaminomethylpyrid-4-ylmethyl)-3-(4-trifluoromethanesulfanylphenyl)imidazolidine-2,4-dione;
5-methyl-1-(3-aminomethylpyrid-4-ylmethyl)-3-(4-trifluoromethanesulfanylphenyl)imidazolidine-2,4-dione;
1-(2-methylpyrid-4-ylmethyl)-3-(4-trifluoromethanesulfanylphenyl)imidazolidine-2,4-dione;
1-(2-ethylpyrid-4-ylmethyl)-3-(4-trifluoromethanesulfanylphenyl)imidazolidine-2,4-dione;
1-(2-isopropylpyrid-4-ylmethyl)-3-(4-trifluoromethanesulfanylphenyl)imidazolidine-2,4-dione;
1-(2-tert-butylpyrid-4-ylmethyl)-3-(4-trifluoromethanesulfanylphenyl)imidazolidine-2,4-dione;
1-(2-isobutylpyrid-4-ylmethyl)-3-(4-trifluoromethanesulfanylphenyl)imidazolidine-2,4-dione;
1-(2-cyclohexylpyrid-4-ylmethyl)-3-(4-trifluoromethanesulfanylphenyl)imidazolidine-2,4-dione;
1-(2-phenylpyrid-4-ylmethyl)-3-(4-trifluoromethanesulfanylphenyl)imidazolidine-2,4-dione;
1-[2-(4-chlorophenyl)pyrid-4-ylmethyl]-3-(4-trifluoromethanesulfanylphenyl)imidazolidine-2,4-dione;
1-[2-(3-chlorophenyl)pyrid-4-ylmethyl]-3-(4-trifluoromethanesulfanylphenyl)imidazolidine-2,4-dione;
1-[2-(2-chlorophenyl)pyrid-4-ylmethyl]-3-(4-trifluoromethanesulfanylphenyl)imidazolidine-2,4-dione;
1-[2-(4-fluorophenyl)pyrid-4-ylmethyl]-3-(4-trifluoromethanesulfanylphenyl)imidazolidine-2,4-dione;
1-[2-(4-methoxyphenyl)pyrid-4-ylmethyl]-3-(4-trifluoromethanesulfanylphenyl)imidazolidine-2,4-dione;
1-(2-benzylpyrid-4-ylmethyl)-3-(4-trifluoromethanesulfanylphenyl)imidazolidine-2,4-dione;
1-(2,2'-bipyrid-4-ylmethyl)-3-(4-trifluoromethanesulfanylphenyl)imidazolidine-2,4-dione;
1-(2-hydroxymethylpyrid-4-ylmethyl)-3-(4-trifluoromethanesulfanylphenyl)imidazolidine-2,4-dione;
1-(2-chloropyrid-4-ylmethyl)-3-(4-trifluoromethanesulfanylphenyl)imidazolidine-2,4-dione;
1-(2-fluoropyrid-4-ylmethyl)-3-(4-trifluoromethanesulfanylphenyl)imidazolidine-2,4-dione;
1-(2-bromopyrid-4-ylmethyl)-3-(4-trifluoromethanesulfanylphenyl)imidazolidine-2,4-dione;
1-(2-aminopyrid-4-ylmethyl)-3-(4-trifluoromethanesulfanylphenyl)imidazolidine-2,4-dione;
1-(2-methylaminopyrid-4-ylmethyl)-3-(4-trifluoromethanesulfanylphenyl)imidazolidine-2,4-dione;
1-(2-ethylaminopyrid-4-ylmethyl)-3-(4-trifluoromethanesulfanylphenyl)imidazolidine-2,4-dione;
1-(2-isopropylaminopyrid-4-ylmethyl)-3-(4-trifluoromethanesulfanylphenyl)imidazolidine-2,4-dione;
1-(2-phenylaminopyrid-4-ylmethyl)-3-(4-trifluoromethanesulfanylphenyl)imidazolidine-2,4-dione;
1-(2-cyclohexylaminopyrid-4-ylmethyl)-3-(4-trifluoromethanesulfanylphenyl)imidazolidine-2,4-dione;
1-(2-diethylaminopyrid-4-ylmethyl)-3-(4-trifluoromethanesulfanylphenyl)imidazolidine-2,4-dione;
1-(2-N-cyclohexyl-N-methylaminopyrid-4-ylmethyl)-3-(4-trifluoromethanesulfanylphenyl)imidazolidine-2,4-dione;
1-(2-piperidinopyrid-4-ylmethyl)-3-(4-trifluoromethanesulfanylphenyl)imidazolidine-2,4-dione;
1-(2-morpholinopyrid-4-ylmethyl)-3-(4-trifluoromethanesulfanylphenyl)imidazolidine-2,4-dione;
1-[2-(4-methylpiperazino)pyrid-4-ylmethyl]-3-(4-trifluoromethanesulfanylphenyl)imidazolidine-2,4-dione;
1-[2-(1H-pyrazol-1-yl)pyrid-4-ylmethyl]-3-(4-trifluoromethanesulfanylphenyl)imidazolidine-2,4-dione;
1-[2-(2-benzoylhydrazino)pyrid-4-ylmethyl]-3-(4-trifluoromethanesulfanylphenyl)imidazolidine-2,4-dione;
1-(2-benzoylaminopyrid-4-ylmethyl)-3-(4-trifluoromethanesulfanylphenyl)imidazolidine-2,4-dione;
1-[2-(4-chlorobenzoylamino)pyrid-4-ylmethyl]-3-(4-trifluoromethanesulfanylphenyl)imidazolidine-2,4-dione;
1-[2-(3-chlorobenzoylamino)pyrid-4-ylmethyl]-3-(4-trifluoromethanesulfanylphenyl)imidazolidine-2,4-dione;
1-[2-(2-chlorobenzoylamino)pyrid-4-ylmethyl]-3-(4-trifluoromethanesulfanylphenyl)imidazolidine-2,4-dione;
1-[2-(4-fluorobenzoylamino)pyrid-4-ylmethyl]-3-(4-trifluoromethanesulfanylphenyl)imidazolidine-2,4-dione;
1-[2-(4-methoxybenzoylamino)pyrid-4-ylmethyl]-3-(4-trifluoromethanesulfanylphenyl)imidazolidine-2,4-dione;
1-(2-acetamidopyrid-4-ylmethyl)-3-(4-trifluoromethanesulfanylphenyl)imidazolidine-2,4-dione;
1-(2-phenylacetamidopyrid-4-ylmethyl)-3-(4-trifluoromethanesulfanylphenyl)imidazolidine-2,4-dione;
1-[2-(4-methylpiperazino)acetamidopyrid-4-ylmethyl]-3-(4-trifluoromethanesulfanylphenyl)imidazolidine-2,4-dione;
1-(2-cyclohexanylcarboxamidopyrid-4-ylmethyl)-3-(4-trifluoromethanesulfanylphenyl)imidazolidine-2,4-dione;
1-[2-(1-methyl-4-piperidinyl)carbonylaminopyrid-4-ylmethyl]-3-(4-trifluoromethanesulfanylphenyl)imidazolidine-2,4-dione;
1-[2-(2-furanylcarbonyl)aminopyrid-4-ylmethyl]-3-(4-trifluoromethanesulfanylphenyl)imidazolidine-2,4-dione;
1-(2-ethoxycarbonylaminopyrid-4-ylmethyl)-3-(4-trifluoromethanesulfanylphenyl)imidazolidine-2,4-dione;
1-(2-isopropoxycarbonylaminopyrid-4-ylmethyl)-3-(4-trifluoromethanesulfanylphenyl)imidazolidine-2,4-dione;
1-(2-butoxycarbonylaminopyrid-4-ylmethyl)-3-(4-trifluoromethanesulfanylphenyl)imidazolidine-2,4-dione;
1-[2-(2-diethylaminoethoxycarbonylamino)pyrid-4-ylmethyl]-3-(4-trifluoromethanesulfanylphenyl)imidazolidine-2,4-dione;
1-(2-phenoxycarbonylaminopyrid-4-ylmethyl)-3-(4-trifluoromethanesulfanylphenyl)imidazolidine-2,4-dione;
1-[2-(4-chloroanilino)carbonylaminopyrid-4-ylmethyl]-3-(4-trifluoromethanesulfanylphenyl)imidazolidine-2,4-dione;
1-(2-anilinocarbonylaminopyrid-4-ylmethyl)-3-(4-trifluoromethanesulfanylphenyl)imidazolidine-2,4-dione;
1-(2-benzylaminocarbonylaminopyrid-4-ylmethyl)-3-(4-trifluoromethanesulfanylphenyl)imidazolidine-2,4-dione;
1-[2-(2-pyridylamino)carbonylaminopyrid-4-ylmethyl]-3-(4-trifluoromethanesulfanylphenyl)imidazolidine-2,4-dione;
1-(2-ureidopyrid-4-ylmethyl)-3-(4-trifluoromethanesulfanylphenyl)imidazolidine-2,4-dione;
1-(2-benzylaminosulfonylaminopyrid-4-ylmethyl)-3-(4-trifluoromethanesulfanylphenyl)imidazolidine-2,4-dione;

1-(2-methylaminosulfonylaminopyrid-4-ylmethyl)-3-(4-trifluoromethanesulfanylphenyl)imidazolidine-2,4-dione;
1-(2-aminosulfonylaminopyrid-4-ylmethyl)-3-(4-trifluoromethanesulfanylphenyl)imidazolidine-2,4-dione;
1-(2-morpholinosulfonylaminopyrid-4-ylmethyl)-3-(4-trifluoromethanesulfanylphenyl)imidazolidine-2,4-dione;
1-(2-dimethylaminosulfonylaminopyrid-4-ylmethyl)-3-(4-trifluoromethanesulfanylphenyl)imidazolidine-2,4-dione;
1-(2-anilinosulfonylaminopyrid-4-ylmethyl)-3-(4-trifluoromethanesulfanylphenyl)imidazolidine-2,4-dione;
1-(2-phenylsulfonylaminopyrid-4-ylmethyl)-3-(4-trifluoromethanesulfanylphenyl)imidazolidine-2,4-dione;
1-[2-(2-thienyl)sulfonylaminopyrid-4-ylmethyl]-3-(4-trifluoromethanesulfanylphenyl)imidazolidine-2,4-dione;
1-(2-methylsulfonylaminopyrid-4-ylmethyl)-3-(4-trifluoromethanesulfanylphenyl)imidazolidine-2,4-dione;
1-[2-(4-chlorophenyl)sulfonylaminopyrid-4-ylmethyl]-3-(4-trifluoromethanesulfanylphenyl)imidazolidine-2,4-dione;
1-(2-benzylsulfonylaminopyrid-4-ylmethyl)-3-(4-trifluoromethanesulfanylphenyl)imidazolidine-2,4-dione;
1-(2-hydroxycarbonylpyrid-4-ylmethyl)-3-(4-trifluoromethanesulfanylphenyl)imidazolidine-2,4-dione;
1-(2-ethoxycarbonylpyrid-4-ylmethyl)-3-(4-trifluoromethanesulfanylphenyl)imidazolidine-2,4-dione;
1-(2-tert-butoxycarbonylpyrid-4-ylmethyl)-3-(4-trifluoromethanesulfanylphenyl)imidazolidine-2,4-dione;
1-(2-phenoxycarbonylpyrid-4-ylmethyl)-3-(4-trifluoromethanesulfanylphenyl)imidazolidine-2,4-dione;
1-[2-(4-methylpiperazinocarbonyl)pyrid-4-ylmethyl]-3-(4-trifluoromethanesulfanylphenyl)imidazolidine-2,4-dione;
1-[2-(methylamino)carbonylpyrid-4-ylmethyl]-3-(4-trifluoromethanesulfanylphenyl)imidazolidine-2,4-dione;
1-[2-(dimethylamino)carbonylpyrid-4-ylmethyl]-3-(4-trifluoromethanesulfanylphenyl)imidazolidine-2,4-dione;
1-(2-piperidinocarbonylpyrid-4-ylmethyl)-3-(4-trifluoromethanesulfanylphenyl)imidazolidine-2,4-dione;
1-(2-morpholinocarbonylpyrid-4-ylmethyl)-3-(4-trifluoromethanesulfanylphenyl)imidazolidine-2,4-dione;
1-[2-(4-phenylpiperazinocarbonyl)pyrid-4-ylmethyl]-3-(4-trifluoromethanesulfanylphenyl)imidazolidine-2,4-dione;
1-(2-phenylaminocarbonylpyrid-4-ylmethyl)-3-(4-trifluoromethanesulfanylphenyl)imidazolidine-2,4-dione;
1-[2-(methylphenylamino)carbonylpyrid-4-ylmethyl]-3-(4-trifluoromethanesulfanylphenyl)imidazolidine-2,4-dione;
1-[2-(4-methoxyphenyl)methylaminocarbonylpyrid-4-ylmethyl]-3-(4-trifluoromethanesulfanylphenyl)imidazolidine-2,4-dione;
1-[2-(4-chlorophenyl)methylaminocarbonylpyrid-4-ylmethyl]-3-(4-trifluoromethanesulfanylphenyl)imidazolidine-2,4-dione;
1-[2-(4-morpholinylamino)carbonylpyrid-4-ylmethyl]-3-(4-trifluoromethanesulfanylphenyl)imidazolidine-2,4-dione;
1-(2-aminocarbonylpyrid-4-ylmethyl)-3-(4-trifluoromethanesulfanylphenyl)imidazolidine-2,4-dione;
1-(2-phenoxypyrid-4-ylmethyl)-3-(4-trifluoromethanesulfanylphenyl)imidazolidine-2,4-dione;
1-(2-methoxypyrid-4-ylmethyl)-3-(4-trifluoromethanesulfanylphenyl)imidazolidine-2,4-dione;
1-(2-ethoxypyrid-4-ylmethyl)-3-(4-trifluoromethanesulfanylphenyl)imidazolidine-2,4-dione;
1-[2-(1-pyrrolidinyl)ethoxypyrid-4-ylmethyl]-3-(4-trifluoromethanesulfanylphenyl)imidazolidine-2,4-dione;
1-(2-benzyloxypyrid-4-ylmethyl)-3-(4-trifluoromethanesulfanylphenyl)imidazolidine-2,4-dione;
1-(2-benzoyloxypyrid-4-ylmethyl)-3-(4-trifluoromethanesulfanylphenyl)imidazolidine-2,4-dione;
1-[2-(4,5-dihydro-1H-imidazol-2-yl)pyrid-4-ylmethyl]-3-(4-trifluoromethanesulfanylphenyl)imidazolidine-2,4-dione;
1-[2-(1H-imidazol-2-yl)pyrid-4-ylmethyl]-3-(4-trifluoromethanesulfanylphenyl)imidazolidine-2,4-dione;
1-[2-(1H-tetrazol-5-yl)pyrid-4-ylmethyl]-3-(4-trifluoromethanesulfanylphenyl)imidazolidine-2,4-dione;
1-(2-amidinopyrid-4-ylmethyl)-3-(4-trifluoromethanesulfanylphenyl)imidazolidine-2,4-dione;
1-(2-dimethylaminomethylpyrid-4-ylmethyl)-3-(4-trifluoromethanesulfanylphenyl)imidazolidine-2,4-dione;
1-(2-aminomethylpyrid-4-ylmethyl)-3-(4-trifluoromethanesulfanylphenyl)imidazolidine-2,4-dione;
1-(3-methylpyrid-4-ylmethyl)-3-(4-trifluoromethanesulfanylphenyl)imidazolidine-2,4-dione;
1-(3-ethylpyrid-4-ylmethyl)-3-(4-trifluoromethanesulfanylphenyl)imidazolidine-2,4-dione;
1-(3-isopropylpyrid-4-ylmethyl)-3-(4-trifluoromethanesulfanylphenyl)imidazolidine-2,4-dione;
1-(3-tert-butylpyrid-4-ylmethyl)-3-(4-trifluoromethanesulfanylphenyl)imidazolidine-2,4-dione;
1-(3-isobutylpyrid-4-ylmethyl)-3-(4-trifluoromethanesulfanylphenyl)imidazolidine-2,4-dione;
1-(3-cyclohexylpyrid-4-ylmethyl)-3-(4-trifluoromethanesulfanylphenyl)imidazolidine-2,4-dione;
1-(3-phenylpyrid-4-ylmethyl)-3-(4-trifluoromethanesulfanylphenyl)imidazolidine-2,4-dione;
1-[3-(4-chlorophenyl)pyrid-4-ylmethyl]-3-(4-trifluoromethanesulfanylphenyl)imidazolidine-2,4-dione;
1-[3-(3-chlorophenyl)pyrid-4-ylmethyl]-3-(4-trifluoromethanesulfanylphenyl)imidazolidine-2,4-dione;
1-[3-(2-chlorophenyl)pyrid-4-ylmethyl]-3-(4-trifluoromethanesulfanylphenyl)imidazolidine-2,4-dione;
1-[3-(4-fluorophenyl)pyrid-4-ylmethyl]-3-(4-trifluoromethanesulfanylphenyl)imidazolidine-2,4-dione;
1-[3-(4-methoxyphenyl)pyrid-4-ylmethyl]-3-(4-trifluoromethanesulfanylphenyl)imidazolidine-2,4-dione;
1-(3-benzylpyrid-4-ylmethyl)-3-(4-trifluoromethanesulfanylphenyl)imidazolidine-2,4-dione;
1-(3,2'-bipyrid-4-ylmethyl)-3-(4-trifluoromethanesulfanylphenyl)imidazolidine-2,4-dione;
1-(3-hydroxymethylpyrid-4-ylmethyl)-3-(4-trifluoromethanesulfanylphenyl)imidazolidine-2,4-dione;
1-(3-chloropyrid-4-ylmethyl)-3-(4-trifluoromethanesulfanylphenyl)imidazolidine-2,4-dione;
1-(3-fluoropyrid-4-ylmethyl)-3-(4-trifluoromethanesulfanylphenyl)imidazolidine-2,4-dione;
1-(3-bromopyrid-4-ylmethyl)-3-(4-trifluoromethanesulfanylphenyl)imidazolidine-2,4-dione;
1-(3-aminopyrid-4-ylmethyl)-3-(4-trifluoromethanesulfanylphenyl)imidazolidine-2,4-dione;
1-(3-methylaminopyrid-4-ylmethyl)-3-(4-trifluoromethanesulfanylphenyl)imidazolidine-2,4-dione;
1-(3-ethylaminopyrid-4-ylmethyl)-3-(4-trifluoromethanesulfanylphenyl)imidazolidine-2,4-dione;
1-(3-isopropylaminopyrid-4-ylmethyl)-3-(4-trifluoromethanesulfanylphenyl)imidazolidine-2,4-dione;
1-(3-phenylaminopyrid-4-ylmethyl)-3-(4-trifluoromethanesulfanylphenyl)imidazolidine-2,4-dione;
1-(3-cyclohexylaminopyrid-4-ylmethyl)-3-(4-trifluoromethanesulfanylphenyl)imidazolidine-2,4-dione;
1-(3-diethylaminopyrid-4-ylmethyl)-3-(4-trifluoromethanesulfanylphenyl)imidazolidine-2,4-dione;
1-(3-N-cyclohexyl-N-methylaminopyrid-4-ylmethyl)-3-(4-trifluoromethanesulfanylphenyl)imidazolidine-2,4-dione;
1-(3-piperidinopyrid-4-ylmethyl)-3-(4-trifluoromethanesulfanylphenyl)imidazolidine-2,4-dione;

1-(3-morpholinopyrid-4-ylmethyl)-3-(4-trifluoromethanesulfanylphenyl)imidazolidine-2,4-dione;
1-[3-(4-methylpiperazino)pyrid-4-ylmethyl]-3-(4-trifluoromethanesulfanylphenyl)imidazolidine-2,4-dione;
1-[3-(1H-pyrazol-1-yl)pyrid-4-ylmethyl]-3-(4-trifluoromethanesulfanylphenyl)imidazolidine-2,4-dione;
1-[3-(2-benzoylhydrazino)pyrid-4-ylmethyl]-3-(4-trifluoromethanesulfanylphenyl)imidazolidine-2,4-dione;
1-(3-benzoylaminopyrid-4-ylmethyl)-3-(4-trifluoromethanesulfanylphenyl)imidazolidine-2,4-dione;
1-[3-(4-chlorobenzoylamino)pyrid-4-ylmethyl]-3-(4-trifluoromethanesulfanylphenyl)imidazolidine-2,4-dione;
1-[3-(3-chlorobenzoylamino)pyrid-4-ylmethyl]-3-(4-trifluoromethanesulfanylphenyl)imidazolidine-2,4-dione;
1-[3-(2-chlorobenzoylamino)pyrid-4-ylmethyl]-3-(4-trifluoromethanesulfanylphenyl)imidazolidine-2,4-dione;
1-[3-(4-fluorobenzoylamino)pyrid-4-ylmethyl]-3-(4-trifluoromethanesulfanylphenyl)imidazolidine-2,4-dione;
1-[3-(4-methoxybenzoylamino)pyrid-4-ylmethyl]-3-(4-trifluoromethanesulfanylphenyl)imidazolidine-2,4-dione;
1-(3-acetamidopyrid-4-ylmethyl)-3-(4-trifluoromethanesulfanylphenyl)imidazolidine-2,4-dione;
1-(3-phenylacetamidopyrid-4-ylmethyl)-3-(4-trifluoromethanesulfanylphenyl)imidazolidine-2,4-dione;
1-[3-(4-methylpiperazino)acetamidopyrid-4-ylmethyl]-3-(4-trifluoromethanesulfanylphenyl)imidazolidine-2,4-dione;
1-(3-cyclohexanylcarboxamidopyrid-4-ylmethyl)-3-(4-trifluoromethanesulfanylphenyl)imidazolidine-2,4-dione;
1-[3-(1-methyl-4-piperidinyl)carbonylaminopyrid-4-ylmethyl]-3-(4-trifluoromethanesulfanylphenyl)imidazolidine-2,4-dione;
1-[3-(2-furanylcarbonyl)aminopyrid-4-ylmethyl]-3-(4-trifluoromethanesulfanylphenyl)imidazolidine-2,4-dione;
1-(3-ethoxycarbonylaminopyrid-4-ylmethyl)-3-(4-trifluoromethanesulfanylphenyl)imidazolidine-2,4-dione;
1-(3-isopropoxycarbonylaminopyrid-4-ylmethyl)-3-(4-trifluoromethanesulfanylphenyl)imidazolidine-2,4-dione;
1-(3-butoxycarbonylaminopyrid-4-ylmethyl)-3-(4-trifluoromethanesulfanylphenyl)imidazolidine-2,4-dione;
1-[3-(2-diethylaminoethoxycarbonylamino)pyrid-4-ylmethyl]-3-(4-trifluoromethanesulfanylphenyl)imidazolidine-2,4-dione;
1-(3-phenoxycarbonylaminopyrid-4-ylmethyl)-3-(4-trifluoromethanesulfanylphenyl)imidazolidine-2,4-dione;
1-[3-(4-chloroanilino)carbonylaminopyrid-4-ylmethyl]-3-(4-trifluoromethanesulfanylphenyl)imidazolidine-2,4-dione;
1-(3-anilinocarbonylaminopyrid-4-ylmethyl)-3-(4-trifluoromethanesulfanylphenyl)imidazolidine-2,4-dione;
1-(3-benzylaminocarbonylaminopyrid-4-ylmethyl)-3-(4-trifluoromethanesulfanylphenyl)imidazolidine-2,4-dione;
1-[3-(2-pyridylamino)carbonylaminopyrid-4-ylmethyl]-3-(4-trifluoromethanesulfanylphenyl)imidazolidine-2,4-dione;
1-(3-ureidopyrid-4-ylmethyl)-3-(4-trifluoromethanesulfanylphenyl)imidazolidine-2,4-dione;
1-(3-benzylaminosulfonylaminopyrid-4-ylmethyl)-3-(4-trifluoromethanesulfanylphenyl)imidazolidine-2,4-dione;
1-(3-methylaminosulfonylaminopyrid-4-ylmethyl)-3-(4-trifluoromethanesulfanylphenyl)imidazolidine-2,4-dione;
1-(3-aminosulfonylaminopyrid-4-ylmethyl)-3-(4-trifluoromethanesulfanylphenyl)imidazolidine-2,4-dione;
1-(3-morpholinosulfonylaminopyrid-4-ylmethyl)-3-(4-trifluoromethanesulfanylphenyl)imidazolidine-2,4-dione;
1-(3-dimethylaminosulfonylaminopyrid-4-ylmethyl)-3-(4-trifluoromethanesulfanylphenyl)imidazolidine-2,4-dione;
1-(3-anilinosulfonylaminopyrid-4-ylmethyl)-3-(4-trifluoromethanesulfanylphenyl)imidazolidine-2,4-dione;
1-(3-phenylsulfonylaminopyrid-4-ylmethyl)-3-(4-trifluoromethanesulfanylphenyl)imidazolidine-2,4-dione;
1-[3-(2-thienyl)sulfonylaminopyrid-4-ylmethyl]-3-(4-trifluoromethanesulfanylphenyl)imidazolidine-2,4-dione;
1-(3-methylsulfonylaminopyrid-4-ylmethyl)-3-(4-trifluoromethanesulfanylphenyl)imidazolidine-2,4-dione;
1-[3-(4-chlorophenyl)sulfonylaminopyrid-4-ylmethyl]-3-(4-trifluoromethanesulfanylphenyl)imidazolidine-2,4-dione;
1-(3-benzylsulfonylaminopyrid-4-ylmethyl)-3-(4-trifluoromethanesulfanylphenyl)imidazolidine-2,4-dione;
1-(3-hydroxycarbonylpyrid-4-ylmethyl)-3-(4-trifluoromethanesulfanylphenyl)imidazolidine-2,4-dione;
1-(3-ethoxycarbonylpyrid-4-ylmethyl)-3-(4-trifluoromethanesulfanylphenyl)imidazolidine-2,4-dione;
1-(3-tert-butoxycarbonylpyrid-4-ylmethyl)-3-(4-trifluoromethanesulfanylphenyl)imidazolidine-2,4-dione;
1-(3-phenoxycarbonylpyrid-4-ylmethyl)-3-(4-trifluoromethanesulfanylphenyl)imidazolidine-2,4-dione;
1-[3-(4-methylpiperazinocarbonyl)pyrid-4-ylmethyl]-3-(4-trifluoromethanesulfanylphenyl)imidazolidine-2,4-dione;
1-[3-(methylamino)carbonylpyrid-4-ylmethyl]-3-(4-trifluoromethanesulfanylphenyl)imidazolidine-2,4-dione;
1-[3-(dimethylamino)carbonylpyrid-4-ylmethyl]-3-(4-trifluoromethanesulfanylphenyl)imidazolidine-2,4-dione;
1-(3-piperidinocarbonylpyrid-4-ylmethyl)-3-(4-trifluoromethanesulfanylphenyl)imidazolidine-2,4-dione;
1-(3-morpholinocarbonylpyrid-4-ylmethyl)-3-(4-trifluoromethanesulfanylphenyl)imidazolidine-2,4-dione;
1-[3-(4-phenylpiperazinocarbonyl)pyrid-4-ylmethyl]-3-(4-trifluoromethanesulfanylphenyl)imidazolidine-2,4-dione;
1-(3-phenylaminocarbonylpyrid-4-ylmethyl)-3-(4-trifluoromethanesulfanylphenyl)imidazolidine-2,4-dione;
1-[3-(methylphenylamino)carbonylpyrid-4-ylmethyl]-3-(4-trifluoromethanesulfanylphenyl)imidazolidine-2,4-dione;
1-[3-(4-methoxyphenyl)methylaminocarbonylpyrid-4-ylmethyl]-3-(4-trifluoromethanesulfanylphenyl)imidazolidine-2,4-dione;
1-[3-(4-chlorophenyl)methylaminocarbonylpyrid-4-ylmethyl]-3-(4-trifluoromethanesulfanylphenyl)imidazolidine-2,4-dione;
1-[3-(4-morpholinylamino)carbonylpyrid-4-ylmethyl]-3-(4-trifluoromethanesulfanylphenyl)imidazolidine-2,4-dione;
1-(3-aminocarbonylpyrid-4-ylmethyl)-3-(4-trifluoromethanesulfanylphenyl)imidazolidine-2,4-dione;
1-(3-phenoxypyrid-4-ylmethyl)-3-(4-trifluoromethanesulfanylphenyl)imidazolidine-2,4-dione;
1-(3-methoxypyrid-4-ylmethyl)-3-(4-trifluoromethanesulfanylphenyl)imidazolidine-2,4-dione;
1-(3-ethoxypyrid-4-ylmethyl)-3-(4-trifluoromethanesulfanylphenyl)imidazolidine-2,4-dione;
1-[3-(1-pyrrolidinyl)ethoxypyrid-4-ylmethyl]-3-(4-trifluoromethanesulfanylphenyl)imidazolidine-2,4-dione;
1-(3-benzyloxypyrid-4-ylmethyl)-3-(4-trifluoromethanesulfanylphenyl)imidazolidine-2,4-dione;
1-(3-benzoyloxypyrid-4-ylmethyl)-3-(4-trifluoromethanesulfanylphenyl)imidazolidine-2,4-dione;
1-[3-(4,5-dihydro-1H-imidazol-2-yl)pyrid-4-ylmethyl]-3-(4-trifluoromethanesulfanylphenyl)imidazolidine-2,4-dione;
1-[3-(1H-imidazol-2-yl)pyrid-4-ylmethyl]-3-(4-trifluoromethanesulfanylphenyl)imidazolidine-2,4-dione;
1-[3-(1H-tetrazol-5-yl)pyrid-4-ylmethyl]-3-(4-trifluoromethanesulfanylphenyl)imidazolidine-2,4-dione;

1-(3-amidinopyrid-4-ylmethyl)-3-(4-trifluoromethanesulfanylphenyl)imidazolidine-2,4-dione;
1-(3-dimethylaminomethylpyridin)-4-ylmethyl]-3-(4-trifluoromethanesulfanylphenyl)imidazolidine-2,4-dione;
1-(3-aminomethylpyrid-4-ylmethyl)-3-(4-trifluoromethanesulfanylphenyl)imidazolidine-2,4-dione;
5,5-dimethyl-1-(2-methylpyrid-4-ylmethyl)-3-(4-trifluoromethanesulfonylphenyl)imidazolidine-2,4-dione;
5,5-dimethyl-1-(2-ethylpyrid-4-ylmethyl)-3-(4-trifluoromethanesulfonylphenyl)imidazolidine-2,4-dione;
5,5-dimethyl-1-(2-isopropylpyrid-4-ylmethyl)-3-(4-trifluoromethanesulfonylphenyl)imidazolidine-2,4-dione;
5,5-dimethyl-1-(2-tert-butylpyrid-4-ylmethyl)-3-(4-trifluoromethanesulfonylphenyl)imidazolidine-2,4-dione;
5,5-dimethyl-1-(2-isobutylpyrid-4-ylmethyl)-3-(4-trifluoromethanesulfonylphenyl)imidazolidine-2,4-dione;
5,5-dimethyl-1-(2-cyclohexylpyrid-4-ylmethyl)-3-(4-trifluoromethanesulfonylphenyl)imidazolidine-2,4-dione;
5,5-dimethyl-1-(2-phenylpyrid-4-ylmethyl)-3-(4-trifluoromethanesulfonylphenyl)imidazolidine-2,4-dione;
5,5-dimethyl-1-[2-(4-chlorophenyl)pyrid-4-ylmethyl]-3-(4-trifluoromethanesulfonylphenyl)imidazolidine-2,4-dione;
5,5-dimethyl-1-[2-(3-chlorophenyl)pyrid-4-ylmethyl]-3-(4-trifluoromethanesulfonylphenyl)imidazolidine-2,4-dione;
5,5-dimethyl-1-[2-(2-chlorophenyl)pyrid-4-ylmethyl]-3-(4-trifluoromethanesulfonylphenyl)imidazolidine-2,4-dione;
5,5-dimethyl-1-[2-(4-fluorophenyl)pyrid-4-ylmethyl]-3-(4-trifluoromethanesulfonylphenyl)imidazolidine-2,4-dione;
5,5-dimethyl-1-[2-(4-methoxyphenyl)pyrid-4-ylmethyl]-3-(4-trifluoromethanesulfonylphenyl)imidazolidine-2,4-dione;
5,5-dimethyl-1-(2-benzylpyrid-4-ylmethyl)-3-(4-trifluoromethanesulfonylphenyl)imidazolidine-2,4-dione;
5,5-dimethyl-1-(2,2'-bipyrid-4-ylmethyl)-3-(4-trifluoromethanesulfonylphenyl)imidazolidine-2,4-dione;
5,5-dimethyl-1-(2-hydroxymethylpyrid-4-ylmethyl)-3-(4-trifluoromethanesulfonylphenyl)imidazolidine-2,4-dione;
5,5-dimethyl-1-(2-chloropyrid-4-ylmethyl)-3-(4-trifluoromethanesulfonylphenyl)imidazolidine-2,4-dione;
5,5-dimethyl-1-(2-fluoropyrid-4-ylmethyl)-3-(4-trifluoromethanesulfonylphenyl)imidazolidine-2,4-dione;
5,5-dimethyl-1-(2-bromopyrid-4-ylmethyl)-3-(4-trifluoromethanesulfonylphenyl)imidazolidine-2,4-dione;
5,5-dimethyl-1-(2-aminopyrid-4-ylmethyl)-3-(4-trifluoromethanesulfonylphenyl)imidazolidine-2,4-dione;
5,5-dimethyl-1-(2-methylaminopyrid-4-ylmethyl)-3-(4-trifluoromethanesulfonylphenyl)imidazolidine-2,4-dione;
5,5-dimethyl-1-(2-ethylaminopyrid-4-ylmethyl)-3-(4-trifluoromethanesulfonylphenyl)imidazolidine-2,4-dione;
5,5-dimethyl-1-(2-isopropylaminopyrid-4-ylmethyl)-3-(4-trifluoromethanesulfonylphenyl)imidazolidine-2,4-dione;
5,5-dimethyl-1-(2-phenylaminopyrid-4-ylmethyl)-3-(4-trifluoromethanesulfonylphenyl)imidazolidine-2,4-dione;
5,5-dimethyl-1-(2-cyclohexylaminopyrid-4-ylmethyl)-3-(4-trifluoromethanesulfonylphenyl)imidazolidine-2,4-dione;
5,5-dimethyl-1-(2-diethylaminopyrid-4-ylmethyl)-3-(4-trifluoromethanesulfonylphenyl)imidazolidine-2,4-dione;
5,5-dimethyl-1-(2-N-cyclohexyl-N-methylaminopyrid-4-ylmethyl)-3-(4-trifluoromethanesulfonylphenyl)imidazolidine-2,4-dione;
5,5-dimethyl-1-(2-piperidinopyrid-4-ylmethyl)-3-(4-trifluoromethanesulfonylphenyl)imidazolidine-2,4-dione;
5,5-dimethyl-1-(2-morpholinopyrid-4-ylmethyl)-3-(4-trifluoromethanesulfonylphenyl)imidazolidine-2,4-dione;
5,5-dimethyl-1-[2-(4-methylpiperazino)diethylaminopyrid-4-ylmethyl]-3-(4-trifluoromethanesulfonylphenyl)imidazolidine-2,4-dione;
5,5-dimethyl-1-[2-(1H-pyrazol-1-yl)pyrid-4-ylmethyl]-3-(4-trifluoromethanesulfonylphenyl)imidazolidine-2,4-dione;
5,5-dimethyl-1-[2-(2-benzoylhydrazino)pyrid-4-ylmethyl]-3-(4-trifluoromethanesulfonylphenyl)imidazolidine-2,4-dione;
5,5-dimethyl-1-[2-(2-benzoylaminopyrid-4-ylmethyl)-3-(4-trifluoromethanesulfonylphenyl)imidazolidine-2,4-dione;
5,5-dimethyl-1-[2-(4-chlorobenzoylamino)pyrid-4-ylmethyl]-3-(4-trifluoromethanesulfonylphenyl)imidazolidine-2,4-dione;
5,5-dimethyl-1-[2-(3-chlorobenzoylamino)pyrid-4-ylmethyl]-3-(4-trifluoromethanesulfonylphenyl)imidazolidine-2,4-dione;
5,5-dimethyl-1-[2-(2-chlorobenzoylamino)pyrid-4-ylmethyl]-3-(4-trifluoromethanesulfonylphenyl)imidazolidine-2,4-dione;
5,5-dimethyl-1-[2-(4-fluorobenzoylamino)pyrid-4-ylmethyl]-3-(4-trifluoromethanesulfonylphenyl)imidazolidine-2,4-dione;
5,5-dimethyl-1-[2-(4-methoxybenzoylamino)pyrid-4-ylmethyl]-3-(4-trifluoromethanesulfonylphenyl)imidazolidine-2,4-dione;
5,5-dimethyl-1-(2-acetamidopyrid-4-ylmethyl)-3-(4-trifluoromethanesulfonylphenyl)imidazolidine-2,4-dione;
5,5-dimethyl-1-(2-phenylacetamidopyrid-4-ylmethyl)-3-(4-trifluoromethanesulfonylphenyl)imidazolidine-2,4-dione;
5,5-dimethyl-1-[2-(4-methylpiperazino)acetamidopyrid-4-ylmethyl]-3-(4-trifluoromethanesulfonylphenyl)imidazolidine-2,4-dione;
5,5-dimethyl-1-(2-cyclohexanylcarboxamidopyrid-4-ylmethyl)-3-(4-trifluoromethanesulfonylphenyl)imidazolidine-2,4-dione;
5,5-dimethyl-1-[2-(1-methyl-4-piperidinyl)carbonylaminopyrid-4-ylmethyl]-3-(4-trifluoromethanesulfonylphenyl)imidazolidine-2,4-dione;
5,5-dimethyl-1-[2-(2-furanylcarbonyl)aminopyrid-4-ylmethyl]-3-(4-trifluoromethanesulfonylphenyl)imidazolidine-2,4-dione;
5,5-dimethyl-1-(2-ethoxycarbonylaminopyrid-4-ylmethyl)-3-(4-trifluoromethanesulfonylphenyl)imidazolidine-2,4-dione;
5,5-dimethyl-1-(2-isopropoxycarbonylaminopyrid-4-ylmethyl)-3-(4-trifluoromethanesulfonylphenyl)imidazolidine-2,4-dione;
5,5-dimethyl-1-(2-butoxycarbonylaminopyrid-4-ylmethyl)-3-(4-trifluoromethanesulfonylphenyl)imidazolidine-2,4-dione;
5,5-dimethyl-1-[2-(2-diethylaminoethoxycarbonylamino)pyrid-4-ylmethyl]-3-(4-trifluoromethanesulfonylphenyl)imidazolidine-2,4-dione;
5,5-dimethyl-1-(2-phenoxycarbonylaminopyrid-4-ylmethyl)-3-(4-trifluoromethanesulfonylphenyl)imidazolidine-2,4-dione;
5,5-dimethyl-1-[2-(4-chloroanilino)carbonylaminopyrid-4-ylmethyl)]-3-(4-trifluoromethanesulfonylphenyl)imidazolidine-2,4-dione;
5,5-dimethyl-1-(2-anilinocarbonylaminopyrid-4-ylmethyl)-3-(4-trifluoromethanesulfonylphenyl)imidazolidine-2,4-dione;
5,5-dimethyl-1-(2-benzylaminocarbonylaminopyrid-4-ylmethyl)-3-(4-trifluoromethanesulfonylphenyl)imidazolidine-2,4-dione;
5,5-dimethyl-1-[2-(2-pyridylamino)carbonylaminopyrid-4-ylmethyl)]-3-(4-trifluoromethanesulfonylphenyl)imidazolidine-2,4-dione;

5,5-dimethyl-1-(2-ureidopyrid-4-ylmethyl)-3-(4-trifluoromethanesulfonylphenyl)imidazolidine-2,4-dione;
5,5-dimethyl-1-(2-benzylaminosulfonylaminopyrid-4-ylmethyl)-3-(4-trifluoromethanesulfonylphenyl)imidazolidine-2,4-dione;
5,5-dimethyl-1-(2-methylaminosulfonylaminopyrid-4-ylmethyl)-3-(4-trifluoromethanesulfonylphenyl)imidazolidine-2,4-dione;
5,5-dimethyl-1-(2-aminosulfonylaminopyrid-4-ylmethyl)-3-(4-trifluoromethanesulfonylphenyl)imidazolidine-2,4-dione;
5,5-dimethyl-1-(2-morpholinosulfonylaminopyrid-4-ylmethyl)-3-(4-trifluoromethanesulfonylphenyl)imidazolidine-2,4-dione;
5,5-dimethyl-1-(2-dimethylaminosulfonylaminopyrid-4-ylmethyl)-3-(4-trifluoromethanesulfonylphenyl)imidazolidine-2,4-dione;
5,5-dimethyl-1-(2-anilinosulfonylaminopyrid-4-ylmethyl)-3-(4-trifluoromethanesulfonylphenyl)imidazolidine-2,4-dione;
5,5-dimethyl-1-(2-phenylsulfonylaminopyrid-4-ylmethyl)-3-(4-trifluoromethanesulfonylphenyl)imidazolidine-2,4-dione;
5,5-dimethyl-1-[2-(2-thienyl)sulfonylaminopyrid-4-ylmethyl]-3-(4-trifluoromethanesulfonylphenyl)imidazolidine-2,4-dione;
5,5-dimethyl-1-(2-methylsulfonylaminopyrid-4-ylmethyl)-3-(4-trifluoromethanesulfonylphenyl)imidazolidine-2,4-dione;
5,5-dimethyl-1-[2-(4-chlorophenyl)sulfonylaminopyrid-4-ylmethyl]-3-(4-trifluoromethanesulfonylphenyl)imidazolidine-2,4-dione;
5,5-dimethyl-1-(2-benzylsulfonylaminopyrid-4-ylmethyl)-3-(4-trifluoromethanesulfonylphenyl)imidazolidine-2,4-dione;
5,5-dimethyl-1-(2-hydroxycarbonylpyrid-4-ylmethyl)-3-(4-trifluoromethanesulfonylphenyl)imidazolidine-2,4-dione;
5,5-dimethyl-1-(2-ethoxycarbonylpyrid-4-ylmethyl)-3-(4-trifluoromethanesulfonylphenyl)imidazolidine-2,4-dione;
5,5-dimethyl-1-(2-tert-butoxycarbonylpyrid-4-ylmethyl)-3-(4-trifluoromethanesulfonylphenyl)imidazolidine-2,4-dione;
5,5-dimethyl-1-(2-phenoxycarbonylpyrid-4-ylmethyl)-3-(4-trifluoromethanesulfonylphenyl)imidazolidine-2,4-dione;
5,5-dimethyl-1-[2-(4-methylpiperazinocarbonyl)pyrid-4-ylmethyl]-3-(4-trifluoromethanesulfonylphenyl)imidazolidine-2,4-dione;
5,5-dimethyl-1-[2-(methylamino)carbonylpyrid-4-ylmethyl]-3-(4-trifluoromethanesulfonylphenyl)imidazolidine-2,4-dione;
5,5-dimethyl-1-[2-dimethylamino)carbonylpyrid-4-ylmethyl]-3-(4-trifluoromethanesulfonylphenyl)imidazolidine-2,4-dione;
5,5-dimethyl-1-(2-piperidinocarbonylpyrid-4-ylmethyl)-3-(4-trifluoromethanesulfonylphenyl)imidazolidine-2,4-dione;
5,5-dimethyl-1-(2-morpholinocarbonylpyrid-4-ylmethyl)-3-(4-trifluoromethanesulfonylphenyl)imidazolidine-2,4-dione;
5,5-dimethyl-1-[2-(4-phenylpiperazinocarbonyl)pyrid-4-ylmethyl]-3-(4-trifluoromethanesulfonylphenyl)imidazolidine-2,4-dione;
5,5-dimethyl-1-(2-phenylaminocarbonylpyrid-4-ylmethyl)-3-(4-trifluoromethanesulfonylphenyl)imidazolidine-2,4-dione;
5,5-dimethyl-1-[2-methylphenylamino)carbonylpyrid-4-ylmethyl]-3-(4-trifluoromethanesulfonylphenyl)imidazolidine-2,4-dione;
5,5-dimethyl-1-[2-(4-methoxyphenyl)methylaminocarbonylpyrid-4-ylmethyl]-3-(4-trifluoromethanesulfonylphenyl)imidazolidine-2,4-dione;
5,5-dimethyl-1-[2-(4-chlorophenyl)methylaminocarbonylpyrid-4-ylmethyl]-3-(4-trifluoromethanesulfonylphenyl)imidazolidine-2,4-dione;
5,5-dimethyl-1-[2-(4-morpholinylamino)carbonylpyrid-4-ylmethyl]-3-(4-trifluoromethanesulfonylphenyl)imidazolidine-2,4-dione;
5,5-dimethyl-1-(2-aminocarbonylpyrid-4-ylmethyl)-3-(4-trifluoromethanesulfonylphenyl)imidazolidine-2,4-dione;
5,5-dimethyl-1-(2-phenoxypyrid-4-ylmethyl)-3-(4-trifluoromethanesulfonylphenyl)imidazolidine-2,4-dione;
5,5-dimethyl-1-(2-methoxypyrid-4-ylmethyl)-3-(4-trifluoromethanesulfonylphenyl)imidazolidine-2,4-dione;
5,5-dimethyl-1-(2-ethoxypyrid-4-ylmethyl)-3-(4-trifluoromethanesulfonylphenyl)imidazolidine-2,4-dione;
5,5-dimethyl-1-[2-(1-pyrrolidinyl)ethoxypyrid-4-ylmethyl]-3-(4-trifluoromethanesulfonylphenyl)imidazolidine-2,4-dione;
5,5-dimethyl-1-(2-benzyloxypyrid-4-ylmethyl)-3-(4-trifluoromethanesulfonylphenyl)imidazolidine-2,4-dione;
5,5-dimethyl-1-(2-benzoyloxypyrid-4-ylmethyl)-3-(4-trifluoromethanesulfonylphenyl)imidazolidine-2,4-dione;
5,5-dimethyl-1-[2-(4,5-dihydro-1H-imidazol-2-yl)pyrid-4-ylmethyl]-3-(4-trifluoromethanesulfonylphenyl)imidazolidine-2,4-dione;
5,5-dimethyl-1-[2-(1H-imidazol-2-yl)pyrid-4-ylmethyl]-3-(4-trifluoromethanesulfonylphenyl)imidazolidine-2,4-dione;
5,5-dimethyl-1-[2-(1H-tetrazol-5-yl)pyrid-4-ylmethyl]-3-(4-trifluoromethanesulfonylphenyl)imidazolidine-2,4-dione;
5,5-dimethyl-1-(2-amidinopyrid-4-ylmethyl)-3-(4-trifluoromethanesulfonylphenyl)imidazolidine-2,4-dione;
5,5-dimethyl-1-(2-dimethylaminomethylpyrid-4-ylmethyl)-3-(4-trifluoromethanesulfonylphenyl)imidazolidine-2,4-dione;
5,5-dimethyl-1-(2-aminomethylpyrid-4-ylmethyl)-3-(4-trifluoromethanesulfonylphenyl)imidazolidine-2,4-dione;
5,5-dimethyl-1-(3-methylpyrid-4-ylmethyl)-3-(4-trifluoromethanesulfonylphenyl)imidazolidine-2,4-dione;
5,5-dimethyl-1-(3-ethylpyrid-4-ylmethyl)-3-(4-trifluoromethanesulfonylphenyl)imidazolidine-2,4-dione;
5,5-dimethyl-1-(3-isopropylpyrid-4-ylmethyl)-3-(4-trifluoromethanesulfonylphenyl)imidazolidine-2,4-dione;
5,5-dimethyl-1-(3-tert-butylpyrid-4-ylmethyl)-3-(4-trifluoromethanesulfonylphenyl)imidazolidine-2,4-dione;
5,5-dimethyl-1-(3-isobutylpyrid-4-ylmethyl)-3-(4-trifluoromethanesulfonylphenyl)imidazolidine-2,4-dione;
5,5-dimethyl-1-(3-cyclohexylpyrid-4-ylmethyl)-3-(4-trifluoromethanesulfonylphenyl)imidazolidine-2,4-dione;
5,5-dimethyl-1-(3-phenylpyrid-4-ylmethyl)-3-(4-trifluoromethanesulfonylphenyl)imidazolidine-2,4-dione;
5,5-dimethyl-1-[3-(4-chlorophenyl)pyrid-4-ylmethyl]-3-(4-trifluoromethanesulfonylphenyl)imidazolidine-2,4-dione;
5,5-dimethyl-1-[3-(3-chlorophenyl)pyrid-4-ylmethyl]-3-(4-trifluoromethanesulfonylphenyl)imidazolidine-2,4-dione;
5,5-dimethyl-1-[3-(2-chlorophenyl)pyrid-4-ylmethyl]-3-(4-trifluoromethanesulfonylphenyl)imidazolidine-2,4-dione;
5,5-dimethyl-1-[3-(4-fluorophenyl)pyrid-4-ylmethyl]-3-(4-trifluoromethanesulfonylphenyl)imidazolidine-2,4-dione;

5,5-dimethyl-1-[3-(4-methoxyphenyl)pyrid-4-ylmethyl]-3-(4-trifluoromethanesulfonylphenyl)imidazolidine-2,4-dione;
5,5-dimethyl-1-(3-benzylpyrid-4-ylmethyl)-3-(4-trifluoromethanesulfonylphenyl)imidazolidine-2,4-dione;
5,5-dimethyl-1-(3,2'-bipyrid-4-ylmethyl)-3-(4-trifluoromethanesulfonylphenyl)imidazolidine-2,4-dione;
5,5-dimethyl-1-(3-hydroxymethylpyrid-4-ylmethyl)-3-(4-trifluoromethanesulfonylphenyl)imidazolidine-2,4-dione;
5,5-dimethyl-1-(3-chloropyrid-4-ylmethyl)-3-(4-trifluoromethanesulfonylphenyl)imidazolidine-2,4-dione;
5,5-dimethyl-1-(3-fluoropyrid-4-ylmethyl)-3-(4-trifluoromethanesulfonylphenyl)imidazolidine-2,4-dione;
5,5-dimethyl-1-(3-bromopyrid-4-ylmethyl)-3-(4-trifluoromethanesulfonylphenyl)imidazolidine-2,4-dione;
5,5-dimethyl-1-(3-aminopyrid-4-ylmethyl)-3-(4-trifluoromethanesulfonylphenyl)imidazolidine-2,4-dione;
5,5-dimethyl-1-(3-methylaminopyrid-4-ylmethyl)-3-(4-trifluoromethanesulfonylphenyl)imidazolidine-2,4-dione;
5,5-dimethyl-1-(3-ethylaminopyrid-4-ylmethyl)-3-(4-trifluoromethanesulfonylphenyl)imidazolidine-2,4-dione;
5,5-dimethyl-1-(3-isopropylaminopyrid-4-ylmethyl)-3-(4-trifluoromethanesulfonylphenyl)imidazolidine-2,4-dione;
5,5-dimethyl-1-(3-phenylaminopyrid-4-ylmethyl)-3-(4-trifluoromethanesulfonylphenyl)imidazolidine-2,4-dione;
5,5-dimethyl-1-(3-cyclohexylaminopyrid-4-ylmethyl)-3-(4-trifluoromethanesulfonylphenyl)imidazolidine-2,4-dione;
5,5-dimethyl-1-(3-diethylaminopyrid-4-ylmethyl)-3-(4-trifluoromethanesulfonylphenyl)imidazolidine-2,4-dione;
5,5-dimethyl-1-(3-N-cyclohexyl-N-methylaminopyrid-4-yl-methyl)-3-(4-trifluoromethanesulfonylphenyl)imidazolidine-2,4-dione;
5,5-dimethyl-1-(3-piperidinopyrid-4-ylmethyl)-3-(4-trifluoromethanesulfonylphenyl)imidazolidine-2,4-dione;
5,5-dimethyl-1-(3-morpholinopyrid-4-ylmethyl)-3-(4-trifluoromethanesulfonylphenyl)imidazolidine-2,4-dione;
5,5-dimethyl-1-[3-(4-methylpiperazino)diethylaminopyrid-4-ylmethyl]-3-(4-trifluoromethanesulfonylphenyl)imidazolidine-2,4-dione;
5,5-dimethyl-1-[3-(1H-pyrazol-1-yl)pyrid-4-ylmethyl]-3-(4-trifluoromethanesulfonylphenyl)imidazolidine-2,4-dione;
5,5-dimethyl-1-[3-(2-benzoylhydrazino)pyrid-4-ylmethyl]-3-(4-trifluoromethanesulfonylphenyl)imidazolidine-2,4-dione;
5,5-dimethyl-1-(3-benzoylaminopyrid-4-ylmethyl)-3-(4-trifluoromethanesulfonylphenyl)imidazolidine-2,4-dione;
5,5-dimethyl-1-[3-(4-chlorobenzoylamino)pyrid-4-ylmethyl]-3-(4-trifluoromethanesulfonylphenyl)imidazolidine-2,4-dione;
5,5-dimethyl-1-[3-(3-chlorobenzoylamino)pyrid-4-ylmethyl]-3-(4-trifluoromethanesulfonylphenyl)imidazolidine-2,4-dione;
5,5-dimethyl-1-[3-(2-chlorobenzoylamino)pyrid-4-ylmethyl]-3-(4-trifluoromethanesulfonylphenyl)imidazolidine-2,4-dione;
5,5-dimethyl-1-[3-(4-fluorobenzoylamino)pyrid-4-ylmethyl]-3-(4-trifluoromethanesulfonylphenyl)imidazolidine-2,4-dione;
5,5-dimethyl-1-[3-(4-methoxybenzoylamino)pyrid-4-ylmethyl]-3-(4-trifluoromethanesulfonylphenyl)imidazolidine-2,4-dione;
5,5-dimethyl-1-(3-acetamidopyrid-4-ylmethyl)-3-(4-trifluoromethanesulfonylphenyl)imidazolidine-2,4-dione;
5,5-dimethyl-1-(3-phenylacetamidopyrid-4-ylmethyl)-3-(4-trifluoromethanesulfonylphenyl)imidazolidine-2,4-dione;
5,5-dimethyl-1-[3-(4-methylpiperazino)acetamidopyrid-4-ylmethyl]-3-(4-trifluoromethanesulfonylphenyl)imidazolidine-2,4-dione;
5,5-dimethyl-1-(3-cyclohexanylcarboxamidopyrid-4-ylmethyl)-3-(4-trifluoromethanesulfonylphenyl)imidazolidine-2,4-dione;
5,5-dimethyl-1-[3-(1-methyl-4-piperidinyl)carbonylaminopyrid-4-ylmethyl]-3-(4-trifluoromethanesulfonylphenyl)imidazolidine-2,4-dione;
5,5-dimethyl-1-[3-(2-furanylcarbonyl)aminopyrid-4-ylmethyl]-3-(4-trifluoromethanesulfonylphenyl)imidazolidine-2,4-dione;
5,5-dimethyl-1-(3-ethoxycarbonylaminopyrid-4-ylmethyl)-3-(4-trifluoromethanesulfonylphenyl)imidazolidine-2,4-dione;
5,5-dimethyl-1-(3-isopropoxycarbonylaminopyrid-4-ylmethyl)-3-(4-trifluoromethanesulfonylphenyl)imidazolidine-2,4-dione;
5,5-dimethyl-1-(3-butoxycarbonylaminopyrid-4-ylmethyl)-3-(4-trifluoromethanesulfonylphenyl)imidazolidine-2,4-dione;
5,5-dimethyl-1-[3-(2-diethylaminoethoxycarbonylamino)pyrid-4-ylmethyl]-3-(4-trifluoromethanesulfonylphenyl)imidazolidine-2,4-dione;
5,5-dimethyl-1-(3-phenoxycarbonylaminopyrid-4-ylmethyl)-3-(4-trifluoromethanesulfonylphenyl)imidazolidine-2,4-dione;
5,5-dimethyl-1-[3-(4-chloroanilino)carbonylaminopyrid-4-ylmethyl)]-3-(4-trifluoromethanesulfonylphenyl)imidazolidine-2,4-dione;
5,5-dimethyl-1-(3-anilinocarbonylaminopyrid-4-ylmethyl)-3-(4-trifluoromethanesulfonylphenyl)imidazolidine-2,4-dione;
5,5-dimethyl-1-(3-benzylaminocarbonylaminopyrid-4-ylmethyl)-3-(4-trifluoromethanesulfonylphenyl)imidazolidine-2,4-dione;
5,5-dimethyl-1-[3-(2-pyridylamino)carbonylaminopyrid-4-ylmethyl)]-3-(4-trifluoromethanesulfonylphenyl)imidazolidine-2,4-dione;
5,5-dimethyl-1-(3-ureidopyrid-4-ylmethyl)-3-(4-trifluoromethanesulfonylphenyl)imidazolidine-2,4-dione;
5,5-dimethyl-1-(3-benzylaminosulfonylaminopyrid-4-ylmethyl)-3-(4-trifluoromethanesulfonylphenyl)imidazolidine-2,4-dione;
5,5-dimethyl-1-(3-methylaminosulfonylaminopyrid-4-ylmethyl)-3-(4-trifluoromethanesulfonylphenyl)imidazolidine-2,4-dione;
5,5-dimethyl-1-(3-aminosulfonylaminopyrid-4-ylmethyl)-3-(4-trifluoromethanesulfonylphenyl)imidazolidine-2,4-dione;
5,5-dimethyl-1-(3-morpholinosulfonylaminopyrid-4-ylmethyl)-3-(4-trifluoromethanesulfonylphenyl)imidazolidine-2,4-dione;
5,5-dimethyl-1-(3-dimethylaminosulfonylaminopyrid-4-ylmethyl)-3-(4-trifluoromethanesulfonylphenyl)imidazolidine-2,4-dione;
5,5-dimethyl-1-(3-anilinosulfonylaminopyrid-4-ylmethyl)-3-(4-trifluoromethanesulfonylphenyl)imidazolidine-2,4-dione;
5,5-dimethyl-1-(3-phenylsulfonylaminopyrid-4-ylmethyl)-3-(4-trifluoromethanesulfonylphenyl)imidazolidine-2,4-dione;
5,5-dimethyl-1-[3-(2-thienyl)sulfonylaminopyrid-4-ylmethyl]-3-(4-trifluoromethanesulfonylphenyl)imidazolidine-2,4-dione;

5,5-dimethyl-1-(3-methylsulfonylaminopyrid-4-ylmethyl)-3-(4-trifluoromethanesulfonylphenyl)imidazolidine-2,4-dione;
5,5-dimethyl-1-[3-(4-chlorophenyl)sulfonylaminopyrid-4-ylmethyl]-3-(4-trifluoromethanesulfonylphenyl)imidazolidine-2,4-dione;
5,5-dimethyl-1-(3-benzylsulfonylaminopyrid-4-ylmethyl)-3-(4-trifluoromethanesulfonylphenyl)imidazolidine-2,4-dione;
5,5-dimethyl-1-(3-hydroxycarbonylpyrid-4-ylmethyl)-3-(4-trifluoromethanesulfonylphenyl)imidazolidine-2,4-dione;
5,5-dimethyl-1-(3-ethoxycarbonylpyrid-4-ylmethyl)-3-(4-trifluoromethanesulfonylphenyl)imidazolidine-2,4-dione;
5,5-dimethyl-1-(3-tert-butoxycarbonylpyrid-4-ylmethyl)-3-(4-trifluoromethanesulfonylphenyl)imidazolidine-2,4-dione;
5,5-dimethyl-1-(3-phenoxycarbonylpyrid-4-ylmethyl)-3-(4-trifluoromethanesulfonylphenyl)imidazolidine-2,4-dione;
5,5-dimethyl-1-[3-(4-methylpiperazinocarbonyl)pyrid-4-ylmethyl]-3-(4-trifluoromethanesulfonylphenyl)imidazolidine-2,4-dione;
5,5-dimethyl-1-[3-(methylamino)carbonylpyrid-4-ylmethyl]-3-(4-trifluoromethanesulfonylphenyl)imidazolidine-2,4-dione;
5,5-dimethyl-1-[3-(dimethylamino)carbonylpyrid-4-ylmethyl]-3-(4-trifluoromethanesulfonylphenyl)imidazolidine-2,4-dione;
5,5-dimethyl-1-(3-piperidinocarbonylpyrid-4-ylmethyl)-3-(4-trifluoromethanesulfonylphenyl)imidazolidine-2,4-dione;
5,5-dimethyl-1-(3-morpholinocarbonylpyrid-4-ylmethyl)-3-(4-trifluoromethanesulfonylphenyl)imidazolidine-2,4-dione;
5,5-dimethyl-1-[3-(4-phenylpiperazinocarbonyl)pyrid-4-ylmethyl]-3-(4-trifluoromethanesulfonylphenyl)imidazolidine-2,4-dione;
5,5-dimethyl-1-(3-phenylaminocarbonylpyrid-4-ylmethyl)-3-(4-trifluoromethanesulfonylphenyl)imidazolidine-2,4-dione;
5,5-dimethyl-1-[3-(methylphenylamino)carbonylpyrid-4-ylmethyl]-3-(4-trifluoromethanesulfonylphenyl)imidazolidine-2,4-dione;
5,5-dimethyl-1-[3-(4-methoxyphenyl)methylaminocarbonylpyrid-4-ylmethyl]-3-(4-trifluoromethanesulfonylphenyl)imidazolidine-2,4-dione;
5,5-dimethyl-1-[3-(4-chlorophenyl)methylaminocarbonylpyrid-4-ylmethyl]-3-(4-trifluoromethanesulfonylphenyl)imidazolidine-2,4-dione;
5,5-dimethyl-1-[3-(4-morpholinylamino)carbonylpyrid-4-ylmethyl]-3-(4-trifluoromethanesulfonylphenyl)imidazolidine-2,4-dione;
5,5-dimethyl-1-(3-aminocarbonylpyrid-4-ylmethyl)-3-(4-trifluoromethanesulfonylphenyl)imidazolidine-2,4-dione;
5,5-dimethyl-1-(3-phenoxypyrid-4-ylmethyl)-3-(4-trifluoromethanesulfonylphenyl)imidazolidine-2,4-dione;
5,5-dimethyl-1-(3-methoxypyrid-4-ylmethyl)-3-(4-trifluoromethanesulfonylphenyl)imidazolidine-2,4-dione;
5,5-dimethyl-1-(3-ethoxypyrid-4-ylmethyl)-3-(4-trifluoromethanesulfonylphenyl)imidazolidine-2,4-dione;
5,5-dimethyl-1-[3-(1-pyrrolidinyl)ethoxypyrid-4-ylmethyl]-3-(4-trifluoromethanesulfonylphenyl)imidazolidine-2,4-dione;
5,5-dimethyl-1-(3-benzyloxypyrid-4-ylmethyl)-3-(4-trifluoromethanesulfonylphenyl)imidazolidine-2,4-dione;
5,5-dimethyl-1-(3-benzoyloxypyrid-4-ylmethyl)-3-(4-trifluoromethanesulfonylphenyl)imidazolidine-2,4-dione;
5,5-dimethyl-1-[3-(4,5-dihydro-1H-imidazol-2-yl)pyrid-4-ylmethyl]-3-(4-trifluoromethanesulfonylphenyl)imidazolidine-2,4-dione;
5,5-dimethyl-1-[3-(1H-imidazol-2-yl)pyrid-4-ylmethyl]-3-(4-trifluoromethanesulfonylphenyl)imidazolidine-2,4-dione;
5,5-dimethyl-1-[3-(1H-tetrazol-5-yl)pyrid-4-ylmethyl]-3-(4-trifluoromethanesulfonylphenyl)imidazolidine-2,4-dione;
5,5-dimethyl-1-(3-amidinopyrid-4-ylmethyl)-3-(4-trifluoromethanesulfonylphenyl)imidazolidine-2,4-dione;
5,5-dimethyl-1-(3-dimethylaminomethylpyrid-4-ylmethyl)-3-(4-trifluoromethanesulfonylphenyl)imidazolidine-2,4-dione;
5,5-dimethyl-1-(3-aminomethylpyrid-4-ylmethyl)-3-(4-trifluoromethanesulfonylphenyl)imidazolidine-2,4-dione;
4-(2-methylpyridin)-4-ylmethyl-6-(4-trifluoromethanesulfonylphenyl)-4,6-diazaspiro[2.4]heptane-5,7-dione;
4-(2-ethylpyridin)-4-ylmethyl-6-(4-trifluoromethanesulfonylphenyl)-4,6-diazaspiro[2.4]heptane-5,7-dione;
4-(2-isopropylpyridin)-4-ylmethyl-6-(4-trifluoromethanesulfonylphenyl)-4,6-diazaspiro[2.4]heptane-5,7-dione;
4-(2-tert-butylpyridin)-4-ylmethyl-6-(4-trifluoromethanesulfonylphenyl)-4,6-diazaspiro[2.4]heptane-5,7-dione;
4-(2-isobutylpyridin)-4-ylmethyl-6-(4-trifluoromethanesulfonylphenyl)-4,6-diazaspiro[2.4]heptane-5,7-dione;
4-(2-cyclohexylpyridin)-4-ylmethyl-6-(4-trifluoromethanesulfonylphenyl)-4,6-diazaspiro[2.4]heptane-5,7-dione;
4-(2-phenylpyridin)-4-ylmethyl-6-(4-trifluoromethanesulfonylphenyl)-4,6-diazaspiro[2.4]heptane-5,7-dione;
4-[2-(4-chlorophenyl)pyridin]-4-ylmethyl-6-(4-trifluoromethanesulfonylphenyl)-4,6-diazaspiro[2.4]heptane-5,7-dione;
4-[2-(3-chlorophenyl)pyridin]-4-ylmethyl-6-(4-trifluoromethanesulfonylphenyl)-4,6-diazaspiro[2.4]heptane-5,7-dione;
4-[2-(2-chlorophenyl)pyridin]-4-ylmethyl-6-(4-trifluoromethanesulfonylphenyl)-4,6-diazaspiro[2.4]heptane-5,7-dione;
4-[2-(4-fluorophenyl)pyridin]-4-ylmethyl-6-(4-trifluoromethanesulfonylphenyl)-4,6-diazaspiro[2.4]heptane-5,7-dione;
4-[2-(4-methoxyphenyl)pyridin]-4-ylmethyl-6-(4-trifluoromethanesulfonylphenyl)-4,6-diazaspiro[2.4]heptane-5,7-dione;
4-(2-benzylpyridin)-4-ylmethyl-6-(4-trifluoromethanesulfonylphenyl)-4,6-diazaspiro[2.4]heptane-5,7-dione;
4-(2,2'-bipyrid-4-ylmethyl-6-(4-trifluoromethanesulfonylphenyl)-4,6-diazaspiro[2.4]heptane-5,7-dione;
4-(2-hydroxymethylpyridine)-4-ylmethyl-6-(4-trifluoromethanesulfonylphenyl)-4,6-diazaspiro[2.4]heptane-5,7-dione;
4-(2-chloropyrid-4-ylmethyl-6-(4-trifluoromethanesulfonylphenyl)-4,6-diazaspiro[2.4]heptane-5,7-dione;
4-(2-fluoropyrid-4-ylmethyl-6-(4-trifluoromethanesulfonylphenyl)-4,6-diazaspiro[2.4]heptane-5,7-dione;
4-(2-bromopyrid-4-ylmethyl-6-(4-trifluoromethanesulfonylphenyl)-4,6-diazaspiro[2.4]heptane-5,7-dione;
4-(2-aminopyrid-4-ylmethyl-6-(4-trifluoromethanesulfonylphenyl)-4,6-diazaspiro[2.4]heptane-5,7-dione;
4-(2-methylaminopyrid-4-ylmethyl-6-(4-trifluoromethanesulfonylphenyl-4,6-diazaspiro[2.4]heptane-5,7-dione;
4-(2-ethylaminopyrid-4-ylmethyl-6-(4-trifluoromethanesulfonylphenyl)-4,6-diazaspiro[2.4]heptane-5,7-dione;
4-(2-isopropylaminopyrid-4-ylmethyl-6-(4-trifluoromethanesulfonylphenyl)-4,6-diazaspiro[2.4]heptane-5,7-dione;

4-(2-phenylaminopyrid-4-ylmethyl-6-(4-trifluoromethanesulfonylphenyl)-4,6-diazaspiro[2.4]heptane-5,7-dione;
4-(2-cyclohexylaminopyrid-4-ylmethyl-6-(4-trifluoromethanesulfonylphenyl)-4,6-diazaspiro[2.4]heptane-5,7-dione;
4-(2-diethylaminopyrid-4-ylmethyl-6-(4-trifluoromethanesulfonylphenyl)-4,6-diazaspiro[2.4]heptane-5,7-dione;
4-(2-N-cyclohexyl-N-methylaminopyrid-4-ylmethyl-6-(4-trifluoromethanesulfonylphenyl)-4,6-diazaspiro[2.4]heptane-5,7-dione;
4-(2-piperidinopyrid-4-ylmethyl-6-(4-trifluoromethanesulfonylphenyl)-4,6-diazaspiro[2.4]heptane-5,7-dione;
4-(2-morpholinopyrid-4-ylmethyl-6-(4-trifluoromethanesulfonylphenyl)-4,6-diazaspiro[2.4]heptane-5,7-dione;
4-[2-(4-methylpiperazino)diethylaminopyrid-4-ylmethyl-6-(4-trifluoromethanesulfonylphenyl)-4,6-diazaspiro[2.4]heptane-5,7-dione;
4-[2-(1H-pyrazol-1-yl)pyridin]-4-ylmethyl-6-(4-trifluoromethanesulfonylphenyl)-4,6-diazaspiro[2.4]heptane-5,7-dione;
4-[2-(2-benzoylhydrazino)pyrid-4-ylmethyl-6-(4-trifluoromethanesulfonylphenyl)-4,6-diazaspiro[2.4]heptane-5,7-dione;
4-(2-benzoylaminopyrid-4-ylmethyl-6-(4-trifluoromethanesulfonylphenyl)-4,6-diazaspiro[2.4]heptane-5,7-dione;
4-[2-(4-chlorobenzoylamino)pyrid-4-ylmethyl-6-(4-trifluoromethanesulfonylphenyl)-4,6-diazaspiro[2.4]heptane-5,7-dione;
4-[2-(3-chlorobenzoylamino)pyrid-4-ylmethyl-6-(4-trifluoromethanesulfonylphenyl)-4,6-diazaspiro[2.4]heptane-5,7-dione;
4-[2-(2-chlorobenzoylamino)pyrid-4-ylmethyl-6-(4-trifluoromethanesulfonylphenyl)-4,6-diazaspiro[2.4]heptane-5,7-dione;
4-[2-(4-fluorobenzoylamino)pyrid-4-ylmethyl-6-(4-trifluoromethanesulfonylphenyl)-4,6-diazaspiro[2.4]heptane-5,7-dione;
4-[2-(4-methoxybenzoylamino)pyrid-4-ylmethyl-6-(4-trifluoromethanesulfonylphenyl)-4,6-diazaspiro[2.4]heptane-5,7-dione;
4-(2-acetamidopyrid-4-ylmethyl-6-(4-trifluoromethanesulfonylphenyl)-4,6-diazaspiro[2.4]heptane-5,7-dione;
4-(2-phenylacetamidopyrid-4-ylmethyl-6-(4-trifluoromethanesulfonylphenyl)-4,6-diazaspiro[2.4]heptane-5,7-dione;
4-[2-(4-methylpiperazino)acetamidopyrid-4-ylmethyl-6-(4-trifluoromethanesulfonylphenyl)-4,6-diazaspiro[2.4]heptane-5,7-dione;
4-(2-cyclohexanylcarboxamidopyrid-4-ylmethyl-6-(4-trifluoromethanesulfonylphenyl)-4,6-diazaspiro[2.4]heptane-5,7-dione;
4-[2-(1-methyl-4-piperidinyl)carbonylaminopyrid-4-ylmethyl-6-(4-trifluoromethanesulfonylphenyl)-4,6-diazaspiro[2.4]heptane-5,7-dione;
4-[2-(2-furanylcarbonyl)aminopyrid-4-ylmethyl-6-(4-trifluoromethanesulfonylphenyl)-4,6-diazaspiro[2.4]heptane-5,7-dione;
4-(2-ethoxycarbonylaminopyrid-4-ylmethyl-6-(4-trifluoromethanesulfonylphenyl)-4,6-diazaspiro[2.4]heptane-5,7-dione;
4-(2-isopropoxycarbonylaminopyrid-4-ylmethyl-6-(4-trifluoromethanesulfonylphenyl)-4,6-diazaspiro[2.4]heptane-5,7-dione;
4-(2-butoxycarbonylaminopyrid-4-ylmethyl-6-(4-trifluoromethanesulfonylphenyl)-4,6-diazaspiro[2.4]heptane-5,7-dione;
4-[2-(2-diethylaminoethoxycarbonylamino)pyrid-4-ylmethyl-6-(4-trifluoromethanesulfonylphenyl)-4,6-diazaspiro[2.4]heptane-5,7-dione;
4-(2-phenoxycarbonylaminopyrid-4-ylmethyl-6-(4-trifluoromethanesulfonylphenyl)-4,6-diazaspiro[2.4]heptane-5,7-dione;
4-[2-(4-chloroanilino)carbonylaminopyrid-4-ylmethyl)-6-(4-trifluoromethanesulfonylphenyl)-4,6-diazaspiro[2.4]heptane-5,7-dione;
4-(2-anilinocarbonylaminopyrid-4-ylmethyl-6-(4-trifluoromethanesulfonylphenyl)-4,6-diazaspiro[2.4]heptane-5,7-dione;
4-(2-benzylaminocarbonylaminopyrid-4-ylmethyl-6-(4-trifluoromethanesulfonylphenyl)-4,6-diazaspiro[2.4]heptane-5,7-dione;
4-[2-(2-pyridylamino)carbonylaminopyrid-4-ylmethyl)-6-(4-trifluoromethanesulfonylphenyl)-4,6-diazaspiro[2.4]heptane-5,7-dione;
4-(2-ureidopyrid-4-ylmethyl-6-(4-trifluoromethanesulfonylphenyl)-4,6-diazaspiro[2.4]heptane-5,7-dione;
4-(2-benzylaminosulfonylaminopyrid-4-ylmethyl-6-(4-trifluoromethanesulfonylphenyl)-4,6-diazaspiro[2.4]heptane-5,7-dione;
4-(2-methylaminosulfonyaminopyrid-4-ylmethyl-6-(4-trifluoromethanesulfonylphenyl)-4,6-diazaspiro[2.4]heptane-5,7-dione;
4-(2-aminosulfonylaminopyrid-4-ylmethyl-6-(4-trifluoromethanesulfonylphenyl)-4,6-diazaspiro[2.4]heptane-5,7-dione;
4-(2-morpholinosulfonylaminopyrid-4-ylmethyl-6-(4-trifluoromethanesulfonylphenyl)-4,6-diazaspiro[2.4]heptane-5,7-dione;
4-(2-dimethylinosulfonylaminopyrid-4-ylmethyl-6-(4-trifluoromethanesulfonylphenyl)-4,6-diazaspiro[2.4]heptane-5,7-dione;
4-(2-anilinosulfonylaminopyrid-4-ylmethyl-6-(4-trifluoromethanesulfonylphenyl)-4,6-diazaspiro[2.4]heptane-5,7-dione;
4-(2-phenylsulfonylaminopyrid-4-ylmethyl-6-(4-trifluoromethanesulfonylphenyl)-4,6-diazaspiro[2.4]heptane-5,7-dione;
4-[2-(2-thienyl)sulfonylaminopyrid-4-ylmethyl-6-(4-trifluoromethanesulfonylphenyl)-4,6-diazaspiro[2.4]heptane-5,7-dione;
4-(2-methylsulfonylaminopyrid-4-ylmethyl-6-(4-trifluoromethanesulfonylphenyl)-4,6-diazaspiro[2.4]heptane-5,7-dione;
4-[2-(4-chlorophenyl)sulfonylaminopyrid-4-ylmethyl-6-(4-trifluoromethanesulfonylphenyl)-4,6-diazaspiro[2.4]heptane-5,7-dione;
4-(2-benzylsulfonylaminopyrid-4-ylmethyl-6-(4-trifluoromethanesulfonylphenyl)-4,6-diazaspiro[2.4]heptane-5,7-dione;
4-(2-hydroxycarbonylpyridin)-4-ylmethyl-6-(4-trifluoromethanesulfonylphenyl)-4,6-diazaspiro[2.4]heptane-5,7-dione;
4-(2-ethoxycarbonylpyridin)-4-ylmethyl-6-(4-trifluoromethanesulfonylphenyl)-4,6-diazaspiro[2.4]heptane-5,7-dione;
4-(2-tert-butoxycarbonylpyridin)-4-ylmethyl-6-(4-trifluoromethanesulfonylphenyl)-4,6-diazaspiro[2.4]heptane-5,7-dione;
4-(2-phenoxycarbonylpyridin)-4-ylmethyl-6-(4-trifluoromethanesulfonylphenyl)-4,6-diazaspiro[2.4]heptane-5,7-dione;

4-[2-(4-methylpiperazinocarbonyl)pyridin]-4-ylmethyl-6-(4-trifluoromethanesulfonylphenyl)-4,6-diazaspiro[2.4]heptane-5,7-dione;
4-[2-(methylamino)carbonylpyridin)-4-ylmethyl-6-(4-trifluoromethanesulfonylphenyl)-4,6-diazaspiro[2.4]heptane-5,7-dione;
4-[2-(dimethylamino)carbonylpyridin)-4-ylmethyl-6-(4-trifluoromethanesulfonylphenyl)-4,6-diazaspiro[2.4]heptane-5,7-dione;
4-(2-piperidinocarbonylpyridin)-4-ylmethyl-6-(4-trifluoromethanesulfonylphenyl)-4,6-diazaspiro[2.4]heptane-5,7-dione;
4-(2-morpholinocarbonylpyridin)-4-ylmethyl-6-(4-trifluoromethanesulfonylphenyl)-4,6-diazaspiro[2.4]heptane-5,7-dione;
4-[2-(4-phenylpiperazinocarbonyl)pyridin]-4-ylmethyl-6-(4-trifluoromethanesulfonylphenyl)-4,6-diazaspiro[2.4]heptane-5,7-dione;
4-(2-phenylaminocarbonylpyridin)-4-ylmethyl-6-(4-trifluoromethanesulfonylphenyl)-4,6-diazaspiro[2.4]heptane-5,7-dione;
4-[2-(methylphenylamino)carbonylpyridin)-4-ylmethyl-6-(4-trifluoromethanesulfonylphenyl)-4,6-diazaspiro[2.4]heptane-5,7-dione;
4-[2-(4-methoxyphenyl)methylaminocarbonylpyridin)-4-ylmethyl-6-(4-trifluoromethanesulfonylphenyl)-4,6-diazaspiro[2.4]heptane-5,7-dione;
4-[2-(4-chlorophenyl)methylaminocarbonylpyridin)-4-ylmethyl-6-(4-trifluoromethanesulfonylphenyl)-4,6-diazaspiro[2.4]heptane-5,7-dione;
4-[2-(4-morpholinylamino)carbonylpyridin)-4-ylmethyl-6-(4-trifluoromethanesulfonylphenyl)-4,6-diazaspiro[2.4]heptane-5,7-dione;
4-(2-aminocarbonylpyridin)-4-ylmethyl-6-(4-trifluoromethanesulfonylphenyl)-4,6-diazaspiro[2.4]heptane-5,7-dione;
4-(2-phenoxypyrid-4-ylmethyl-6-(4-trifluoromethanesulfonylphenyl)-4,6-diazaspiro[2.4]heptane-5,7-dione;
4-(2-methoxypyrid-4-ylmethyl-6-(4-trifluoromethanesulfonylphenyl)-4,6-diazaspiro[2.4]heptane-5,7-dione;
4-(2-ethoxypyrid-4-ylmethyl-6-(4-trifluoromethanesulfonylphenyl)-4,6-diazaspiro[2.4]heptane-5,7-dione;
4-[2-(1-pyrrolidinyl)ethoxypyrid-4-ylmethyl-6-(4-trifluoromethanesulfonylphenyl)-4,6-diazaspiro[2.4]heptane-5,7-dione;
4-(2-benzyloxypyrid-4-ylmethyl-6-(4-trifluoromethanesulfonylphenyl)-4,6-diazaspiro[2.4]heptane-5,7-dione;
4-(2-benzoyloxypyrid-4-ylmethyl-6-(4-trifluoromethanesulfonylphenyl)-4,6-diazaspiro[2.4]heptane-5,7-dione;
4-[2-(4,5-dihydro-1H-imidazol-2-yl)pyridin]-4-ylmethyl-6-(4-trifluoromethanesulfonylphenyl)-4,6-diazaspiro[2.4]heptane-5,7-dione;
4-[2-(1H-imidazol-2-yl)pyridin]-4-ylmethyl-6-(4-trifluoromethanesulfonylphenyl)-4,6-diazaspiro[2.4]heptane-5,7-dione;
4-[2-(H-tetrazol-5-yl)pyridin]-4-ylmethyl-6-(4-trifluoromethanesulfonylphenyl)-4,6-diazaspiro[2.4]heptane-5,7-dione;
4-(2-amidinopyrid-4-ylmethyl-6-(4-trifluoromethanesulfonylphenyl)-4,6-diazaspiro[2.4]heptane-5,7-dione;
4-(2-dimethylaminomethylpyridin)-4-ylmethyl-6-(4-trifluoromethanesulfonylphenyl)-4,6-diazaspiro[2.4]heptane-5,7-dione;
4-(2-aminomethylpyridin)-4-ylmethyl-6-(4-trifluoromethanesulfonylphenyl)-4,6-diazaspiro[2.4]heptane-5,7-dione;
4-(3-methylpyridin)-4-ylmethyl-6-(4-trifluoromethanesulfonylphenyl)-4,6-diazaspiro[2.4]heptane-5,7-dione;
4-(3-ethylpyridin)-4-ylmethyl-6-(4-trifluoromethanesulfonylphenyl)-4,6-diazaspiro[2.4]heptane-5,7-dione;
4-(3-isopropylpyridin)-4-ylmethyl-6-(4-trifluoromethanesulfonylphenyl)-4,6-diazaspiro[2.4]heptane-5,7-dione;
4-(3-tert-butylpyridin)-4-ylmethyl-6-(4-trifluoromethanesulfonylphenyl)-4,6-diazaspiro[2.4]heptane-5,7-dione;
4-(3-isobutylpyridin)-4-ylmethyl-6-(4-trifluoromethanesulfonylphenyl)-4,6-diazaspiro[2.4]heptane-5,7-dione;
4-(3-cyclohexylpyridin)-4-ylmethyl-6-(4-trifluoromethanesulfonylphenyl)-4,6-diazaspiro[2.4]heptane-5,7-dione;
4-(3-phenylpyridin)-4-ylmethyl-6-(4-trifluoromethanesulfonylphenyl)-4,6-diazaspiro[2.4]heptane-5,7-dione;
4-[3-(4-chlorophenyl)pyridin]-4-ylmethyl-6-(4-trifluoromethanesulfonylphenyl)-4,6-diazaspiro[2.4]heptane-5,7-dione;
4-[3-(3-chlorophenyl)pyridin]-4-ylmethyl-6-(4-trifluoromethanesulfonylphenyl)-4,6-diazaspiro[2.4]heptane-5,7-dione;
4-[3-(2-chlorophenyl)pyridin]-4-ylmethyl-6-(4-trifluoromethanesulfonylphenyl)-4,6-diazaspiro[2.4]heptane-5,7-dione;
4-[3-(4-fluorophenyl)pyridin]-4-ylmethyl-6-(4-trifluoromethanesulfonylphenyl)-4,6-diazaspiro[2.4]heptane-5,7-dione;
4-[3-(4-methoxyphenyl)pyridin]-4-ylmethyl-6-(4-trifluoromethanesulfonylphenyl)-4,6-diazaspiro[2.4]heptane-5,7-dione;
4-(3-benzylpyridin)-4-ylmethyl-6-(4-trifluoromethanesulfonylphenyl)-4,6-diazaspiro[2.4]heptane-5,7-dione;
4-(3,2'-bipyrid-4-ylmethyl-6-(4-trifluoromethanesulfonylphenyl)-4,6-diazaspiro[2.4]heptane-5,7-dione;
4-(3-hydroxymethylpyridine)-4-ylmethyl-6-(4-trifluoromethanesulfonylphenyl)-4,6-diazaspiro[2.4]heptane-5,7-dione;
4-(3-chloropyrid-4-ylmethyl-6-(4-trifluoromethanesulfonylphenyl)-4,6-diazaspiro[2.4]heptane-5,7-dione;
4-(3-fluoropyrid-4-ylmethyl-6-(4-trifluoromethanesulfonylphenyl)-4,6-diazaspiro[2.4]heptane-5,7-dione;
4-(3-bromopyrid-4-ylmethyl-6-(4-trifluoromethanesulfonylphenyl)-4,6-diazaspiro[2.4]heptane-5,7-dione;
4-(3-aminopyrid-4-ylmethyl-6-(4-trifluoromethanesulfonylphenyl)-4,6-diazaspiro[2.4]heptane-5,7-dione;
4-(3-methylaminopyrid-4-ylmethyl-6-(4-trifluoromethanesulfonylphenyl)-4,6-diazaspiro[2.4]heptane-5,7-dione;
4-(3-ethylaminopyrid-4-ylmethyl-6-(4-trifluoromethanesulfonylphenyl)-4,6-diazaspiro[2.4]heptane-5,7-dione;
4-(3-isopropylaminopyrid-4-ylmethyl-6-(4-trifluoromethanesulfonylphenyl)-4,6-diazaspiro[2.4]heptane-5,7-dione;
4-(3-phenylaminopyrid-4-ylmethyl-6-(4-trifluoromethanesulfonylphenyl)-4,6-diazaspiro[2.4]heptane-5,7-dione;
4-(3-cyclohexylaminopyrid-4-ylmethyl-6-(4-trifluoromethanesulfonylphenyl)-4,6-diazaspiro[2.4]heptane-5,7-dione;
4-(3-diethylaminopyrid-4-ylmethyl-6-(4-trifluoromethanesulfonylphenyl)-4,6-diazaspiro[2.4]heptane-5,7-dione;
4-(3-N-cyclohexyl-N-methylaminopyrid-4-ylmethyl-6-(4-trifluoromethanesulfonylphenyl)-4,6-diazaspiro[2.4]heptane-5,7-dione;
4-(3-piperidinopyrid-4-ylmethyl-6-(4-trifluoromethanesulfonylphenyl)-4,6-diazaspiro[2.4]heptane-5,7-dione;
4-(3-morpholinopyrid-4-ylmethyl-6-(4-trifluoromethanesulfonylphenyl)-4,6-diazaspiro[2.4]heptane-5,7-dione;

4-[3-(4-methylpiperazino)diethylaminopyrid-4-ylmethyl-6-(4-trifluoromethanesulfonylphenyl)-4,6-diazaspiro[2.4]heptane-5,7-dione;
4-[3-(1H-pyrazol-1-yl)pyridin]-4-ylmethyl-6-(4-trifluoromethanesulfonylphenyl)-4,6-diazaspiro[2.4]heptane-5,7-dione;
4-[3-(2-benzoylhydrazino)pyrid-4-ylmethyl-6-(4-trifluoromethanesulfonylphenyl)-4,6-diazaspiro[2.4]heptane-5,7-dione;
4-(3-benzoylaminopyrid-4-ylmethyl-6-(4-trifluoromethanesulfonylphenyl)-4,6-diazaspiro[2.4]heptane-5,7-dione;
4-[3-(4-chlorobenzoylamino)pyrid-4-ylmethyl-6-(4-trifluoromethanesulfonylphenyl)-4,6-diazaspiro[2.4]heptane-5,7-dione;
4-[3-(3-chlorobenzoylamino)pyrid-4-ylmethyl-6-(4-trifluoromethanesulfonylphenyl)-4,6-diazaspiro[2.4]heptane-5,7-dione;
4-[3-(2-chlorobenzoylamino)pyrid-4-ylmethyl-6-(4-trifluoromethanesulfonylphenyl)-4,6-diazaspiro[2.4]heptane-5,7-dione;
4-[3-(4-fluorobenzoylamino)pyrid-4-ylmethyl-6-(4-trifluoromethanesulfonylphenyl)-4,6-diazaspiro[2.4]heptane-5,7-dione;
4-[3-(4-methoxybenzoylamino)pyrid-4-ylmethyl-6-(4-trifluoromethanesulfonylphenyl)-4,6-diazaspiro[2.4]heptane-5,7-dione;
4-(3-acetamidopyrid-4-ylmethyl-6-(4-trifluoromethanesulfonylphenyl)-4,6-diazaspiro[2.4]heptane-5,7-dione;
4-(3-phenylacetamidopyrid-4-ylmethyl-6-(4-trifluoromethanesulfonylphenyl)-4,6-diazaspiro[2.4]heptane-5,7-dione;
4-[3-(4-methylpiperazino)acetamidopyrid-4-ylmethyl-6-(4-trifluoromethanesulfonylphenyl)-4,6-diazaspiro[2.4]heptane-5,7-dione;
4-(3-cyclohexanylcarboxamidopyrid-4-ylmethyl-6-(4-trifluoromethanesulfonylphenyl)-4,6-diazaspiro[2.4]heptane-5,7-dione;
4-[3-(1-methyl-4-piperidinyl)carbonylaminopyrid-4-ylmethyl-6-(4-trifluoromethanesulfonylphenyl)-4,6-diazaspiro[2.4]heptane-5,7-dione;
4-[3-(2-furanylcarbonyl)aminopyrid-4-ylmethyl-6-(4-trifluoromethanesulfonylphenyl)-4,6-diazaspiro[2.4]heptane-5,7-dione;
4-(3-ethoxycarbonylaminopyrid-4-ylmethyl-6-(4-trifluoromethanesulfonylphenyl)-4,6-diazaspiro[2.4]heptane-5,7-dione;
4-(3-isopropoxycarbonylaminopyrid-4-ylmethyl-6-(4-trifluoromethanesulfonylphenyl)-4,6-diazaspiro[2.4]heptane-5,7-dione;
4-(3-butoxycarbonylaminopyrid-4-ylmethyl-6-(4-trifluoromethanesulfonylphenyl)-4,6-diazaspiro[2.4]heptane-5,7-dione;
4-[3-(2-diethylaminoethoxycarbonylamino)pyrid-4-ylmethyl-6-(4-trifluoromethanesulfonylphenyl)-4,6-diazaspiro[2.4]heptane-5,7-dione;
4-(3-phenoxycarbonylaminopyrid-4-ylmethyl-6-(4-trifluoromethanesulfonylphenyl)-4,6-diazaspiro[2.4]heptane-5,7-dione;
4-[3-(4-chloroanilino)carbonylaminopyrid-4-ylmethyl-6-(4-trifluoromethanesulfonylphenyl)-4,6-diazaspiro[2.4]heptane-5,7-dione;
4-(3-anilinocarbonylaminopyrid-4-ylmethyl-6-(4-trifluoromethanesulfonylphenyl)-4,6-diazaspiro[2.4]heptane-5,7-dione;
4-(3-benzylaminocarbonylaminopyrid-4-ylmethyl-6-(4-trifluoromethanesulfonylphenyl)-4,6-diazaspiro[2.4]heptane-5,7-dione;
4-[3-(2-pyridylamino)carbonylaminopyrid-4-ylmethyl)-6-(4-trifluoromethanesulfonylphenyl)-4,6-diazaspiro[2.4]heptane-5,7-dione;
4-(3-ureidopyrid-4-ylmethyl-6-(4-trifluoromethanesulfonylphenyl)-4,6-diazaspiro[2.4]heptane-5,7-dione;
4-(3-benzylaminosulfonylaminopyrid-4-ylmethyl-6-(4-trifluoromethanesulfonylphenyl)-4,6-diazaspiro[2.4]heptane-5,7-dione;
4-(3-methylaminosulfonylaminopyrid-4-ylmethyl-6-(4-trifluoromethanesulfonylphenyl)-4,6-diazaspiro[2.4]heptane-5,7-dione;
4-(3-aminosulfonylaminopyrid-4-ylmethyl-6-(4-trifluoromethanesulfonylphenyl)-4,6-diazaspiro[2.4]heptane-5,7-dione;
4-(3-morpholinosulfonylaminopyrid-4-ylmethyl-6-(4-trifluoromethanesulfonylphenyl)-4,6-diazaspiro[2.4]heptane-5,7-dione;
4-(3-dimethylaminosulfonylaminopyrid-4-ylmethyl-6-(4-trifluoromethanesulfonylphenyl)-4,6-diazaspiro[2.4]heptane-5,7-dione;
4-(3-anilinosulfonylaminopyrid-4-ylmethyl-6-(4-trifluoromethanesulfonylphenyl)-4,6-diazaspiro[2.4]heptane-5,7-dione;
4-(3-phenylsulfonylaminopyrid-4-ylmethyl-6-(4-trifluoromethanesulfonylphenyl)-4,6-diazaspiro[2.4]heptane-5,7-dione;
4-[3-(2-thienyl)sulfonylaminopyrid-4-ylmethyl-6-(4-trifluoromethanesulfonylphenyl)-4,6-diazaspiro[2.4]heptane-5,7-dione;
4-(3-methylsulfonylaminopyrid-4-ylmethyl-6-(4-trifluoromethanesulfonylphenyl)-4,6-diazaspiro[2.4]heptane-5,7-dione;
4-[3-(4-chlorophenyl)sulfonylaminopyrid-4-ylmethyl-6-(4-trifluoromethanesulfonylphenyl)-4,6-diazaspiro[2.4]heptane-5,7-dione;
4-(3-benzylsulfonylaminopyrid-4-ylmethyl-6-(4-trifluoromethanesulfonylphenyl)-4,6-diazaspiro[2.4]heptane-5,7-dione;
4-(3-hydroxycarbonylpyridin)-4-ylmethyl-6-(4-trifluoromethanesulfonylphenyl)-4,6-diazaspiro[2.4]heptane-5,7-dione;
4-(3-ethoxycarbonylpyridin)-4-ylmethyl-6-(4-trifluoromethanesulfonylphenyl)-4,6-diazaspiro[2.4]heptane-5,7-dione;
4-(3-tert-butoxycarbonylpyridin)-4-ylmethyl-6-(4-trifluoromethanesulfonylphenyl)-4,6-diazaspiro[2.4]heptane-5,7-dione;
4-(3-phenoxycarbonylpyridin)-4-ylmethyl-6-(4-trifluoromethanesulfonylphenyl)-4,6-diazaspiro[2.4]heptane-5,7-dione;
4-[3-(4-methylpiperazinocarbonyl)pyridin]-4-ylmethyl-6-(4-trifluoromethanesulfonylphenyl)-4,6-diazaspiro[2.4]heptane-5,7-dione;
4-[3-(methylamino)carbonylpyridin)-4-ylmethyl-6-(4-trifluoromethanesulfonylphenyl)-4,6-diazaspiro[2.4]heptane-5,7-dione;
4-[3-(dimethylamino)carbonylpyridin)-4-ylmethyl-6-(4-trifluoromethanesulfonylphenyl)-4,6-diazaspiro[2.4]heptane-5,7-dione;
4-(3-piperidinocarbonylpyridin)-4-ylmethyl-6-(4-trifluoromethanesulfonylphenyl)-4,6-diazaspiro[2.4]heptane-5,7-dione;
4-(3-morpholinocarbonylpyridin)-4-ylmethyl-6-(4-trifluoromethanesulfonylphenyl)-4,6-diazaspiro[2.4]heptane-5,7-dione;

4-[3-(4-phenylpiperazinocarbonyl)pyridin]-4-ylmethyl-6-(4-trifluoromethanesulfonylphenyl)-4,6-diazaspiro[2.4]heptane-5,7-dione;
4-(3-phenylaminocarbonylpyridin)-4-ylmethyl-6-(4-trifluoromethanesulfonylphenyl)-4,6-diazaspiro[2.4]heptane-5,7-dione;
4-[3-(methylphenylamino)carbonylpyridin)-4-ylmethyl-6-(4-trifluoromethanesulfonylphenyl)-4,6-diazaspiro[2.4]heptane-5,7-dione;
4-[3-(4-methoxyphenyl)methylaminocarbonylpyridin)-4-ylmethyl-6-(4-trifluoromethanesulfonylphenyl)-4,6-diazaspiro[2.4]heptane-5,7-dione;
4-[3-(4-chlorophenyl)methylaminocarbonylpyridin)-4-ylmethyl-6-(4-trifluoromethanesulfonylphenyl)-4,6-diazaspiro[2.4]heptane-5,7-dione;
4-[3-(4-morpholinylamino)carbonylpyridin)-4-ylmethyl-6-(4-trifluoromethanesulfonylphenyl)-4,6-diazaspiro[2.4]heptane-5,7-dione;
4-(3-aminocarbonylpyridin)-4-ylmethyl-6-(4-trifluoromethanesulfonylphenyl)-4,6-diazaspiro[2.4]heptane-5,7-dione;
4-(3-phenoxypyrid-4-ylmethyl-6-(4-trifluoromethanesulfonylphenyl)-4,6-diazaspiro[2.4]heptane-5,7-dione;
4-(3-methoxypyrid-4-ylmethyl-6-(4-trifluoromethanesulfonylphenyl)-4,6-diazaspiro[2.4]heptane-5,7-dione;
4-(3-ethoxypyrid-4-ylmethyl-6-(4-trifluoromethanesulfonylphenyl)-4,6-diazaspiro[2.4]heptane-5,7-dione;
4-[3-(1-pyrrolidinyl)ethoxypyrid-4-ylmethyl-6-(4-trifluoromethanesulfonylphenyl)-4,6-diazaspiro[2.4]heptane-5,7-dione;
4-(3-benzyloxypyrid-4-ylmethyl-6-(4-trifluoromethanesulfonylphenyl)-4,6-diazaspiro[2.4]heptane-5,7-dione;
4-(3-benzoyloxypyrid-4-ylmethyl-6-(4-trifluoromethanesulfonylphenyl)-4,6-diazaspiro[2.4]heptane-5,7-dione;
4-[3-(4,5-dihydro-1H-imidazol-2-yl)pyridin]-4-ylmethyl-6-(4-trifluoromethanesulfonylphenyl)-4,6-diazaspiro[2.4]heptane-5,7-dione;
4-[3-(1H-imidazol-2-yl)pyridin]-4-ylmethyl-6-(4-trifluoromethanesulfonylphenyl)-4,6-diazaspiro[2.4]heptane-5,7-dione;
4-[3-(1H-tetrazol-5-yl)pyridin]-4-ylmethyl-6-(4-trifluoromethanesulfonylphenyl)-4,6-diazaspiro[2.4]heptane-5,7-dione;
4-(3-amidinopyrid-4-ylmethyl-6-(4-trifluoromethanesulfonylphenyl)-4,6-diazaspiro[2.4]heptane-5,7-dione;
4-(3-dimethylaminomethylpyridin)-4-ylmethyl-6-(4-trifluoromethanesulfonylphenyl)-4,6-diazaspiro[2.4]heptane-5,7-dione;
4-(3-aminomethylpyridin)-4-ylmethyl-6-(4-trifluoromethanesulfonylphenyl)-4,6-diazaspiro[2.4]heptane-5,7-dione;
5-methyl-1-(2-methylpyrid-4-ylmethyl)-3-(4-trifluoromethanesulfonylphenyl)imidazolidine-2,4-dione;
5-methyl-1-(2-ethylpyrid-4-ylmethyl)-3-(4-trifluoromethanesulfonylphenyl)imidazolidine-2,4-dione;
5-methyl-1-(2-isopropylpyrid-4-ylmethyl)-3-(4-trifluoromethanesulfonylphenyl)imidazolidine-2,4-dione;
5-methyl-1-(2-tert-butylpyrid-4-ylmethyl)-3-(4-trifluoromethanesulfonylphenyl)imidazolidine-2,4-dione;
5-methyl-1-(2-isobutylpyrid-4-ylmethyl)-3-(4-trifluoromethanesulfonylphenyl)imidazolidine-2,4-dione;
5-methyl-1-(2-cyclohexylpyrid-4-ylmethyl)-3-(4-trifluoromethanesulfonylphenyl)imidazolidine-2,4-dione;
5-methyl-1-(2-phenylpyrid-4-ylmethyl)-3-(4-trifluoromethanesulfonylphenyl)imidazolidine-2,4-dione;
5-methyl-1-[2-(4-chlorophenyl)pyrid-4-ylmethyl]-3-(4-trifluoromethanesulfonylphenyl)imidazolidine-2,4-dione;
5-methyl-1-[2-(3-chlorophenyl)pyrid-4-ylmethyl]-3-(4-trifluoromethanesulfonylphenyl)imidazolidine-2,4-dione;
5-methyl-1-[2-(2-chlorophenyl)pyrid-4-ylmethyl]-3-(4-trifluoromethanesulfonylphenyl)imidazolidine-2,4-dione;
5-methyl-1-[2-(4-fluorophenyl)pyrid-4-ylmethyl]-3-(4-trifluoromethanesulfonylphenyl)imidazolidine-2,4-dione;
5-methyl-1-[2-(4-methoxyphenyl)pyrid-4-ylmethyl]-3-(4-trifluoromethanesulfonylphenyl)imidazolidine-2,4-dione;
5-methyl-1-(2-benzylpyrid-4-ylmethyl)-3-(4-trifluoromethanesulfonylphenyl)imidazolidine-2,4-dione;
5-methyl-1-(2,2'-bipyrid-4-ylmethyl)-3-(4-trifluoromethanesulfonylphenyl)imidazolidine-2,4-dione;
5-methyl-1-(2-hydroxymethylpyrid-4-ylmethyl)-3-(4-trifluoromethanesulfonylphenyl)imidazolidine-2,4-dione;
5-methyl-1-(2-chloropyrid-4-ylmethyl)-3-(4-trifluoromethanesulfonylphenyl)imidazolidine-2,4-dione;
5-methyl-1-(2-fluoropyrid-4-ylmethyl)-3-(4-trifluoromethanesulfonylphenyl)imidazolidine-2,4-dione;
5-methyl-1-(2-bromopyrid-4-ylmethyl)-3-(4-trifluoromethanesulfonylphenyl)imidazolidine-2,4-dione;
5-methyl-1-(2-aminopyrid-4-ylmethyl)-3-(4-trifluoromethanesulfonylphenyl)imidazolidine-2,4-dione;
5-methyl-1-(2-methylaminopyrid-4-ylmethyl)-3-(4-trifluoromethanesulfonylphenyl)imidazolidine-2,4-dione;
5-methyl-1-(2-ethylaminopyrid-4-ylmethyl)-3-(4-trifluoromethanesulfonylphenyl)imidazolidine-2,4-dione;
5-methyl-1-(2-isopropylaminopyrid-4-ylmethyl)-3-(4-trifluoromethanesulfonylphenyl)imidazolidine-2,4-dione;
5-methyl-1-(2-phenylaminopyrid-4-ylmethyl)-3-(4-trifluoromethanesulfonylphenyl)imidazolidine-2,4-dione;
5-methyl-1-(2-cyclohexylaminopyrid-4-ylmethyl)-3-(4-trifluoromethanesulfonylphenyl)imidazolidine-2,4-dione;
5-methyl-1-(2-diethylaminopyrid-4-ylmethyl)-3-(4-trifluoromethanesulfonylphenyl)imidazolidine-2,4-dione;
5-methyl-1-(2-N-cyclohexyl-N-methylaminopyrid-4-ylmethyl)-3-(4-trifluoromethanesulfonylphenyl)imidazolidine-2,4-dione;
5-methyl-1-(2-piperidinopyrid-4-ylmethyl)-3-(4-trifluoromethanesulfonylphenyl)imidazolidine-2,4-dione;
5-methyl-1-(2-morpholinopyrid-4-ylmethyl)-3-(4-trifluoromethanesulfonylphenyl)imidazolidine-2,4-dione;
5-methyl-1-[2-(4-methylpiperazino)diethylaminopyrid-4-ylmethyl]-3-(4-trifluoromethanesulfonylphenyl)imidazolidine-2,4-dione;
5-methyl-1-[2-(1H-pyrazol-1-yl)pyrid-4-ylmethyl]-3-(4-trifluoromethanesulfonylphenyl)imidazolidine-2,4-dione;
5-methyl-1-[2-(2-benzoylhydrazino)pyrid-4-ylmethyl]-3-(4-trifluoromethanesulfonylphenyl)imidazolidine-2,4-dione;
5-methyl-1-(2-benzoylaminopyrid-4-ylmethyl)-3-(4-trifluoromethanesulfonylphenyl)imidazolidine-2,4-dione;
5-methyl-1-[2-(4-chlorobenzoylamino)pyrid-4-ylmethyl]-3-(4-trifluoromethanesulfonylphenyl)imidazolidine-2,4-dione;
5-methyl-1-[2-(3-chlorobenzoylamino)pyrid-4-ylmethyl]-3-(4-trifluoromethanesulfonylphenyl)imidazolidine-2,4-dione;
5-methyl-1-[2-(2-chlorobenzoylamino)pyrid-4-ylmethyl]-3-(4-trifluoromethanesulfonylphenyl)imidazolidine-2,4-dione;
5-methyl-1-[2-(4-fluorobenzoylamino)pyrid-4-ylmethyl]-3-(4-trifluoromethanesulfonylphenyl)imidazolidine-2,4-dione;
5-methyl-1-[2-(4-methoxybenzoylamino)pyrid-4-ylmethyl]-3-(4-trifluoromethanesulfonylphenyl)imidazolidine-2,4-dione;

5-methyl-1-(2-acetamidopyrid-4-ylmethyl)-3-(4-trifluoromethanesulfonylphenyl)imidazolidine-2,4-dione;
5-methyl-1-(2-phenylacetamidopyrid-4-ylmethyl)-3-(4-trifluoromethanesulfonylphenyl)imidazolidine-2,4-dione;
5-methyl-1-[2-(4-methylpiperazino)acetamidopyrid-4-ylmethyl]-3-(4-trifluoromethanesulfonylphenyl)imidazolidine-2,4-dione;
5-methyl-1-(2-cyclohexanylcarboxamidopyrid-4-ylmethyl)-3-(4-trifluoromethanesulfonylphenyl)imidazolidine-2,4-dione;
5-methyl-1-[2-(1-methyl-4-piperidinyl)carbonylaminopyrid-4-ylmethyl]-3-(4-trifluoromethanesulfonylphenyl)imidazolidine-2,4-dione;
5-methyl-1-[2-(2-furanylcarbonyl)aminopyrid-4-ylmethyl]-3-(4-trifluoromethanesulfonylphenyl)imidazolidine-2,4-dione;
5-methyl-1-(2-ethoxycarbonylaminopyrid-4-ylmethyl)-3-(4-trifluoromethanesulfonylphenyl)imidazolidine-2,4-dione;
5-methyl-1-(2-isopropoxycarbonylaminopyrid-4-ylmethyl)-3-(4-trifluoromethanesulfonylphenyl)imidazolidine-2,4-dione;
5-methyl-1-(2-butoxycarbonylaminopyrid-4-ylmethyl)-3-(4-trifluoromethanesulfonylphenyl)imidazolidine-2,4-dione;
5-methyl-1-[2-(2-diethylaminoethoxycarbonylamino)pyrid-4-ylmethyl]-3-(4-trifluoromethanesulfonylphenyl)imidazolidine-2,4-dione;
5-methyl-1-(2-phenoxycarbonylaminopyrid-4-ylmethyl)-3-(4-trifluoromethanesulfonylphenyl)imidazolidine-2,4-dione;
5-methyl-1-[2-(4-chloroanilino)carbonylaminopyrid-4-ylmethyl)]-3-(4-trifluoromethanesulfonylphenyl)imidazolidine-2,4-dione;
5-methyl-1-(2-anilinocarbonylaminopyrid-4-ylmethyl)-3-(4-trifluoromethanesulfonylphenyl)imidazolidine-2,4-dione;
5-methyl-1-(2-benzylaminocarbonylaminopyrid-4-ylmethyl)-3-(4-trifluoromethanesulfonylphenyl)imidazolidine-2,4-dione;
5-methyl-1-[2-(2-pyridylamino)carbonylaminopyrid-4-ylmethyl)]-3-(4-trifluoromethanesulfonylphenyl)imidazolidine-2,4-dione;
5-methyl-1-(2-ureidopyrid-4-ylmethyl)-3-(4-trifluoromethanesulfonylphenyl)imidazolidine-2,4-dione;
5-methyl-1-(2-benzylaminosulfonylaminopyrid-4-ylmethyl)-3-(4-trifluoromethanesulfonylphenyl)imidazolidine-2,4-dione;
5-methyl-1-(2-methylaminosulfonylaminopyrid-4-ylmethyl)-3-(4-trifluoromethanesulfonylphenyl)imidazolidine-2,4-dione;
5-methyl-1-(2-aminosulfonylaminopyrid-4-ylmethyl)-3-(4-trifluoromethanesulfonylphenyl)imidazolidine-2,4-dione;
5-methyl-1-(2-morpholinosulfonylaminopyrid-4-ylmethyl)-3-(4-trifluoromethanesulfonylphenyl)imidazolidine-2,4-dione;
5-methyl-1-(2-dimethylaminosulfonylaminopyrid-4-ylmethyl)-3-(4-trifluoromethanesulfonylphenyl)imidazolidine-2,4-dione;
5-methyl-1-(2-anilinosulfonylaminopyrid-4-ylmethyl)-3-(4-trifluoromethanesulfonylphenyl)imidazolidine-2,4-dione;
5-methyl-1-(2-phenylsulfonylaminopyrid-4-ylmethyl)-3-(4-trifluoromethanesulfonylphenyl)imidazolidine-2,4-dione;
5-methyl-1-[2-(2-thienyl)sulfonylaminopyrid-4-ylmethyl]-3-(4-trifluoromethanesulfonylphenyl)imidazolidine-2,4-dione;
5-methyl-1-(2-methylsulfonylaminopyrid-4-ylmethyl)-3-(4-trifluoromethanesulfonylphenyl)imidazolidine-2,4-dione;
5-methyl-1-[2-(4-chlorophenyl)sulfonylaminopyrid-4-ylmethyl]-3-(4-trifluoromethanesulfonylphenyl)imidazolidine-2,4-dione;
5-methyl-1-(2-benzylsulfonylaminopyrid-4-ylmethyl)-3-(4-trifluoromethanesulfonylphenyl)imidazolidine-2,4-dione;
5-methyl-1-(2-hydroxycarbonylpyrid-4-ylmethyl)-3-(4-trifluoromethanesulfonylphenyl)imidazolidine-2,4-dione;
5-methyl-1-(2-ethoxycarbonylpyrid-4-ylmethyl)-3-(4-trifluoromethanesulfonylphenyl)imidazolidine-2,4-dione;
5-methyl-1-(2-tert-butoxycarbonylpyrid-4-ylmethyl)-3-(4-trifluoromethanesulfonylphenyl)imidazolidine-2,4-dione;
5-methyl-1-(2-phenoxycarbonylpyrid-4-ylmethyl)-3-(4-trifluoromethanesulfonylphenyl)imidazolidine-2,4-dione;
5-methyl-1-[2-(4-methylpiperazinocarbonyl)pyrid-4-ylmethyl]-3-(4-trifluoromethanesulfonylphenyl)imidazolidine-2,4-dione;
5-methyl-1-[2-(methylamino)carbonylpyrid-4-ylmethyl]-3-(4-trifluoromethanesulfonylphenyl)imidazolidine-2,4-dione;
5-methyl-1-[2-(dimethylamino)carbonylpyrid-4-ylmethyl]-3-(4-trifluoromethanesulfonylphenyl)imidazolidine-2,4-dione;
5-methyl-1-(2-piperidinocarbonylpyrid-4-ylmethyl)-3-(4-trifluoromethanesulfonylphenyl)imidazolidine-2,4-dione;
5-methyl-1-(2-morpholinocarbonylpyrid-4-ylmethyl)-3-(4-trifluoromethanesulfonylphenyl)imidazolidine-2,4-dione;
5-methyl-1-[2-(4-phenylpiperazinocarbonyl)pyrid-4-ylmethyl]-3-(4-trifluoromethanesulfonylphenyl)imidazolidine-2,4-dione;
5-methyl-1-(2-phenylaminocarbonylpyrid-4-ylmethyl)-3-(4-trifluoromethanesulfonylphenyl)imidazolidine-2,4-dione;
5-methyl-1-[2-(methylphenylamino)carbonylpyrid-4-ylmethyl]-3-(4-trifluoromethanesulfonylphenyl)imidazolidine-2,4-dione;
5-methyl-1-[2-(4-methoxyphenyl)methylaminocarbonylpyrid-4-ylmethyl]-3-(4-trifluoromethanesulfonylphenyl)imidazolidine-2,4-dione;
5-methyl-1-[2-(4-chlorophenyl)methylaminocarbonylpyrid-4-ylmethyl]-3-(4-trifluoromethanesulfonylphenyl)imidazolidine-2,4-dione;
5-methyl-1-[2-(4-morpholinylamino)carbonylpyrid-4-ylmethyl]-3-(4-trifluoromethanesulfonylphenyl)imidazolidine-2,4-dione;
5-methyl-1-(2-aminocarbonylpyrid-4-ylmethyl)-3-(4-trifluoromethanesulfonylphenyl)imidazolidine-2,4-dione;
5-methyl-1-(2-phenoxypyrid-4-ylmethyl)-3-(4-trifluoromethanesulfonylphenyl)imidazolidine-2,4-dione;
5-methyl-1-(2-methoxypyrid-4-ylmethyl)-3-(4-trifluoromethanesulfonylphenyl)imidazolidine-2,4-dione;
5-methyl-1-(2-ethoxypyrid-4-ylmethyl)-3-(4-trifluoromethanesulfonylphenyl)imidazolidine-2,4-dione;
5-methyl-1-[2-(1-pyrrolidinyl)ethoxypyrid-4-ylmethyl]-3-(4-trifluoromethanesulfonylphenyl)imidazolidine-2,4-dione;
5-methyl-1-(2-benzyloxypyrid-4-ylmethyl)-3-(4-trifluoromethanesulfonylphenyl)imidazolidine-2,4-dione;
5-methyl-1-(2-benzoyloxypyrid-4-ylmethyl)-3-(4-trifluoromethanesulfonylphenyl)imidazolidine-2,4-dione;
5-methyl-1-[2-(4,5-dihydro-1H-imidazol-2-yl)pyrid-4-ylmethyl]-3-(4-trifluoromethanesulfonylphenyl)imidazolidine-2,4-dione;
5-methyl-1-[2-(1H-imidazol-2-yl)pyrid-4-ylmethyl]-3-(4-trifluoromethanesulfonylphenyl)imidazolidine-2,4-dione;

5-methyl-1-[2(1H-tetrazol-5-yl)pyrid-4-ylmethyl]-3-(4-trifluoromethanesulfonylphenyl)imidazolidine-2,4-dione;
5-methyl-1-(2-amidinopyrid-4-ylmethyl)-3-(4-trifluoromethanesulfonylphenyl)imidazolidine-2,4-dione;
5-methyl-1-(2-dimethylaminomethylpyrid-4-ylmethyl)-3-(4-trifluoromethanesulfonylphenyl)imidazolidine-2,4-dione;
5-methyl-1-(2-aminomethylpyrid-4-ylmethyl)-3-(4-trifluoromethanesulfonylphenyl)imidazolidine-2,4-dione;
5-methyl-1-(3-methylpyrid-4-ylmethyl)-3-(4-trifluoromethanesulfonylphenyl)imidazolidine-2,4-dione;
5-methyl-1-(3-ethylpyrid-4-ylmethyl)-3-(4-trifluoromethanesulfonylphenyl)imidazolidine-2,4-dione;
5-methyl-1-(3-isopropylpyrid-4-ylmethyl)-3-(4-trifluoromethanesulfonylphenyl)imidazolidine-2,4-dione;
5-methyl-1-(3-tert-butylpyrid-4-ylmethyl)-3-(4-trifluoromethanesulfonylphenyl)imidazolidine-2,4-dione;
5-methyl-1-(3-isobutylpyrid-4-ylmethyl)-3-(4-trifluoromethanesulfonylphenyl)imidazolidine-2,4-dione;
5-methyl-1-(3-cyclohexylpyrid-4-ylmethyl)-3-(4-trifluoromethanesulfonylphenyl)imidazolidine-2,4-dione;
5-methyl-1-(3-phenylpyrid-4-ylmethyl)-3-(4-trifluoromethanesulfonylphenyl)imidazolidine-2,4-dione;
5-methyl-1-[3-(4-chlorophenyl)pyrid-4-ylmethyl]-3-(4-trifluoromethanesulfonylphenyl)imidazolidine-2,4-dione;
5-methyl-1-[3-(3-chlorophenyl)pyrid-4-ylmethyl]-3-(4-trifluoromethanesulfonylphenyl)imidazolidine-2,4-dione;
5-methyl-1-[3-(2-chlorophenyl)pyrid-4-ylmethyl]-3-(4-trifluoromethanesulfonylphenyl)imidazolidine-2,4-dione;
5-methyl-1-[3-(4-fluorophenyl)pyrid-4-ylmethyl]-3-(4-trifluoromethanesulfonylphenyl)imidazolidine-2,4-dione;
5-methyl-1-[3-(4-methoxyphenyl)pyrid-4-ylmethyl]-3-(4-trifluoromethanesulfonylphenyl)imidazolidine-2,4-dione;
5-methyl-1-(3-benzylpyrid-4-ylmethyl)-3-(4-trifluoromethanesulfonylphenyl)imidazolidine-2,4-dione;
5-methyl-1-(3,2'-bipyrid-4-ylmethyl)-3-(4-trifluoromethanesulfonylphenyl)imidazolidine-2,4-dione;
5-methyl-1-(3-hydroxymethylpyrid-4-ylmethyl)-3-(4-trifluoromethanesulfonylphenyl)imidazolidine-2,4-dione;
5-methyl-1-(3-chloropyrid-4-ylmethyl)-3-(4-trifluoromethanesulfonylphenyl)imidazolidine-2,4-dione;
5-methyl-1-(3-fluoropyrid-4-ylmethyl)-3-(4-trifluoromethanesulfonylphenyl)imidazolidine-2,4-dione;
5-methyl-1-(3-bromopyrid-4-ylmethyl)-3-(4-trifluoromethanesulfonylphenyl)imidazolidine-2,4-dione;
5-methyl-1-(3-aminopyrid-4-ylmethyl)-3-(4-trifluoromethanesulfonylphenyl)imidazolidine-2,4-dione;
5-methyl-1-(3-methylaminopyrid-4-ylmethyl)-3-(4-trifluoromethanesulfonylphenyl)imidazolidine-2,4-dione;
5-methyl-1-(3-ethylaminopyrid-4-ylmethyl)-3-(4-trifluoromethanesulfonylphenyl)imidazolidine-2,4-dione;
5-methyl-1-(3-isopropylaminopyrid-4-ylmethyl)-3-(4-trifluoromethanesulfonylphenyl)imidazolidine-2,4-dione;
5-methyl-1-(3-phenylaminopyrid-4-ylmethyl)-3-(4-trifluoromethanesulfonylphenyl)imidazolidine-2,4-dione;
5-methyl-1-(3-cyclohexylaminopyrid-4-ylmethyl)-3-(4-trifluoromethanesulfonylphenyl)imidazolidine-2,4-dione;
5-methyl-1-(3-diethylaminopyrid-4-ylmethyl)-3-(4-trifluoromethanesulfonylphenyl)imidazolidine-2,4-dione;
5-methyl-1-(3-N-cyclohexyl-N-methylaminopyrid-4-ylmethyl)-3-(4-trifluoromethanesulfonylphenyl)imidazolidine-2,4-dione;
5-methyl-1-(3-piperidinopyrid-4-ylmethyl)-3-(4-trifluoromethanesulfonylphenyl)imidazolidine-2,4-dione;
5-methyl-1-(3-morpholinopyrid-4-ylmethyl)-3-(4-trifluoromethanesulfonylphenyl)imidazolidine-2,4-dione;
5-methyl-1-[3-(4-methylpiperazino)diethylaminopyrid-4-ylmethyl]-3-(4-trifluoromethanesulfonylphenyl)imidazolidine-2,4-dione;
5-methyl-1-[3-(1H-pyrazol-1-yl)pyrid-4-ylmethyl]-3-(4-trifluoromethanesulfonylphenyl)imidazolidine-2,4-dione;
5-methyl-1-[3-(2-benzoylhydrazino)pyrid-4-ylmethyl]-3-(4-trifluoromethanesulfonylphenyl)imidazolidine-2,4-dione;
5-methyl-1-(3-benzoylaminopyrid-4-ylmethyl)-3-(4-trifluoromethanesulfonylphenyl)imidazolidine-2,4-dione;
5-methyl-1-[3-(4-chlorobenzoylamino)pyrid-4-ylmethyl]-3-(4-trifluoromethanesulfonylphenyl)imidazolidine-2,4-dione;
5-methyl-1-[3-(3-chlorobenzoylamino)pyrid-4-ylmethyl]-3-(4-trifluoromethanesulfonylphenyl)imidazolidine-2,4-dione;
5-methyl-1-[3-(2-chlorobenzoylamino)pyrid-4-ylmethyl]-3-(4-trifluoromethanesulfonylphenyl)imidazolidine-2,4-dione;
5-methyl-1-[3-(4-fluorobenzoylamino)pyrid-4-ylmethyl]-3-(4-trifluoromethanesulfonylphenyl)imidazolidine-2,4-dione;
5-methyl-1-[3-(4-methoxybenzoylamino)pyrid-4-ylmethyl]-3-(4-trifluoromethanesulfonylphenyl)imidazolidine-2,4-dione;
5-methyl-1-(3-acetamidopyrid-4-ylmethyl)-3-(4-trifluoromethanesulfonylphenyl)imidazolidine-2,4-dione;
5-methyl-1-(3-phenylacetamidopyrid-4-ylmethyl)-3-(4-trifluoromethanesulfonylphenyl)imidazolidine-2,4-dione;
5-methyl-1-[3-(4-methylpiperazino)acetamidopyrid-4-ylmethyl]-3-(4-trifluoromethanesulfonylphenyl)imidazolidine-2,4-dione;
5-methyl-1-(3-cyclohexanylcarboxamidopyrid-4-ylmethyl)-3-(4-trifluoromethanesulfonylphenyl)imidazolidine-2,4-dione;
5-methyl-1-[3-(1-methyl-4-piperidinyl)carbonylaminopyrid-4-ylmethyl]-3-(4-trifluoromethanesulfonylphenyl)imidazolidine-2,4-dione;
5-methyl-1-[3-(2-furanylcarbonyl)aminopyrid-4-ylmethyl]-3-(4-trifluoromethanesulfonylphenyl)imidazolidine-2,4-dione;
5-methyl-1-(3-ethoxycarbonylaminopyrid-4-ylmethyl)-3-(4-trifluoromethanesulfonylphenyl)imidazolidine-2,4-dione;
5-methyl-1-(3-isopropoxycarbonylaminopyrid-4-ylmethyl)-3-(4-trifluoromethanesulfonylphenyl)imidazolidine-2,4-dione;
5-methyl-1-(3-butoxycarbonylaminopyrid-4-ylmethyl)-3-(4-trifluoromethanesulfonylphenyl)imidazolidine-2,4-dione;
5-methyl-1-[3-(2-diethylaminoethoxycarbonylamino)pyrid-4-ylmethyl]-3-(4-trifluoromethanesulfonylphenyl)imidazolidine-2,4-dione;
5-methyl-1-(3-phenoxycarbonylaminopyrid-4-ylmethyl)-3-(4-trifluoromethanesulfonylphenyl)imidazolidine-2,4-dione;
5-methyl-1-[3-(4-chloroanilino)carbonylaminopyrid-4-ylmethyl]-3-(4-trifluoromethanesulfonylphenyl)imidazolidine-2,4-dione;
5-methyl-1-(3-anilinocarbonylaminopyrid-4-ylmethyl)-3-(4-trifluoromethanesulfonylphenyl)imidazolidine-2,4-dione;
5-methyl-1-(3-benzylaminocarbonylaminopyrid-4-ylmethyl)-3-(4-trifluoromethanesulfonylphenyl)imidazolidine-2,4-dione;

5-methyl-1-[3-(2-pyridylamino)carbonylaminopyrid-4-ylmethyl)]-3-(4-trifluoromethanesulfonylphenyl)imidazolidine-2,4-dione;
5-methyl-1-(3-ureidopyrid-4-ylmethyl)-3-(4-trifluoromethanesulfonylphenyl)imidazolidine-2,4-dione;
5-methyl-1-(3-benzylaminosulfonylaminopyrid-4-ylmethyl)-3-(4-trifluoromethanesulfonylphenyl)imidazolidine-2,4-dione;
5-methyl-1-(3-methylaminosulfonylaminopyrid-4-ylmethyl)-3-(4-trifluoromethanesulfonylphenyl)imidazolidine-2,4-dione;
5-methyl-1-(3-aminosulfonylaminopyrid-4-ylmethyl)-3-(4-trifluoromethanesulfonylphenyl)imidazolidine-2,4-dione;
5-methyl-1-(3-morpholinosulfonylaminopyrid-4-ylmethyl)-3-(4-trifluoromethanesulfonylphenyl)imidazolidine-2,4-dione;
5-methyl-1-(3-dimethylaminosulfonylaminopyrid-4-ylmethyl)-3-(4-trifluoromethanesulfonylphenyl)imidazolidine-2,4-dione;
5-methyl-1-(3-anilinosulfonylaminopyrid-4-ylmethyl)-3-(4-trifluoromethanesulfonylphenyl)imidazolidine-2,4-dione;
5-methyl-1-(3-phenylsulfonylaminopyrid-4-ylmethyl)-3-(4-trifluoromethanesulfonylphenyl)imidazolidine-2,4-dione;
5-methyl-1-[3-(2-thienyl)sulfonylaminopyrid-4-ylmethyl]-3-(4-trifluoromethanesulfonylphenyl)imidazolidine-2,4-dione;
5-methyl-1-(3-methylsulfonylaminopyrid-4-ylmethyl)-3-(4-trifluoromethanesulfonylphenyl)imidazolidine-2,4-dione;
5-methyl-1-[3-(4-chlorophenyl)sulfonylaminopyrid-4-ylmethyl]-3-(4-trifluoromethanesulfonylphenyl)imidazolidine-2,4-dione;
5-methyl-1-(3-benzylsulfonylaminopyrid-4-ylmethyl)-3-(4-trifluoromethanesulfonylphenyl)imidazolidine-2,4-dione;
5-methyl-1-(3-hydroxycarbonylpyrid-4-ylmethyl)-3-(4-trifluoromethanesulfonylphenyl)imidazolidine-2,4-dione;
5-methyl-1-(3-ethoxycarbonylpyrid-4-ylmethyl)-3-(4-trifluoromethanesulfonylphenyl)imidazolidine-2,4-dione;
5-methyl-1-(3-tert-butoxycarbonylpyrid-4-ylmethyl)-3-(4-trifluoromethanesulfonylphenyl)imidazolidine-2,4-dione;
5-methyl-1-(3-phenoxycarbonylpyrid-4-ylmethyl)-3-(4-trifluoromethanesulfonylphenyl)imidazolidine-2,4-dione;
5-methyl-1-[3-(4-methylpiperazinocarbonyl)pyrid-4-ylmethyl]-3-(4-trifluoromethanesulfonylphenyl)imidazolidine-2,4-dione;
5-methyl-1-[3-(methylamino)carbonylpyrid-4-ylmethyl]-3-(4-trifluoromethanesulfonylphenyl)imidazolidine-2,4-dione;
5-methyl-1-[3-dimethylamino)carbonylpyrid-4-ylmethyl]-3-(4-trifluoromethanesulfonylphenyl)imidazolidine-2,4-dione;
5-methyl-1-(3-piperidinocarbonylpyrid-4-ylmethyl)-3-(4-trifluoromethanesulfonylphenyl)imidazolidine-2,4-dione;
5-methyl-1-(3-morpholinocarbonylpyrid-4-ylmethyl)-3-(4-trifluoromethanesulfonylphenyl)imidazolidine-2,4-dione;
5-methyl-1-[3-(4-phenylpiperazinocarbonyl)pyrid-4-ylmethyl]-3-(4-trifluoromethanesulfonylphenyl)imidazolidine-2,4-dione;
5-methyl-1-(3-phenylaminocarbonylpyrid-4-ylmethyl)-3-(4-trifluoromethanesulfonylphenyl)imidazolidine-2,4-dione;
5-methyl-1-[3-(methylphenylamino)carbonylpyrid-4-ylmethyl]-3-(4-trifluoromethanesulfonylphenyl)imidazolidine-2,4-dione;
5-methyl-1-[3-(4-methoxyphenyl)methylaminocarbonylpyrid-4-ylmethyl]-3-(4-trifluoromethanesulfonylphenyl)imidazolidine-2,4-dione;
5-methyl-1-[3-(4-chlorophenyl)methylaminocarbonylpyrid-4-ylmethyl]-3-(4-trifluoromethanesulfonylphenyl)imidazolidine-2,4-dione;
5-methyl-1-[3-(4-morpholinylamino)carbonylpyrid-4-ylmethyl]-3-(4-trifluoromethanesulfonylphenyl)imidazolidine-2,4-dione;
5-methyl-1-(3-aminocarbonylpyrid-4-ylmethyl)-3-(4-trifluoromethanesulfonylphenyl)imidazolidine-2,4-dione;
5-methyl-1-(3-phenoxypyrid-4-ylmethyl)-3-(4-trifluoromethanesulfonylphenyl)imidazolidine-2,4-dione;
5-methyl-1-(3-methoxypyrid-4-ylmethyl)-3-(4-trifluoromethanesulfonylphenyl)imidazolidine-2,4-dione;
5-methyl-1-(3-ethoxypyrid-4-ylmethyl)-3-(4-trifluoromethanesulfonylphenyl)imidazolidine-2,4-dione;
5-methyl-1-[3-(1-pyrrolidinyl)ethoxypyrid-4-ylmethyl]-3-(4-trifluoromethanesulfonylphenyl)imidazolidine-2,4-dione;
5-methyl-1-(3-benzyloxypyrid-4-ylmethyl)-3-(4-trifluoromethanesulfonylphenyl)imidazolidine-2,4-dione;
5-methyl-1-(3-benzoyloxypyrid-4-ylmethyl)-3-(4-trifluoromethanesulfonylphenyl)imidazolidine-2,4-dione;
5-methyl-1-[3-(4,5-dihydro-1H-imidazol-2-yl)pyrid-4-ylmethyl]-3-(4-trifluoromethanesulfonylphenyl)imidazolidine-2,4-dione;
5-methyl-1-[3-(1H-imidazol-2-yl)pyrid-4-ylmethyl]-3-(4-trifluoromethanesulfonylphenyl)imidazolidine-2,4-dione;
5-methyl-1-[3-(1H-tetrazol-5-yl)pyrid-4-ylmethyl]-3-(4-trifluoromethanesulfonylphenyl)imidazolidine-2,4-dione;
5-methyl-1-(3-amidinopyrid-4-ylmethyl)-3-(4-trifluoromethanesulfonylphenyl)imidazolidine-2,4-dione;
5-methyl-1-(3-dimethylaminomethylpyrid-4-ylmethyl)-3-(4-trifluoromethanesulfonylphenyl)imidazolidine-2,4-dione;
5-methyl-1-(3-aminomethylpyrid-4-ylmethyl)-3-(4-trifluoromethanesulfonylphenyl)imidazolidine-2,4-dione;
1-(2-methylpyrid-4-ylmethyl)-3-(4-trifluoromethanesulfonylphenyl)imidazolidine-2,4-dione;
1-(2-ethylpyrid-4-ylmethyl)-3-(4-trifluoromethanesulfonylphenyl)imidazolidine-2,4-dione;
1-(2-isopropylpyrid-4-ylmethyl)-3-(4-trifluoromethanesulfonylphenyl)imidazolidine-2,4-dione;
1-(2-tert-butylpyrid-4-ylmethyl)-3-(4-trifluoromethanesulfonylphenyl)imidazolidine-2,4-dione;
1-(2-isobutylpyrid-4-ylmethyl)-3-(4-trifluoromethanesulfonylphenyl)imidazolidine-2,4-dione;
1-(2-cyclohexylpyrid-4-ylmethyl)-3-(4-trifluoromethanesulfonylphenyl)imidazolidine-2,4-dione;
1-(2-phenylpyrid-4-ylmethyl)-3-(4-trifluoromethanesulfonylphenyl)imidazolidine-2,4-dione;
1-[2-(4-chlorophenyl)pyrid-4-ylmethyl]-3-(4-trifluoromethanesulfonylphenyl)imidazolidine-2,4-dione;
1-[2-(3-chlorophenyl)pyrid-4-ylmethyl]-3-(4-trifluoromethanesulfonylphenyl)imidazolidine-2,4-dione;
1-[2-(2-chlorophenyl)pyrid-4-ylmethyl]-3-(4-trifluoromethanesulfonylphenyl)imidazolidine-2,4-dione;
1-[2-(4-fluorophenyl)pyrid-4-ylmethyl]-3-(4-trifluoromethanesulfonylphenyl)imidazolidine-2,4-dione;
1-[2-(4-methoxyphenyl)pyrid-4-ylmethyl]-3-(4-trifluoromethanesulfonylphenyl)imidazolidine-2,4-dione;
1-(2-benzylpyrid-4-ylmethyl)-3-(4-trifluoromethanesulfonylphenyl)imidazolidine-2,4-dione;
1-(2,2'-bipyrid-4-ylmethyl)-3-(4-trifluoromethanesulfonylphenyl)imidazolidine-2,4-dione;
1-(2-hydroxymethylpyrid-4-ylmethyl)-3-(4-trifluoromethanesulfonylphenyl)imidazolidine-2,4-dione;
1-(2-chloropyrid-4-ylmethyl)-3-(4-trifluoromethanesulfonylphenyl)imidazolidine-2,4-dione;

1-(2-fluoropyrid-4-ylmethyl)-3-(4-trifluoromethanesulfonylphenyl)imidazolidine-2,4-dione;
1-(2-bromopyrid-4-ylmethyl)-3-(4-trifluoromethanesulfonylphenyl)imidazolidine-2,4-dione;
1-(2-aminopyrid-4-ylmethyl)-3-(4-trifluoromethanesulfonylphenyl)imidazolidine-2,4-dione;
1-(2-methylaminopyrid-4-ylmethyl)-3-(4-trifluoromethanesulfonylphenyl)imidazolidine-2,4-dione;
1-(2-ethylaminopyrid-4-ylmethyl)-3-(4-trifluoromethanesulfonylphenyl)imidazolidine-2,4-dione;
1-(2-isopropylaminopyrid-4-ylmethyl)-3-(4-trifluoromethanesulfonylphenyl)imidazolidine-2,4-dione;
1-(2-phenylaminopyrid-4-ylmethyl)-3-(4-trifluoromethanesulfonylphenyl)imidazolidine-2,4-dione;
1-(2-cyclohexylaminopyrid-4-ylmethyl)-3-(4-trifluoromethanesulfonylphenyl)imidazolidine-2,4-dione;
1-(2-diethylaminopyrid-4-ylmethyl)-3-(4-trifluoromethanesulfonylphenyl)imidazolidine-2,4-dione;
1-(2-N-cyclohexyl-N-methylaminopyrid-4-ylmethyl)-3-(4-trifluoromethanesulfonylphenyl)imidazolidine-2,4-dione;
1-(2-piperidinopyrid-4-ylmethyl)-3-(4-trifluoromethanesulfonylphenyl)imidazolidine-2,4-dione;
1-(2-morpholinopyrid-4-ylmethyl)-3-(4-trifluoromethanesulfonylphenyl)imidazolidine-2,4-dione;
1-[2-(4-methylpiperazino)diethylaminopyrid-4-ylmethyl]-3-(4-trifluoromethanesulfonylphenyl)imidazolidine-2,4-dione;
1-[2-(1H-pyrazol-1-yl)pyrid-4-ylmethyl]-3-(4-trifluoromethanesulfonylphenyl)imidazolidine-2,4-dione;
1-[2-(2-benzoylhydrazino)pyrid-4-ylmethyl]-3-(4-trifluoromethanesulfonylphenyl)imidazolidine-2,4-dione;
1-(2-benzoylaminopyrid-4-ylmethyl)-3-(4-trifluoromethanesulfonylphenyl)imidazolidine-2,4-dione;
1-[2-(4-chlorobenzoylamino)pyrid-4-ylmethyl]-3-(4-trifluoromethanesulfonylphenyl)imidazolidine-2,4-dione;
1-[2-(3-chlorobenzoylamino)pyrid-4-ylmethyl]-3-(4-trifluoromethanesulfonylphenyl)imidazolidine-2,4-dione;
1-[2-(2-chlorobenzoylamino)pyrid-4-ylmethyl]-3-(4-trifluoromethanesulfonylphenyl)imidazolidine-2,4-dione;
1-[2-(4-fluorobenzoylamino)pyrid-4-ylmethyl]-3-(4-trifluoromethanesulfonylphenyl)imidazolidine-2,4-dione;
1-[2-(4-methoxybenzoylamino)pyrid-4-ylmethyl]-3-(4-trifluoromethanesulfonylphenyl)imidazolidine-2,4-dione;
1-(2-acetamidopyrid-4-ylmethyl)-3-(4-trifluoromethanesulfonylphenyl)imidazolidine-2,4-dione;
1-(2-phenylacetamidopyrid-4-ylmethyl)-3-(4-trifluoromethanesulfonylphenyl)imidazolidine-2,4-dione;
1-[2-(4-methylpiperazino)acetamidopyrid-4-ylmethyl]-3-(4-trifluoromethanesulfonylphenyl)imidazolidine-2,4-dione;
1-(2-cyclohexanylcarboxamidopyrid-4-ylmethyl)-3-(4-trifluoromethanesulfonylphenyl)imidazolidine-2,4-dione;
1-[2-(1-methyl-4-piperidinyl)carbonylaminopyrid-4-ylmethyl]-3-(4-trifluoromethanesulfonylphenyl)imidazolidine-2,4-dione;
1-[2-(2-furanylcarbonyl)aminopyrid-4-ylmethyl]-3-(4-trifluoromethanesulfonylphenyl)imidazolidine-2,4-dione;
1-(2-ethoxycarbonylaminopyrid-4-ylmethyl)-3-(4-trifluoromethanesulfonylphenyl)imidazolidine-2,4-dione;
1-(2-isopropoxycarbonylaminopyrid-4-ylmethyl)-3-(4-trifluoromethanesulfonylphenyl)imidazolidine-2,4-dione;
1-(2-butoxycarbonylaminopyrid-4-ylmethyl)-3-(4-trifluoromethanesulfonylphenyl)imidazolidine-2,4-dione;
1-[2-(2-diethylaminoethoxycarbonylamino)pyrid-4-ylmethyl]-3-(4-trifluoromethanesulfonylphenyl)imidazolidine-2,4-dione;
1-(2-phenoxycarbonylaminopyrid-4-ylmethyl)-3-(4-trifluoromethanesulfonylphenyl)imidazolidine-2,4-dione;
1-[2-(4-chloroanilino)carbonylaminopyrid-4-ylmethyl]-3-(4-trifluoromethanesulfonylphenyl)imidazolidine-2,4-dione;
1-(2-anilinocarbonylaminopyrid-4-ylmethyl)-3-(4-trifluoromethanesulfonylphenyl)imidazolidine-2,4-dione;
1-(2-benzylaminocarbonylaminopyrid-4-ylmethyl)-3-(4-trifluoromethanesulfonylphenyl)imidazolidine-2,4-dione;
1-[2-(2-pyridylamino)carbonylaminopyrid-4-ylmethyl]-3-(4-trifluoromethanesulfonylphenyl)imidazolidine-2,4-dione;
1-(2-ureidopyrid-4-ylmethyl)-3-(4-trifluoromethanesulfonylphenyl)imidazolidine-2,4-dione;
1-(2-benzylaminosulfonylaminopyrid-4-ylmethyl)-3-(4-trifluoromethanesulfonylphenyl)imidazolidine-2,4-dione;
1-(2-methylaminosulfonylaminopyrid-4-ylmethyl)-3-(4-trifluoromethanesulfonylphenyl)imidazolidine-2,4-dione;
1-(2-aminosulfonylaminopyrid-4-ylmethyl)-3-(4-trifluoromethanesulfonylphenyl)imidazolidine-2,4-dione;
1-(2-morpholinosulfonylaminopyrid-4-ylmethyl)-3-(4-trifluoromethanesulfonylphenyl)imidazolidine-2,4-dione;
1-(2-dimethylaminosulfonylaminopyrid-4-ylmethyl)-3-(4-trifluoromethanesulfonylphenyl)imidazolidine-2,4-dione;
1-(2-anilinosulfonylaminopyrid-4-ylmethyl)-3-(4-trifluoromethanesulfonylphenyl)imidazolidine-2,4-dione;
1-(2-phenylsulfonylaminopyrid-4-ylmethyl)-3-(4-trifluoromethanesulfonylphenyl)imidazolidine-2,4-dione;
1-[2-(2-thienyl)sulfonylaminopyrid-4-ylmethyl]-3-(4-trifluoromethanesulfonylphenyl)imidazolidine-2,4-dione;
1-(2-methylsulfonylaminopyrid-4-ylmethyl)-3-(4-trifluoromethanesulfonylphenyl)imidazolidine-2,4-dione;
1-[2-(4-chlorophenyl)sulfonylaminopyrid-4-ylmethyl]-3-(4-trifluoromethanesulfonylphenyl)imidazolidine-2,4-dione;
1-(2-benzylsulfonylaminopyrid-4-ylmethyl)-3-(4-trifluoromethanesulfonylphenyl)imidazolidine-2,4-dione;
1-(2-hydroxycarbonylpyrid-4-ylmethyl)-3-(4-trifluoromethanesulfonylphenyl)imidazolidine-2,4-dione;
1-(2-ethoxycarbonylpyrid-4-ylmethyl)-3-(4-trifluoromethanesulfonylphenyl)imidazolidine-2,4-dione;
1-(2-tert-butoxycarbonylpyrid-4-ylmethyl)-3-(4-trifluoromethanesulfonylphenyl)imidazolidine-2,4-dione;
1-(2-phenoxycarbonylpyrid-4-ylmethyl)-3-(4-trifluoromethanesulfonylphenyl)imidazolidine-2,4-dione;
1-[2-(4-methylpiperazinocarbonyl)pyrid-4-ylmethyl]-3-(4-trifluoromethanesulfonylphenyl)imidazolidine-2,4-dione;
1-[2-methylamino)carbonylpyrid-4-ylmethyl]-3-(4-trifluoromethanesulfonylphenyl)imidazolidine-2,4-dione;
1-[2-(dimethylamino)carbonylpyrid-4-ylmethyl]-3-(4-trifluoromethanesulfonylphenyl)imidazolidine-2,4-dione;
1-(2-piperidinocarbonylpyrid-4-ylmethyl)-3-(4-trifluoromethanesulfonylphenyl)imidazolidine-2,4-dione;
1-(2-morpholinocarbonylpyrid-4-ylmethyl)-3-(4-trifluoromethanesulfonylphenyl)imidazolidine-2,4-dione;
1-[2-(4-phenylpiperazinocarbonyl)pyrid-4-ylmethyl]-3-(4-trifluoromethanesulfonylphenyl)imidazolidine-2,4-dione;
1-(2-phenylaminocarbonylpyrid-4-ylmethyl)-3-(4-trifluoromethanesulfonylphenyl)imidazolidine-2,4-dione;
1-[2-(methylphenylamino)carbonylpyrid-4-ylmethyl]-3-(4-trifluoromethanesulfonylphenyl)imidazolidine-2,4-dione;
1-[2-(4-methoxyphenyl)methylaminocarbonylpyrid-4-ylmethyl]-3-(4-trifluoromethanesulfonylphenyl)imidazolidine-2,4-dione;
1-[2-(4-chlorophenyl)methylaminocarbonylpyrid-4-ylmethyl]-3-(4-trifluoromethanesulfonylphenyl)imidazolidine-2,4-dione;

1-[2-(4-morpholinylamino)carbonylpyrid-4-ylmethyl]-3-(4-trifluoromethanesulfonylphenyl)imidazolidine-2,4-dione;
1-(2-aminocarbonylpyrid-4-ylmethyl)-3-(4-trifluoromethanesulfonylphenyl)imidazolidine-2,4-dione;
1-(2-phenoxypyrid-4-ylmethyl)-3-(4-trifluoromethanesulfonylphenyl)imidazolidine-2,4-dione;
1-(2-methoxypyrid-4-ylmethyl)-3-(4-trifluoromethanesulfonylphenyl)imidazolidine-2,4-dione;
1-(2-ethoxypyrid-4-ylmethyl)-3-(4-trifluoromethanesulfonylphenyl)imidazolidine-2,4-dione;
1-[2-(1-pyrrolidinyl)ethoxypyrid-4-ylmethyl]-3-(4-trifluoromethanesulfonylphenyl)imidazolidine-2,4-dione;
1-(2-benzyloxypyrid-4-ylmethyl)-3-(4-trifluoromethanesulfonylphenyl)imidazolidine-2,4-dione;
1-(2-benzoyloxypyrid-4-ylmethyl)-3-(4-trifluoromethanesulfonylphenyl)imidazolidine-2,4-dione;
1-[2-(4,5-dihydro-1H-imidazol-2-yl)pyrid-4-ylmethyl]-3-(4-trifluoromethanesulfonylphenyl)imidazolidine-2,4-dione;
1-[2-(1H-imidazol-2-yl)pyrid-4-ylmethyl]-3-(4-trifluoromethanesulfonylphenyl)imidazolidine-2,4-dione;
1-[2-(1H-tetrazol-5-yl)pyrid-4-ylmethyl]-3-(4-trifluoromethanesulfonylphenyl)imidazolidine-2,4-dione;
1-(2-amidinopyrid-4-ylmethyl)-3-(4-trifluoromethanesulfonylphenyl)imidazolidine-2,4-dione;
1-(2-dimethylaminomethylpyrid-4-ylmethyl)-3-(4-trifluoromethanesulfonylphenyl)imidazolidine-2,4-dione;
1-(2-aminomethylpyrid-4-ylmethyl)-3-(4-trifluoromethanesulfonylphenyl)imidazolidine-2,4-dione;
1-(3-methylpyrid-4-ylmethyl)-3-(4-trifluoromethanesulfonylphenyl)imidazolidine-2,4-dione;
1-(3-ethylpyrid-4-ylmethyl)-3-(4-trifluoromethanesulfonylphenyl)imidazolidine-2,4-dione;
1-(3-isopropylpyrid-4-ylmethyl)-3-(4-trifluoromethanesulfonylphenyl)imidazolidine-2,4-dione;
1-(3-tert-butylpyrid-4-ylmethyl)-3-(4-trifluoromethanesulfonylphenyl)imidazolidine-2,4-dione;
1-(3-isobutylpyrid-4-ylmethyl)-3-(4-trifluoromethanesulfonylphenyl)imidazolidine-2,4-dione;
1-(3-cyclohexylpyrid-4-ylmethyl)-3-(4-trifluoromethanesulfonylphenyl)imidazolidine-2,4-dione;
1-(3-phenylpyrid-4-ylmethyl)-3-(4-trifluoromethanesulfonylphenyl)imidazolidine-2,4-dione;
1-[3-(4-chlorophenyl)pyrid-4-ylmethyl]-3-(4-trifluoromethanesulfonylphenyl)imidazolidine-2,4-dione;
1-[3-(3-chlorophenyl)pyrid-4-ylmethyl]-3-(4-trifluoromethanesulfonylphenyl)imidazolidine-2,4-dione;
1-[3-(2-chlorophenyl)pyrid-4-ylmethyl]-3-(4-trifluoromethanesulfonylphenyl)imidazolidine-2,4-dione;
1-[3-(4-fluorophenyl)pyrid-4-ylmethyl]-3-(4-trifluoromethanesulfonylphenyl)imidazolidine-2,4-dione;
1-[3-(4-methoxyphenyl)pyrid-4-ylmethyl]-3-(4-trifluoromethanesulfonylphenyl)imidazolidine-2,4-dione;
1-(3-benzylpyrid-4-ylmethyl)-3-(4-trifluoromethanesulfonylphenyl)imidazolidine-2,4-dione;
1-(3,2'-bipyrid-4-ylmethyl)-3-(4-trifluoromethanesulfonylphenyl)imidazolidine-2,4-dione;
1-(3-hydroxymethylpyrid-4-ylmethyl)-3-(4-trifluoromethanesulfonylphenyl)imidazolidine-2,4-dione;
1-(3-chloropyrid-4-ylmethyl)-3-(4-trifluoromethanesulfonylphenyl)imidazolidine-2,4-dione;
1-(3-fluoropyrid-4-ylmethyl)-3-(4-trifluoromethanesulfonylphenyl)imidazolidine-2,4-dione;
1-(3-bromopyrid-4-ylmethyl)-3-(4-trifluoromethanesulfonylphenyl)imidazolidine-2,4-dione;
1-(3-aminopyrid-4-ylmethyl)-3-(4-trifluoromethanesulfonylphenyl)imidazolidine-2,4-dione;
1-(3-methylaminopyrid-4-ylmethyl)-3-(4-trifluoromethanesulfonylphenyl)imidazolidine-2,4-dione;
1-(3-ethylaminopyrid-4-ylmethyl)-3'-4-trifluoromethanesulfonylphenyl)imidazolidine-2,4-dione;
1-(3-isopropylaminopyrid-4-ylmethyl)-3-(4-trifluoromethanesulfonylphenyl)imidazolidine-2,4-dione;
1-(3-phenylaminopyrid-4-ylmethyl)-3-(4-trifluoromethanesulfonylphenyl)imidazolidine-2,4-dione;
1-(3-cyclohexylaminopyrid-4-ylmethyl)-3-(4-trifluoromethanesulfonylphenyl)imidazolidine-2,4-dione;
1-(3-diethylaminopyrid-4-ylmethyl)-3-(4-trifluoromethanesulfonylphenyl)imidazolidine-2,4-dione;
1-(3-N-cyclohexyl-N-methylaminopyrid-4-ylmethyl)-3-(4-trifluoromethanesulfonylphenyl)imidazolidine-2,4-dione;
1-(3-piperidinopyrid-4-ylmethyl)-3-(4-trifluoromethanesulfonylphenyl)imidazolidine-2,4-dione;
1-(3-morpholinopyrid-4-ylmethyl)-3-(4-trifluoromethanesulfonylphenyl)imidazolidine-2,4-dione;
1-[3-(4-methylpiperazino)diethylaminopyrid-4-ylmethyl]-3-(4-trifluoromethanesulfonylphenyl)imidazolidine-2,4-dione;
1-[3-(1H-pyrazol-1-yl)pyrid-4-ylmethyl]-3-(4-trifluoromethanesulfonylphenyl)imidazolidine-2,4-dione;
1-[3-(2-benzoylhydrazino)pyrid-4-ylmethyl]-3-(4-trifluoromethanesulfonylphenyl)imidazolidine-2,4-dione;
1-(3-benzoylaminopyrid-4-ylmethyl)-3-(4-trifluoromethanesulfonylphenyl)imidazolidine-2,4-dione;
1-[3-(4-chlorobenzoylamino)pyrid-4-ylmethyl]-3-(4-trifluoromethanesulfonylphenyl)imidazolidine-2,4-dione;
1-[3-(3-chlorobenzoylamino)pyrid-4-ylmethyl]-3-(4-trifluoromethanesulfonylphenyl)imidazolidine-2,4-dione;
1-[3-(2-chlorobenzoylamino)pyrid-4-ylmethyl]-3-(4-trifluoromethanesulfonylphenyl)imidazolidine-2,4-dione;
1-[3-(4-fluorobenzoylamino)pyrid-4-ylmethyl]-3-(4-trifluoromethanesulfonylphenyl)imidazolidine-2,4-dione;
1-[3-(4-methoxybenzoylamino)pyrid-4-ylmethyl]-3-(4-trifluoromethanesulfonylphenyl)imidazolidine-2,4-dione;
1-(3-acetamidopyrid-4-ylmethyl)-3-(4-trifluoromethanesulfonylphenyl)imidazolidine-2,4-dione;
1-(3-phenylacetamidopyrid-4-ylmethyl)-3-(4-trifluoromethanesulfonylphenyl)imidazolidine-2,4-dione;
1-[3-(4-methylpiperazino)acetamidopyrid-4-ylmethyl]-3-(4-trifluoromethanesulfonylphenyl)imidazolidine-2,4-dione;
1-(3-cyclohexanylcarboxamidopyrid-4-ylmethyl)-3-(4-trifluoromethanesulfonylphenyl)imidazolidine-2,4-dione;
1-[3-(1-methyl-4-piperidinyl)carbonylaminopyrid-4-ylmethyl]-3-(4-trifluoromethanesulfonylphenyl)imidazolidine-2,4-dione;
1-[3-(2-furanylcarbonyl)aminopyrid-4-ylmethyl]-3-(4-trifluoromethanesulfonylphenyl)imidazolidine-2,4-dione;
1-(3-ethoxycarbonylaminopyrid-4-ylmethyl)-3-(4-trifluoromethanesulfonylphenyl)imidazolidine-2,4-dione;
1-(3-isopropoxycarbonylaminopyrid-4-ylmethyl)-3-(4-trifluoromethanesulfonylphenyl)imidazolidine-2,4-dione;
1-(3-butoxycarbonylaminopyrid-4-ylmethyl)-3-(4-trifluoromethanesulfonylphenyl)imidazolidine-2,4-dione;
1-[3-(2-diethylaminoethoxycarbonylamino)pyrid-4-ylmethyl]-3-(4-trifluoromethanesulfonylphenyl)imidazolidine-2,4-dione;
1-(3-phenoxycarbonylaminopyrid-4-ylmethyl)-3-(4-trifluoromethanesulfonylphenyl)imidazolidine-2,4-dione;
1-[3-(4-chloroanilino)carbonylaminopyrid-4-ylmethyl]-3-(4-trifluoromethanesulfonylphenyl)imidazolidine-2,4-dione;
1-(3-anilinocarbonylaminopyrid-4-ylmethyl)-3-(4-trifluoromethanesulfonylphenyl)imidazolidine-2,4-dione;

1-(3-benzylaminocarbonylaminopyrid-4-ylmethyl)-3-(4-trifluoromethanesulfonylphenyl)imidazolidine-2,4-dione;
1-[3-(2-pyridylamino)carbonylaminopyrid-4-ylmethyl)]-3-(4-trifluoromethanesulfonylphenyl)imidazolidine-2,4-dione;
1-(3-ureidopyrid-4-ylmethyl)-3-(4-trifluoromethanesulfonylphenyl)imidazolidine-2,4-dione;
1-(3-benzylaminosulfonylaminopyrid-4-ylmethyl)-3-(4-trifluoromethanesulfonylphenyl)imidazolidine-2,4-dione;
1-(3-methylaminosulfonylaminopyrid-4-ylmethyl)-3-(4-trifluoromethanesulfonylphenyl)imidazolidine-2,4-dione;
1-(3-aminosulfonylaminopyrid-4-ylmethyl-3-(4-trifluoromethanesulfonylphenyl)imidazolidine-2,4-dione;
1-(3-morpholinosulfonylaminopyrid-4-ylmethyl)-3-(4-trifluoromethanesulfonylphenyl)imidazolidine-2,4-dione;
1-(3-dimethylaminosulfonylaminopyrid-4-ylmethyl)-3-(4-trifluoromethanesulfonylphenyl)imidazolidine-2,4-dione;
1-(3-anilinosulfonylaminopyrid-4-ylmethyl)-3-(4-trifluoromethanesulfonylphenyl)imidazolidine-2,4-dione;
1-(3-phenylsulfonylaminopyrid-4-ylmethyl)-3-(4-trifluoromethanesulfonylphenyl)imidazolidine-2,4-dione;
1-[3-(2-thienyl)sulfonylaminopyrid-4-ylmethyl]-3-(4-trifluoromethanesulfonylphenyl)imidazolidine-2,4-dione;
1-(3-methylsulfonylaminopyrid-4-ylmethyl)-3-(4-trifluoromethanesulfonylphenyl)imidazolidine-2,4-dione;
1-[3-(4-chlorophenyl)sulfonylaminopyrid-4-ylmethyl]-3-(4-trifluoromethanesulfonylphenyl)imidazolidine-2,4-dione;
1-(3-benzylsulfonylaminopyrid-4-ylmethyl)-3-(4-trifluoromethanesulfonylphenyl)imidazolidine-2,4-dione;
1-(3-hydroxycarbonylpyrid-4-ylmethyl)-3-(4-trifluoromethanesulfonylphenyl)imidazolidine-2,4-dione;
1-(3-ethoxycarbonylpyrid-4-ylmethyl)-3-(4-trifluoromethanesulfonylphenyl)imidazolidine-2,4-dione;
1-(3-tert-butoxycarbonylpyrid-4-ylmethyl)-3-(4-trifluoromethanesulfonylphenyl)imidazolidine-2,4-dione;
1-(3-phenoxycarbonylpyrid-4-ylmethyl)-3-(4-trifluoromethanesulfonylphenyl)imidazolidine-2,4-dione;
1-[3-(4-methylpiperazinocarbonyl)pyrid-4-ylmethyl]-3-(4-trifluoromethanesulfonylphenyl)imidazolidine-2,4-dione;
1-[3-(methylamino)carbonylpyrid-4-ylmethyl]-3-(4-trifluoromethanesulfonylphenyl)imidazolidine-2,4-dione;
1-[3-(dimethylamino)carbonylpyrid-4-ylmethyl]-3-(4-trifluoromethanesulfonylphenyl)imidazolidine-2,4-dione;
1-(3-piperidinocarbonylpyrid-4-ylmethyl)-3-(4-trifluoromethanesulfonylphenyl)imidazolidine-2,4-dione;
1-(3-morpholinocarbonylpyrid-4-ylmethyl)-3-(4-trifluoromethanesulfonylphenyl)imidazolidine-2,4-dione;
1-[3-(4-phenylpiperazinocarbonyl)pyrid-4-ylmethyl]-3-(4-trifluoromethanesulfonylphenyl)imidazolidine-2,4-dione;
1-(3-phenylaminocarbonylpyrid-4-ylmethyl)-3-(4-trifluoromethanesulfonylphenyl)imidazolidine-2,4-dione;
1-[3-(methylphenylamino)carbonylpyrid-4-ylmethyl]-3-(4-trifluoromethanesulfonylphenyl)imidazolidine-2,4-dione;
1-[3-(4-methoxyphenyl)methylaminocarbonylpyrid-4-ylmethyl]-3-(4-trifluoromethanesulfonylphenyl)imidazolidine-2,4-dione;
1-[3-(4-chlorophenyl)methylaminocarbonylpyrid-4-ylmethyl]-3-(4-trifluoromethanesulfonylphenyl)imidazolidine-2,4-dione;
1-[3-(4-morpholinylamino)carbonylpyrid-4-ylmethyl]-3-(4-trifluoromethanesulfonylphenyl)imidazolidine-2,4-dione;
1-(3-aminocarbonylpyrid-4-ylmethyl)-3-(4-trifluoromethanesulfonylphenyl)imidazolidine-2,4-dione;
1-(3-phenoxypyrid-4-ylmethyl)-3-(4-trifluoromethanesulfonylphenyl)imidazolidine-2,4-dione;
1-(3-methoxypyrid-4-ylmethyl)-3-(4-trifluoromethanesulfonylphenyl)imidazolidine-2,4-dione;
1-(3-ethoxypyrid-4-ylmethyl)-3-(4-trifluoromethanesulfonylphenyl)imidazolidine-2,4-dione;
1-[3-(1-pyrrolidinyl)ethoxypyrid-4-ylmethyl]-3-(4-trifluoromethanesulfonylphenyl)imidazolidine-2,4-dione;
1-(3-benzyloxypyrid-4-ylmethyl)-3-(4-trifluoromethanesulfonylphenyl)imidazolidine-2,4-dione;
1-(3-benzoyloxypyrid-4-ylmethyl)-3-(4-trifluoromethanesulfonylphenyl)imidazolidine-2,4-dione;
1-[3-(4,5-dihydro-1H-imidazol-2-yl)pyrid-4-ylmethyl]-3-(4-trifluoromethanesulfonylphenyl)imidazolidine-2,4-dione;
1-[3-(1H-imidazol-2-yl)pyrid-4-ylmethyl]-3-(4-trifluoromethanesulfonylphenyl)imidazolidine-2,4-dione;
1-[3-(1H-tetrazol-5-yl)pyrid-4-ylmethyl]-3-(4-trifluoromethanesulfonylphenyl)imidazolidine-2,4-dione;
1-(3-amidinopyrid-4-ylmethyl)-3-(4-trifluoromethanesulfonylphenyl)imidazolidine-2,4-dione;
1-(3-dimethylaminomethylpyridin)-4-ylmethyl]-3-(4-trifluoromethanesulfonylphenyl)imidazolidine-2,4-dione;
1-(3-aminomethylpyrid-4-ylmethyl)-3-(4-trifluoromethanesulfonylphenyl)imidazolidine-2,4-dione;
5,5-dimethyl-1-(2-methylquinolin-4-ylmethyl)-3-(4-trifluoromethoxyphenyl)imidazolidine-2,4-dione;
5,5-dimethyl-1-(2-methoxyquinolin-4-ylmethyl)-3-(4-trifluoromethoxyphenyl)imidazolidine-2,4-dione;
5,5-dimethyl-1-(2-chloroquinoline-4-ylmethyl)-3-(4-trifluoromethoxyphenyl)imidazolidine-2,4-dione;
5,5-dimethyl-1-(2-fluoroquinoline-4-ylmethyl)-3-(4-trifluoromethoxyphenyl)imidazolidine-2,4-dione;
5,5-dimethyl-1-(2-aminoquinoline-4-ylmethyl)-3-(4-trifluoromethoxyphenyl)imidazolidine-2,4-dione;
5,5-dimethyl-1-(2-methylaminoquinolin-4-ylmethyl)-3-(4-trifluoromethoxyphenyl)imidazolidine-2,4-dione;
5,5-dimethyl-1-(2-dimethylaminoquinolin-4-ylmethyl)-3-(4-trifluoromethoxyphenyl)imidazolidine-2,4-dione;
5,5-dimethyl-1-(2-piperidinoquinolin-4-ylmethyl)-3-(4-trifluoromethoxyphenyl)imidazolidine-2,4-dione;
5,5-dimethyl-1-(3-methylquinolin-4-ylmethyl)-3-(4-trifluoromethoxyphenyl)imidazolidine-2,4-dione;
5,5-dimethyl-1-(3-methoxyquinolin-4-ylmethyl)-3-(4-trifluoromethoxyphenyl)imidazolidine-2,4-dione;
5,5-dimethyl-1-(3-chloroquinoline-4-ylmethyl)-3-(4-trifluoromethoxyphenyl)imidazolidine-2,4-dione;
5,5-dimethyl-1-(3-fluoroquinoline-4-ylmethyl)-3-(4-trifluoromethoxyphenyl)imidazolidine-2,4-dione;
5,5-dimethyl-1-(3-aminoquinoline-4-ylmethyl)-3-(4-trifluoromethoxyphenyl)imidazolidine-2,4-dione;
5,5-dimethyl-1-(3-methylaminoquinolin-4-ylmethyl)-3-(4-trifluoromethoxyphenyl)imidazolidine-2,4-dione;
5,5-dimethyl-1-(3-dimethylaminoquinolin-4-ylmethyl)-3-(4-trifluoromethoxyphenyl)imidazolidine-2,4-dione;
5,5-dimethyl-1-(3-piperidinoquinolin-4-ylmethyl)-3-(4-trifluoromethoxyphenyl)imidazolidine-2,4-dione;
5,5-dimethyl-1-(5-methylquinolin-4-ylmethyl)-3-(4-trifluoromethoxyphenyl)imidazolidine-2,4-dione;
5,5-dimethyl-1-(5-methoxyquinolin-4-ylmethyl)-3-(4-trifluoromethoxyphenyl)imidazolidine-2,4-dione;
5,5-dimethyl-1-(5-chloroquinoline-4-ylmethyl)-3-(4-trifluoromethoxyphenyl)imidazolidine-2,4-dione;
5,5-dimethyl-1-(5-fluoroquinoline-4-ylmethyl)-3-(4-trifluoromethoxyphenyl)imidazolidine-2,4-dione;
5,5-dimethyl-1-(5-aminoquinoline-4-ylmethyl)-3-(4-trifluoromethoxyphenyl)imidazolidine-2,4-dione;
5,5-dimethyl-1-(5-methylaminoquinolin-4-ylmethyl)-3-(4-trifluoromethoxyphenyl)imidazolidine-2,4-dione;

5,5-dimethyl-1-(5-dimethylaminoquinolin-4-ylmethyl)-3-(4-trifluoromethoxyphenyl)imidazolidine-2,4-dione;
5,5-dimethyl-1-(5-piperidinoquinolin-4-ylmethyl)-3-(4-trifluoromethoxyphenyl)imidazolidine-2,4-dione;
5,5-dimethyl-1-(6-methylquinolin-4-ylmethyl)-3-(4-trifluoromethoxyphenyl)imidazolidine-2,4-dione;
5,5-dimethyl-1-(6-methoxyquinolin-4-ylmethyl)-3-(4-trifluoromethoxyphenyl)imidazolidine-2,4-dione;
5,5-dimethyl-1-(6-chloroquinoline-4-ylmethyl)-3-(4-trifluoromethoxyphenyl)imidazolidine-2,4-dione;
5,5-dimethyl-1-(6-fluoroquinoline-4-ylmethyl)-3-(4-trifluoromethoxyphenyl)imidazolidine-2,4-dione;
5,5-dimethyl-1-(6-aminoquinoline-4-ylmethyl)-3-(4-trifluoromethoxyphenyl)imidazolidine-2,4-dione;
5,5-dimethyl-1-(6-methylaminoquinolin-4-ylmethyl)-3-(4-trifluoromethoxyphenyl)imidazolidine-2,4-dione;
5,5-dimethyl-1-(6-dimethylaminoquinolin-4-ylmethyl)-3-(4-trifluoromethoxyphenyl)imidazolidine-2,4-dione;
5,5-dimethyl-1-(6-piperidinoquinolin-4-ylmethyl)-3-(4-trifluoromethoxyphenyl)imidazolidine-2,4-dione;
5,5-dimethyl-1-(7-methylquinolin-4-ylmethyl)-3-(4-trifluoromethoxyphenyl)imidazolidine-2,4-dione;
5,5-dimethyl-1-(7-methoxyquinolin-4-ylmethyl)-3-(4-trifluoromethoxyphenyl)imidazolidine-2,4-dione;
5,5-dimethyl-1-(7-chloroquinoline-4-ylmethyl)-3-(4-trifluoromethoxyphenyl)imidazolidine-2,4-dione;
5,5-dimethyl-1-(7-fluoroquinoline-4-ylmethyl)-3-(4-trifluoromethoxyphenyl)imidazolidine-2,4-dione;
5,5-dimethyl-1-(7-aminoquinoline-4-ylmethyl)-3-(4-trifluoromethoxyphenyl)imidazolidine-2,4-dione;
5,5-dimethyl-1-(7-methylaminoquinolin-4-ylmethyl)-3-(4-trifluoromethoxyphenyl)imidazolidine-2,4-dione;
5,5-dimethyl-1-(7-dimethylaminoquinolin-4-ylmethyl)-3-(4-trifluoromethoxyphenyl)imidazolidine-2,4-dione;
5,5-dimethyl-1-(7-piperidinoquinolin-4-ylmethyl)-3-(4-trifluoromethoxyphenyl)imidazolidine-2,4-dione;
5,5-dimethyl-1-(8-methylquinolin-4-ylmethyl)-3-(4-trifluoromethoxyphenyl)imidazolidine-2,4-dione;
5,5-dimethyl-1-(8-methoxyquinolin-4-ylmethyl)-3-(4-trifluoromethoxyphenyl)imidazolidine-2,4-dione;
5,5-dimethyl-1-(8-chloroquinoline-4-ylmethyl)-3-(4-trifluoromethoxyphenyl)imidazolidine-2,4-dione;
5,5-dimethyl-1-(8-fluoroquinoline-4-ylmethyl)-3-(4-trifluoromethoxyphenyl)imidazolidine-2,4-dione;
5,5-dimethyl-1-(8-aminoquinoline-4-ylmethyl)-3-(4-trifluoromethoxyphenyl)imidazolidine-2,4-dione;
5,5-dimethyl-1-(8-methylaminoquinolin-4-ylmethyl)-3-(4-trifluoromethoxyphenyl)imidazolidine-2,4-dione;
5,5-dimethyl-1-(8-dimethylaminoquinolin-4-ylmethyl)-3-(4-trifluoromethoxyphenyl)imidazolidine-2,4-dione;
5,5-dimethyl-1-(8-piperidinoquinolin-4-ylmethyl)-3-(4-trifluoromethoxyphenyl)imidazolidine-2,4-dione;
4-(2-methylquinolin)-4-ylmethyl-6-(4-trifluoromethoxyphenyl)-4,6-diazaspiro[2.4]heptane-5,7-dione;
4-(2-methoxyquinolin)-4-ylmethyl-6-(4-trifluoromethoxyphenyl)-4,6-diazaspiro[2.4]heptane-5,7-dione;
4-(2-chloroquinoline)-4-ylmethyl-6-(4-trifluoromethoxyphenyl)-4,6-diazaspiro[2.4]heptane-5,7-dione;
4-(2-fluoroquinoline)-4-ylmethyl-6-(4-trifluoromethoxyphenyl)-4,6-diazaspiro[2.4]heptane-5,7-dione;
4-(2-aminoquinoline)-4-ylmethyl-6-(4-trifluoromethoxyphenyl)-4,6-diazaspiro[2.4]heptane-5,7-dione;
4-(2-methylaminoquinolin)-4-ylmethyl-6-(4-trifluoromethoxyphenyl)-4,6-diazaspiro[2.4]heptane-5,7-dione;
4-(2-dimethylaminoquinolin)-4-ylmethyl-6-(4-trifluoromethoxyphenyl)-4,6-diazaspiro[2.4]heptane-5,7-dione;
4-(2-piperidinoquinolin)-4-ylmethyl-6-(4-trifluoromethoxyphenyl)-4,6-diazaspiro[2.4]heptane-5,7-dione;
4-(3-methylquinolin)-4-ylmethyl-6-(4-trifluoromethoxyphenyl)-4,6-diazaspiro[2.4]heptane-5,7-dione;
4-(3-methoxyquinolin)-4-ylmethyl-6-(4-trifluoromethoxyphenyl)-4,6-diazaspiro[2.4]heptane-5,7-dione;
4-(3-chloroquinoline)-4-ylmethyl-6-(4-trifluoromethoxyphenyl)-4,6-diazaspiro[2.4]heptane-5,7-dione;
4-(3-fluoroquinoline)-4-ylmethyl-6-(4-trifluoromethoxyphenyl)-4,6-diazaspiro[2.4]heptane-5,7-dione;
4-(3-aminoquinoline)-4-ylmethyl-6-(4-trifluoromethoxyphenyl)-4,6-diazaspiro[2.4]heptane-5,7-dione;
4-(3-methylaminoquinolin)-4-ylmethyl-6-(4-trifluoromethoxyphenyl)-4,6-diazaspiro[2.4]heptane-5,7-dione;
4-(3-dimethylaminoquinolin)-4-ylmethyl-6-(4-trifluoromethoxyphenyl)-4,6-diazaspiro[2.4]heptane-5,7-dione;
4-(3-piperidinoquinolin)-4-ylmethyl-6-(4-trifluoromethoxyphenyl)-4,6-diazaspiro[2.4]heptane-5,7-dione;
4-(5-methylquinolin)-4-ylmethyl-6-(4-trifluoromethoxyphenyl)-4,6-diazaspiro[2.4]heptane-5,7-dione;
4-(5-methoxyquinolin)-4-ylmethyl-6-(4-trifluoromethoxyphenyl)-4,6-diazaspiro[2.4]heptane-5,7-dione;
4-(5-chloroquinoline)-4-ylmethyl-6-(4-trifluoromethoxyphenyl)-4,6-diazaspiro[2.4]heptane-5,7-dione;
4-(5-fluoroquinoline)-4-ylmethyl-6-(4-trifluoromethoxyphenyl)-4,6-diazaspiro[2.4]heptane-5,7-dione;
4-(5-aminoquinoline)-4-ylmethyl-6-(4-trifluoromethoxyphenyl)-4,6-diazaspiro[2.4]heptane-5,7-dione;
4-(5-methylaminoquinolin)-4-ylmethyl-6-(4-trifluoromethoxyphenyl)-4,6-diazaspiro[2.4]heptane-5,7-dione;
4-(5-dimethylaminoquinolin)-4-ylmethyl-6-(4-trifluoromethoxyphenyl)-4,6-diazaspiro[2.4]heptane-5,7-dione;
4-(5-piperidinoquinolin)-4-ylmethyl-6-(4-trifluoromethoxyphenyl)-4,6-diazaspiro[2.4]heptane-5,7-dione;
4-(6-methylquinolin)-4-ylmethyl-6-(4-trifluoromethoxyphenyl)-4,6-diazaspiro[2.4]heptane-5,7-dione;
4-(6-methoxyquinolin)-4-ylmethyl-6-(4-trifluoromethoxyphenyl)-4,6-diazaspiro[2.4]heptane-5,7-dione;
4-(6-chloroquinoline)-4-ylmethyl-6-(4-trifluoromethoxyphenyl)-4,6-diazaspiro[2.4]heptane-5,7-dione;
4-(6-fluoroquinoline)-4-ylmethyl-6-(4-trifluoromethoxyphenyl)-4,6-diazaspiro[2.4]heptane-5,7-dione;
4-(6-aminoquinoline)-4-ylmethyl-6-(4-trifluoromethoxyphenyl)-4,6-diazaspiro[2.4]heptane-5,7-dione;
4-(6-methylaminoquinolin)-4-ylmethyl-6-(4-trifluoromethoxyphenyl)-4,6-diazaspiro[2.4]heptane-5,7-dione;
4-(6-dimethylaminoquinolin)-4-ylmethyl-6-(4-trifluoromethoxyphenyl)-4,6-diazaspiro[2.4]heptane-5,7-dione;
4-(6-piperidinoquinolin)-4-ylmethyl-6-(4-trifluoromethoxyphenyl)-4,6-diazaspiro[2.4]heptane-5,7-dione;
4-(7-methylquinolin)-4-ylmethyl-6-(4-trifluoromethoxyphenyl)-4,6-diazaspiro[2.4]heptane-5,7-dione;
4-(7-methoxyquinolin)-4-ylmethyl-6-(4-trifluoromethoxyphenyl)-4,6-diazaspiro[2.4]heptane-5,7-dione;
4-(7-chloroquinoline)-4-ylmethyl-6-(4-trifluoromethoxyphenyl)-4,6-diazaspiro[2.4]heptane-5,7-dione;
4-(7-fluoroquinoline)-4-ylmethyl-6-(4-trifluoromethoxyphenyl)-4,6-diazaspiro[2.4]heptane-5,7-dione;
4-(7-aminoquinoline)-4-ylmethyl-6-(4-trifluoromethoxyphenyl)-4,6-diazaspiro[2.4]heptane-5,7-dione;
4-(7-methylaminoquinolin)-4-ylmethyl-6-(4-trifluoromethoxyphenyl)-4,6-diazaspiro[2.4]heptane-5,7-dione;
4-(7-dimethylaminoquinolin)-4-ylmethyl-6-(4-trifluoromethoxyphenyl)-4,6-diazaspiro[2.4]heptane-5,7-dione;
4-(7-piperidinoquinolin)-4-ylmethyl-6-(4-trifluoromethoxyphenyl)-4,6-diazaspiro[2.4]heptane-5,7-dione;

4-(8-methylquinolin)-4-ylmethyl-6-(4-trifluoromethoxyphenyl)-4,6-diazaspiro[2.4]heptane-5,7-dione;
4-(8-methoxyquinolin)-4-ylmethyl-6-(4-trifluoromethoxyphenyl)-4,6-diazaspiro[2.4]heptane-5,7-dione;
4-(8-chloroquinoline)-4-ylmethyl-6-(4-trifluoromethoxyphenyl)-4,6-diazaspiro[2.4]heptane-5,7-dione;
4-(8-fluoroquinoline)-4-ylmethyl-6-(4-trifluoromethoxyphenyl)-4,6-diazaspiro[2.4]heptane-5,7-dione;
4-(8-aminoquinoline)-4-ylmethyl-6-(4-trifluoromethoxyphenyl)-4,6-diazaspiro[2.4]heptane-5,7-dione;
4-(8-methylaminoquinolin)-4-ylmethyl-6-(4-trifluoromethoxyphenyl)-4,6-diazaspiro[2.4]heptane-5,7-dione;
4-(8-dimethylaminoquinolin)-4-ylmethyl-6-(4-trifluoromethoxyphenyl)-4,6-diazaspiro[2.4]heptane-5,7-dione;
4-(8-piperidinoquinolin)-4-ylmethyl-6-(4-trifluoromethoxyphenyl)-4,6-diazaspiro[2.4]heptane-5,7-dione;
5-methyl-1-(2-methylquinolin-4-ylmethyl)-3-(4-trifluoromethoxyphenyl)imidazolidine-2,4-dione;
5-methyl-1-(2-methoxyquinolin-4-ylmethyl)-3-(4-trifluoromethoxyphenyl)imidazolidine-2,4-dione;
5-methyl-1-(2-chloroquinoline-4-ylmethyl)-3-(4-trifluoromethoxyphenyl)imidazolidine-2,4-dione;
5-methyl-1-(2-fluoroquinoline-4-ylmethyl)-3-(4-trifluoromethoxyphenyl)imidazolidine-2,4-dione;
5-methyl-1-(2-aminoquinoline-4-ylmethyl)-3-(4-trifluoromethoxyphenyl)imidazolidine-2,4-dione;
5-methyl-1-(2-methylaminoquinolin-4-ylmethyl)-3-(4-trifluoromethoxyphenyl)imidazolidine-2,4-dione;
5-methyl-1-(2-dimethylaminoquinolin-4-ylmethyl)-3-(4-trifluoromethoxyphenyl)imidazolidine-2,4-dione;
5-methyl-1-(2-piperidinoquinolin-4-ylmethyl)-3-(4-trifluoromethoxyphenyl)imidazolidine-2,4-dione;
5-methyl-1-(3-methylquinolin-4-ylmethyl)-3-(4-trifluoromethoxyphenyl)imidazolidine-2,4-dione;
5-methyl-1-(3-methoxyquinolin-4-ylmethyl)-3-(4-trifluoromethoxyphenyl)imidazolidine-2,4-dione;
5-methyl-1-(3-chloroquinoline-4-ylmethyl)-3-(4-trifluoromethoxyphenyl)imidazolidine-2,4-dione;
5-methyl-1-(3-fluoroquinoline-4-ylmethyl)-3-(4-trifluoromethoxyphenyl)imidazolidine-2,4-dione;
5-methyl-1-(3-aminoquinoline-4-ylmethyl)-3-(4-trifluoromethoxyphenyl)imidazolidine-2,4-dione;
5-methyl-1-(3-methylaminoquinolin-4-ylmethyl)-3-(4-trifluoromethoxyphenyl)imidazolidine-2,4-dione;
5-methyl-1-(3-dimethylaminoquinolin-4-ylmethyl)-3-(4-trifluoromethoxyphenyl)imidazolidine-2,4-dione;
5-methyl-1-(3-piperidinoquinolin-4-ylmethyl)-3-(4-trifluoromethoxyphenyl)imidazolidine-2,4-dione;
5-methyl-1-(5-methylquinolin-4-ylmethyl)-3-(4-trifluoromethoxyphenyl)imidazolidine-2,4-dione;
5-methyl-1-(5-methoxyquinolin-4-ylmethyl)-3-(4-trifluoromethoxyphenyl)imidazolidine-2,4-dione;
5-methyl-1-(5-chloroquinoline-4-ylmethyl)-3-(4-trifluoromethoxyphenyl)imidazolidine-2,4-dione;
5-methyl-1-(5-fluoroquinoline-4-ylmethyl)-3-(4-trifluoromethoxyphenyl)imidazolidine-2,4-dione;
5-methyl-1-(5-aminoquinoline-4-ylmethyl)-3-(4-trifluoromethoxyphenyl)imidazolidine-2,4-dione;
5-methyl-1-(5-methylaminoquinolin-4-ylmethyl)-3-(4-trifluoromethoxyphenyl)imidazolidine-2,4-dione;
5-methyl-1-(5-dimethylaminoquinolin-4-ylmethyl)-3-(4-trifluoromethoxyphenyl)imidazolidine-2,4-dione;
5-methyl-1-(5-piperidinoquinolin-4-ylmethyl)-3-(4-trifluoromethoxyphenyl)imidazolidine-2,4-dione;
5-methyl-1-(6-methylquinolin-4-ylmethyl)-3-(4-trifluoromethoxyphenyl)imidazolidine-2,4-dione;
5-methyl-1-(6-methoxyquinolin-4-ylmethyl)-3-(4-trifluoromethoxyphenyl)imidazolidine-2,4-dione;
5-methyl-1-(6-chloroquinoline-4-ylmethyl)-3-(4-trifluoromethoxyphenyl)imidazolidine-2,4-dione;
5-methyl-1-(6-fluoroquinoline-4-ylmethyl)-3-(4-trifluoromethoxyphenyl)imidazolidine-2,4-dione;
5-methyl-1-(6-aminoquinoline-4-ylmethyl)-3-(4-trifluoromethoxyphenyl)imidazolidine-2,4-dione;
5-methyl-1-(6-methylaminoquinolin-4-ylmethyl)-3-(4-trifluoromethoxyphenyl)imidazolidine-2,4-dione;
5-methyl-1-(6-dimethylaminoquinolin-4-ylmethyl)-3-(4-trifluoromethoxyphenyl)imidazolidine-2,4-dione;
5-methyl-1-(6-piperidinoquinolin-4-ylmethyl)-3-(4-trifluoromethoxyphenyl)imidazolidine-2,4-dione;
5-methyl-1-(7-methylquinolin-4-ylmethyl)-3-(4-trifluoromethoxyphenyl)imidazolidine-2,4-dione;
5-methyl-1-(7-methoxyquinolin-4-ylmethyl)-3-(4-trifluoromethoxyphenyl)imidazolidine-2,4-dione;
5-methyl-1-(7-chloroquinoline-4-ylmethyl)-3-(4-trifluoromethoxyphenyl)imidazolidine-2,4-dione;
5-methyl-1-(7-fluoroquinoline-4-ylmethyl)-3-(4-trifluoromethoxyphenyl)imidazolidine-2,4-dione;
5-methyl-1-(7-aminoquinoline-4-ylmethyl)-3-(4-trifluoromethoxyphenyl)imidazolidine-2,4-dione;
5-methyl-1-(7-methylaminoquinolin-4-ylmethyl)-3-(4-trifluoromethoxyphenyl)imidazolidine-2,4-dione;
5-methyl-1-(7-dimethylaminoquinolin-4-ylmethyl)-3-(4-trifluoromethoxyphenyl)imidazolidine-2,4-dione;
5-methyl-1-(7-piperidinoquinolin-4-ylmethyl)-3-(4-trifluoromethoxyphenyl)imidazolidine-2,4-dione;
5-methyl-1-(8-methylquinolin-4-ylmethyl)-3-(4-trifluoromethoxyphenyl)imidazolidine-2,4-dione;
5-methyl-1-(8-methoxyquinolin-4-ylmethyl)-3-(4-trifluoromethoxyphenyl)imidazolidine-2,4-dione;
5-methyl-1-(8-chloroquinoline-4-ylmethyl)-3-(4-trifluoromethoxyphenyl)imidazolidine-2,4-dione;
5-methyl-1-(8-fluoroquinoline-4-ylmethyl)-3-(4-trifluoromethoxyphenyl)imidazolidine-2,4-dione;
5-methyl-1-(8-aminoquinoline-4-ylmethyl)-3-(4-trifluoromethoxyphenyl)imidazolidine-2,4-dione;
5-methyl-1-(8-methylaminoquinolin-4-ylmethyl)-3-(4-trifluoromethoxyphenyl)imidazolidine-2,4-dione;
5-methyl-1-(8-dimethylaminoquinolin-4-ylmethyl)-3-(4-trifluoromethoxyphenyl)imidazolidine-2,4-dione;
5-methyl-1-(8-piperidinoquinolin-4-ylmethyl)-3-(4-trifluoromethoxyphenyl)imidazolidine-2,4-dione;
1-(2-methylquinolin-4-ylmethyl)-3-(4-trifluoromethoxyphenyl)imidazolidine-2,4-dione;
1-(2-methoxyquinolin-4-ylmethyl)-3-(4-trifluoromethoxyphenyl)imidazolidine-2,4-dione;
1-(2-chloroquinoline-4-ylmethyl)-3-(4-trifluoromethoxyphenyl)imidazolidine-2,4-dione;
1-(2-fluoroquinoline-4-ylmethyl)-3-(4-trifluoromethoxyphenyl)imidazolidine-2,4-dione;
1-(2-aminoquinoline-4-ylmethyl)-3-(4-trifluoromethoxyphenyl)imidazolidine-2,4-dione;
1-(2-methylaminoquinolin-4-ylmethyl)-3-(4-trifluoromethoxyphenyl)imidazolidine-2,4-dione;
1-(2-dimethylaminoquinolin-4-ylmethyl)-3-(4-trifluoromethoxyphenyl)imidazolidine-2,4-dione;
1-(2-piperidinoquinolin-4-ylmethyl)-3-(4-trifluoromethoxyphenyl)imidazolidine-2,4-dione;
1-(3-methylquinolin-4-ylmethyl)-3-(4-trifluoromethoxyphenyl)imidazolidine-2,4-dione;
1-(3-methoxyquinolin-4-ylmethyl)-3-(4-trifluoromethoxyphenyl)imidazolidine-2,4-dione;

1-(3-chloroquinoline-4-ylmethyl)-3-(4-trifluoromethoxyphenyl)imidazolidine-2,4-dione;
1-(3-fluoroquinoline-4-ylmethyl)-3-(4-trifluoromethoxyphenyl)imidazolidine-2,4-dione;
1-(3-aminoquinoline-4-ylmethyl)-3-(4-trifluoromethoxyphenyl)imidazolidine-2,4-dione;
1-(3-methylaminoquinolin-4-ylmethyl)-3-(4-trifluoromethoxyphenyl)imidazolidine-2,4-dione;
1-(3-dimethylaminoquinolin-4-ylmethyl)-3-(4-trifluoromethoxyphenyl)imidazolidine-2,4-dione;
1-(3-piperidinoquinolin-4-ylmethyl)-3-(4-trifluoromethoxyphenyl)imidazolidine-2,4-dione;
1-(5-methylquinolin-4-ylmethyl)-3-(4-trifluoromethoxyphenyl)imidazolidine-2,4-dione;
1-(5-methoxyquinolin-4-ylmethyl)-3-(4-trifluoromethoxyphenyl)imidazolidine-2,4-dione;
1-(5-chloroquinoline-4-ylmethyl)-3-(4-trifluoromethoxyphenyl)imidazolidine-2,4-dione;
1-(5-fluoroquinoline-4-ylmethyl)-3-(4-trifluoromethoxyphenyl)imidazolidine-2,4-dione;
1-(5-aminoquinoline-4-ylmethyl)-3-(4-trifluoromethoxyphenyl)imidazolidine-2,4-dione;
1-(5-methylaminoquinolin-4-ylmethyl)-3-(4-trifluoromethoxyphenyl)imidazolidine-2,4-dione;
1-(5-dimethylaminoquinolin-4-ylmethyl)-3-(4-trifluoromethoxyphenyl)imidazolidine-2,4-dione;
1-(5-piperidinoquinolin-4-ylmethyl)-3-(4-trifluoromethoxyphenyl)imidazolidine-2,4-dione;
1-(6-methylquinolin-4-ylmethyl)-3-(4-trifluoromethoxyphenyl)imidazolidine-2,4-dione;
1-(6-methoxyquinolin-4-ylmethyl)-3-(4-trifluoromethoxyphenyl)imidazolidine-2,4-dione;
1-(6-chloroquinoline-4-ylmethyl)-3-(4-trifluoromethoxyphenyl)imidazolidine-2,4-dione;
1-(6-fluoroquinoline-4-ylmethyl)-3-(4-trifluoromethoxyphenyl)imidazolidine-2,4-dione;
1-(6-aminoquinoline-4-ylmethyl)-3-(4-trifluoromethoxyphenyl)imidazolidine-2,4-dione;
1-(6-methylaminoquinolin-4-ylmethyl)-3-(4-trifluoromethoxyphenyl)imidazolidine-2,4-dione;
1-(6-dimethylaminoquinolin-4-ylmethyl)-3-(4-trifluoromethoxyphenyl)imidazolidine-2,4-dione;
1-(6-piperidinoquinolin-4-ylmethyl)-3-(4-trifluoromethoxyphenyl)imidazolidine-2,4-dione;
1-(7-methylquinolin-4-ylmethyl)-3-(4-trifluoromethoxyphenyl)imidazolidine-2,4-dione;
1-(7-methoxyquinolin-4-ylmethyl)-3-(4-trifluoromethoxyphenyl)imidazolidine-2,4-dione;
1-(7-chloroquinoline-4-ylmethyl)-3-(4-trifluoromethoxyphenyl)imidazolidine-2,4-dione;
1-(7-fluoroquinoline-4-ylmethyl)-3-(4-trifluoromethoxyphenyl)imidazolidine-2,4-dione;
1-(7-aminoquinoline-4-ylmethyl)-3-(4-trifluoromethoxyphenyl)imidazolidine-2,4-dione;
1-(7-methylaminoquinolin-4-ylmethyl)-3-(4-trifluoromethoxyphenyl)imidazolidine-2,4-dione;
1-(7-dimethylaminoquinolin-4-ylmethyl)-3-(4-trifluoromethoxyphenyl)imidazolidine-2,4-dione;
1-(7-piperidinoquinolin-4-ylmethyl)-3-(4-trifluoromethoxyphenyl)imidazolidine-2,4-dione;
1-(8-methylquinolin-4-ylmethyl)-3-(4-trifluoromethoxyphenyl)imidazolidine-2,4-dione;
1-(8-methoxyquinolin-4-ylmethyl)-3-(4-trifluoromethoxyphenyl)imidazolidine-2,4-dione;
1-(8-chloroquinoline-4-ylmethyl)-3-(4-trifluoromethoxyphenyl)imidazolidine-2,4-dione;
1-(8-fluoroquinoline-4-ylmethyl)-3-(4-trifluoromethoxyphenyl)imidazolidine-2,4-dione;
1-(8-aminoquinoline-4-ylmethyl)-3-(4-trifluoromethoxyphenyl)imidazolidine-2,4-dione;
1-(8-methylaminoquinolin-4-ylmethyl)-3-(4-trifluoromethoxyphenyl)imidazolidine-2,4-dione;
1-(8-dimethylaminoquinolin-4-ylmethyl)-3-(4-trifluoromethoxyphenyl)imidazolidine-2,4-dione;
1-(8-piperidinoquinolin-4-ylmethyl)-3-(4-trifluoromethoxyphenyl)imidazolidine-2,4-dione;
5,5-dimethyl-1-(2-methylquinolin-4-ylmethyl)-3-(4-trifluoromethanesulfanylphenyl)imidazolidine-2,4-dione;
5,5-dimethyl-1-(2-methoxyquinolin-4-ylmethyl)-3-(4-trifluoromethanesulfanylphenyl)imidazolidine-2,4-dione;
5,5-dimethyl-1-(2-chloroquinoline-4-ylmethyl)-3-(4-trifluoromethanesulfanylphenyl)imidazolidine-2,4-dione;
5,5-dimethyl-1-(2-fluoroquinoline-4-ylmethyl)-3-(4-trifluoromethanesulfanylphenyl)imidazolidine-2,4-dione;
5,5-dimethyl-1-(2-aminoquinoline-4-ylmethyl)-3-(4-trifluoromethanesulfanylphenyl)imidazolidine-2,4-dione;
5,5-dimethyl-1-(2-methylaminoquinolin-4-ylmethyl)-3-(4-trifluoromethanesulfanylphenyl)imidazolidine-2,4-dione;
5,5-dimethyl-1-(2-dimethylaminoquinolin-4-ylmethyl)-3-(4-trifluoromethanesulfanylphenyl)imidazolidine-2,4-dione;
5,5-dimethyl-1-(2-piperidinoquinolin-4-ylmethyl)-3-(4-trifluoromethanesulfanylphenyl)imidazolidine-2,4-dione;
5,5-dimethyl-1-(3-methylquinolin-4-ylmethyl)-3-(4-trifluoromethanesulfanylphenyl)imidazolidine-2,4-dione;
5,5-dimethyl-1-(3-methoxyquinolin-4-ylmethyl)-3-(4-trifluoromethanesulfanylphenyl)imidazolidine-2,4-dione;
5,5-dimethyl-1-(3-chloroquinoline-4-ylmethyl)-3-(4-trifluoromethanesulfanylphenyl)imidazolidine-2,4-dione;
5,5-dimethyl-1-(3-fluoroquinoline-4-ylmethyl)-3-(4-trifluoromethanesulfanylphenyl)imidazolidine-2,4-dione;
5,5-dimethyl-1-(3-aminoquinoline-4-ylmethyl)-3-(4-trifluoromethanesulfanylphenyl)imidazolidine-2,4-dione;
5,5-dimethyl-1-(3-methylaminoquinolin-4-ylmethyl)-3-(4-trifluoromethanesulfanylphenyl)imidazolidine-2,4-dione;
5,5-dimethyl-1-(3-dimethylaminoquinolin-4-ylmethyl)-3-(4-trifluoromethanesulfanylphenyl)imidazolidine-2,4-dione;
5,5-dimethyl-1-(3-piperidinoquinolin-4-ylmethyl)-3-(4-trifluoromethanesulfanylphenyl)imidazolidine-2,4-dione;
5,5-dimethyl-1-(5-methylquinolin-4-ylmethyl)-3-(4-trifluoromethanesulfanylphenyl)imidazolidine-2,4-dione;
5,5-dimethyl-1-(5-methoxyquinolin-4-ylmethyl)-3-(4-trifluoromethanesulfanylphenyl)imidazolidine-2,4-dione;
5,5-dimethyl-1-(5-chloroquinoline-4-ylmethyl)-3-(4-trifluoromethanesulfanylphenyl)imidazolidine-2,4-dione;
5,5-dimethyl-1-(5-fluoroquinoline-4-ylmethyl)-3-(4-trifluoromethanesulfanylphenyl)imidazolidine-2,4-dione;
5,5-dimethyl-1-(5-aminoquinoline-4-ylmethyl)-3-(4-trifluoromethanesulfanylphenyl)imidazolidine-2,4-dione;
5,5-dimethyl-1-(5-methylaminoquinolin-4-ylmethyl)-3-(4-trifluoromethanesulfanylphenyl)imidazolidine-2,4-dione;
5,5-dimethyl-1-(5-dimethylaminoquinolin-4-ylmethyl)-3-(4-trifluoromethanesulfanylphenyl)imidazolidine-2,4-dione;
5,5-dimethyl-1-(5-piperidinoquinolin-4-ylmethyl)-3-(4-trifluoromethanesulfanylphenyl)imidazolidine-2,4-dione;
5,5-dimethyl-1-(6-methylquinolin-4-ylmethyl)-3-(4-trifluoromethanesulfanylphenyl)imidazolidine-2,4-dione;
5,5-dimethyl-1-(6-methoxyquinolin-4-ylmethyl)-3-(4-trifluoromethanesulfanylphenyl)imidazolidine-2,4-dione;
5,5-dimethyl-1-(6-chloroquinoline-4-ylmethyl)-3-(4-trifluoromethanesulfanylphenyl)imidazolidine-2,4-dione;

5,5-dimethyl-1-(6-fluoroquinoline-4-ylmethyl)-3-(4-trifluoromethanesulfanylphenyl)imidazolidine-2,4-dione;
5,5-dimethyl-1-(6-aminoquinoline-4-ylmethyl)-3-(4-trifluoromethanesulfanylphenyl)imidazolidine-2,4-dione;
5,5-dimethyl-1-(6-methylaminoquinolin-4-ylmethyl)-3-(4-trifluoromethanesulfanylphenyl)imidazolidine-2,4-dione;
5,5-dimethyl-1-(6-dimethylaminoquinolin-4-ylmethyl)-3-(4-trifluoromethanesulfanylphenyl)imidazolidine-2,4-dione;
5,5-dimethyl-1-(6-piperidinoquinolin-4-ylmethyl)-3-(4-trifluoromethanesulfanylphenyl)imidazolidine-2,4-dione;
5,5-dimethyl-1-(7-methylquinolin-4-ylmethyl)-3-(4-trifluoromethanesulfanylphenyl)imidazolidine-2,4-dione;
5,5-dimethyl-1-(7-methoxyquinolin-4-ylmethyl)-3-(4-trifluoromethanesulfanylphenyl)imidazolidine-2,4-dione;
5,5-dimethyl-1-(7-chloroquinoline-4-ylmethyl)-3-(4-trifluoromethanesulfanylphenyl)imidazolidine-2,4-dione;
5,5-dimethyl-1-(7-fluoroquinoline-4-ylmethyl)-3-(4-trifluoromethanesulfanylphenyl)imidazolidine-2,4-dione;
5,5-dimethyl-1-(7-aminoquinoline-4-ylmethyl)-3-(4-trifluoromethanesulfanylphenyl)imidazolidine-2,4-dione;
5,5-dimethyl-1-(7-methylaminoquinolin-4-ylmethyl)-3-(4-trifluoromethanesulfanylphenyl)imidazolidine-2,4-dione;
5,5-dimethyl-1-(7-dimethylaminoquinolin-4-ylmethyl)-3-(4-trifluoromethanesulfanylphenyl)imidazolidine-2,4-dione;
5,5-dimethyl-1-(7-piperidinoquinolin-4-ylmethyl)-3-(4-trifluoromethanesulfanylphenyl)imidazolidine-2,4-dione;
5,5-dimethyl-1(8-methylquinolin-4-ylmethyl)-3-(4-trifluoromethanesulfanylphenyl)imidazolidine-2,4-dione;
5,5-dimethyl-1-(8-methoxyquinolin-4-ylmethyl)-3-(4-trifluoromethanesulfanylphenyl)imidazolidine-2,4-dione;
5,5-dimethyl-1-(8-chloroquinoline-4-ylmethyl)-3-(4-trifluoromethanesulfanylphenyl)imidazolidine-2,4-dione;
5,5-dimethyl-1-(8-fluoroquinoline-4-ylmethyl)-3-(4-trifluoromethanesulfanylphenyl)imidazolidine-2,4-dione;
5,5-dimethyl-1-(8-aminoquinoline-4-ylmethyl)-3-(4-trifluoromethanesulfanylphenyl)imidazolidine-2,4-dione;
5,5-dimethyl-1-(8-methylaminoquinolin-4-ylmethyl)-3-(4-trifluoromethanesulfanylphenyl)imidazolidine-2,4-dione;
5,5-dimethyl-1-(8-dimethylaminoquinolin-4-ylmethyl)-3-(4-trifluoromethanesulfanylphenyl)imidazolidine-2,4-dione;
5,5-dimethyl-1-(8-piperidinoquinolin-4-ylmethyl)-3-(4-trifluoromethanesulfanylphenyl)imidazolidine-2,4-dione;
4-(2-methylquinolin)-4-ylmethyl-6-(4-trifluoromethanesulfanylphenyl)-4,6-diazaspiro[2.4]heptane-5,7-dione;
4-(2-methoxyquinolin)-4-ylmethyl-6-(4-trifluoromethanesulfanylphenyl)-4,6-diazaspiro[2.4]heptane-5,7-dione;
4-(2-chloroquinoline)-4-ylmethyl-6-(4-trifluoromethanesulfanylphenyl)-4,6-diazaspiro[2.4]heptane-5,7-dione;
4-(2-fluoroquinoline)-4-ylmethyl-6-(4-trifluoromethanesulfanylphenyl)-4,6-diazaspiro[2.4]heptane-5,7-dione;
4-(2-aminoquinoline)-4-ylmethyl-6-(4-trifluoromethanesulfanylphenyl)-4,6-diazaspiro[2.4]heptane-5,7-dione;
4-(2-methylaminoquinolin)-4-ylmethyl-6-(4-trifluoromethanesulfanylphenyl)-4,6-diazaspiro[2.4]heptane-5,7-dione;
4-(2-dimethylaminoquinolin)-4-ylmethyl-6-(4-trifluoromethanesulfanylphenyl)-4,6-diazaspiro[2.4]heptane-5,7-dione;
4-(2-piperidinoquinolin)-4-ylmethyl-6-(4-trifluoromethanesulfanylphenyl)-4,6-diazaspiro[2.4]heptane-5,7-dione;
4-(3-methylquinolin)-4-ylmethyl-6-(4-trifluoromethanesulfanylphenyl)-4,6-diazaspiro[2.4]heptane-5,7-dione;
4-(3-methoxyquinolin)-4-ylmethyl-6-(4-trifluoromethanesulfanylphenyl)-4,6-diazaspiro[2.4]heptane-5,7-dione;
4-(3-chloroquinoline)-4-ylmethyl-6-(4-trifluoromethanesulfanylphenyl)-4,6-diazaspiro[2.4]heptane-5,7-dione;
4-(3-fluoroquinoline)-4-ylmethyl-6-(4-trifluoromethanesulfanylphenyl)-4,6-diazaspiro[2.4]heptane-5,7-dione;
4-(3-aminoquinoline)-4-ylmethyl-6-(4-trifluoromethanesulfanylphenyl)-4,6-diazaspiro[2.4]heptane-5,7-dione;
4-(3-methylaminoquinolin)-4-ylmethyl-6-(4-trifluoromethanesulfanylphenyl)-4,6-diazaspiro[2.4]heptane-5,7-dione;
4-(3-dimethylaminoquinolin)-4-ylmethyl-6-(4-trifluoromethanesulfanylphenyl)-4,6-diazaspiro[2.4]heptane-5,7-dione;
4-(3-piperidinoquinolin)-4-ylmethyl-6-(4-trifluoromethanesulfanylphenyl)-4,6-diazaspiro[2.4]heptane-5,7-dione;
4-(5-methylquinolin)-4-ylmethyl-6-(4-trifluoromethanesulfanylphenyl)-4,6-diazaspiro[2.4]heptane-5,7-dione;
4-(5-methoxyquinolin)-4-ylmethyl-6-(4-trifluoromethanesulfanylphenyl)-4,6-diazaspiro[2.4]heptane-5,7-dione;
4-(5-chloroquinoline)-4-ylmethyl-6-(4-trifluoromethanesulfanylphenyl)-4,6-diazaspiro[2.4]heptane-5,7-dione;
4-(5-fluoroquinoline)-4-ylmethyl-6-(4-trifluoromethanesulfanylphenyl)-4,6-diazaspiro[2.4]heptane-5,7-dione;
4-(5-aminoquinoline)-4-ylmethyl-6-(4-trifluoromethanesulfanylphenyl)-4,6-diazaspiro[2.4]heptane-5,7-dione;
4-(5-methylaminoquinolin)-4-ylmethyl-6-(4-trifluoromethanesulfanylphenyl)-4,6-diazaspiro[2.4]heptane-5,7-dione;
4-(5-dimethylaminoquinolin)-4-ylmethyl-6-(4-trifluoromethanesulfanylphenyl)-4,6-diazaspiro[2.4]heptane-5,7-dione;
4-(5-piperidinoquinolin)-4-ylmethyl-6-(4-trifluoromethanesulfanylphenyl)-4,6-diazaspiro[2.4]heptane-5,7-dione;
4-(6-methylquinolin)-4-ylmethyl-6-(4-trifluoromethanesulfanylphenyl)-4,6-diazaspiro[2.4]heptane-5,7-dione;
4-(6-methoxyquinolin)-4-ylmethyl-6-(4-trifluoromethanesulfanylphenyl)-4,6-diazaspiro[2.4]heptane-5,7-dione;
4-(6-chloroquinoline)-4-ylmethyl-6-(4-trifluoromethanesulfanylphenyl)-4,6-diazaspiro[2.4]heptane-5,7-dione;
4-(6-fluoroquinoline)-4-ylmethyl-6-(4-trifluoromethanesulfanylphenyl)-4,6-diazaspiro[2.4]heptane-5,7-dione;
4-(6-aminoquinoline)-4-ylmethyl-6-(4-trifluoromethanesulfanylphenyl)-4,6-diazaspiro[2.4]heptane-5,7-dione;
4-(6-methylaminoquinolin)-4-ylmethyl-6-(4-trifluoromethanesulfanylphenyl)-4,6-diazaspiro[2.4]heptane-5,7-dione;
4-(6-dimethylaminoquinolin)-4-ylmethyl-6-(4-trifluoromethanesulfanylphenyl)-4,6-diazaspiro[2.4]heptane-5,7-dione;
4-(6-piperidinoquinolin)-4-ylmethyl-6-(4-trifluoromethanesulfanylphenyl)-4,6-diazaspiro[2.4]heptane-5,7-dione;
4-(7-methylquinolin)-4-ylmethyl-6-(4-trifluoromethanesulfanylphenyl)-4,6-diazaspiro[2.4]heptane-5,7-dione;
4-(7-methoxyquinolin)-4-ylmethyl-6-(4-trifluoromethanesulfanylphenyl)-4,6-diazaspiro[2.4]heptane-5,7-dione;
4-(7-chloroquinoline)-4-ylmethyl-6-(4-trifluoromethanesulfanylphenyl)-4,6-diazaspiro[2.4]heptane-5,7-dione;
4-(7-fluoroquinoline)-4-ylmethyl-6-(4-trifluoromethanesulfanylphenyl)-4,6-diazaspiro[2.4]heptane-5,7-dione;
4-(7-aminoquinoline)-4-ylmethyl-6-(4-trifluoromethanesulfanylphenyl)-4,6-diazaspiro[2.4]heptane-5,7-dione;
4-(7-methylaminoquinolin)-4-ylmethyl-6-(4-trifluoromethanesulfanylphenyl)-4,6-diazaspiro[2.4]heptane-5,7-dione;
4-(7-dimethylaminoquinolin)-4-ylmethyl-6-(4-trifluoromethanesulfanylphenyl)-4,6-diazaspiro[2.4]heptane-5,7-dione;

4-(7-piperidinoquinolin)-4-ylmethyl-6-(4-trifluoromethane-sulfanylphenyl)-4,6-diazaspiro[2.4]heptane-5,7-dione;
4-(8-methylquinolin)-4-ylmethyl-6-(4-trifluoromethane-sulfanylphenyl)-4,6-diazaspiro[2.4]heptane-5,7-dione;
4-(8-methoxyquinolin)-4-ylmethyl-6-(4-trifluoromethane-sulfanylphenyl)-4,6-diazaspiro[2.4]heptane-5,7-dione;
4-(8-chloroquinoline)-4-ylmethyl-6-(4-trifluoromethane-sulfanylphenyl)-4,6-diazaspiro[2.4]heptane-5,7-dione;
4-(8-fluoroquinoline)-4-ylmethyl-6-(4-trifluoromethane-sulfanylphenyl)-4,6-diazaspiro[2.4]heptane-5,7-dione;
4-(8-aminoquinoline)-4-ylmethyl-6-(4-trifluoromethane-sulfanylphenyl)-4,6-diazaspiro[2.4]heptane-5,7-dione;
4-(8-methylaminoquinolin)-4-ylmethyl-6-(4-trifluoromethanesulfanylphenyl)-4,6-diazaspiro[2.4]heptane-5,7-dione;
4-(8-dimethylaminoquinolin)-4-ylmethyl-6-(4-trifluoromethanesulfanylphenyl)-4,6-diazaspiro[2.4]heptane-5,7-dione;
4-(8-piperidinoquinolin)-4-ylmethyl-6-(4-trifluoromethane-sulfanylphenyl)-4,6-diazaspiro[2.4]heptane-5,7-dione;
5-methyl-1-(2-methylquinolin-4-ylmethyl)-3-(4-trifluoromethanesulfanylphenyl)imidazolidine-2,4-dione;
5-methyl-1-(2-methoxyquinolin-4-ylmethyl)-3-(4-trifluoromethanesulfanylphenyl)imidazolidine-2,4-dione;
5-methyl-1-(2-chloroquinoline-4-ylmethyl)-3-(4-trifluoromethanesulfanylphenyl)imidazolidine-2,4-dione;
5-methyl-1-(2-fluoroquinoline-4-ylmethyl)-3-(4-trifluoromethanesulfanylphenyl)imidazolidine-2,4-dione;
5-methyl-1-(2-aminoquinoline-4-ylmethyl)-3-(4-trifluoromethanesulfanylphenyl)imidazolidine-2,4-dione;
5-methyl-1-(2-methylaminoquinolin-4-ylmethyl)-3-(4-trifluoromethanesulfanylphenyl)imidazolidine-2,4-dione;
5-methyl-1-(2-dimethylaminoquinolin-4-ylmethyl)-3-(4-trifluoromethanesulfanylphenyl)imidazolidine-2,4-dione;
5-methyl-1-(2-piperidinoquinolin-4-ylmethyl)-3-(4-trifluoromethanesulfanylphenyl)imidazolidine-2,4-dione;
5-methyl-1-(3-methylquinolin-4-ylmethyl)-3-(4-trifluoromethanesulfanylphenyl)imidazolidine-2,4-dione;
5-methyl-1-(3-methoxyquinolin-4-ylmethyl)-3-(4-trifluoromethanesulfanylphenyl)imidazolidine-2,4-dione;
5-methyl-1-(3-chloroquinoline-4-ylmethyl)-3-(4-trifluoromethanesulfanylphenyl)imidazolidine-2,4-dione;
5-methyl-1-(3-fluoroquinoline-4-ylmethyl)-3-(4-trifluoromethanesulfanylphenyl)imidazolidine-2,4-dione;
5-methyl-1-(3-aminoquinoline-4-ylmethyl)-3-(4-trifluoromethanesulfanylphenyl)imidazolidine-2,4-dione;
5-methyl-1-(3-methylaminoquinolin-4-ylmethyl)-3-(4-trifluoromethanesulfanylphenyl)imidazolidine-2,4-dione;
5-methyl-1-(3-dimethylaminoquinolin-4-ylmethyl)-3-(4-trifluoromethanesulfanylphenyl)imidazolidine-2,4-dione;
5-methyl-1-(3-piperidinoquinolin-4-ylmethyl)-3-(4-trifluoromethanesulfanylphenyl)imidazolidine-2,4-dione;
5-methyl-1-(5-methylquinolin-4-ylmethyl)-3-(4-trifluoromethanesulfanylphenyl)imidazolidine-2,4-dione;
5-methyl-1-(5-methoxyquinolin-4-ylmethyl)-3-(4-trifluoromethanesulfanylphenyl)imidazolidine-2,4-dione;
5-methyl-1-(5-chloroquinoline-4-ylmethyl)-3-(4-trifluoromethanesulfanylphenyl)imidazolidine-2,4-dione;
5-methyl-1-(5-fluoroquinoline-4-ylmethyl)-3-(4-trifluoromethanesulfanylphenyl)imidazolidine-2,4-dione;
5-methyl-1-(5-aminoquinoline-4-ylmethyl)-3-(4-trifluoromethanesulfanylphenyl)imidazolidine-2,4-dione;
5-methyl-1-(5-methylaminoquinolin-4-ylmethyl)-3-(4-trifluoromethanesulfanylphenyl)imidazolidine-2,4-dione;
5-methyl-1-(5-dimethylaminoquinolin-4-ylmethyl)-3-(4-trifluoromethanesulfanylphenyl)imidazolidine-2,4-dione;
5-methyl-1-(5-piperidinoquinolin-4-ylmethyl)-3-(4-trifluoromethanesulfanylphenyl)imidazolidine-2,4-dione;
5-methyl-1-(6-methylquinolin-4-ylmethyl)-3-(4-trifluoromethanesulfanylphenyl)imidazolidine-2,4-dione;
5-methyl-1-(6-methoxyquinolin-4-ylmethyl)-3-(4-trifluoromethanesulfanylphenyl)imidazolidine-2,4-dione;
5-methyl-1-(6-chloroquinoline-4-ylmethyl)-3-(4-trifluoromethanesulfanylphenyl)imidazolidine-2,4-dione;
5-methyl-1-(6-fluoroquinoline-4-ylmethyl)-3-(4-trifluoromethanesulfanylphenyl)imidazolidine-2,4-dione;
5-methyl-1-(6-aminoquinoline-4-ylmethyl)-3-(4-trifluoromethanesulfanylphenyl)imidazolidine-2,4-dione;
5-methyl-1-(6-methylaminoquinolin-4-ylmethyl)-3-(4-trifluoromethanesulfanylphenyl)imidazolidine-2,4-dione;
5-methyl-1-(6-dimethylaminoquinolin-4-ylmethyl)-3-(4-trifluoromethanesulfanylphenyl)imidazolidine-2,4-dione;
5-methyl-1-(6-piperidinoquinolin-4-ylmethyl)-3-(4-trifluoromethanesulfanylphenyl)imidazolidine-2,4-dione;
5-methyl-1-(7-methylquinolin-4-ylmethyl)-3-(4-trifluoromethanesulfanylphenyl)imidazolidine-2,4-dione;
5-methyl-1-(7-methoxyquinolin-4-ylmethyl)-3-(4-trifluoromethanesulfanylphenyl)imidazolidine-2,4-dione;
5-methyl-1-(7-chloroquinoline-4-ylmethyl)-3-(4-trifluoromethanesulfanylphenyl)imidazolidine-2,4-dione;
5-methyl-1-(7-fluoroquinoline-4-ylmethyl)-3-(4-trifluoromethanesulfanylphenyl)imidazolidine-2,4-dione;
5-methyl-1-(7-aminoquinoline-4-ylmethyl)-3-(4-trifluoromethanesulfanylphenyl)imidazolidine-2,4-dione;
5-methyl-1-(7-methylaminoquinolin-4-ylmethyl)-3-(4-trifluoromethanesulfanylphenyl)imidazolidine-2,4-dione;
5-methyl-1-(7-dimethylaminoquinolin-4-ylmethyl)-3-(4-trifluoromethanesulfanylphenyl)imidazolidine-2,4-dione;
5-methyl-1-(7-piperidinoquinolin-4-ylmethyl)-3-(4-trifluoromethanesulfanylphenyl)imidazolidine-2,4-dione;
5-methyl-1-(8-methylquinolin-4-ylmethyl)-3-(4-trifluoromethanesulfanylphenyl)imidazolidine-2,4-dione;
5-methyl-1-(8-methoxyquinolin-4-ylmethyl)-3-(4-trifluoromethanesulfanylphenyl)imidazolidine-2,4-dione;
5-methyl-1-(8-chloroquinoline-4-ylmethyl)-3-(4-trifluoromethanesulfanylphenyl)imidazolidine-2,4-dione;
5-methyl-1-(8-fluoroquinoline-4-ylmethyl)-3-(4-trifluoromethanesulfanylphenyl)imidazolidine-2,4-dione;
5-methyl-1-(8-aminoquinoline-4-ylmethyl)-3-(4-trifluoromethanesulfanylphenyl)imidazolidine-2,4-dione;
5-methyl-1-(8-methylaminoquinolin-4-ylmethyl)-3-(4-trifluoromethanesulfanylphenyl)imidazolidine-2,4-dione;
5-methyl-1-(8-dimethylaminoquinolin-4-ylmethyl)-3-(4-trifluoromethanesulfanylphenyl)imidazolidine-2,4-dione;
5-methyl-1-(8-piperidinoquinolin-4-ylmethyl)-3-(4-trifluoromethanesulfanylphenyl)imidazolidine-2,4-dione;
1-(2-methylquinolin-4-ylmethyl)-3-(4-trifluoromethane-sulfanylphenyl)imidazolidine-2,4-dione;
1-(2-methoxyquinolin-4-ylmethyl)-3-(4-trifluoromethane-sulfanylphenyl)imidazolidine-2,4-dione;
1-(2-chloroquinoline-4-ylmethyl)-3-(4-trifluoromethane-sulfanylphenyl)imidazolidine-2,4-dione;
1-(2-fluoroquinoline-4-ylmethyl)-3-(4-trifluoromethane-sulfanylphenyl)imidazolidine-2,4-dione;
1-(2-aminoquinoline-4-ylmethyl)-3-(4-trifluoromethane-sulfanylphenyl)imidazolidine-2,4-dione;
1-(2-methylaminoquinolin-4-ylmethyl)-3-(4-trifluoromethanesulfanylphenyl)imidazolidine-2,4-dione;
1-(2-dimethylaminoquinolin-4-ylmethyl)-3-(4-trifluoromethanesulfanylphenyl)imidazolidine-2,4-dione;
1-(2-piperidinoquinolin-4-ylmethyl)-3-(4-trifluoromethanesulfanylphenyl)imidazolidine-2,4-dione;

1-(3-methylquinolin-4-ylmethyl)-3-(4-trifluoromethane-sulfanylphenyl)imidazolidine-2,4-dione;
1-(3-methoxyquinolin-4-ylmethyl)-3-(4-trifluoromethane-sulfanylphenyl)imidazolidine-2,4-dione;
1-(3-chloroquinoline-4-ylmethyl)-3-(4-trifluoromethane-sulfanylphenyl)imidazolidine-2,4-dione;
1-(3-fluoroquinoline-4-ylmethyl)-3-(4-trifluoromethane-sulfanylphenyl)imidazolidine-2,4-dione;
1-(3-aminoquinoline-4-ylmethyl)-3-(4-trifluoromethane-sulfanylphenyl)imidazolidine-2,4-dione;
1-(3-methylaminoquinolin-4-ylmethyl)-3-(4-trifluoromethanesulfanylphenyl)imidazolidine-2,4-dione;
1-(3-dimethylaminoquinolin-4-ylmethyl)-3-(4-trifluoromethanesulfanylphenyl)imidazolidine-2,4-dione;
1-(3-piperidinoquinolin-4-ylmethyl)-3-(4-trifluoromethane-sulfanylphenyl)imidazolidine-2,4-dione;
1-(5-methylquinolin-4-ylmethyl)-3-(4-trifluoromethane-sulfanylphenyl)imidazolidine-2,4-dione;
1-(5-methoxyquinolin-4-ylethyl)-3-(4-trifluoromethane-sulfanylphenyl)imidazolidine-2,4-dione;
1-(5-chloroquinoline-4-ylmethyl)-3-(4-trifluoromethane-sulfanylphenyl)imidazolidine-2,4-dione;
1-(5-fluoroquinoline-4-ylmethyl)-3-(4-trifluoromethane-sulfanylphenyl)imidazolidine-2,4-dione;
1-(5-aminoquinoline-4-ylmethyl)-3-(4-trifluoromethane-sulfanylphenyl)imidazolidine-2,4-dione;
1-(5-methylaminoquinolin-4-ylmethyl)-3-(4-trifluoromethanesulfanylphenyl)imidazolidine-2,4-dione;
1-(5-dimethylaminoquinolin-4-ylmethyl)-3-(4-trifluoromethanesulfanylphenyl)imidazolidine-2,4-dione;
1-(5-piperidinoquinolin-4-ylmethyl)-3-(4-trifluoromethane-sulfanylphenyl)imidazolidine-2,4-dione;
1-(6-methylquinolin-4-ylmethyl)-3-(4-trifluoromethane-sulfanylphenyl)imidazolidine-2,4-dione;
1-(6-methoxyquinolin-4-ylmethyl)-3-(4-trifluoromethane-sulfanylphenyl)imidazolidine-2,4-dione;
1-(6-chloroquinoline-4-ylmethyl)-3-(4-trifluoromethane-sulfanylphenyl)imidazolidine-2,4-dione;
1-(6-fluoroquinoline-4-ylmethyl)-3-(4-trifluoromethane-sulfanylphenyl)imidazolidine-2,4-dione;
1-(6-aminoquinoline-4-ylmethyl)-3-(4-trifluoromethane-sulfanylphenyl)imidazolidine-2,4-dione;
1-(6-methylaminoquinolin-4-ylmethyl)-3-(4-trifluoromethanesulfanylphenyl)imidazolidine-2,4-dione;
1-(6-dimethylaminoquinolin-4-ylmethyl)-3-(4-trifluoromethanesulfanylphenyl)imidazolidine-2,4-dione;
1-(6-piperidinoquinolin-4-ylmethyl)-3-(4-trifluoromethane-sulfanylphenyl)imidazolidine-2,4-dione;
1-(7-methylquinolin-4-ylmethyl)-3-(4-trifluoromethane-sulfanylphenyl)imidazolidine-2,4-dione;
1-(7-methoxyquinolin-4-ylmethyl)-3-(4-trifluoromethane-sulfanylphenyl)imidazolidine-2,4-dione;
1-(7-chloroquinoline-4-ylmethyl)-3-(4-trifluoromethane-sulfanylphenyl)imidazolidine-2,4-dione;
1-(7-fluoroquinoline-4-ylmethyl-3-(4-trifluoromethane-sulfanylphenyl)imidazolidine-2,4-dione;
1-(7-aminoquinoline-4-ylmethyl)-3-(4-trifluoromethane-sulfanylphenyl)imidazolidine-2,4-dione;
1-(7-methylaminoquinolin-4-ylmethyl)-3-(4-trifluoromethanesulfanylphenyl)imidazolidine-2,4-dione;
1-(7-dimethylaminoquinolin-4-ylmethyl)-3-(4-trifluoromethanesulfanylphenyl)imidazolidine-2,4-dione;
1-(7-piperidinoquinolin-4-ylmethyl)-3-(4-trifluoromethane-sulfanylphenyl)imidazolidine-2,4-dione;
1-(8-methylquinolin-4-ylmethyl)-3-(4-trifluoromethane-sulfanylphenyl)imidazolidine-2,4-dione;
1-(8-methoxyquinolin-4-ylmethyl)-3-(4-trifluoromethane-sulfanylphenyl)imidazolidine-2,4-dione;
1-(8-chloroquinoline-4-ylmethyl)-3-(4-trifluoromethane-sulfanylphenyl)imidazolidine-2,4-dione;
1-(8-fluoroquinoline-4-ylmethyl)-3-(4-trifluoromethane-sulfanylphenyl)imidazolidine-2,4-dione;
1-(8-aminoquinoline-4-ylmethyl)-3-(4-trifluoromethane-sulfanylphenyl)imidazolidine-2,4-dione;
1-(8-methylaminoquinolin-4-ylmethyl)-3-(4-trifluoromethanesulfanylphenyl)imidazolidine-2,4-dione;
1-(8-dimethylaminoquinolin-4-ylmethyl)-3-(4-trifluoromethanesulfanylphenyl)imidazolidine-2,4-dione;
1-(8-piperidinoquinolin-4-ylmethyl)-3-(4-trifluoromethane-sulfanylphenyl)imidazolidine-2,4-dione;
5,5-dimethyl-1-(2-methylquinolin-4-ylmethyl)-3-(4-trifluoromethanesulfonylphenyl)imidazolidine-2,4-dione;
5,5-dimethyl-1-(2-methoxyquinolin-4-ylmethyl)-3-(4-trifluoromethanesulfonylphenyl)imidazolidine-2,4-dione;
5,5-dimethyl-1-(2-chloroquinoline-4-ylmethyl)-3-(4-trifluoromethanesulfonylphenyl)imidazolidine-2,4-dione;
5,5-dimethyl-1-(2-fluoroquinoline-4-ylmethyl)-3-(4-trifluoromethanesulfonylphenyl)imidazolidine-2,4-dione;
5,5-dimethyl-1-(2-aminoquinoline-4-ylmethyl)-3-(4-trifluoromethanesulfonylphenyl)imidazolidine-2,4-dione;
5,5-dimethyl-1-(2-methylaminoquinolin-4-ylmethyl)-3-(4-trifluoromethanesulfonylphenyl)imidazolidine-2,4-dione;
5,5-dimethyl-1-(2-dimethylaminoquinolin-4-ylmethyl)-3-(4-trifluoromethanesulfonylphenyl)imidazolidine-2,4-dione;
5,5-dimethyl-1-(2-piperidinoquinolin-4-ylmethyl)-3-(4-trifluoromethanesulfonylphenyl)imidazolidine-2,4-dione;
5,5-dimethyl-1-(3-methylquinolin-4-ylmethyl)-3-(4-trifluoromethanesulfonylphenyl)imidazolidine-2,4-dione;
5,5-dimethyl-1-(3-methoxyquinolin-4-ylmethyl)-3-(4-trifluoromethanesulfonylphenyl)imidazolidine-2,4-dione;
5,5-dimethyl-1-(3-chloroquinoline-4-ylmethyl)-3-(4-trifluoromethanesulfonylphenyl)imidazolidine-2,4-dione;
5,5-dimethyl-1-(3-fluoroquinoline-4-ylmethyl)-3-(4-trifluoromethanesulfonylphenyl)imidazolidine-2,4-dione;
5,5-dimethyl-1-(3-aminoquinoline-4-ylmethyl)-3-(4-trifluoromethanesulfonylphenyl)imidazolidine-2,4-dione;
5,5-dimethyl-1-(3-methylaminoquinolin-4-ylmethyl)-3-(4-trifluoromethanesulfonylphenyl)imidazolidine-2,4-dione;
5,5-dimethyl-1-(3-dimethylaminoquinolin-4-ylmethyl)-3-(4-trifluoromethanesulfonylphenyl)imidazolidine-2,4-dione;
5,5-dimethyl-1-(3-piperidinoquinolin-4-ylmethyl)-3-(4-trifluoromethanesulfonylphenyl)imidazolidine-2,4-dione;
5,5-dimethyl-1-(5-methylquinolin-4-ylmethyl)-3-(4-trifluoromethanesulfonylphenyl)imidazolidine-2,4-dione;
5,5-dimethyl-1-(5-methoxyquinolin-4-ylmethyl)-3-(4-trifluoromethanesulfonylphenyl)imidazolidine-2,4-dione;
5,5-dimethyl-1-(5-chloroquinoline-4-ylmethyl)-3-(4-trifluoromethanesulfonylphenyl)imidazolidine-2,4-dione;
5,5-dimethyl-1-(5-fluoroquinoline-4-ylmethyl)-3-(4-trifluoromethanesulfonylphenyl)imidazolidine-2,4-dione;
5,5-dimethyl-1-(5-aminoquinoline-4-ylmethyl)-3-(4-trifluoromethanesulfonylphenyl)imidazolidine-2,4-dione;
5,5-dimethyl-1-(5-methylaminoquinolin-4-ylmethyl)-3-(4-trifluoromethanesulfonylphenyl)imidazolidine-2,4-dione;
5,5-dimethyl-1-(5-dimethylaminoquinolin-4-ylmethyl)-3-(4-trifluoromethanesulfonylphenyl)imidazolidine-2,4-dione;
5,5-dimethyl-1-(5-piperidinoquinolin-4-ylmethyl)-3-(4-trifluoromethanesulfonylphenyl)imidazolidine-2,4-dione;
5,5-dimethyl-1-(6-methylquinolin-4-ylmethyl)-3-(4-trifluoromethanesulfonylphenyl)imidazolidine-2,4-dione;

5,5-dimethyl-1-(6-methoxyquinolin-4-ylmethyl)-3-(4-trifluoromethanesulfonylphenyl)imidazolidine-2,4-dione;
5,5-dimethyl-1-(6-chloroquinoline-4-ylmethyl)-3-(4-trifluoromethanesulfonylphenyl)imidazolidine-2,4-dione;
5,5-dimethyl-1-(6-fluoroquinoline-4-ylmethyl)-3-(4-trifluoromethanesulfonylphenyl)imidazolidine-2,4-dione;
5,5-dimethyl-1-(6-aminoquinoline-4-ylmethyl)-3-(4-trifluoromethanesulfonylphenyl)imidazolidine-2,4-dione;
5,5-dimethyl-1-(6-methylaminoquinolin-4-ylmethyl)-3-(4-trifluoromethanesulfonylphenyl)imidazolidine-2,4-dione;
5,5-dimethyl-1-(6-dimethylaminoquinolin-4-ylmethyl)-3-(4-trifluoromethanesulfonylphenyl)imidazolidine-2,4-dione;
5,5-dimethyl-1-(6-piperidinoquinolin-4-ylmethyl)-3-(4-trifluoromethanesulfonylphenyl)imidazolidine-2,4-dione;
5,5-dimethyl-1-(7-methylquinolin-4-ylmethyl)-3-(4-trifluoromethanesulfonylphenyl)imidazolidine-2,4-dione;
5,5-dimethyl-1-(7-methoxyquinolin-4-ylmethyl)-3-(4-trifluoromethanesulfonylphenyl)imidazolidine-2,4-dione;
5,5-dimethyl-1-(7-chloroquinoline-4-ylmethyl)-3-(4-trifluoromethanesulfonylphenyl)imidazolidine-2,4-dione;
5,5-dimethyl-1-(7-fluoroquinoline-4-ylmethyl)-3-(4-trifluoromethanesulfonylphenyl)imidazolidine-2,4-dione;
5,5-dimethyl-1-(7-aminoquinoline-4-ylmethyl)-3-(4-trifluoromethanesulfonylphenyl)imidazolidine-2,4-dione;
5,5-dimethyl-1-(7-methylaminoquinolin-4-ylmethyl)-3-(4-trifluoromethanesulfonylphenyl)imidazolidine-2,4-dione;
5,5-dimethyl-1-(7-dimethylaminoquinolin-4-ylmethyl)-3-(4-trifluoromethanesulfonylphenyl)imidazolidine-2,4-dione;
5,5-dimethyl-1-(7-piperidinoquinolin-4-ylmethyl)-3-(4-trifluoromethanesulfonylphenyl)imidazolidine-2,4-dione;
5,5-dimethyl-1-(8-methylquinolin-4-ylmethyl)-3-(4-trifluoromethanesulfonylphenyl)imidazolidine-2,4-dione;
5,5-dimethyl-1-(8-methoxyquinolin-4-ylmethyl)-3-(4-trifluoromethanesulfonylphenyl)imidazolidine-2,4-dione;
5,5-dimethyl-1-(8-chloroquinoline-4-ylmethyl)-3-(4-trifluoromethanesulfonylphenyl)imidazolidine-2,4-dione;
5,5-dimethyl-1-(8-fluoroquinoline-4-ylmethyl)-3-(4-trifluoromethanesulfonylphenyl)imidazolidine-2,4-dione;
5,5-dimethyl-1-(8-aminoquinoline-4-ylmethyl)-3-(4-trifluoromethanesulfonylphenyl)imidazolidine-2,4-dione;
5,5-dimethyl-1-(8-methylaminoquinolin-4-ylmethyl)-3-(4-trifluoromethanesulfonylphenyl)imidazolidine-2,4-dione;
5,5-dimethyl-1-(8-dimethylaminoquinolin-4-ylmethyl)-3-(4-trifluoromethanesulfonylphenyl)imidazolidine-2,4-dione;
5,5-dimethyl-1-(8-piperidinoquinolin-4-ylmethyl)-3-(4-trifluoromethanesulfonylphenyl)imidazolidine-2,4-dione;
4-(2-methylquinolin)-4-ylmethyl-6-(4-trifluoromethanesulfonylphenyl)-4,6-diazaspiro[2.4]heptane-5,7-dione;
4-(2-methoxyquinolin)-4-ylmethyl-6-(4-trifluoromethanesulfonylphenyl)-4,6-diazaspiro[2.4]heptane-5,7-dione;
4-(2-chloroquinoline)-4-ylmethyl-6-(4-trifluoromethanesulfonylphenyl)-4,6-diazaspiro[2.4]heptane-5,7-dione;
4-(2-fluoroquinoline)-4-ylmethyl-6-(4-trifluoromethanesulfonylphenyl)-4,6-diazaspiro[2.4]heptane-5,7-dione;
4-(2-aminoquinoline)-4-ylmethyl-6-(4-trifluoromethanesulfonylphenyl)-4,6-diazaspiro[2.4]heptane-5,7-dione;
4-(2-methylaminoquinolin)-4-ylmethyl-6-(4-trifluoromethanesulfonylphenyl)-4,6-diazaspiro[2.4]heptane-5,7-dione;
4-(2-dimethylaminoquinolin)-4-ylmethyl-6-(4-trifluoromethanesulfonylphenyl)-4,6-diazaspiro[2.4]heptane-5,7-dione;
4-(2-piperidinoquinolin)-4-ylmethyl-6-(4-trifluoromethanesulfonylphenyl)-4,6-diazaspiro[2.4]heptane-5,7-dione;
4-(3-methylquinolin)-4-ylmethyl-6-(4-trifluoromethanesulfonylphenyl)-4,6-diazaspiro[2.4]heptane-5,7-dione;
4-(3-methoxyquinolin)-4-ylmethyl-6-(4-trifluoromethanesulfonylphenyl)-4,6-diazaspiro[2.4]heptane-5,7-dione;
4-(3-chloroquinoline)-4-ylmethyl-6-(4-trifluoromethanesulfonylphenyl)-4,6-diazaspiro[2.4]heptane-5,7-dione;
4-(3-fluoroquinoline)-4-ylmethyl-6-(4-trifluoromethanesulfonylphenyl)-4,6-diazaspiro[2.4]heptane-5,7-dione;
4-(3-aminoquinoline)-4-ylmethyl-6-(4-trifluoromethanesulfonylphenyl)-4,6-diazaspiro[2.4]heptane-5,7-dione;
4-(3-methylaminoquinolin)-4-ylmethyl-6-(4-trifluoromethanesulfonylphenyl)-4,6-diazaspiro[2.4]heptane-5,7-dione;
4-(3-dimethylaminoquinolin)-4-ylmethyl-6-(4-trifluoromethanesulfonylphenyl)-4,6-diazaspiro[2.4]heptane-5,7-dione;
4-(3-piperidinoquinolin)-4-ylmethyl-6-(4-trifluoromethanesulfonylphenyl)-4,6-diazaspiro[2.4]heptane-5,7-dione;
4-(5-methylquinolin)-4-ylmethyl-6-(4-trifluoromethanesulfonylphenyl)-4,6-diazaspiro[2.4]heptane-5,7-dione;
4-(5-methoxyquinolin)-4-ylmethyl-6-(4-trifluoromethanesulfonylphenyl)-4,6-diazaspiro[2.4]heptane-5,7-dione;
4-(5-chloroquinoline)-4-ylmethyl-6-(4-trifluoromethanesulfonylphenyl)-4,6-diazaspiro[2.4]heptane-5,7-dione;
4-(5-fluoroquinoline)-4-ylmethyl-6-(4-trifluoromethanesulfonylphenyl)-4,6-diazaspiro[2.4]heptane-5,7-dione;
4-(5-aminoquinoline)-4-ylmethyl-6-(4-trifluoromethanesulfonylphenyl)-4,6-diazaspiro[2.4]heptane-5,7-dione;
4-(5-methylaminoquinolin)-4-ylmethyl-6-(4-trifluoromethanesulfonylphenyl)-4,6-diazaspiro[2.4]heptane-5,7-dione;
4-(5-dimethylaminoquinolin)-4-ylmethyl-6-(4-trifluoromethanesulfonylphenyl)-4,6-diazaspiro[2.4]heptane-5,7-dione;
4-(5-piperidinoquinolin)-4-ylmethyl-6-(4-trifluoromethanesulfonylphenyl)-4,6-diazaspiro[2.4]heptane-5,7-dione;
4-(6-methylquinolin)-4-ylmethyl-6-(4-trifluoromethanesulfonylphenyl)-4,6-diazaspiro[2.4]heptane-5,7-dione;
4-(6-methoxyquinolin)-4-ylmethyl-6-(4-trifluoromethanesulfonylphenyl)-4,6-diazaspiro[2.4]heptane-5,7-dione;
4-(6-chloroquinoline)-4-ylmethyl-6-(4-trifluoromethanesulfonylphenyl)-4,6-diazaspiro[2.4]heptane-5,7-dione;
4-(6-fluoroquinoline)-4-ylmethyl-6-(4-trifluoromethanesulfonylphenyl)-4,6-diazaspiro[2.4]heptane-5,7-dione;
4-(6-aminoquinoline)-4-ylmethyl-6-(4-trifluoromethanesulfonylphenyl)-4,6-diazaspiro[2.4]heptane-5,7-dione;
4-(6-methylaminoquinolin)-4-ylmethyl-6-(4-trifluoromethanesulfonylphenyl)-4,6-diazaspiro[2.4]heptane-5,7-dione;
4-(6-dimethylaminoquinolin)-4-ylmethyl-6-(4-trifluoromethanesulfonylphenyl)-4,6-diazaspiro[2.4]heptane-5,7-dione;
4-(6-piperidinoquinolin)-4-ylmethyl-6-(4-trifluoromethanesulfonylphenyl)-4,6-diazaspiro[2.4]heptane-5,7-dione;
4-(7-methylquinolin)-4-ylmethyl-6-(4-trifluoromethanesulfonylphenyl)-4,6-diazaspiro[2.4]heptane-5,7-dione;
4-(7-methoxyquinolin)-4-ylmethyl-6-(4-trifluoromethanesulfonylphenyl)-4,6-diazaspiro[2.4]heptane-5,7-dione;
4-(7-chloroquinoline)-4-ylmethyl-6-(4-trifluoromethanesulfonylphenyl)-4,6-diazaspiro[2.4]heptane-5,7-dione;
4-(7-fluoroquinoline)-4-ylmethyl-6-(4-trifluoromethanesulfonylphenyl)-4,6-diazaspiro[2.4]heptane-5,7-dione;
4-(7-aminoquinoline)-4-ylmethyl-6-(4-trifluoromethanesulfonylphenyl)-4,6-diazaspiro[2.4]heptane-5,7-dione;
4-(7-methylaminoquinolin)-4-ylmethyl-6-(4-trifluoromethanesulfonylphenyl)-4,6-diazaspiro[2.4]heptane-5,7-dione;

4-(7-dimethylaminoquinolin)-4-ylmethyl-6-(4-trifluoromethanesulfonylphenyl)-4,6-diazaspiro[2.4]heptane-5,7-dione;
4-(7-piperidinoquinolin)-4-ylmethyl-6-(4-trifluoromethanesulfonylphenyl)-4,6-diazaspiro[2.4]heptane-5,7-dione;
4-(8-methylquinolin)-4-ylmethyl-6-(4-trifluoromethanesulfonylphenyl)-4,6-diazaspiro[2.4]heptane-5,7-dione;
4-(8-methoxyquinolin)-4-ylmethyl-6-(4-trifluoromethanesulfonylphenyl)-4,6-diazaspiro[2.4]heptane-5,7-dione;
4-(8-chloroquinoline)-4-ylmethyl-6-(4-trifluoromethanesulfonylphenyl)-4,6-diazaspiro[2.4]heptane-5,7-dione;
4-(8-fluoroquinoline)-4-ylmethyl-6-(4-trifluoromethanesulfonylphenyl)-4,6-diazaspiro[2.4]heptane-5,7-dione;
4-(8-aminoquinoline)-4-ylmethyl-6-(4-trifluoromethanesulfonylphenyl)-4,6-diazaspiro[2.4]heptane-5,7-dione;
4-(8-methylaminoquinolin)-4-ylmethyl-6-(4-trifluoromethanesulfonylphenyl)-4,6-diazaspiro[2.4]heptane-5,7-dione;
4-(8-dimethylaminoquinolin)-4-ylmethyl-6-(4-trifluoromethanesulfonylphenyl)-4,6-diazaspiro[2.4]heptane-5,7-dione;
4-(8-piperidinoquinolin)-4-ylmethyl-6-(4-trifluoromethanesulfonylphenyl)-4,6-diazaspiro[2.4]heptane-5,7-dione;
5-methyl-1-(2-methylquinolin-4-ylmethyl)-3-(4-trifluoromethanesulfonylphenyl)imidazolidine-2,4-dione;
5-methyl-1-(2-methoxyquinolin-4-ylmethyl)-3-(4-trifluoromethanesulfonylphenyl)imidazolidine-2,4-dione;
5-methyl-1-(2-chloroquinoline-4-ylmethyl)-3-(4-trifluoromethanesulfonylphenyl)imidazolidine-2,4-dione;
5-methyl-1-(2-fluoroquinoline-4-ylmethyl)-3-(4-trifluoromethanesulfonylphenyl)imidazolidine-2,4-dione;
5-methyl-1-(2-aminoquinoline-4-ylmethyl)-3-(4-trifluoromethanesulfonylphenyl)imidazolidine-2,4-dione;
5-methyl-1-(2-methylaminoquinolin-4-ylmethyl)-3-(4-trifluoromethanesulfonylphenyl)imidazolidine-2,4-dione;
5-methyl-1-(2-dimethylaminoquinolin-4-ylmethyl)-3-(4-trifluoromethanesulfonylphenyl)imidazolidine-2,4-dione;
5-methyl-1-(2-piperidinoquinolin-4-ylmethyl)-3-(4-trifluoromethanesulfonylphenyl)imidazolidine-2,4-dione;
5-methyl-1-(3-methylquinolin-4-ylmethyl)-3-(4-trifluoromethanesulfonylphenyl)imidazolidine-2,4-dione;
5-methyl-1-(3-methoxyquinolin-4-ylmethyl)-3-(4-trifluoromethanesulfonylphenyl)imidazolidine-2,4-dione;
5-methyl-1-(3-chloroquinoline-4-ylmethyl)-3-(4-trifluoromethanesulfonylphenyl)imidazolidine-2,4-dione;
5-methyl-1-(3-fluoroquinoline-4-ylmethyl)-3-(4-trifluoromethanesulfonylphenyl)imidazolidine-2,4-dione;
5-methyl-1-(3-aminoquinoline-4-ylmethyl)-3-(4-trifluoromethanesulfonylphenyl)imidazolidine-2,4-dione;
5-methyl-1-(3-methylaminoquinolin-4-ylmethyl)-3-(4-trifluoromethanesulfonylphenyl)imidazolidine-2,4-dione;
5-methyl-1-(3-dimethylaminoquinolin-4-ylmethyl)-3-(4-trifluoromethanesulfonylphenyl)imidazolidine-2,4-dione;
5-methyl-1-(3-piperidinoquinolin-4-ylmethyl)-3-(4-trifluoromethanesulfonylphenyl)imidazolidine-2,4-dione;
5-methyl-1-(5-methylquinolin-4-ylmethyl)-3-(4-trifluoromethanesulfonylphenyl)imidazolidine-2,4-dione;
5-methyl-1-(5-methoxyquinolin-4-ylmethyl)-3-(4-trifluoromethanesulfonylphenyl)imidazolidine-2,4-dione;
5-methyl-1-(5-chloroquinoline-4-ylmethyl)-3-(4-trifluoromethanesulfonylphenyl)imidazolidine-2,4-dione;
5-methyl-1-(5-fluoroquinoline-4-ylmethyl)-3-(4-trifluoromethanesulfonylphenyl)imidazolidine-2,4-dione;
5-methyl-1-(5-aminoquinoline-4-ylmethyl)-3-(4-trifluoromethanesulfonylphenyl)imidazolidine-2,4-dione;
5-methyl-1-(5-methylaminoquinolin-4-ylmethyl)-3-(4-trifluoromethanesulfonylphenyl)imidazolidine-2,4-dione;
5-methyl-1-(5-piperidinoquinolin-4-ylmethyl)-3-(4-trifluoromethanesulfonylphenyl)imidazolidine-2,4-dione;
5-methyl-1-(6-methylquinolin-4-ylmethyl)-3-(4-trifluoromethanesulfonylphenyl)imidazolidine-2,4-dione;
5-methyl-1-(6-methoxyquinolin-4-ylmethyl)-3-(4-trifluoromethanesulfonylphenyl)imidazolidine-2,4-dione;
5-methyl-1-(6-chloroquinoline-4-ylmethyl)-3-(4-trifluoromethanesulfonylphenyl)imidazolidine-2,4-dione;
5-methyl-1-(6-fluoroquinoline-4-ylmethyl)-3-(4-trifluoromethanesulfonylphenyl)imidazolidine-2,4-dione;
5-methyl-1-(6-aminoquinoline-4-ylmethyl)-3-(4-trifluoromethanesulfonylphenyl)imidazolidine-2,4-dione;
5-methyl-1-(6-methylaminoquinolin-4-ylmethyl)-3-(4-trifluoromethanesulfonylphenyl)imidazolidine-2,4-dione;
5-methyl-1-(6-dimethylaminoquinolin-4-ylmethyl)-3-(4-trifluoromethanesulfonylphenyl)imidazolidine-2,4-dione;
5-methyl-1-(6-piperidinoquinolin-4-ylmethyl)-3-(4-trifluoromethanesulfonylphenyl)imidazolidine-2,4-dione;
5-methyl-1-(7-methylquinolin-4-ylmethyl)-3-(4-trifluoromethanesulfonylphenyl)imidazolidine-2,4-dione;
5-methyl-1-(7-methoxyquinolin-4-ylmethyl)-3-(4-trifluoromethanesulfonylphenyl)imidazolidine-2,4-dione;
5-methyl-1-(7-chloroquinoline-4-ylmethyl)-3-(4-trifluoromethanesulfonylphenyl)imidazolidine-2,4-dione;
5-methyl-1-(7-fluoroquinoline-4-ylmethyl)-3-(4-trifluoromethanesulfonylphenyl)imidazolidine-2,4-dione;
5-methyl-1-(7-aminoquinoline-4-ylmethyl)-3-(4-trifluoromethanesulfonylphenyl)imidazolidine-2,4-dione;
5-methyl-1-(7-methylaminoquinolin-4-ylmethyl)-3-(4-trifluoromethanesulfonylphenyl)imidazolidine-2,4-dione;
5-methyl-1-(7-dimethylaminoquinolin-4-ylmethyl)-3-(4-trifluoromethanesulfonylphenyl)imidazolidine-2,4-dione;
5-methyl-1-(7-piperidinoquinolin-4-ylmethyl)-3-(4-trifluoromethanesulfonylphenyl)imidazolidine-2,4-dione;
5-methyl-1-(8-methylquinolin-4-ylmethyl)-3-(4-trifluoromethanesulfonylphenyl)imidazolidine-2,4-dione;
5-methyl-1-(8-methoxyquinolin-4-ylmethyl)-3-(4-trifluoromethanesulfonylphenyl)imidazolidine-2,4-dione;
5-methyl-1-(8-chloroquinoline-4-ylmethyl)-3-(4-trifluoromethanesulfonylphenyl)imidazolidine-2,4-dione;
5-methyl-1-(8-fluoroquinoline-4-ylmethyl)-3-(4-trifluoromethanesulfonylphenyl)imidazolidine-2,4-dione;
5-methyl-1-(8-aminoquinoline-4-ylmethyl)-3-(4-trifluoromethanesulfonylphenyl)imidazolidine-2,4-dione;
5-methyl-1-(8-methylaminoquinolin-4-ylmethyl)-3-(4-trifluoromethanesulfonylphenyl)imidazolidine-2,4-dione;
5-methyl-1-(8-dimethylaminoquinolin-4-ylmethyl)-3-(4-trifluoromethanesulfonylphenyl)imidazolidine-2,4-dione;
5-methyl-1-(8-piperidinoquinolin-4-ylmethyl)-3-(4-trifluoromethanesulfonylphenyl)imidazolidine-2,4-dione;
1-(2-methylquinolin-4-ylmethyl)-3-(4-trifluoromethanesulfonylphenyl)imidazolidine-2,4-dione;
1-(2-methoxyquinolin-4-ylmethyl)-3-(4-trifluoromethanesulfonylphenyl)imidazolidine-2,4-dione;
1-(2-chloroquinoline-4-ylmethyl)-3-(4-trifluoromethanesulfonylphenyl)imidazolidine-2,4-dione;
1-(2-fluoroquinoline-4-ylmethyl)-3-(4-trifluoromethanesulfonylphenyl)imidazolidine-2,4-dione;
1-(2-aminoquinoline-4-ylmethyl)-3-(4-trifluoromethanesulfonylphenyl)imidazolidine-2,4-dione;
1-(2-methylaminoquinolin-4-ylmethyl)-3-(4-trifluoromethanesulfonylphenyl)imidazolidine-2,4-dione;
1-(2-dimethylaminoquinolin-4-ylmethyl)-3-(4-trifluoromethanesulfonylphenyl)imidazolidine-2,4-dione;

1-(2-piperidinoquinolin-4-ylmethyl)-3-(4-trifluoromethane-sulfonylphenyl)imidazolidine-2,4-dione;
1-(3-methylquinolin-4-ylmethyl)-3-(4-trifluoromethane-sulfonylphenyl)imidazolidine-2,4-dione;
1-(3-methoxyquinolin-4-ylmethyl)-3-(4-trifluoromethane-sulfonylphenyl)imidazolidine-2,4-dione;
1-(3-chloroquinoline-4-ylmethyl)-3-(4-trifluoromethane-sulfonylphenyl)imidazolidine-2,4-dione;
1-(3-fluoroquinoline-4-ylmethyl)-3-(4-trifluoromethane-sulfonylphenyl)imidazolidine-2,4-dione;
1-(3-aminoquinoline-4-ylmethyl)-3-(4-trifluoromethane-sulfonylphenyl)imidazolidine-2,4-dione;
1-(3-methylaminoquinolin-4-ylmethyl)-3-(4-trifluoromethanesulfonylphenyl)imidazolidine-2,4-dione;
1-(3-dimethylaminoquinolin-4-ylmethyl)-3-(4-trifluoromethanesulfonylphenyl)imidazolidine-2,4-dione;
1-(3-piperidinoquinolin-4-ylmethyl)-3-(4-trifluoromethane-sulfonylphenyl)imidazolidine-2,4-dione;
1-(5-methylquinolin-4-ylmethyl)-3-(4-trifluoromethane-sulfonylphenyl)imidazolidine-2,4-dione;
1-(5-methoxyquinolin-4-ylmethyl)-3-(4-trifluoromethane-sulfonylphenyl)imidazolidine-2,4-dione;
1-(5-chloroquinoline-4-ylmethyl)-3-(4-trifluoromethane-sulfonylphenyl)imidazolidine-2,4-dione;
1-(5-fluoroquinoline-4-ylmethyl)-3-(4-trifluoromethane-sulfonylphenyl)imidazolidine-2,4-dione;
1-(5-aminoquinoline-4-ylmethyl)-3-(4-trifluoromethane-sulfonylphenyl)imidazolidine-2,4-dione;
1-(5-methylaminoquinolin-4-ylmethyl)-3-(4-trifluoromethanesulfonylphenyl)imidazolidine-2,4-dione;
1-(5-dimethylaminoquinolin-4-ylmethyl)-3-(4-trifluoromethanesulfonylphenyl)imidazolidine-2,4-dione;
1-(5-piperidinoquinolin-4-ylmethyl)-3-(4-trifluoromethane-sulfonylphenyl)imidazolidine-2,4-dione;
1-(6-methylquinolin-4-ylmethyl)-3-(4-trifluoromethane-sulfonylphenyl)imidazolidine-2,4-dione;
1-(6-methoxyquinolin-4-ylmethyl)-3-(4-trifluoromethane-sulfonylphenyl)imidazolidine-2,4-dione;
1-(6-chloroquinoline-4-ylmethyl)-3-(4-trifluoromethane-sulfonylphenyl)imidazolidine-2,4-dione;
1-(6-fluoroquinoline-4-ylmethyl)-3-(4-trifluoromethane-sulfonylphenyl)imidazolidine-2,4-dione;
1-(6-aminoquinoline-4-ylmethyl)-3-(4-trifluoromethane-sulfonylphenyl)imidazolidine-2,4-dione;
1-(6-methylaminoquinolin-4-ylmethyl)-3-(4-trifluoromethanesulfonylphenyl)imidazolidine-2,4-dione;
1-(6-dimethylaminoquinolin-4-ylmethyl)-3-(4-trifluoromethanesulfonylphenyl)imidazolidine-2,4-dione;
1-(6-piperidinoquinolin-4-ylmethyl)-3-(4-trifluoromethane-sulfonylphenyl)imidazolidine-2,4-dione;
1-(7-methylquinolin-4-ylmethyl)-3-(4-trifluoromethane-sulfonylphenyl)imidazolidine-2,4-dione;
1-(7-methoxyquinolin-4-ylmethyl)-3-(4-trifluoromethane-sulfonylphenyl)imidazolidine-2,4-dione;
1-(7-chloroquinoline-4-ylmethyl)-3-(4-trifluoromethane-sulfonylphenyl)imidazolidine-2,4-dione;
1-(7-fluoroquinoline-4-ylmethyl)-3-(4-trifluoromethane-sulfonylphenyl)imidazolidine-2,4-dione;
1-(7-aminoquinoline-4-ylmethyl)-3-(4-trifluoromethane-sulfonylphenyl)imidazolidine-2,4-dione;
1-(7-methylaminoquinolin-4-ylmethyl)-3-(4-trifluoromethanesulfonylphenyl)imidazolidine-2,4-dione;
1-(7-dimethylaminoquinolin-4-ylmethyl)-3-(4-trifluoromethanesulfonylphenyl)imidazolidine-2,4-dione;
1-(7-piperidinoquinolin-4-ylmethyl)-3-(4-trifluoromethane-sulfonylphenyl)imidazolidine-2,4-dione;
1-(8-methylquinolin-4-ylmethyl)-3-(4-trifluoromethane-sulfonylphenyl)imidazolidine-2,4-dione;
1-(8-methoxyquinolin-4-ylmethyl)-3-(4-trifluoromethane-sulfonylphenyl)imidazolidine-2,4-dione;
1-(8-chloroquinoline-4-ylmethyl)-3-(4-trifluoromethane-sulfonylphenyl)imidazolidine-2,4-dione;
1-(8-fluoroquinoline-4-ylmethyl)-3-(4-trifluoromethane-sulfonylphenyl)imidazolidine-2,4-dione;
1-(8-aminoquinoline-4-ylmethyl)-3-(4-trifluoromethane-sulfonylphenyl)imidazolidine-2,4-dione;
1-(8-methylaminoquinolin-4-ylmethyl)-3-(4-trifluoromethanesulfonylphenyl)imidazolidine-2,4-dione;
1-(8-dimethylaminoquinolin-4-ylmethyl)-3-(4-trifluoromethanesulfonylphenyl)imidazolidine-2,4-dione;
1-(8-piperidinoquinolin-4-ylmethyl)-3-(4-trifluoromethane-sulfonylphenyl)imidazolidine-2,4-dione

TABLE 1

(Ex. 264 to 332)

| Examples | Structure |
|---|---|
| 264 | 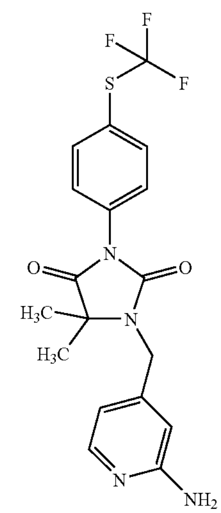 |
| 265 | 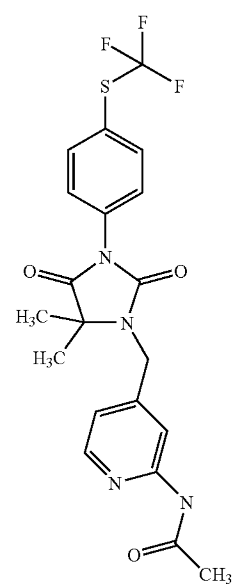 |

TABLE 1-continued
(Ex. 264 to 332)
| Examples | Structure |
|---|---|
| 266 | 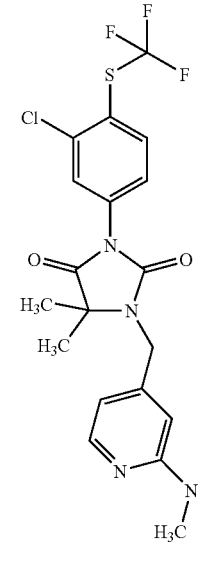 |
| 267 | 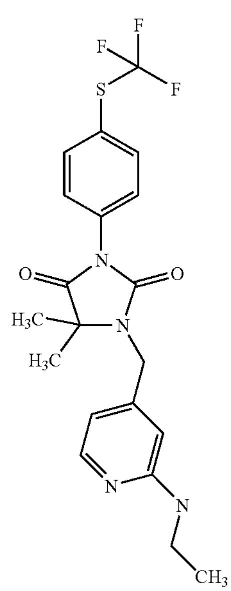 |
| 268 | 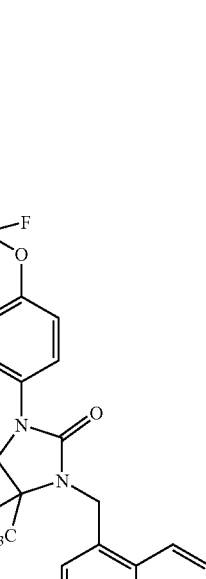 |
| 269 | 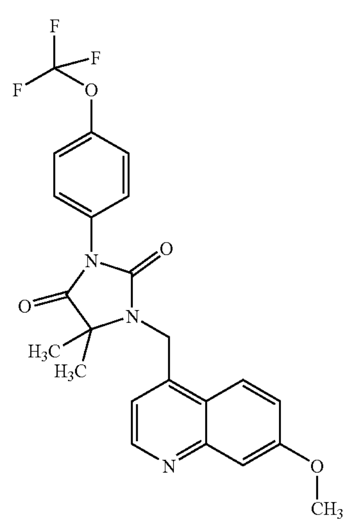 |

TABLE 1-continued
(Ex. 264 to 332)
| Examples | Structure |
|---|---|
| 270 | 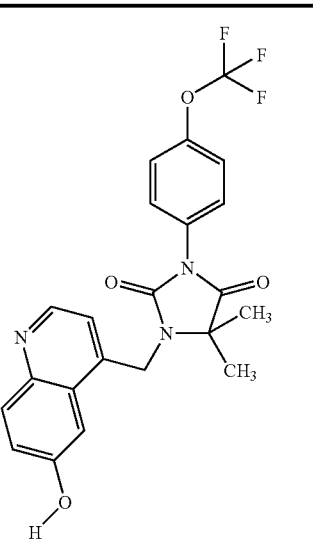 |
| 271 | 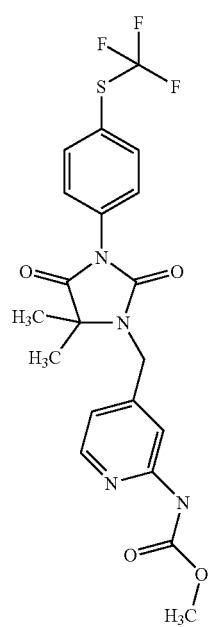 |
| 272 | 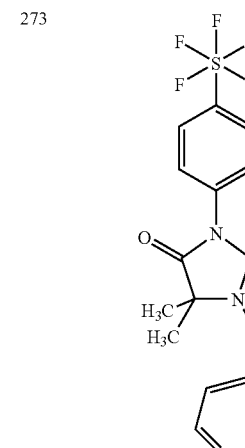 |
| 273 | 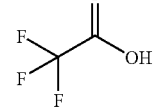 |

TABLE 1-continued (Ex. 264 to 332)

| Examples | Structure |
|---|---|
| 274 | (structure with 4-trifluoromethoxyphenyl, dimethylhydantoin, and 6-methoxyquinolin-4-ylmethyl groups) |
| 275 | (structure with 4-(trifluoromethylthio)phenyl, dimethylhydantoin, and 2-(phenylamino)pyridin-4-ylmethyl groups) |
| 276 | (structure with 4-(pentafluorosulfanyl)phenyl, dimethylhydantoin, and pyridin-4-ylmethyl groups; trifluoroacetic acid salt) |
| 277 | (structure with 3-bromo-4-trifluoromethoxyphenyl, dimethylhydantoin, and quinolin-4-ylmethyl groups) |
| 278 | (structure with 3-chloro-4-trifluoromethoxyphenyl, dimethylhydantoin, and quinolin-4-ylmethyl groups) |

TABLE 1-continued (Ex. 264 to 332)

| Examples | Structure |
|---|---|
| 279 | 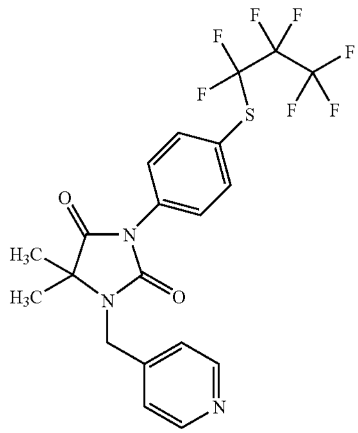 |
| 280 | 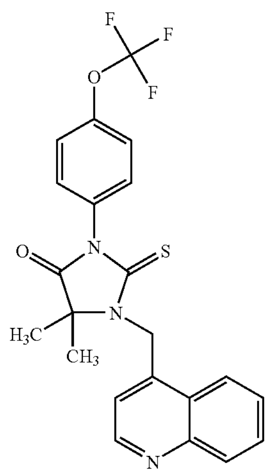 |
| 281 | 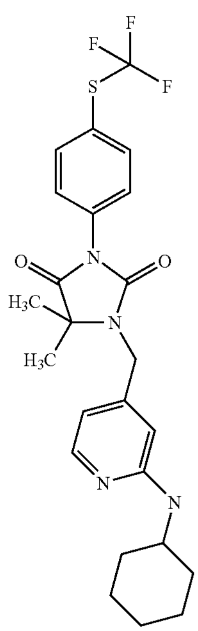 |
| 282 | 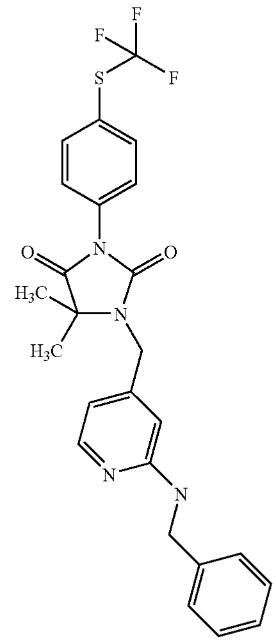 |
| 283 | 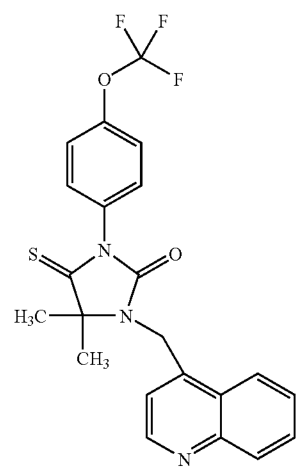 |
| 284 | 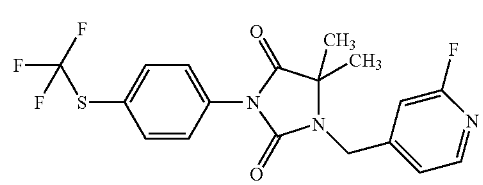 |

TABLE 1-continued
(Ex. 264 to 332)
| Examples | Structure |
|---|---|
| 285 | 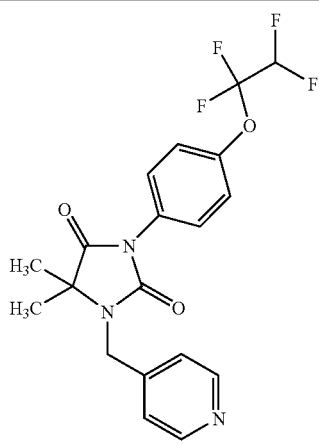 |
| 286 | 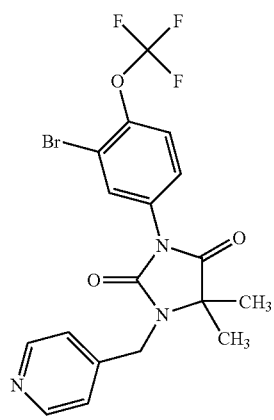 |
| 287 | 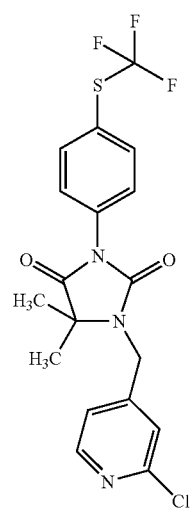 |
| 288 | 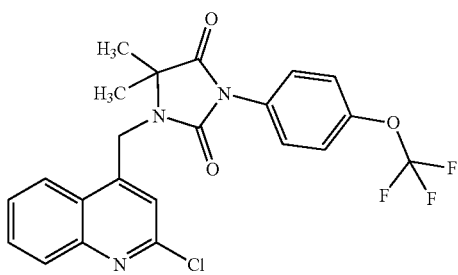 |
| 289 | 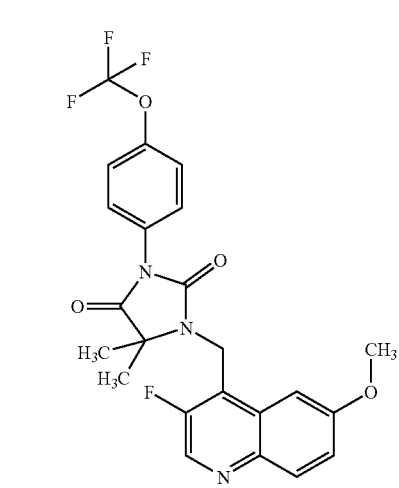 |
| 290 | 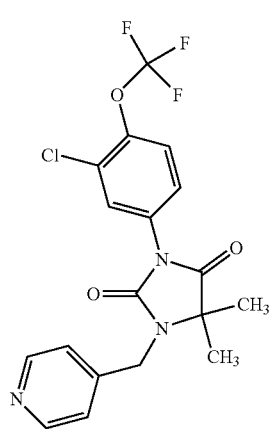 |

TABLE 1-continued (Ex. 264 to 332)

| Examples | Structure |
|---|---|
| 291 | *[Chemical structure: 3-(4-trifluoromethoxyphenyl)-5,5-dimethyl-1-((2-ethylpyridin-4-yl)methyl)imidazolidine-2,4-dione]* |
| 292 | *[Chemical structure: 3-(4-trifluoromethylthiophenyl)-5,5-dimethyl-1-((2-piperidin-1-ylpyridin-4-yl)methyl)imidazolidine-2,4-dione]* |
| 293 | *[Chemical structure: 3-(2-chloro-4-trifluoromethoxyphenyl)-5,5-dimethyl-1-(pyridin-3-ylmethyl)imidazolidine-2,4-dione]* |
| 294 | *[Chemical structure: 3-(4-trifluoromethoxyphenyl)-5,5-dimethyl-1-((2-ethoxypyridin-4-yl)methyl)imidazolidine-2,4-dione]* |
| 295 | *[Chemical structure: 3-(3-chloro-4-trifluoromethylthiophenyl)-5,5-dimethyl-1-(pyridin-4-ylmethyl)imidazolidine-2,4-dione]* |
| 296 | *[Chemical structure: 3-(3-chloro-4-trifluoromethylthiophenyl)-5,5-dimethyl-1-((2-aminopyridin-4-yl)methyl)imidazolidine-2,4-dione]* |

TABLE 1-continued (Ex. 264 to 332)

| Examples | Structure |
|---|---|
| 297 | 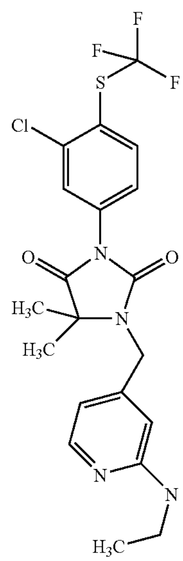 |
| 298 | 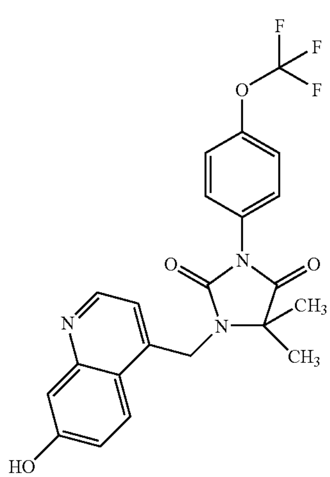 |
| 299 | 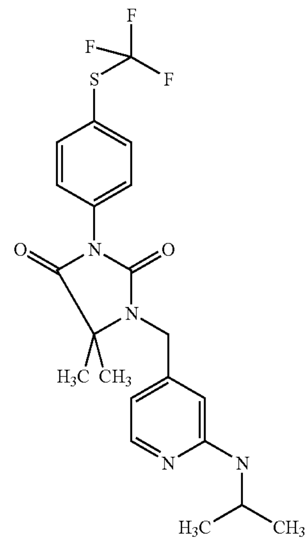 |
| 300 | 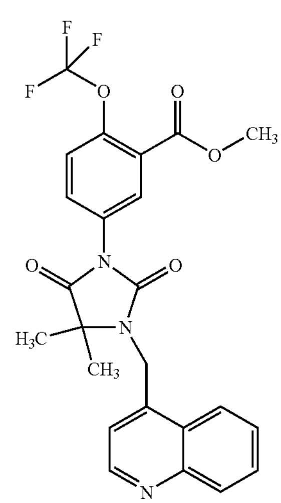 |

TABLE 1-continued (Ex. 264 to 332)

| Examples | Structure |
|---|---|
| 301 | (structure) |
| 302 | (structure) |
| 303 | (structure) |
| 304 | (structure) |

TABLE 1-continued
(Ex. 264 to 332)
| Examples | Structure |
|---|---|
| 305 | 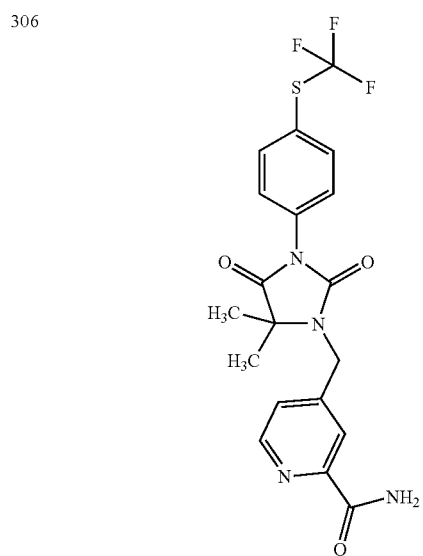 |
| 306 | 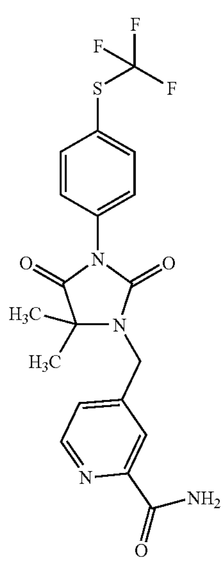 |
| 307 | 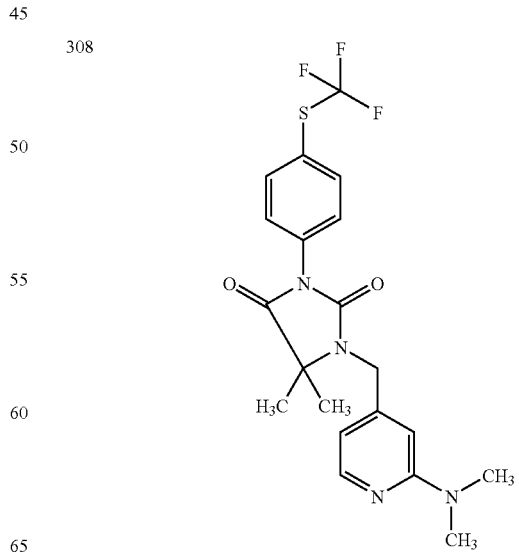 |
| 308 | |

TABLE 1-continued
(Ex. 264 to 332)
| Examples | Structure |
|---|---|
| 309 | 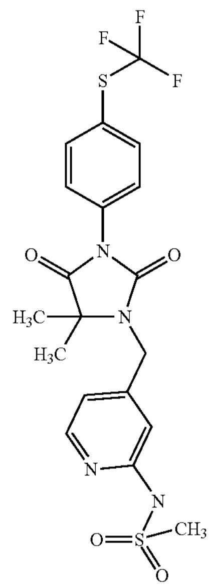 |
| 310 | 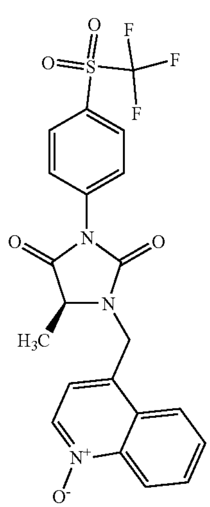 |
| 311 | 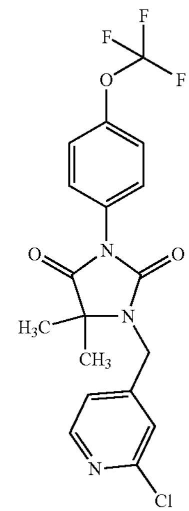 |
| 312 | 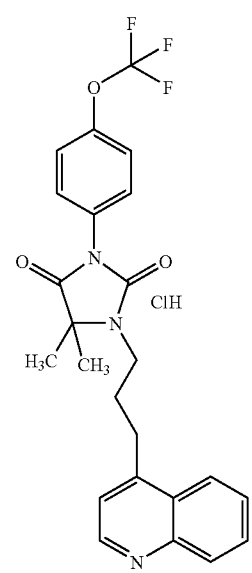 |
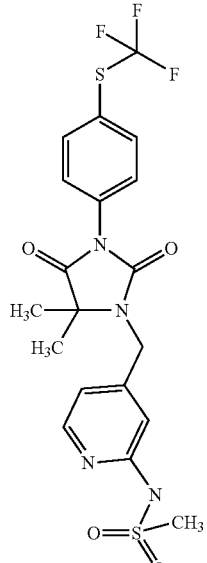

331
TABLE 1-continued
(Ex. 264 to 332)
| Examples | Structure |
|---|---|
| 313 | 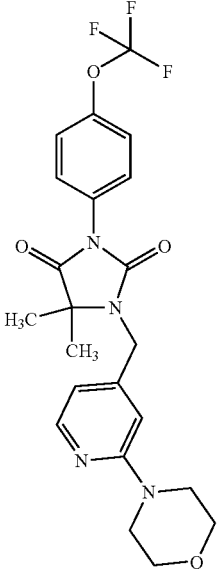 |
| 314 | 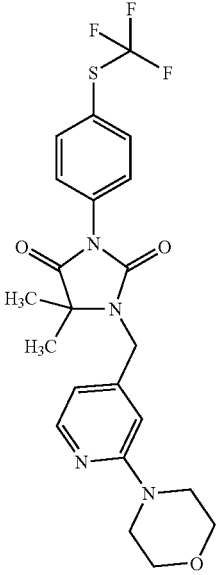 |
332
TABLE 1-continued
(Ex. 264 to 332)
| Examples | Structure |
|---|---|
| 315 | 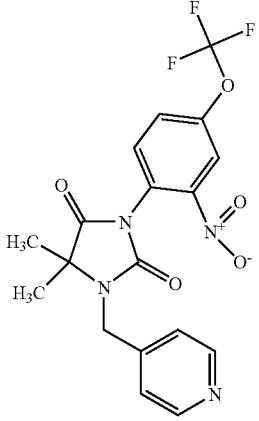 |
| 316 | 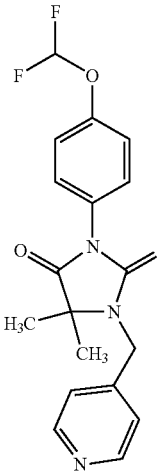 |
| 317 | 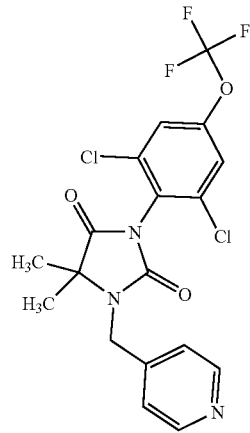 |

TABLE 1-continued (Ex. 264 to 332)

| Examples | Structure |
|---|---|
| 318 | 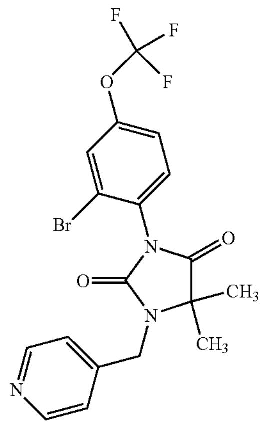 |
| 319 | 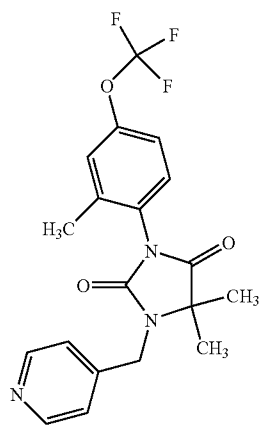 |
| 320 | 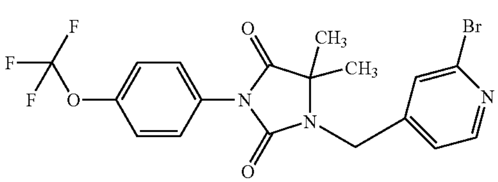 |
| 321 | |
| 322 | |
| 323 | |

TABLE 1-continued
(Ex. 264 to 332)
| Examples | Structure |
|---|---|
| 324 | 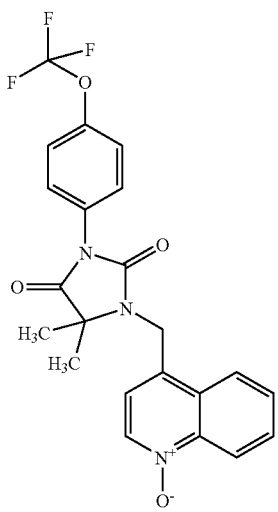 |
| 325 | 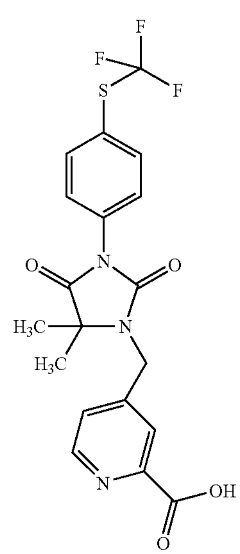 |
| 326 | 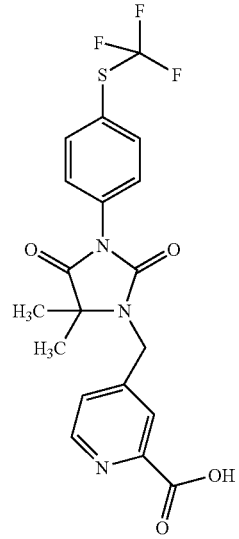 |
| 327 | 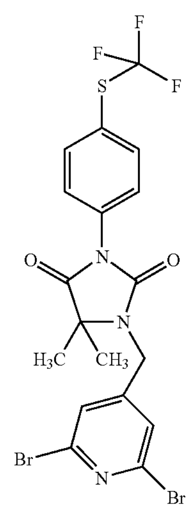 |
| 328 | 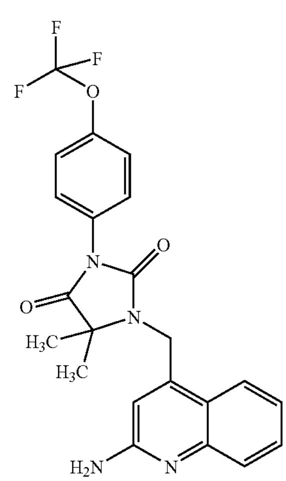 |

TABLE 1-continued (Ex. 264 to 332)

| Examples | Structure |
|---|---|
| 329 | 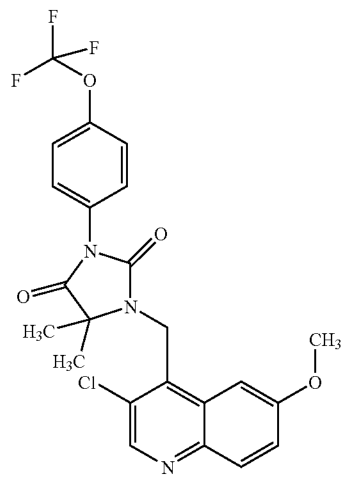 |
| 330 | 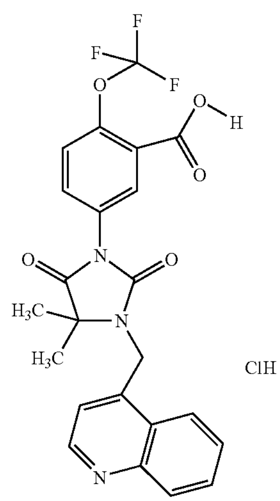 |
| 331 | 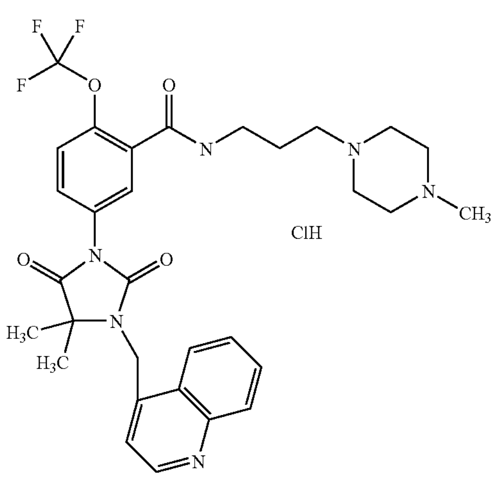 |
| 332 | 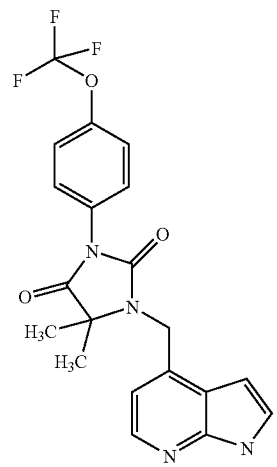 |

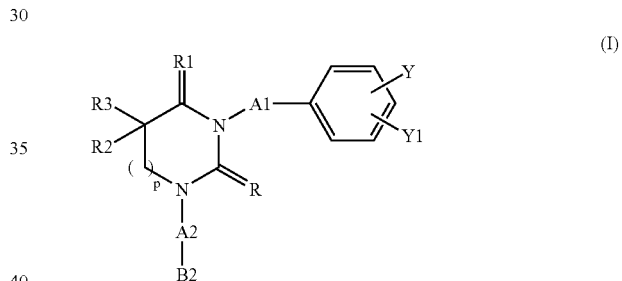

The invention claimed is:
1. The compound of formula I:

(I)

wherein
p is 0,
R and R1, which may be identical or different, are O or NH,
R2 and R3, which may be identical or different, are hydrogen, alkyl, alkenyl, alkynyl, cycloalkyl, hydroxyphenylalkyl, thienylbenzothienylalkyl, phenylalkyl, pyridylalkyl, benzothienylalkyl, aryl or heteroaryl, the phenylalkyl, pyridylalkyl, and benzothienylalkyl being optionally substituted with one or more radicals chosen from halogen, hydroxyl, alkyl and alkoxy containing from one to four carbon atoms,
A1 is single bond, alkyl, alkenyl or alkynyl,
Y and Y1, which may be identical or different, are such that one of Y and Y1 is —OCF$_3$, —O—CF$_2$—CHF$_2$, —O—CHF$_2$, —O—CH$_2$—CF$_3$, —SO$_2$NR5R6, —SF$_5$ or —S(O)$_n$-alkyl and the other of Y and Y1 is —OCF$_3$, —O—CF$_2$—CHF$_2$, —O—CHF$_2$, —O—CH$_2$—CF$_3$, SO$_2$NR5R6, —SF$_5$, —S(O)$_n$-alkyl, hydrogen, halogen, hydroxyl, alkoxy, nitro, —CN, —NR5R6, alkyl, aryl, heteroaryl, —CF$_3$, —O-alkenyl, —O-alkynyl, —O-cycloalkyl, —S(O)$_n$-alkenyl, —S(O)$_n$-alkynyl, —S(O)$_n$-cycloalkyl, —CONR5R6, or free, salified or esterified carboxyl, or the

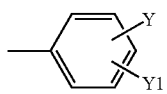

is

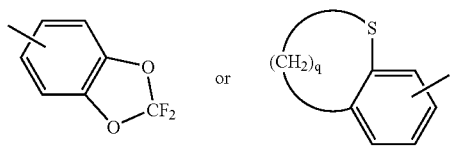

that is optionally substituted with one or more alkyl that are optionally substituted, q is 2, 3 or 4, R5 and R6, which may be identical or different, are hydrogen, alkyl, alkenyl, alkynyl, cycloalkyl, cycloalkenyl, heterocyclyl, aryl or heteroaryl, or R5 and R6 taken together with the nitrogen atom to which they are attached form a 3- to 10-membered heterocyclyl containing one or more hetero atoms chosen from O, S, N and NR7, A2, which may be identical to or different from A1, is defined as A1 or is CO or $SO_2$, B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2, R7 is hydrogen, alkyl, cycloalkyl, phenyl, acyl, —$S(O)_2$Alk, —$S(O)_2$Aryl, —$S(O)_2$heteroaryl or —$S(O)_2$NR5R6, Y2 is hydrogen, halogen, hydroxyl, cyano, alkyl, alkoxy, cycloalkyl, heterocyclyl, aryl, phenyl optionally substituted with —NR5R6, heteroaryl, —O-alkenyl, —O-alkynyl, —O-cycloalkyl, —$S(O)_n$-alkyl, —$S(O)_n$-alkenyl, —$S(O)_n$-alkynyl, —$S(O)_n$-cycloalkyl, —COOR13, —COOR9, —OCOR13, —OCOR8, NR5R6, CONR5R6, —$S(O)_n$—NR5R6, —NR10-CO—R13, —NHCOR8, —NHS$(O)_n$R8, —NH—S$(O)_n$ $CF_3$, —NR10-$SO_2$—R13, NH—$SO_2$—NR5R6, —NR10-CO—NR5R6, —NR10-CS—NR5R6 or —NR10-COOR13, all of which are optionally substituted, all the alkyl, alkenyl, alkynyl and alkoxy above are linear or branched and contain not more than 6 carbon atoms, all the cycloalkyl and heterocyclyl above contain not more than 7 carbon atoms, all the aryl and heteroaryl above contain not more than 10 carbon atoms, all the carbocyclyl, alkyl, alkenyl, alkynyl, alkoxy, cycloalkyl, heterocyclyl, aryl and heteroaryl above, and also the ring formed by R5 and R6 with the nitrogen atom to which they are attached, are optionally substituted with one or more substituents, which may be identical or different, selected from the group consisting of halogen, cyano, hydroxyl, alkoxy, —$CF_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S$(O)_n$—R8, —$S(O)_n$—R8, —N(R10)-S$(O)_n$—NR11R12 and —$S(O)_n$—NR11R12, all the aryl and heteroaryl above are optionally substituted with one or more substituents selected from the group consisting of alkyl, alkoxy and alkylenedioxy, all the cyclic radicals above, and also the ring formed by R5 and R6 with the nitrogen atom to which they are attached, are optionally substituted with one or more substituents selected from the group consisting of oxo and thioxo, n is 0 to 2, R8 is alkyl, alkenyl, cycloalkyl, cycloalkylalkyl, heterocyclyl, heterocyclylalkyl, aryl, arylalkyl, heteroaryl or heteroarylalkyl, R9 is defined as R8 or is hydrogen, R10 is hydrogen or alkyl, R11 and R12, which may be identical or different, are hydrogen, $C_3$-$C_6$ cycloalkyl, cycloalkylalkyl, $C_1$-$C_4$ alkyl, phenyl, or phenylalkyl, optionally substituted with one or more substituents, which may be identical or different, selected from the group consisting of $C_1$-$C_4$ alkyl, halogen, cyano, hydroxyl, alkoxy, —$CF_3$, nitro, phenyl, and free, salified, esterified or amidated carboxyl, or R11 and R12 taken together with the nitrogen atom to which they are attached form a 5- to 7-membered cyclic radical containing one or more hetero atoms chosen from O, S, N and NR7, and R13, which may be identical to or different from R5 or R6, is defined as R5 or R6, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —$OCF_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —$S(O)_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —$SO_2$Alk or $SO_2NH_2$ and the other is NR5R6, A2 is single bond or alkylene and B2 is optionally substituted 5- to 10-membered heterocyclyl, then R2 and R3 are not both hydrogen.

2. The compound according to claim 1 wherein p is 0,

R and R1, which may be identical or different, are O or NH,

R2 and R3, which may be identical or different, are hydrogen, alkyl, alkenyl, alkynyl, cycloalkyl, aryl or heteroaryl, A1 is single bond, alkyl, allyl or propynyl, Y and Y1, which may be identical or different, are such that one of Y and Y1 is selected from the group consisting of —$OCF_3$, —$S(O)_nCF_3$, —$S(O)_n$-alk, —$SO_2CHF_2$, —$SO_2CF_2CF_3$ and —$SO_2NR5R6$ and the other of Y and Y1 is selected from the group consisting of —OCF$_3$, —S(O)$_n$CF$_3$, —S(O)$_n$-alk, —SO$_2$CHF$_2$, —SO$_2$CF$_2$CF$_3$, —SO$_2$NR5R6, hydrogen, halogen, hydroxyl, alkoxy, —NR5R6, alkyl, aryl, heteroaryl, —CF$_3$, —O-allyl, —O-propynyl, —O-cycloalkyl, —S(O)$_n$-allyl, —S(O)$_n$-propynyl, —S(O)$_n$-cycloalkyl, —CONR5R6 and free, salified or esterified carboxyl, wherein R5 and R6, which may be identical or different, are selected from the group consisting of hydrogen, alkyl, alkenyl, cycloalkyl, cycloalkenyl, heterocyclyl, aryl and heteroaryl, or R5 and R6 taken together with the nitrogen atom to which they are attached form a 3- to 10-membered heterocyclyl containing one or more hetero atoms chosen from O, S, N and NR7, A2, which may be identical to or different from A1, is defined as A1 or CO or SO$_2$, B2 is a saturated or unsaturated heterocyclyl containing 1 or more identical or different hetero atoms chosen from O, S, N and NR7, optionally substituted with one or more identical or different substituents defined as Y2, R7 is hydrogen, alkyl, cycloalkyl, phenyl, acyl, —S(O)$_2$Alk, —S(O)$_2$Aryl, S(O)$_2$heteroaryl or —S(O)$_2$NR5R6 radical, Y2 is hydrogen, halogen, hydroxyl, alkyl, alkoxy, cycloalkyl, heterocyclyl, aryl, heteroaryl, —O-allyl, —O-propynyl, —O-cycloalkyl, —S(O)$_n$-alkyl, —S(O)$_n$-allyl, —S(O)$_n$-propynyl, —S(O)$_n$-cycloalkyl, —COOR9, —OCOR8, —NR5R6, —CONR5R6, —S(O)$_n$—R5R6, —NHCOR8, —NH—S(O)$_n$R8, —NH—S(O)$_n$CF$_3$ or —NH—SO$_2$—NR5R6, all these radicals being optionally substituted, all the carbocyclyl, alkyl, alkenyl, alkynyl, alkoxy, cycloalkyl, heterocyclyl, aryl and heteroaryl above are optionally substituted with one or more substituents, which may be identical or different, selected from the group consisting of halogen, cyano, hydroxyl, alkoxy, —CF$_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, N(R10)-C(=O)—NR11R12, —N(R10)-S(O)$_n$—R8, —S(O)$_n$—R8, —N(R10)-S(O)$_n$—NR11R12 and —S(O)$_n$—NR11R12, and all the aryl and heteroaryl above are optionally substituted with one or more substituents selected from the group consisting of alkyl and alkylenedioxy radicals, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —SO$_2$Alk or SO$_2$NH$_2$ and the other is NR5R6, A2 is single bond or alkylene and B2 is optionally substituted 5- to 10-membered heterocyclyl, then R2 and R3 are not both hydrogen.

3. The compound according to claim 1 wherein p is 0,

R and R1, which may be identical or different, are O or NH,

R2 and R3, which may be identical or different, are hydrogen, alkyl, alkenyl, cycloalkyl, phenyl or heteroaryl, A1 is single bond, alkyl, allyl or propynyl, Y and Y1, which may be identical or different, are such that one of Y and Y1 is selected from the group consisting of —OCF$_3$, —S(O)$_n$CF$_3$, S(O)$_n$-alk, —SO$_2$CHF$_2$, —SO$_2$CF$_2$CF$_3$ and —SO$_2$NR5R6 and the other from Y and Y1 is selected from the group consisting of —OCF$_3$, —S(O)$_n$CF$_3$, S(O)$_n$-alk, —SO$_2$CHF$_2$, —SO$_2$CF$_2$CF$_3$, —SO$_2$NR5R6, hydrogen, halogen, hydroxyl, alkoxy, NR5R6, alkyl, phenyl, optionally substituted pyrazolyl and optionally substituted pyridyl, R5 and R6, which may be identical or different, are hydrogen, alkyl, alkenyl, cycloalkyl, heterocyclyl, phenyl or heteroaryl, or R5 and R6 taken together with the nitrogen atom to which they are attached form a 3- to 10-membered heterocyclyl that contains one or more hetero atoms chosen from O, S, N and NR7, A2, which may be identical to or different from A1, is defined as A1 or is CO or SO$_2$, B2 is a saturated or unsaturated 3- to 10-membered heterocyclyl containing one or more hetero atoms, which may be identical or different, chosen from O, S, N and NR7, optionally substituted with one or more substituents, which may be identical or different substituents defined as Y2, R7 is hydrogen or an alkyl, cycloalkyl or phenyl radical, Y2 is hydrogen, halogen, hydroxyl, alkyl, alkoxy, cycloalkyl, heterocyclyl, phenyl, heteroaryl, —O-cycloalkyl, —S(O)$_n$-alk, —S(O)$_n$-cycloalkyl, —COOR9, —OCOR8, —NR5R6, —CONR5R6, S(O)$_n$—R5R6, —NHCOR8 or —NH—S(O)$_n$R8, all these radicals being optionally substituted, all the alkyl, alkenyl, alkynyl and alkoxy radicals above being linear or branched and contain not more than 6 carbon atoms, all the cycloalkyl and heterocyclyl radicals above containing not more than 7 carbon atoms, all the aryl and heteroaryl radicals above containing not more than 10 carbon atoms, all the carbocyclyl, alkyl, alkenyl, alkynyl, alkoxy, cycloalkyl, heterocyclyl, aryl and heteroaryl radicals above being optionally substituted with one or more radicals, which may be identical or different, chosen from halogen atoms and cyano, hydroxyl, alkoxy, —CF$_3$, nitro, phenyl, heteroaryl, —C(=O)—OR9, —C(=O)—R8, —NR11R12, —C(=O)—NR11R12, —N(R10)-C(=O)—R8, —N(R10)-C(=O)—OR9, N(R10)-C(=O)—NR11R12, —N(R10)-S(O)$_n$—R8, —S(O)$_n$—R8, —N(R10)-S(O)$_n$—NR11R12 and —S(O)$_n$—NR11R12, all the aryl and heteroaryl radicals above are optionally substituted with one or more radicals chosen from alkyl and alkylenedioxy, n is 0 to 2, R8 is alkyl, cycloalkyl, cycloalkylalkyl, heterocyclyl, heterocyclylalkyl, phenyl or phenylalkyl, R9 is defined as R8 or is hydrogen, R10 is hydrogen or alkyl, and R11 and R12, which may be identical or different, are hydrogen, $C_1$-$C_4$ alkyl or phenyl, which are optionally substituted with one or more radicals, which may be identical or different, chosen from halogen, hydroxyl, alkoxy, —$CF_3$, nitro, phenyl and free, salified, esterified or amidated carboxyl, or R11 and R12 taken together with the nitrogen atom to which they are attached form a 5- to 7-membered cyclic radical containing one or more hetero atoms chosen from O, S, N and NR7, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —$OCF_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —$S(O)_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —$SO_2$Alk or $SO_2NH_2$ and the other is NR5R6, A2 is single bond or alkylene and B2 is optionally substituted 5- to 10-membered heterocyclyl, then R2 and R3 are not both hydrogen.

4. The compound according to claim 1 wherein one of Y and Y1 is hydrogen and the other is chosen from —$OCF_3$, —$S(O)_nCF_3$, —$S(O)_n$-alk, —$SO_2CHF_2$, —$SO_2CF_2CF_3$ and —$SO_2NR5R6$, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —$OCF_3$ or —S-alk, A2 is single bond or alkyl and B2 is an optionally substituted heterocyclyl, then R2 and R3 are not one hydrogen and the other imidazolylalkyl;

or b) when p is 0, R and R1 are oxygen, A1 is a single bond or alkyl, Y and Y1, which may be identical or different, are at least one is —$S(O)_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl.

5. The compound according to claim 1 wherein one of Y and Y1 is hydrogen and the other is chosen from —$S(O)_nCF_3$, —SO-Alk, —$S(O)_2$Alk, —$SO_2CHF_2$, —$SO_2CF_2CF_3$ and —$SO_2NR5R6$, or a racemic, enantiomeric or diastereoisomeric isomer form of the compound of formula I, or an addition salt with a mineral or organic acid or with a mineral or organic base thereof, with the proviso:

when p is 0, R and R1 are oxygen, A1 is a single bond or alkyl, Y and Y1, which may be identical or different, are at least one is —SO-Alk or —$S(O)_2$Alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl.

6. The compound according to claim 1 wherein one of Y and Y1 is hydrogen and the other is chosen from —$S(O)_nCF_3$, —$SO_2CHF_2$, —$SO_2CF_2CF_3$ and —$SO_2NR5R6$, or a racemic, enantiomeric or diastereoisomeric isomer form of the compound of formula I, or an addition salt with a mineral or organic acid or with a mineral or organic base thereof.

7. The compound according to claim 1 wherein one of Y and Y1 is hydrogen and the other is chosen from —$S(O)_nCF_3$, —$SO_2CHF_2$ and —$SO_2CF_2CF_3$, or a racemic, enantiomeric or diastereoisomeric isomer form of the compound of formula I, or an addition salt with a mineral or organic acid or with a mineral or organic base thereof.

8. A compound of formula I wherein

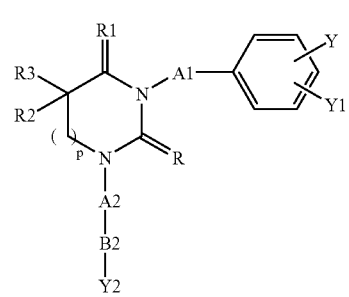

(I)

p is 0,

R and R1, which may be identical or different, are O or NH,

R2 and R3, which may be identical or different, are hydrogen, alkyl, alkenyl, alkynyl, cycloalkyl, hydroxyphenylalkyl, thienylbenzothienylalkyl, phenylalkyl, pyridylalkyl, benzothienylalkyl, aryl or heteroaryl, the phenylalkyl, pyridylalkyl, and benzothienylalkyl being optionally substituted with one or more radicals chosen from halogen, hydroxyl, alkyl and alkoxy containing from one to four carbon atoms, A1 is single bond, alkyl, alkenyl or alkynyl, Y and Y1, which may be identical or different, are such that one of Y and Y1 is —$OCF_3$, —O—$CF_2$—$CHF_2$, —O—$CHF_2$, —O—$CH_2$—$CF_3$, —$SO_2NR5R6$, —$SF_5$ or —$S(O)_n$-alkyl and the other of Y and Y1 is —$OCF_3$, —O—$CF_2$—$CHF_2$, —O—$CHF_2$, —O—$CH_2$—$CF_3$, $SO_2NR5R6$, —$SF_5$, —$S(O)_n$-alkyl, hydrogen, halogen, hydroxyl, alkoxy, nitro, —CN, —NR5R6, alkyl, aryl, heteroaryl, —$CF_3$, —O-alkenyl, —O-alkynyl, —O-cycloalkyl, —$S(O)_n$-alkenyl, —$S(O)_n$-alkynyl, —$S(O)_n$-cycloalkyl, —$CONR5R6$, or free, salified or esterified carboxyl, or the

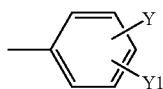

is

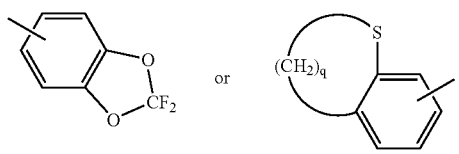

that is optionally substituted with one or more alkyl that are optionally substituted, q is 2, 3 or 4, R5 and R6, which may be identical or different, are hydrogen, alkyl, alkenyl, alkynyl, cycloalkyl, cycloalkenyl, heterocyclyl, aryl or heteroaryl, or R5 and R6 taken together with the nitrogen atom to which they are attached form a 3- to 10-membered heterocyclyl containing one or more hetero atoms chosen from O, S, N and NR7, A2, which may be identical to or different from A1, is defined as A1 or is CO or $SO_2$, B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2, R7 is hydrogen, alkyl, cycloalkyl, phenyl, acyl, —$S(O)_2$Alk, —$S(O)_2$Aryl, —$S(O)_2$heteroaryl or —$S(O)_2$NR5R6, Y2 is hydrogen, halogen, hydroxyl, cyano, alkyl, alkoxy, cycloalkyl, heterocyclyl, aryl, phenyl optionally substituted with —NR5R6, heteroaryl, —O-alkenyl, —O-alkynyl, —O-cycloalkyl, —$S(O)_n$-alkyl, —$S(O)_n$-alkenyl, —$S(O)_n$-alkynyl, —$S(O)_n$-cycloalkyl, —COOR13, —COOR9, —OCOR13, —OCOR8, NR5R6, CONR5R6, —$S(O)_n$—NR5R6, —NR10-CO—R13, —NHCOR8, —$NHS(O)_n$R8, —NH—S$(O)_n$ $CF_3$, —NR10-$SO_2$—R13, NH—$SO_2$—NR5R6, —NR10-CO—NR5R6, —NR10-CS—NR5R6 or —NR10-COOR13, all of which are optionally substituted, all the alkyl, alkenyl, alkynyl and alkoxy above are linear or branched and contain not more than 6 carbon atoms, all the cycloalkyl and heterocyclyl above contain not more than 7 carbon atoms, all the aryl and heteroaryl above contain not more than 10 carbon atoms, all the alkyl, alkenyl, alkynyl, cycloalkyl, heterocyclyl, aryl or heteroaryl are optionally substituted with one or more radicals, which may be identical or different, chosen from halogen, cyano, hydroxyl, alkoxy, —$CF_3$, nitro, phenyl, carboxyl which is free, salified, esterified with an alkyl radical or amidated with —NR11aR12a, —C(=O)—R9a, —NR11 aR12a, —C(=O)—NR11aR12a, —N(R10a)-C(=O)—R9a, —N(R10a)-C(=O)—OR8a, —N(R10a)-C(=O)—NR11 aR12a, —N(R10a)-$S(O)_n$—R9a, —$S(O)_n$—R9a, —N(R10a)-$S(O)_n$—NR11aR12a or —$S(O)_n$—NR11 aR12a, all the aryl and heteroaryl above furthermore being optionally substituted with an ethylenedioxy, R8 is alkyl, alkenyl, cycloalkyl, cycloalkylalkyl, heterocyclyl, heterocyclylalkyl, aryl, arylalkyl, heteroaryl or heteroarylalkyl, R8a is hydrogen, alkyl, alkenyl, phenyl, phenylalkyl, heteroaryl or heteroarylalkyl, R9 is defined as R8 or is hydrogen, R9a is alkyl, cycloalkyl, cycloalkylalkyl, heterocyclyl, heterocyclylalkyl, phenyl, phenylalkyl, heteroaryl or heteroarylalkyl, R10 is hydrogen or alkyl, R10a is hydrogen or alkyl, R11a and R2a, which may be identical or different, are hydrogen, alkyl, cycloalkyl, cycloalkylalkyl, phenyl, or phenylalkyl, optionally substituted with one or more substituents, which may be identical or different, chosen from halogen, hydroxyl, $C_1$-$C_4$ alkyl and $C_1$-$C_4$ alkoxy, or R11a and R12a taken together with the nitrogen atom to which they are attached forma cyclic radical chosen from pyrrolidyl, piperidyl, piperazinyl, morpholinyl, indolinyl, tetrahydroquinolyl, thiazolidinyl and naphthyridyl, R13, which may be identical to or different from R5 or R6, is defined as R5 or R6, or a racemic, enantiomeric or diastereoisomeric isomer form of the compound of formula I, or an addition salt with a mineral or organic acid or with a mineral or organic base thereof;

with the proviso:

a) when p is 0, R and R1 are oxygen, A1 is single bond or alkyl, Y and Y1, which may be identical or different, are at least one is —$OCF_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —$S(O)_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —$SO_2$Alk or $SO_2NH_2$ and the other is NR5R6, A2 is single bond or alkylene and B2 is optionally substituted 5- to 10-membered heterocyclyl, then R2 and R3 are not both hydrogen.

9. The compound according to claim 1 wherein R1 is O.

10. The compound according to claim 1 wherein R is O.

11. The compound of formula I:

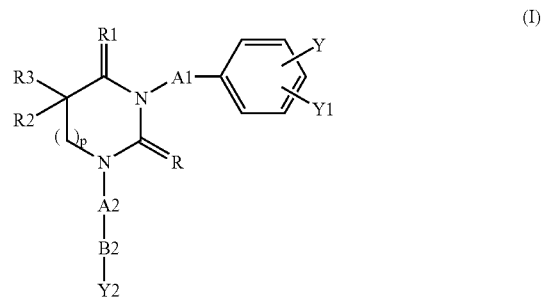

wherein
p is 0,
R and R1, which may be identical or different, are O or NH,
R2 and R3, which may be identical or different, are hydrogen, alkyl, alkenyl, cycloalkyl, cycloalkylalkyl, phenyl, phenylalkyl, heterocyclyl, heterocyclylalkyl, heteroaryl or heteroarylalkyl, which are optionally substituted,
all the above R2 and R3 radicals being optionally substituted with one or more radicals chosen from halogen, cyano, hydroxyl, alkyl and alkoxy containing 1 to 4 carbon atoms, —$CF_3$, nitro, phenyl, carboxyl which is free, salified, esterified with alkyl or amidated with —NR11bR12b, —C(=O)—R9b, —NR11bR12b and —C(=O)—NR11bR12b,
R7b is hydrogen, alkyl or phenyl,
R9b is hydrogen, alkyl, cycloalkyl, cycloalkylalkyl or phenyl,
R11b and R12b, which may be identical or different, are hydrogen, alkyl, cycloalkyl or phenyl, or R11b and R12b taken together with the nitrogen atom to which they are attached form an optionally substituted piperazinyl,
A1 is single bond, alkyl, alkenyl or alkynyl,
Y and Y1, which may be identical or different, are such that one of Y and Y1 is —$OCF_3$, —O—$CF_2$—$CHF_2$, —O—$CHF_2$, —O—$CH_2$—$CF_3$, —$SO_2NR5R6$, —$SF_5$ or —$S(O)_n$-alkyl and the other of Y and Y1 is —$OCF_3$, —O—$CF_2$—$CHF_2$, —O—$CHF_2$, —O—$CH_2$—$CF_3$, $SO_2NR5R6$, —$SF_5$, —$S(O)_n$-alkyl, hydrogen, halogen, hydroxyl, alkoxy, nitro, —CN, —NR5R6, alkyl, aryl, heteroaryl, —$CF_3$, —O-alkenyl, —O-alkynyl, —O-cycloalkyl, —$S(O)_n$-alkenyl, —$S(O)_n$-alkynyl, —$S(O)_n$-cycloalkyl, —CONR5R6, or free, salified or esterified carboxyl,
or the

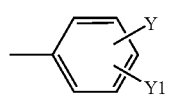

is

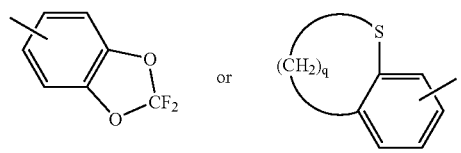

that is optionally substituted with one or more alkyl that are optionally substituted,
q is 2, 3 or 4,
R5 and R6, which may be identical or different, are hydrogen, alkyl, alkenyl, alkynyl, cycloalkyl, cycloalkenyl, heterocyclyl, aryl or heteroaryl, or R5 and R6 taken together with the nitrogen atom to which they are attached form a 3- to 10-membered heterocyclyl containing one or more hetero atoms chosen from O, S, N and NR7
A2, which may be identical to or different from A1, is defined as A1 or is CO or $SO_2$, B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2,
R7 is hydrogen, alkyl, cycloalkyl, phenyl, acyl, —$S(O)_2$Alk, —$S(O)_2$Aryl, —$S(O)_2$heteroaryl or —$S(O)_2$NR5R6,
Y2 is hydrogen, halogen, hydroxyl, cyano, alkyl, alkoxy, cycloalkyl, heterocyclyl, aryl, heteroaryl, —O-alkenyl, —O-alkynyl, —O-cycloalkyl, —$S(O)_n$-alkyl, —$S(O)_n$-alkenyl, —$S(O)_n$-alkynyl, —$S(O)_n$-cycloalkyl, —COOR13, —OCOR13, NR5R6, CONR5R6, —$S(O)_n$—NR5R6, —NR10-CO—R13, —NR10-$SO_2$—R13, NH—$SO_2$—NR5R6, —NR10-CO—NR5R6, —NR10-CS—NR5R6 or —NR10-COOR13, all of which are optionally substituted,
all the alkyl, alkenyl, alkynyl and alkoxy above are linear or branched and contain not more than 6 carbon atoms,
all the cycloalkyl and heterocyclyl above contain not more than 7 carbon atoms,
all the aryl and heteroaryl above contain not more than 10 carbon atoms,
all the carbocyclyl, alkyl, alkenyl, alkynyl, alkoxy, cycloalkyl, heterocyclyl, aryl and heteroaryl above, and also the ring formed by R5 and R6 with the nitrogen atom to which they are attached, except for the radicals of R2 and R3, are optionally substituted with one or more substituents, which may be identical or different, selected from the group consisting of halogen, cyano, hydroxyl, alkoxy, —$CF_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S(O)$_n$—R8, —S(O)$_n$—R8, —N(R10)-S(O)$_n$—NR11R12 and —S(O)$_n$—NR11R12,
all the aryl and heteroaryl above are optionally substituted with one or more substituents selected from the group consisting of alkyl, alkoxy and alkylenedioxy,
all the cyclic radicals above, and also the ring formed by R5 and R6 with the nitrogen atom to which they are attached, are optionally substituted with one or more substituents selected from the group consisting of oxo and thioxo,
n is 0 to 2,
R8 is alkyl, alkenyl, cycloalkyl, cycloalkylalkyl, heterocyclyl, heterocyclylalkyl, aryl, arylalkyl, heteroaryl or heteroarylalkyl,
R9 is defined as R8 or is hydrogen,
R10 is hydrogen or alkyl,
R11 and R12, which may be identical or different, are hydrogen, $C_3$-$C_6$ cycloalkyl, $C_1$-$C_4$ alkyl or phenyl optionally substituted with one or more substituents, which may be identical or different, selected from the group consisting of halogen, cyano, hydroxyl, alkoxy, —$CF_3$, nitro, phenyl, and free, salified, esterified or amidated carboxyl,
or R11 and R12 taken together with the nitrogen atom to which they are attached form a 5- to 7-membered cyclic radical containing one or more hetero atoms chosen from O, S, N and NR7, and R13, which may be identical to or different from R5 or R6, is defined as R5 or R6, or a racemic, enantiomeric or diastereoisomeric isomer form of the compound of formula I, or an addition salt with a mineral or organic acid or with a mineral or organic base thereof,
with the proviso:
  a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;
  b) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or
  c) when p is 0, R and R1 are oxygen, A1 is single bond, Y and Y1, which may be identical or different, are one is —SO$_2$Alk or SO$_2$NH$_2$ and the other is NR5R6, A2 is single bond or alkylene and B2 is optionally substituted 5- to 10-membered heterocyclyl, then R2 and R3 are not both hydrogen.

12. The compound according to claim 1 wherein R2 and R3, which may be identical or different, are chosen from hydrogen, alkyl, phenylalkyl, pyridylalkyl and benzothienylalkyl, which are optionally substituted with one or more radicals chosen from halogen, hydroxyl, alkyl and alkoxy containing from one to 4 carbon atoms.

13. The compound according to claim 1 wherein R2 and R3, which may be identical or different, are chosen from hydrogen, alkyl, hydroxyalkyl, phenylalkyl, hydroxyphenylalkyl, pyridylalkyl or thienylbenzothienylallyl.

14. The compound according to claim 1 wherein R2 and R3, which may be identical or different, are chosen from hydrogen, alkyl, hydroxyalkyl, phenylalkyl and hydroxyphenylalkyl.

15. The compound according to claim 1 wherein one of R2 and R3 is chosen from hydrogen and alkyl, and the other R2 and R3 is chosen from among the broadest definitions of R2 and R3.

16. The compound according to claim 1 wherein R2 and R3, which may be identical or different, are hydrogen or alkyl.

17. The compound according to claim 1 wherein R2 and R3, which may be identical or different, are hydrogen or methyl.

18. The compound according to claim 1 wherein A1 is single bond and A2 is chosen from single bond, a linear or branched alkyl containing not more than 6 carbon atoms and allyl, propynyl, C=O and SO$_2$ radicals, the other substituents of said compound of formula I are as defined in claim 1.

19. The compound according to claim 1 wherein A1 is single bond and A2 is chosen from single bond, alkyl, allyl, propynyl, C=O and SO$_2$.

20. The compound according to claim 1 wherein A1 is single bond and A2 is chosen from alkyl, allyl, propynyl, C=O and SO$_2$.

21. The compound according to claim 1 wherein A1 is single bond and A2 is alkyl or C=O.

22. The compound according to claim 1 wherein A1 is single bond and A2 is C=O, ethylene or methylene.

23. The compound according to claim 1 wherein A1 is single bond and A2 is methylene.

24. The compound according to claim 1 wherein Y and Y1 are such that one is hydrogen, halogen or amino and the other is chosen from —OCF$_3$, —O—CF$_2$—CHF$_2$, —O—CHF$_2$, —O—CH$_2$—CF$_3$, —SF$_5$, —S(O)$_n$—CF$_3$, —S(O)$_n$-alk, —SO$_2$CHF$_2$, —SO$_2$CF$_2$CF$_3$, —SO$_2$NH$_2$, —S—CF$_2$—CF$_2$—CF$_3$, —S-Alk-O-Alk, —S-Alk-OH, —S-Alk-CN, —S-Alk-morpholino, —S-Alk-pyrrolidinyl and —S-Alk-piperazinyl, wherein the morpholino, pyrrolidinyl and piperazinyl are optionally substituted with Alk, in which Alk is alkyl containing from 1 to 4 carbon atoms.

25. The compound according to claim 1 wherein Y is hydrogen and Y1 is chosen from —OCF$_3$, S(O)$_n$—CF$_3$, —S(O)$_n$—CH3, —SO$_2$CHF$_2$ and —SO$_2$NH$_2$.

26. The compound according to claim 1 wherein Y is hydrogen and Y1 is chosen from —OCF$_3$, —S(O)$_n$—CF$_3$ and —SO$_2$CHF$_2$.

27. The compound according to claim 1 wherein Y is hydrogen and Y1 is chosen from —OCF$_3$ and S(O)$_n$—CF$_3$.

28. The compound according to claim 1 wherein Y is hydrogen and Y1 is chosen from —OCF$_3$, S—CF$_3$ and S(O)2—CF$_3$.

29. The compound according to claim 1 wherein B2 is monocyclic or bicyclic heteroaryl chosen from pyridyl, pyrimidinyl, quinolyl, azaindolyl, 1H-pyrrolo[2,3-b]pyridinyl, quinazolyl, thiazolyl, imidazolyl, pyrazolyl, furazanyl, isoxazolyl, morpholinyl, pyrrolidinyl, furyl, piperidyl, thienyl, chromenyl, oxochromenyl, indolyl, pyrrolyl, purinyl, benzoxazinyl, benzimidazolyl and benzofuranyl, which are optionally substituted with one or more radicals chosen from the definition of Y2.

30. The compound according to claim 1 wherein B2 is heteroaryl chosen from 3- or 4-pyridyl, 3- or 4-quinolyl, imidazolyl, thiazolyl, indolyl, pyrazolyl, pyrrolyl, pyrimidyl, purinyl, benzoxazinyl, benzimidazolyl and benzofuranyl, which are optionally substituted with one or more radicals chosen from the definition of Y2.

31. The compound according to claim 1 wherein B2 is heteroaryl chosen from 4-pyridyl, 4-quinolyl, imidazolyl, thiazolyl, pyrazolyl, pyrrolyl, pyrimidyl and purinyl radicals, which are optionally substituted with one or more radicals chosen from the definition of Y2.

32. The compound according to claim 1 wherein B2 is heteroaryl chosen from 3- or 4-pyridyl, pyrimidinyl, 3- or 4-quinolyl, azaindolyl, quinazolyl, thiazolyl, imidazolyl, pyrazolyl, furazanyl and isoxazolyl, which are optionally substituted with one or more radicals chosen from the definition of Y2.

33. The compound according to claim 1 wherein B2 is heteroaryl chosen from 3- or 4-pyridyl, pyrimidyl, 3- or 4-quinolyl, azaindolyl and quinazolyl, which are optionally substituted with one or more radicals chosen from the definition of Y2.

34. The compound according to claim 1 wherein B2 is 4-pyridyl, 4-quinolyl or 1H-pyrrolo[2,3-b]pyrid-4-yl, which are optionally substituted with one or more radicals chosen from the definition of Y2.

35. The compound according to claim 1 wherein Y2 is 2-amino-4-pyridyl in which the amino is optionally substituted as indicated for the radical —NR5R6 as defined in claim 1.

36. The compound of formula I:

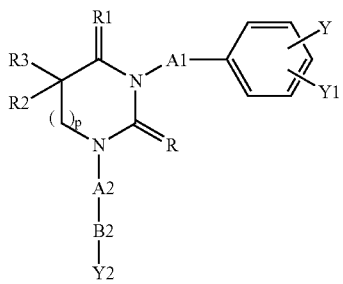

wherein p is 0,

R and R1, which may be identical or different, are O or NH,

R2 and R3, which may be identical or different, are hydrogen, alkyl, alkenyl, alkynyl, cycloalkyl, aryl or heteroaryl, A1 is single bond, alkyl, alkenyl or alkynyl, Y and Y1, which may be identical or different, are such that one of Y and Y1 is —OCF$_3$, —O—CF$_2$—CHF$_2$, —O—CHF$_2$, —O—CH$_2$—CF$_3$, —SO$_2$NR5R6, —SF$_5$ or —S(O)$_n$-alkyl and the other of Y and Y1 is —OCF$_3$, —O—CF$_2$—CHF$_2$, —O—CHF$_2$, —O—CH$_2$—CF$_3$, SO$_2$NR5R6, —SF$_5$, —S(O)$_n$-alkyl, hydrogen, halogen, hydroxyl, alkoxy, nitro, —CN, —NR5R6, alkyl, aryl, heteroaryl, —CF$_3$, —O-alkenyl, —O-alkynyl, —O-cycloalkyl, —S(O)$_n$-alkenyl, —S(O)$_n$-alkynyl, —S(O)$_n$-cycloalkyl, —CONR5R6, or free, salified or esterified carboxyl, or the

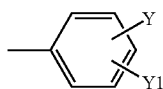

is

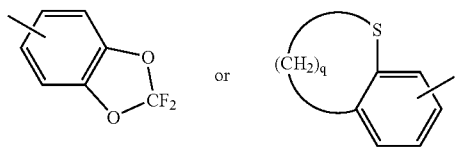

that is optionally substituted with one or more alkyl that are optionally substituted, q is 2, 3 or 4, A2, which may be identical to or different from A1, is defined as A1 or is CO or SO$_2$, B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2, R7 is hydrogen, alkyl, cycloalkyl, phenyl, acyl, —S(O)$_2$Alk, —S(O)$_2$Aryl, —S(O)$_2$heteroaryl or —S(O)$_2$NR5R6, Y2 is hydrogen, halogen, hydroxyl, cyano, alkyl, alkoxy, phenyl, —COOH, —COOAlk, —CONR5R6, —NR5R6, —NR10-COOR6, —NR10-CO—R6, —NR10-CS—NR5R6, —NR10-CO—NR5R6 or —NR10-SO$_2$—R6, which are all optionally substituted, R5 and R6, which may be identical or different, are chosen from hydrogen, alkyl, cycloalkyl, phenyl and 5- or 6-membered heteroaryl containing 1 to 3 hetero atoms chosen from O, N and S, which are all optionally substituted, or R5 and R6 taken together with the nitrogen atom to which they are attached form an optionally substituted pyrrolidinyl, piperidyl, piperazinyl, morpholinyl or quinazolinyl, R10 is hydrogen or alkyl, all the alkyl, alkoxy, cycloalkyl and phenyl of Y2, R5, R6 and R10, and also the ring formed by R5 and R6 with the atom to which they are attached, are optionally substituted with one or more radicals, which may be identical or different, chosen from halogen, cyano, hydroxyl, alkyl, alkoxy, OCF$_3$, —CF$_3$, —S(O)$_n$—CF$_3$, nitro, oxo, thioxo, —OCOAlk; and phenyl, which is optionally substituted with one or more radicals chosen from halogen, alkyl, alkoxy; —OCOAlk; —NH$_2$, —NHAlk, —N(Alk)$_2$, —N(alk)(phenylalkyl), —N(Alk)(aminoalkyl), —N(Alk)(alkylaminoalkyl), —N(Alk)(dialkylaminoalkyl), and carboxyl in free form or esterified with an alkyl, all Y2, R5, and R6 phenyl are optionally substituted with alkylenedioxy, all Y2, R5, R6, and R10 alkyl are optionally substituted with one or more saturated or partially unsaturated 4- to 7-membered heterocyclyl containing at least one nitrogen atom N and 0 to 2 other hetero atoms chosen from O, N and S, all the pyrrolidinyl and quinazolinyl of Y2, R5, and R6 are optionally substituted with oxo or thioxo, all the aryl and heteroaryl above contain not more than 10 carbon atoms, except for the radicals of Y2, R5, R6 and R10, all the carbocyclyl, heterocyclyl, alkyl, alkenyl, alkynyl, alkoxy, cycloalkyl, aryl and heteroaryl above, are optionally substituted with one or more substituents, which may be identical or different, selected from the group consisting of halogen, cyano, hydroxyl, alkoxy, —CF$_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S(O)$_n$—R8, —S(O)$_n$—R8, —N(R10)-S(O)$_n$—NR11R12 and —S(O)$_n$—NR11R12, except for the radicals of Y2, R5, and R6, all the aryl and heteroaryl above are optionally substituted with one or more substituents selected from the group consisting of alkyl, alkoxy and alkylenedioxy, except for the radicals of Y2, R5, and R6, all the cyclic radicals above are optionally substituted with one or more substituents selected from the group consisting of oxo and thioxo, all the alkyl alkenyl, alkynyl and alkoxy being linear or branched and containing not more than 6 carbon atoms, all the cycloalkyl and heterocyclyl containing not more than 7 carbon atoms, n is 0 to 2, R8 is alkyl, alkenyl, cycloalkyl, cycloalkylalkyl, heterocyclyl, heterocyclylalkyl, aryl, arylalkyl, heteroaryl or heteroarylalkyl, R9 is defined as R8 or is hydrogen,
R11 and R12, which may be identical or different, are hydrogen, $C_3$-$C_6$ cycloalkyl, $C_1$-$C_4$ alkyl or phenyl, optionally substituted with one or more substituents, which may be identical or different, selected from the group consisting of halogen, cyano, hydroxyl, alkoxy, —$CF_3$, nitro, phenyl, and free, salified, esterified or amidated carboxyl,
or R11 and R12 taken together with the nitrogen atom to which they are attached form a 5- to 7-membered cyclic radical containing one or more hetero atoms chosen from O, S, N and NR7, and
R13, which may be identical to or different from R5 or R6, is defined as R5 or R6, or
a racemic, enantiomeric or diastereoisomeric isomer form of the compound of formula I, or an addition salt with a mineral or organic acid or with a mineral or organic base thereof,
with the proviso:
a) when p is 0, R and R1 are oxygen, A1 is single bond or alkyl, Y and Y1, which may be identical or different, are at least one is —$OCF_3$ or —S-alk, A2 is single bond or alkyl and B2 is an optionally substituted heterocyclyl, then R2 and R3 are not one hydrogen and the other imidazolylalkyl;
b) when p is 0, R and R1 are oxygen, A1 is a single bond or alkyl, Y and Y1, which may be identical or different, are at least one is —$S(O)_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or
c) when p is 0, R and R1 are oxygen, A1 is single bond, Y and Y1, which may be identical or different, are one is —$SO_2$Alk or $SO_2NH_2$ and the other is NR5R6, A2 is single bond or alkylene and B2 is optionally substituted 5- to 10-membered heterocyclyl, then R2 and R3 are not both hydrogen.

37. The compound according to claim 1 wherein R5 and R6 are pyridyl, pyrazinyl, pyrimidinyl, thienyl, thiazolyl or oxazolyl, which are all optionally substituted.

38. The compound of formula I:

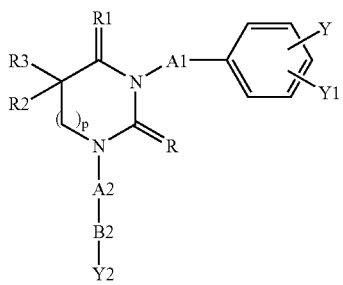

(I)

wherein
p is 0,
R and R1, which may be identical or different, are O or NH,
R2 and R3, which may be identical or different, are hydrogen, alkyl, alkenyl, alkynyl, cycloalkyl, aryl or heteroaryl,
A1 is single bond, alkyl, alkenyl or alkynyl,
Y and Y1, which may be identical or different, are such that one of Y and Y1 is —$OCF_3$, —O—$CF_2$—$CHF_2$, —O—$CHF_2$, —O—$CH_2$—$CF_3$, —$SO_2NR5R6$, —$SF_5$ or —$S(O)_n$-alkyl and the other of Y and Y1 is —$OCF_3$, —O—$CF_2$—$CHF_2$, —O—$CHF_2$, —O—$CH_2$—$CF_3$, $SO_2NR5R6$, —$SF_5$, —$S(O)_n$-alkyl, hydrogen, halogen, hydroxyl, alkoxy, nitro, —CN, —NR5R6, alkyl, aryl, heteroaryl, —$CF_3$, —O-alkenyl, —O-alkynyl, —O-cycloalkyl, —$S(O)_n$-alkenyl, —$S(O)_n$-alkynyl, —$S(O)_n$-cycloalkyl, —$CONR5R6$, or free, salified or esterified carboxyl,
or the

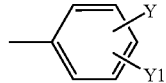

is

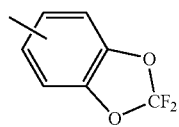 or 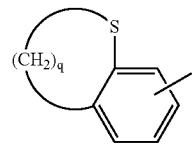

that is optionally substituted with one or more alkyl that are optionally substituted,
q is 2, 3 or 4,
R5 and R6, which may be identical or different, are hydrogen, alkyl, alkenyl, alkynyl, cycloalkyl, cycloalkenyl, heterocyclyl, aryl or heteroaryl, or R5 and R6 taken together with the nitrogen atom to which they are attached form a 3- to 10-membered heterocyclyl containing one or more hetero atoms chosen from O, S, N and NR7,
A2, which may be identical to or different from A1, is defined as A1 or is CO or $SO_2$,
B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2,
R7 is hydrogen, alkyl, cycloalkyl, phenyl, acyl, —$S(O)_2$Alk, —$S(O)_2$Aryl, —$S(O)_2$heteroaryl or —$S(O)_2$NR5R6,
Y2 is hydrogen, halogen, hydroxyl, cyano, alkyl, alkoxy, cycloalkyl, heterocyclyl, aryl, heteroaryl, —O-alkenyl, —O-alkynyl, —O-cycloalkyl, —$S(O)_n$-alkyl, —$S(O)_n$-alkenyl, —$S(O)_n$-alkynyl, —$S(O)_n$-cycloalkyl, —COOR13, —OCOR13, NR5R6, CONR5R6, —$S(O)_n$—NR5R6, —NR10-CO—R13, —NR10-$SO_2$—R13, NH—$SO_2$—NR5R6, —NR10-CO—NR5R6, —NR10-CS—NR5R6 or —NR10-COOR13, all of which are optionally substituted,
all the alkyl, alkenyl, alkynyl and alkoxy above are linear or branched and contain not more than 6 carbon atoms,
all the cycloalkyl and heterocyclyl above contain not more than 7 carbon atoms,
all the aryl and heteroaryl above contain not more than 10 carbon atoms,
all the alkyl above are optionally substituted with heterocyclyl chosen from thiomorpholin-4-yl, thiazolidin-3-yl, azetidin-1-yl, piperazinyl, imidazolyl, morpholinyl, pyrrolidinyl, piperidyl and azepanyl, all of which are optionally substituted with one or more radicals chosen from alkyl, hydroxyalkyl, oxo, pyridyl and phenyl optionally substituted with one or more radicals chosen from halogen, alkyl, hydroxyl, alkoxy, —CN, carboxyl or amino, which are themselves optionally substituted, all the carbocyclyl, alkenyl, alkynyl, alkoxy, cycloalkyl, heterocyclyl, aryl and heteroaryl above, and also the ring formed by R5 and R6 with the nitrogen atom to which they are attached, are optionally substituted with one or more substituents, which may be identical or different, selected from the group consisting of halogen, cyano, hydroxyl, alkoxy, —CF$_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S(O)$_n$—R8, —S(O)$_n$—R8, —N(R10)-S(O)$_n$—NR11R12 and —S(O)$_n$—NR11R12, all the aryl and heteroaryl above are optionally substituted with one or more substituents selected from the group consisting of alkyl, alkoxy and alkylenedioxy, all the cyclic radicals above, and also the ring formed by R5 and R6 with the nitrogen atom to which they are attached, are optionally substituted with one or more substituents selected from the group consisting of oxo and thioxo, n is 0 to 2, R8 is alkyl, alkenyl, cycloalkyl, cycloalkylalkyl, heterocyclyl, heterocyclylalkyl, aryl, arylalkyl, heteroaryl or heteroarylalkyl, R9 is defined as R8 or is hydrogen, R10 is hydrogen or alkyl, R11 and R12, which may be identical or different, are hydrogen, $C_3$-$C_6$ cycloalkyl, $C_1$-$C_4$ alkyl, or phenyl, optionally substituted with one or more substituents, which may be identical or different, selected from the group consisting of halogen, cyano, hydroxyl, alkoxy, —CF$_3$, nitro, phenyl, and free, salified, esterified or amidated carboxyl, or R11 and R12 taken together with the nitrogen atom to which they are attached form a 5- to 7-membered cyclic radical containing one or more hetero atoms chosen from O, S, N and NR7, and R13, which may be identical to or different from R5 or R6, is defined as R5 or R6, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —SO$_2$Alk or SO$_2$NH$_2$ and the other is NR5R6, A2 is single bond or alkylene and B2 is optionally substituted 5- to 10-membered heterocyclyl, then R2 and R3 are not both hydrogen.

39. The compound of formula I:

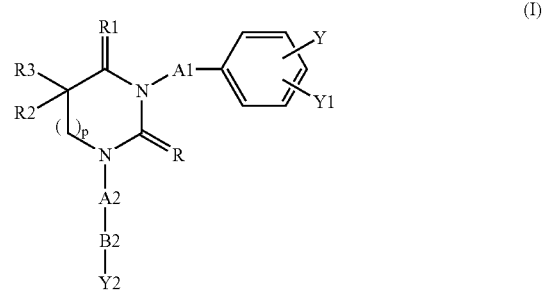

wherein p is 0,

R and R1, which may be identical or different, are O or NH,

R2 and R3, which may be identical or different, are hydrogen, alkyl, alkenyl, alkynyl, cycloalkyl, aryl or heteroaryl, A1 is single bond, alkyl, alkenyl or alkynyl, Y and Y1, which may be identical or different, are such that one of Y and Y1 is —OCF$_3$, —O—CF$_2$—CHF$_2$, —O—CHF$_2$, —O—CH$_2$—CF$_3$, —SO$_2$NR5R6, —SF$_5$ or —S(O)$_n$-alkyl and the other of Y and Y1 is —OCF$_3$, —O—CF$_2$—CHF$_2$, —O—CHF$_2$, —O—CH$_2$—CF$_3$, SO$_2$NR5R6, —SF$_5$, —S(O)$_n$-alkyl, hydrogen, halogen, hydroxyl, alkoxy, nitro, —CN, —NR5R6, alkyl, aryl, heteroaryl, —CF$_3$, —O-alkenyl, —O-alkynyl, —O-cycloalkyl, —S(O)$_n$-alkenyl, —S(O)$_n$-alkynyl, —S(O)$_n$-cycloalkyl, —CONR5R6, or free, salified or esterified carboxyl, or the

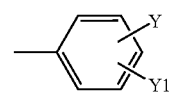

is

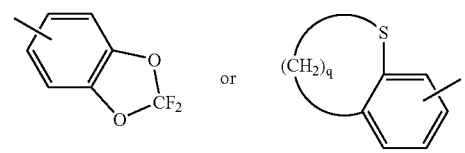

that is optionally substituted with one or more alkyl that are optionally substituted, q is 2, 3 or 4, A2, which may be identical to or different from A1, is defined as A1 or is CO or SO$_2$, B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2, R7 is hydrogen, alkyl, cycloalkyl, phenyl, acyl, —S(O)$_2$Alk, —S(O)$_2$Aryl, —S(O)$_2$heteroaryl or —S(O)$_2$NR5R6, Y2 is hydrogen, halogen, hydroxyl, cyano, alkyl, alkoxy, phenyl, —CONR5R6, —NR5R6, —NR10-COOH, —NR10-COOAlk, —NR10-CO—R6, —NR10-CS—NR5R6, —NR10-CO—NR5R6 or —NR10-SO$_2$—R6, R5 and R6, which may be identical or different, are chosen from hydrogen; alkyl; cycloalkyl; phenyl; pyrimidinyl; thienyl; pyridyl; quinolyl; thiazolyl optionally substituted with one or two halogen; pyran optionally substituted with one or more —OCOAlk; phenyl substituted with one or more radicals chosen from halogen, alkyl, alkoxy, amino, alkylamino, dialkylamino and carboxyl in free form or esterified with an alkyl radical; alkyl substituted with phenyl, which is itself optionally substituted with one or more radicals chosen from halogen, alkyl, alkoxy, amino, alkylamino, dialkylamino, carboxyl in free form or esterified with an alkyl radical; alkyl substituted with piperazinyl, which is itself optionally substituted with one or more radicals chosen from Alk, Alk-OH and pyridyl; alkyl substituted with imidazolyl; alkyl substituted with one or more radicals chosen from —NH$_2$, —NHAlk, —N(Alk)$_2$, —N(alk)(phenylalkyl), —N(Alk)(aminoalkyl), —N(Alk)(alkylaminoalkyl) and —N(Alk)(dialkylaminoalkyl); alkyl substituted with morpholinyl optionally substituted with one or two Alk; alkyl substituted with pyrrolidinyl; alkyl substituted with piperidyl, which is itself optionally substituted with one or two Alk; alkyl substituted with thiomorpholinyl; alkyl substituted with azetidinyl; and alkyl substituted with azepanyl, which is optionally substituted with oxo, or R5 and R6 taken together with the nitrogen atom to which they are attached form pyrrolidinyl; piperidyl; piperazinyl; morpholinyl; or quinazolinyl, all of which are optionally substituted with one or more radicals, which may be identical or different, chosen from halogen, alkyl, hydroxyl and alkoxy, and phenyl which is optionally substituted with one or more radicals chosen from halogen, alkyl and alkoxy, the pyrrolidinyl and quinazolinyl are optionally substituted with oxo or thioxo, the piperazinyl itself is optionally substituted with one or more radicals chosen from Alk, Alk-OH and pyridyl, except for the radicals of Y2, R5, R6 and R10, all the carbocyclyl, alkyl, alkenyl, alkynyl, alkoxy, cycloalkyl, heterocyclyl, aryl and heteroaryl above, are optionally substituted with one or more substituents, which may be identical or different, selected from the group consisting of halogen, cyano, hydroxyl, alkoxy, —CF$_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S(O)$_n$—R8, —S(O)$_n$—R8, —N(R10)-S(O)$_n$—NR11R12 and —S(O)$_n$—NR11R12, except for the radicals of Y2, R5, and R6, all the aryl and heteroaryl above are optionally substituted with one or more substituents selected from the group consisting of alkyl, alkoxy and alkylenedioxy, except for the radicals of Y2, R5, and R6, all the cyclic radicals above, are optionally substituted with one or more substituents selected from the group consisting of oxo and thioxo, R10 is hydrogen or alkyl, all alkyl, Alk, alkenyl, alkynyl and alkoxy above being linear or branched and containing not more than 6 carbon atoms, all the cycloalkyl and heterocyclyl containing not more than 7 carbon atoms, all the aryl and heteroaryl above contain not more than 10 carbon atoms, all the phenyl of Y2, R5, and R6 are optionally substituted with a radical chosen from —CF$_3$, —OCF$_3$, nitro and alkylenedioxy, n is 0 to 2, R8 is alkyl, alkenyl, cycloalkyl, cycloalkylalkyl, heterocyclyl, heterocyclylalkyl, aryl, arylalkyl, heteroaryl or heteroarylalkyl, R9 is defined as R8 or is hydrogen, R11 and R12, which may be identical or different, are hydrogen, C$_3$-C$_6$ cycloalkyl, C$_1$-C$_4$ alkyl or phenyl, optionally substituted with one or more substituents, which may be identical or different, selected from the group consisting of halogen, cyano, hydroxyl, alkoxy, —CF$_3$, nitro, phenyl, and free, salified, esterified or amidated carboxyl, or R11 and R12 taken together with the nitrogen atom to which they are attached form a 5- to 7-membered cyclic radical containing one or more hetero atoms chosen from O, S, N and NR7, and R13, which may be identical to or different from R5 or R6, is defined as R5 or R6, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —SO$_2$Alk or SO$_2$NH$_2$ and the other is NR5R6, A2 is single bond or alkylene and B2 is optionally substituted 5- to 10-membered heterocyclyl, then R2 and R3 are not both hydrogen.

40. The compound according to claim 1 in which —A2-B2-Y2 is selected from the following radicals:

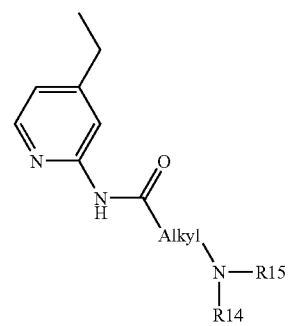

-continued

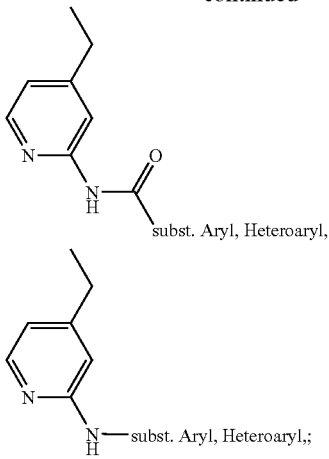
subst. Aryl, Heteroaryl,

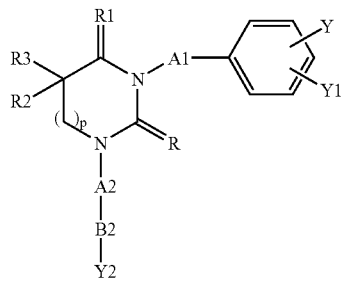
subst. Aryl, Heteroaryl,;

wherein NR14R15 is defined as —NR5R6 and the definition for Alkyl, Aryl and Heteroaryl are chosen from the values of the alkyl, aryl and heteroaryl as defined in claim 1 and optionally substituted as defined in claim 1.

41. The compound according to claim 1 wherein B2 is selected from the group consisting of 4-pyridyl and 4-quinolyl, which are optionally substituted with one or more radicals chosen from the definition of Y2.

42. The compound of formula I:

(I)

$$\text{R1, R2, R3, A1, N, R, A2, B2, Y, Y1, Y2, (}\,)_p$$

wherein p is 0,

R and R1, which may be identical or different, are O or NH,

R2 and R3, which may be identical or different, are hydrogen, alkyl, alkenyl, alkynyl, cycloalkyl, aryl or heteroaryl, A1 is single bond, alkyl, alkenyl or alkynyl, Y and Y1, which may be identical or different, are such that one of Y and Y1 is —OCF$_3$, —O—CF$_2$—CHF$_2$, —O—CHF$_2$, —O—CH$_2$—CF$_3$, —SO$_2$NR5R6, —SF$_5$ or —S(O)$_n$-alkyl and the other of Y and Y1 is —OCF$_3$, —O—CF$_2$—CHF$_2$, —O—CHF$_2$, —O—CH$_2$—CF$_3$, SO$_2$NR5R6, —SF$_5$, —S(O)$_n$-alkyl, hydrogen, halogen, hydroxyl, alkoxy, nitro, —CN, —NR5R6, alkyl, aryl, heteroaryl, —CF$_3$, —O-alkenyl, —O-alkynyl, —O-cycloalkyl, —S(O)$_n$-alkenyl, —S(O)$_n$-alkynyl, —S(O)$_n$-cycloalkyl, —CONR5R6, or free, salified or esterified carboxyl, or the

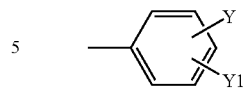

is

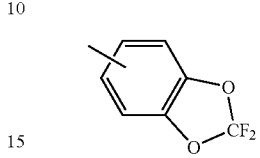 or 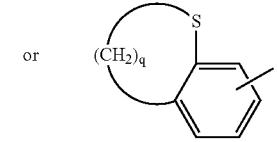

that is optionally substituted with one or more alkyl that are optionally substituted, q is 2, 3 or 4, R5 and R6, which may be identical or different, are hydrogen, alkyl, alkenyl, alkynyl, cycloalkyl, cycloalkenyl, heterocyclyl, aryl or heteroaryl, or R5 and R6 taken together with the nitrogen atom to which they are attached form a 3- to 10-membered heterocyclyl containing one or more hetero atoms chosen from O, S, N and NR7, A2, which may be identical to or different from A1, is defined as A1 or is CO or SO$_2$, B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2, R7 is hydrogen, alkyl, cycloalkyl, phenyl, acyl, —S(O)$_2$Alk, —S(O)$_2$Aryl, —S(O)$_2$heteroaryl or —S(O)$_2$NR5R6, Y2 is V1, halogen, hydroxyl, —C(═NH)NH$_2$, OV1, O—CO—V1, COOV1, COV1, CO—NV1V2, —NV1V2, —NH—CO—V1, —NH—COO—V1, —NH—NH—CO—V1, —NV1-CO—NV1V2, —NV1-CO—NHV1, —NH—CO—NHV1, —NH—SO$_2$—NHV1 and —NH—SO$_2$—V1, in which V1 and V2, which may be identical or different, are hydrogen, alkyl, cycloalkyl or phenyl or heterocyclyl, all the alkyl, phenyl and heterocyclyl of V1 and V2 being optionally substituted with one or more radicals chosen from halogen, hydroxyl, alkyl, alkoxy, —CF$_3$, NH$_2$, NH-alk, N(Alk)$_2$ and phenyl, itself optionally substituted with one or more substituents chosen from halogen, hydroxyl and alkoxy radicals, all the phenyl and heterocyclyl of V1 and V2 are optionally substituted with one or more alkyl, the phenyl of V1 and V2 is optionally substituted with —NR5R6, all the alkyl, alkenyl, alkynyl and alkoxy above are linear or branched and contain not more than 6 carbon atoms, all the cycloalkyl and heterocyclyl above contain not more than 7 carbon atoms, all the aryl and heteroaryl above contain not more than 10 carbon atoms, except for V1 and V2, all the carbocyclyl, alkenyl, alkynyl, alkoxy, cycloalkyl, aryl and heteroaryl above, and also the ring formed by R5 and R6 with the nitrogen atom to which they are attached, are optionally substituted with one or more substituents, which may be identical or different, selected from the group consisting of halogen, cyano, hydroxyl, alkoxy, —CF₃, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S(O)ₙ—R8, —S(O)ₙ—R8, —N(R10)-S(O)ₙ—NR11R12 and —S(O)ₙ—NR11R12, except for V1 and V2, all the aryl and heteroaryl above are optionally substituted with one or more substituents selected from the group consisting of alkyl, alkoxy and alkylenedioxy, except for V1 and V2, all the cyclic radicals above, and also the ring formed by R5 and R6 with the nitrogen atom to which they are attached, are optionally substituted with one or more substituents selected from the group consisting of oxo and thioxo, n is 0 to 2, R8 is alkyl, alkenyl, cycloalkyl, cycloalkylalkyl, heterocyclyl, heterocyclylalkyl, aryl, arylalkyl, heteroaryl or heteroarylalkyl, R9 is defined as R8 or is hydrogen, R10 is hydrogen or alkyl, R11 and R12, which may be identical or different, are hydrogen, C₃-C₆ cycloalkyl, C₁-C₄ alkyl or phenyl, optionally substituted with one or more substituents, which may be identical or different, selected from the group consisting of halogen, cyano, hydroxyl, alkoxy, —CF₃, nitro, phenyl, and free, salified, esterified or amidated carboxyl, or R11 and R12 taken together with the nitrogen atom to which they are attached form a 5- to 7-membered cyclic radical containing one or more hetero atoms chosen from O, S, N and NR7, and R13, which may be identical to or different from R5 or R6, is defined as R5 or R6, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —OCF₃ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —S(O)ₙ-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —SO₂Alk or SO₂NH₂ and the other is NR5R6, A2 is single bond or alkylene and B2 is optionally substituted 5- to 10-membered heterocyclyl, then R2 and R3 are not both hydrogen.

43. The compound of formula I:

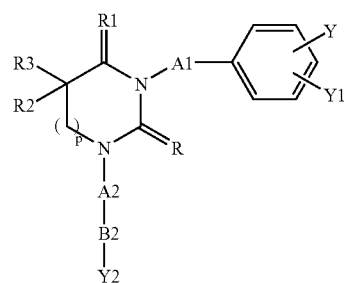

(I)

wherein
p is 0,
R and R1, which may be identical or different, are O or NH,
R2 and R3, which may be identical or different, are hydrogen, alkyl, alkenyl, alkynyl, cycloalkyl aryl or heteroaryl,
A1 is single bond, alkyl, alkenyl or alkynyl,
Y and Y1, which may be identical or different, are such that one of Y and Y1 is —OCF₃, —O—CF₂—CHF₂, —O—CHF₂, —O—CH₂—CF₃, —SO₂NR5R6, —SF₅ or —S(O)ₙ-alkyl and the other of Y and Y1 is —OCF₃, —O—CF₂—CHF₂, —O—CHF₂, —O—CH₂—CF₃, SO₂NR5R6, —SF₅, —S(O)ₙ-alkyl, hydrogen, halogen, hydroxyl, alkoxy, nitro, —CN, —NR5R6, alkyl, aryl, heteroaryl, —CF₃, —O-alkenyl, —O-alkynyl, —O-cycloalkyl, —S(O)ₙ-alkenyl, —S(O)ₙ-alkynyl, —S(O)ₙ-cycloalkyl, —CONR5R6, or free, salified or esterified carboxyl, or the

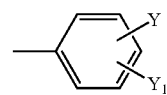

is

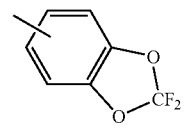 or 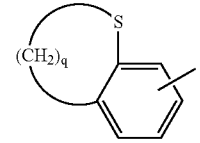

that is optionally substituted with one or more alkyl that are optionally substituted, q is 2, 3 or 4, R5 and R6, which may be identical or different, are hydrogen, alkyl, alkenyl, alkynyl, cycloalkyl, cycloalkenyl, heterocyclyl, aryl or heteroaryl, or R5 and R6 taken together with the nitrogen atom to which they are attached form a 3- to 10-membered heterocyclyl containing one or more hetero atoms chosen from O, S, N and NR7, A2, which may be identical to or different from A1, is defined as A1 or is CO or SO₂, B2 is a saturated or unsaturated 3- to 10-membered monocyclic or bicyclic heterocyclyl containing one or more hetero atoms chosen from O, S, N and NR7 that is optionally substituted with one or more identical or different substituents defined as Y2, R7 is hydrogen, alkyl, cycloalkyl, phenyl, acyl, —S(O)$_2$Alk, —S(O)$_2$Aryl, —S(O)$_2$heteroaryl or —S(O)$_2$NR5R6, Y2 is hydrogen, halogen, alkyl, cycloalkyl, hydroxyl, alkoxy, carboxyl which is free or esterified with an alkyl or phenyl, —NH$_2$, —NHalk, —N(Alk)$_2$ or phenyl, all the Y2 alkyl, alkoxy and phenyl are optionally substituted with one or more radicals chosen from halogen, hydroxyl, $C_1$-$C_4$ alkyl, $C_1$-$C_4$ alkoxy, —CF$_3$, —NH$_2$, —NH-alk, N(Alk)$_2$ and phenyl, which is itself optionally substituted with one or more substituents chosen from halogen, hydroxyl and alkoxy, all the Y2 phenyl are optionally substituted with one or more $C_1$-$C_4$ alkyl and optionally substituted with —NR5R6, all the alkyl, alkenyl, alkynyl and alkoxy above are linear or branched and contain not more than 6 carbon atoms, all the cycloalkyl and heterocyclyl above contain not more than 7 carbon atoms, all the aryl and heteroaryl above contain not more than 10 carbon atoms, except for Y2, all the carbocyclyl, heterocyclyl, alkyl, alkenyl, alkynyl, alkoxy, cycloalkyl, aryl and heteroaryl above, and also the ring formed by R5 and R6 with the nitrogen atom to which they are attached, are optionally substituted with one or more substituents, which may be identical or different, selected from the group consisting of halogen, cyano, hydroxyl, alkoxy, —CF$_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S(O)$_n$—R8, —S(O)$_n$—R8, —N(R10)-S(O)$_n$—NR11R12 and —S(O)$_n$—NR11R12, except for Y2, all the aryl and heteroaryl above are optionally substituted with one or more substituents selected from the group consisting of alkyl, alkoxy and alkylenedioxy, except for Y2, all the cyclic radicals above, and also the ring formed by R5 and R6 with the nitrogen atom to which they are attached, are optionally substituted with one or more substituents selected from the group consisting of oxo and thioxo, n is 0 to 2, R8 is alkyl, alkenyl, cycloalkyl, cycloalkylalkyl, heterocyclyl, heterocyclylalkyl, aryl, arylalkyl, heteroaryl or heteroarylalkyl, R9 is defined as R8 or is hydrogen, R10 is hydrogen or alkyl, R11 and R12, which may be identical or different, are hydrogen, $C_3$-$C_6$ cycloalkyl, $C_1$-$C_4$ alkyl or phenyl, optionally substituted with one or more substituents, which may be identical or different, selected from the group consisting of halogen, cyano, hydroxyl, alkoxy, —CF$_3$, nitro, phenyl, and free, salified, esterified or amidated carboxyl, or R11 and R12 taken together with the nitrogen atom to which they are attached form a 5- to 7-membered cyclic radical containing one or more hetero atoms chosen from O, S, N and NR7, and R13, which may be identical to or different from R5 or R6, is defined as R5 or R6, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —OCF$_3$ or —S-alk, A2 is single bond or alkyl and B2 is an optionally substituted heterocyclyl, then R2 and R3 are not one hydrogen and the other imidazolylalkyl;

b) when p is 0, R and R1 are oxygen, A1 is a single bond or alkyl, Y and Y1, which may be identical or different, are at least one is —S(O)$_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl; or c) when p is 0, R and R1 are oxygen, A1 is single bond, Y and Y1, which may be identical or different, are one is —SO$_2$Alk or SO$_2$NH$_2$ and the other is NR5R6, A2 is single bond or alkylene and B2 is optionally substituted 5- to 10-membered heterocyclyl, then R2 and R3 are not both hydrogen.

44. The compound according to claim 1 wherein Y2 is hydrogen, F, Cl, —CH$_3$, —CH$_2$CH$_3$, —OH, —OCH$_3$, —NH$_2$, —NH-Alk or phenyl optionally substituted with —NR5R6 in which R5 and R6 are as defined in claim 1.

45. The compound according to claim 1 wherein B2 is selected from 4-pyridyl and 4-quinolyl substituted with one or two radicals chosen from F, Cl, —OH and —OCH$_3$.

46. The compound according to claim 1 wherein

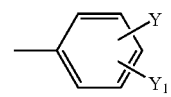

is selected from the group consisting of:

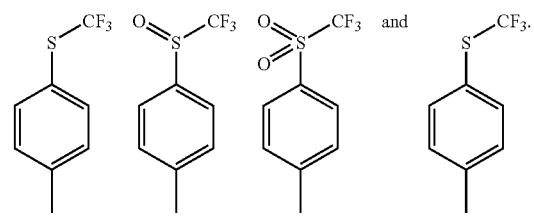

47. The compound according to claim 1 wherein —A2-B2-Y2 are selected from the following radicals:

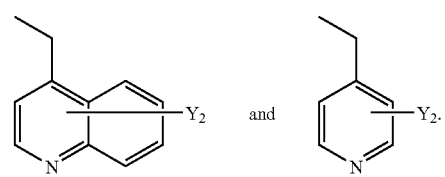

48. The compound of formula (IC):

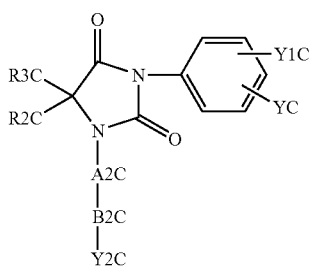

in which YC and Y1C are such that one is hydrogen, halogen, or amino and the other is chosen from —OCF$_3$, —O—CF$_2$—CHF$_2$, —O—CHF$_2$, —O—CH$_2$—CF$_3$, —SF$_5$, —S(O)$_n$—CF$_3$, —S(O)$_n$-alk, —SO$_2$CHF$_2$, SO$_2$CF$_2$CF$_3$, —SO$_2$NH$_2$, —S—CF$_2$—CF$_2$—CF$_3$, —S-Alk-O-Alk, —S-Alk-OH, —S-Alk-CN, —S-Alk-morpholino, —S-Alk-pyrrolidyl and —S-Alk-piperazinyl, the morpholino, pyrrolidyl and piperazinyl are optionally substituted with Alk, with Alk being alkyl containing from 1 to 4 carbon atoms, or the phenyl thereof with its substituents YC and Y1C forms one of the two following radicals:

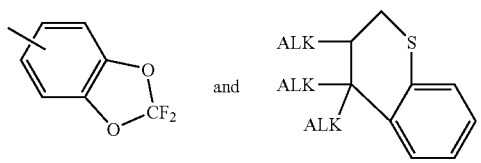

R2C and R3C, which may be identical or different, are hydrogen or optionally substituted alkyl, A2C is single bond or CH$_2$, B2C is pyridyl, pyrimidyl, quinolyl, azaindolyl, quinazolyl, thiazolyl, imidazolyl, pyrazolyl, furazanyl, isoxazolyl, morpholinyl, pyrrolidyl, furyl, piperidyl, chromenyl, oxochromenyl, quinazolyl, thienyl, indolyl, pyrrolyl, purinyl, benzoxazinyl, benzimidazolyl or benzofuryl, that are optionally substituted with one or more radicals chosen from the definition of Y2C, Y2C is hydrogen, halogen, hydroxyl, cyano, alkyl, alkoxy, phenyl, —COOH, —COOAlk, —CONR5R6, —NR5R6, —NR10-COOH, —NR10-COOAlk, —NR10-CO—R6, —NR10-CS—NR5R6, —NR10-CO—NR5R6 or —NR10-SO$_2$—R6, all these radicals are optionally substituted, R5 and R6, which may be identical or different, are chosen from hydrogen, alkyl, cycloalkyl, phenyl, pyrimidyl, thienyl, pyridyl, quinolyl, thiazolyl and pyran, all these radicals are optionally substituted, or R5 and R6 taken together with the nitrogen atom to which they are attached form an optionally substituted pyrrolidyl, piperidyl, piperazinyl, morpholinyl or quinazolinyl, R10 is hydrogen or alkyl, all the alkyl, Alk or ALK, alkoxy, cycloalkyl and phenyl radicals, and also the ring formed by R5 and R6 with the atom to which they are attached, are optionally substituted with one or more radicals, which may be identical or different, chosen from halogen, cyano, hydroxyl, alkyl, alkoxy, —OCF$_3$, —CF$_3$, —S(O)$_n$— CF$_3$, nitro, oxo, thioxo, —OCOAlk, and phenyl, itself optionally substituted with one or more radicals chosen from halogen, alkyl, alkoxy; —OCOAlk; —NH$_2$, —NHAlk, —N(Alk)$_2$, —N(alk)(phenylalkyl), —N(Alk)(aminoalkyl)-N(Alk)(alkylaminoalkyl), —N(Alk)(dialkylaminoalkyl); carboxyl in free form or esterified with alkyl, all the phenyl are optionally substituted with alkylenedioxy, all the alkyl are optionally substituted with one or more radicals chosen from piperazinyl, itself optionally substituted with Alk, Alk-OH and pyridyl; imidazolyl; morpholinyl; pyrrolidyl; piperidyl, itself optionally substituted with one or two alk; azepanyl optionally substituted with oxo, all the pyrrolidyl and quinazolinyl are optionally substituted with oxo or thioxo, all the alkyl and alkoxy being linear or branched and containing not more than 6 carbon atoms, all the cycloalkyl containing not more than 7 carbon atoms, and n is 0 to 2, or a racemic, enantiomeric or diastereoisomeric isomer form of the compound of formula I, or an addition salt with a mineral or organic acid or with a mineral or organic base thereof.

49. The compound according to claim 48 wherein the radical

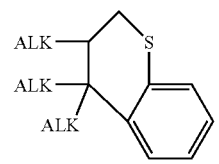

is

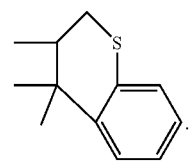.

50. The compound of formula (IA):

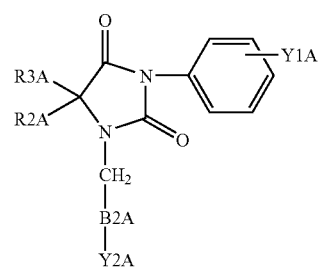

in which:

Y1A is —OCF$_3$, —S(O)$_n$—CF$_3$ or —SO$_2$CHF$_2$,

B2a is 4-quinolyl or 4-pyridyl optionally substituted with one or more radicals chosen from the definition of Y2A, Y2A is defined as Y2, R2A and R3A, which may be identical or different, are hydrogen or optionally substituted alkyl, all the alkyl and phenyl above are optionally substituted with one or more radicals chosen from halogen, —OH, alk, —O-alk, —OCF$_3$, —S(O)$_n$—CF$_3$, —CF$_3$, —NH$_2$, —NH-Alk and —N(Alk)$_2$, and Y2 is hydrogen, halogen, hydroxyl, cyano, alkyl, alkoxy, cycloalkyl, heterocyclyl, aryl, heteroaryl, —O-alkenyl, —O-alkynyl, —O-cycloalkyl, —S(O)$_n$-alkyl, —S(O)$_n$-alkenyl, —S(O)$_n$-alkynyl, —S(O)$_n$-cycloalkyl, —COOR13, —OCOR13, NR5R6, CONR5R6, —S(O)$_n$—NR5R6, —NR10-CO—R13, —NR10-SO$_2$—R13, NH—SO$_2$—NR5R6, —NR10-CO—NR5R6, —NR10-CS—NR5R6 or —NR10-COOR13, all of which are optionally substituted, R5 and R6, which may be identical or different, are hydrogen, alkyl, alkenyl, alkynyl, cycloalkyl, cycloalkenyl, heterocyclyl, aryl or heteroaryl, or R5 and R6 taken together with the nitrogen atom to which they are attached form a 3- to 10-membered heterocyclyl containing one or more hetero atoms chosen from O, S, N and NR7, R7 is hydrogen, alkyl, cycloalkyl, phenyl, acyl, —S(O)$_2$Alk, —S(O)$_2$Aryl, —S(O)$_2$heteroaryl or —S(O)$_2$NR5R6, except for Y1A, B2a, R2A, and R3A, all the carbocyclyl, heterocyclyl, alkyl, alkenyl, alkynyl, alkoxy, cycloalkyl, heterocyclyl, aryl and heteroaryl above, and also the ring formed by R5 and R6 with the nitrogen atom to which they are attached, are optionally substituted with one or more substituents, which may be identical or different, selected from the group consisting of halogen, cyano, hydroxyl, alkoxy, —CF$_3$, nitro, aryl, heteroaryl, —C(=O)—OR9, —C(=O)—R8, —NR11R12, —C(=O)—NR11R12, —N(R10)-C(=O)—R8, —N(R10)-C(=O)—OR9, —N(R10)-C(=O)—NR11R12, —N(R10)-S(O)$_n$—R8, —S(O)$_n$—R8, —N(R10)-S(O)$_n$—NR11R12 and —S(O)$_n$—NR11R12, except for B2a, all the aryl and heteroaryl above are optionally substituted with one or more substituents selected from the group consisting of alkyl, alkoxy and alkylenedioxy, except for B2a, R2A, and R3A, all the cyclic radicals above, and also the ring formed by R5 and R6 with the nitrogen atom to which they are attached, are optionally substituted with one or more substituents selected from the group consisting of oxo and thioxo, R8 is alkyl, alkenyl, cycloalkyl, cycloalkylalkyl, heterocyclyl, heterocyclylalkyl, aryl, arylalkyl, heteroaryl or heteroarylalkyl, R9 is defined as R8 or is hydrogen, R10 is hydrogen or alkyl, R11 and R12, which may be identical or different, are hydrogen, C$_3$-C$_6$ cycloalkyl, C$_1$-C$_4$ alkyl, or phenyl, optionally substituted with one or more substituents, which may be identical or different, selected from the group consisting of halogen, cyano, hydroxyl, alkoxy, —CF$_3$, nitro, phenyl, and free, salified, esterified or amidated carboxyl, or R11 and R12 taken together with the nitrogen atom to which they are attached form 5- to 7-membered cyclic radical containing one or more hetero atoms chosen from O, S, N and NR7, R13, which may be identical to or different from R5 or R6, is defined as R5 or R6, and n is 0 to 2, or a racemic, enantiomeric or diastereoisomeric isomer form of said compound, or an addition salt with a mineral or organic acid or with a mineral or organic base thereof.

51. The compound according to claim 50 wherein Y1A, B2a, R2A and R3A are as defined in claim 50 and Y2A is halogen, —OH, -alk, —Oalk, —Oacyl, —NR5AR6A, —CO2H, —CO2alk, —CO—NR5AR6A, —S(O)$_n$—CF$_3$, —NH—S(O)$_n$—CF$_3$ or phenyl; alk is a linear or branched alkyl radical containing not more than 6 carbon atoms; all the alkyl, alkoxy and phenyl are optionally substituted, R5A and R6A, which may be identical or different, are hydrogen, alkyl, cycloalkyl or phenyl, the alkyl and phenyl are optionally substituted, or R5A and R6A taken together with the nitrogen atom to which they are attached form cyclic radical chosen from pyrrolidyl, piperidyl, piperazinyl, morpholinyl, indolinyl, tetrahydroquinolyl and azetidinyl, all the alkyl, alkoxy and phenyl are optionally substituted with one or more radicals chosen from halogen, —OH, alk, —Oalk, —OCF$_3$, —S(O)$_n$—CF$_3$, —CF$_3$, —NH$_2$, —NH-Alk and —N(Alk)$_2$, and n is 0 to 2, or a racemic, enantiomeric or diastereoisomeric isomer form of said compound, or an addition salt with a mineral or organic acid or with a mineral or organic base thereof.

52. The compound according to claim 50 wherein

Y1A is —OCF$_3$, SCF$_3$ or S(O)2-CF$_3$,

B2a is a 4-quinolyl or 4-pyridyl radical optionally substituted with one or two radicals chosen from halogen, —OH, alk, —Oalk, —CO2H, —CO2alk, —NR5AR6A, —CF$_3$, —OCF$_3$ and optionally substituted phenyl, R5A and R6A, which may be identical or different, are hydrogen, alkyl, cycloalkyl or phenyl, the alkyl and phenyl radicals being optionally substituted, or R5A and R6A taken together with the nitrogen atom to which they are attached forma cyclic radical chosen from pyrrolidyl, piperidyl, piperazinyl, morpholinyl, piperazinyl and azetidinyl radicals, R2A and R3A, which may be identical or different, are hydrogen or optionally substituted alkyl, all the alkyl and phenyl radicals being optionally substituted with one or more radicals chosen from halogen, OH, alk, Oalk, OCF$_3$, S(O)$_n$—CF$_3$, —CF$_3$, NH$_2$, NHalk and N(Alk)$_2$, or a racemic, enantiomeric or diastereoisomeric isomer form of said compound, or an addition salt with a mineral or organic acid or with a mineral or organic base thereof.

53. The compound according to claim 50 wherein

Y1A is —OCF$_3$, —SCF$_3$ or —S(O)$_2$—CF$_3$,

B2a is 4-quinolyl or 4-pyridyl optionally substituted with one or two radicals chosen from halogen, —OH, alk and —Oalk, and R2A and R3A, which may be identical or different, are hydrogen or linear or branched alkyl containing not more than 4 carbon atoms optionally substituted with hydroxyl, or a racemic, enantiomeric or diastereoisomeric isomer form of said compound, or an addition salt with a mineral or organic acid or with a mineral or organic base thereof.

54. The compound according to claim 50 wherein Y1a is —OCF$_3$, —SCF$_3$ or —S(O)$_2$CF$_3$, and R2A and R3A, which may be identical or different, are hydrogen or CH3, or a diastereoisomeric isomer form of said compound, or an addition salt with a mineral or organic acid or with a mineral or organic base thereof.

55. A compound selected from the group consisting of:
(S)-5-methyl-1-quinol-4-ylmethyl-3-(4-trifluoromethanesulfonylphenyl)imidazolidine-2,4-dione trifluoroacetate;
(S)-5-methyl-1-pyrid-4-ylmethyl-3-(4-trifluoromethanesulfonylphenyl)imidazolidine-2,4-dione trifluoroacetate;
(S)-5-methyl-1-quinol-4-ylmethyl-3-(4-trifluoromethylsulfanylphenyl)imidazolidine-2,4-dione trifluoroacetate;
5,5-dimethyl-1-quinol-4-ylmethyl-3-(4-trifluoromethanesulfonylphenyl)imidazolidine-2,4-dione trifluoroacetate;
(R)-5-methyl-1-quinol-4-ylmethyl-3-(4-trifluoromethanesulfonylphenyl)imidazolidine-2,4-dione trifluoroacetate;
(R)-5-methyl-1-quinol-4-ylmethyl-3-(4-trifluoromethylsulfanylphenyl)imidazolidine-2,4-dione trifluoroacetate;
(R)-5-methyl-1-pyrid-4-ylmethyl-3-(4-trifluoromethanesulfonylphenyl)imidazolidine-2,4-dione trifluoroacetate;
(R)-5-methyl-1-(3-methylpyrid-4-ylmethyl)-3-(4-trifluoromethanesulfonylphenyl)imidazolidine-2,4-dione trifluoroacetate;
(R)-4-methyl-3-quinol-4-ylmethyl-5-thioxo-1-(4-trifluoromethylsulfanylphenyl)imidazolidin-2-one trifluoroacetate;
(R)-5-isopropyl-1-quinol-4-ylmethyl-3-(4-trifluoromethylsulfanylphenyl)imidazolidine-2,4-dione trifluoroacetate;
(R)-5-isopropyl-1-quinol-4-ylmethyl-3-(4-trifluoromethanesulfonylphenyl)imidazolidine-2,4-dione trifluoroacetate;
(R)-5-(4-hydroxybenzyl)-1-quinol-4-ylmethyl-3-(4-trifluoromethanesulfonylphenyl)imidazolidine-2,4-dione trifluoroacetate;
(R)-5-(4-hydroxybenzyl)-1-pyrid-4-ylmethyl-3-(4-trifluoromethanesulfonylphenyl)imidazolidine-2,4-dione trifluoroacetate;
(R)-5-(1-hydroxyethyl)-1-quinol-4-ylmethyl-3-(4-trifluoromethanesulfonylphenyl)imidazolidine-2,4-dione trifluoroacetate;
(R)-1-(3-hydroxypyrid-4-ylmethyl)-5-methyl-3-(4-trifluoromethylsulfanylphenyl)imidazolidine-2,4-dione trifluoroacetate;
5,5-dimethyl-1-quinol-4-ylmethyl-3-(4-trifluoromethoxyphenyl)imidazolidine-2,4-dione trifluoroacetate;
5,5-dimethyl-1-quinol-4-ylmethyl-3-(4-trifluoromethylsulfanylphenyl)imidazolidine-2,4-dione trifluoroacetate;
5,5-dimethyl-1-(3-methylpyrid-4-ylmethyl)-3-(4-trifluoromethoxyphenyl)imidazolidine-2,4-dione trifluoroacetate;
5,5-dimethyl-1-(3-methylpyrid-4-ylmethyl)-3-(4-trifluoromethylsulfanylphenyl)imidazolidine-2,4-dione trifluoroacetate;
5,5-dimethyl-1-(3-methylpyrid-4-ylmethyl)-3-(4-trifluoromethanesulfonylphenyl)imidazolidine-2,4-dione trifluoroacetate;
1-(3-hydroxypyrid-4-ylmethyl)-5,5-dimethyl-3-(4-trifluoromethoxyphenyl)imidazolidine-2,4-dione trifluoroacetate;
1-(3-hydroxypyrid-4-ylmethyl)-5,5-dimethyl-3-(4-trifluoromethylsulfanylphenyl)imidazolidine-2,4-dione trifluoroacetate
1-(3-hydroxypyrid-4-ylmethyl)-5,5-dimethyl-3-(4-trifluoromethanesulfonylphenyl)imidazolidine-2,4-dione trifluoroacetate;
{4-[5,5-dimethyl-2,4-dioxo-3-(4-trifluoromethylsulfanylphenyl)imidazolidin-1-ylmethyl]pyrid-2-yl} cyclopropanecarboxamide trifluoroacetate;
5,5-dimethyl-1-[2-(pyrid-2-ylamino)pyrid-4-ylmethyl]-3-(4-trifluoromethylsulfanylphenyl)imidazolidine-2,4-dione; compound with trifluoroacetic acid;
N-{4-[5,5-dimethyl-2,4-dioxo-3-(4-trifluoromethylsulfanylphenyl)imidazolidin-1-ylmethyl]pyrid-2-yl}isobutyramide; compound with trifluoroacetic acid;
N-{4-[5,5-dimethyl-2,4-dioxo-3-(4-trifluoromethylsulfanylphenyl)imidazolidin-1-ylmethyl]pyrid-2-yl}propionamide; compound with trifluoroacetic acid;
1-(2-aminopyrid-4-ylmethyl)-5,5-dimethyl-3-(4-trifluoromethylsulfanylphenyl)imidazolidine-2,4-dione hydrochloride;
{4-[5,5-dimethyl-2,4-dioxo-3-(4-trifluoromethylsulfanylphenyl)imidazolidin-1-ylmethyl]pyrid-2-yl}pyridine-2-carboxamide trifluoroacetate;
N-{4-[5,5-dimethyl-2,4-dioxo-3-(4-trifluoromethylsulfanylphenyl)imidazolidin-1-ylmethyl]pyrid-2-yl}-3-piperid-1-ylpropionamide trifluoroacetate;
N-{4-[5,5-dimethyl-2,4-dioxo-3-(4-trifluoromethylsulfanylphenyl)imidazolidin-1-ylmethyl]pyrid-2-yl}-3-[4-(2-hydroxyethyl)piperazin-1-yl]propionamide trifluoroacetate;
N-{4-[5,5-dimethyl-2,4-dioxo-3-(4-trifluoromethylsulfanylphenyl)imidazolidin-1-ylmethyl]pyrid-2-yl}-3-morpholin-4-ylpropionamide trifluoroacetate;
N-{4-[5,5-dimethyl-2,4-dioxo-3-(4-trifluoromethylsulfanylphenyl)imidazolidin-1-ylmethyl]pyrid-2-yl}-3-pyrrolidin-1-ylpropionamide trifluoroacetate;
N-{4-[5,5-dimethyl-2,4-dioxo-3-(4-trifluoromethylsulfanylphenyl)imidazolidin-1-ylmethyl]pyrid-2-yl}-3-(4-methylpiperazin-1-yl)propionamide trifluoroacetate;
1-{4-[5,5-dimethyl-2,4-dioxo-3-(4-trifluoromethylsulfanylphenyl)imidazolidin-1-ylmethyl]pyrid-2-yl}-3-phenylurea;
1-[2-(6-ethylpyrid-2-ylamino)pyrid-4-ylmethyl]-5,5-dimethyl-3-(4-trifluoromethylsulfanylphenyl)imidazolidine-2,4-dione;
5,5-dimethyl-1-[2-(4-methylpyrid-2-ylamino)pyrid-4-ylmethyl]-3-(4-trifluoromethylsulfanylphenyl)imidazolidine-2,4-dione;
5,5-dimethyl-1-[2-(6-methylpyrid-2-ylamino)pyrid-4-ylmethyl]-3-(4-trifluoromethylsulfanylphenyl)imidazolidine-2,4-dione;
1-[2-(4,6-dimethylpyrid-2-ylamino)pyrid-4-ylmethyl]-5,5-dimethyl-3-(4-trifluoromethyl sulfanylphenyl)-imidazolidine-2,4-dione;
1-[2-(3,5-dichloropyrid-2-ylamino)pyrid-4-ylmethyl]-5,5-dimethyl-3-(4-trifluoromethylsulfanylphenyl)-imidazolidine-2,4-dione;
5,5-dimethyl-1-[2-(pyrid-4-ylamino)pyrid-4-ylmethyl]-3-(4-trifluoromethylsulfanylphenyl)imidazolidine-2,4-dione;
5,5-dimethyl-1-[2-(pyrid-3-ylamino)pyrid-4-ylmethyl]-3-(4-trifluoromethylsulfanylphenyl)imidazolidine-2,4-dione;
N-{4-[5,5-dimethyl-2,4-dioxo-3-(4-trifluoromethylsulfanylphenyl)imidazolidin-1-ylmethyl]pyrid-2-yl}-3-(2-oxoazepan-1-yl)propionamide;
3-(benzylmethylamino)-N-{4-[5,5-dimethyl-2,4-di-oxo-3-(4-trifluoromethylsulfanylphenyl)imidazolidin-1-ylmethyl]pyrid-2-yl}propionamide;
4,5-diacetoxy-6-acetoxymethyl-2-(3-{4-[5,5-dimethyl-2,4-dioxo-3-(4-trifluoromethylsulfanylphenyl)-imidazolidin-1-ylmethyl]pyrid-2-yl}thioureidoacetic acid;
5,5-dimethyl-1-[2-(5-methylpyrid-2-ylamino)pyridin-4-ylmethyl]-3-(4-trifluoromethylsulfanylphenyl)-imidazolidine-2,4-dione;
N-{4-[5,5-dimethyl-2,4-dioxo-3-(4-trifluoromethylsulfanylphenyl)imidazolidin-1-ylmethyl]pyrid-2-yl}-3,5-dimethoxybenzamide trifluoroacetate;
5,5-dimethyl-1-[2-(pyrazin-2-ylamino)pyrid-4-ylmethyl]-3-(4-trifluoromethylsulfanylphenyl)imidazolidine-2,4-dione trifluoroacetate;
N-{4-[5,5-dimethyl-2,4-dioxo-3-(4-trifluoromethylsulfanylphenyl)imidazolidin-1-ylmethyl]pyrid-2-yl}-3-(3-methylpiperid-1-yl)propionamide trifluoroacetate;

N-{4-[5,5-dimethyl-2,4-dioxo-3-(4-trifluoromethylsulfanylphenyl)imidazolidin-1-ylmethyl]pyrid-2-yl}-3-(3,5-dimethylpiperid-1-yl)propionamide trifluoroacetate;
N-{4-[5,5-dimethyl-2,4-dioxo-3-(4-trifluoromethylsulfanylphenyl)imidazolidin-1-ylmethyl]pyrid-2-yl}-3-methoxybenzamide trifluoroacetate;
{4-[5,5-dimethyl-2,4-dioxo-3-(4-trifluoromethylsulfanylphenyl)imidazolidin-1-ylmethyl]pyrid-2-yl}pyrazine-2-carboxamide trifluoroacetate;
{4-[5,5-dimethyl-2,4-dioxo-3-(4-trifluoromethylsulfanylphenyl)imidazolidin-1-ylmethyl]pyrid-2-yl}thiophene-2-carboxamide trifluoroacetate;
N-{4-[5,5-dimethyl-2,4-dioxo-3-(4-trifluoromethylsulfanylphenyl)imidazolidin-1-ylmethyl]pyrid-2-yl}-4-methylbenzamide; compound with trifluoroacetic acid;
1-isoquinolin-5-yl-5,5-dimethyl-3-(4-trifluoro-methylsulfanylphenyl)imidazolidine-2,4-dione;
3-(4-acetylpiperazin-1-yl)-N-{4-[5,5-dimethyl-2,4-dioxo-3-(4-trifluoromethylsulfanylphenyl)imidazolidin-1-ylmethyl]pyrid-2-yl}propionamide;
3-[4-(2-diethylaminoethyl)piperazin-1-yl]-N-{4-[5,5-dimethyl-2,4-dioxo-3-(4-trifluoromethylsulfanylphenyl)imidazolidin-1-ylmethyl]pyrid-2-yl}propionamide;
N-{4-[5,5-dimethyl-2,4-dioxo-3-(4-trifluoromethylsulfanylphenyl)imidazolidin-1-ylmethyl]pyrid-2-yl}-3-(2,6-dimethylmorpholin-4-yl)propionamide;
N-{4-[5,5-dimethyl-2,4-dioxo-3-(4-trifluoromethylsulfanylphenyl)imidazolidin-1-ylmethyl]pyrid-2-yl}-3-(4-pyrrolidin-1-ylpiperid-1-yl)propionamide;
N-{4-[5,5-dimethyl-2,4-dioxo-3-(4-trifluoromethylsulfanylphenyl)imidazolidin-1-ylmethyl]pyrid-2-yl}-2-(4-pyrrolidin-1-ylpiperid-1-yl)acetamide;
5,5-dimethyl-1-[2-(4-methylpyrid-3-ylamino)pyrid-4-ylmethyl]-3-(4-trifluoromethylsulfanylphenyl)imidazolidine-2,4-dione;
5,5-dimethyl-1-[2-(6-morpholin-4-ylpyrid-3-ylamino)pyrid-4-ylmethyl]-3-(4-trifluoromethylsulfanylphenyl)imidazolidine-2,4-dione;
1-[2-(2,6-dimethylpyrid-3-ylamino)pyrid-4-ylmethyl]-5,5-dimethyl-3-(4-trifluoromethylsulfanylphenyl)-imidazolidine-2,4-dione;
methyl 5-{4-[5,5-dimethyl-2,4-dioxo-3-(4-trifluoromethylsulfanylphenyl)imidazolidin-1-ylmethyl]pyrid-2-ylamino}pyridine-2-carboxylate;
1-[2-(2,6-dimethoxypyrid-3-ylamino)pyrid-4-ylmethyl]-5,5-dimethyl-3-(4-trifluoromethylsulfanylphenyl)imidazolidine-2,4-dione;
1-[2-(6-fluoropyrid-3-ylamino)pyrid-4-ylmethyl]-5,5-dimethyl-3-(4-trifluoromethylsulfanylphenyl)-imidazolidine-2,4-dione; and
1-[2-(6-methoxypyrid-3-ylamino)pyrid-4-ylmethyl]-5,5-dimethyl-3-(4-trifluoromethylsulfanylphenyl)-imidazolidine-2,4-dione, or
a racemic, enantiomeric or diastereoisomeric isomer form of the compound of formula I, or an addition salt with a mineral or organic acid or with a mineral or organic base thereof.

56. A pharmaceutical composition comprising a pharmaceutically effective amount of a compound according to claim 1 and a pharmaceutically acceptable adjuvant.

57. A method for treating a patient suffering from rheumatoid arthritis, comprising administering to the patient a physiologically effective amount of the compound according to claim 1.

58. The compound according to claim 1 wherein
Y and Y1, which may be identical or different, are such that one of Y and Y1 is selected from the group consisting of $OCF_3$, —O—$CF_2$—$CHF_2$, —O—$CHF_2$, —O—$CH_2$—$CF_3$, —$S(O)_n CF_3$, —S—$CF_2$—$CF_2$—$CF_3$, —$S(O)_n$-alk, —S-Alk-O-Alk, —S-Alk-OH, —S-Alk-CN, —S-Alk-heterocyclyl, —$SO_2 CHF_2$, —$SO_2 CF_2 CF_3$, —$SO_2 NR5R6$ and —$SF_5$, in which Alk is alkyl containing from 1 to 4 carbon atoms, and the other of Y and Y1 is chosen from the group consisting of hydrogen, halogen, nitro, —NR5R6, free or esterified carboxyl, and —CONR5R6,
or the

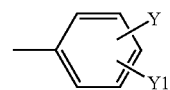

is

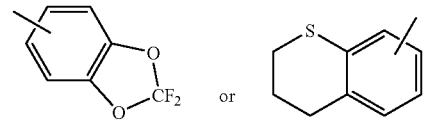

being optionally substituted with one or more alkyl, which are themselves optionally substituted, or a racemic, enantiomeric or diastereoisomeric isomer form of the compound of formula I, or an addition salt with a mineral or organic acid or with a mineral or organic base thereof, with the proviso:

a) when p is 0, R and R1 are oxygen, A1 is single bond or alkyl, Y and Y1, which may be identical or different, are at least one is —$OCF_3$ or —S-alk, A2 is single bond or alkyl and B2 is an optionally substituted heterocyclyl, then R2 and R3 are not one hydrogen and the other imidazolylalkyl;

or b) when p is 0, R and R1 are oxygen, A1 is a single bond or alkyl, Y and Y1, which may be identical or different, are at least one is —$S(O)_n$-alk, A2 is single bond and B2 is an optionally substituted 5- or 6-membered aromatic heterocyclyl, then R2 and R3 are not selected from the group consisting of hydrogen, alkyl, arylalkyl, aryl and heteroaryl.

* * * * *